United States Patent
Kick et al.

(10) Patent No.: US 11,008,317 B2
(45) Date of Patent: May 18, 2021

(54) TRIAZOLOPYRIDINE INHIBITORS OF MYELOPEROXIDASE AND/OR EPX

(71) Applicant: BRISTOL-MYERS SQUIBB COMPANY, Princeton, NJ (US)

(72) Inventors: Ellen K. Kick, Pennington, NJ (US); Joanne M. Smallheer, Yardley, PA (US); Scott A. Shaw, Lawrence Township, NJ (US); Benjamin P. Vokits, New York City, NY (US); Andrew K. Dilger, Ewing, NJ (US); Charles G. Clark, Cherry Hill, NJ (US); Meriah Neissel Valente, Bedminster, NJ (US); Sutjano Jusuf, Princeton, NJ (US); Nicholas R. Wurtz, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 231 days.

(21) Appl. No.: 16/083,958

(22) PCT Filed: Mar. 16, 2017

(86) PCT No.: PCT/US2017/022756
§ 371 (c)(1),
(2) Date: Sep. 11, 2018

(87) PCT Pub. No.: WO2017/161145
PCT Pub. Date: Sep. 21, 2017

(65) Prior Publication Data
US 2020/0291016 A1  Sep. 17, 2020

Related U.S. Application Data

(60) Provisional application No. 62/310,017, filed on Mar. 18, 2016.

(51) Int. Cl.
*C07D 471/04* (2006.01)
*C07D 519/00* (2006.01)

(52) U.S. Cl.
CPC .......... *C07D 471/04* (2013.01); *C07D 519/00* (2013.01)

(58) Field of Classification Search
CPC .................................................. C07D 471/04
See application file for complete search history.

(56) References Cited

U.S. PATENT DOCUMENTS 9,920,075 B2    3/2018  Wurtz et al.
10,214,527 B2 *  2/2019  Shaw ..................... A61P 25/00
2018/0282320 A1  10/2018 Shaw et al.

FOREIGN PATENT DOCUMENTS

WO   WO 2016/040419 A1   3/2016
WO   WO 2017/040449 A1   3/2017

OTHER PUBLICATIONS

Schönherr "Profound Methyl Effects in Drug Discovery and a Call for New C-H Methylation Reactions" Angew. Chem. Int. Ed. 2013, 52, 12256-12267.*
Patani "Bioisosterism: A Rational Approach in Drug Design" Chemical Reviews 1996, 96, 3147-3176.*
Wermuth, Camille G. "Molecular Variation Based on Isosteric Replacements" in Chapter 13, The Practice of Medicinal Chemistry, Academic: 1996.*
Nakamura, Toshio "Imidazole derivatives as new potent and selective 20-HETE synthase inhibitors." Bioorganic & Medicinal Chemistry Letters 2004, 14, 333-336.*
Li, Bing et. al. "N-(Arylacetyl)-biphenylalanines as Potent VLA-4 Antagonists" Bioorganic & Medicinal Chemistry Letters 2002, 12, 2141-2144.*

\* cited by examiner

*Primary Examiner* — David K O'Dell
(74) *Attorney, Agent, or Firm* — Elliott Korsen

(57) ABSTRACT

The present invention provides compounds of Formula (I); wherein the substituents are each as defined in the specification, and compositions comprising any of such novel compounds. These compounds are myeloperoxidase (MPO) inhibitors and/or eosinophil peroxidase (EPX) inhibitors, and may be useful for the treatment and/or prophylaxis of atherosclerosis, heart failure, chronic obstructive pulmonary disease (COPD), and related diseases.

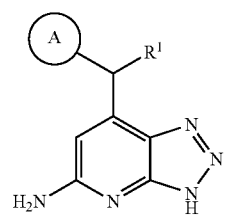

5 Claims, No Drawings

TRIAZOLOPYRIDINE INHIBITORS OF MYELOPEROXIDASE AND/OR EPX

CROSS REFERENCE TO RELATED APPLICATION

This application claims priority to U.S. Provisional Patent Application Ser. No. 62/310,017, filed Mar. 18, 2016, which is incorporated by reference in its entirety.

FIELD OF THE INVENTION

The present invention relates to novel macrocyclic compounds, which are myeloperoxidase (MPO) inhibitors and/or eosinophil peroxidase (EPX) inhibitors, compositions containing them, and methods of using them, for example, for the treatment and/or prophylaxis of atherosclerosis, heart failure, chronic obstructive pulmonary disease (COPD), and related diseases.

BACKGROUND OF THE INVENTION

Cardiovascular disease is a major health risk throughout the industrialized world. Atherosclerosis, the most prevalent of cardiovascular diseases, is the principal cause of heart attack and stroke, and thereby the principal cause of death in the United States. Atherosclerosis is a complex disease involving many cell types and molecular factors (for a detailed review, see Weber et al., Nature Med, 17(11):1410-1422 (2011)).

MPO inhibitors have been suggested to reduce the atherosclerotic burden and/or the vulnerability of existing atherosclerotic lesions and thereby decrease the risk of acute myocardial infarction, unstable angina or stroke, and reduce ischemia-reperfusion injury during acute coronary syndrome and ischemic cerebrovascular events. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al., J. Clin. Invest., 94(1):437-444 (1994)). Moreover, HOCl-modified lipoproteins have been detected in advanced human atherosclerotic lesions (Hazell, L. J. et al., J. Clin. Invest., 97:1535-1544 (1996)). In eroded and ruptured human lesions, as compared to fatty streaks, an increased number of MPO expressing macrophages have been demonstrated, suggesting a particular role for MPO in acute coronary syndromes (Sugiyama, S. et al., Am. J. Pathol. 158(3):879-891 (2001); Tavora, F. R., BMC Cardiovasc. Disord., 9:27 (Jun. 23, 2009)).

Data accumulated during the last fifteen years indicate that the pro-atherogenic actions of MPO include oxidation of lipoproteins, induction of endothelial dysfunction via consuming nitric oxide and destabilization of atherosclerotic lesions by activation of proteases (Nicholls, S. J. et al., Arterioscler. Thromb. Vasc. Biol., 25(6): 1102-1111 (2005); Nicholls, S. J. et al., JLR, S346-S351 (2009)). Several studies have focused on nitro- and chlorotyrosine modifications of LDL and HDL lipoproteins. Since chlorotyrosine modifications in vivo are generated by hypochlorous acid produced by MPO these modifications are regarded as specific markers of MPO activity (Hazen, S. et al., J. Clin. Invest., 99(9):2075-2081 (1997)).

ApoA-I isolated from atherosclerotic lesions is modified by reactive chlorine and nitrogen species as well as by reactive carbonyls (Pennathur, S. et al., J. Biol. Chem., 279:42977-42983 (2004); Shao, B. et al., J. Biol. Chem., 279:7856-7866 (2004); Zheng, L. et al., J. Clin. Invest., 114(4):529-541 (2004); Shao, B. et al., JBC in press (2012)). Chlorotyrosine modification of apoA1, the main apolipoprotein of HDL cholesterol, was associated with impaired cholesterol acceptor function (Bergt, C. S. et al., Proc. Natl. Acad. Sci. USA, 101(35):13032-13037 (2004); Zheng, L. et al., J. Clin. Invest., 114(4):529-541 (2004)). Thus, oxidation of apoA-I amino acid residues by the MPO—$H_2O_2$—$Cl^-$ system is one mechanism for loss of its biological activities.

The lipid and protein content of LDL are also targets for MPO oxidation and presence of chlorotyrosine in LDL extracted from human atherosclerotic tissues has been shown (Hazen, S. et al., J. Clin. Invest., 2075-2081 (1997)). LDL particles exposed to MPO in vitro become aggregated, leading to facilitated uptake via macrophage scavenger receptors and foam cell formation (Hazell, L. J. et al., Biochem. J., 290 (Pt. 1): 165-172 (1993); Podrez, E. A. et al., J Clin. Invest. 105:1095-1108 (2000)). Thus, MPO appears to play a role in the generation of oxidized LDL, which contributes to atherosclerosis plaque development.

Further evidence implicating MPO in the pathophysiology of atherosclerosis comes from the study of hMPO transgenic mice crossed with LDL-R KO mice (Castelini L. W. et al., J. Lipid Res., 47:1366-1377 (2006)). These mice expressed MPO in lesions and developed significantly larger aortic lesions than control LDL-R KO mice.

Many clinical studies have implicated MPO in cardiovascular disease in human patients. Patients with established coronary artery disease have higher plasma and leukocyte MPO levels than healthy controls (Zhang, R. et al., JAMA, 286(17):2136-2142 (2001)). Moreover, in three large prospective studies plasma levels of MPO predicted the risk of future coronary events or revascularization (Baldus, S. et al., Circulation, 108(12):1440-1445 (2003); Brennan, M. et al., N. Engl. J. Med., 349(17):1595-1604 (2003); Kohli, P. et al., Circulation, 122:A13175 (2010)). In two recent large nested case control prospective studies, the EPIC-Norfolk and MONICA-/KORA Augsburg studies, baseline MPO levels in these initially healthy populations turned out to be an excellent predictor of future risk of CAD and CHD respectively, showing that this inflammatory marker precedes the presentation of clinical symptoms of CVD (Meuwese, M. C. et al., J. Am. Coll. Cardiol., 50:159-165 (2007); Karakas et al., J. Int. Med., 271:43-50 (2011)). Interestingly, MPO deficient humans are less affected by cardiovascular disease than controls with normal MPO levels (Kutter, D. et al., Acta Haematol., 104:10-15 (2000)). A polymorphism in the MPO promoter affects expression leading to high and low MPO expressing individuals. In three different studies the high expression genotype has been associated with an increased risk of cardiovascular disease (Nikpoor, B. et al., Am. Heart J., 142(2):336-339 (2001); Makela, R. et al., Lab. Invest. 83(7):919-925 (2003); Asselbergs, F. W. et al., Am. J. Med., 116(6):429-430 (2004)).

MPO inhibitors are expected to preserve heart function and reduce heart failure burden in patients. In MPO null mice, preservation of left ventricular (LV) function has been observed in both a coronary artery ligation model (Askari, A. T. et al., J. Exp. Med., 197:615-624 (2003)) and an ischemia reperfusion model (Vasilyev, N. et al., Circulation, 112:2812-2820 (2005)), suggesting that MPO may provide a mechanistic link between inflammation, oxidant stress, and impaired cardiac remodeling. High circulating levels of MPO have also been linked to chronic heart failure in patients. Systemic MPO was increased in patients with established chronic systolic HF and correlated with diastolic dysfunction independent of age and plasma B-type natriuretic peptide (Tang, W. H. et al., *Am. J. Cardiol.*, 98:796-799 (2006)). Studies also showed that systemic MPO in subjects with myocardial infarction (MI) (Mocatta, T. J. et al., *J. Am. Coll. Cardiol.*, 49:1993-2000 (2007)) or chronic systolic HF (Tang, W. H. et al., *J. Am. Coll. Cardiol.*, 49:2364-2370 (2007)) may predict long-term adverse clinical events.

Inhibitors of MPO or EPX may be used to treat other neuroinflammatory diseases, including multiple sclerosis, Alzheimer's disease, Parkinson's disease, multiple system atrophy, and stroke as well as other inflammatory diseases or conditions like asthma, COPD, cystic fibrosis, inflammatory bowel disease, chronic kidney disease, renal glomerular damage and rheumatoid arthritis.

In these chronic inflammatory diseases, a role of MPO in the development of tissue injury has been suggested. In lesional tissues of patients with Alzheimer's disease, MPO protein was detected along with elevated levels of chlorotyrosine (Green, P. S. et al., *J Neurochem.*, 90:724-733 (2004)). In an animal model of Parkinson's disease, increased levels of chlorotyrosine and HOCl-modified proteins in brain tissues have been reported (Choi, D. K. et al., *J. Neuroscience*, 25(28):6394-6600 (2005)). In asthmatic patients the level of bromotyrosine, a molecular fingerprint of eosinophil-catalyzed oxidation was associated with symptom severity (Wedes, S. H. et al., *J. Pediatr.*, 248-255 (2011)). Upon allergen challenge, a model that elicits primarily a strong eosinophilic response, lung segments of asthmatic subjects exhibit a >10 fold increase in bronchioalveolar lavage 3-bromotyrosine an indicator of eosinophil activity vs. a 3-fold increase in 3-chlorotyrosine characteristic of MPO activity (Wu, W. et al., JCI, 105:1455-1463 (2000)). The presence of HOCl-modified protein was also detected in patients with membranous glomerulonephritis (Grone et al., *Lab. Invest.*, 82:5-14 (2002)). High MPO circulating levels have been implicated in the development of cardiovascular and chronic kidney disease in patients on hemodialysis (Honda, H. et al., *Clin. J. Am. Soc., Nephrol.*, 142-151 (2009). In addition MPO activity and 3-chlorotyrosine levels were also increased during hemodyalisis in patients with end-stage renal disease (Delporte, C et al., *Talanta*, 99:603-609 (2012)). Similarly, there is accumulation of neutrophils and eosinophils in conjunction with MPO and EPX seen in intestinal mucosa of patients with inflammatory bowel disease (Kruidenier, L. et al., *J. Pathol.*, 201:17-27 (2003); Carlson, M. et al., *Am. J. Gastrol.*, 94(7):1876-1883 (1999)) and in synovial fluids of rheumatoid arthritis patients (Edwards, S. W. et al., *Biochem. J.*, 250:81-85 (1988); Nucombe, H. L. et al., *Ann. Rheum. Dis.*, 50:237-242 (1991)).

Thus, there is considerable evidence that MPO and/or EPX derived oxidants contribute to tissue injury in chronic inflammatory disorders. MPO and/or EPX inhibitors are anticipated to reduce the levels of oxidants and tissue injury associated with the progression of these diseases.

SUMMARY OF THE INVENTION

The present disclosure provides novel triazolopyridine compounds, including stereoisomers, tautomers, pharmaceutically acceptable salts, or solvates thereof, which are useful as MPO inhibitors and/or EPX inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of diseases or disorders associated with the activity of MPO and/or EPX.

The compounds of the invention may be used in therapy.

The compounds of the invention may be used for the manufacture of a medicament for the treatment and/or prophylaxis of diseases or disorders associated with the activity of MPO and/or EPX.

Examples of diseases or disorders associated with the activity of MPO and/or EPX include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

The compounds of the invention can be used alone, in combination with other compounds of the present invention, or in combination with one or more, preferably one to two other agent(s).

Other features and advantages of the invention will be apparent from the following detailed description and claims.

I. Compounds of the Invention

In a first aspect, the present invention provides a compound of Formula (I):

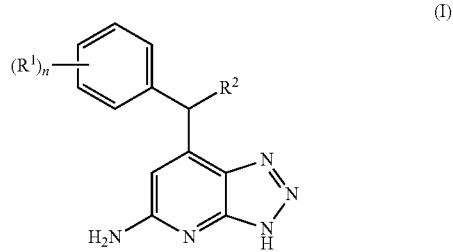

wherein
$R^1$ is independently one or more hydrogen, halogen, $C_{1-4}$ alkyl, $C_{1-4}$ alkoxy, $C_{1-4}$ haloalkyl, $C_{1-4}$ haloalkoxy, CN, $CO_2$ ($C_{1-4}$ alkyl), $CH_2OH$, $CH_2NH_2$, $SO_2Me$, or $SO_2NH_2$;

n is 0, 1, or 2;

$R^2$ is $C_1$-$C_6$ alkyl, benzyl, $C_3$-$C_8$ cycloalkyl $C_1$-$C_6$ alkyl-, hydroxy $C_1$-$C_6$ alkyl-, aryl $C_1$-$C_6$ alkyl-, —$(CH_2)_2C_1$-$C_6$ alkoxy aryl, heteroaryl $C_1$-$C_6$ alkyl-, —$(CH_2)_2C_1$-$C_6$ alkoxy, —$(CH_2)_mNR^3COaryl$, —$(CH_2)_mNR^3C_1$-$C_6$ alkyl, —$(CH_2)_m NR^3$ aryl $C_1$-$C_6$ alkyl; —$(CH_2)_mNR^3$ heteroaryl $C_1$-$C_6$ alkyl, —$(CH_2)_mNR^3C_3$-$C_8$ cycloalkyl, —$(CH_2)_mNR^3$ heterocyclyl, —$(CH_2)_mNR^3C_3$-$C_8$ cycloalkyl $C_1$-$C_6$ alkyl, —$(CH_2)_mNR^3C_3$-$C_8$ cycloalkyl aryl, —$(CH_2)_m NR^3C_9$-$C_{10}$ bicyclic carbocyclyl, —$(CH_2)_mNR^3$ bridged carbocyclyl, —$(CH_2)_mNR^3$ bridged heterocyclyl, —$(CH_2)_m NHSO_2$ aryl, —$(CH_2)_{20}C_3$-$C_{10}$ carbocyclyl, —$(CH_2)_m$ CO aryl $C_1$-$C_6$ alkyl, —$(CH_2)_p$ heterocyclyl, or —$CH_2CO NR^3C_3$-$C_{10}$ carbocyclyl; any of which is substituted with 0-3 $R^4$ groups, m is 1, 2, 3, or 4;

p is 2 or 3;

$R^3$ is hydrogen, $C_{1-4}$ alkyl, 2-($C_{1-4}$ alkoxy)ethyl-, hydroxy $C_2$-$C_4$ alkyl, $C_{1-4}$ haloalkyl, —$CH_2CH(OH)CF_3$, —$(CH_2)$ heterocyclyl or —$CH_2CONR^xR^y$;

$R^x$ is hydrogen or $C_{1-4}$ alkyl;

$R^y$ is hydrogen or $C_{1-4}$ alkyl;

$R^4$ is, independently at each occurrence, one or more hydrogen, halogen, hydroxy, amino, cyano, hydroxy $C_1$-$C_6$ alkyl, halo $C_1$-$C_6$ alkyl, $C_1$-$C_6$ alkyl, $C_1$-$C_4$ alkoxy, —$C_{3-6}$ cycloalkyl, aryl, aryloxy, aryl $C_1$-$C_6$ alkyl-, heterocycle, —COO $C_1$-$C_6$ alkyl, or $CONR^xR^y$;

said —$C_{3-6}$ cycloalkyl substituted with 0-3 $R^a$, aryl substituted with 0-4 $R^a$, or a 5- to 10-membered heterocycle comprising carbon atoms and 1-4 heteroatoms selected from N, $NR^b$, O, and S; wherein said heterocycle is substituted with 0-3 $R^a$;

$R^a$ is, independently at each occurrence, hydrogen, OH, CN, —$CONH_2$, halogen, $C_{1-4}$ alkyl, $C_{1-4}$ alkoxy, $C_{1-4}$ haloalkyl or $C_{1-4}$ haloalkoxy;

$R^b$ is, independently at each occurrence, hydrogen, $C_{1-4}$ alkyl, $C_{1-4}$ haloalkyl, CO($C_{1-4}$ alkyl), $CO_2$($C_{1-4}$ alkyl), $SO_2$ ($C_{1-4}$ alkyl) or —$(CH_2)_t$-phenyl, said —$(CH_2)_t$-phenyl substituted with 0-1 $R^d$;

$R^d$ is hydrogen, $C_{1-4}$ alkyl or halogen;

t is 1 or 2;

and/or a pharmaceutically acceptable salt, a stereoisomer, a tautomer, or a solvate thereof.

In a second aspect, the invention provides, within the scope of the first aspect, a compound of Formula (II);

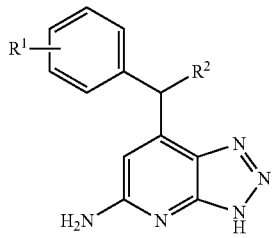

(II)

wherein $R^1$ is hydrogen, halogen, OMe, $OCF_3$, $OCF_2H$, methyl, $CH_2OH$, $SO_2NH_2$ or CN; $R^2$ is $C_1$-$C_6$ alkyl, benzyl, $C_3$-$C_8$ cycloalkyl $C_1$-$C_6$ alkyl-, hydroxy $C_1$-$C_6$ alkyl-, aryl $C_1$-$C_6$ alkyl-, —$(CH_2)_2C_1$-$C_6$ alkoxy aryl, heteroaryl $C_1$-$C_6$ alkyl-, —$(CH_2)_2C_1$-$C_6$ alkoxy, —$(CH_2)_mNR^3COaryl$, —$(CH_2)_m NR^3C_1$-$C_6$ alkyl, —$(CH_2)_mNR^3$ aryl $C_1$-$C_6$ alkyl; —$(CH_2)_m NR^3$ heteroaryl $C_1$-$C_6$ alkyl, —$(CH_2)_mNR^3C_3$-$C_8$ cycloalkyl, —$(CH_2)_mNR^3$ heterocyclyl, —$(CH_2)_mNR^3C_3$-$C_8$ cycloalkyl $C_1$-$C_6$ alkyl, —$(CH_2)_mNR^3C_3$-$C_8$ cycloalkyl aryl, —$(CH_2)_m NR^3C_9$-$C_{10}$ bicyclic carbocyclyl, —$(CH_2)_m NR^3$ bridged carbocyclyl, —$(CH_2)_mNR^3$ bridged heterocyclyl, —$(CH_2)_m$ $NHSO_2$ aryl, —$(CH_2)_{20}C_3$-$C_{10}$ carbocyclyl, —$(CH_2)_mCO$ aryl $C_1$-$C_6$ alkyl, —$(CH_2)_p$ heterocyclyl, or —$CH_2CONR^3C_3$-$C_{10}$ carbocyclyl; any of which is substituted with 0-3 $R^4$ groups, m is 2 or 3;

p is 2 or 3;

$R^3$ is hydrogen, $C_{1-4}$ alkyl, 2-($C_{1-4}$ alkoxy)ethyl-, hydroxy $C_2$-$C_4$ alkyl, $C_{1-4}$ haloalkyl, —$(CH_2)$ heterocyclyl or —$CH_2CONR^xR^y$;

$R^x$ is hydrogen or $C_{1-4}$ alkyl;

$R^y$ is hydrogen or $C_{1-4}$ alkyl;

$R^4$ is, independently at each occurrence, one or more halogen, hydroxy, cyano, hydroxy $C_1$-$C_6$ alkyl, halo $C_1$-$C_6$ alkyl, $C_1$-$C_4$ alkoxy, $C_1$-$C_6$ alkyl, —$C_{3-6}$ cycloalkyl, aryl, aryloxy, aryl $C_1$-$C_6$ alkyl-, —COO $C_1$-$C_6$ alkyl, or $CONR^xR^y$;

said —$C_{3-6}$ cycloalkyl is substituted with 0-3 $R^a$; said aryl is substituted with 0-4 $R^a$, or a 5- to 10-membered heterocycle comprising carbon atoms and 1-4 heteroatoms selected from N, $NR^b$, O, and S; wherein said heterocycle is substituted with 0-3 $R^a$;

$R^a$ is, independently at each occurrence, OH, CN, —$CONH_2$, halogen, $C_{1-4}$ alkyl, $C_{1-4}$ alkoxy, $C_{1-4}$ haloalkyl, or $C_{1-4}$ haloalkoxy;

$R^b$ is, independently at each occurrence, hydrogen, $C_{1-4}$ alkyl, $C_{1-4}$ haloalkyl, CO($C_{1-4}$ alkyl), $CO_2$($C_{1-4}$ alkyl), $SO_2$ ($C_{1-4}$ alkyl) or —$(CH_2)_t$-phenyl, said —$(CH_2)_t$-phenyl substituted with 0-1 $R^d$;

$R^d$ is F or Cl;

and/or a pharmaceutically acceptable salt, a stereoisomer, a tautomer, or a solvate thereof.

In a third aspect, the present invention includes a compound of Formula (III);

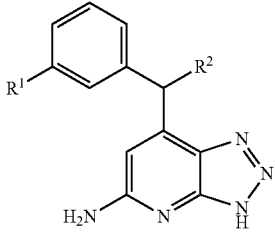

(III)

wherein $R^1$ is hydrogen, halogen, OMe, $OCF_3$, $OCF_2H$, methyl, $CH_2OH$, $SO_2NH_2$ or cyano;

$R^3$ is hydrogen, $C_{1-4}$ alkyl, 2-($C_{1-4}$ alkoxy)ethyl-, hydroxy ethyl, $C_{1-4}$ haloalkyl, —$(CH_2)$ heterocyclyl or —$CH_2CONR^xR^y$;

$R^2$ is, Me, ethyl, propyl, 2-methylpropyl, 3-phenylpropyl, 2-benzyloxyethyl, 3,3,-diphenylpropyl, 3-cyclohexylethyl, 1-naphthylpropyl, 2-naphthylpropyl, 1-indanylpropyl, 2-(tetrahydro-2H-pyran-4-yl)ethyl, 3-(1,2,3,4-tetrahydroisoquinolin-1-yl)propyl, —$(CH_2)_2NR^3C_1$-$C_6$ alkyl, —$(CH_2)_mNR^3$ aryl $C_1$-$C_6$ alkyl; —$(CH_2)_mNR^3$ heteroaryl $C_1$-$C_6$ alkyl, —$(CH_2)_mNR^3C_3$-$C_8$ cycloalkyl, —$(CH_2)_mNR^3$ heterocyclyl, —$(CH_2)_mNR^3C_3$-$C_8$ cycloalkyl $C_1$-$C_6$ alkyl, —$(CH_2)_mNR^3C_3$-$C_8$ cycloalkyl aryl, —$(CH_2)_m NR^3C_9$-$C_{10}$ bicyclic carbocyclyl, —$(CH_2)_mNR^3$ bridged carbocyclyl, —$(CH_2)_mNR^3$ bridged heterocyclyl,

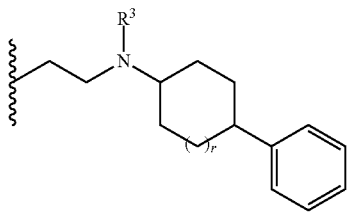

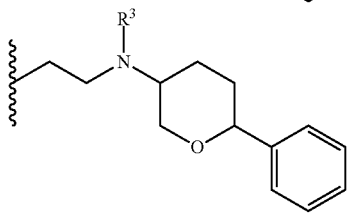

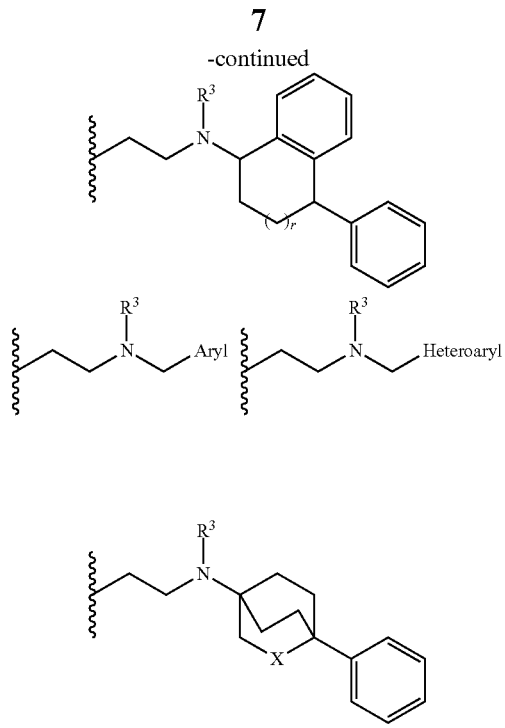

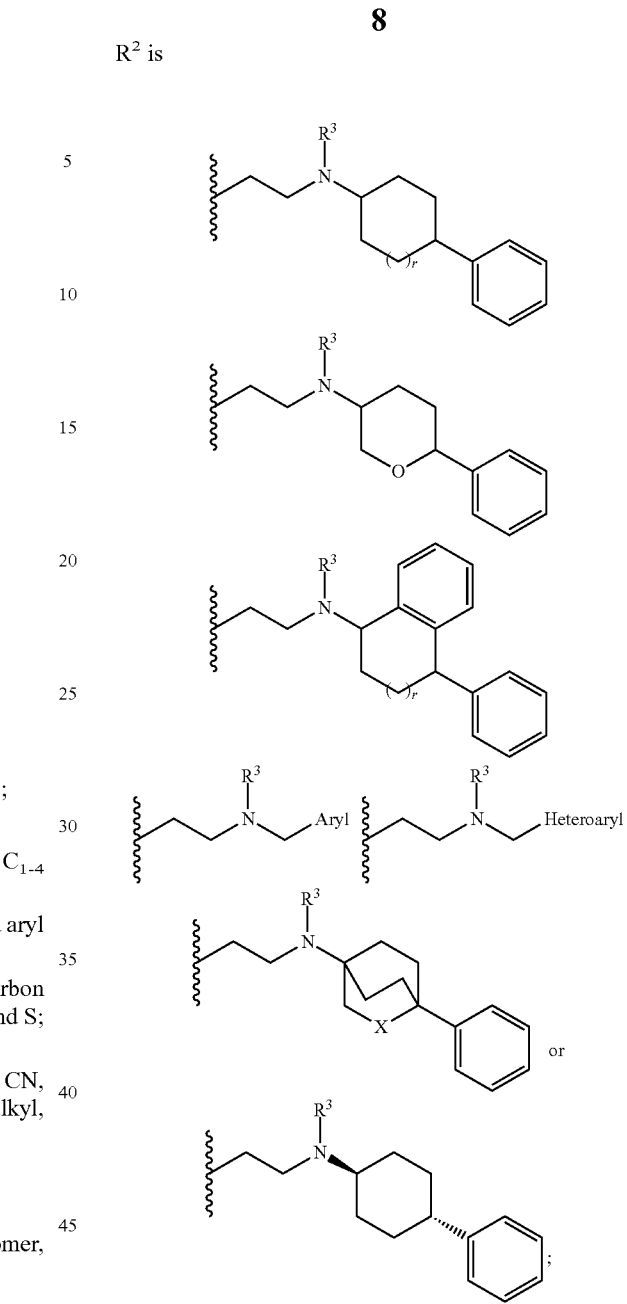

any of which can be substituted with 0-3 $R^4$ groups;

m is 2;

$R^4$ is hydrogen, halogen, hydroxyl, $C_{1-4}$ alkyl, $C_{1-4}$ alkoxy, $C_{1-2}$ haloalkyl, phenoxy, aryl or benzyl;

said —$C_{3-6}$ cycloalkyl is substituted with 0-3 $R^a$; said aryl is substituted with 0-4 $R^a$ or a 5- to 10-membered heterocycle comprising carbon atoms and 1-4 heteroatoms selected from N, $NR^b$, O, and S; wherein said heterocycle is substituted with 0-3 $R^a$;

$R^a$ is, independently at each occurrence, OH, CN, —$CONH_2$, halogen, $C_{1-4}$ alkyl, $C_{1-4}$ alkoxy, $C_{1-4}$ haloalkyl, or $C_{1-4}$ haloalkoxy;

r is 0 or 1;

X is $CH_2$ or O;

and/or a pharmaceutically acceptable salt, a stereoisomer, a tautomer, or a solvate thereof.

In a fourth aspect, the present invention includes a compound of Formula (III);

(III)

wherein $R^3$ is hydrogen, $C_{1-4}$ alkyl, $C_{1-4}$ alkoxyalkyl, $C_{2-4}$ hydroxyalkyl, $C_{1-4}$ haloalkyl, —$CH_2$-heterocyclyl or —$(CH_2)$ $CONH_2$;

$R^2$ is any of which can be substituted with 0-1 $R^4$ groups;

r is 0 or 1;

$R^4$ is hydrogen, halogen, hydroxyl, $C_{1-4}$ alkyl, $C_{1-4}$ alkoxy, $C_{1-2}$ haloalkyl, phenoxy, aryl or benzyl;

and/or a pharmaceutically acceptable salt, a stereoisomer, a tautomer, or a solvate thereof.

In another aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the prior aspect.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a pharmaceutical composition as defined above further comprising additional therapeutic agent(s).

In another embodiment, the present invention provides a process for making a compound of the present invention.

In another embodiment, the present invention provides an intermediate for making a compound of the present invention.

In another embodiment, the present invention provides a compound of the present invention, for use in therapy, alone, or optionally in combination with another compound of the present invention and/or at least one other type of therapeutic agent.

In another embodiment, the present invention provides a compound of the present invention for use in therapy, for the treatment and/or prophylaxis of diseases or disorders associated with the activity of MPO and/or EPX, alone, or optionally in combination with another compound of the present invention and/or at least one other type of therapeutic agent.

In another embodiment, the present invention provides a method for the treatment and/or prophylaxis of diseases or disorders associated with the activity of MPO and/or EPX, comprising administering to a patient in need of such treatment and/or prophylaxis a therapeutically effective amount of at least one of the compounds of the present invention, alone, or optionally in combination with another compound of the present invention and/or at least one other type of therapeutic agent.

In another embodiment, the present invention provides a method for the treatment and/or prophylaxis of diseases or disorders associated with the activity of MPO and/or EPX, comprising administering to a patient in need thereof a therapeutically effective amount of a first and second therapeutic agent, wherein the first therapeutic agent is a compound of the present invention and the second therapeutic agent is one other type of therapeutic agent.

In another embodiment, the present invention also provides the use of a compound of the present invention for the manufacture of a medicament for the treatment and/or prophylaxis of diseases or disorders associated with the activity of MPO and/or EPX, alone, or optionally in combination with another compound of the present invention and/or at least one other type of therapeutic agent.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of diseases or disorders associated with the activity of MPO and/or EPX.

Examples of diseases or disorders associated with the activity of MPO and/or EPX that may be prevented, modulated, or treated according to the present invention include, but are not limited to, atherosclerosis, coronary heart disease, coronary artery disease, coronary vascular disease, cerebrovascular disorders, peripheral vascular disease, dyslipidemias and the sequelae thereof, cardiovascular disorders, angina, ischemia, cardiac ischemia, heart failure, stroke, myocardial infarction, reperfusion injury, angioplastic restenosis, hypertension, vascular complications of diabetes, obesity or endotoxemia.

In one embodiment, examples of diseases or disorders include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, transient ischemic attack and stroke. In one embodiment, examples of diseases or disorders include atherosclerosis, coronary heart disease, cerebrovascular disorders and dyslipidemias and the sequelae thereof. In one embodiment, examples of diseases or disorders include coronary artery disease and acute coronary syndrome. In one embodiment, examples of diseases or disorders include dyslipidemias and the sequelae thereof. In one embodiment, examples of diseases or disorders include heart failure. In one embodiment, examples of diseases or disorders include lung diseases including asthma, COPD and cystic fibrosis. In one embodiment, examples of diseases or disorders include neuroinflammatory diseases, including multiple sclerosis, Alzheimer's disease, Parkinson's disease, multiple system atrophy, and stroke.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, diuretics, mineralocorticoid receptor antagonists, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma high-density lipoprotein (HDL)-raising agents, anti-hypercholesterolemic agents, cholesterol biosynthesis inhibitors (such as HMG CoA reductase inhibitors), acyl-coenzyme A: cholesterol acytransferase (ACAT) inhibitors, cholesterylester transfer protein (CETP) inhibitors, liver X receptor (LXR) agonists, anti-probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, diuretics, mineralocorticoid receptor antagonists, calcium channel blockers, anti-diabetes agents, angiotensin II receptor antagonists, angiotensin converting enzyme inhibitors, platelet aggregation inhibitors, factor Xa inhibitors, anti-thrombotic agents, renin inhibitors, fibrinogen receptor antagonists, aspirin and fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, [2.2.2]bicyclooctane, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 15th Edition, John Wiley & Sons, Inc., New York (2007). "$C_6$ or $C_{10}$ aryl" or "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N—O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium (R$_n$NH$_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene, T. W. et al., *Protecting Groups in Organic Synthesis*, 4th Edition, *Wiley* (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH). Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of the present invention may have prodrug forms. Any compound that will be converted in vivo to provide the bioactive agent (i.e., a compound of Formula (I) or Formula (II)) is a prodrug within the scope and spirit of the invention. Various forms of prodrugs are well known in the art. For examples of such prodrug derivatives, see:

(a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield Formula (I) or Formula (II) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) or Formula (II) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., Medicinal Chemistry: Principles and Practice, The Royal Society of Chemistry, Cambridge, UK (2nd Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "µwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Ac | acetic |
| AcOH | acetic acid, |
| ACN (or MeCN) | acetonitrile |
| APF | aminophenyl fluorescein |
| Aq. | aqueous |
| BINAP | 2,2'-bis(diphenylphosphino)-1,1'-binaphthyl |
| Bn | benzyl |
| Boc | tert-butyl carbonyl |
| Boc$_2$O | di-tert-butyl dicarbonate |
| Bu | butyl |
| dba (Pd$_2$(dba)3) | dibenzylideneacetone |
| DCM | dichloromethane |
| DEAD | diethyl azodicarboxylate |
| DIAD | diisopropyl azodicarboxylate |
| DIEA | diisopropylethylamine |
| DMAP | 4-dimethylaminopyridine |
| DME | dimethoxyethane |
| DMF | dimethylformamide |
| DMSO | dimethyl sulfoxide |
| DPPA | DPPA: diphenyl phosphoryl azide |
| dppf | 1,1'-bis(diphenylphosphino)ferrocene |
| (DtBPF)PdCl$_2$ | 1,1'-bis(di-tert-butylphosphino)ferrocene palladium dichloride |
| EDC | 1-Ethyl-3-(3-dimethylaminopropyl)carbodiimide |
| ELSD | evaporative light scattering detector |
| EPX | eosinophil peroxidase |
| Et | ethyl |
| EtOH | ethanol |
| EtOAc | ethyl acetate |
| HATU | 2-(7-aza-1H-benzotriazole-1-yl)-1,1,3,3-tetramethyluronium hexafluorophosphate |
| HBTU | 2-(1H-benzotriazole-1-yl)-1,1,3,3-tetramethyluronium hexafluorophosphate |
| i-Bu | isobutyl |
| IBCF | isobutylchloroformate |
| i-Pr | isopropyl |
| KHMDS | |
| LAH | lithium aluminum hydride |

-continued

| | |
|---|---|
| m-CPBA | meta-chloroperbenzoic acid |
| Me | methyl |
| MeOH | methanol |
| MPO | myeloperoxidase |
| NMM | N-methylmorpholine |
| NMO | N-methyl morpholine N-oxide |
| NMP | N-methylpyrrolidone |
| PCC | pyridinium chlorochromate |
| Ph | phenyl |
| Pr | propyl |
| Psia | pounds per square inch absolute |
| psia | absolute pressure in pounds per square inch |
| rt | Room temperature |
| t-Bu | tert-butyl |
| tetrakis | tetrakis(triphenylphosphine) palladium |
| T3P | propylphosphonic anhydride |
| TBDMS-Cl | t-butyldimethylchlorosilane |
| TBDMS | t-butyldimethylsilyl |
| TBDPS | t-butyldiphenylsilyl |
| TCA | trichloroacetic acid |
| TEA | triethylamine |
| TES | triethylsilyl |
| TFA | trifluoroacetic acid |
| TFAA | trifluoroacetic acid anhydride |
| THF | tetrahydrofuran |
| TIPS | triisopropylsilyl |
| TIPS-Cl | tri-isopropylsilyl chloride |
| TMAD | N,N,N',N'-tetramethylazodicarbonamide (1,1'azobis(N,N-dimethylformamide)) |
| TMS | trimethylsilyl |
| TPAP | tetrapropylammonium perruthenate |
| Tr | trityl (triphenylmethyl) |
| Ts | tosyl |
| Xphos | 2-Dicyclohexylphosphino-2',4',6'-triisopropylbiphenyl |

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 3rd Edition, Wiley-Interscience (1999)).

Compounds having the general Formula (I):

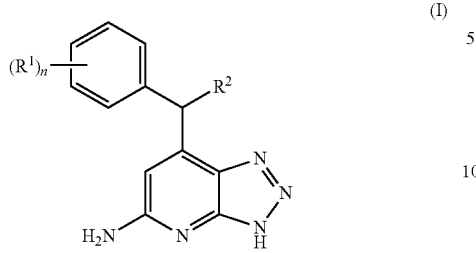

wherein $R^1$ and $R^2$ are each defined above, can be prepared by the following one or more of the synthetic schemes:

Schemes 1-12 describe synthetic routes for making intermediates and compounds of the present invention. Scheme 1 shows the elaboration of advanced intermediates prepared according to Schemes 2-6 to compounds of Formula (I). Schemes 7-12 demonstrates alternative methods for the preparation of compounds of Formula (I).Scheme 1 outlines a general procedure for the elaboration of C-4 alkylated 2,6-diaminopyridines 1-1 (syntheses of which are described in Schemes 2-6) to compounds of Formula (I) via diazotization with 4-chlorophenyldiazonium chloride (adapted from Yao et al. *Arch. Pharm. Chem. Life Sci.* 2009, 342, 274). The resulting diazo intermediates 1-2 were then reduced either with zinc/AcOH or hydrazine to furnish triamine intermediates 1-3. These triamine intermediates were then cyclized by treatment with isoamylnitrite in THF, where AcOH may or may not be added to increase reaction rate, to furnish compounds of Formula (I).

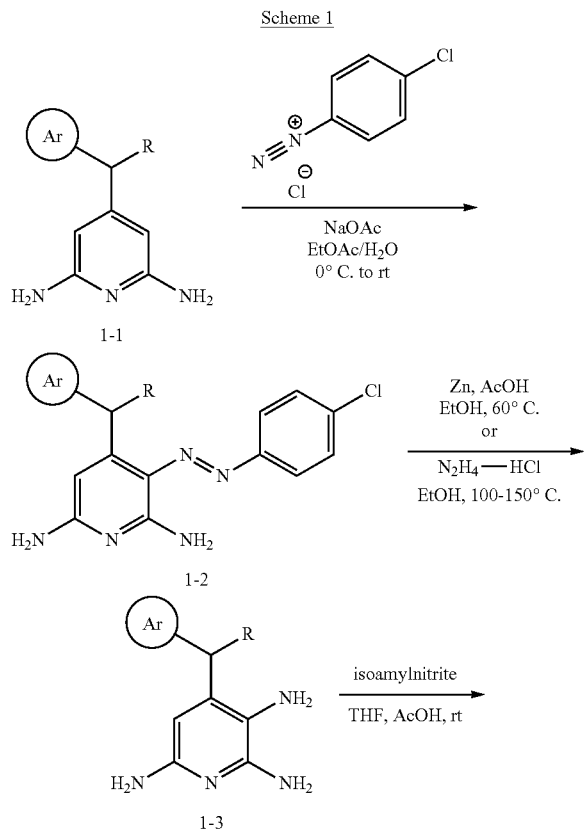

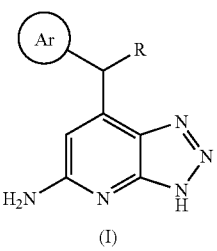

Scheme 2 demonstrates a method for the production of diamine intermediates 1-1 from commercially available 4-bromo-2,6-diaminopyridine 2-1. Vinylzinc (2-3, M=—ZnX) or vinylboronic acid (2-4, M=—B(OH)$_2$) intermediates, prepared from the corresponding halides 2-2, were coupled with 2-1 under standard Negishi (Netherton, M. R.; Fu, G. C. *Org. Lett.* 2001, 3, 4295) or Suzuki (Suzuki, A. *Pure Appl. Chem.* 1991, 63, 419) cross-coupling conditions to furnish vinyl intermediate 2-5, which was then hydrogenated using Pd/C in EtOH at 14-65 psia to furnish diamine 1-1, R=—CH$_2$R'.

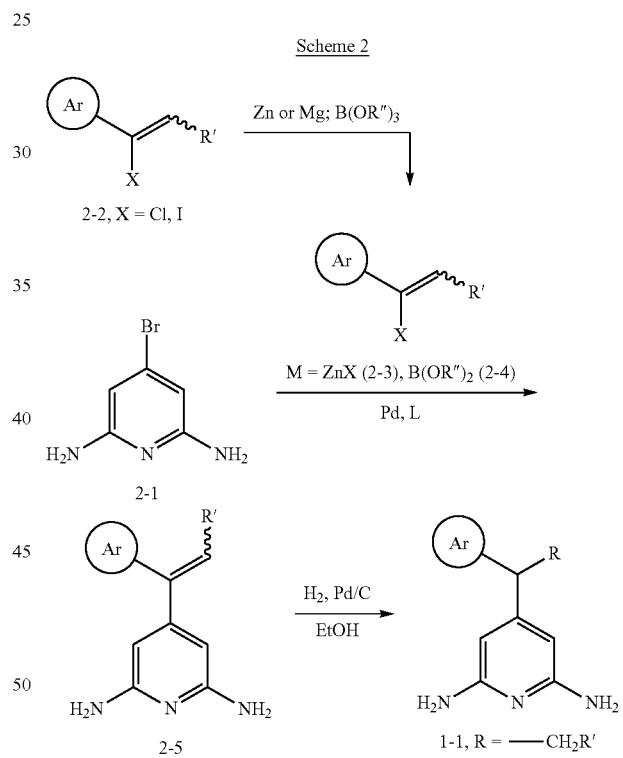

Scheme 3 illustrates an alternative the preparation of diamine intermediates 1-1 from boronic acid 3-1. Boronic acid 3-1 was coupled to vinyl iodide 3-2 (Miroslav, H.; Per, S.; Ingrid, P. US2010/210653A1, Aug. 19, 2010) according to standard Suzuki cross-coupling procedures employing Pd2(dba)$_3$, tBu$_3$P-HBF$_4$ and sodium carbonate solution. The resulting allylic alcohol 3-3 was treated with mesyl chloride, lithium chloride and Hunig's base to furnish allyl chloride 3-4. Chloride 3-4 was treated with a variety of nucleophiles (Nu-H) including alkoxides, amines, and sulfides in the presence of Hunig's base to furnish pyridine 3-5. The pyrrole protecting groups were removed via treatment of intermediate 3-5 with hydroxylamine hydrochloride and TEA in an alcoholic solvent where water may or may not be added as a cosolvent resulting in the formation of styrene 2-5 (R'=—CH₂Nu). Hydrogenation of styrene 2-5 with a heterogeneous metal catalyst such as Pd/C or PtO₂ in an alcoholic solvent under 14-65 psia results in the formation of key diamine intermediate 1-1 (R=—CH₂CH₂Nu).

Alternatively, Scheme 4 illustrates how allylic alcohol 3-3 can be converted into a variety of key diamine intermediates 1-1. Alcohol 3-3 was converted to enal 4-1 by treatment with manganese dioxide. The resulting aldehyde 4-1 was treated with a variety of commercially available primary amines (R'NH₂), NaBH₄ with or without catalytic nickel chloride to furnish secondary amine 4-2 (R=—CH₂CH₂NHR'). Treatment of intermediate 4-2 with hydroxylamine hydrochloride and TEA in an alcoholic solvent where water may or may not be added as a cosolvent results in the formation of key diamine intermediate 1-1.

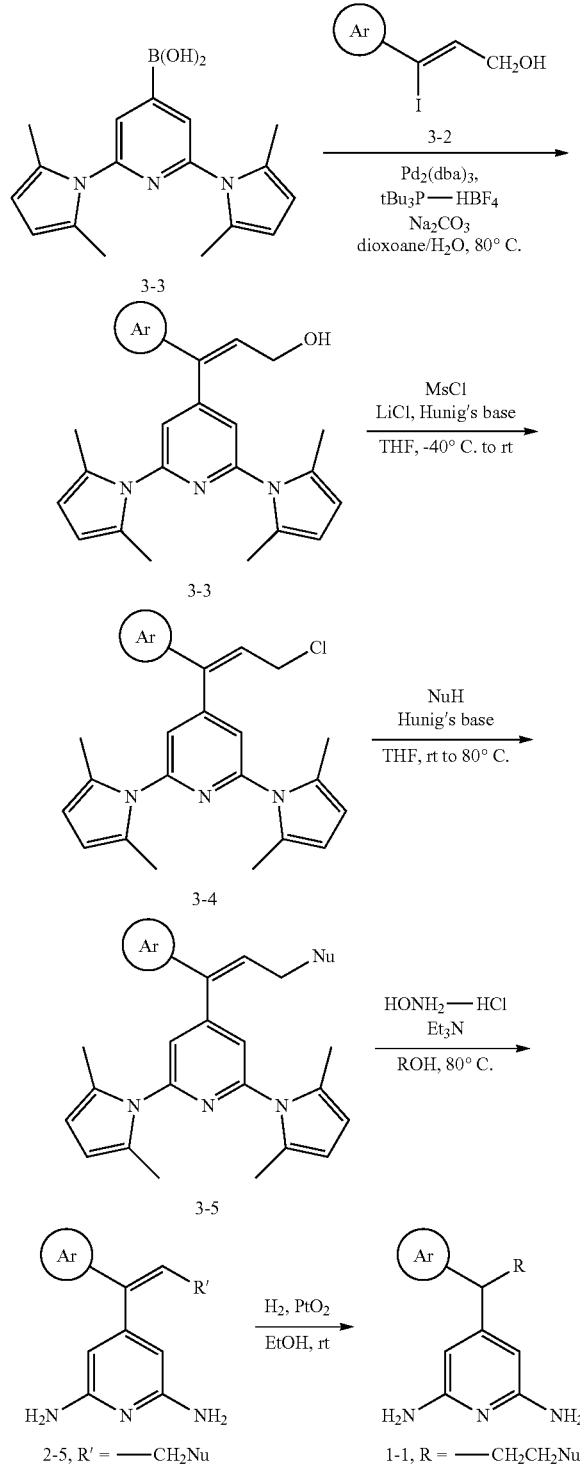

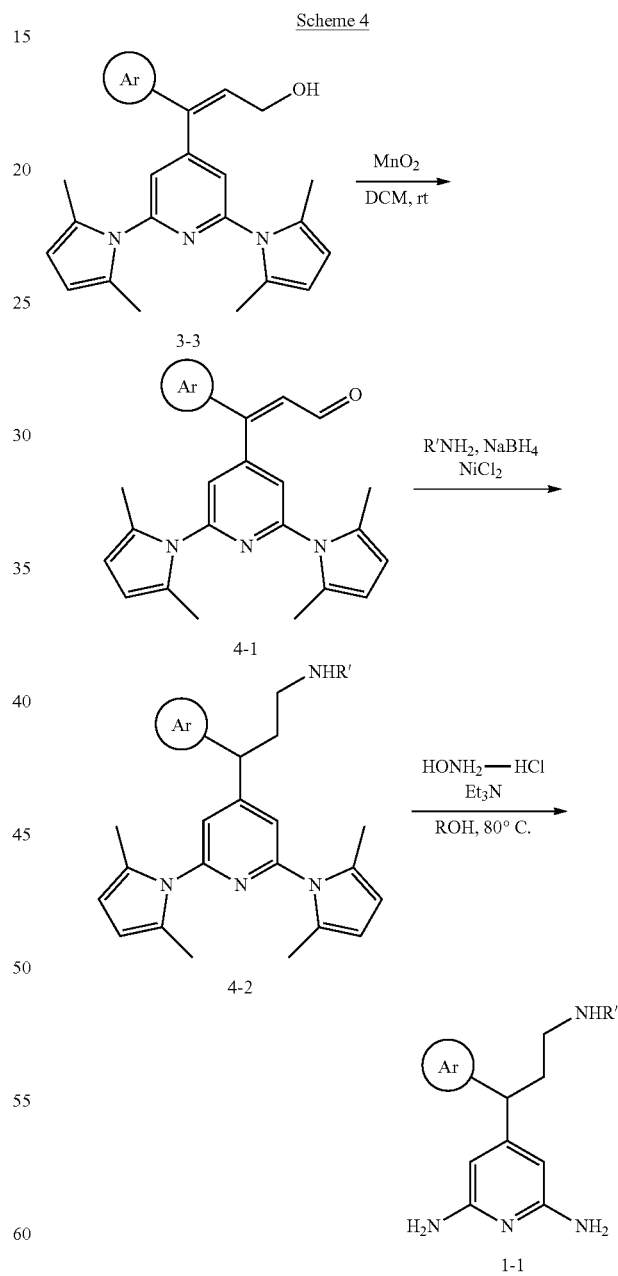

Scheme 5 shows an alternative method for the conversion of bromopyridine intermediate 2-1 (or its protected analog 5-1) into key diamine intermediates 1-1. Treatment of 2-1 or 5-1 with a ketohydrazone (prepared according from the corresponding ketone and tosylhydrazone), Buchwald's pre-catalyst (Buchwald et al. *J. Am. Chem. Soc.* 2010, 132, 14073), and lithium tert-butoxide according to the procedure of Barluenga (Barluenga et al. *Chem. Eur. J.* 2009, 15, 13291) resulted in the formation of styrene 2-5 or protected styrene 5-2. Protected styrene 5-2 was converted to styrene 2-5 via treatment with hydroxylamine hydrochloride and TEA in an alcoholic solvent where water may or may not be added as a cosolvent. Hydrogenation of styrene 2-5 with a heterogeneous metal catalyst such as Pd/C or PtO$_2$ in an alcoholic solvent under 14-65 psia results in the formation of key diamine intermediate 1-1.

Scheme 6

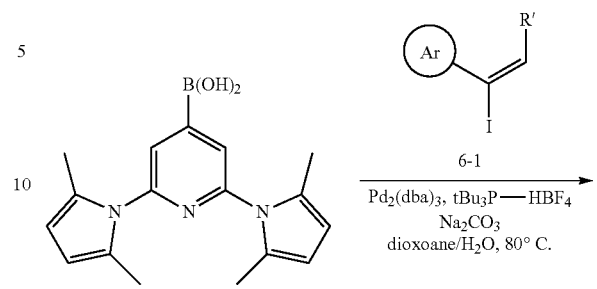

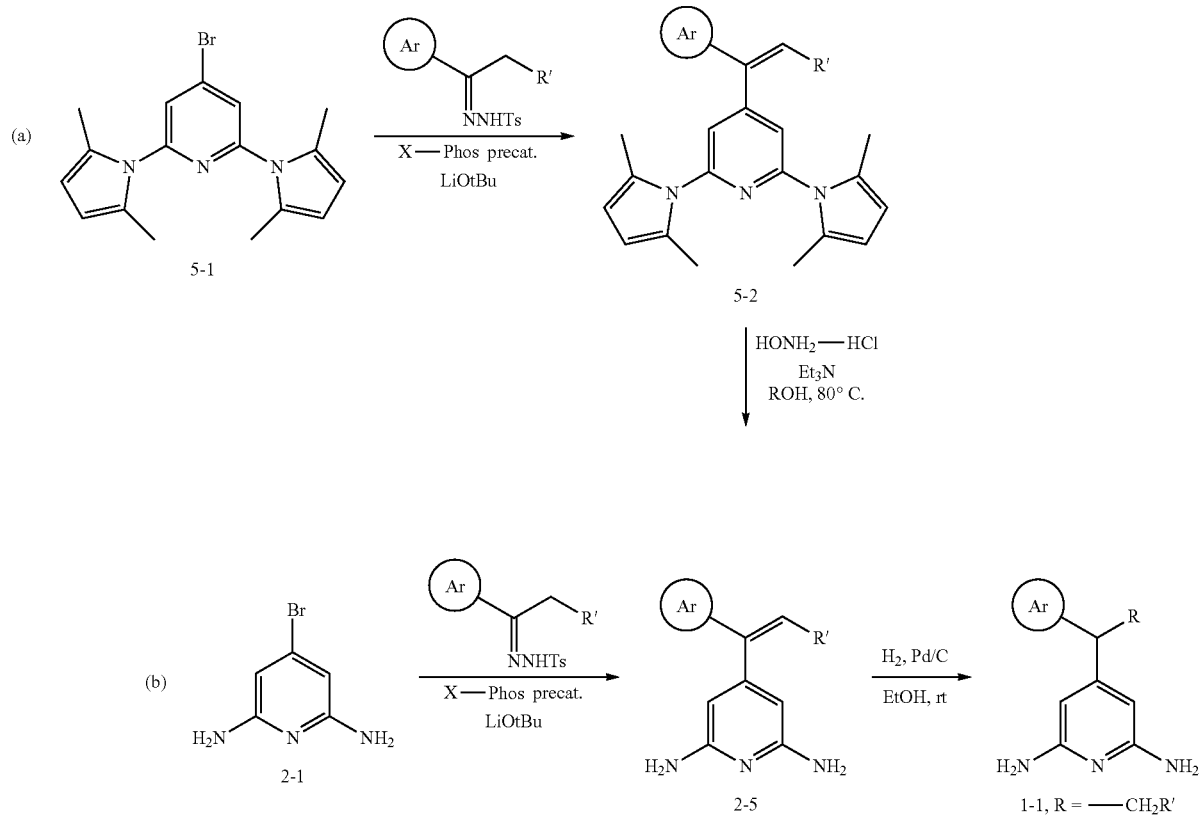

Scheme 6 illustrates an alternative method for conversion of pyridyl boronic acid 3-1 into diamine intermediates 1-1. Treatment of boronic acid 3-1 with vinyl iodide 6-1 under standard Suzuki conditions to furnish styrene 5-3, which is treated with hydroxylamine hydrochloride and TEA in an alcoholic solvent where water may or may not be added as a co-solvent results in the formation of styrene 2-5. Hydrogenation of styrene intermediate 2-5 with a heterogeneous metal catalyst such as Pd/C or PtO$_2$ in an alcoholic solvent under 14-65 psia results in the formation of key diamine intermediate 1-1.

-continued

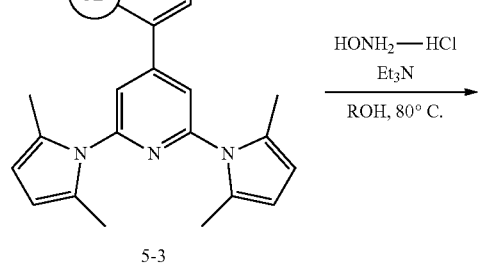

-continued

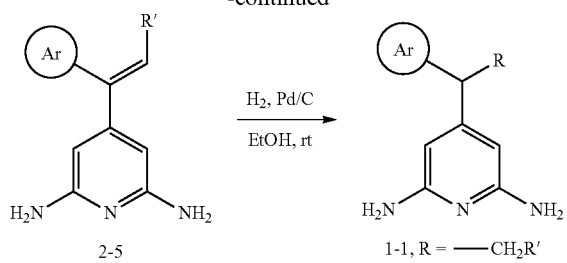

Scheme 7 shows a process for conversion of known halide 7-1 into compounds of Formula (I). Aryl bromide 7-1 was subjected to a Miyaura borylation, with the resulting boronate coupled to vinyl iodide 7-2 under standard Suzuki reaction conditions. The resulting allylic alcohol 7-3 was converted to enal 7-4 using $MnO_2$. Reductive amination of intermediate 7-4 with a variety of amines ($R—NH_2$) under standard conditions led to the formation of allyl amines 7-5. Removal of the trityl protecting groups (Tr=trityl=triphenylmethyl) from 7-5 under standard conditions followed by hydrogenation of resulting intermediate over $PtO_2$ under 15-65 psia hydrogen gas led to the formation of compounds of the Formula (I).

Scheme 7

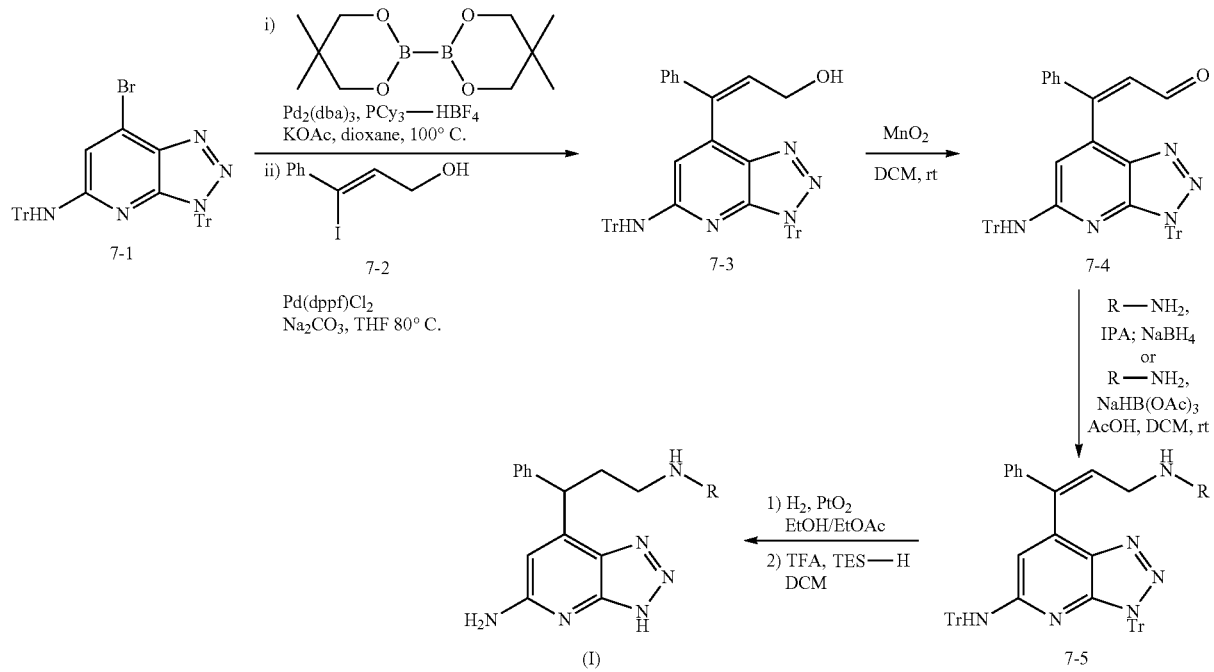

Scheme 8 illustrates an alternative method for the conversion of intermediate 7-1 to compounds of Formula (I). Intermediate 7-1 is subjected to standard Sonongashira conditions with propargyl alcohol to furnish alkynol 8-1. Alkynol 8-1 is then converted to vinyl iodide 8-2 with $LiAlH_4$, followed by $I_2$. Iodide 8-2 is then treated with an aryl boronic acid under standard Suzuki reaction conditions to furnish alcohol 8-3, which is elaborated to compounds of Formula (I) via methods analogous to those described in Scheme 7.

Scheme 8

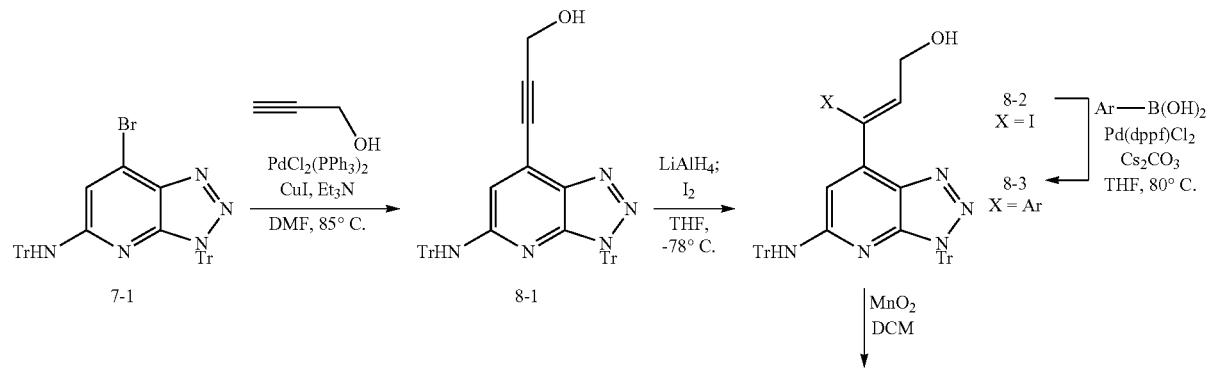

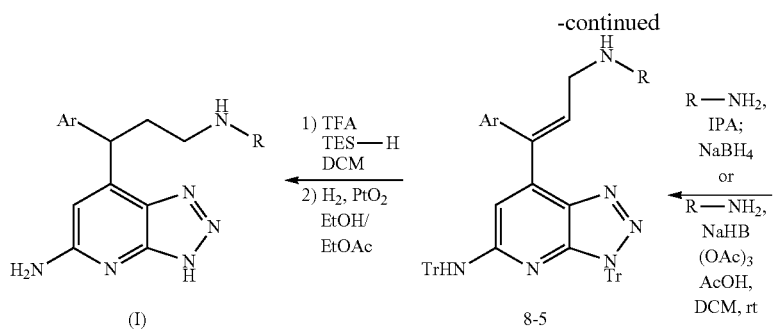

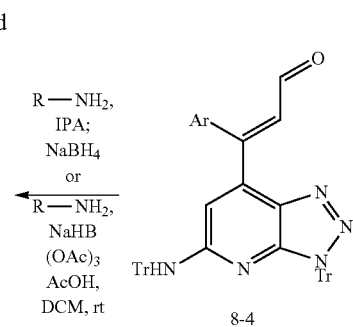

Scheme 9 demonstrates an enantioselective method for the preparation of compounds of Formula (I). Alcohol 9-2 was prepared from the intermediate 9-1 via treatment with KHMDS and ethylene oxide followed by separation of the resulting enantiomers via supercritical fluid chromatography (SFC). Alternatively, 9-2 can be prepared from 7-1 via Heck reaction, followed by enantioselective conjugate arylation to form 9-3 and L-selectride mediated reduction to furnish 9-2. Intermediate 9-2 can be converted to the corresponding bromide 9-4 via treatment with $CBr_4$ and $PPh_3$. Displacement of this bromide with a variety of amines using KI and $K_2CO_3$ followed by removal of the trityl groups under standard conditions furnishes compounds of the Formula (I).

Scheme 9

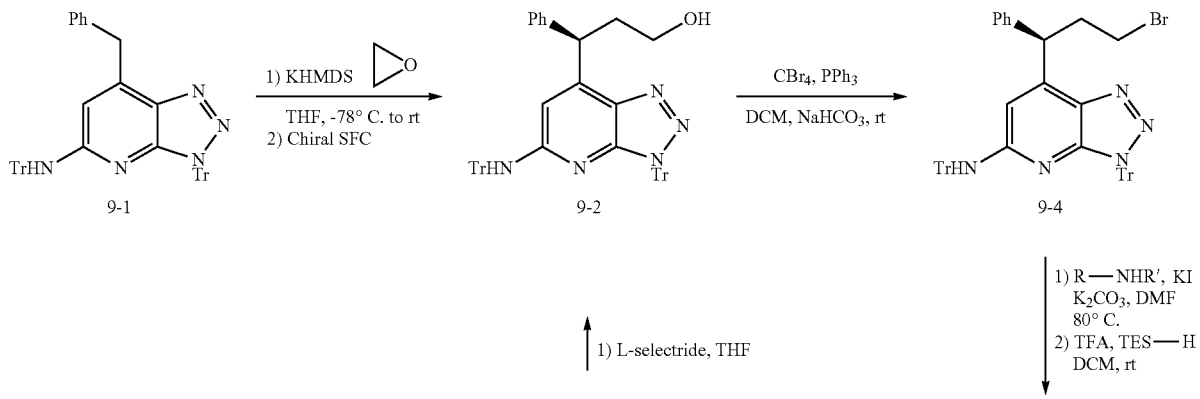

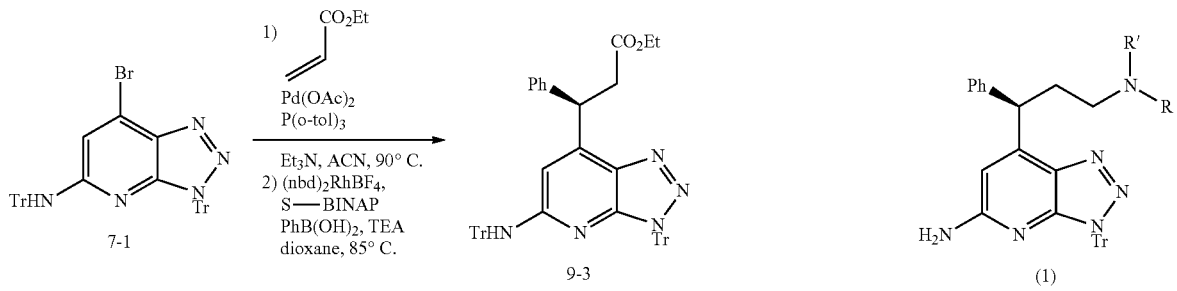

Scheme 10 illustrates an alternative method for the elaboration of alcohol 9-2 to compounds of Formula (I). Oxidation of 9-2 with TPAP and NMO furnished aldehyde 10-1. Treatment of 10-1 with a variety of amines R-NHR" under standard reductive amination conditions, followed by removal of the trityl groups furnished compounds of Formula (I).

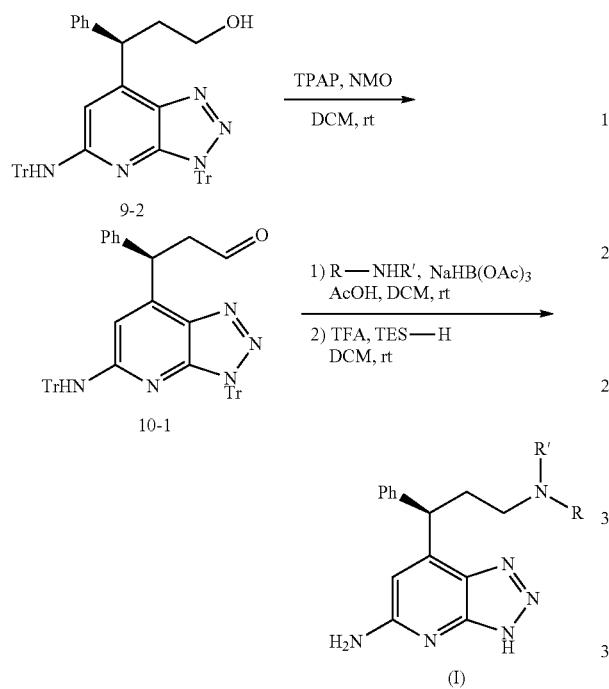

Scheme 11 shows a method for the preparation of amide-compounds of the Formula (I) from intermediate 9-3. Ester 9-3 was saponified with LiOH, and the resulting acid 11-1 was treated with amines and HATU under standard amide forming reactions to furnish compounds of Formula (I).

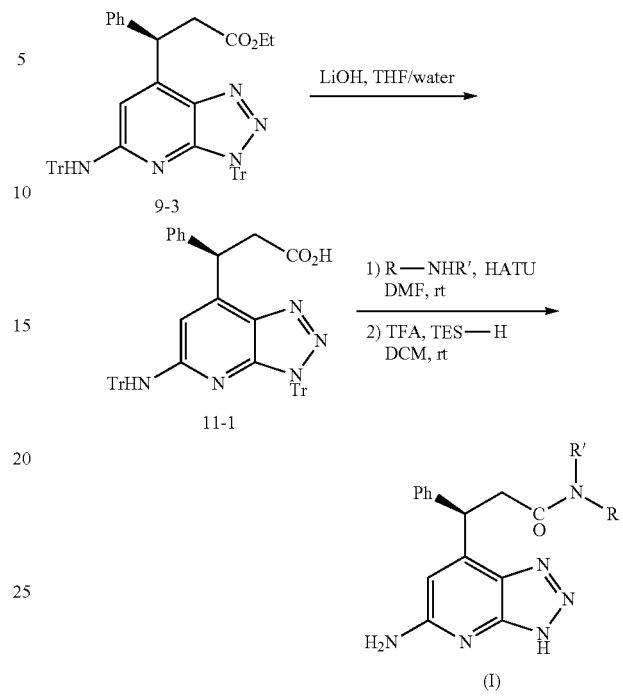

Scheme 12 shows an alternative method for the conversion of intermediate 9-1 to compounds of Formula (I). Intermediate 9-1 was alkylated with KHMDS and a commercially available bromide 12-1. The resulting silyl ether 12-1 was deprotected with TBAF, and the enantiomers separated by chiral SFC to furnish alcohol 12-3. Oxidation of alcohol 12-3 to aldehyde 12-4 was accomplished with TPAP/NMO. Reductive amination of 12-4 with an amine R-NHR' under standard conditions followed by removal of the trityl groups furnished compounds of the Formula (I).

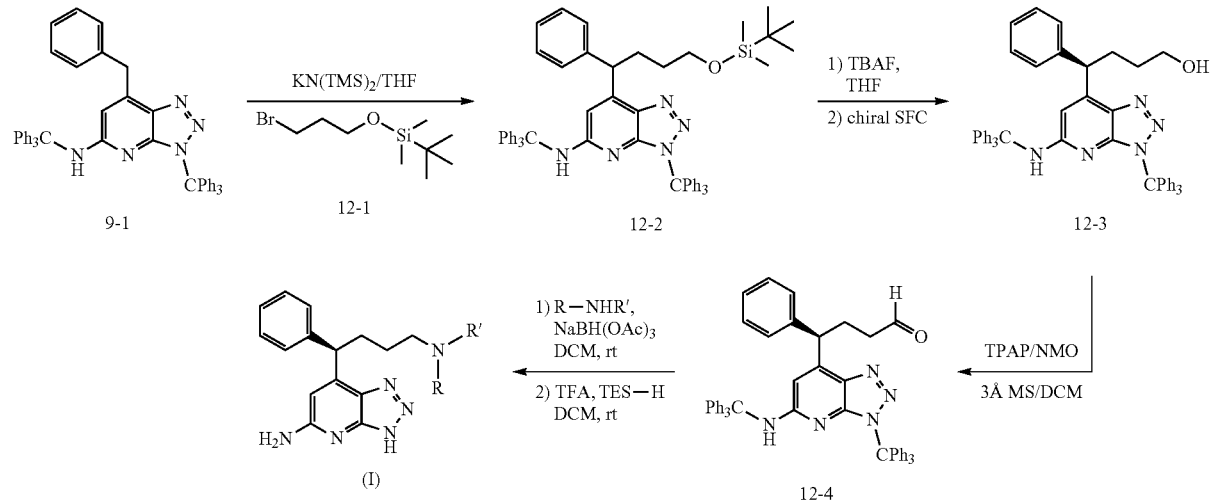

Scheme 13 shows an alternative method for the conversion of intermediate 9-1 to compounds of Formula (I). Intermediate 9-1 was alkylated with KHMDS and a prepared alkyl halide, followed by removal of the trityl groups to furnish compounds of the Formula (I).

Scheme 13

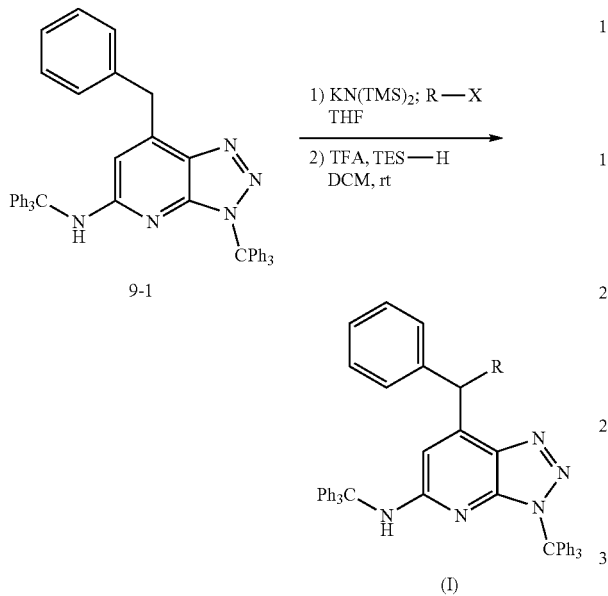

General Methods

The following methods were used in the exemplified Examples, except where noted otherwise.

Analytical HPLC Methods Employed in Characterization of Examples

Products were analyzed by reverse phase analytical HPLC: carried out on a Shimadzu Analytical HPLC: system running Discovery VP software. RT=retention time.

Method A: Linear gradient of 0 to 100% B over 10 min, with 5 min hold at 100% B;
 UV visualization at 254 nm
 Column: SunFire C18; 3.5 m; 4.6×150 mm
 Flow rate: 1 mL/min.
 Solvent A: 10% acetonitrile, 90% water, 0.05% TFA
 Solvent B: 10% water, 90% acetonitrile, 0.05% TFA Method B: Linear gradient of 0 to 100% B over 10 min, with 5 min hold at 100% B;
 UV visualization at 254 nm
 Column: SunFire C18; 3.5 m; 4.6×150 mm
 Flow rate: 1 mL/min.
 Solvent A: 10% acetonitrile, 90% water, 0.05% ammonium carbonate
 Solvent B: 10% water, 90% acetonitrile, 0.05% ammonium carbonate Method C: Linear gradient: 0-100% B over 3 min, then a 0.75-min hold at 100% B
 Temperature: 50° C.
 UV visualization at 220 nm
 Column: Waters Acquity UPLC BEH C18, 1.7 m; 2.1×50 mm
 Flow: 1.11 mL/min (Method A).
 Solvent A: 5:95 acetonitrile:water with 0.1% TFA
 Solvent B: 95:5 acetonitrile:water with 0.1% TFA Method D: Linear gradient: 0-100% B over 3 min, then a 0.75-min hold at 100% B
 Temperature: 50° C.
 UV visualization at 220 nm
 Column: Waters Acquity UPLC BEH C18, 1.7 m; 2.1×50 mm
 Flow: 1.11 mL/min
 Solvent A: 5:95 acetonitrile:water with 10 mM ammonium acetate
 Solvent B: 95:5 acetonitrile:water with 10 mM ammonium acetate LC/MS Methods Employed in Characterization of Examples Reverse phase analytical HPLC/MS was performed on Shimadzu LC10AS systems coupled with Waters ZMD Mass Spectrometers (Methods A-E) or Waters Acquity system coupled with a Waters MICROMASS® ZQ Mass Spectrometer Method A: Linear gradient of 0 to 100% B over 4 min, with 1 min hold at 100% B;
 UV visualization at 220 nm
 Column: PHENOMENEX® Luna C18 4.6×50 mm
 Flow rate: 4 mL/min
 Solvent A: 0.1% trifluoroacetic acid, 90% water, 10% acetonitrile
 Solvent B: 0.1% trifluoroacetic acid, 90% acetonitrile, 10% water.

Method B: Linear gradient of 0 to 100% B over 4 min, with 1 min hold at 100% B;
 UV visualization at 220 nm
 Column: PHENOMENEX® Luna C18 2×50 mm
 Flow rate: 4 mL/min
 Solvent A: 98% water, 2% methanol, 0.1% formic acid
 Solvent B: Methanol, 0.1% formic acid.

Method C: Linear gradient of 0 to 100% B over 4 min, with 1 min hold at 100% B;
 UV visualization at 220 nm
 Column: PHENOMENEX® Luna C18 4.6×50 mm
 Flow rate: 4 mL/min
 Solvent A: 0.1% trifluoroacetic acid, 90% water, 10% methanol
 Solvent B: 0.1% trifluoroacetic acid, 90% methanol, 10% water.

Method D: Linear gradient of 0 to 100% B over 2 min, with 1 min hold at 100% B;
 UV visualization at 220 nm
 Column: PHENOMENEX® Luna C18 2.0×30 mm
 Flow rate: 1 mL/min
 Solvent A: 0.1% trifluoroacetic acid, 90% water, 10% methanol
 Solvent B: 0.1% trifluoroacetic acid, 90% methanol, 10% water.

Method E: Linear gradient of 0 to 100% B over 2 min, with 1 min hold at 100% B;
 UV visualization at 220 nm
 Column: PHENOMENEX® Luna C18 2.0×30 mm
 Flow rate: 1 mL/min
 Solvent A: 98% water, 2% methanol, 0.1% formic acid
 Solvent B: Methanol, 0.1% formic acid.

Method F: Linear gradient of 2 to 98% B over 1 min, with 0.5 min hold time at 98% B;
 UV visualization at 220 nm
 Column: Waters BEH C18 2.1×50 mm
 Flow rate: 0.8 mL/min
 Solvent A: 0.05% TFA, 100% water
 Solvent B: 0.05% TFA, 100% acetonitrile Preparative HPLC: Methods Employed in the Purification of Products Method G: Linear gradient of 20 to 100% B over 10 min, with 2 min hold time at 100% B
  Shimadzu LC-8A binary pumps
  Shimadzu SPD-10 A or 20A UV detector
  UV visualization at 220 nm
  Column: Waters SunFire 19×100 mm 5 µm C18
  Flow rate: 20 mL/min
  Solvent A: 0.1% TFA, 10% MeOH, 90% water
  Solvent B: 0.1% TFA, 90% MeOH, 10% water Method J: Linear gradient of 20 to 100% B over 10 min, with 2 min hold time at 100% B
  Shimadzu LC-8A binary pumps
  Shimadzu SPD-10A or 20A UV detector
  UV visualization at 220 nm
  Column: PHENOMENEX® Luna Axia 30×100 mm 5 µm C18
  Flow rate: 20 mL/min
  Peak collection triggered by UV absorbance
  Solvent A: 0.1% TFA, 10% MeOH, 90% water
  Solvent B: 0.1% TFA, 90% MeOH, 10% water Method K: Linear gradient of 0 to 100% B over 10 min, with 2 min hold time at 100% B
  Shimadzu LC-8A binary pumps
  Shimadzu SPD-20A UV detector
  UV visualization at 220 nm
  Column: PHENOMENEX® Luna Axia 30×75 mm 5 µm C18
  Flow rate: 20 mL/min
  Peak collection triggered by UV absorbance
  Solvent A: 0.1% TFA, 10% ACN, 90% water
  Solvent B: 0.1% TFA, 90% ACN, 10% water NMR Employed in Characterization of Examples $^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®).

Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$.

Biology

Myeloperoxidase (MPO) and eosinophil peroxidase (EPX) are heme-containing enzymes and are members of the family of mammalian heme peroxidases that also includes salivary peroxidase, lactoperoxidase (LPO), thyroid peroxidase (TPO), prostaglandin H synthase and others. Both MPO and EPX use hydrogen peroxide to oxidize an array of substrates to either hypohalous acids or free radicals. Whereas both EPX and MPO are able to oxidize bromine ($Br^-$), iodine ($I^-$) and thiocyanate (—SCN), MPO is also able to oxidize chloride ($Cl^-$) to hypochlorous acid (HOCl) efficiently.

MPO is present predominantly in neutrophils and to a lesser extent in monocytes and subtypes of tissue macrophages. The processed mature form of the enzyme is a glycosylated 146 kDa homodimer. Each subunit is made of a light and heavy polypeptide chain and contains a protoporphyrin IX group with a central iron. The three-fold linkage of the heme is unique compared to other heme proteins and provides specific spectral and catalytic properties to MPO. MPO uses hydrogen peroxide to oxidize an array of substrates to either hypohalous acids or free radicals. The main substrate for MPO is generally accepted to be chloride, which is oxidized to hypochlorous acid. This is one of the most reactive oxidants produced in vivo. Other substrates include thiocyanate, bromide, tyrosine, tryptophan, sulfhydryls, phenol and indole derivatives, ascorbate, nitrite, nitric oxide, and urate.

The physiological role of MPO is to participate in the killing of invading bacterial and fungal pathogens (Klebanoff, S. J., *J. Exp Med.*, 126:1063-1078 (1967); Klebanoff, S. J., *J. Bacteriol.*, 95:2131-2138 (1968); Klebanoff, S. J., *Science*, 169:1095-1097 (1970)). However, excessive generation of oxidants by MPO and other peroxidases has been linked to tissue damage in many diseases, especially those characterized by acute or chronic inflammation. At sites of inflammation, PMNs or tissue macrophages can generate hydrogen peroxide and upon activation also produce myeloperoxidase. This is evidenced by the fact that, in many cases, enzymatically active MPO in conjunction with 3-chlorotyrosine, a tissue marker for HOCl-mediated damage, or HOCl-modified proteins can be detected in diseased tissues colocalized with neutrophils or macrophages (Daugherty, A. et al., JCI, 94:437-444 (1994); Bergt et al., *Proc. Natl. Acad. Sci.*, 101:13032-13037 (2004); Pennathur, S. et al., *JBC*, 279:42977-42983 (2004); Choi D. K. et al., *J. Neurosci.*, 25(28):6394-6600 (2005)).

Eosinophil peroxidase (EPX) is a cationic heme-containing protein, and represents nearly 25% of the total mass of the secondary granule protein in eosinophils. It is a highly basic 77 kDa protein made up of two subunits containing a modified Fe-protoporphyrin-IX prosthetic group. EPX shares with MPO the ability to use $H_2O_2$ to oxidize thiocyanate, bromide, and nitrite in vivo to kill bacteria, and viruses (Jong, E. C. et al., *J. Immunol.*, 124:1949-1953 (1980)). Eosinophils play a unique role in host defense mechanisms but increased levels of circulating and tissue eosinophils are implicated in promoting cellular and tissue injury in particular in asthma, and during allergic inflammatory responses of lung diseases.

MPO Peroxidation Assay (Amplex Red Assay)

MPO peroxidation activity was measured in 100 mM KPi (pH 7.4) by utilizing the non-fluorescent reagent Amplex Red (Invitrogen Cat. #A12222) which can be oxidized to the highly fluorescent resorufin. Amplex Red is oxidized by the peroxidase action of MPO to resorufin. Reactions were carried out in 50 µL total volume by adding a 25 µL mixture of 200 pM myeloperoxidase and 40 nM $H_2O_2$ (Sigma #349887) to 100 nL inhibitor in 100% DMSO in a 384 well Perkin Elmer Optiplate. Enzyme and compound were preincubated for ten minutes at rt.

After the ten minute preincubation, 25 µL of an Amplex Red mixture containing 200 µM Amplex Red and 10 mM $H_2O_2$ was added to the plate. Kinetic determinations were carried out immediately on a Perkin Elmer Envision (15 minute kinetic read, Ex: 535 nm, Em: 590 nm).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B-A}{1+(C/x)^D}$$

where A=minimal Y value (activity level of inhibited sample), B=maximal Y value (activity level of uninhibited sample), C=Log $IC_{50}$, D=Hill Slope, x=concentration of inhibitor.

MPO Chlorination Assay (APF Assay)

MPO chlorination activity was measured in 100 mM KPi (pH 7.4) by utilizing the non-fluorescent reagent Aminophenyl fluorescein (APF, Invitrogen Cat. #A36003). APF is cleaved by (—OCl) to yield the fluorescent compound fluorescein. Reactions were carried out in 50 μL total volume by adding a 25 μL mixture of 200 pM myeloperoxidase and 120 mM NaCl to 100 nL inhibitor in 100% DMSO in a 384 well, non-binding surface clear bottom plate (Corning #3655). Enzyme, inhibitor, and chloride were preincubated for ten minutes at rt.

After the ten minute preincubation, 25 μL of an APF mixture containing 10 mM APF, 120 mM NaCl and 10 μM $H_2O_2$ was added to the plate using the internal dispensing system of a Hammatsu FDSS 6000. Kinetic determinations were carried out immediately on the FDSS 6000 (3 minute kinetic read, 1 read every second, ex: 485 nm, em: 535 nm). $IC_{50}$ values for inhibitors were calculated by taking the slope of the linear portion of the kinetic measurement (20 seconds to ~80-120 secs).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B-A}{1+(C/x)^D}$$

where A=minimal Y value (activity level of inhibited sample), B=maximal Y value (activity level of uninhibited sample), C=Log $IC_{50}$, D=Hill Slope, x=concentration of inhibitor.

EPX Bromination Assay

EPX bromination activity was measured in 100 mM KPi (pH 7.4) by monitoring the $H_2O_2$ catalyzed formation of 3-bromo tyrosine from tyrosine and potassium bromide. A 50 μL mixture of 0.6 μM EPX (Lee Biosolutions Cat. #342-60) was added to 100 nL inhibitor in 100% DMSO in a 384 well REMP plate. Enzyme and compound were preincubated for ten minutes at rt.

After the ten minute preincubation of enzyme and inhibitor, 25 μL of a mixture containing 400 μM tyrosine and 1200 μM potassium bromide was added to the plate containing enzyme and inhibitor, followed by the addition of 25 μL of 20 μM $H_2O_2$. The reaction was allowed to proceed for 15 minutes, at which time it was quenched with 10 μL of 20% TCA. The final concentrations of all components were 0.3 μM EPX, 100 μM tyrosine, 400 μM potassium bromide, 5 μM $H_2O_2$, 0.1% DMSO, 2.0% TCA.

$IC_{50}$ values were determined by determining the peak areas of 3-bromo-tyrosine present at the end of the 15 minute reaction and fitting the data to:

$$Y = A + \frac{B-A}{1+(C/x)^D}$$

where A=minimal Y value (activity level of inhibited sample), B=maximal Y value (activity level of uninhibited sample), C=Log $IC_{50}$, D=Hill Slope, x=concentration of inhibitor.

Reversed-phase analysis was performed on a Waters Acquity Ultra Performance LC system using an Acquity UPLC BEH $C_{18}$ 1.7 μM, 2.1×50 mm analytical column. The column was maintained at 60° C. Samples were eluted using a gradient of 0%-100% B over 2.5 minutes, followed by equilibration with 100% A for 1 minute where A consisted of 0.1% TFA and B consisted of 90% MeOH/0.1% TFA at a flow rate of 0.6 mL/min. The retention time of 3-bromo tyrosine was 1.22 min (Method A).

The exemplified Examples disclosed below were tested in the MPO peroxidation assay described above and found to have MPO inhibitory activity. A range of $IC_{50}$ values of ≤10 μM (10000 nM) was observed.

Most of the exemplified Examples disclosed below were tested in the MPO chlorination assay described above and found to have MPO inhibitory activity. A range of $IC_{50}$ values of ≤10 μM (10000 nM) was observed. Table 1 below lists $IC_{50}$ value range in the MPO peroxidation (Amplex Red) assay and MPO chlorination assay (APF) measured for the following Examples. Potency ranges A=1-100 nM; B=101-999 nM; C=1000-10000 nM.

TABLE 1

| Example No. | Amplex Red Assay $IC_{50}$ value (μM) | APF Assay $IC_{50}$ value (μM) |
|---|---|---|
| 1 | A | — |
| 2 | A | B |
| 3 | A | — |
| 4 | B | — |
| 5 | B | — |
| 6 | B | — |
| 7 | A | B |
| 8 | A | B |
| 9 | B | B |
| 10 | A | A |
| 11 | A | A |
| 12 | B | B |
| 13 | B | B |
| 14 | B | B |
| 15 | A | B |
| 16 | B | A |
| 17 | B | A |
| 18 | B | B |
| 19 | B | — |
| 20 | B | C |
| 21 | B | B |
| 22 | B | B |
| 23 | B | B |
| 24 | B | C |
| 25 | B | A |
| 26 | B | A |
| 27 | B | B |
| 28 | A | A |
| 29 | A | A |
| 30 | A | B |
| 31 | B | — |
| 32 | B | — |
| 33 | B | — |
| 34 | B | — |
| 35 | B | — |
| 36 | B | — |
| 37 | C | — |
| 38 | B | B |

TABLE 1-continued

| Example No. | Amplex Red Assay IC$_{50}$ value (μM) | APF Assay IC$_{50}$ value (μM) |
|---|---|---|
| 39 | B | C |
| 40 | B | — |
| 41 | B | B |
| 42 | A | A |
| 43 | B | B |
| 44 | A | A |
| 45 | B | B |
| 46 | B | B |
| 47 | C | B |
| 48 | B | A |
| 51 | A | — |
| 52 | C | A |
| 53 | B | B |
| 54 | B | B |
| 55 | C | B |
| 56 | B | A |
| 57 | B | A |
| 58 | B | A |
| 59 | B | B |
| 60 | B | A |
| 61 | B | B |
| 62 | B | B |
| 63 | B | A |
| 64 | B | A |
| 65 | B | B |
| 66 | B | A |
| 67 | B | A |
| 68 | B | A |
| 69 | C | A |
| 70 | B | B |
| 72 | B | B |
| 73 | C | A |
| 74 | B | A |
| 75 | B | A |
| 76 | B | A |
| 78 | B | A |
| 80 | B | A |
| 81 | C | A |
| 82 | C | A |
| 83 | C | A |
| 84 | C | B |
| 85 | B | A |
| 86 | C | A |
| 87 | B | A |
| 88 | B | B |
| 89 | C | B |
| 90 | B | A |
| 91 | B | A |
| 92 | C | A |
| 93 | A | A |
| 94 | C | A |
| 95 | B | A |
| 96 | C | B |
| 97 | B | A |
| 98 | B | A |
| 99 | B | A |
| 100 | A | A |
| 101 | C | A |
| 102 | C | B |
| 103 | B | A |
| 104 | B | B |
| 105 | C | A |
| 106 | B | B |
| 107 | B | A |
| 108 | B | A |
| 109 | B | B |
| 110 | B | B |
| 111 | B | A |
| 112 | B | B |
| 113 | C | A |
| 114 | A | A |
| 115 | B | A |
| 116 | B | A |
| 117 | B | A |
| 118 | B | B |
| 119 | B | A |
| 120 | C | A |
| 121 | B | B |
| 122 | A | — |
| 123 | B | B |
| 124 | C | B |
| 125 | B | A |
| 126 | C | A |
| 127 | C | A |
| 128 | C | A |
| 129 | C | A |
| 130 | B | A |
| 131 | — | A |
| 132 | C | C |
| 133 | B | B |
| 134 | B | B |
| 135 | B | A |
| 136 | C | B |
| 137 | C | B |
| 138 | C | C |
| 139 | B | A |
| 140 | B | A |
| 141 | B | B |
| 142 | C | B |
| 143 | B | B |
| 144 | C | B |
| 145 | A | A |
| 146 | C | B |
| 147 | A | A |
| 148 | A | A |
| 149 | C | B |
| 150 | B | A |
| 151 | C | C |
| 152 | A | A |
| 153 | A | A |
| 154 | A | A |
| 155 | B | A |
| 156 | B | A |
| 157 | B | A |
| 158 | B | A |
| 159 | B | C |
| 160 | B | C |
| 161 | C | B |
| 162 | B | A |
| 163 | — | A |
| 164 | C | A |
| 165 | B | B |
| 166 | B | A |
| 168 | C | A |
| 171 | A | A |
| 172 | B | A |
| 174 | B | — |
| 175 | B | B |
| 176 | B | A |
| 177 | B | A |
| 178 | B | A |
| 179 | A | A |
| 180 | B | A |
| 181 | A | A |
| 182 | B | A |
| 183 | C | A |
| 184 | B | A |
| 185 | C | A |
| 186 | C | B |
| 187 | C | A |
| 188 | B | A |
| 189 | — | A |
| 190 | B | A |
| 191 | B | A |
| 192 | C | A |
| 193 | A | A |
| 195 | B | A |
| 196 | B | A |
| 197 | B | A |
| 198 | A | A |
| 199 | A | A |
| 200 | B | A |
| 201 | B | A |
| 202 | B | A |

TABLE 1-continued

| Example No. | Amplex Red Assay IC$_{50}$ value (µM) | APF Assay IC$_{50}$ value (µM) |
|---|---|---|
| 203 | C | B |
| 204 | B | A |
| 205 | C | C |
| 206 | C | A |
| 207 | B | A |
| 208 | C | B |
| 209 | B | B |
| 210 | B | A |
| 211 | B | A |
| 212 | B | A |
| 213 | B | B |
| 214 | B | A |
| 215 | B | A |
| 216 | B | A |
| 217 | B | B |
| 218 | B | A |
| 219 | B | A |
| 220 | B | B |
| 221 | B | B |
| 222 | C | A |
| 223 | B | B |
| 224 | A | — |
| 225 | B | B |
| 226 | B | B |
| 111 | B | B |
| 228 | C | C |
| 229 | A | B |
| 230 | A | C |
| 231 | B | B |
| 232 | B | B |
| 233 | A | B |
| 234 | B | B |
| 235 | B | B |
| 236 | C | A |
| 237 | B | B |
| 238 | B | A |
| 239 | A | B |
| 240 | B | B |
| 241 | B | A |
| 242 | A | A |
| 243 | B | A |
| 244 | B | A |
| 245 | B | A |
| 246 | B | A |
| 247 | B | A |
| 248 | B | A |
| 249 | B | A |
| 250 | B | A |
| 251 | C | A |
| 252 | C | A |
| 253 | C | A |
| 254 | C | A |
| 255 | C | A |
| 256 | B | B |
| 257 | C | B |
| 258 | C | B |
| 259 | B | B |
| 260 | C | B |
| 261 | B | C |
| 262 | C | C |
| 263 | B | B |

Accordingly, the compounds of the present invention may be administered to mammals, preferably humans, for the treatment of a variety of conditions and disorders, including, but not limited to, atherosclerosis, coronary artery disease, acute coronary syndrome, dyslipidemias and the sequelae thereof, angina, ischemia, cardiac ischemia, myocardial infarction, reperfusion injury, angioplastic restenosis, hypertension, vascular complications of diabetes, obesity or endotoxemia, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors, antihypertensives or other pharmaceutically active material.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, $DHEA-SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, 133-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the myeloperoxidase. Such compounds may be provided in a commercial kit, for example, for use in pharmaceutical research involving myeloperoxidase activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving myeloperoxidase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

General Synthesis Procedures:

For Schemes 1-6, the following general procedures are applicable as performed in sequences defined in the appropriate Scheme:

General Diazotization Procedure:

According to the procedure of Yao et al. (*Arch. Pharm. Chem. Life. Sci.* 2009, 342, 274), to a solution or slurry of p-chloroaniline (1.0 eq) in 6N HCl (3.8 eq) at 0° C. was added an aqueous solution of sodium nitrite (1.0 eq). After stirring for 30 min at 0° C., this solution was added to a solution of diaminopyridine (1-1, 1.0 eq) either in water or a biphasic mixture of water and EtOAc (approximately 1:1 v/v). After 30-60 min of stirring, the resulting mixture may or may not be treated with sodium acetate to facilitate homogenization of the reaction mixture. The mixture was then allowed to stir 0.5-24 h, and then was partitioned between water and EtOAc. The organic layer was then concentrated and purified by silica gel chromatography to yield the desired diazopyridine intermediates (1-2).

General Zinc Diazo Reduction Procedure:

A solution of diazopyridine intermediate (1-2,) in EtOH was treated with AcOH (1-5 eq) and zinc powder (2-10 eq) and stirred at 60° C. After 10-120 min, the solution was filtered through Celite and concentrated, and the residue purified by silica gel chromatography to yield the desired triamine intermediate (1-3).

General Hydrazine Diazo Reduction Procedure:

Diazo intermediate (1-2,) were suspended in EtOH in a sealable pressure vial and excess hydrazine (20-40% v/v) added. Vial was sealed and heated either at 100° C. on the bench for 24-48 h or at 150° C. for 2 h in a microwave reactor. After cooling to room temperature, the reaction mixture was either evaporated to dryness or diluted with EtOAc and washed with water and brine, dried over anhydrous $Na_2SO_4$, filtered and evaporated, then purified by silica gel chromatography to provide triamine intermediate (1-3).

General Triazole Formation Procedure:

A solution of triamine intermediate (1-3, 1.0 eq) in THF was treated with isoamylnitrite (0.9 eq). Several drops of AcOH may or may not have been added to enhance reaction rate. In the event of incomplete conversion, additional isoamylnitrite may have been added. After 2-72 h, the reaction mixture may have been treated with 7N MeOH in $NH_3$ or urea to consume residual isoamylnitrite. The solution was concentrated, and the residue purified by column chromatography or preparative HPLC to furnish examples of the general formula (I).

General Negishi Cross-Coupling Procedure:

A solution of aryl bromide intermediate (e.g., 2-1, 1.0 eq), tris(dibenzylidineacetone)dipalladium (0.05 eq), and (tri-tert-butylphosphonium) tetrafluoroborate (0.1 eq) in THF was added a solution of organozinc reagent (1-10 eq in THF). The solution was allowed to stir overnight, then concentrated and purified by column chromatography or preparative HPLC to furnish alkylated pyridines intermediate (e.g., 2-5).

Intermediate 1a: 7-(1-phenylvinyl)-3H-[1,2,3]triazolo[4,5-b]pyridin-5-amine

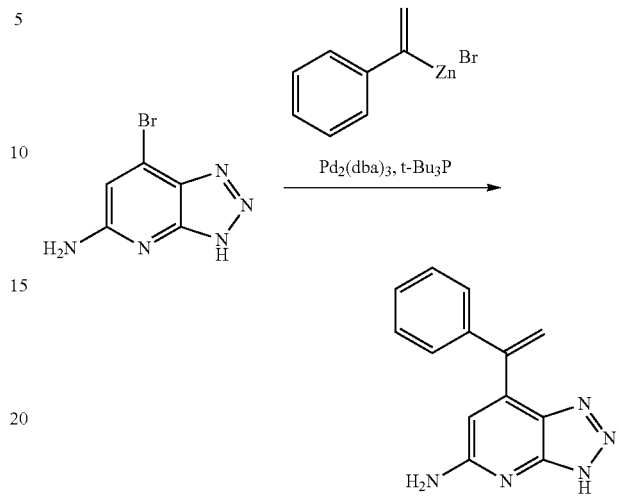

To 7-bromo-3H-[1,2,3]triazolo[4,5-b]pyridin-5-amine (0.10 g, 0.47 mmol) dissolved in THF (4.7 mL) and sparged with Ar was added tri-t-butylphosphonium tetrafluoroborate (0.014 g, 0.047 mmol), tris(dibenzylideneacetone)dipalladium(0) (0.021 g, 0.023 mmol) and (1-phenylvinyl)zinc(II) bromide (6 mL, 3 mmol). The reaction mixture was heated to 50° C., stirred for 3 hours, and purified via flash chromatography to furnish 7-(1-phenylvinyl)-3H-[1,2,3]triazolo[4,5-b]pyridin-5-amine (0.0779 g, 0.312 mmol, 66.8% yield). MS (ESI) m/z 238.3 (M+H).

Example 1: 7-(1-phenylethyl)-3H-[1,2,3]triazolo[4,5-b]pyridin-5-amine

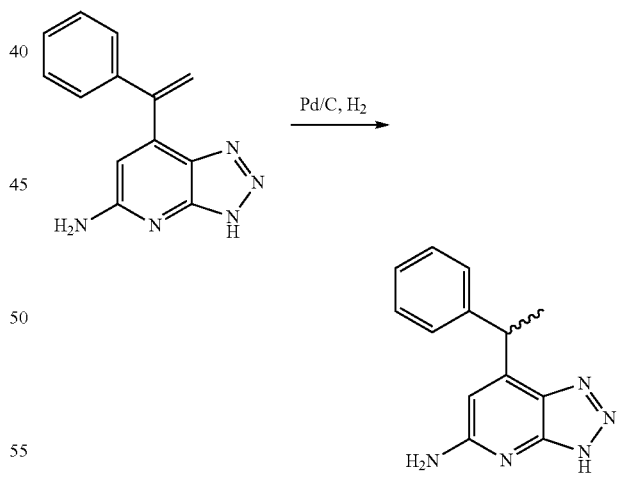

To 7-(1-phenylvinyl)-3H-[1,2,3]triazolo[4,5-b]pyridin-5-amine (0.070 g, 0.29 mmol) was added Pd/C (0.031 g, 0.030 mmol), and the mixture was stirred under hydrogen at 55 psi(g) overnight. The reaction was purified via flash chromatography to furnish racemic 7-(1-phenylethyl)-3H-[1,2,3]triazolo[4,5-b]pyridin-5-amine (0.028 g, 0.11 mmol, 38% yield). MS (ESI) m/z 240.1 (M+H). $^1$H NMR (400 MHz, $CD_3CN$) δ 7.40 (d, J=7.1 Hz, 2H), 7.31 (t, J=7.7 Hz, 2H), 7.24-7.15 (m, 1H), 6.45 (s, 1H), 5.34 (br. s., 2H), 4.76-4.59 (m, 1H), 1.76 (d, J=7.1 Hz, 3H). LC: 4.97 min, Method A Enantiomers were separated via Chiralcel OJ-H, (250×21 mm ID 5 µM, 60 mL/min, 100 bar BP, 35° C., 20% isopropanol/80% CO$_2$). Peak two R-isomer (Example R-8) determined by X-ray co-crystallography, chiral analytical retention 5.112 min (Chiralcel OJ-H, 250×4.6 mm ID, 5 µm, 3.0 mL/min, 100 Bar BP, 35° C., 20% isopropanol/88% CO$_2$).

General Route 1 (see Scheme 1):

For all diamines prepared according to Schemes 2-6, the resulting diamines were converted to the corresponding examples of the general formula (I) according to the previously described general procedures in the sequence outlined as follows: diamine intermediates 1-1 were diazotized according to the General Diazotization Procedure to furnish diazopyridine 1-2. Diazopyridine 1-2 was reduced either according to General Zinc Diazo Reduction Procedure or General Hydrazine Diazo Reduction Procedure to furnish triamine 1-3 which was immediately treated according to the General Triazole Formation Procedure to furnish compounds of the general formula (I).

General Route 2 (see Scheme 2):

Vinyl halides 2-2 were either commercially available, prepared via literature methods or prepared according to the general methods described below. Similarly, vinyl organometallic reagents 2-3 and 2-4 were either commercially available, prepared via literature methods or prepared according to the general methods described below.

General Vinylstannane Synthetic Procedure: (adapted from Sakaguchi et al. *Tetrahedron*, 2009, 65, 10355)

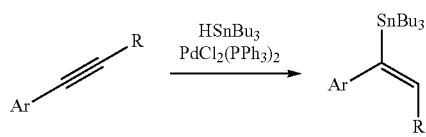

To alkyne (1 eq) dissolved in THF and cooled to 0° C., was added bis(triphenylphosphine)palladium(II) chloride (0.01 eq) followed by dropwise addition of tri-n-butyltin hydride (1.2 eq). The reaction mixture was allowed to warm to room temperature, and was stirred for 3-72 hours. The resulting solution was concentrated and purified via silica gel chromatography to furnish product.

General Vinyl iodide 2-2 Synthetic Procedure: (adapted from Cushman et al. *J. Org. Chem.* 2001, 66, 5958)

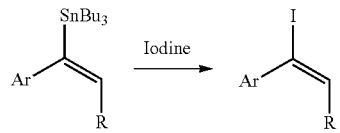

To vinylstannane (1 eq) dissolved in DCM was added iodine (1.25 eq) portion wise and the mixture was stirred 30 minutes. Excess iodine was quenched with 20% wt Na$_2$S$_2$O$_4$ solution. The organic layer separated, dried over MgSO$_4$, filtered, concentrated and purified via silica gel chromatography to furnish vinyl halide 2-2.

General Vinyl Boronic Acid 2-4 Synthetic Procedure

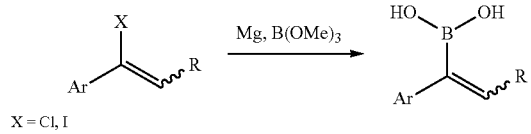

To a slurry of magnesium (2 eq) in THF was added 1,2-dibromoethane (0.12 eq) and iodine (0.06 eq). The mixture was heated until activation of metal was apparent by gas evolution. The slurry was heated to reflux and vinylhalide (2-2, 1 eq) was added. The reaction mixture was refluxed for 16 hours at which time it was cannulated to a solution of trimethyl borate (1.32 eq) dissolved in ether at 0° C. The mixture was then allowed to warm to room temperature. HCl (1.45 eq) was added to the crude borate, layers were separated, and aqueous material was extracted with ether. The organic layers were combined, dried over MgSO$_4$, filtered and concentrated to yield borate 2-4.

General Olefin Suzuki Coupling Procedure

To a mixture of bromopyridinediamine 2-1 (1 eq) and boronic acid or ester (2-4, 1.4 eq) dissolved in mixture of 1 M aq Na$_2$CO$_3$:DME (1:3, 0.2 M) was added bis(triphenylphosphine)palladium(II) chloride (0.1 eq) or dichloropalladium(II)(dppf) DCM adduct (0.1 eq), and the mixture was heated to 70° C. for 12-24 hours. The solution was concentrated, and the resulting residue dissolved in DCM, filtered, and purified by flash chromatography to furnish olefin 2-5.

General Olefin Hydrogenation Procedure

To olefin 2-5 (1 eq) dissolved in EtOH, EtOAc, THF, or any multi-component mixture therein was added 10% wt. palladium on carbon (0.1 eq) or platinum oxide (0.1-0.5 eq). The vessel was evacuated and atmosphere replaced with 15-65 psia hydrogen, and the mixture was stirred until product formation was complete. The solution was filtered, concentrated, and the resulting residue purified by flash chromatography to furnish reduced branched diaminopyridine 1-1.

Intermediate 2a: (E)-4-(1,2-diphenylvinyl)pyridine-2,6-diamine:

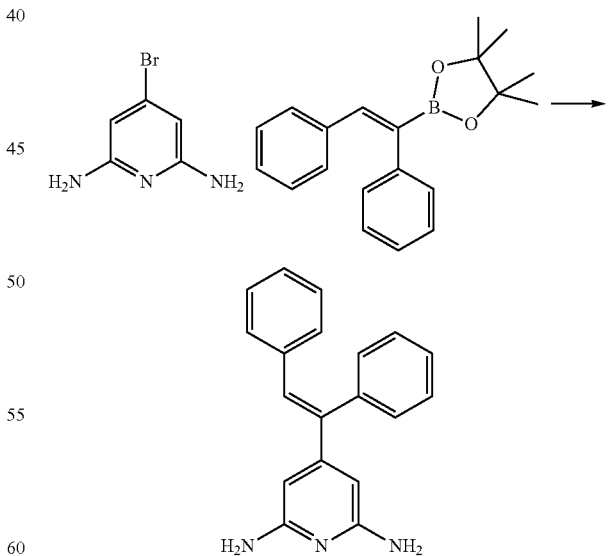

To 4-bromopyridine-2,6-diamine (0.100 g, 0.532 mmol), (Z)-2-(1,2-diphenylvinyl)-4,4,5,5-tetramethyl-1,3,2-dioxaborolane (0.228 g, 0.745 mmol) in DME (2.0 mL) was added 1 M Na$_2$CO$_3$ (aq) (0.67 mL) and bis(triphenylphosphine)palladium(II) chloride (0.037 g, 0.053 mmol), and the mixture was heated to 70° C. for 16 hours. The solvent was removed and the residue was purified via flash chromatography to furnish a yellow oil, (E)-4-(1,2-diphenylvinyl)pyridine-2,6-diamine (0.115 g, 0.400 mmol, 75% yield). MS (ESI) m/z 288.1 (M+H).

Intermediate 2b: 4-(1.2-diphenethyl)pyridine-2,6-diamine:

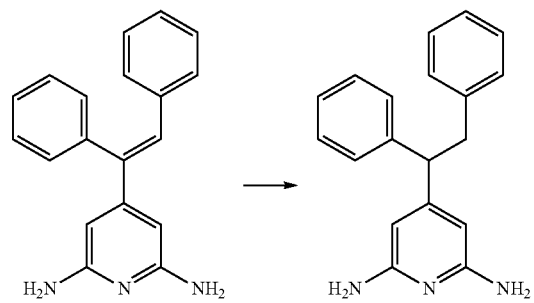 [SMILES: Nc1cc(/C(=C/c2ccccc2)c2ccccc2)cc(N)n1 ; Nc1cc(C(Cc2ccccc2)c2ccccc2)cc(N)n1]

To (E)-4-(1,2-diphenylvinyl)pyridine-2,6-diamine (0.412 g, 1.43 mmol) dissolved in EtOAc (14 mL) and EtOH (14 mL) was added Pd/C (0.381 g, 0.358 mmol). The mixture was placed under hydrogen atmosphere at 55 psi(g) and stirred for 6 days. The mixture was filtered and the solvents were removed to yield 4-(1.2-diphenethyl)pyridine-2,6-diamine (0.399 g, 1.38 mmol, 96% yield). MS (ESI) m/z 290.0 (M+H).

Intermediate 2c: 3-(4-chlorophenyl)diazenyl)-4-(1,2-diphenylethyl)pyridine-2,6-diamine:

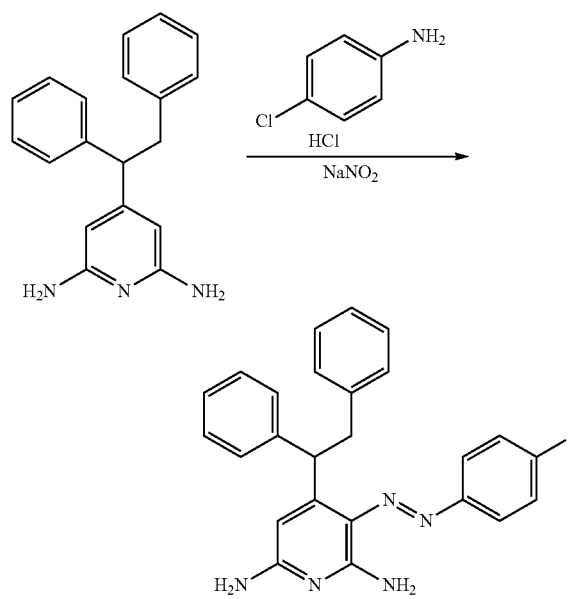

To a solution of 4-chloroaniline (0.194 g, 1.52 mmol) in 6N HCl (0.87 mL, 5.2 mmol) a solution of sodium nitrite (0.095 g, 1.4 mmol) in water (0.19 mL) was added, and the reaction mixture was stirred for 30 min. The above solution was poured into a suspension of 4-(1,2-diphenylethyl)pyridine-2,6-diamine (0.399 g, 1.38 mmol) in EtOAc (4.8 mL). After 16 hrs, sodium acetate (0.025 g, 0.30 mmol) was added, and the reaction mixture was allowed to stir for 10 min. The mixture was partitioned between water and EtOAc. The aqueous material was extracted 3× with EtOAc. The organics were combined, dried over MgSO₄, filtered, concentrated and purified via flash chromatography to furnish orange oil, 3-((4-chlorophenyl)diazenyl)-4-(1,2-diphenylethyl)pyridine-2,6-diamine (0.560 g, 1.31 mmol, 95% yield). MS (ESI) m/z 428.1 (M+H).

Intermediate 2d:
4-(1,2-diphenylethyl)pyridine-2,3,6-triamine

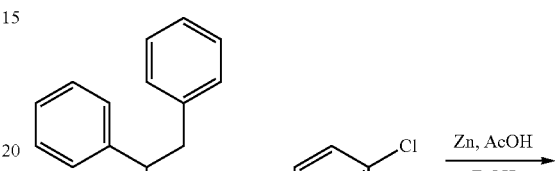

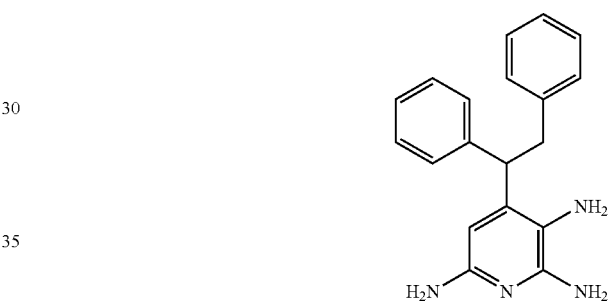

To a solution of 3-((4-chlorophenyl)diazenyl)-4-(1,2-diphenylethyl)pyridine-2,6-diamine (0.560 g, 1.31 mmol) in EtOH (13 mL) was added AcOH (0.23 mL, 3.9 mmol) and zinc powder (0.257 g, 3.92 mmol), and the reaction mixture was heated to 50° C. for 10 min. The mixture was then filtered and concentrated, and the residue purified by silica gel chromatography to furnish 4-(1,2-diphenylethyl)pyridine-2,3,6-triamine (0.373 g, 1.22 mmol, 94% yield); MS (ESI) m/z 305.1 (M+H).

Example 2: (R)-7-(1,2-diphenylethyl)-1-methyl-1H-[1,2,3]triazolo[4,5-b]pyridin-5-amine

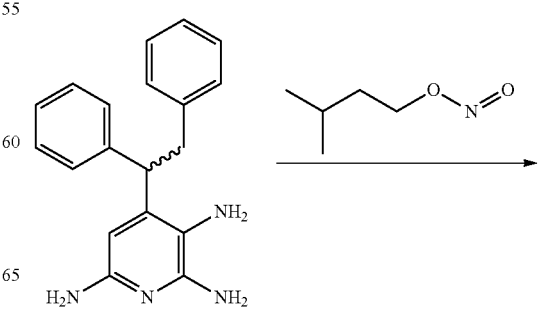

-continued

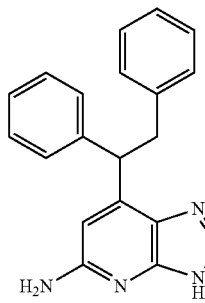

To a solution of 4-(1,2-diphenylethyl)pyridine-2,3,6-triamine (0.373 g, 1.22 mmol) in THF (12.3 mL) was added isoamyl nitrite (0.16 mL, 1.2 mmol). The reaction mixture was allowed to stir overnight. The solution was concentrated, and the residue purified by reverse phase method K to furnish racemate 7-(1,2-diphenylethyl)-3H-[1,2,3]triazolo[4,5-b]pyridin-5-amine (0.291 g, 0.924 mmol, 75% yield), light tan foam.

Enantiomers separated via Chiralcel OJ-H, 250×21 mm ID 5 μM, 65 mL/min, 150 bar BP, 40° C., 10% MeOH/90% CO$_2$, peak one R isomer determined by X-ray co-crystallography, chiral analytical retention 25.983 min (Chiralcel OJ-H, 250×4.6 mm ID, 5 μm, 3.5 mL/min, 150 Bar BP, 40° C., 15% MeOH/85% CO$_2$). MS (ESI) m/z 316.1. $^1$H NMR (400 MHz, CD$_3$CN) δ 7.49 (d, J=7.1 Hz, 2H), 7.33-7.23 (m, 2H), 7.21-7.05 (m, 6H), 6.51 (s, 1H), 5.33 (br. s., 2H), 4.82 (t, J=8.0 Hz, 1H), 3.77 (dd, J=13.7, 8.2 Hz, 1H), 3.51 (dd, J=13.7, 8.2 Hz, 1H). LC: 7.42 min, Method A Examples 3-10 were prepared according the procedures described for Example 2 and as described in General Route 2 by using the appropriate boronate species, which were commercially available, known or prepared according to the methods summarized below, followed by further elaboration via General Route 1.

Example 6: 7-(3-cyclohexyl-1-phenylpropyl)-3H-[1,2,3]triazolo[4,5-b]pyridin-5-amine

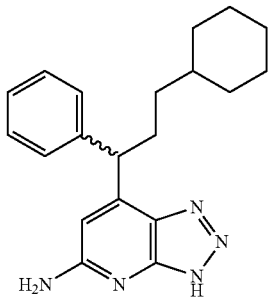 [SMILES: Nc1cc(C(CCC2CCCCC2)c2ccccc2)c2nn[nH]c2n1]

Prepared from (1-chloro-3-cyclohexylprop-1-en-1-yl)benzene, according to the procedure summarized below.

Intermediate 6a: (1-chloro-3-cyclohexylprop-1-en-1-yl)benzene: (adapted from *J. Am. Chem. Soc.* 1965, 87, 258)

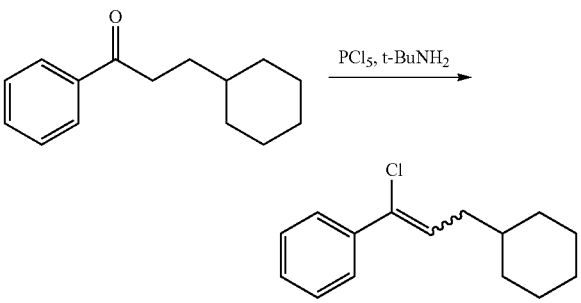

To 3-cyclohexyl-1-phenylpropan-1-one (5.0 g, 23 mmol) dissolved in ether (29 mL) at 0° C. was added PCl$_5$ (5.25 g, 25.2 mmol) and tert-butylamine (2.69 mL, 25.4 mmol), and the mixture was stirred overnight. The solids were filtered and washed with ether, and the resulting solution was washed with 1.5 μM pH 7.4 potassium phosphate buffer. The ether layer was concentrated, dried over MgSO$_4$ and purified via flash chromatography to yield clear oil (1-chloro-3-cyclohexylprop-1-en-1-yl)benzene (2.41 g, 44%).

Intermediate 6b: (3-cyclohexyl-1-phenylprop-1-en-1-yl)boronic acid

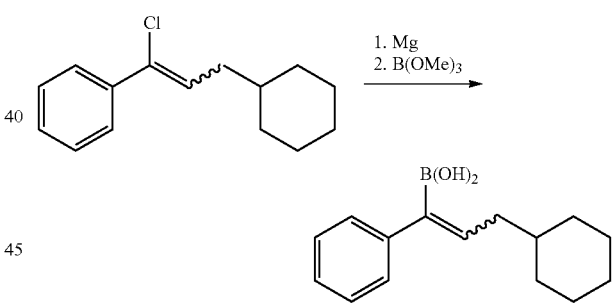

To magnesium (0.207 g, 8.52 mmol) slurried in THF (8.8 mL) was added 0.08 mL of 1,2-dibromoethane and iodine (0.092 g, 0.36 mmol), and the mixture was heated until activation of metal was apparent by gas evolution. The slurry was heated to reflux and (1-chloro-3-cyclohexylprop-1-en-1-yl)benzene (1.0 g, 4.3 mmol) was added, and let mixture reflux overnight. The reaction solution was cannulated into a solution of trimethylborate (0.628 mL, 5.62 mmol) dissolved in ether (1.9 mL) at 0° C., and then allowed to warm to rt. To the crude borate was added HCl (2.1 mL, 6.2 mmol), the layers separated, and aqueous layer extracted with ether 2×. The organic layers were combined, dried over MgSO$_4$, filtered and concentrated to yield crude (3-cyclohexyl-1-phenylprop-1-en-1-yl)boronic acid (1.00 g, 1.65 mmol, 38.7% yield) MS (ESI) m/z 267.1 (M+Na).

Example 7: 7-(1,4-diphenylbutyl)-3H-[1,2,3]triazolo[4,5-b]pyridin-5-amine

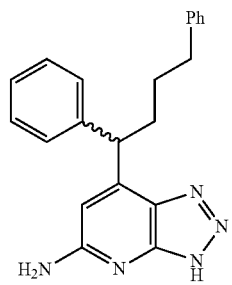 [SMILES: Nc1cc(C(CCCc2ccccc2)c2ccccc2)c2nn[nH]c2n1]

Prepared from (1-chlorobut-1-ene-1,4-diyl)dibenzene (*J. Org. Chem.* 1978, 43, 2402-10)

Enantiomers were separated on a Chiralpak AD-H, 250×30 mm ID, 5 μm, 65 mL/min, 150 bar BP, 40° C., 25% Isopropanol/75% $CO_2$, to furnish 7-(1,4-diphenylbutyl)-3H-[1,2,3]triazolo[4,5-b]pyridin-5-amine 0.5 iPrOH, active peak 2, chiral analytical retention 17.114 min (Chiralpak AD-H, 250×4.6 mm ID, 5 μm, 3.0 mL/min, 150 Bar BP, 35° C., 20% isopropanol/80% $CO_2$). MS (ESI) m/z 344.1 (M+H). $^1$H NMR (400 MHz, $CD_3CN$) δ 7.43 (d, J=7.7 Hz, 2H), 7.34-7.05 (m, 8H), 6.49 (s, 1H), 4.49 (t, J=8.0 Hz, 1H), 2.65 (t, J=7.4 Hz, 2H), 2.44-2.28 (m, 1H), 2.26-2.11 (m, 1H), 1.70-1.47 (m, 2H). LC: 8.46 min, Method A

Example 8: 7-(3-(benzyloxy)-1-phenylpropyl)-3H-[1,2,3]triazolo[4,5-b]pyridin-5-amine

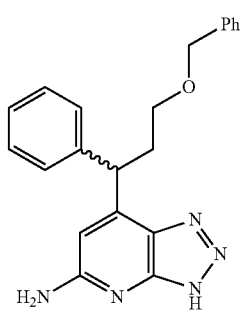 [SMILES: Nc1cc(C(CCOCc2ccccc2)c2ccccc2)c2nn[nH]c2n1]

From (3-(benzyloxy)prop-1-yn-1-yl)benzene (*Tetrahedron* 1998, 54, 1299) isolated from olefin hydrogenation without reduction of benzyl ether.

Enantiomers were separated on a Chiralcel OJ-H, 250×21 mm ID, 5 μm, 65 mL/min, 150 bar BP, 40° C., 25% MeOH/75% $CO_2$ to furnish 7-(3-(benzyloxy)-1-phenylpropyl)-3H-[1,2,3]triazolo[4,5-b]pyridin-5-amine, peak 2 active, chiral analytical retention 12.340 (Chiralcel OJ-H, 250×4.6 mm ID, 5 μm, 2 mL/min, 150 Bar BP, 35° C., 25% MeOH/75% $CO_2$). MS (ESI) m/z 360.1 (M+H), 1H, LC: 7.64 min, Method A

Intermediate 9a: (Z)-2-(1-(2-fluorophenyl)-2-phenylvinyl)-4,4,5,5-tetramethyl-1,3,2-dioxaborolane compound with (Z)-2-(2-(2-fluorophenyl)-1-phenylvinyl)-4,4,5,5-tetramethyl-1,3,2-dioxaborolane

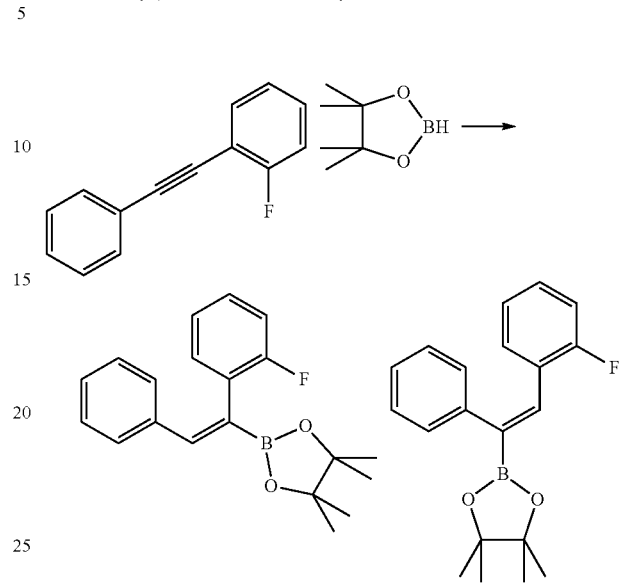

(Adapted from *J. Clin. Res.* 2002, 3, 142) To carbonylchlorohydridotris (triphenylphosphine)ruthenium(II) (0.322 g, 0.338 mmol) in toluene (45 mL) under Ar was added 4,4,5,5-tetramethyl-1,3,2-dioxaborolane (1.8 mL, 12 mmol) and then 1-fluoro-2-(phenylethynyl)benzene (2.21 g, 11.2 mmol) (*Tetrahedron,* 2009, 65, 4085), and the mixture was heated to 50° C. for 16 hours. The mixture was diluted with ether, washed with water, and the organic layer was dried over $MgSO_4$, filtered and concentrated. The residue was purified via flash chromatography to furnish a mix of regioisomers, (Z)-2-(1-(2-fluorophenyl)-2-phenylvinyl)-4,4,5,5-tetramethyl-1,3,2-dioxaborolane compound with (Z)-2-(2-(2-fluorophenyl)-1-phenylvinyl)-4,4,5,5-tetramethyl-1,3,2-dioxaborolane (1:1) (2.40 g, 3.70 mmol, 65.7% yield). Used as is, MS (ES) m/z 325.2 (M+H).

Example 9: 7-(2-(2-fluorophenyl)-1-phenylethyl)-3H-[1,2,3]triazolo[4,5-b]pyridin-5-amine

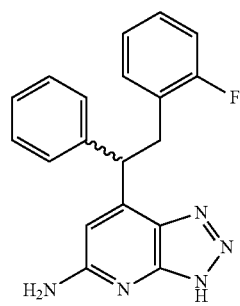 [SMILES: Nc1cc(C(Cc2ccccc2F)c2ccccc2)c2nn[nH]c2n1]

Prepared from 6a by procedures described herein. Separation of regioisomers and enantiomers achieved on a Chiralcel OJ-H, 21×250 mm ID, 5 μm, 45 mL/min, 150 bar BP, 40° C., 15% MeOH-0.1% Diethylamine/85% $CO_2$. Chiral analytical retention 12.475 min (Chiralcel OJ-H, 4.6×250 mm ID, 5 μm, 3.0 mL/min, 150 bar BP, 35° C., 15%

MeOH-0.1% Diethylamine/85% $CO_2$). MS (ES) m/z 334.0 (M+H). $^1$H NMR (500 MHz, $CD_3CN$) δ 7.48 (dd, J=8.3, 1.1 Hz, 2H), 7.30-7.24 (m, 2H), 7.21-7.10 (m, 3H), 7.03-6.91 (m, 2H), 6.54 (d, J=0.6 Hz, 1H), 5.33 (br. s., 2H), 4.85 (t, J=8.3 Hz, 1H), 3.76 (dd, J=13.9, 8.1 Hz, 1H), 3.60 (dd, J=14.0, 8.0 Hz, 1H). LC: 7.24 min, Method A Example 10: 7-(1-(2-fluorophenyl)-2-phenylethyl)-3H-[1,2,3]triazolo[4,5-b]pyridin-5-amine

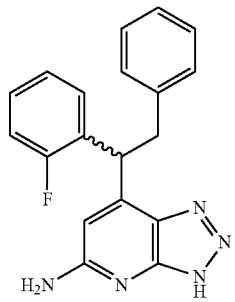 [SMILES: Nc1cc(C(Cc2ccccc2)c2ccccc2F)c2nn[nH]c2n1]

Prepared from 6a by procedures described herein. Purification of enantiomers achieved on a Chiralcel OJ-H, 21×250 mm ID, 5 μm, 45 mL/min, 150 bar BP, 40° C., 15% MeOH-0.1% Diethylamine/85% $CO_2$. Chiral analytical retention 12.806 min (Chiralcel OJ-H, 4.6×250 mm ID, 5 μm, 3.0 mL/min, 150 bar BP, 35° C., 15% MeOH-0.1% Diethylamine/85% $CO_2$). MS (ES) m/z 334.1 (M+H). $^1$H NMR (400 MHz, THF-d8) δ 7.85 (td, J=7.7, 1.6 Hz, 1H), 7.24-6.89 (m, 8H), 6.26 (s, 1H), 5.81 (s, 2H), 4.99 (t, J=8.0 Hz, 1H), 4.03 (dd, J=13.7, 7.7 Hz, 1H), 3.51 (dd, J=13.7, 8.2 Hz, 1H). LC: 7.73 min, Method A Preparation of 2,6-(2,5-dimethylpyrrol-1-yl)-pyridylboronic acid 3-1.

Pyridine-2,6-diamine (2.000 g, 18.33 mmol) was dissolved in HCl (10.3 mL, 41.2 mmol) with sufficient MeOH added to ensure homogeneity. The solution was concentrated, MeOH was added to form an azeotrope to remove residual solvents The solid residue was triturated with ether, and placed under vacuum overnight. The material was diluted in DMF (36.7 mL), then treated with hexane-2,5-dione (6.45 mL, 55.0 mmol) and $MgSO_4$ (11 g, 92 mmol) and allowed to stir for 1 h at 120° C. The solution was filtered and partitioned between water and EtOAc. The organic layer was washed with water and brine, dried over $Na_2SO_4$, filtered through a silica gel plug and concentrated. The residue was triturated with a minimal quantity of ether to furnish 2,6-bis(2,5-dimethyl-1H-pyrrol-1-yl)pyridine (2.06 g, 7.77 mmol, 42.4% yield). MS (ES) m/z 266.1 (M+H). $^1$H NMR (500 MHz, $CDCl_3$) δ 7.98 (t, J=7.7 Hz, 1H), 7.27 (d, J=8.0 Hz, 2H), 5.92 (s, 4H), 2.17 (s, 12H).

A solution of 2,6-bis(2,5-dimethyl-1H-pyrrol-1-yl)pyridine (1.00 g, 3.77 mmol) in THF (18.8 mL) was cooled to 0° C. and nBuLi (1.80 mL, 4.15 mmol) was added slowly. After 10 min, the solution was transferred to a solution of trimethyl borate (0.55 mL, 4.9 mmol) in ether (18.8 mL) and stirred for 1 h warming to rt. The solution was cooled to 0° C., treated with HCl (1.8 mL, 5.4 mmol), and stirred for 10 min. The ether layer was then dried over $Na_2SO_4$, filtered and concentrated to furnish (2,6-bis(2,5-dimethyl-1H-pyrrol-1-yl)pyridin-4-yl)boronic acid (3-1, 1.17 g, 3.78 mmol, 100% yield). $^1$H NMR (500 MHz, DMSO-d6) δ 7.67 (s, 2H), 5.83 (s, 4H), 2.06 (s, 12H)

General Bis-pyrrole Deprotection Procedure:

A 0.1 M solution of bis-pyrrolylpyridine 3-5 (1.0 eq) in either IPA/water (4:1), EtOH/water (4:1) or neat EtOH was treated with $H_3NOHCl$ (20 eq) and TEA (10 eq). The resulting mixture was heated to 80° C. over 16-96 hours, treated with $NaHCO_3$ solution and extracted with EtOAc. The organic layer was concentrated, and the residue was purified by column chromatography to furnish diaminopyridine intermediate 1-1 or styrene 2-5 which were elaborated to compounds of the general formula (I) according to the general procedures outlined in General Route 1 (Scheme 1) or General Route 2 (Scheme 2).

General Route 3 (see Scheme 3):

Intermediate 3-1a:
2,6-(2,5-Dimethylpyrrol-1-yl)-pyridine

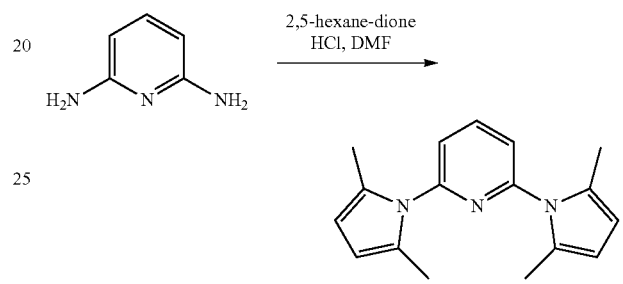

Pyridine-2,6-diamine (2.00 g, 18.3 mmol) was dissolved in HCl (10.3 mL, 41.2 mmol) with sufficient MeOH added to ensure homogeneity. The solution was concentrated using MeOH as an azeotrope, then the solid residue was triturated with ether and placed under vacuum overnight. The material was diluted in DMF (37 mL), then treated with hexane-2,5-dione (6.45 mL, 55.0 mmol) and $MgSO_4$ (11 g, 92 mmol), and allowed to stir for 1 h at 120° C. The solution was then filtered and partitioned between water and EtOAc. The organic layer was extracted with water and brine, dried over $Na_2SO_4$, filtered through a silica gel plug and concentrated. The residue was triturated with a minimal quantity of ether to furnish the title compound (2.062 g, 7.77 mmol, 42.4% yield). MS(ESI) m/z 266.1 (M+H). $^1$H NMR (500 MHz, $CDCl_3$) δ 7.98 (t, J=7.7 Hz, 1H), 7.27 (d, J=8.0 Hz, 2H), 5.92 (s, 4H), 2.17 (s, 12H).

Intermediate 3-1:
2,6-(2,5-Dimethylpyrrol-1-yl)-pyridylboronic acid

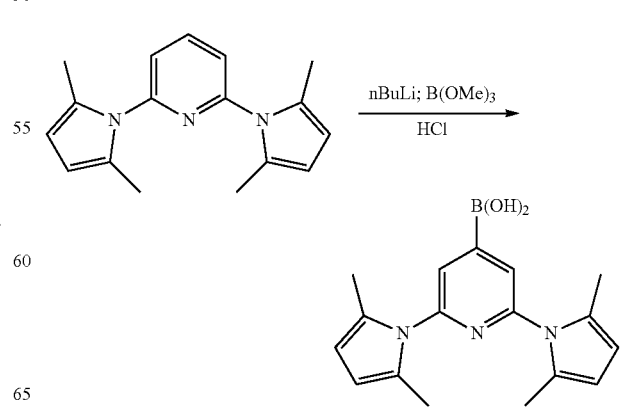

A solution of 2,6-bis(2,5-dimethyl-1H-pyrrol-1-yl)pyridine (1.00 g, 3.77 mmol) in THF (19 mL) was cooled to 0° C. and treated with nBuLi (1.80 mL, 4.15 mmol) added slowly. After 10 min the solution was transferred to a solution of trimethyl borate (0.55 mL, 4.9 mmol) in ether (19 mL) and allowed to stir for 1 h while warming to rt. The solution was cooled to 0° C. and treated with HCl (1.8 mL, 5.5 mmol), then stirred for 10 min. The ether layer was then dried over Na$_2$SO$_4$, filtered and concentrated to furnish the title compound (1.17 g, 3.78 mmol, 100% yield). $^1$H NMR (500 MHz, DMSO-d$_6$) δ 7.67 (s, 2H), 5.83 (s, 4H), 2.06 (s, 12H).

Intermediate 3-3: (Z)-3-(2,6-bis(2,5-dimethyl-1H-pyrrol-1-yl)pyridin-4-yl)-3-phenylprop-2-en-1-ol

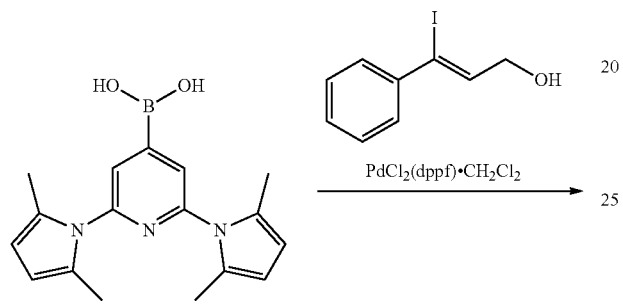

To (Z)-3-iodo-3-phenylprop-2-en-1-ol (7.07 g, 27.2 mmol) and (2,6-bis(2,5-dimethyl-1H-pyrrol-1-yl)pyridin-4-yl)boronic acid (9.25 g, 29.9 mmol) in DME (102 mL) blanketed under Ar was added 2 M Na$_2$CO$_3$ in water (34.0 mL) and PdCl$_2$(dppf)•DCM adduct (2.22 g, 2.72 mmol). The reaction mixture was heated to 70° C. overnight, concentrated and purified via flash chromatography to furnish (Z)-3-(2,6-bis(2,5-dimethyl-1H-pyrrol-1-yl)pyridin-4-yl)-3-phenylprop-2-en-1-ol (3-3, 7.94 g, 19.9 mmol, 73.5% yield). MS (ESI) m/z 398.3 (M+H). $^1$H NMR (400 MHz, CDCl$_3$-d) δ 7.45-7.32 (m, 3H), 7.28-7.21 (m, 2H), 7.08 (s, 2H), 6.41 (t, J=6.9 Hz, 1H), 5.91 (s, 4H), 4.36 (dd, J=6.8, 5.5 Hz, 2H), 2.20-2.14 (m, 12H).

General Allyl chloride synthesis:

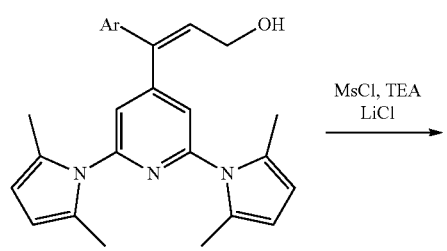

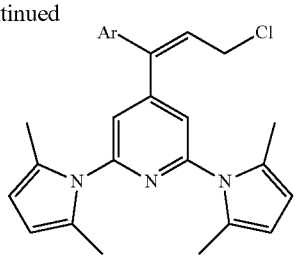

(Adapted from *Chem. Bio. Chem.* 2009, 10, 2060-71) To allyl alcohol 3-3 (1 eq) dissolved in DCM (0.45 M) at −40° C. was added methanesulfonyl chloride (0.95 eq) followed by drop-wise addition of TEA (1.1 eq). After 30 minutes was added a 0.72 M solution of lithium chloride (2 eq) dissolved in THF: DMF (3:1), and the reaction mixture was allowed to warm to 0° C. for 1 hour. The solution was partitioned between water and EtOAc, and the organic layer was dried over MgSO$_4$, filtered, and concentrated to furnish allyl chloride 3-4.

Intermediate 3-4: (Z)-4-(3-chloro-1-phenylprop-1-en-1-yl)-2,6-bis(2,5-dimethyl-1H-pyrrol-1-yl)pyridine

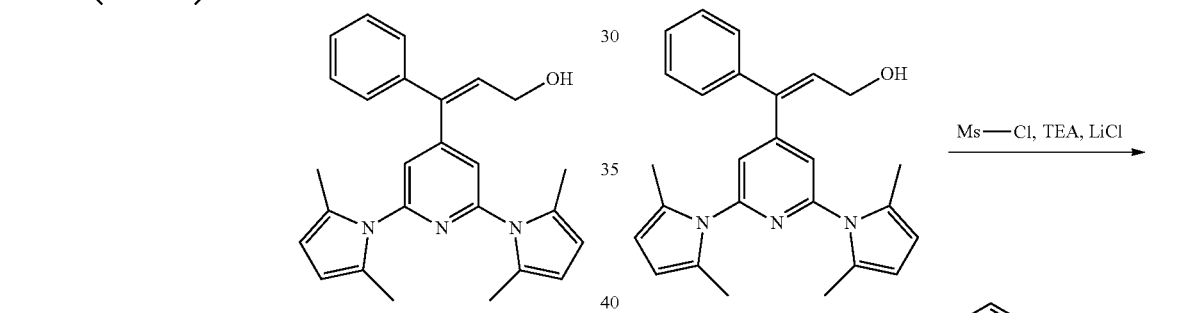

To (Z)-3-(2,6-bis(2,5-dimethyl-1H-pyrrol-1-yl)pyridin-4-yl)-3-phenylprop-2-en-1-ol (3.00 g, 7.55 mmol) in DCM (16.8 mL) cooled to −40° C. was added methanesulfonyl chloride (0.56 mL, 7.2 mmol) followed by dropwise addition of Et$_3$N (1.2 mL, 8.3 mmol), and the mixture was stirred 30 minutes prior to addition of LiCl (0.640 g, 15.1 mmol) dissolved in THF/DMF 3:1 (21 mL). The reaction mixture was warmed to 0° C. for 1 hour, partitioned between water and EtOAc. The layers were separated, and the aqueous washed 1× with EtOAc. The organics were combined and washed with water and brine. The organic phase was dried over MgSO$_4$, filtered, and concentrated to furnish crude (Z)-4-(3-chloro-1-phenylprop-1-en-1-yl)-2,6-bis(2,5-dimethyl-1H-pyrrol-1-yl)pyridine (3.39 g, 7.50 mmol, 99% yield). MS (ESI) m/z$^2$ 416.1 (M+H), $^1$H NMR (400 MHz, CDCl$_3$-d) δ 7.40-7.33 (m, 3H), 7.25-7.18 (m, 2H), 7.12 (s, 2H), 6.40 (t, J=8.2 Hz, 1H), 5.90 (s, 4H), 4.19 (d, J=8.2 Hz, 2H), 2.18 (s, 12H).

Intermediate 11a: (Z)-N-benzyl-3-(2,6-bis(2,5-dimethyl-1H-pyrrol-1-yl)pyridin-4-yl)-3-phenylprop-2-en-1-amine

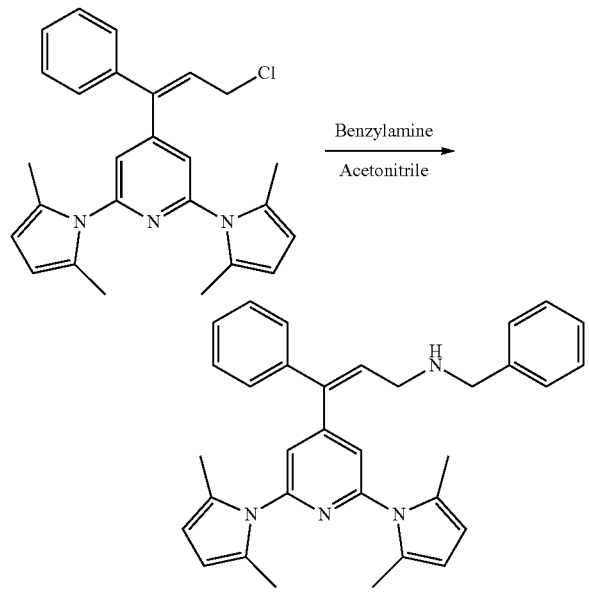

To benzylamine (0.788 g, 7.35 mmol) in acetonitrile was added (Z)-4-(3-chloro-1-phenylprop-1-en-1-yl)-2,6-bis(2,5-dimethyl-1H-pyrrol-1-yl)pyridine (1.02 g, 2.45 mmol), and the mixture was refluxed for 2 hours. The mixture was partitioned between DCM and water. The aqueous layer was washed 3× with DCM, and the organics were dried over MgSO$_4$, filtered, concentrated and purified via flash chromatography to furnish (Z)-N-benzyl-3-(2,6-bis(2,5-dimethyl-1H-pyrrol-1-yl)pyridin-4-yl)-3-phenylprop-2-en-1-amine (1.07 g, 2.2 mmol, 90% yield). MS (ESI) m/z 487.1 (M+H).

Intermediate 11b: (Z)-4-(3-(benzylamino)-1-phenylprop-1-en-1-yl)pyridine-2,6-diamine

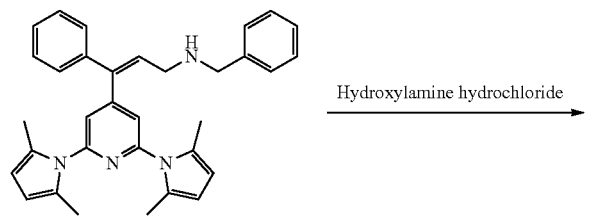

To (Z)-N-benzyl-3-(2,6-bis(2,5-dimethyl-1H-pyrrol-1-yl)pyridin-4-yl)-3-phenylprop-2-en-1-amine (0.870 g, 1.79 mmol) in EtOH (17.9 mL) was added Et$_3$N (2.5 mL, 18 mmol) and hydroxylamine hydrochloride (2.48 g, 35.8 mmol), and the mixture was heated to 80° C. for 16 hours. The reaction mixture was concentrated, partitioned between DCM and 1N NaOH. The aqueous was washed 2× with DCM, and the organic layers were combined, dried over MgSO$_4$, filtered and concentrated to furnish crude (Z)-4-(3-(benzylamino)-1-phenylprop-1-en-1-yl)pyridine-2,6-diamine, with residual TEA (0.925 g, 1.44 mmol, 80% yield). MS (ESI) m/z=331.0 (M+H).

Intermediate 11c: 4-(3-(benzylamino)-1-phenylpropyl)pyridine-2,6-diamine

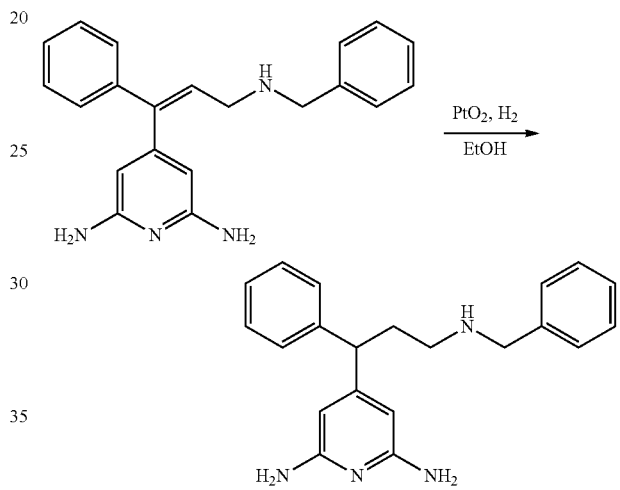

To (Z)-4-(3-(benzylamino)-1-phenylprop-1-en-1-yl)pyridine-2,6-diamine (0.474 g, 1.44 mmol) in EtOH (14 mL) was added PtO$_2$ (0.033 g, 0.14 mmol), and the reaction vessel was evacuated under vacuum and flushed with N$_2$ 3×. Then the vessel was charged with 10 psi(g) hydrogen gas, and the mixture was stirred 16 hrs. The reaction mixture was filtered and concentrated to furnish 4-(3-(benzylamino)-1-phenylpropyl)pyridine-2,6-diamine, with residual EtOH (0.638 g, 1.35 mmol, 94% yield). MS (ESI) m/z 333.0 (M+H).

Intermediate 11d: 4-(3-(benzylamino)-1-phenylpropyl)pyridine-2,3,6-triamine

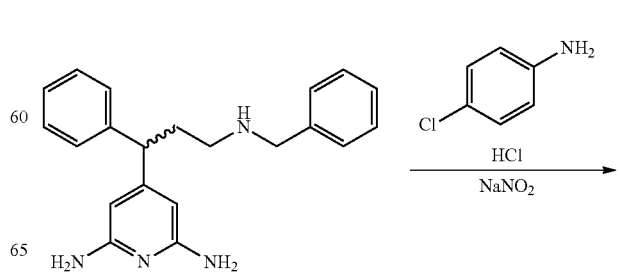

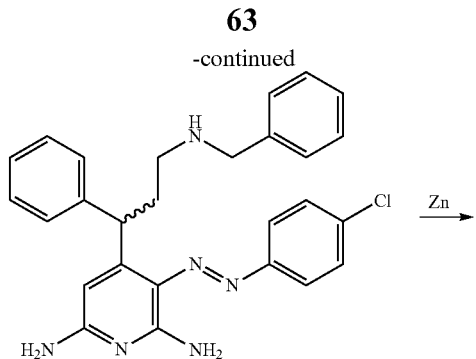

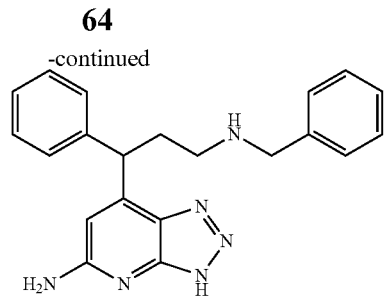

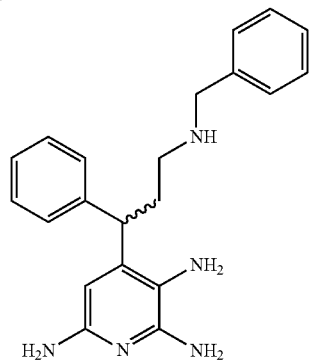

To a solution of 4-chloroaniline (0.295 g, 2.31 mmol) in water (26.3 mL) was added 6N HCl (8 mL, 50 mmol). A solution of sodium nitrite (0.145 g, 2.10 mmol) in water (0.2 mL) was added, and the reaction mixture was stirred for 30 min. The above solution was poured into a solution of 4-(3-(benzylamino)-1-phenylpropyl)pyridine-2,6-diamine (0.698 g, 2.10 mmol) in 0.1 M HCl (aq) (26.3 mL) and let stir for 16 hrs. To the reaction was added 1 M sodium hydroxide (50 mL, 50 mmol), and the mixture was allowed to stir for 10 min. The mixture was partitioned between water and EtOAc, and the aqueous was extracted 3× with EtOAc. The organics were combined, dried over MgSO$_4$, filtered, concentrated and purified via flash chromatography to furnish orange solid (E)-4-(3-(benzylamino)-1-phenylpropyl)-3-((4-chlorophenyl)diazenyl)pyridine-2,6-diamine (0.40 g, 0.85 mmol, 40%). MS (ES) m/z 471.0 (M+H).

To a solution of (E)-4-(3-(benzylamino)-1-phenylpropyl)-3-((4-chlorophenyl)diazenyl)pyridine-2,6-diamine (0.30 g, 0.64 mmol) in EtOH (6.4 mL) was added zinc (0.108 g, 1.66 mmol) and AcOH (0.10 mL, 1.7 mmol), and the reaction mixture was heated to 50° C. After 10 min, the reaction slurry was filtered through celite and concentrated, and the residue was purified by silica gel chromatography to furnish 4-(3-(benzylamino)-1-phenylpropyl)pyridine-2,3,6-triamine (0.165 g, 0.475 mmol, 74.6% yield). MS (ESI) m/z 348.1 (M+H).

Example 11: 7-(3-(benzylamino)-1-phenylpropyl)-3H-[1,2,3]triazolo[4,5-b]pyridin-5-amine

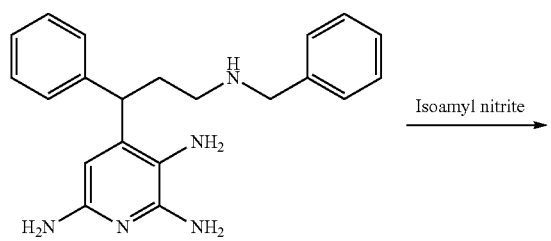

(Adapted from *J. Org. Chem.* 2008, 73, 4199) To a solution of 4-(3-(benzylamino)-1-phenylpropyl)pyridine-2,3,6-triamine (0.014 g, 0.034 mmol) in THF (3.4 mL) was added 3 drops of AcOH and isoamyl nitrite (4.4 µL, 0.032 mmol). The resulting reaction solution was stirred at rt for 16 hours. To the reaction mixture was added 2 mL of 7N NH$_3$ in MeOH. The mixture was concentrated and purified via reverse phase Method K to furnish 7-(3-(benzylamino)-1-phenylpropyl)-3H-[1,2,3]triazolo[4,5-b]pyridin-5-amine, TFA (0.0049 g, 9.9 µmol, 29% yield). MS (ESI) m/z 359.0 (M+H). $^1$H NMR (500 MHz, CD$_3$CN) δ 7.47-7.38 (m, 7H), 7.37-7.32 (m, 2H), 7.31-7.25 (m, 1H), 6.78 (s, 1H), 4.58 (t, J=7.8 Hz, 1H), 4.12 (s, 2H), 3.13-2.97 (m, 2H), 2.80-2.69 (m, 1H), 2.65-2.51 (m, 1H). LC: 3.93 min, Method A Enantiomers were separated on a Regis Whelk-01 (R,R), 21×250 mm, 5 micron; 45 mL/min, 100 bar BP, 35° C.; 25% MeOH-0.1% DEA/75% CO$_2$ to furnish both stereoisomers of 7-(3-(benzylamino)-1-phenylpropyl)-3H-[1,2,3]triazolo[4,5-b]pyridin-5-amine. Peak 2 active (Example 11), Chiral analytical retention 10.87 min (Regis Whelk-01 (R,R), 21×250 mm, 5 micron, 3.0 mL/min, 100 Bar BP, 35° C., 25% MeOH-0.1% DEA/75% CO$_2$). MS (ESI) m/z 359.0 (M+H). $^1$H NMR (400 MHz, CD$_3$CN) δ 7.48 (d, J=7.1 Hz, 2H), 7.39-7.10 (m, 8H), 6.52 (s, 1H), 5.35 (br. s., 1H), 4.66 (t, J=7.5 Hz, 1H), 3.75 (s, 2H), 2.67-2.51 (m, 3H), 2.48-2.28 (m, 1H).

Examples 12-13 were prepared according the procedures described for Example 11 by using the appropriate nucleophile, which were commercially available, followed by further elaboration by methods described herein.

Examples 12-13: 7-(1-phenyl-3-((1-phenylethyl)amino)propyl)-3H-[1,2,3]triazolo[4,5-b]pyridin-5-amine

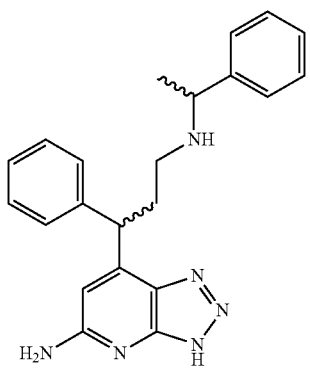 [SMILES: CC(NCCC(c1ccccc1)c1cc(N)nc2[nH]nnc12)c1ccccc1]

Diastereomer pairs were separated via Regis Whelk-O1 (R, R 30×250 mm, 5 micron), 25% MeOH:DEA/75% CO$_2$, 85 mL/min, 40° C., 125 Bar, and further separation of each pair achieved via Chiralpak IC, 250×21 mm ID, 5 µm, 40 mL/min, 100 bar BP, 35° C., 20% EtOH 0.1% DEA/80% CO$_2$ for peak 1&2, 15% EtOH 0.1% DEA/85% CO$_2$ for peak 3&4. Active peaks 3 & 4: Peak 3 chiral analytical retention 12.72 min; Peak 4 chiral analytical retention 16.69 min (Chiralpak IC, 250×21 mm ID, 5 µm, 2.0 mL/min, 100 Bar BP, 35° C., 15% EtOH 0.1% DEA/85% CO$_2$ for peak 3&4).

Peak 3 (Example 12): MS (ESI) m/z 373.0 (M+H). $^1$H NMR (500 MHz, CD$_3$CN) δ 7.48-7.41 (m, 2H), 7.27 (t, J=7.6 Hz, 2H), 7.22-7.09 (m, 6H), 6.46 (s, 1H), 5.30 (br. s., 2H), 4.63 (t, J=7.6 Hz, 1H), 3.66 (q, J=6.6 Hz, 1H), 2.62-2.49 (m, 1H), 2.46-2.36 (m, 1H), 2.33-2.17 (m, 2H), 1.22 (d, J=6.6 Hz, 3H). LC: 4.02 min, Method A Peak 4 (Example 13): MS (ESI) m/z 373.0 (M+H). $^1$H NMR (400 MHz, CD$_3$CN) δ 7.44-7.37 (m, 2H), 7.30-7.21 (m, 6H), 7.19-7.11 (m, 2H), 6.46 (s, 1H), 5.30 (br. s., 2H), 4.61 (t, J=7.1 Hz, 1H), 3.67 (q, J=6.6 Hz, 1H), 2.46-2.37 (m, 2H), 2.34-2.23 (m, 2H), 1.23 (d, J=6.8 Hz, 3H). LC: 4.14 min, Method A Intermediate 15a: N-benzyl-3-(2,6-bis(2,5-dimethyl-1H-pyrrol-1-yl)pyridin-4-yl)-3-phenylpropan-1-amine

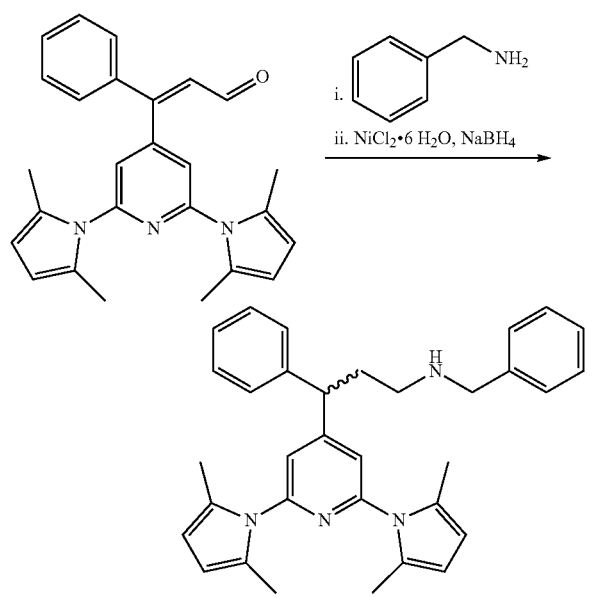

To (Z)-3-(2,6-bis(2,5-dimethyl-1H-pyrrol-1-yl)pyridin-4-yl)-3-phenylacrylaldehyde (Intermediate 4-1, 1.00 g, 2.53 mmol) suspended in EtOH (25.3 mL) was added phenylmethanamine (0.406 g, 3.79 mmol), and the mixture was heated until all the material dissolved. The solution was cooled to 0° C., and THF (25.3 mL) was added followed by nickel (II) chloride hexahydrate (1.80 g, 7.59 mmol), and the mixture was stirred for 10 minutes. To this mixture was added a 0.5 M NaBH$_4$ in diglyme (24.3 mL, 12.1 mmol) dropwise for 45 minutes and then 5 mL of saturated NH$_4$Cl was added, and the mixture was stirred over the weekend. The mixture was partitioned between water and EtOAc, and the aqueous was extracted 3× with EtOAc. The organics were combined, dried over MgSO$_4$, filtered, concentrated and purified via flash chromatography to furnish N-benzyl-3-(2,6-bis(2,5-dimethyl-1H-pyrrol-1-yl)pyridin-4-yl)-3-phenylpropan-1-amine (15a, 0.500 g, 1.02 mmol, 40.5% yield). MS (ESI) m/z 489.1 (M+H).

Intermediate 15b: N-benzyl-N-(3-(2,6-bis(2,5-dimethyl-1H-pyrrol-1-yl)pyridin-4-yl)-3-phenylpropyl)benzenesulfonamide

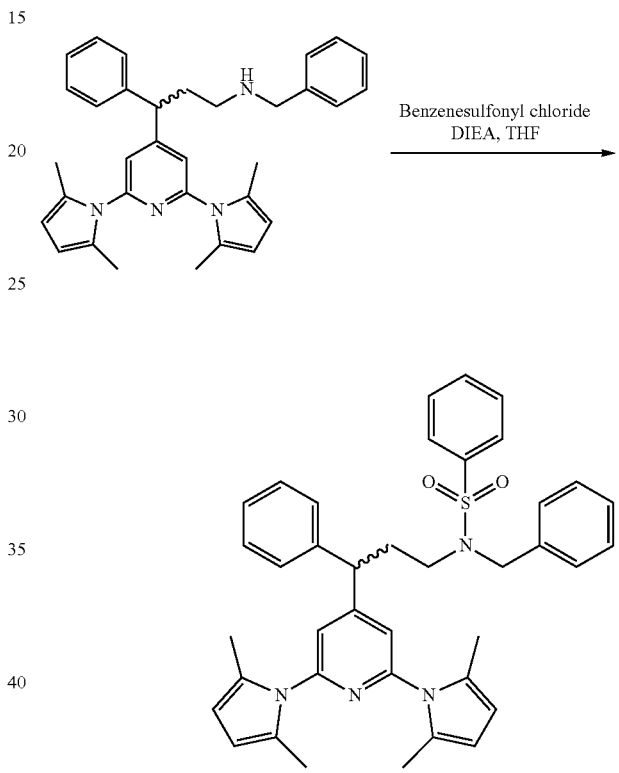

To N-benzyl-3-(2,6-bis(2,5-dimethyl-1H-pyrrol-1-yl)pyridin-4-yl)-3-phenylpropan-1-amine (0.300 g, 0.614 mmol) dissolved in THF (6.1 mL) was added diisopropylethylamine (0.54 mL, 3.1 mmol), and the mixture was cooled to 0° C. followed by addition of benzenesulfonyl chloride (0.087 mL, 0.68 mmol). The mixture was allowed to warm to rt and was stirred for 2 hours. The mixture was concentrated, partitioned between DCM and water. The organic layer was separated, dried over MgSO$_4$, filtered, concentrated and purified via flash chromatography to furnish N-benzyl-N-(3-(2,6-bis(2,5-dimethyl-1H-pyrrol-1-yl)pyridin-4-yl)-3-phenylpropyl)benzenesulfonamide (0.266 g, 0.423 mmol, 68.9% yield), MS (ESI) m/z 629.2 (M+H). $^1$H NMR (400 MHz, CDCl$_3$) δ 7.83-7.71 (m, 2H), 7.56 (d, J=7.3 Hz, 1H), 7.52-7.44 (m, 2H), 7.31-7.14 (m, 8H), 6.97 (d, J=6.6 Hz, 2H), 6.77 (s, 2H), 5.86 (s, 4H), 4.40-4.31 (m, 1H), 4.24-4.16 (m, 1H), 3.93-3.74 (m, 1H), 3.18-3.05 (m, 1H), 3.03-2.89 (m, 1H), 2.22-2.07 (m, 2H).

Intermediate 15c: N-benzyl-N-(3-(2,6-diaminopyridin-4-yl)-3-phenylpropyl)benzenesulfonamide

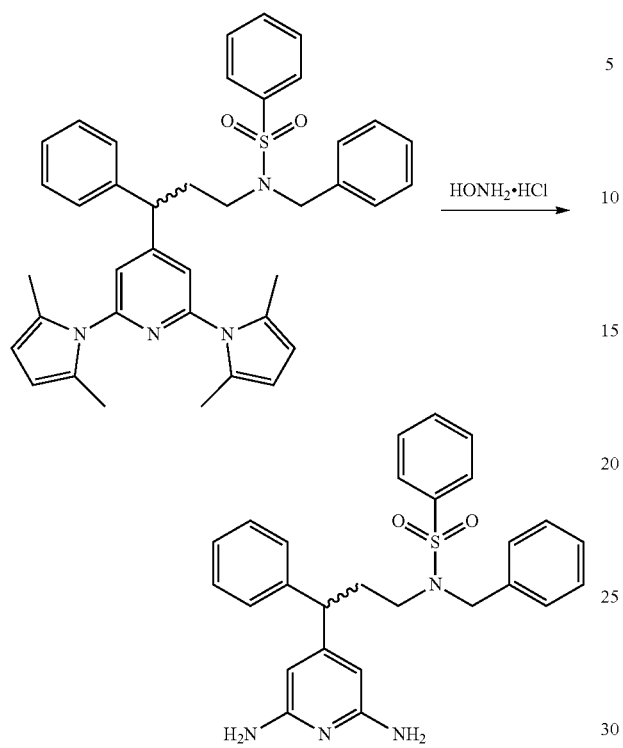

To N-benzyl-N-(3-(2,6-bis(2,5-dimethyl-1H-pyrrol-1-yl)pyridin-4-yl)-3-phenylpropyl)benzenesulfonamide (0.266 g, 0.423 mmol) suspended in EtOH (4.2 mL) was added TEA (0.59 mL, 4.2 mmol) and hydroxylamine hydrochloride (0.588 g, 8.46 mmol), and the mixture was heated to 80° C. for two days. The reaction mixture was partitioned between DCM and 1N NaOH. The aqueous layer was washed 2× with DCM. The organics were dried over MgSO$_4$, filtered, concentrated and purified via flash chromatography to furnish N-benzyl-N-(3-(2,6-diaminopyridin-4-yl)-3-phenylpropyl)benzenesulfonamide (0.114 g, 0.241 mmol, 57.0% yield). MS (ESI) m/z 473.2 (M+H). $^1$H NMR (400 MHz, CDCl$_3$) δ 7.83-7.72 (m, 2H), 7.62-7.55 (m, 1H), 7.53-7.45 (m, 2H), 7.36-7.27 (m, 3H), 7.24-7.10 (m, 5H), 7.03-6.94 (m, 2H), 5.53 (s, 2H), 4.37-4.22 (m, 2H), 4.10-4.03 (m, 4H), 3.47-3.39 (m, 1H), 3.08-2.90 (m, 2H), 2.15-1.95 (m, 2H).

Intermediate 15d: N-(3-(2,6-diaminopyridin-4-yl)-3-phenylpropyl)benzenesulfonamide

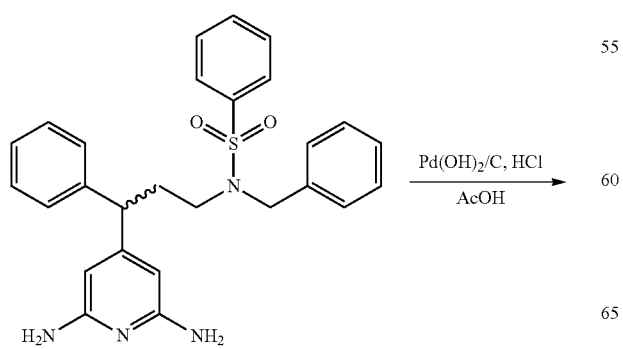

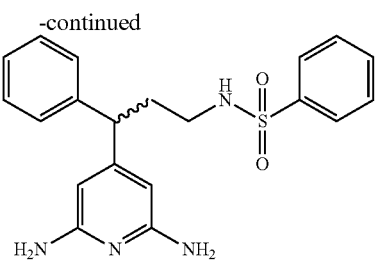

To N-benzyl-N-(3-(2,6-diaminopyridin-4-yl)-3-phenylpropyl)benzenesulfonamide (0.114 g, 0.241 mmol) suspended in AcOH (2.4 mL) was added 12N HCl (0.48 mL, 5.8 mmol) and palladium hydroxide on carbon (10% wt) (0.034 g, 0.024 mmol), and the mixture was stirred under 55 psi(g) hydrogen gas overnight. The reaction mixture was diluted with EtOH, filtered, concentrated and purified via flash chromatography to furnish N-(3-(2,6-diaminopyridin-4-yl)-3-phenylpropyl)benzenesulfonamide (0.029 g, 0.076 mmol, 31% yield). MS (ESI) m/z 383.0 (M+H). $^1$H NMR (400 MHz, CDCl$_3$) δ 7.85-7.75 (m, 2H), 7.58-7.51 (m, 1H), 7.49-7.39 (m, 2H), 7.29-7.14 (m, 3H), 7.13-7.05 (m, 2H), 5.67 (s, 2H), 3.68 (t, J=7.8 Hz, 1H), 2.88 (t, J=6.9 Hz, 2H), 2.09 (q, J=7.4 Hz, 2H).

Intermediate 15e: (E)-N-(3-(2,6-diamino-3-((4-chlorophenyl)diazenyl)pyridin-4-yl)-3-phenylpropyl)benzenesulfonamide

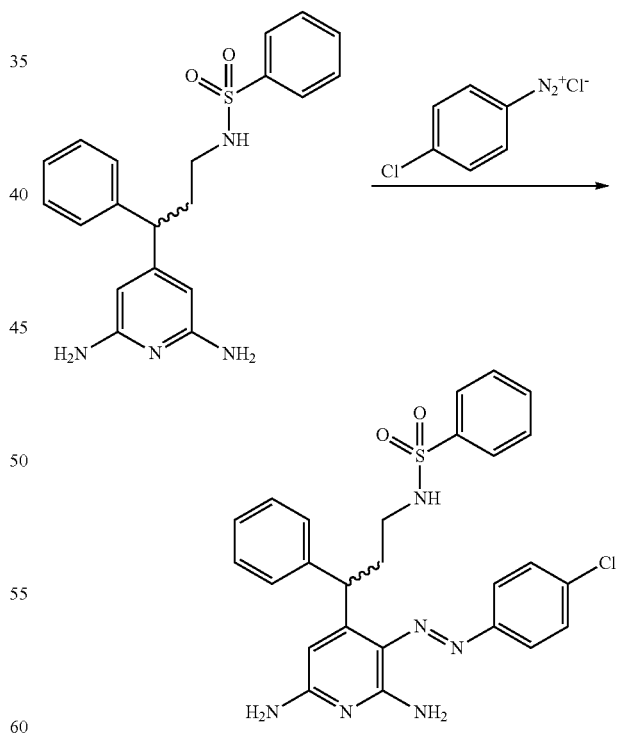

To a solution of N-(3-(2,6-diaminopyridin-4-yl)-3-phenylpropyl) benzenesulfonamide (0.029 g, 0.076 mmol) dissolved in EtOAc (0.95 mL) was added a solution of 4-chlorobenzenediazonium (1.0 mL, 0.076 mmol), and the mixture was stirred overnight. The reaction mixture was diluted with EtOAc and 3 mL of 1 M NaOH solution, and the layers were separated. The organic layer was dried over MgSO₄, filtered and concentrated to furnish crude (E)-N-(3-(2,6-diamino-3-((4-chlorophenyl)diazenyl)pyridin-4-yl)-3-phenylpropyl)benzenesulfonamide (0.040 g, 0.076 mmol, 100% yield). MS (ESI) m/z 521.0 (M+H).

Intermediate 15f: N-(3-phenyl-3-(2,3,6-triaminopyridin-4-yl)propyl)benzenesulfonamide

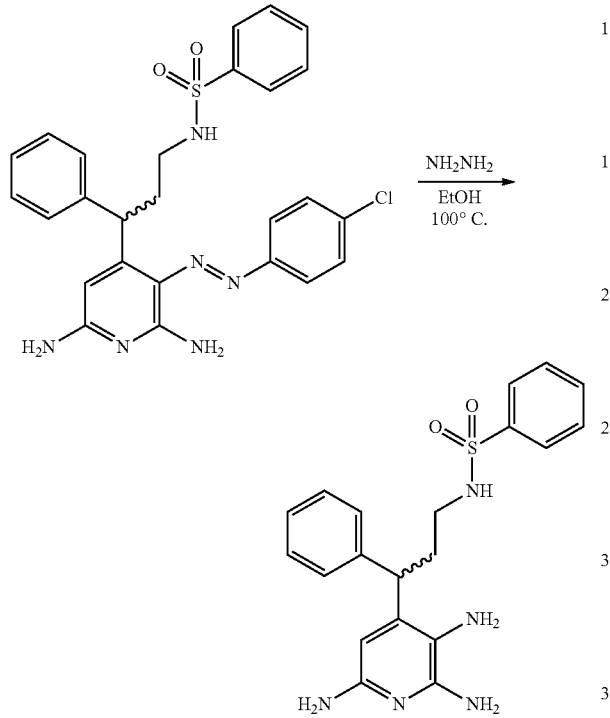

To crude (E)-N-(3-(2,6-diamino-3-((4-chlorophenyl)diazenyl)pyridin-4-yl)-3-phenylpropyl)benzenesulfonamide (0.040 g, 0.076 mmol) suspended in EtOH (0.5 mL) in a 20 mL microwave vial was added hydrazine (0.09 mL, 3 mmol), and the vial was sealed and heated with stirring at 100° C. in a pie block behind a blast shield over weekend. The reaction mixture was concentrated, and the residue was purified via flash chromatography to furnish N-(3-phenyl-3-(2,3,6-triaminopyridin-4-yl)propyl)benzenesulfonamide (0.022 g, 0.055 mmol, 73% yield). MS (ESI) m/z 397.9 (M+H).

Example 15: N-(3-(5-amino-3H-[1,2,3]triazolo[4,5-b]pyridin-7-yl)-3-phenylpropyl)benzenesulfonamide, TFA

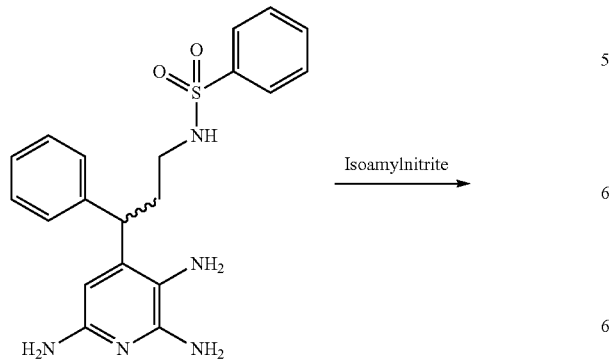

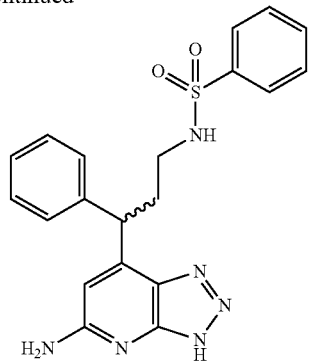

To N-(3-phenyl-3-(2,3,6-triaminopyridin-4-yl)propyl)benzenesulfonamide (15f, 0.022 g, 0.055 mmol) dissolved in THF (0.6 mL) was added AcOH (6 µL, 0.1 mmol) and isoamylnitrite (7 µL, 0.05 mmol), and the mixture was stirred overnight. To the reaction was added 7N NH₃ in MeOH. The mixture was concentrated and purified via preparative reverse phase chromatography to furnish N-(3-(5-amino-3H-[1,2,3]triazolo[4,5-b]pyridin-7-yl)-3-phenylpropyl)benzenesulfonamide, TFA (0.010 g, 0.017 mmol, 31% yield) MS (ESI) m/z 409.1 (M+H)$^1$H NMR (400 MHz, CD₃CN) δ 7.79-7.70 (m, 2H), 7.65-7.44 (m, 3H), 7.40-7.16 (m, 5H), 6.71 (s, 1H), 5.71 (t, J=5.6 Hz, 1H), 4.50 (t, J=7.8 Hz, 1H), 2.96-2.67 (m, 2H), 2.45 (dq, J=13.9, 7.0 Hz, 1H), 2.35-2.24 (m, 1H). LC: 5.82 min, Method A
General Route 4 (see Scheme 4):

Intermediate 4-1: (Z)-3-(2,6-bis(2,5-dimethyl-1H-pyrrol-1-yl)pyridin-4-yl)-3-phenylacrylaldehyde

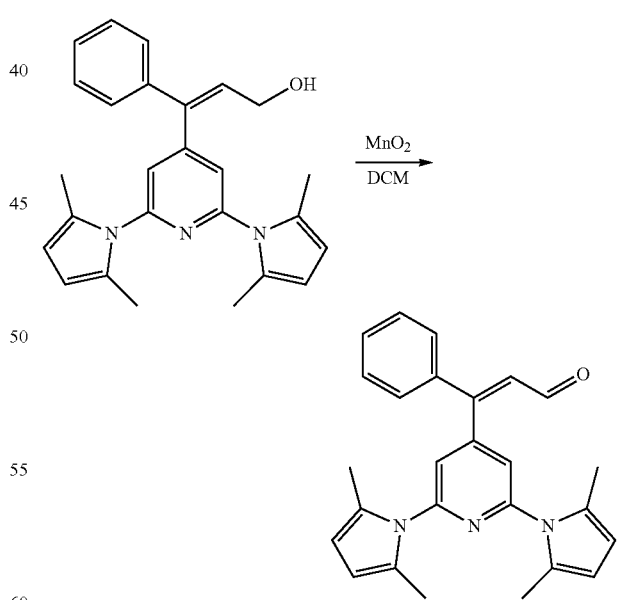

(Adapted from *J Org. Chem.* 1954, 19, 1608) To (Z)-3-(2,6-bis(2,5-dimethyl-1H-pyrrol-1-yl)pyridin-4-yl)-3-phenyl-prop-2-en-1-ol (2.00 g, 5.03 mmol) in DCM (50 mL) was added manganese dioxide (7.4 g, 86 mmol), and the mixture was stirred overnight. The reaction mixture was filtered, concentrated and purified via silica gel chromatography to furnish (Z)-3-(2,6-bis(2,5-dimethyl-1H-pyrrol-1-yl)pyridin-4-yl)-3-phenylacrylaldehyde (4-1, 1.34 g, 3.39 mmol, 67.3% yield). MS (ESI) m/z 428.0 (M+H). $^1$H NMR (400 MHz, CDCl$_3$) δ 9.70 (d, J=7.8 Hz, 1H), 7.55-7.40 (m, 3H), 7.39-7.31 (m, 2H), 7.17 (s, 2H), 6.74 (d, J=8.1 Hz, 1H), 5.92 (s, 4H), 2.19 (s, 12H).

General Enal Reductive Amination Procedure:

To aldehyde 4-1 (1 eq) in EtOH (0.1 M) was added amine (free based with an equivalent of Et$_3$N) (1-1.5 eq), and the mixture was heated until all the solids dissolved. The resultant solution was cooled to 0° C., and THF or EtOH (0.1 M) and NiCl$_2$ hexahydrate (3 eq) were added, and the mixture was stirred for 10 minutes (the nickel salt may or may not be added to the reaction with similar results). To the solution was added either NaBH$_4$ (5.5 eq) portion wise or drop-wise in an ethereal solution, and the mixture was stirred at 0° C. for 30-60 minutes. To the solution was added an excess of saturated NH$_4$Cl, and the reaction mixture was stirred 1-20 hours. The crude was diluted with EtOAc, and the aqueous phase was washed 3× with EtOAc. The combined organic phases were dried with MgSO$_4$, filtered and concentrated. The residue was purified by silica gel chromatography to furnish aminoalkane 4-2 which was deprotected according to the General Bis-pyrrole Deprotection Procedure to furnish intermediate 1-1. The compounds of the invention were processed to compounds of the general formula (I) according to the general procedures outlined herein.

Intermediate 17a: 3-(2,6-bis(2,5-dimethyl-1H-pyrrol-1-yl)pyridin-4-yl)-N-(naphthalen-1-ylmethyl)-3-phenylpropan-1-amine

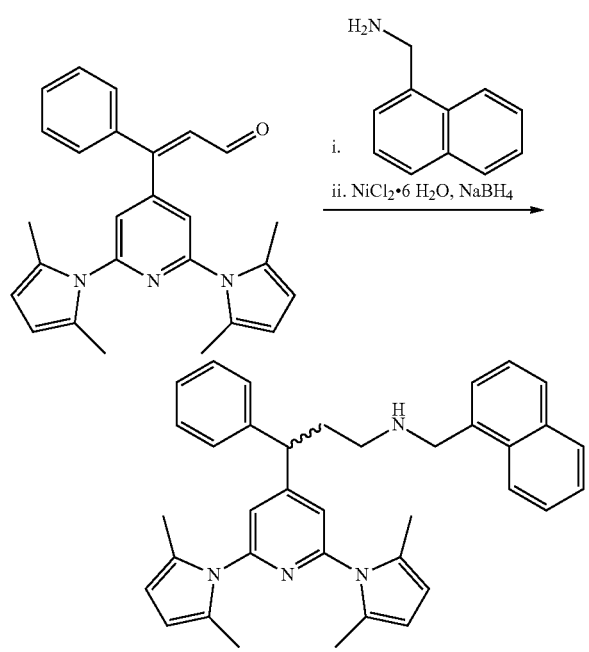

To naphthalen-1-ylmethanamine (0.103 g, 0.652 mmol) in EtOH (6.5 mL) was added (Z)-3-(2,6-bis(2,5-dimethyl-1H-pyrrol-1-yl)pyridin-4-yl)-3-phenylacrylaldehyde (0.258 g, 0.652 mmol), and the mixture was heated until the solids dissolved. THF (6.5 mL) and nickel(II) chloride hexahydrate (0.253 g, 1.96 mmol) were added, and the mixture was stirred at 0° C. under Ar. To this was added NaBH$_4$ (0.136 g, 3.59 mmol) portion wise, and the mixture was stirred at 0° C. for 45 min. The reaction was quenched with saturated NH$_4$Cl and diluted with EtOAc. The aq. phase was washed 3× with EtOAc, and the combined organic phases were dried with MgSO$_4$, filtered, concentrated, and purified via flash chromatography to furnish 3-(2,6-bis(2,5-dimethyl-1H-pyrrol-1-yl)pyridin-4-yl)-N-(naphthalen-1-ylmethyl)-3-phenylpropan-1-amine (0.249 g, 0.463 mmol, 71.0% yield). MS (ESI) m/z 539.1 (M+H). $^1$H NMR (400 MHz, CDCl$_3$) δ 8.16-8.07 (m, 1H), 7.89-7.81 (m, 1H), 7.78-7.71 (m, 1H), 7.56-7.44 (m, 2H), 7.41-7.28 (m, 4H), 7.26-7.11 (m, 3H), 7.00 (s, 2H), 5.88 (s, 4H), 4.20 (s, 3H), 2.74 (t, J=6.3 Hz, 2H), 2.30 (q, J=6.8 Hz, 2H), 2.07 (s, 12H).

Example 17: 7-(3-((naphthalen-1-ylmethyl)amino)-1-phenylpropyl)-3H-[1,2,3]triazolo[4,5-b]pyridin-5-amine

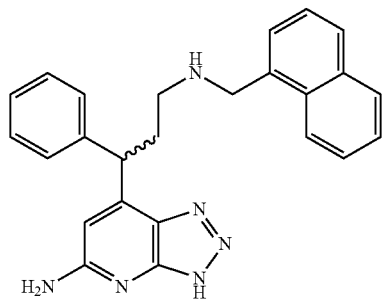 [SMILES: Nc1cc(C(CCNCc2cccc3ccccc23)c2ccccc2)c2nn[nH]c2n1]

To 3-(2,6-bis(2,5-dimethyl-1H-pyrrol-1-yl)pyridin-4-yl)-N-(naphthalen-1-ylmethyl)-3-phenylpropan-1-amine (0.249 g, 0.463 mmol) dissolved in EtOH (4.6 mL) was added TEA (0.65 mL, 4.6 mmol) and hydroxylamine hydrochloride (0.643 g, 9.26 mmol), and the mixture was heated to 80° C. overnight. The reaction mixture was concentrated, partitioned between DCM and 1N NaOH, the aqueous layer was washed with DCM, and the combined organic layer dried over MgSO$_4$, filtered and concentrated to furnish crude 4-(3-((naphthalen-1-ylmethyl)amino)-1-phenylpropyl)pyridine-2,6-diamine (0.300 g, 0.463 mmol, 100% yield). MS (ESI) m/z 383.0 (M+H).

To a solution of 4-chloroaniline (0.065 g, 0.51 mmol) in water (5.8 mL) was added 6N HCl (0.31 mL, 1.9 mmol). A solution of sodium nitrite (0.032 g, 0.46 mmol) in water (0.5 mL) was added, and the reaction mixture was stirred for 30 min. The above solution was poured into a solution of 4-(3-((naphthalen-1-ylmethyl)amino)-1-phenylpropyl)pyridine-2,6-diamine (0.177 g, 0.463 mmol) in 0.1 M HCl (aq) (5.8 mL) and stirred overnight. To the reaction mixture was added 1 M sodium hydroxide (14 mL, 14 mmol), and the reaction mixture was stirred for 10 min. The reaction mixture was partitioned between water and EtOAc, the aqueous was extracted 3× with EtOAc, and the organics were combined, dried over MgSO$_4$, filtered, concentrated and purified via flash chromatography to furnish orange solid (E)-3-((4-chlorophenyl)diazenyl)-4-(3-((naphthalen-1-ylmethyl)amino)-1-phenylpropyl)pyridine-2,6-diamine (0.218 g, 0.418 mmol, 90%). MS (ESI) m/z 520.0 (M+H).

To (E)-3-((4-chlorophenyl)diazenyl)-4-(3-((naphthalen-1-ylmethyl)amino)-1-phenylpropyl)pyridine-2,6-diamine (0.241 g, 0.463 mmol) in EtOH (4.63 mL) was added zinc (0.079 g, 1.2 mmol) and AcOH (0.069 mL, 1.2 mmol), and the mixture was heated to 50° C. for 5 min. The reaction mixture was filtered, diluted with 7N NH₃ in MeOH, concentrated and purified via flash chromatography to furnish 4-(3-((naphthalen-1-ylmethyl)amino)-1-phenylpropyl)pyridine-2,3,6-triamine, with residual MeOH (0.140 g, 0.266 mmol, 57.5% yield) which was used as is.

To 4-(3-((naphthalen-1-ylmethyl)amino)-1-phenylpropyl)pyridine-2,3,6-triamine (0.106 g, 0.266 mmol) in THF (2.7 mL) was added AcOH (0.030 mL, 0.53 mmol) and isoamyl nitrite (0.034 mL, 0.25 mmol), and the mixture was stirred for 16 hours. The reaction was quenched with 3 mL 7N NH₃ in MeOH, and the solvents were concentrated. The residue was purified via preparative reverse phase HPLC to furnish 7-(3-((naphthalen-1-ylmethyl)amino)-1-phenylpropyl)-3H-[1,2,3]triazolo[4,5-b]pyridin-5-amine, TFA (0.0090 g, 0.016 mmol, 6.2% yield. MS (ESI) m/z 408.9 (M+H). ¹H NMR (500 MHz, CD₃CN) δ 8.08 (d, J=8.3 Hz, 1H), 7.99-7.90 (m, 2H), 7.67-7.54 (m, 3H), 7.50 (dd, J=8.3, 7.2 Hz, 1H), 7.44-7.38 (m, 2H), 7.34 (t, J=7.6 Hz, 2H), 7.30-7.23 (m, 1H), 6.72 (s, 1H), 4.62 (s, 2H), 4.58 (t, J=7.8 Hz, 1H), 3.24-3.08 (m, 2H), 2.85-2.72 (m, 1H), 2.67-2.55 (m, 1H). LC: 4.01 min, Method A Examples 16, and 18-29 were prepared according the procedures described for Example 17 and as described in General Route 4 by using the appropriate amine, which was commercially available, followed by further elaboration via General Route 1.

Intermediate 30a: IV-(1-(3-fluorophenyl)ethylidene)-4-methylbenzenesulfonohydrazide

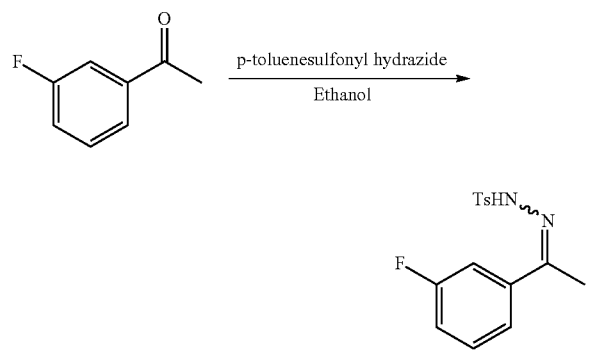

To 1-(3-fluorophenyl)ethanone (1.00 g, 7.24 mmol) dissolved in EtOH (7.2 mL) was added 4-methylbenzenesulfonohydrazide (1.35 g, 7.24 mmol), and the mixture was stirred overnight at rt. Product was recrystallized from the reaction solution, filtered, washed with cold EtOH to yield N-(1-(3-fluorophenyl)ethylidene)-4-methylbenzenesulfonohydrazide (1.50 g, 4.90 mmol, 67.6% yield). MS (ESI) m/z 307.0 (M+H). ¹H NMR (400 MHz, CDCl₃) δ 7.91 (d, J=8.2 Hz, 2H), 7.52 (s, 1H), 7.45-7.27 (m, 5H), 7.06 (td, J=8.2, 2.7 Hz, 1H), 2.43 (s, 3H), 2.13 (s, 3H).

Intermediate 30b: 7-(1-(3-fluorophenyl)vinyl)-3H-[1,2,3]triazolo[45-b]pyridin-5-amine

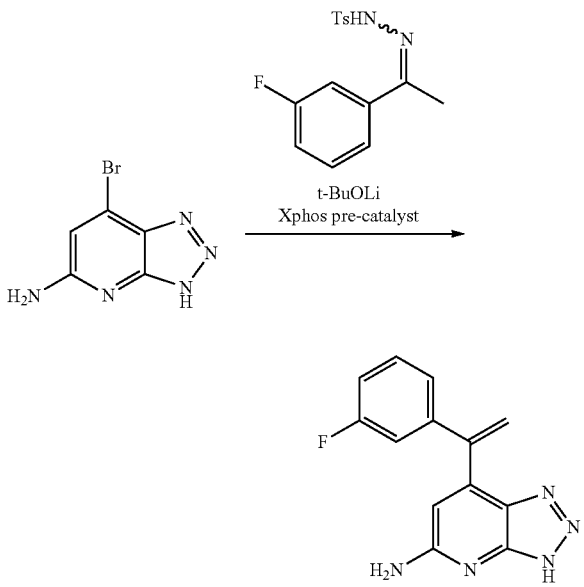

To N-(1-(3-fluorophenyl)ethylidene)-4-methylbenzenesulfonohydrazide (0.079 g, 0.26 mmol), chloro(2-dicyclohexylphosphino-2',4',6'-tri-i-propyl-1,1'-biphenyl)[2-(aminoethyl)phenyl]palladium(II) methyl-t-butylether adduct (0.048 g, 0.058 mmol), and lithium 2-methylpropan-2-olate (0.064 g, 0.79 mmol) dissolved in dioxane (0.9 mL) and blanketed under Ar was added 7-bromo-3H-[1,2,3]triazolo[4,5-b]pyridin-5-amine (0.05 g, 0.2 mmol), and the mixture was heated to 90° C. overnight. The mixture was partitioned between EtOAc and sat. NH₄Cl, and washed 3× with EtOAc. The organics were dried over MgSO₄, filtered and concentrated. The residue was purified via reverse phase to furnish 7-(1-(3-fluorophenyl)vinyl)-3H-[1,2,3]triazolo[4,5-b]pyridin-5-amine (0.0134 g, 0.052 mmol, 22.5% yield). MS (ESI) m/z 256.0 (M+H). ¹H NMR (400 MHz, CD₃CN) δ 7.51-7.38 (m, 1H), 7.27-7.09 (m, 3H), 6.61 (s, 1H), 6.50 (s, 1H), 6.03 (s, 1H).

Example 30: 7-(1-(3-fluorophenyl)ethyl)-3H-[1,2,3]triazolo[4,5-b]pyridin-5-amine

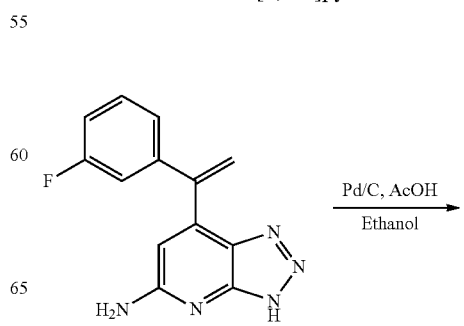

-continued

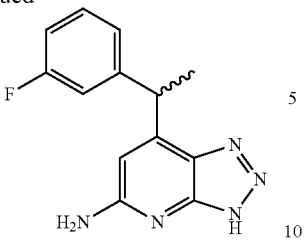

To 7-(1-(3-fluorophenyl)vinyl)-3H-[1,2,3]triazolo[4,5-b]pyridin-5-amine (0.019 g, 0.073 mmol) dissolved in EtOH (3.6 mL) was added AcOH (0.01 mL, 0.2 mmol) and Pd/C (10 wt %) (7.8 mg, 7.3 µmol). The flask was evacuated and charged to 55 psi(g) with hydrogen, and the mixture was stirred overnight. The reaction mixture was filtered to remove Pd/C, concentrated and purified via reverse phase to furnish racemic 7-(1-(3-fluorophenyl)ethyl)-3H-[1,2,3]triazolo[4,5-b]pyridin-5-amine (0.0087 g, 0.032 mmol, 44% yield), MS (ESI) m/z 258.0 (M+H). $^1$H NMR (400 MHz, CD$_3$CN) δ 7.35 (td, J=8.0, 6.0 Hz, 1H), 7.20 (d, J=7.7 Hz, 1H), 7.15 (dt, J=10.4, 1.9 Hz, 1H), 7.00 (td, J=8.5, 2.7 Hz, 1H), 6.65 (s, 1H), 4.69 (q, J=7.1 Hz, 1H), 1.74 (d, J=7.1 Hz, 3H). LC: 6.07 min, Method A General Route 5 (see Scheme 5):
General Hydrazone Formation Procedure:

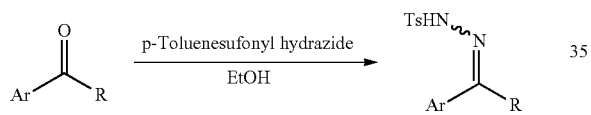

To a ketone (1 eq) dissolved in EtOH (1 M) was added 4-methylbenzenesulfonohydrazide (1 eq), and the mixture was stirred at room temperature or reflux for 1-20 hours. Solids were filtered and washed with cold EtOH to yield hydrazone intermediate.

General Palladium Mediated Barluenga Procedure:

(Adapted from *Chem. Eur. J.* 2009, 15, 13291) To a mixture of bromopyridine 2-1 or 5-1 (1 eq), tosylhydrazone (1.1 eq, prepared according to the General Hydrazone Formation Procedure) and chloro(2-dicyclohexylphosphino-2',4',6'-tri-i-propyl-1,1'-biphenyl)[2-(aminoethyl)phenyl]palladium(II) methyl-t-butylether adduct (0.04 eq) in dioxane (0.25 M), was added lithium 2-methylpropan-2-olate (2.4 eq). The vessel was purged with Ar, sealed and heated between 80-90° C. for 12-20 hours until the starting bromopyridine was consumed. The solution was partitioned between DCM and water, washed 3× with DCM. The organic layer was dried over MgSO$_4$, filtered, and concentrated. The resulting residue was purified by flash chromatography to furnish olefin 5-2 in the case of starting material 5-1, which was deprotected according to the General Bispyrrole Deprotection Procedure to furnish 2-5, or in the case of starting material 2-1, to furnish 2-5 directly. In either case the material was hydrogenated according to the General Olefin Hydrogenation Procedure and the resulting intermediate 1-1 processed to compounds of the general formula (I) according to the methods outlined in General Route 1 (Scheme 1).

Intermediate 5-1:
2,6-(2,5-Dimethylpyrrol-1-yl)-4-bromo-pyridine

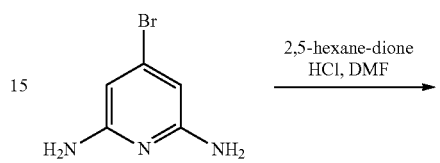

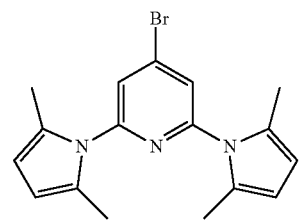

4-Bromopyridine-2,6-diamine (20 g, 106 mmol) was suspended in iPrOH (100 mL) and conc HBr (29.9 mL, 266 mmol). The mixture was stirred at rt under argon overnight. The precipitated hydrobromide salt was collected by filtration and washed with a minimal amount of iPrOH and dried under vacuum. The filtrate was evaporated, and the residue was dried under vacuum for several hours then triturated with Et$_2$O three times. The resulting solid was dried in vacuo and combined with the first crop for a total of 26.9 g of yellow 4-bromopyridine-2,6-diamine, hydrobromide. 4-bromopyridine-2,6-diamine, hydrobromide (26.9 g, 100 mmol) was taken up in DMF (200 mL), and 2,5-hexanedione (36.7 mL, 300 mmol) and MgSO$_4$ (60.2 g, 500 mmol) were added. The mixture was heated under argon at 120° C. for ~4 hr, then cooled to rt and filtered. The solid was washed thoroughly with EtOAc. The combined filtrate and washings were extracted with aq. sat. NaHCO$_3$, 10% aq LiCl and brine, then dried over MgSO$_4$, filtered, and evaporated. The residue was taken up in DCM, and absorbed onto a silica gel pad, which was then eluted with 10% Et$_2$O in hexanes until most of the orange color had eluted. The eluent was evaporated and the solid dried thoroughly in vacuo to provide 2,6-(2,5-dimethylpyrrol-1-yl)-4-bromo-pyridine (25.1 g, 72.7%). MS(ESI) m/z: 344.0 (M+H)$^+$ 1H NMR (500 MHz, CDCl$_3$) δ 7.40 (s, 2H), 5.91 (s, 4H), 2.18 (s, 12H).

Intermediate 34a: 2,6-bis(2,5-dimethyl-1H-pyrrol-1-yl)-4-(1-(3-methoxyphenyl)-2-phenylvinyl)pyridine

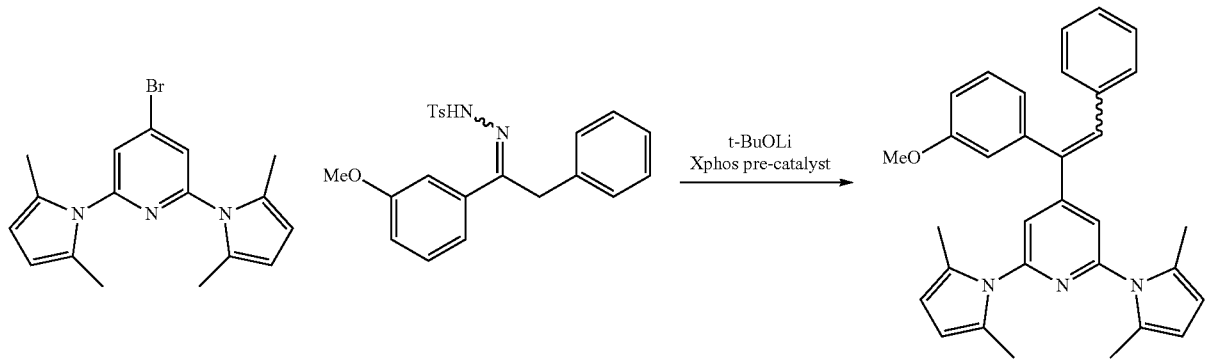

To N-(1-(3-methoxyphenyl)-2-phenylethylidene)-4-methylbenzene sulfonohydrazide (0.353 g, 0.895 mmol), chloro(2-dicyclohexylphosphino-2',4',6'-tri-i-propyl-1,1'-biphenyl)[2-(aminoethyl)phenyl]palladium(II) methyl-t-butyl-ether adduct (0.027 g, 0.033 mmol), and 4-bromo-2,6-bis(2,5-dimethyl-1H-pyrrol-1-yl)pyridine (0.28 g, 0.81 mmol) in dioxane (3.2 mL) blanketed under Ar was added lithium 2-methylpropan-2-olate (0.156 g, 1.95 mmol), and the mixture was heated to 90° C. overnight. The reaction mixture was partitioned between EtOAc and water, and the aqueous layer was washed 3× with EtOAc. The organics were dried over MgSO$_4$, filtered and concentrated. The residue was purified via flash chromatography to furnish 2,6-bis(2,5-dimethyl-1H-pyrrol-1-yl)-4-(1-(3-methoxyphenyl)-2-phenylvinyl)pyridine (0.326 g, 85% yield). MS (ESI) m/z 474.2 (M+H).

Intermediate 34b: 4-(1-(3-methoxyphenyl)-2-phenylvinyl)pyridine-2,6-diamine

To 2,6-bis(2,5-dimethyl-1H-pyrrol-1-yl)-4-(1-(3-methoxyphenyl)-2-phenylvinyl)pyridine (0.325 g, 0.686 mmol) dissolved in 2-propanol (5.5 mL) and water (1.4 mL) was added TEA (0.96 mL, 6.9 mmol) and hydroxylamine hydrochloride (0.954 g, 13.7 mmol), and the mixture was heated to 80° C. for two days. The reaction mixture was partitioned between EtOAc and water, and extracted 3× with EtOAc. The organic layer was dried over MgSO$_4$, filtered and purified via flash chromatography to furnish 4-(1-(3-methoxyphenyl)-2-phenylvinyl)pyridine-2,6-diamine (0.169 g, 0.532 mmol, 78% yield). MS (ESI) m/z 318.0 (M+H).

Intermediate 34c: 4-(1-(3-methoxyphenyl)-2-phenylethyl)pyridine-2,6-diamine

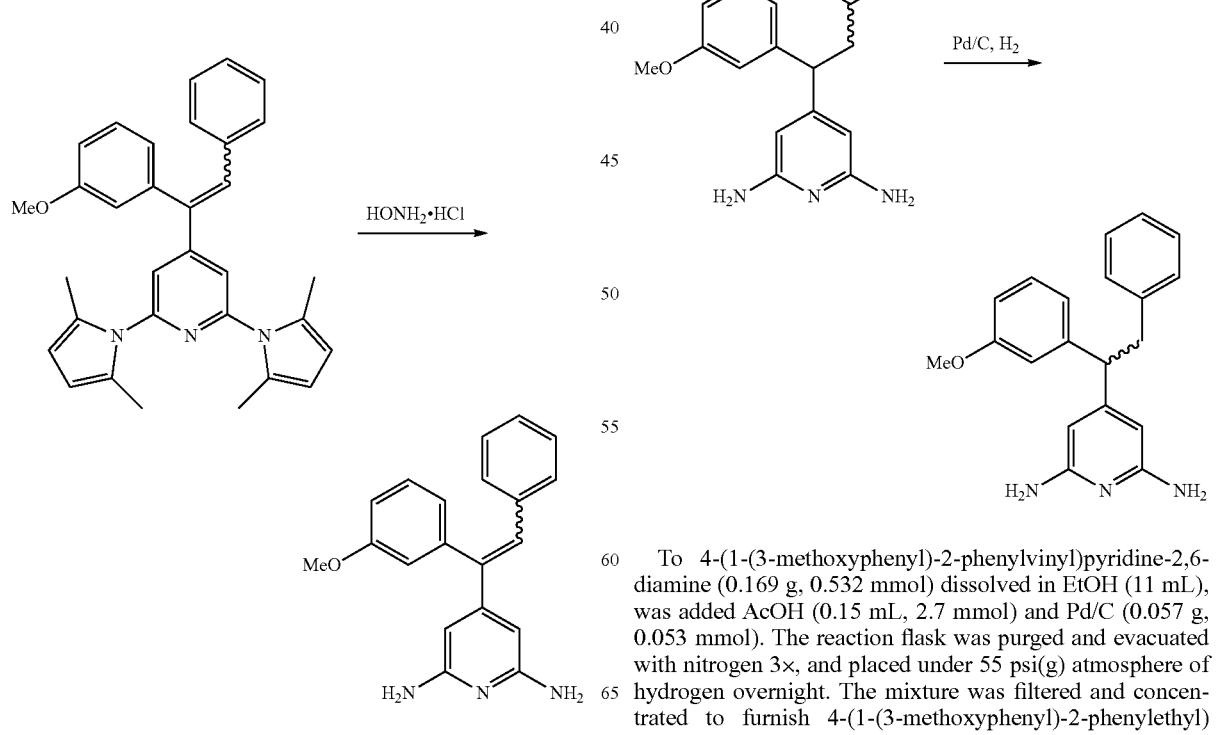

To 4-(1-(3-methoxyphenyl)-2-phenylvinyl)pyridine-2,6-diamine (0.169 g, 0.532 mmol) dissolved in EtOH (11 mL), was added AcOH (0.15 mL, 2.7 mmol) and Pd/C (0.057 g, 0.053 mmol). The reaction flask was purged and evacuated with nitrogen 3×, and placed under 55 psi(g) atmosphere of hydrogen overnight. The mixture was filtered and concentrated to furnish 4-(1-(3-methoxyphenyl)-2-phenylethyl)pyridine-2,6-diamine (0.121 g, 0.242 mmol, 45.4% yield)

contaminated with residual AcOH. MS (ESI) m/z 320.1 (M+H). $^1$H NMR (400 MHz, CDCl$_3$) δ 7.25-7.11 (m, 4H), 7.06-6.97 (m, 2H), 6.82-6.67 (m, 3H), 5.67 (s, 2H), 3.92 (t, J=7.7 Hz, 1H), 3.76 (s, 3H), 3.23 (d, J=7.7 Hz, 2H).

Intermediate 34d: (E)-3-((4-chlorophenyl)diazenyl)-4-(1-(3-methoxyphenyl)-2-phenylethyl)pyridine-2,6-diamine

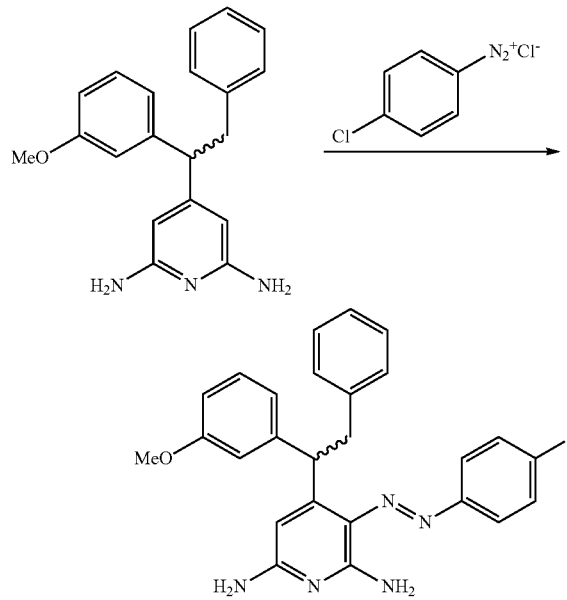

To solution of 4-(1-(3-methoxyphenyl)-2-phenylethyl)pyridine-2,6-diamine (0.077 g, 0.24 mmol) in EtOAc (5.8 mL) was added 4-chlorobenzenediazonium chloride solution (0.41 mL, 0.24 mmol), and the mixture was stirred overnight. Then NaOAc (0.069 g, 0.85 mmol) was added followed by dilution with EtOAc, and separation of the layers. The organic layers were dried over MgSO$_4$, filtered and concentrated. The residue was purified via flash chromatography to furnish (E)-3-((4-chlorophenyl)diazenyl)-4-(1-(3-methoxyphenyl)-2-phenylethyl)pyridine-2,6-diamine, (0.130 g, -) contaminated with residual EtOAc. MS (ESI) m/z 458.0 (M+H).

Intermediate 34e: 4-(1-(3-methoxyphenyl)-2-phenylethyl)pyridine-2,3,6-triamine

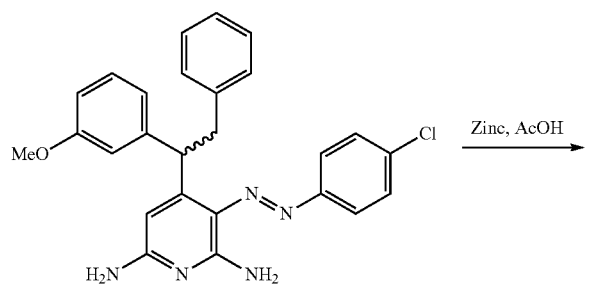

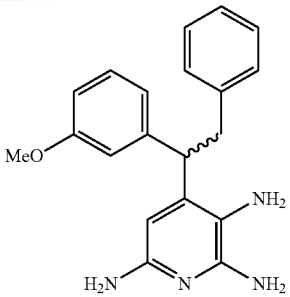

To (E)-3-((4-chlorophenyl)diazenyl)-4-(1-(3-methoxyphenyl)-2-phenylethyl)pyridine-2,6-diamine (0.130 g, 0.285 mmol) dissolved in EtOH (2.9 mL), was added zinc (0.228 g, 2.90 mmol) and AcOH (0.19 mL, 3.4 mmol), and the mixture was heated to 50° C. for 15 minutes. The reaction mixture was filtered, concentrated, and diluted with 7N NH$_3$ in MeOH followed by concentration under vacuum. The residue was purified via flash chromatography to afford 4-(1-(3-methoxyphenyl)-2-phenylethyl)pyridine-2,3,6-triamine (0.116 g, 0.220 mmol, 77% yield), contaminated with residual MeOH. MS (ESI) m/z 335.1 (M+H).

Example 34: 7-(1-(3-methoxyphenyl)-2-phenylethyl)-3H-[1,2,3]triazolo[4,5-b]pyridin-5-amine

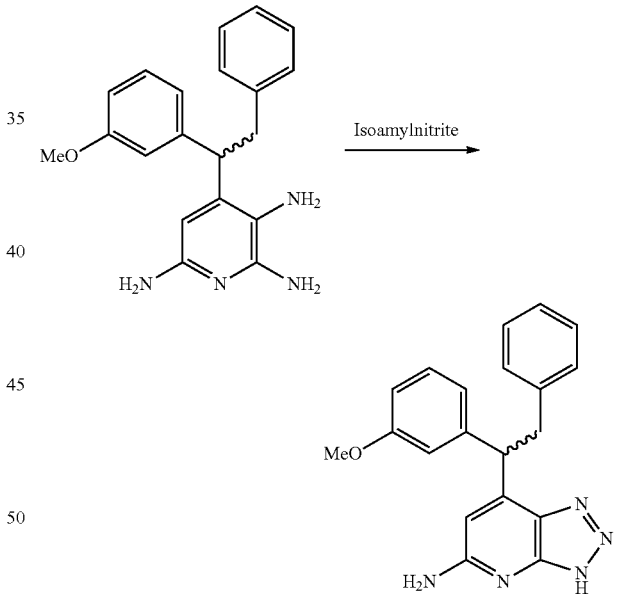

To a solution of 4-(1-(3-methoxyphenyl)-2-phenylethyl)pyridine-2,3,6-triamine (0.116 g, 0.220 mmol) dissolved in THF (22 mL) was added 1 drop of AcOH and isoamyl nitrite (29 µL, 0.21 mmol), and the mixture was stirred overnight. To the mixture 2 mL of 7N NH$_3$ in MeOH was added. The solution was concentrated and purified via preparative reverse phase to furnish 7-(1-(3-methoxyphenyl)-2-phenylethyl)-3H-[1,2,3]triazolo[4,5-b]pyridin-5-amine (0.030 g, 0.083 mmol, 38% yield). MS (ESI) m/z 346.1 (M+H). $^1$H NMR (400 MHz, CD$_3$CN) δ 7.25-7.10 (m, 6H), 7.03-6.96 (m, 2H), 6.80-6.75 (m, 1H), 6.73 (s, 1H), 4.81 (t, J=8.0 Hz, 1H), 3.73 (s, 3H), 3.65 (dd, J=14.0, 7.4 Hz, 1H), 3.47 (dd, J=13.7, 8.8 Hz, 1H). LC: 6.84 min, Method A Examples 31-33, 35, and 36 were prepared according the procedures described for Example 34 described in General Route 5 by using the appropriate bromo pyridine species, and hydrazone generated by appropriate ketone which were commercially available.

General Route 6 (see Scheme 6):

Intermediate 38a: (E)-2-(2-phenyl-1-(tributylstannyl)vinyl)pyridine compound with (E)-2-(2-phenyl-2-(tributylstannyl)vinyl)pyridine

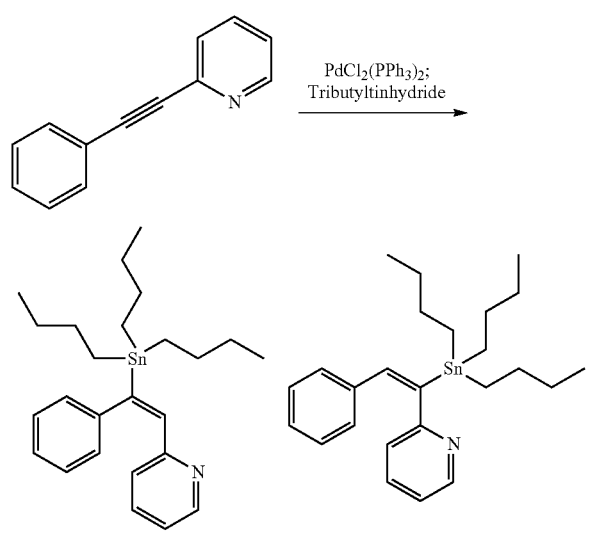

To 2-(phenylethynyl)pyridine (1.12 g, 6.45 mmol) dissolved in THF (13 mL) was added bis(triphenylphosphine)palladium(II) chloride (0.045 g, 0.065 mmol), and the mixture was cooled to 0° C. To this solution was added dropwise tri-n-butyltinhydide (2.1 mL, 7.7 mmol), and the reaction mixture stirred at room temperature overnight. The solvent was concentrated and the residue was purified via flash chromatography to furnish as a mixture of regioisomers (E)-2-(2-phenyl-1-(tributylstannyl)vinyl)pyridine compound with (E)-2-(2-phenyl-2-(tributylstannyl)vinyl)pyridine (1.5 g, 1.6 mmol, 49% yield). MS (ESI) m/z 472.3 (M+H).

Intermediate 38b: (E)-2-(1-iodo-2-phenylvinyl)pyridine compound with (E)-2-(2-iodo-2-phenylvinyl)pyridine

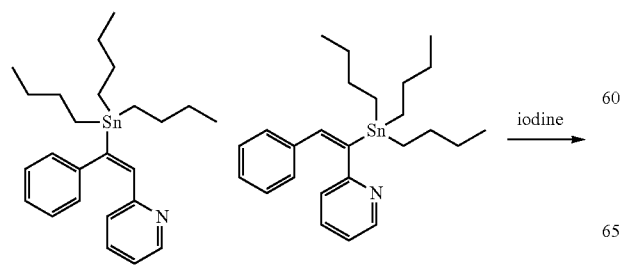

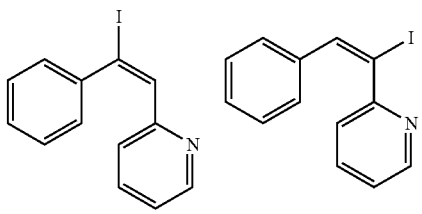

To a mixture of (E)-2-(2-phenyl-1-(tributylstannyl)vinyl)pyridine compound with (E)-2-(2-phenyl-2-(tributylstannyl)vinyl)pyridine (1.5 g, 1.6 mmol) dissolved in DCM (32 mL) was added iodine (0.97 g, 3.8 mmol), and the mixture was stirred at rt overnight in the dark. The reaction mixture was partitioned between DCM and 20% wt Na$_2$S203. The aqueous phase was washed with DCM 3x. The organic layers were combined, dried over MgSO$_4$, filtered, concentrated, and purified via flash chromatography to furnish (E)-2-(1-iodo-2-phenylvinyl)pyridine compound with (E)-2-(2-iodo-2-phenylvinyl)pyridine (0.96 g, 1.6 mmol, 49% yield). MS (ESI) m/z 308.0 (M+H).

Intermediate 38c: (E)-2,6-bis(2,5-dimethyl-1H-pyrrol-1-yl)-4-(1-phenyl-2-(pyridin-2-yl)vinyl)pyridine compound with (Z)-2,6-bis(2,5-dimethyl-1H-pyrrol-1-yl)-4-(2-phenyl-1-(pyridin-2-yl)vinyl)pyridine

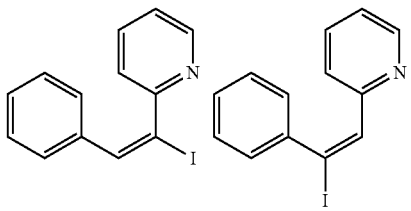

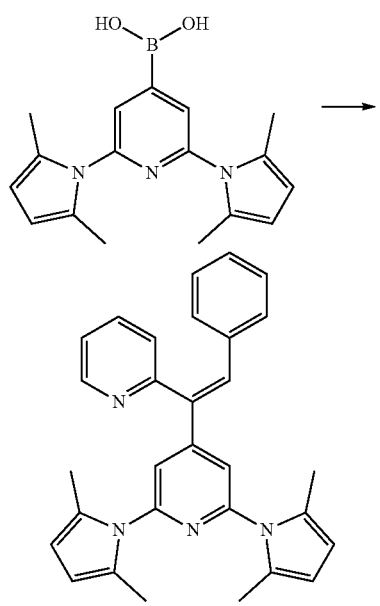

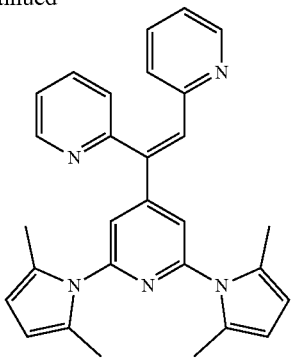

To a mixture of (E)-2-(1-iodo-2-phenylvinyl)pyridine compound with (E)-2-(2-iodo-2-phenylvinyl)pyridine (0.96 g, 1.6 mmol) and (2,6-bis(2,5-dimethyl-1H-pyrrol-1-yl)pyridin-4-yl)boronic acid (1.1 g, 3.4 mmol) dissolved in DME (12 mL) was added 2 M Na₂CO₃ in water (4 mL), and the mixture was blanketed under Ar. Following the addition of PdCl₂ (dppf)-DCM adduct (0.26 g, 0.31 mmol), the reaction mixture was heated to 70° C. overnight. The solvent was concentrated, and the residue purified via flash chromatography to furnish mixture (E)-2,6-bis(2,5-dimethyl-1H-pyrrol-1-yl)-4-(1-phenyl-2-(pyridin-2-yl)vinyl)pyridine compound with (Z)-2,6-bis(2,5-dimethyl-1H-pyrrol-1-yl)-4-(2-phenyl-1-(pyridin-2-yl)vinyl)pyridine (0.84 g, 0.95 mmol, 61% yield). MS (ESI) m/z 445.2 (M+H).

Intermediate 38d: (E)-4-(2-phenyl-1-(pyridin-2-yl)vinyl)pyridine-2,6-diamine

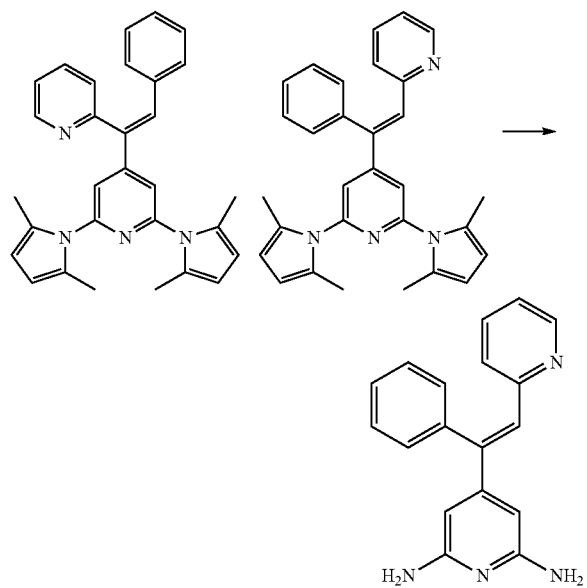

To a mixture of (E)-2,6-bis(2,5-dimethyl-1H-pyrrol-1-yl)-4-(1-phenyl-2-(pyridin-2-yl)vinyl)pyridine compound with (Z)-2,6-bis(2,5-dimethyl-1H-pyrrol-1-yl)-4-(2-phenyl-1-(pyridin-2-yl)vinyl)pyridine (0.85 g, 0.95 mmol) dissolved in 2-propanol (15 mL) and water (4 mL) was added Et₃N (2.7 mL, 19 mmol) and hydroxylamine hydrochloride (2.6 g, 38 mmol), and the mixture was heated to 80° C. overnight. The solvent was concentrated, and residue partitioned between EtOAc and saturated bicarbonate solution. The aqueous layer was extracted 3× with EtOAc. The combined organic phase was dried over MgSO₄, filtered, concentrated and purified via flash chromatography to furnish (E)-4-(2-phenyl-1-(pyridin-2-yl)vinyl)pyridine-2,6-diamine (0.38 g, 0.66 mmol, 69% yield). MS (ESI) m/z 289.1 (M+H).

Intermediate 38e: 4-(2-phenyl-1-(pyridin-2-yl)ethyl)pyridine-2,6-diamine

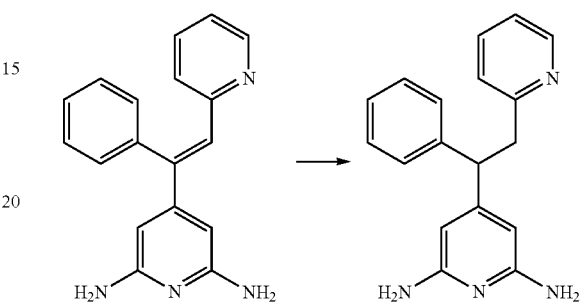

To (E)-4-(1-phenyl-2-(pyridin-2-yl)vinyl)pyridine-2,6-diamine compound with (Z)-4-(2-phenyl-1-(pyridin-2-yl)vinyl)pyridine-2,6-diamine (0.38 g, 0.66 mmol) dissolved in EtOH (4 mL) was added AcOH (0.38 mL, 6.6 mmol) and 10% wt. Pd/C (0.14 g, 0.13 mmol), and the vessel was evacuated and pressurized with 50 psi(g) of hydrogen gas overnight. The reaction mixture was filtered and concentrated to furnish 4-(2-phenyl-1-(pyridin-2-yl)ethyl)pyridine-2,6-diamine (0.38 g, 0.65 mmol, 100% yield) MS (ESI) m/z 291.1 (M+H). ¹H NMR (400 MHz, CDCl₃-d) δ 8.55-8.49 (m, 1H), 7.51 (td, J=7.7, 1.6 Hz, 1H), 7.30-7.24 (m, 2H), 7.23-7.17 (m, 3H), 7.13-7.08 (m, 1H), 6.94 (d, J=7.7 Hz, 1H), 5.69 (s, 2H), 4.36 (t, J=8.0 Hz, 1H), 3.41 (dd, J=8.0, 1.4 Hz, 2H).

Example 38: 7-(1-phenyl-2-(pyridin-2-yl)ethyl)-3H-[1,2,3]triazolo[4,5-b]pyridine-5-amine

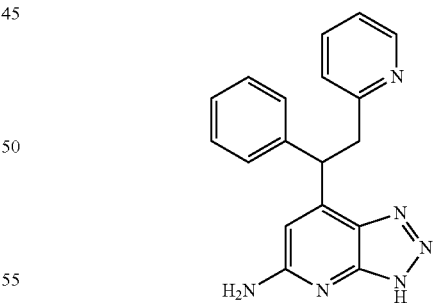

4-(2-phenyl-1-(pyridin-2-yl)ethyl)pyridine-2,6-diamine was further elaborated via Scheme 1 and purified via standard HPLC gradient in ACN in TFA buffered water on an Phenomonex AXIA 5u C18 30×100 mm column. MS (ESI) m/z 317.1 (M+H). ¹H NMR (400 MHz, THF-d) δ 8.44-8.39 (m, 1H), 7.54 (d, J=7.1 Hz, 2H), 7.38 (td, J=7.7, 1.6 Hz, 1H), 7.20-7.13 (m, 2H), 7.10-6.99 (m, 2H), 6.98-6.92 (m, 1H), 6.31 (s, 1H), 5.76 (br. s., 2H), 5.05 (t, J=7.7 Hz, 1H), 4.10 (dd, J=13.7, 8.2 Hz, 1H), 3.67 (dd, J=13.7, 7.7 Hz, 1H). LC: 3.22 min, Method A Example 37 was prepared according the procedures described for Example 38 described in General Route 6 by using the appropriate vinyl iodide, which was commercially available, and further elaborated according to the procedures described in General Route 1.

Intermediate 39a:
N-formyl-N-(3-phenylprop-2-yn-1-yl)formamide

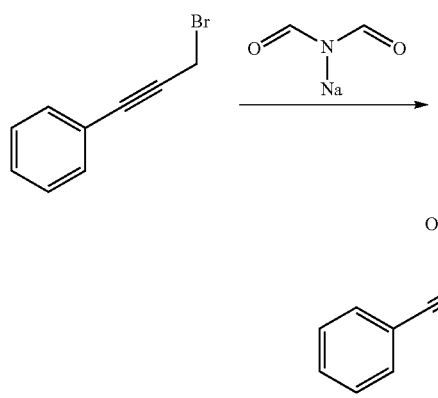

(Adapted from: *Synthesis*, 1990, 2, 122.) To (3-bromoprop-1-yn-1-yl)benzene (3.00 g, 15.4 mmol) (*J. Am. Chem. Soc.*, 2009, 131,9178) dissolved in acetonitrile (154 mL) was added sodium formimide (1.53 g, 16.1 mmol), and the mixture was stirred overnight at 50° C. The crude reaction mixture was concentrated, dissolved in DCM/hexanes, filtered and purified via flash chromatography to furnish N-formyl-N-(3-phenylprop-2-yn-1-yl)formamide. $^1$H NMR (400 MHz, CDCl$_3$) δ 8.91 (br. s., 2H), 7.46-7.36 (m, 2H), 7.34-7.27 (m, 3H), 4.63 (s, 2H).

Intermediate 39b: (E)-N-formyl-N-(3-phenyl-3-(tributylstannyl)allyl)formamide

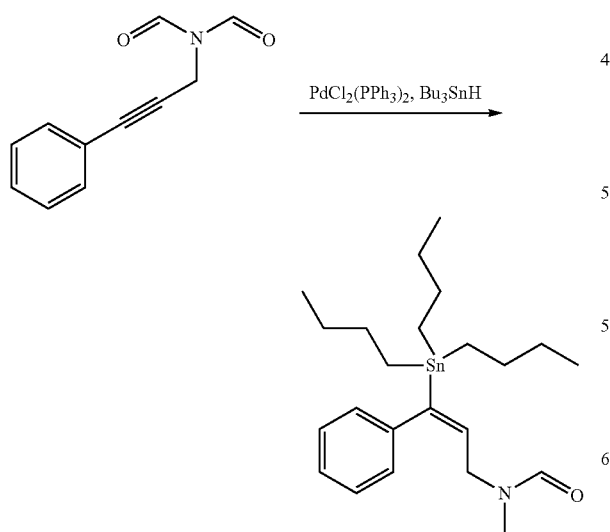

To N-formyl-N-(3-phenylprop-2-yn-1-yl)formamide (2.93 g, 15.7 mmol) dissolved in THF (31 mL) and cooled to 0° C., was added bis(triphenylphosphine)palladium(II) chloride (0.110 g, 0.157 mmol), followed by dropwise addition of tri-n-butyltin hydride (5.0 mL, 18 mmol). The mixture was allowed to warm to rt, and stirred for 3 days. The resulting solution was concentrated and purified via flash chromatography furnish (E)-N-formyl-N-(3-phenyl-3-(tributylstannyl)allyl)formamide (1.00 g, 2.09 mmol, 13.4% yield). MS (ESI) m/z 502.1 (M+Na).

Intermediate 39c:
(E)-N-(3-iodo-3-phenylallyl)formamide

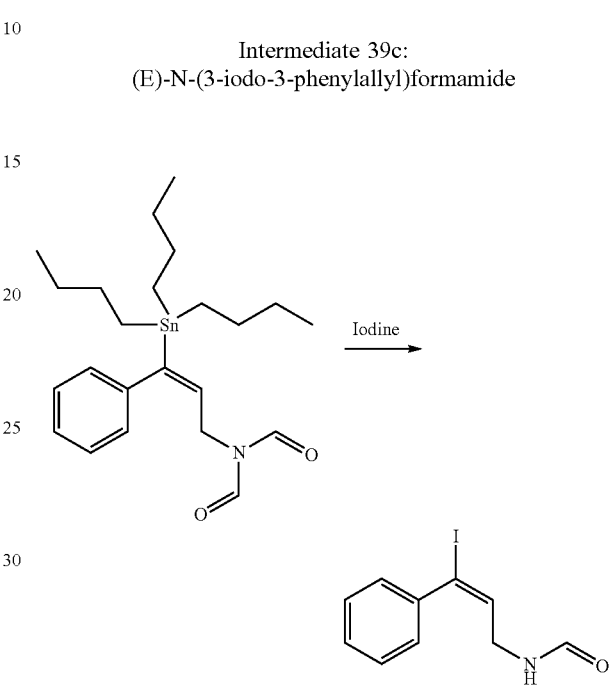

To (E)-N-formyl-N-(3-phenyl-3-(tributylstannyl)allyl)formamide (1.00 g, 2.09 mmol) dissolved in DCM (42 mL) iodine (0.638 g, 2.51 mmol) was gradually added. The mixture was stirred for 30 minutes. Excess iodine was quenched with 20% wt Na$_2$S204 solution, and the layers were separated. The organic layer was dried over MgSO$_4$, filtered, concentrated and purified via flash chromatography to furnish white solid (E)-N-(3-iodo-3-phenylallyl)formamide (0.531 g, 1.85 mmol, 88% yield). MS (ESI) m/z 309.9 (M+Na). $^1$H NMR (400 MHz, CDCl$_3$) δ 8.13 (s, 1H), 7.42-7.19 (m, 5H), 6.57-6.46 (m, 1H), 3.90-3.77 (m, 2H).

Intermediate 39d: (E)-N-(3-(2,6-bis(2,5-dimethyl-1H-pyrrol-1-yl)pyridin-4-yl)-3-phenylallyl)formamide

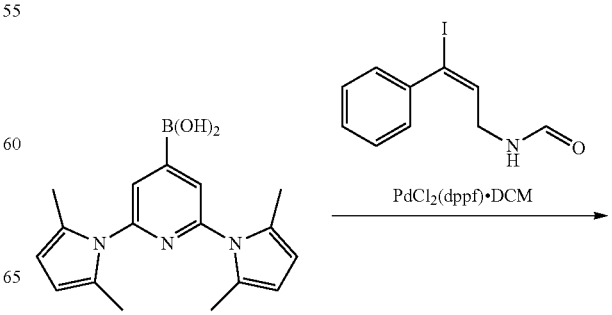

-continued

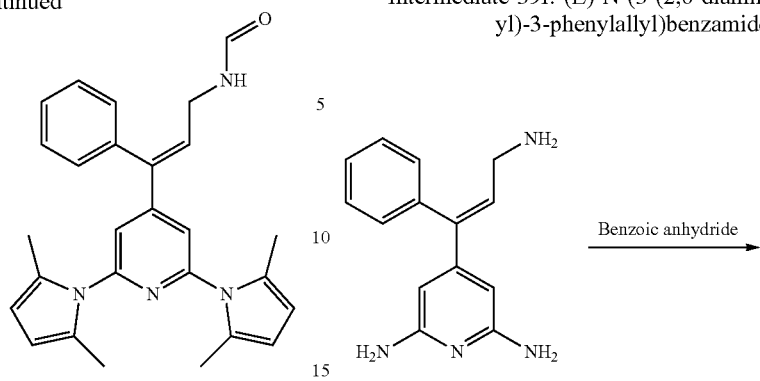

To (E)-N-(3-iodo-3-phenylallyl)formamide 39c and (2,6-bis(2,5-dimethyl-1H-pyrrol-1-yl)pyridin-4-yl)boronic acid (0.223 g, 0.722 mmol) dissolved in DME (2.5 mL) was added 2 M $Na_2CO_3$ in water (0.82 mL), and the mixture was blanketed under Ar followed by addition of $PdCl_2$(dppf)-DCM (0.054 g, 0.066 mmol). The reaction mixture was heated to 70° C. overnight, concentrated and purified via flash chromatography to furnish (E)-N-(3-(2,6-bis(2,5-dimethyl-1H-pyrrol-1-yl)pyridin-4-yl)-3-phenylallyl)formamide (0.667 g, 0.157 mmol, 24% yield). MS (ESI) m/z 425.1 (M+H).

Intermediate 39e: (E)-4-(3-amino-1-phenylprop-1-en-1-yl)pyridine-2,6-diamine

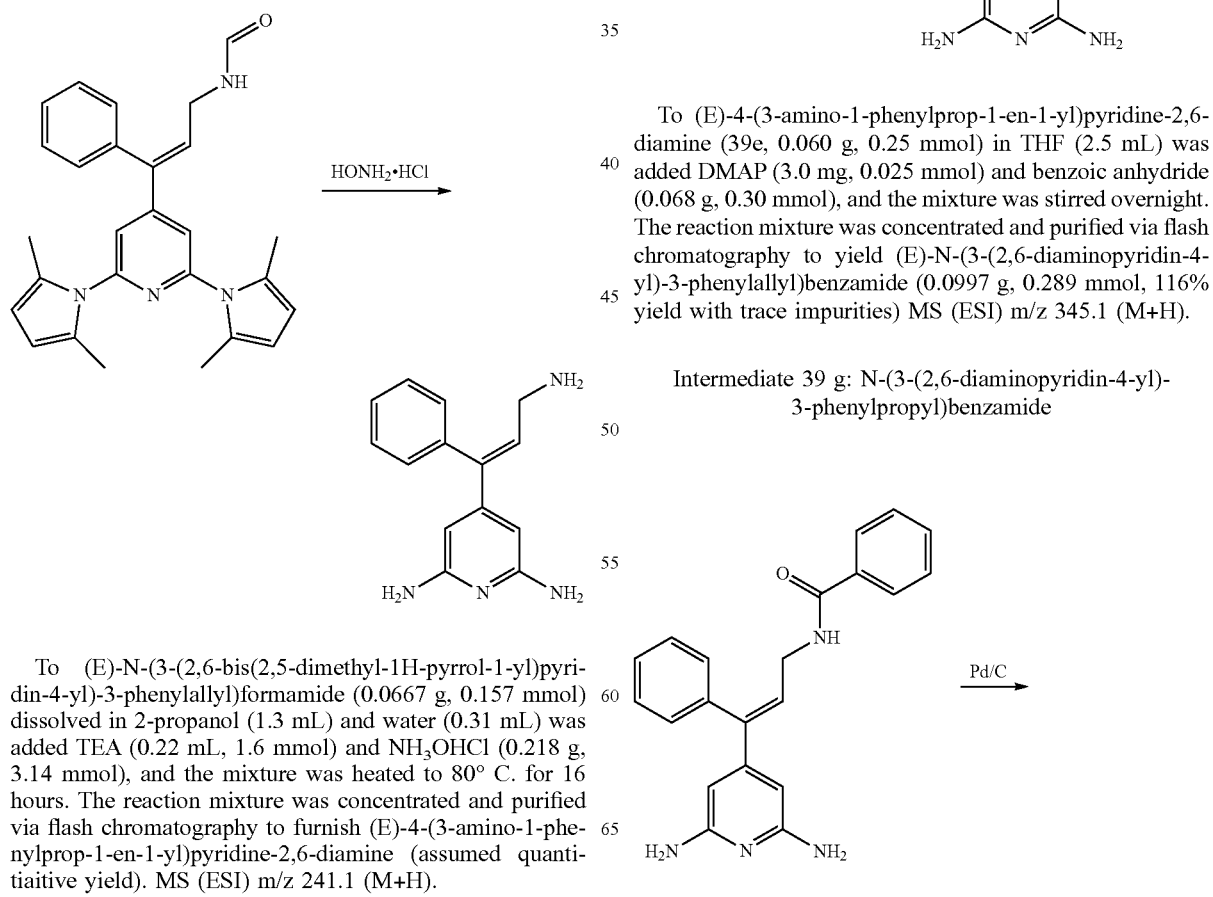

To (E)-N-(3-(2,6-bis(2,5-dimethyl-1H-pyrrol-1-yl)pyridin-4-yl)-3-phenylallyl)formamide (0.0667 g, 0.157 mmol) dissolved in 2-propanol (1.3 mL) and water (0.31 mL) was added TEA (0.22 mL, 1.6 mmol) and $NH_3OHCl$ (0.218 g, 3.14 mmol), and the mixture was heated to 80° C. for 16 hours. The reaction mixture was concentrated and purified via flash chromatography to furnish (E)-4-(3-amino-1-phenylprop-1-en-1-yl)pyridine-2,6-diamine (assumed quantitaitive yield). MS (ESI) m/z 241.1 (M+H).

Intermediate 39f: (E)-N-(3-(2,6-diaminopyridin-4-yl)-3-phenylallyl)benzamide

To (E)-4-(3-amino-1-phenylprop-1-en-1-yl)pyridine-2,6-diamine (39e, 0.060 g, 0.25 mmol) in THF (2.5 mL) was added DMAP (3.0 mg, 0.025 mmol) and benzoic anhydride (0.068 g, 0.30 mmol), and the mixture was stirred overnight. The reaction mixture was concentrated and purified via flash chromatography to yield (E)-N-(3-(2,6-diaminopyridin-4-yl)-3-phenylallyl)benzamide (0.0997 g, 0.289 mmol, 116% yield with trace impurities) MS (ESI) m/z 345.1 (M+H).

Intermediate 39 g: N-(3-(2,6-diaminopyridin-4-yl)-3-phenylpropyl)benzamide

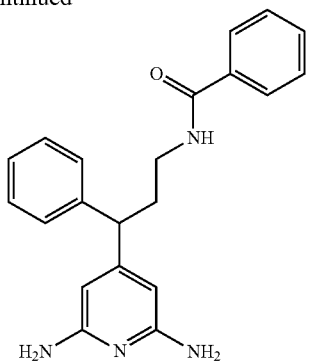

To (E)-N-(3-(2,6-diaminopyridin-4-yl)-3-phenylallyl)benzamide (0.0997 g, 0.289 mmol) dissolved in EtOH (2.9 mL) was added AcOH (0.02 mL, 0.3 mmol) and Pd/C (10 wt %) (0.031 g, 0.029 mmol), and the mixture was placed under 55 psi(g) of hydrogen gas overnight. The reaction mixture was filtered and concentrated to furnish N-(3-(2,6-diaminopyridin-4-yl)-3-phenylpropyl)benzamide which was contaminated with impurities and used directly. MS (ESI) m/z 347.1 (M+H).

Intermediate 39h: (E)-N-(3-(2,6-diamino-3-((4-chlorophenyl)diazenyl)pyridin-4-yl)-3-phenylpropyl)benzamide

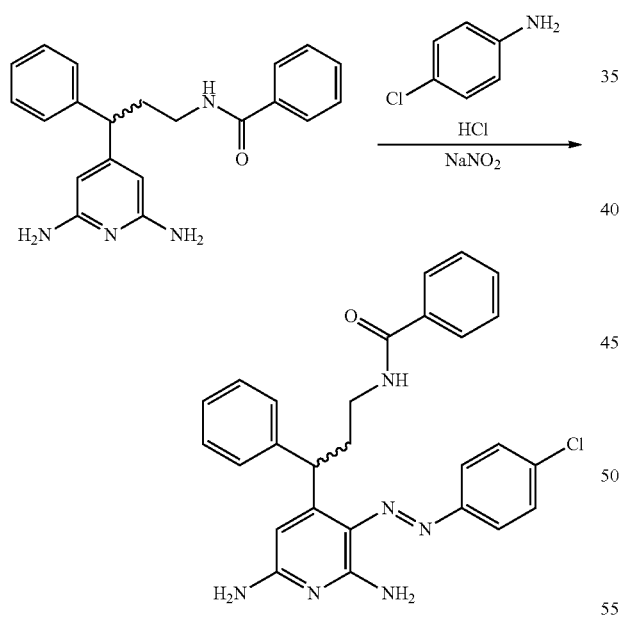

To a solution of 4-chloroaniline (0.028 g, 0.22 mmol) in 6N HCl (0.13 mL, 0.76 mmol) a solution of sodium nitrite (0.014 g, 0.20 mmol) in water (0.02 mL) was added, and the reaction mixture was stirred for 30 min. The above solution was poured into a suspension of N-(3-(2,6-diaminopyridin-4-yl)-3-phenylpropyl)benzamide (approximately 0.2 mmol) in EtOAc (4.8 mL). After 3 hrs, sodium acetate (0.057 g, 0.70 mmol) was added, and the reaction was stirred for 10 min. The reaction mixture was partitioned between water and EtOAc. The aqueous was extracted 3× with EtOAc, and the organics were combined, dried over MgSO$_4$, filtered, concentrated and purified via flash chromatography to furnish crude orange solid (E)-N-(3-(2,6-diamino-3-((4-chlorophenyl)diazenyl)pyridin-4-yl)-3-phenylpropyl)benzamide (0.0543 g, 0.112 mmol, 56.0% yield). MS (ESI) m/z 485.2 (M+H).

Intermediate 39i: N-(3-phenyl-3-(2,3,6-triaminopyridin-4-yl)propyl)benzamide

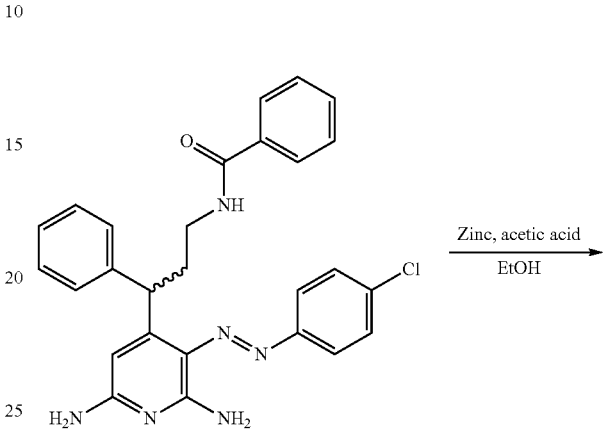

To a solution of (E)-N-(3-(2,6-diamino-3-((4-chlorophenyl)diazenyl)pyridin-4-yl)-3-phenylpropyl)benzamide (0.0543 g, 0.112 mmol) dissolved in EtOH (1.1 mL) was added AcOH (0.04 mL, 0.7 mmol) and zinc powder (0.044 g, 0.67 mmol), and the reaction mixture was heated to 50° C. After 10 min, the reaction slurry was filtered through celite and concentrated. The residue purified by silica gel chromatography to furnish N-(3-phenyl-3-(2,3,6-triaminopyridin-4-yl)propyl)benzamide, contaminated with residual MeOH (0.0530 g, 0.116 mmol, 103% yield). MS (ESI) m/z 362.1 (M+H). $^1$H NMR (400 MHz, THF-d8) δ 7.86-7.77 (m, 2H), 7.73 (br. s., 1H), 7.45-7.33 (m, 3H), 7.30 (d, J=7.1 Hz, 2H), 7.22 (t, J=7.7 Hz, 2H), 7.15-7.03 (m, 1H), 5.78-5.70 (m, 1H), 4.23 (t, J=7.7 Hz, 1H), 3.49-3.38 (m, 1H), 3.33-3.20 (m, 1H), 2.23 (br. q, J=7.0 Hz, 2H).

Example 39: N-(3-(5-amino-3H-[1,2,3]triazolo[4,5-b]pyridin-7-yl)-3-phenylpropyl)benzamide

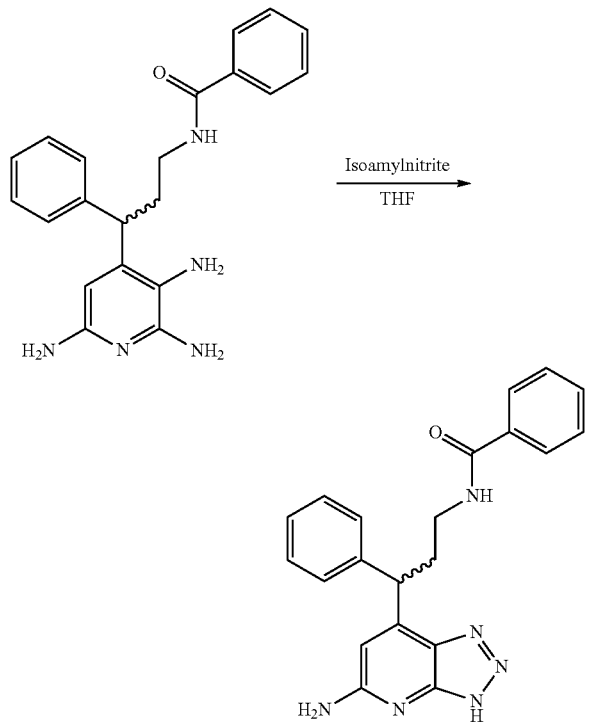

To N-(3-phenyl-3-(2,3,6-triaminopyridin-4-yl)propyl) benzamide (0.040 g, 0.11 mmol) dissolved in THF (2.2 mL) was added isoamyl nitrite (0.02 mL, 0.1 mmol), and the mixture was stirred overnight. The reaction mixture was concentrated and purified via reverse phase method K to furnish N-(3-(5-amino-3H-[1,2,3]triazolo[4,5-b]pyridin-7-yl)-3-phenylpropyl)benzamide. MS (ES) m/z 317.1 (M+H). $^1$H NMR (400 MHz, THF-d8) δ 7.88 (br. s., 1H), 7.85-7.81 (m, 2H), 7.52 (d, J=7.7 Hz, 2H), 7.45-7.33 (m, 3H), 7.27 (t, J=7.7 Hz, 2H), 7.20-7.12 (m, 1H), 6.38 (s, 1H), 4.62 (t, J=7.7 Hz, 1H), 3.47-3.37 (m, 1H), 3.33-3.22 (m, 1H), 2.76-2.48 (m, 2H). LC: 6.27 min, Method A General Route 7 (see Scheme 7):

Intermediate 9-1a: (E)-4-Bromo-3-((4-chlorophenyl)diazenyl)pyridine-2,6-diamine

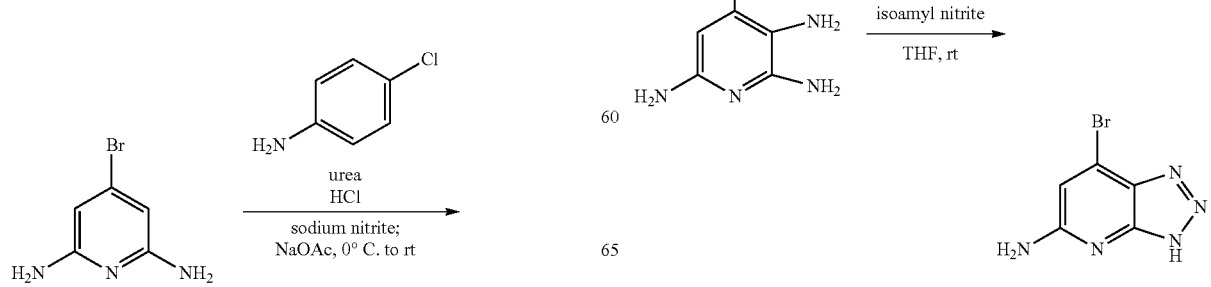

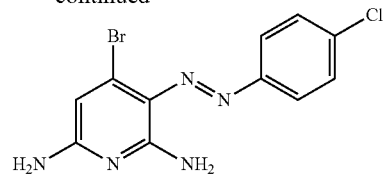

To a solution of 4-chloroaniline (0.678 g, 5.32 mmol) in 6 N HCl (3.4 mL, 20. mmol) at 0° C. was added a solution of sodium nitrite (0.367 g, 5.32 mmol) in water (0.58 mL), and the reaction mixture was stirred for 30 min. The reaction mixture was then treated with urea (0.032 g, 0.53 mmol). The solution was then poured into a solution of 4-bromopyridine-2,6-diamine (1.00 g, 5.32 mmol) in water (14.5 mL). After 30 min, sodium acetate (1.963 g, 23.93 mmol) was added, and the reaction mixture was allowed to stir overnight. The reaction mixture was then filtered, and the filtrate was dried under reduced pressure to furnish the title compound (1.19 g, 3.65 mmol, 68.7% yield). MS(ESI) m/z 328.0 (M+H).

Intermediate 9-1b: 4-Bromopyridine-2,3,6-triamine

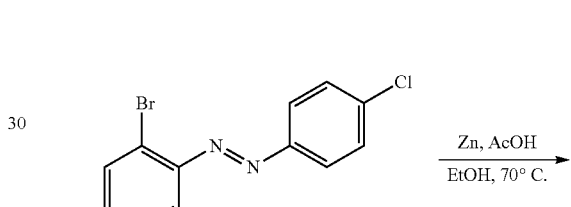

To a solution of (E)-4-bromo-3-((4-chlorophenyl)diazenyl)pyridine-2,6-diamine (1.19 g, 3.65 mmol) in EtOH (12 mL) was added acetic acid (0.63 mL, 11 mmol) and zinc powder (0.717 g, 11.0 mmol), and the reaction mixture was heated to 70° C. After 90 min, the reaction mixture was filtered through CELITE and concentrated. The residue was purified by silica gel chromatography to furnish the title compound (0.568 g, 2.80 mmol, 77.0% yield).

Intermediate 9-1c: 7-Bromo-3H-[1,2,3]triazolo[4,5-b]pyridin-5-amine

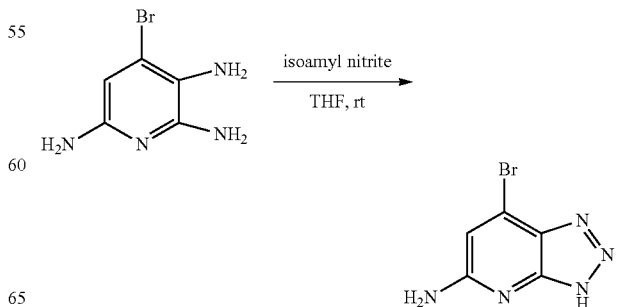

To a solution of 4-bromopyridine-2,3,6-triamine (0.568 g, 2.80 mmol) in THF (28 mL) was added isoamylnitrite (0.38 mL, 2.8 mmol). The reaction mixture was allowed to stir overnight. The solution was then treated with an additional 0.20 mL of isoamylnitrite and the solution was allowed to stir overnight. The solution was then concentrated, and the residue purified by silica gel chromatography to furnish the title compound (0.185 g, 0.864 mmol, 30.9% yield). MS(ESI) m/z 214.0 (M+H).

Intermediate 9-1d: 7-bromo-N,3-ditrityl-3H-[1,2,3] triazolo[4,5-b]pyridin-5-amine

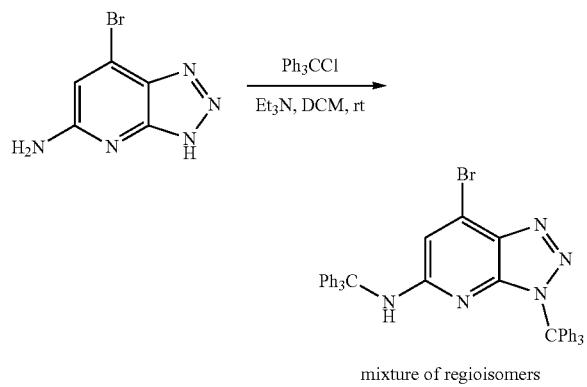

mixture of regioisomers

To a suspension 7-bromo-3H-[1,2,3]triazolo[4,5-b]pyridin-5-amine (1.31, 6.12 mmol), and trityl chloride (3.41 g, 12.2 mmol) slurried in dichloromethane (61 mL) was added triethylamine (2.6 mL, 18 mmol) and the reaction mixture was allowed to stir under argon overnight. The reaction mixture was then concentrated and purified via flash chromatography to furnish the title compound as a mixture of trityl regioisomers (2.69 g, 3.85 mmol, 62.9% yield). MS(ESI) m/z 699.9, 697.9 (M+H).

Intermediate 9-1: 7-benzyl-N,3-ditrityl-3H-[1,2,3] triazolo[4,5-b]pyridin-5-amine

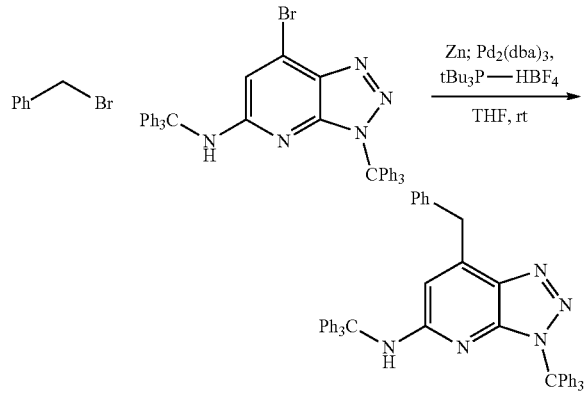

Zinc powder (16.9 g, 258 mmol) in THF (129 mL) was treated with 1,2-dibromoethane (1.7 mL, 19 mmol) and TMS-C$_1$ (2.5 mL, 19 mmol) under argon. After 30 min, the solution was treated with benzylbromide (15 mL, 130 mmol). After 30 min, the solution was canulated into a mixture of 7-bromo-N,3-ditrityl-3H-[1,2,3]triazolo[4,5-b] pyridin-5-amine (30 g, 43 mmol), tri-t-butylphosphonium tetrafluoroborate (0.623 g, 2.15 mmol) and tris(dibenzylideneacetone)dipalladium(0) (0.983 g, 1.073 mmol) dissolved in THF (130 mL), and the reaction mixture was allowed to stir under argon overnight at rt. The solution was concentrated and partitioned between NH$_4$Cl and EtOAc, extracted with EtOAc. The organic layers were concentrated and the residue purified by silica gel chromatography to furnish the title compound (18.1 g, 25.6 mmol, 59.5% yield). MS(ESI) m/z 710.1 (M+H). $^1$H NMR major regioisomer (400 MHz, chloroform-d) δ 7.25-7.20 (m, 10H), 7.19-7.10 (m, 19H), 7.08-7.01 (m, 6H), 6.98-6.92 (m, 2H), 5.71 (s, 1H), 5.60 (s, 1H), 4.06 (s, 2H).

Intermdiate 7-3: (Z)-3-phenyl-3-(3-trityl-5-(tritylamino)-3H-[1,2,3]triazolo[4,5-b]pyridin-7-yl)prop-2-en-1-ol

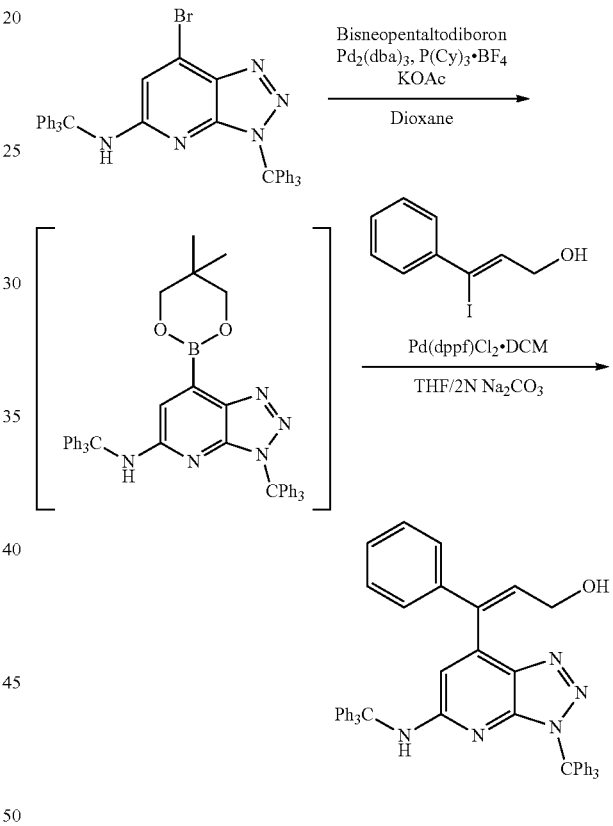

To an Ar sparged mixture of 7-bromo-N,3-ditrityl-3H-[1, 2,3]triazolo[4,5-b]pyridin-5-amine (13 g, 19 mmol), 5,5,5', 5'-tetramethyl-2,2'-bi(1,3,2-dioxaborinane) (4.6 g, 21 mmol), and potassium acetate (2.8 g, 28 mmol) in dioxane (62 mL) were added Pd$_2$(dba)$_3$ (0.86 g, 0.93 mmol) and tricyclohexylphosphonium tetrafluoroborate (0.69 g, 1.9 mmol). The mixture was heated to 100° C. overnight. To the reaction solution was added PdCl$_2$(dppf)-DCM adduct (0.76 g, 0.94 mmol), aqueous 2N Na$_2$CO$_3$ (47 mL), and (Z)-3-iodo-3-phenylprop-2-en-1-ol (5.4 g, 21 mmol) dissolved in THF (50 mL). The reaction mixture was blanketed under Ar and heated to 80° C. overnight. The mixture was concentrated and the residue purified via flash chromatography to furnish (Z)-3-phenyl-3-(3-trityl-5-(tritylamino)-3H-[1,2,3] triazolo[4,5-b]pyridin-7-yl)prop-2-en-1-ol (8.22 g, 10.9 mmol, 59% yield). MS (ESI) m/z 752.3 (M+H).

Intermediate 7-4: (Z)-3-phenyl-3-(3-trityl-5-(tritylamino)-3H-[1,2,3]triazolo[4,5-b]pyridin-7-yl)acrylaldehyde

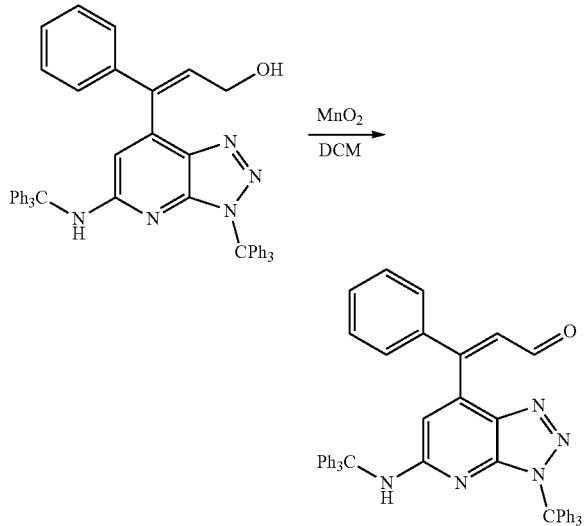

To a solution of (Z)-3-phenyl-3-(3-trityl-5-(tritylamino)-3H-[1,2,3]triazolo[4,5-b]pyridin-7-yl)prop-2-en-1-ol (8.2 g, 11 mmol) dissolved in DCM (110 mL) was added manganese dioxide (16 g, 190 mmol), and the resultant slurry was stirred at rt overnight. Additional manganese dioxide (2.0 g, 23 mmol) was added, and the slurry was stirred an additional 5 days. The slurry was filtered and the resultant solution was concentrated to furnish (Z)-3-phenyl-3-(3-trityl-5-(tritylamino)-3H-[1,2,3]triazolo[4,5-b]pyridin-7-yl)acrylaldehyde (7.88 g, 10.5 mmol, 96% yield). MS (ESI) m/z 750.2 (M+H).

Intermediate 114a: (Z)-7-(1-phenyl-3-((4-phenylbicyclo[2.2.2]octan-1-yl)amino)prop-1-en-1-yl)-N,3-ditrityl-3H-[1,2,3]triazolo[4,5-b]pyridin-5-amine

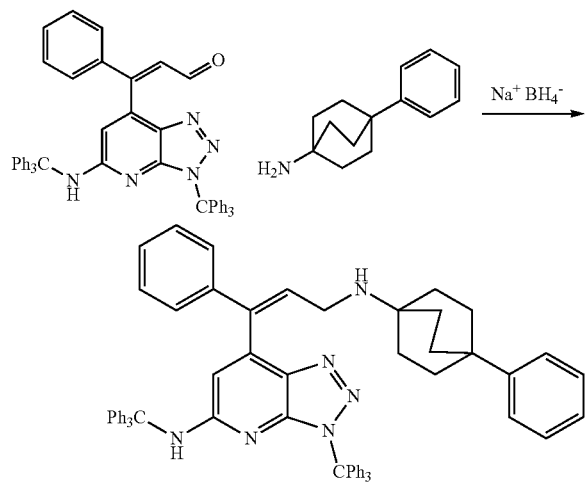

To (Z)-3-phenyl-3-(3-trityl-5-(tritylamino)-3H-[1,2,3]triazolo[4,5-b]pyridin-7-yl)acrylaldehyde (0.25 g, 0.33 mmol) in EtOH (3.3 mL) with TEA (0.42 mL, 3.0 mmol) was added 4-phenylbicyclo[2.2.2]octan-1-amine AcOH salt (0.32 g, 1.0 mmol). The mixture was heated to 60° C. for 2 hours, at which time imine formation was detected via LCMS. The reaction was allowed to cool and THF (3.3 mL) and NaBH$_4$ (0.069 g, 1.8 mmol) were added, and the mixture was stirred overnight. The mixture was partitioned between EtOAc and 1N NaOH, extracted into DCM, dried over MgSO$_4$, filtered and concentrated to furnish (Z)-7-(1-phenyl-3-((4-phenylbicyclo[2.2.2]octan-1-yl)amino)prop-1-en-1-yl)-N,3-ditrityl-3H-[1,2,3]triazolo[4,5-b]pyridin-5-amine. The crude material was used for subsequent transformations assuming a quantitative yield. MS (ESI) m/z 935.4 (M+H).

Example 114: 7-(1-phenyl-3-((4-phenylbicyclo[2.2.2]octan-1-yl)amino)propyl)-3H-[1,2,3]triazolo[4,5-b]pyridin-5-amine

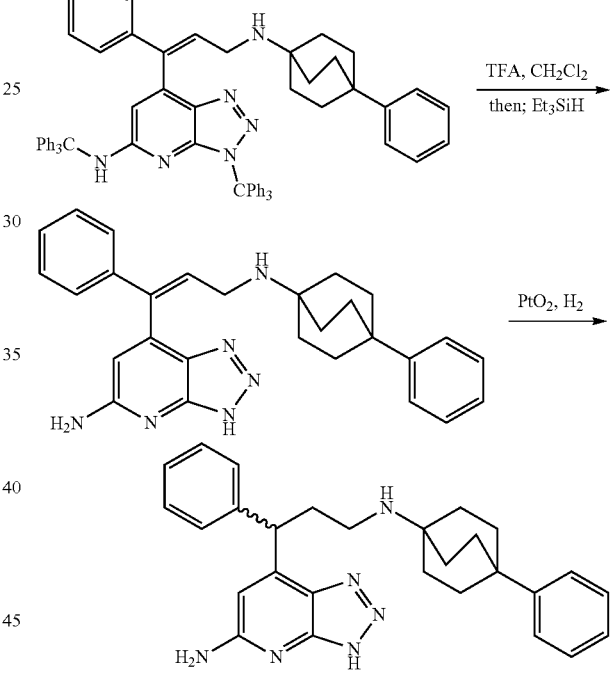

To a solution of (Z)-7-(1-phenyl-3-((4-phenylbicyclo[2.2.2]octan-1-yl)amino)prop-1-en-1-yl)-N,3-ditrityl-3H-[1,2,3]triazolo[4,5-b]pyridin-5-amine (0.31 g, 0.33 mmol) and triethylsilane (0.21 mL, 1.3 mmol) dissolved in DCM (12 mL) was added TFA (2.9 mL). After 60 minutes the reaction mixture was concentrated in vacuo. The sample was triturated with ether/hexanes, and the solids were filtered to furnish (Z)-7-(1-phenyl-3-((4-phenylbicyclo[2.2.2]octan-1-yl)amino)prop-1-en-1-yl)-3H-[1,2,3]triazolo[4,5-b]pyridin-5-amine, TFA salt, which was used for subsequent transformations assuming a quantitative yield. MS (ESI) m/z 451.3 (M+H).

To (Z)-7-(1-phenyl-3-((4-phenylbicyclo[2.2.2]octan-1-yl)amino)prop-1-en-1-yl)-3H-[1,2,3]triazolo[4,5-b]pyridin-5-amine, TFA salt (0.19 g, 0.33 mmol) dissolved in a mixture of EtOH (30 mL) and EtOAc (3 mL) was added platinum oxide (8 mg, 0.03 mmol). The solution was degassed and pressurized with 15 psi(g) hydrogen for two nights. The reaction mixture was filtered, concentrated and purified on a Sunfire 5µ30×100 mm column 10-80% ACN in TFA buffered water. The product was concentrated to furnish racemic 7-(1-phenyl-3-((4-phenylbicyclo[2.2.2]octan-1-yl)amino)propyl)-3H-[1,2,3]triazolo[4,5-b]pyridin-5-amine (0.076 g, 0.11 mmol, 33% yield). ¹H NMR (400 MHz, CD₃OD) δ 7.56-7.47 (m, 2H), 7.39 (t, J=7.5 Hz, 2H), 7.34-7.22 (m, 5H), 7.19-7.10 (m, 1H), 6.73 (s, 1H), 4.64 (dd, J=9.0, 6.4 Hz, 1H), 3.13-2.99 (m, 1H), 2.90 (td, J=11.3, 4.6 Hz, 1H), 2.85-2.72 (m, 1H), 2.70-2.56 (m, 1H), 2.07-1.95 (m, 6H), 1.93-1.78 (m, 6H). MS (ESI) m/z 453.3 (M+H). LC: 1.34 min, Method C Examples 40-113, and 115-154 were prepared according the procedures described for Example 38 and 114 described in General Route 7 by using the appropriate amines. The amines were either known, commercially available, or prepared according to the procedures below unless otherwise indicated. Amine intermediates for Examples 57, 58, 60, 65, 73, 121, 123 and 124 were prepared according to the procedures in Ellman et al., *J Org. Chem.* 2007, 72, 626. Amine intermediates for examples 142-144 were prepared according to the procedures in Ellman et al., *J. Am. Chem. Soc.* 1999, 121, 268. Any vestigial aryl bromides or olefins present in the amine fragment prior to reductive amination were subsequently reduced during the final hydrogenation step.

Intermediate 63a: (2-benzylphenyl)methanamine

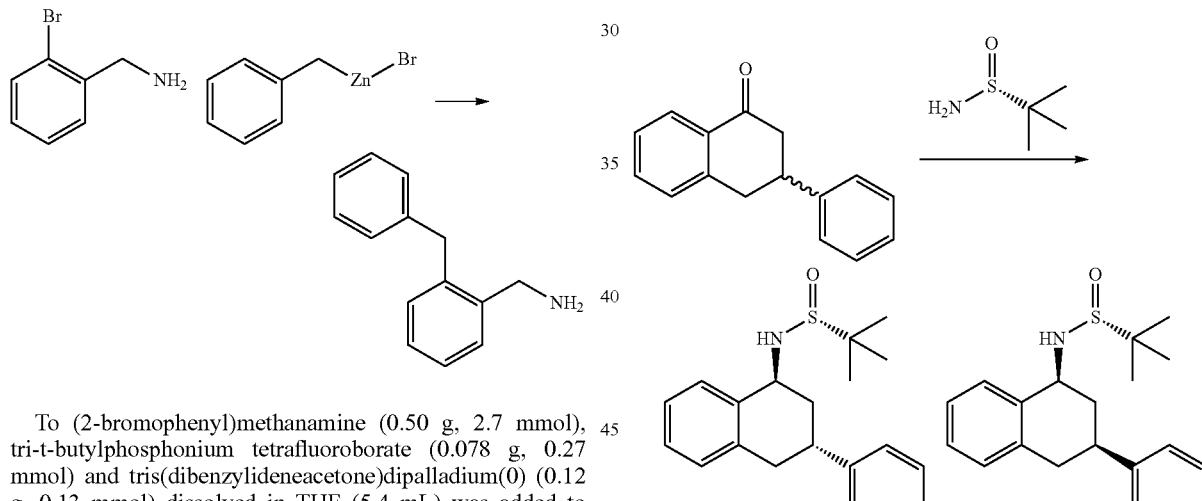

To (2-bromophenyl)methanamine (0.50 g, 2.7 mmol), tri-t-butylphosphonium tetrafluoroborate (0.078 g, 0.27 mmol) and tris(dibenzylideneacetone)dipalladium(0) (0.12 g, 0.13 mmol) dissolved in THF (5.4 mL) was added to benzylzinc(II) bromide (8.0 mL, 8.0 mmol), and the mixture was stirred at room temperature overnight. The reaction was quenched with sat NH₄Cl, extracted with EtOAc, and dried over Na₂SO₄. The organics were filtered, concentrated, and purified via flash chromatography to furnish (2-benzylphenyl)methanamine (0.80, 2.0 mmol, 75% yield. MS (ESI) m/z 198.1 (M+H).

Intermediate 78a: (2-(naphthalen-2-ylmethyl)phenyl)methanamine

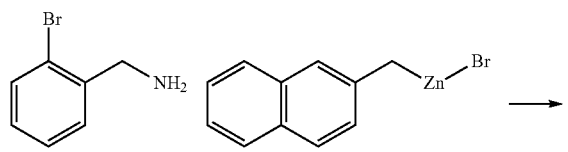

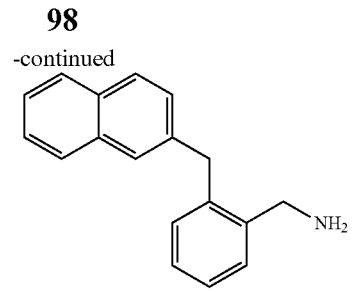

To a solution of (2-bromophenyl)methanamine (0.50 g, 2.7 mmol), tri-t-butylphosphonium tetrafluoroborate (0.078 g, 0.27 mmol) and tris(dibenzylideneacetone)dipalladium(0) (0.12 g, 0.13 mmol) dissolved in THF (5.4 mL) was added (naphthalen-2-ylmethyl)zinc(II) bromide (8.1 mL, 8.1 mmol) and allowed to react at room temperature overnight. The reaction was diluted with sat. NH₄Cl and extracted with ether 2×. The organic layer was dried over MgSO₄, filtered, concentrated and purified via flash chromatography to furnish (2-(naphthalen-2-ylmethyl)phenyl)methanamine (0.20 g, 0.79 mmol, 29% yield). ¹H NMR (400 MHz, CDCl₃) δ 7.79-7.68 (m, 3H), 7.55-7.48 (m, 2H), 7.44-7.37 (m, 2H), 7.26-7.21 (m, 3H), 7.19-7.12 (m, 1H), 4.25 (s, 2H), 4.12 (s, 2H). MS (ESI) m/z 248.1 (M+H).

Intermediates: 82a: (R)-2-methyl-N-((1S,3R)-3-phenyl-1,2,3,4-tetrahydronaphthalen-1-yl)propane-2-sulfinamide

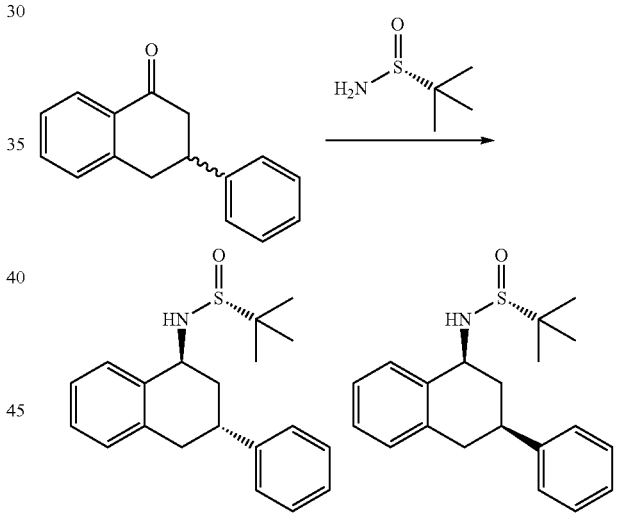

To a solution of 3-phenyl-3,4-dihydronaphthalen-1(2H)-one (1.0 g, 4.5 mmol) and (R)-2-methylpropane-2-sulfinamide (0.71 g, 5.9 mmol) dissolved in THF (2.2 mL) was added tetraethoxytitanium (1.9 mL, 9.0 mmol), and the reaction was heated to 75° C. overnight. The correct mass was detected (MS (ESI) m/z 326.1 (M+H)) and the crude material was carried forward. To a prepared solution of (R)-2-methyl-N-(3-phenyl-3,4-dihydronaphthalen-1(21H)-ylidene)propane-2-sulfinamide (1.5 g, 4.5 mmol) was added THF (4.5 mL) and the mixture was cooled to −50° C. To this solution was added L-Selectride (13.5 mL, 13.5 mmol) slowly. The solution was allowed to warm slowly to ambient temperature, and subsequently was cooled to 0° C., and MeOH was slowly added to quench the excess hydride. The reaction mixture was poured into saturated brine and stirred vigorously. The resultant slurry was filtered over a bed of celite, and the filter cake was washed with EtOAc. The mother liquor was diluted with EtOAc, and the aqueous layer separated. The organic layer was dried over MgSO₄, filtered, concentrated and purified via flash chromatography to furnish a mixture of diastereomers that were separated via SFC Regis Whelk-01(R,R), 250×30 mm ID 5 μm. 85 mL/min, 150 bar BP, 40° C., 18% MeOH-DEA/82% CO₂.
Peak 1: (R)-2-methyl-N-((1S,3R)-3-phenyl-1,2,3,4-tetrahydronaphthalen-1-yl)propane-2-sulfinamide (0.24 g, 0.72 mmol, 16% yield): ¹H NMR (400 MHz, CDCl₃) δ 7.61-7.49 (m, 1H), 7.38-7.17 (m, 7H), 7.15-7.09 (m, 1H), 4.68 (td, J=10.6, 5.7 Hz, 1H), 3.36 (d, J=10.6 Hz, 1H), 3.22-2.90 (m, 3H), 2.83 (ddt, J=12.8, 5.9, 2.1 Hz, 1H), 2.00 (td, J=12.4, 11.0 Hz, 1H), 1.30 (s, 9H).
Peak 2: (R)-2-methyl-N-((1S,3S)-3-phenyl-1,2,3,4-tetrahydronaphthalen-1-yl)propane-2-sulfinamide (0.22 g, 0.67 mmol, 15% yield): ¹H NMR (400 MHz, CDCl₃) δ 7.42-7.36 (m, 1H), 7.35-7.29 (m, 4H), 7.25-7.13 (m, 4H), 4.64-4.55 (m, 1H), 3.57 (d, J=9.0 Hz, 1H), 3.25 (tdd, J=11.5, 4.9, 2.6 Hz, 1H), 3.17-3.07 (m, 1H), 3.01-2.88 (m, 1H), 2.60-2.51 (m, 1H), 2.26 (ddd, J=13.6, 12.1, 4.6 Hz, 1H), 1.24 (s, 9H).
Intermediates 83a ((R)-2-methyl-N-((1R,3R)-3-phenyl-1,2,3,4-tetrahydronaphthalen-1-yl)propane-2-sulfinamide) and 84a ((R)-2-methyl-N-((1R,3S)-3-phenyl-1,2,3,4-tetrahydronaphthalen-1-yl)propane-2-sulfinamide)

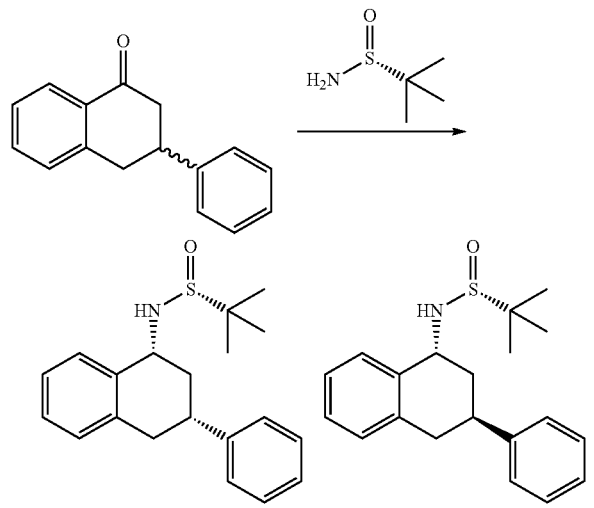

To a solution of 3-phenyl-3,4-dihydronaphthalen-1(2H)-one (1.0 g, 4.5 mmol) and (R)-2-methylpropane-2-sulfinamide (0.71 g, 5.9 mmol) dissolved in THF (2.2 mL) was added tetraethoxytitanium (1.9 mL, 9.0 mmol). The reaction mixture was heated to 75° C. overnight. The correct mass ion was detects (MS (ESI) m/z 326.1 (M+H)) so the crude material was used. To this solution was added THF (4.5 mL), and the reaction mixture was cooled to −50° C., followed by slow addition of a prepared suspension of NaBH₄ (0.68 g, 18 mmol). The solution was allowed to warm slowly to ambient temperature, and subsequently was cooled to 0° C. followed by slow addition of MeOH to quench the excess hydride. The reaction mixture was poured into saturated brine and stirred vigorously. The resultant slurry was filtered over a bed of celite, and the filter cake was washed with EtOAc. The mother liquor was diluted with EtOAc, the aqueous layer separated. The organic layer was dried over MgSO₄, filtered, concentrated and purified via flash chromatography to furnish a mixture of diastereomers that were separated via SFC Regis Whelk-01(R,R), 250×30 mm ID 5 μm. 85 mL/min, 150 bar BP, 40° C., 18% MeOH-DEA/82% CO₂.
Peak 1 (R)-2-methyl-N-((1R,3R)-3-phenyl-1,2,3,4-tetrahydronaphthalen-1-yl)propane-2-sulfinamide (0.22 g, 0.67 mmol, 15% yield): ¹H NMR (400 MHz, CDCl₃) δ 7.47-7.40 (m, 1H), 7.38-7.32 (m, 2H), 7.29-7.21 (m, 5H), 7.18-7.12 (m, 1H), 4.80-4.70 (m, 1H), 3.37-3.24 (m, 1H), 3.20 (s, 1H), 3.13-3.02 (m, 1H), 2.97-2.85 (m, 1H), 2.37-2.26 (m, 1H), 2.13-1.99 (m, 1H).
Peak 2 (R)-2-methyl-N-((1R,3S)-3-phenyl-1,2,3,4-tetrahydronaphthalen-1-yl)propane-2-sulfinamide (0.22 g, 0.67 mmol, 15% yield): ¹H NMR (400 MHz, CDCl₃) δ 7.80 (d, J=7.7 Hz, 1H), 7.38-7.31 (m, 2H), 7.31-7.18 (m, 5H), 7.11 (d, J=7.5 Hz, 1H), 4.86-4.68 (m, 1H), 3.58 (d, J=7.0 Hz, 1H), 3.18-2.95 (m, 3H), 2.43 (dd, J=12.7, 5.8 Hz, 1H), 2.11-1.91 (m, 1H), 1.31-1.15 (m, 1H).

Intermediate 82b: (1S,3R)-3-phenyl-1,2,3,4-tetrahydronaphalen-1-amine, HCl salt

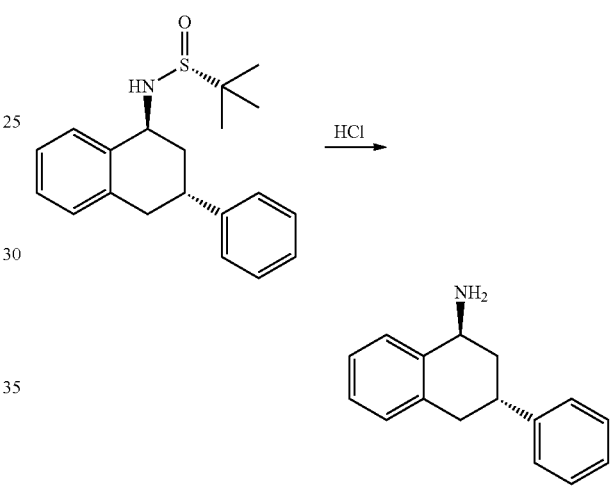

To (R)-2-methyl-N-((1S,3R)-3-phenyl-1,2,3,4-tetrahydronaphthalen-1-yl)propane-2-sulfinamide (0.24 g, 0.72 mmol) dissolved in MeOH (2.9 mL) was added 4N HCl in dioxane (0.36 mL, 1.4 mmol), and the mixture was stirred overnight. The reaction was concentrated to furnish (1S, 3R)-3-phenyl-1,2,3,4-tetrahydronaphalen-1-amine, HCl salt. (0.16 g, 0.72 mmol, 100%). ¹H NMR (400 MHz, CDCl₃) δ 7.83-7.68 (m, 1H), 7.36-7.30 (m, 2H), 7.28-7.21 (m, 5H), 7.17-7.12 (m, 1H), 4.72 (dd, J=11.1, 6.3 Hz, 1H), 3.02 (d, J=3.3 Hz, 2H), 2.71 (dd, J=12.5, 6.2 Hz, 1H), 2.30-2.05 (m, 2H). MS (ESI) m/z 224.0 (M+H).

Intermediate 83b: (1R,3R)-3-phenyl-1,2,3,4-tetrahydronaphalen-1-amine, HCl salt

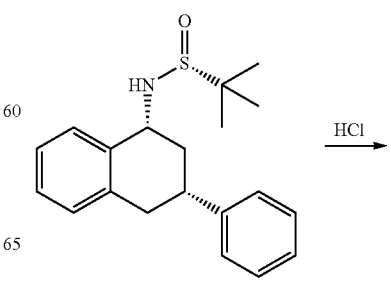

101

-continued

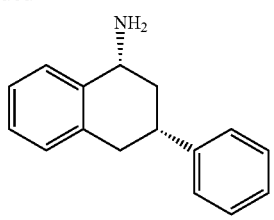

Prepared analogously to Intermediate 82b ¹H NMR (400 MHz, CDCl₃) δ 7.64-7.54 (m, 1H), 7.37-7.29 (m, 6H), 7.28-7.22 (m, 1H), 7.21-7.16 (m, 1H), 4.60 (d, J=2.2 Hz, 1H), 3.44-3.32 (m, 2H), 3.22-3.09 (m, 1H), 3.00-2.86 (m, 1H), 2.56-2.32 (m, 5H), 2.26 (td, J=13.8, 5.1 Hz, 2H). MS (ESI) m/z 224.0 (M+H).

Intermediate 84b: (1R,3S)-3-phenyl-1,2,3,4-tetrahydronaphalen-1-amine HCl salt

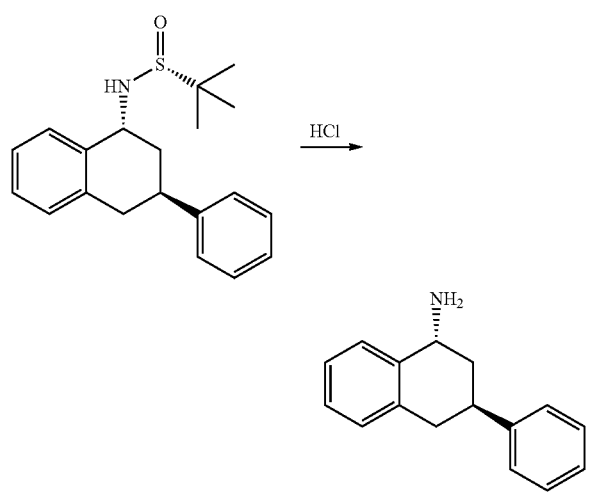

Prepared analogously to Intermediate 82b. ¹H NMR (400 MHz, CDCl₃) δ 7.67 (d, J=7.3 Hz, 1H), 7.39-7.31 (m, 3H), 7.29-7.23 (m, 2H), 7.17 (d, J=7.0 Hz, 1H), 4.71 (dd, J=10.6, 5.5 Hz, 1H), 3.14-2.95 (m, 3H), 2.67 (dd, J=12.0, 5.8 Hz, 1H), 2.09 (q, J=11.7 Hz, 1H), 1.38 (t, J=7.3 Hz, 1H). MS (ESI) m/z 224.0 (M+H).

Intermediate 91a

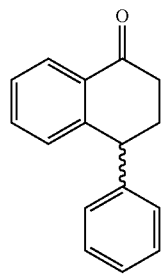

102

-continued

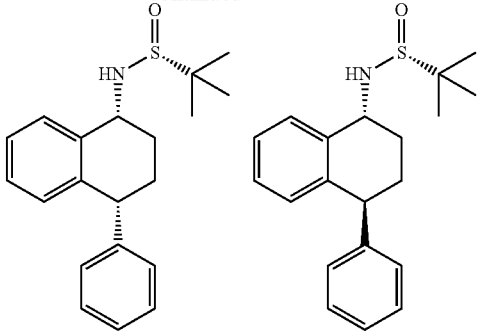

To a solution of 4-phenyl-3,4-dihydronaphthalen-1(2H)-one (0.50 g, 2.2 mmol) and (R)-2-methylpropane-2-sulfinamide (0.35 g, 2.9 mmol) dissolved in THF (1.1 mL) was added tetraethoxytitanium (0.93 mL, 4.5 mmol), and the reaction was heated to 75° C. overnight (MS (ESI) m/z 325.9 (M+H)). To the above solution of (R)-2-methyl-N-(4-phenyl-3,4-dihydronaphthalen-1(2H)-ylidene)propane-2-sulfinamide (0.73 g, 2.2 mmol) was added THF (2.2 mL), and the reaction mixture was cooled to −50° C. A prepared suspension of NaBH₄ (0.34 g, 9.0 mmol) was added slowly to the solution. The solution was allowed to warm slowly to rt and subsequently was cooled to 0° C., followed by slow addition of MeOH to quench the excess hydride. The reaction mixture was poured into saturated brine and stirred vigorously. The resultant slurry was filtered over a bed of celite, and the filter cake was washed with EtOAc. The mother liquor was diluted with EtOAc, and the aqueous layer separated. The organic layer was dried over MgSO₄, filtered, concentrated and purified via flash chromatography to furnish a mixture of diastereomers. The mixture was further purified via SFC Chiralpak AD, 250×30 mm ID 5 μm. 85 mL/min, 150 bar BP, 40° C., 20% MeOH-DEA/80% CO₂.

Peak 1: ¹H NMR (400 MHz, CDCl₃) δ 7.45 (d, J=7.7 Hz, 1H), 7.35-7.28 (m, 2H), 7.27-7.18 (m, 2H), 7.17-7.07 (m, 3H), 6.85 (d, J=7.7 Hz, 1H), 4.66 (q, J=3.4 Hz, 1H), 4.01 (dd, J=9.8, 6.1 Hz, 1H), 3.28 (d, J=2.0 Hz, 1H), 2.23-1.88 (m, 4H), 1.29-1.18 (m, 9H)

Peak 2 (91a): ¹H NMR (400 MHz, CDCl₃) δ 7.58 (d, J=7.5 Hz, 1H), 7.33-7.23 (m, 3H), 7.22-7.11 (m, 2H), 7.03-6.97 (m, 2H), 6.92 (d, J=7.7 Hz, 1H), 4.67 (q, J=4.7 Hz, 1H), 4.20 (t, J=5.4 Hz, 1H), 3.31 (d, J=4.0 Hz, 1H), 2.43-2.29 (m, 1H), 2.11-1.97 (m, 1H), 1.90-1.77 (m, 2H), 1.28-1.19 (m, 9H)

Intermediates 86a and 94a

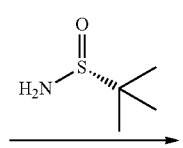 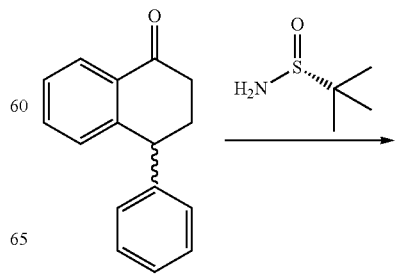

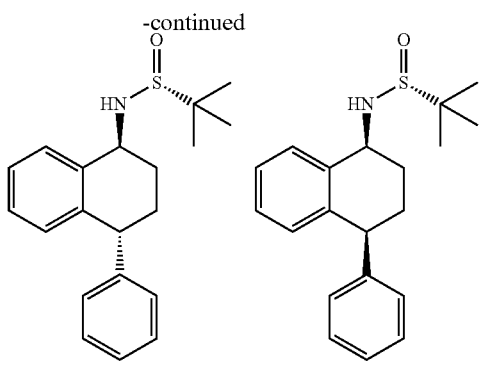

To a solution of 4-phenyl-3,4-dihydronaphthalen-1(2H)-one (0.50 g, 2.2 mmol) and (R)-2-methylpropane-2-sulfinamide (0.35 g, 2.9 mmol) dissolved in THF (1.1 mL) was added tetraethoxytitanium (0.93 mL, 4.5 mmol), and the reaction was heated to 75° C. overnight. The desired mass ion was observed (MS (ESI) m/z 325.9 (M+H)). To the above solution of (R)-2-methyl-N-(4-phenyl-3,4-dihydronaphthalen-1(2H)-ylidene)propane-2-sulfinamide (0.73 g, 2.2 mmol) was added THF (2.2 mL), and the reaction mixture was cooled to −50° C. To this solution was added L-Selectride (6.8 mL, 6.8 mmol) slowly. The solution was allowed to warm slowly to rt and subsequently was cooled to 0° C. MeOH was added to quench the excess hydride. The mixture was poured into saturated brine and stirred vigorously. The resultant slurry was filtered over a bed of celite, and the filter cake was washed with EtOAc. The mother liquor was diluted with EtOAc, and the aqueous layer was separated. The organic layer was dried over MgSO₄, filtered, concentrated and purified via flash chromatography to furnish a mixture of diastereomers. The mixture was further purified via SFC Chiralpak AD, 250×30 mm ID 5 µm. 85 mL/min, 150 bar BP, 40° C., 20% MeOH-DEA/80% CO₂. Peak 1 (86a): ¹H NMR (400 MHz, CDCl₃) δ 7.47 (d, J=7.5 Hz, 1H), 7.33-7.24 (m, 2H), 7.24-7.18 (m, 2H), 7.14 (td, J=7.4, 1.2 Hz, 1H), 7.10-7.03 (m, 2H), 6.89 (d, J=7.7 Hz, 1H), 4.64-4.45 (m, 1H), 4.08 (t, J=6.6 Hz, 1H), 3.46 (d, J=9.2 Hz, 1H), 2.31-1.92 (m, 4H), 1.37-1.22 (m, 9H)
Peak 2 (94a): ¹H NMR (400 MHz, CDCl₃) δ 7.51 (d, J=7.7 Hz, 1H), 7.33-7.24 (m, 2H), 7.24-7.17 (m, 2H), 7.12 (td, J=7.5, 1.0 Hz, 1H), 7.08-7.02 (m, 2H), 6.85 (d, J=7.7 Hz, 1H), 4.71-4.52 (m, 1H), 4.13 (t, J=6.8 Hz, 1H), 3.41 (d, J=10.1 Hz, 1H), 2.49 (ddd, J=11.0, 7.6, 5.4 Hz, 1H), 2.27 (ddd, J=11.3, 7.7, 5.8 Hz, 1H), 1.99-1.85 (m, 2H), 1.30 (s, 9H)

Intermediate 94b: (1S,4S)-4-phenyl-1,2,3,4-tetrahydronaphthalen-1-amine, HCl

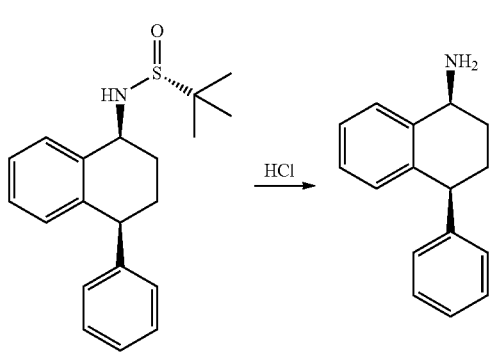 [SMILES: CC(C)(C)[S@@](=O)N[C@H]1CC[C@@H](c2ccccc2)c2ccccc21 ; Cl ; N[C@H]1CC[C@@H](c2ccccc2)c2ccccc21]

Prepared analogously to Intermediate 82b ¹H NMR (400 MHz, CDCl₃) δ 8.98 (br. s., 3H), 7.62 (d, J=7.5 Hz, 1H), 7.25-7.14 (m, 5H), 7.12-7.05 (m, 1H), 7.00 (t, J=7.4 Hz, 1H), 6.79 (d, J=7.7 Hz, 1H), 4.55 (br. s., 1H), 4.05-3.89 (m, 1H), 2.42-2.26 (m, 1H), 2.25-2.10 (m, 2H), 2.08-1.93 (m, 1H). MS (ESI) m/z 224.0 (M+H)

Intermediates 91a, and 86a were deprotected by similar procedure used for Intermediate 82b.

Intermediate 115a: (4-hydroxy-4-phenylcyclohexane-1,1-diyl)bis(methylene) bis(4-methylbenzenesulfonate)

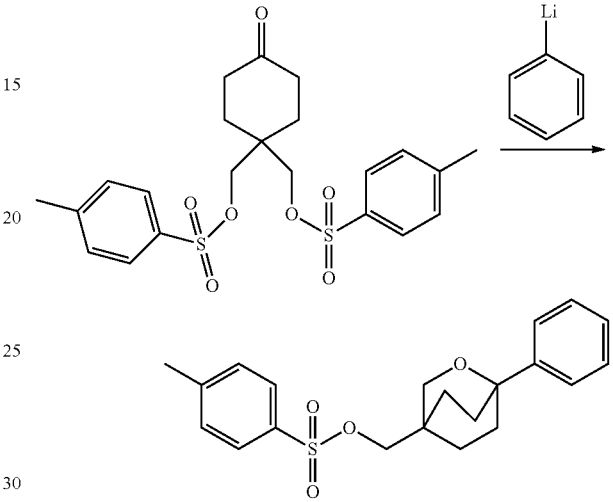

To a solution of (4-oxocyclohexane-1,1-diyl)bis(methylene) bis(4-methylbenzenesulfonate-(US2014/275173 A1) (0.91 g, 2.0 mmol) dissolved in THF (11 mL) at 0° C. was added phenyllithium (1.3 mL, 2.3 mmol). The mixture was stirred 2 hours, at which time crushed NaOH (0.32 g, 7.8 mmol) was added, and the mixture was refluxed over 2 days. The reaction was extracted into DCM, and the organic phase was dried over MgSO₄, filtered, concentrated and purified via flash chromatography to furnish (4-hydroxy-4-phenylcyclohexane-1,1-diyl)bis(methylene) bis(4-methylbenzenesulfonate) (0.51 g, 0.94 mmol, 48% yield). ¹H NMR (400 MHz, CDCl₃) δ 7.83-7.71 (m, 4H), 7.42-7.30 (m, 5H), 4.02 (s, 2H), 3.80 (s, 2H), 2.48 (s, 3H), 1.77-1.50 (m, 8H). MS (ESI) m/z 562.4 (M+18)

Intermediate 115b: (1-phenyl-2-oxabicyclo[2.2.2]octan-4-yl)methanol

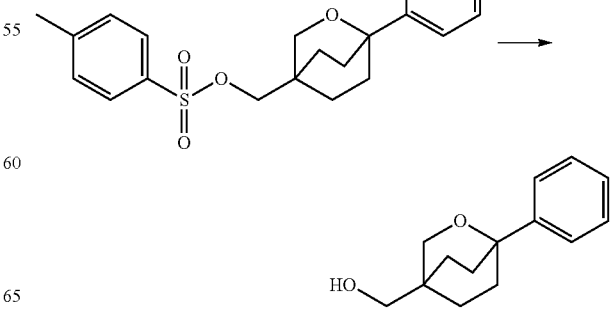

To (1-phenyl-2-oxabicyclo[2.2.2]octan-4-yl)methyl 4-methylbenzenesulfonate (0.13 g, 0.35 mmol) suspended in MeOH (7 mL) was added magnesium turnings (0.085 g, 3.5 mmol), and the mixture was stirred overnight. The reaction was quenched with sat. NH$_4$Cl and extracted with ether. The organic layer was dried over MgSO$_4$, filtered and concentrated to furnish (1-phenyl-2-oxabicyclo[2.2.2]octan-4-yl)methanol (0.076 g, 0.35 mmol, 100% yield). $^1$H NMR (400 MHz, CDCl$_3$) δ 7.44-7.38 (m, 2H), 7.34-7.28 (m, 2H), 7.24-7.18 (m, 1H), 3.95 (t, J=1.4 Hz, 2H), 3.41 (s, 2H), 2.15-1.99 (m, 4H), 1.87-1.72 (m, 2H), 1.71-1.59 (m, 2H). MS (ESI) m/z 219.1 (M+H).

Intermediate 115c: 1-phenyl-2-oxabicyclo[2.2.2]octane-4-carboxylic acid

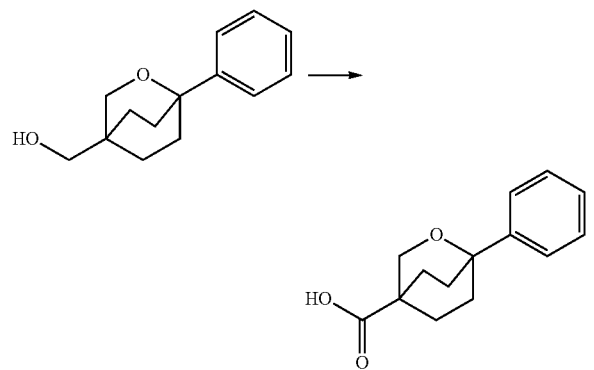

To (1-phenyl-2-oxabicyclo[2.2.2]octan-4-yl)methanol (0.040 g, 0.18 mmol) dissolved in DMF (0.61 mL) was added PDC (0.24 g, 0.64 mmol), and the mixture was stirred for 7 hrs. The reaction mixture was diluted with 10× volume water and extracted into ether 2×. Ether was dried over MgSO$_4$, filtered and concentrated to furnish 1-phenyl-2-oxabicyclo[2.2.2]octane-4-carboxylic acid (0.033 g, 0.14 mmol, 78% yield). $^1$H NMR (400 MHz, CDCl$_3$) δ 7.43-7.37 (m, 2H), 7.36-7.29 (m, 2H), 7.25-7.20 (m, 1H), 4.20 (s, 2H), 2.21-2.01 (m, 8H). MS (ESI) m/z 233.2 (M+H).

Intermediate 115d: tert-butyl (1-phenyl-2-oxabicyclo[2.2.2]octan-4-yl)carbamate

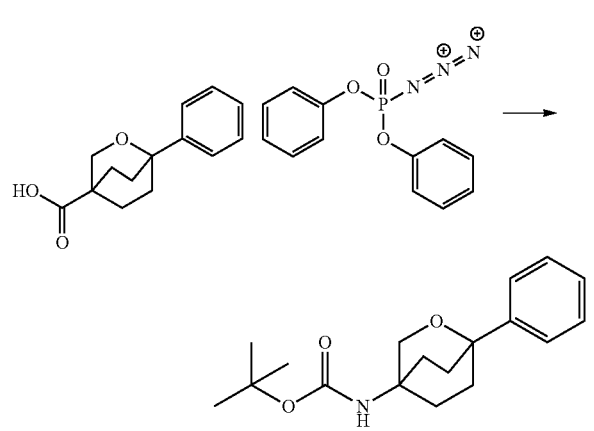

To a solution of 1-phenyl-2-oxabicyclo[2.2.2]octane-4-carboxylic acid (0.12 g, 0.50 mmol) dissolved in t-butanol (1.7 mL) was added Et$_3$N (0.14 mL, 0.99 mmol). The solution was heated to 80° C., and diphenyl phosphorazidate (0.16 mL, 0.74 mmol) was added dropwise. The mixture was stirred overnight. The solvent was concentrated, and the residue partitioned between 1.5 M pH 7.4 phosphate buffer and EtOAc. The aqueous was washed 3× with EtOAc. The combined organic layers were dried over MgSO$_4$, filtered, concentrated, and purified via flash chromatography to furnish tert-butyl (1-phenyl-2-oxabicyclo[2.2.2]octan-4-yl)carbamate (0.12 g, 0.41 mmol, 82% yield). MS (ESI) m/z 204.0 (M-BOC+H).

Intermediate 115e: 1-phenyl-2-oxabicyclo[2.2.2]octan-4-amine, TFA salt

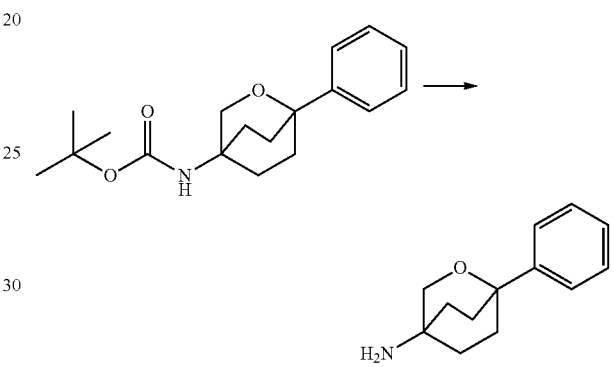

To a solution of tert-butyl (1-phenyl-2-oxabicyclo[2.2.2]octan-4-yl)carbamate (0.12 g, 0.41 mmol) dissolved in DCM (3.2 mL) was added TFA (0.81 mL), and the mixture was stirred for 2 hours. The solvent was concentrated, and an azeotrope with toluene removed residual solvents to furnish 1-phenyl-2-oxabicyclo[2.2.2]octan-4-amine, TFA salt (0.13 g, 0.41 mmol, 100%), suitable for direct use. MS (ESI) m/z 204.0 (M+H).

Intermediate 117a: 4-((tert-butoxycarbonyl)amino)cyclohex-1-en-1-yl trifluoromethanesulfonate

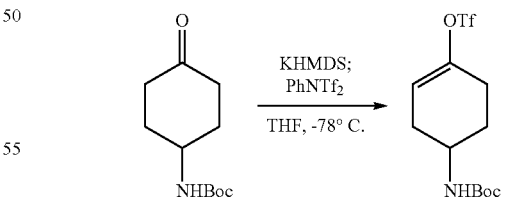

To a solution of tert-butyl (4-oxocyclohexyl)carbamate (0.300 g, 1.41 mmol) in THF (14 mL) was added KHMDS (3.1 mL, 3.1 mmol) at −78° C. The solution was stirred for 30 min, then treated with N-phenylbistriflimide (0.653 g, 1.83 mmol) and warmed to rt. The reaction mixture was then extracted from brine with EtOAc, filtered through a silica gel plug and used as is as 4-((tert-butoxycarbonyl)amino)cyclohex-1-en-1-yl trifluoromethanesulfonate (0.486 g, 1.41 mmol).

Intermediate 117b: tert-butyl (4'-carbamoyl-2,3,4,5-tetrahydro-[1,1'-biphenyl]-4-yl)carbamate

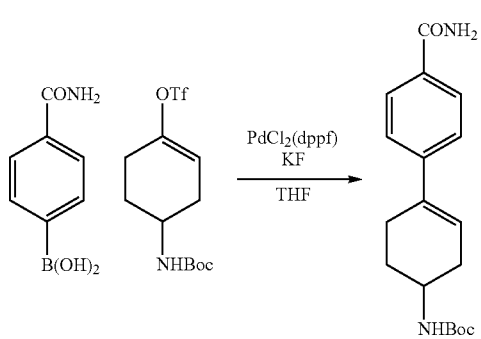

To a solution of 4-((tert-butoxycarbonyl)amino)cyclohex-1-en-1-yl trifluoromethanesulfonate (0.486 g, 1.41 mmol) in THF (7.0 mL) were added (4-carbamoylphenyl)boronic acid (0.255 g, 1.55 mmol), PdCl$_2$(dppf) (0.051 g, 0.070 mmol) and KF (0.270 g, 4.64 mmol), and the reaction mixture was stirred under Ar overnight. The mixture was partitioned between EtOAc and water. The organic layer was concentrated and purified by silica gel chromatography (0-20% MeOH/DCM) to furnish tert-butyl (4'-carbamoyl-2,3,4,5-tetrahydro-[1,1'-biphenyl]-4-yl)carbamate (0.095 g, 0.30 mmol, 21% yield).

Intermediate 117c: 4'-amino-2',3',4',5'-tetrahydro-[1,1'-biphenyl]-4-carboxamide, TFA

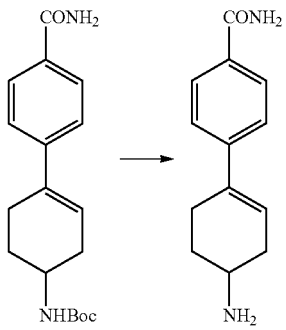 [SMILES: CC(C)(C)OC(=O)NC1CC=C(c2ccc(C(N)=O)cc2)CC1 ; NC(=O)c1ccc(C2=CCC(N)CC2)cc1]

To a solution of tert-butyl (4'-carbamoyl-2,3,4,5-tetrahydro-[1,1'-biphenyl]-4-yl)carbamate (0.095 g, 0.30 mmol) in DCM (2.0 mL) was added TFA (1.0 mL), and the reaction mixture was stirred overnight. The mixture was concentrated to furnish 4'-amino-2',3',4',5'-tetrahydro-[1,1'-biphenyl]-4-carboxamide, TFA (0.099 g, 0.30 mmol, 100% yield), which was used directly in the reductive amination procedure as described for Example 114 to provide Example 117.

Intermediates for the preparation of Examples 118, 125, 132, 133-134, 137-139, and 141 were prepared analogous to Example 117.

Intermediates 135a: (R)-3-((tert-butyldimethylsilyl)oxy)-2-(tritylamino)propan-1-ol

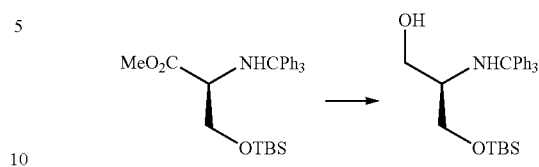

To a solution of commercially available (S)-methyl 3-((tert-butyldimethylsilyl)oxy)-2-(tritylamino)propanoate (3.06 g, 6.43 mmol) in toluene (64 mL) was added DIBAL-H (19.3 mL, 19.3 mmol) at 0° C. The solution was allowed to warm to rt slowly overnight. The reaction was quenched with sat. aqueous Rochelle's salt and extracted with DCM. The organic layer was concentrated to furnish (R)-3-((tert-butyldimethylsilyl)oxy)-2-(tritylamino)propan-1-ol (2.88 g, 6.43 mmol, 100% yield), which was used directly.

Intermediate 135b: (S)-3-((tert-butyldimethylsilyl)oxy)-2-(tritylamino)propanal

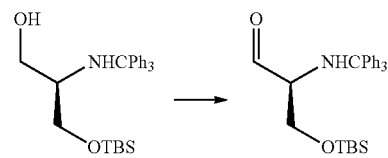

To a solution of DMSO (0.55 mL, 7.8 mmol) in DCM (12 mL) at −78° C. was added oxallyl chloride (0.51 mL, 5.9 mmol) in DCM (12 mL). After 5 min, the solution was treated with (R)-3-((tert-butyldimethylsilyl)oxy)-2-(tritylamino)propan-1-ol (2.18 g, 4.88 mmol) in DCM (24 mL). After 10 min, the solution was treated with Hinig's base (2.73 mL, 15.6 mmol), stirred for 30 min and then allowed to warm for 30 min. The solution was extracted from 10% citric acid with DCM. The organic layer was concentrated to furnish (S)-3-((tert-butyldimethylsilyl)oxy)-2-(tritylamino)propanal (2.18 g, 4.88 mmol, 100% yield) which was used directly.

Intermediate 135c: (R,E)-5-((tert-butyldimethylsilyl)oxy)-1-phenyl-4-(tritylamino)pent-2-en-1-one

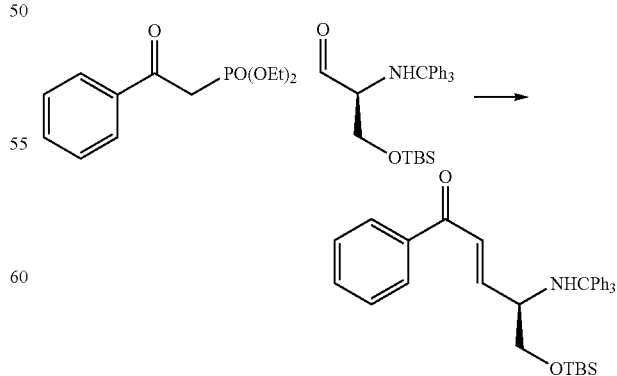

To a solution of diethyl (2-oxo-2-phenylethyl)phosphonate (1.17 mL, 5.37 mmol) in THF (27 mL) at 0° C. was added NaH (0.234 g, 5.86 mmol). The solution was warmed to rt and stirred for 1 h. A solution of (S)-3-((tert-butyldimethylsilyl)oxy)-2-(tritylamino)propanal (2.17 g, 4.88 mmol) in THF (22 mL) was added, and the reaction mixture was stirred overnight. The mixture was partitioned between water and EtOAc, and the organic layer was concentrated. The residue was purified by silica gel chromatography (0-100% EtOAc/hex) to furnish (R,E)-5-((tert-butyldimethylsilyl)oxy)-1-phenyl-4-(tritylamino)pent-2-en-1-one (0.985 g, 1.80 mmol, 36.8% yield). MS (ESI) m/z=548.3

Intermediate 135d: (R,E)-4-amino-5-((tert-butyldimethylsilyl)oxy)-1-phenylpent-2-en-1-one

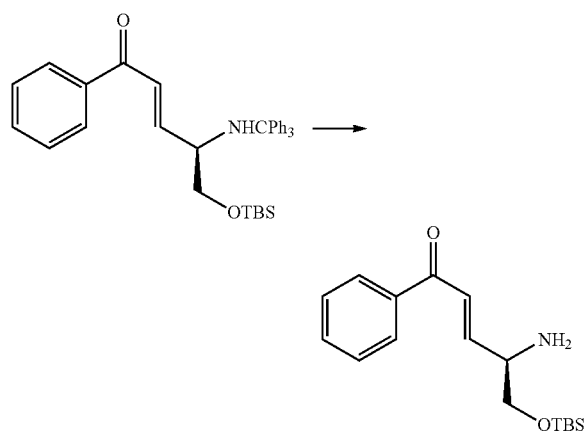

To a solution of (R,E)-5-((tert-butyldimethylsilyl)oxy)-1-phenyl-4-(tritylamino)pent-2-en-1-one (0.985 g, 1.80 mmol) in DCM (18 mL)/water (0.18 mL) was added TFA (0.42 mL, 5.4 mmol). The reaction was monitored by LCMS. After 2 min, the reaction was complete. The solution was concentrated to furnish (R,E)-4-amino-5-((tert-butyldimethylsilyl)oxy)-1-phenylpent-2-en-1-one (0.549 g, 1.80 mmol, 100% yield), which was used directly. MS (ESI) m/z=306.1

Intermediate 135e: (R,E)-N-(1-((tert-butyldimethylsilyl)oxy)-5-oxo-5-phenylpent-3-en-2-yl)-2,2,2-trifluoroacetamide

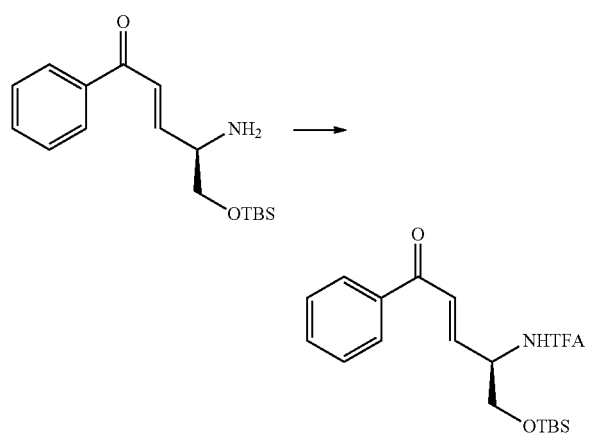

To a solution of (R,E)-4-amino-5-((tert-butyldimethylsilyl)oxy)-1-phenylpent-2-en-1-one (0.550 g, 1.80 mmol) in DCM (18 mL) at 0° C. was added Hünig's base (1.3 mL, 7.2 mmol) followed by TFAA (0.28 mL, 2.0 mmol). After 1 h, the reaction was treated with additional TFAA (0.28 mL, 2.0 mmol). After 2 h, the reaction mixture was extracted from dilute HCl with DCM, and the organic layer was concentrated to furnish (R,E)-N-(1-((tert-butyldimethylsilyl)oxy)-5-oxo-5-phenylpent-3-en-2-yl)-2,2,2-trifluoroacetamide (0.723 g, 1.80 mmol, 100% yield), which was used without further manipulation. MS (ESI) m/z=402.1

Intermediate 135f: (R)—N-(1-((tert-butyldimethylsilyl)oxy)-5-oxo-5-phenylpentan-2-yl)-2,2,2-trifluoroacetamide

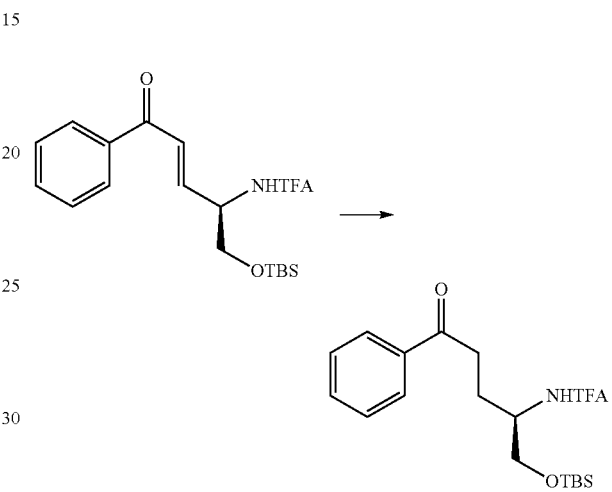

To a solution of (R,E)-N-(1-((tert-butyldimethylsilyl)oxy)-5-oxo-5-phenylpent-3-en-2-yl)-2,2,2-trifluoroacetamide (0.723 g, 1.80 mmol) in EtOAc (18 mL) was added Pd/C (0.192 g, 0.180 mmol), and the reaction mixture was blanketed under $H_2$ (balloon) and stirred overnight. The slurry was filtered and the filtrate was concentrated. The residue was purified by silica gel chromatography (0-100% EtOAc/hex) to furnish (R)—N-(1-((tert-butyldimethylsilyl)oxy)-5-oxo-5-phenylpentan-2-yl)-2,2,2-trifluoroacetamide (0.726 g, 1.80 mmol, 100% yield).

Intermediate 135 g: 2,2,2-trifluoro-N-((3R,6S)-6-phenyltetrahydro-2H-pyran-3-yl)acetamide and 136 g: 2,2,2-trifluoro-N-((3R,6R)-6-phenyltetrahydro-2H-pyran-3-yl)acetamide

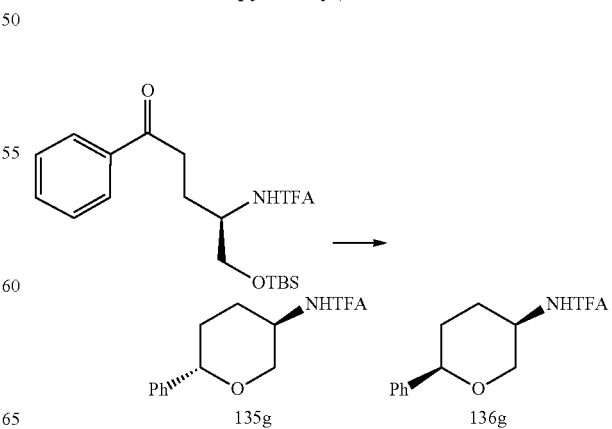

To a solution of (R)—N-(1-((tert-butyldimethylsilyl)oxy)-5-oxo-5-phenylpentan-2-yl)-2,2,2-trifluoroacetamide (0.726 g, 1.80 mmol) and Et₃SiH (0.58 mL, 3.6 mmol) in DCM (18 mL) was added BF₃•OEt₂ (0.228 mL, 1.80 mmol), and the reaction was monitored by LCMS. After 30 min, the crude product was extracted from brine with DCM. The organic layer was concentrated, and the residue containing 135 g, 136 g and 2,2,2-trifluoro-N-((3R,6S)-6-hydroxy-6-phenyltetrahydro-2H-pyran-3-yl)acetamide was treated with TES-H (0.58 mL, 3.6 mmol) in DCM (18 mL). To this solution was added BF₃•OEt₂ (0.228 mL, 1.80 mmol), and the reaction was monitored by LCMS. After 2 min, the starting material was consumed by LCMS. The reaction mixture was extracted from brine with DCM. The organic layer was concentrated, and the residue purified by silica gel chromatography (0-100% EtOAc/hex) to furnish 2,2,2-trifluoro-N-((3R,6S)-6-phenyltetrahydro-2H-pyran-3-yl)acetamide (0.170 g, 0.622 mmol, 34.6% yield) as a mixture of 135 g and 136 g. MS (ESI) m/z=274.1

Intermediates 135h: (3R,6S)-6-phenyltetrahydro-2H-pyran-3-amine and 136h: (3R,6R)-6-phenyltetrahydro-2H-pyran-3-amine

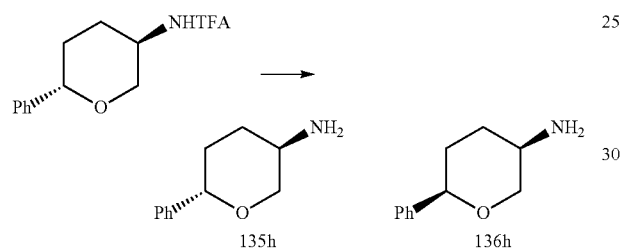

135h                    136h

To a solution of 135h (0.170 g, 0.622 mmol) contaminated with 136 g in MeOH (11.31 mL) was added K₂CO₃ (0.567 g, 4.11 mmol), and the mixture was heated to 65° C. overnight. The reaction mixture was extracted from brine with EtOAc and concentrated to furnish (3R,6S)-6-phenyltetrahydro-2H-pyran-3-amine (0.110 g, 0.622 mmol, 100% yield) as a mixture with epimer 136h. MS (ESI) m/z=178.1

The amine for Example 140 was prepared analogous to that for Example 135.

Intermediate 147a: N-benzyl-3-methylene-4-phenylbicyclo[2.2.2]octan-1-amine

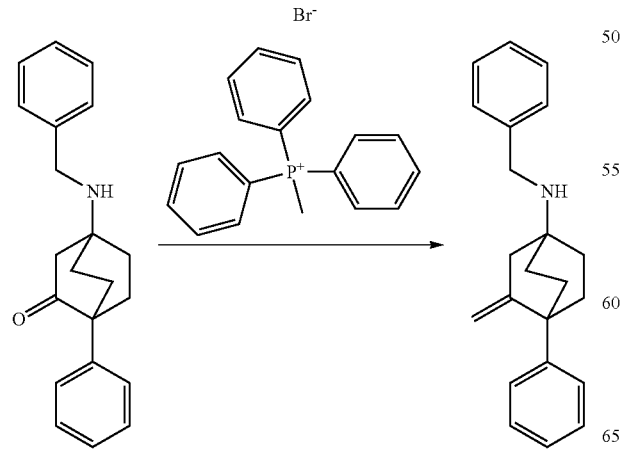

To a slurry of methyltriphenylphosphonium bromide (0.23 g, 0.66 mmol) in THF (6.6 mL) at 0° C., BuLi (0.32 mL, 0.66 mmol) was added dropwise. The mixture was stirred for 30 minutes. To the resulting solution was added 4-(benzylamino)-1-phenylbicyclo[2.2.2]octan-2-one (0.20 g, 0.66 mmol), and the reaction mixture was allowed to warm to rt overnight. The mixture was partitioned between EtOAc and brine. The organic layer was dried over MgSO₄, filtered, concentrated, and purified via flash chromatography to furnish N-benzyl-3-methylene-4-phenylbicyclo[2.2.2]octan-1-amine (0.080 g, 0.26 mmol, 40% yield).

Intermediate 147b: 3-methyl-4-phenylbicyclo[2.2.2]octan-1-amine

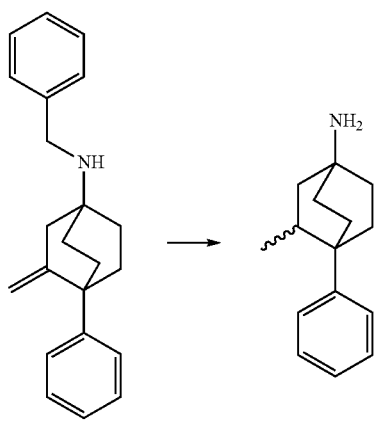 [SMILES: C=C1CC2(NCc3ccccc3)CCC1(c1ccccc1)CC2 ; CC1CC2(N)CCC1(c1ccccc1)CC2]

To N-benzyl-3-methylene-4-phenylbicyclo[2.2.2]octan-1-amine (0.080 g, 0.26 mmol) dissolved in EtOH (2.6 mL) was added Pd/C 10% wt. (0.028 g, 0.026 mmol). The reaction vessel atmosphere was evacuated and submitted to 55 psi(g) hydrogen overnight. The reaction mixture was filtered and concentrated for furnish 3-methyl-4-phenylbicyclo[2.2.2]octan-1-amine (0.057 g, 0.26 mmol, 100% yield). MS (ESI) m/z 216.2 (M+H).

Intermediate 148a: 4-(benzylamino)-1-phenylbicyclo[2.2.2]octan-2-one

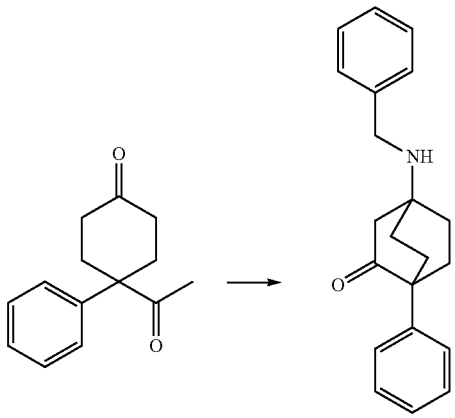 [SMILES: CC(=O)C1(c2ccccc2)CCC(=O)CC1 ; O=C1CC2(NCc3ccccc3)CCC1(c1ccccc1)CC2]

To a solution of 4-acetyl-4-phenylcyclohexanone (2.2 g, 10. mmol) dissolved in toluene (21 mL) was added benzylamine (3.3 mL, 30 mmol) and tosic acid (0.02 g, 0.1 mmol), and the mixture was heated to reflux with a Dean-Stark trap. After 2 hours the reaction mixture was cooled to rt, partitioned between EtOAc and 1.5 M pH 7.4 phosphate buffer. The organic layer was dried over MgSO$_4$, filtered and concentrated. The tan residue was purified via flash chromatography to furnish 4-(benzylamino)-1-phenylbicyclo[2.2.2]octan-2-one (2.2 g, 7.2 mmol, 76% yield) $^1$H NMR (400 MHz, CDCl$_3$) δ 7.38-7.30 (m, 6H), 7.29-7.24 (m, 2H), 7.23-7.16 (m, 2H), 3.80 (s, 2H), 2.56 (t, J=1.3 Hz, 2H), 2.35-2.23 (m, 2H), 2.19-2.08 (m, 2H), 2.01-1.83 (m, 4H). MS (ESI) m/z 306.1 (M+H).

Intermediate 148b: tert-butyl benzyl(3-oxo-4-phenylbicyclo[2.2.2]octan-1-yl)carbamate

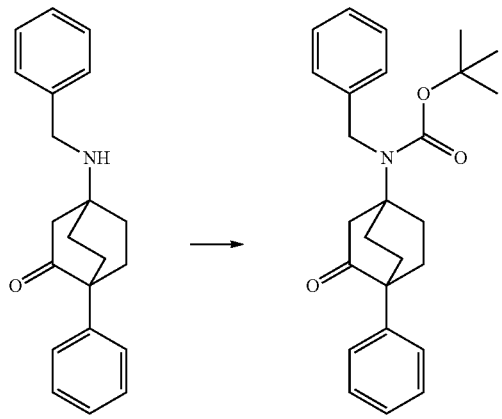 [SMILES: O=C1CC2(NCc3ccccc3)CCC1(c1ccccc1)CC2 ; CC(C)(C)OC(=O)N(Cc1ccccc1)C12CCC(c3ccccc3)(CC1)C(=O)C2]

To 4-(benzylamino)-1-phenylbicyclo[2.2.2]octan-2-one (0.41 g, 1.3 mmol) dissolved in THF (2.2 mL) was added 1N NaOH (2.2 mL, 2.2 mmol) followed by Boc$_2$O (1.3 mL, 1.3 mmol). The biphasic mixture was stirred overnight. The reaction was monitored and additional Boc$_2$O was added until the reaction was complete. The reaction mixture was concentrated, and the residue was purified via flash chromatography utilizing ELSD to furnish tert-butyl benzyl(3-oxo-4-phenylbicyclo[2.2.2]octan-1-yl)carbamate (0.42 g, 1.0 mmol, 78% yield). $^1$H NMR (400 MHz, CDCl$_3$) δ 7.36-7.27 (m, 4H), 7.25-7.18 (m, 4H), 7.16-7.11 (m, 2H), 4.64 (s, 2H), 3.06 (s, 2H), 2.35-2.12 (m, 6H), 2.10-1.97 (m, 2H), 1.47 (s, 9H). MS (ESI) m/z 350.2 (M+H).

Intermediate 148c: tert-butyl benzyl(3-hydroxy-4-phenylbicyclo[2.2.2]octan-1-yl)carbamate

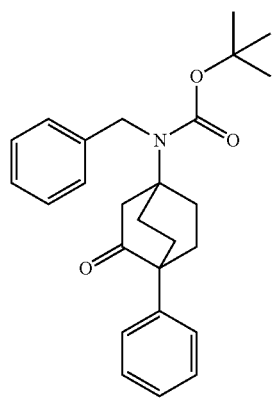

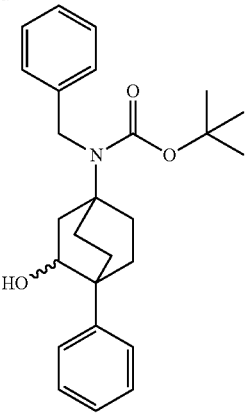

To tert-butyl benzyl(3-oxo-4-phenylbicyclo[2.2.2]octan-1-yl)carbamate (0.42 g, 1.0 mmol) dissolved in a mixture of THF (5.2 mL) and MeOH (5.2 mL) was added NaBH$_4$ (0.080 g, 2.0 mmol). The mixture was stirred overnight. The reaction mixture was concentrated, and the residue was partitioned between EtOAc and water. The organic layer was dried over MgSO$_4$, filtered and concentrated to furnish tert-butyl benzyl(3-hydroxy-4-phenylbicyclo[2.2.2]octan-1-yl)carbamate (0.38 g, 0.93 mmol, 89% yield). $^1$H NMR (400 MHz, CDCl$_3$) δ 7.35-7.28 (m, 6H), 7.24-7.18 (m, 4H), 4.69-4.49 (m, 2H), 4.20-4.07 (m, 1H), 2.74 (ddd, J=13.1, 9.6, 3.1 Hz, 1H), 2.44-2.32 (m, 1H), 2.29-1.88 (m, 6H), 1.82-1.65 (m, 2H), 1.44 (s, 9H), 1.25 (d, J=2.4 Hz, 1H). MS (ESI) m/z 408.2 (M+H)

Intermediate 148d: tert-butyl benzyl(3-methoxy-4-phenylbicyclo[2.2.2]octan-1-yl)carbamate

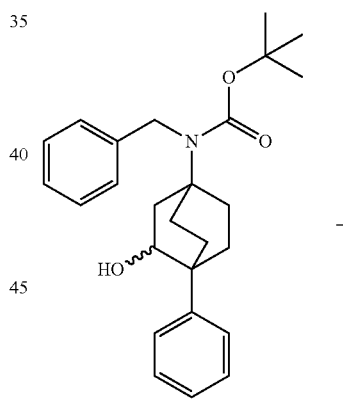

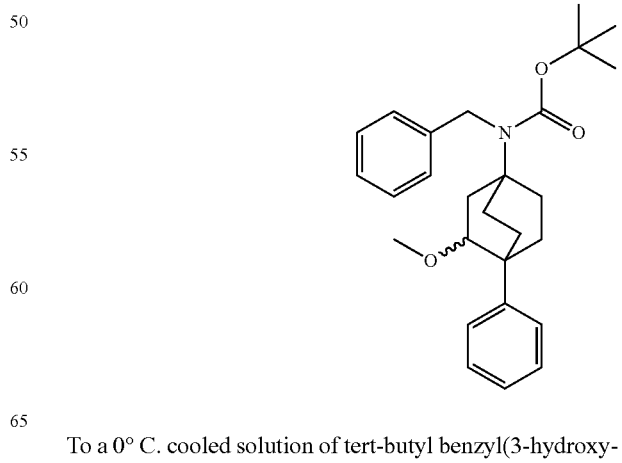

To a 0° C. cooled solution of tert-butyl benzyl(3-hydroxy-4-phenylbicyclo[2.2.2]octan-1-yl)carbamate (0.38 g, 0.92 mmol) dissolved in THF (3.1 mL) was added NaH 60% wt. (0.040 g, 1.0 mmol), and the mixture was stirred for 30 min. The resulting solution was warmed to rt over 30 minutes, and methyl iodide (0.058 mL, 0.92 mmol) was added. The resulting solution was stirred overnight. The solution was concentrated and purified via flash chromatography to furnish tert-butyl benzyl(3-methoxy-4-phenylbicyclo[2.2.2]octan-1-yl)carbamate (0.33 g, 0.78 mmol, 85% yield). MS (ESI) m/z 422.3 (M+H). $^1$H NMR (400 MHz, CDCl$_3$) δ 7.34-7.26 (m, 6H), 7.25-7.12 (m, 4H), 4.71-4.46 (m, 2H), 3.66 (d, J=8.6 Hz, 1H), 3.06 (s, 3H), 2.70-2.55 (m, 1H), 2.39-2.08 (m, 3H), 2.08-1.71 (m, 5H), 1.69-1.59 (m, 1H), 1.44 (s, 9H).

Intermediate 148e: N-benzyl-3-methoxy-4-phenylbicyclo[2.2.2]octan-1-amine, TFA salt

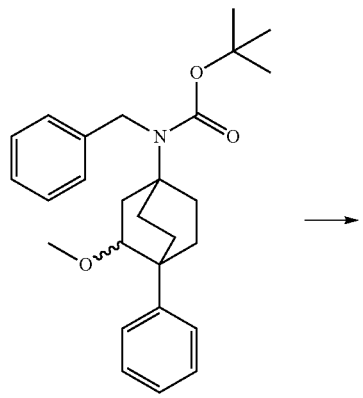

To tert-butyl benzyl(3-methoxy-4-phenylbicyclo[2.2.2]octan-1-yl)carbamate (0.33 g, 0.78 mmol) dissolved in DCM (6.3 mL) was added TFA (1.6 mL), and the mixture was stirred for 2 days. The sample was concentrated to afford crude N-benzyl-3-methoxy-4-phenylbicyclo[2.2.2]octan-1-amine, TFA salt (0.34 g, 0.78 mmol, 100% yield). MS (ESI) m/z 322.2 (M+H)

Intermediate 148f: 3-methoxy-4-phenylbicyclo[2.2.2]octan-1-amine

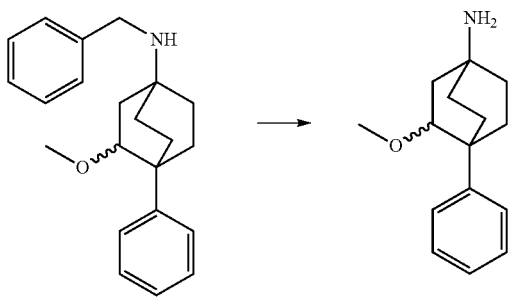 [SMILES: COC1CC2(NCc3ccccc3)CCC1(c1ccccc1)CC2 ; COC1CC2(N)CCC1(c1ccccc1)CC2]

To N-benzyl-3-methoxy-4-phenylbicyclo[2.2.2]octan-1-amine, TFA salt (0.34 g, 0.78 mmol) dissolved in EtOH (7.8 mL) was added Pd—C 10% wt. (0.08 g, 0.08 mmol), and the mixture was stirred under 55 psi(g) hydrogen overnight. The solution was filtered and concentrated to furnish 3-methoxy-4-phenylbicyclo[2.2.2]octan-1-amine suitable for direct use. MS (ESI) m/z 232.1 (M+H)

Intermediate 149a: Benzyl (8-oxobicyclo[3.2.1]octan-3-yl)carbamate

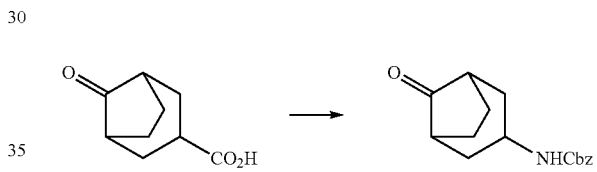

To a solution of the known 8-oxo-[3.2.1]octane-3-carboxylic acid (0.50 g, 2.3 mmol), TEA (0.33 mL, 2.3 mmol), and BnOH (0.73 mL, 7.0 mmol) in toluene (13 mL) was added DPPA (0.50 mL, 2.3 mmol), and the reaction was heated to 110° C. overnight. The reaction mixture was extracted from water with EtOAc and concentrated. The residue was purified by Silica gel chromatography (0-50% EtOAc/hex) to furnish benzyl (8-oxobicyclo[3.2.1]octan-3-yl)carbamate (0.627 mg, 2.29 mmol, 98% yield)

Intermediate 149b: benzyl (8-hydroxy-8-phenylbicyclo[3.2.1]octan-3-yl)carbamate

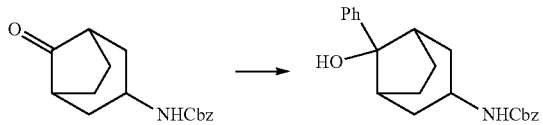 [SMILES: O=C(NC1CC2CCC(C1)C2=O)OCc1ccccc1 ; O=C(NC1CC2CCC(C1)C2(O)c1ccccc1)OCc1ccccc1]

To a solution of benzyl (8-oxobicyclo[3.2.1]octan-3-yl)carbamate (0.627 g, 2.29 mmol) in THF (23 mL) was added PhMgBr (5.0 mL, 5.0 mmol) at −78° C., and the reaction was allowed to warm to rt overnight. The reaction mixture was quenched with brine and extracted with EtOAc, filtered through a silica gel plug and concentrated to furnish benzyl (8-hydroxy-8-phenylbicyclo[3.2.1]octan-3-yl)carbamate (0.713 g, 2.03 mmol, 88% yield).

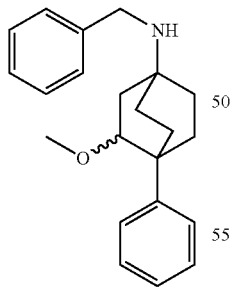

Intermediate 149c:
8-phenylbicyclo[3.2.1]octan-3-amine

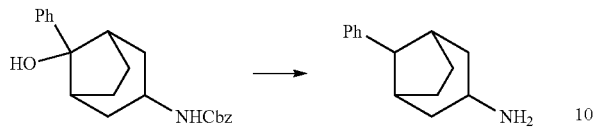

To a solution of benzyl (8-hydroxy-8-phenylbicyclo[3.2.1]octan-3-yl)carbamate (0.713 g, 2.03 mmol) in EtOH (20 mL) was added Pd—C(0.216 g, 0.203 mmol), and the reaction mixture was blanketed under $H_2$ (balloon). The reaction mixture was filtered through celite and concentrated to furnish 8-phenylbicyclo[3.2.1]octan-3-amine (0.327 g, 1.62 mmol, 80% yield). The resulting amine was used directly in the reductive amination procedure.

Intermediate 150a: 4'-amino-2',3',4',5'-tetrahydro-[1,1'-biphenyl]-4-carboxamide, TFA

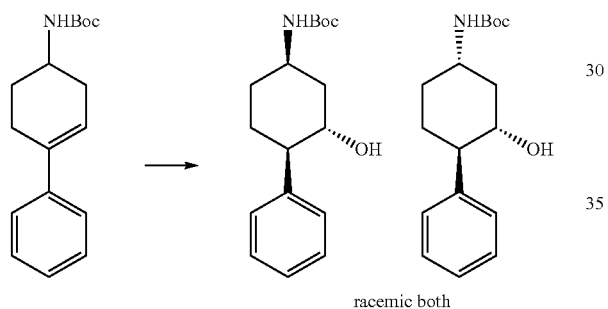

racemic both

To a THF solution (37 mL) of tert-butyl (2,3,4,5-tetrahydro-[1,1'-biphenyl]-4-yl)carbamate (1.10 g, 4.02 mmol), prepared analogous to Intermediate 117b, was added $BH_3 \cdot THF$ (4.0 mL, 4.0 mmol) at 0° C., and the reaction mixture was warmed to rt slowly overnight. The reaction mixture was treated with EtOH (18 mL)/Water (18 mL) then treated with hydrogen peroxide (0.62 mL, 20 mmol) and NaOH (2.0 mL, 10 mmol). After 24 h, additional $H_2O_2$ (0.62 mL, 20 mmol) and NaOH (2.0 mL, 10 mmol) were added. The reaction mixture was partitioned between brine and EtOAc. The organic layer was concentrated, and the residue was purified by silica gel chromatography (0-100% EtOAc/hex) to furnish tert-butyl 3-hydroxy-4-phenylcyclohexyl carbamate (0.526 g, 1.81 mmol, 44.9% yield). The intermediate was deprotected according to the procedure outlined for Intermediate 117c and the resulting amine used in the reductive amination step directly as described for Example 114.

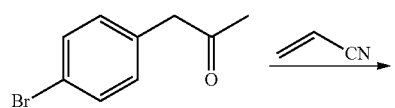

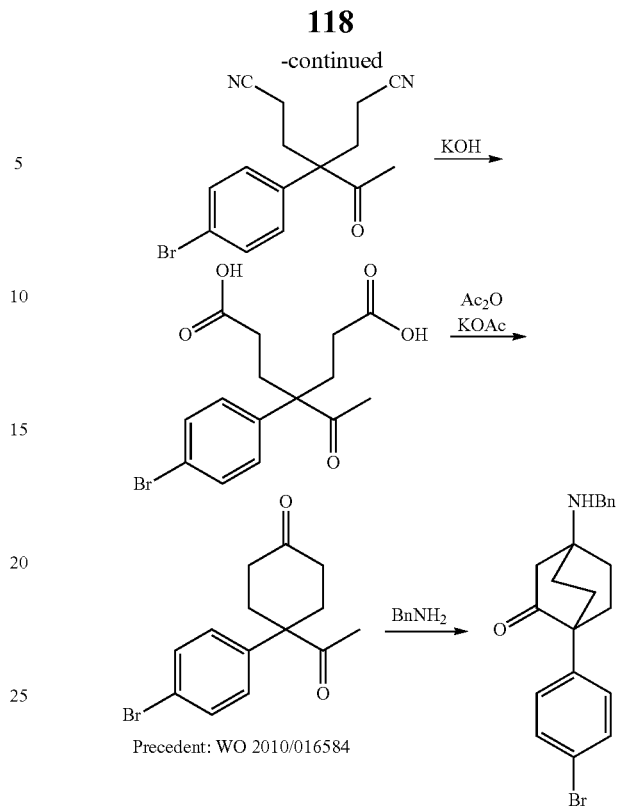

Precedent: WO 2010/016584

Intermediate 152a:
4-acetyl-4-(4-bromophenyl)heptanedinitrile

To 1-(4-bromophenyl)propan-2-one (15.0 g, 70.4 mmol) dissolved in t-butanol (17.6 mL) was added N,N,N-trimethyl-1-phenylmethanaminium hydroxide in MeOH (1.9 mL, 4.2 mmol), followed by dropwise addition of acrylonitrile (9.3 mL, 140 mmol) to a flask sitting in a water cooling bath in case exothermic heat was generated. After the addition was complete, the reaction mixture was stirred an additional hour to furnish a thick biphasic goo. The reaction was diluted with water, further diluted with toluene and ether, neutralized with 4.3 mL 1N HCl, and the layers were separated. The aqueous layer was washed 1× with ether, and combined with the organic layer. The combined organic layers were washed with water and brine. The organic layer was concentrated and used as is, 4-acetyl-4-(4-bromophenyl)heptanedinitrile (28.1 g, 70.4 mmol, 100% yield). MS (ESI) m/z 321.1 (M+H).

Intermediate 152b:
4-acetyl-4-(4-bromophenyl)heptanedioic acid

To a slurry of 4-acetyl-4-(4-bromophenyl)heptanedinitrile (28.1 g, 70.4 mmol) in water (78 mL) was added KOH (11 g, 200 mmol). The mixture was heated to reflux overnight. The reaction mixture was cooled, and the aqueous phase was washed with ether. The aqueous layer was collected and acidified with 16.4 mL of concentrated HCl. The resulting precipitate was filtered and washed with water to furnish 4-acetyl-4-(4-bromophenyl)heptanedioic acid (26 g, 73 mmol, 103% yield). MS (ESI) m/z 359.0 (M+H).

Intermediate 152c:
4-acetyl-4-(4-bromophenyl)cyclohexanone

To a slurry of 4-acetyl-4-(4-bromophenyl)heptanedioic acid (16.8 g, 46.9 mmol) in $Ac_2O$ (22.1 mL, 235 mmol) was added potassium acetate (0.138 g, 1.41 mmol). The mixture was heated to reflux for 2 hours. The AcOH and acetic anhydride were removed via evaporation. The flask containing product residue was fitted with a 6" glass condensing tube and was heated to 210° C. in an oil bath with 1 hour of stirring. The residue was purified via flash chromatorgraphy to furnish 4-acetyl-4-(4-bromophenyl)cyclohexanone (3.2 g, 11 mmol, 23% yield). MS (ESI) m/z 297.0 (M+H). ¹H NMR (500 MHz, CDCl₃) δ 7.56 (d, J=8.5 Hz, 2H), 7.25 (d, J=8.8 Hz, 2H), 2.66-2.58 (m, 2H), 2.56-2.47 (m, 2H), 2.46-2.38 (m, 2H), 2.34-2.25 (m, 2H), 2.03 (s, 3H).

Intermediate 152d: 4-(benzylamino)-1-(4-bromophenyl)bicyclo[2.2.2]octan-2-one

To a solution of 4-acetyl-4-(4-bromophenyl)cyclohexanone (0.20 g, 0.68 mmol) dissolved in toluene (1.4 mL) was added benzylamine (0.22 mL, 2.0 mmol) and tosic acid (1 mg, 7 µmol). The solution was heated to reflux with a Dean-Stark trap. After 2 hours, the reaction mixture was cooled to rt, and 0.66 mL of 3 M HCl was added. The mixture was stirred overnight. The mixture was then partitioned between 1.5 M pH 7.4 buffer and EtOAc, and the layers were separated. The organic layer was dried over MgSO₄, filtered and concentrated to furnish a brown residue. The residue was purified via flash chromatography to furnish 4-(benzylamino)-1-(4-bromophenyl)bicyclo[2.2.2]octan-2-one (0.23 g, 0.60 mmol, 88% yield). MS (ESI) m/z 386.1 (M+H), ¹H NMR (400 MHz, CDCl₃) δ 7.47 (d, J=8.6 Hz, 2H), 7.36-7.32 (m, 5H), 7.07 (d, J=8.6 Hz, 2H), 3.79 (s, 2H), 2.56 (s, 2H), 2.30-2.18 (m, 2H), 2.16-2.03 (m, 2H), 2.02-1.83 (m, 4H).

Intermediate 152e: 4-(benzylamino)-1-(4-bromophenyl)bicyclo[2.2.2]octan-2-yl methanesulfonate

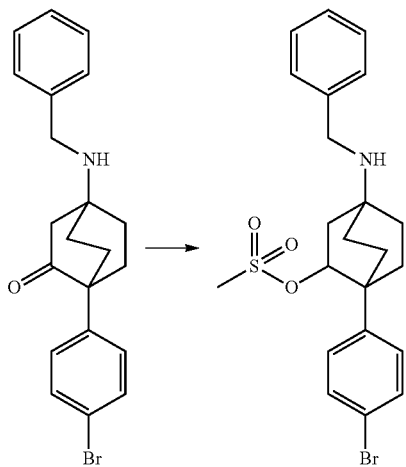 [SMILES: O=C1CC2(NCc3ccccc3)CCC1(c1ccc(Br)cc1)CC2 ; CS(=O)(=O)OC1CC2(NCc3ccccc3)CCC1(c1ccc(Br)cc1)CC2]

To 4-(benzylamino)-1-phenylbicyclo[2.2.2]octan-2-one (2.3 g, 6.0 mmol) dissolved in MeOH (16 mL) was added NaBH₄ (0.36 g, 9.9 mmol), and the mixture was stirred overnight. The reaction mixture was partitioned between EtOAc and water. The organic layer was dried over MgSO₄, filtered and concentrated to furnish 4-(benzylamino)-1-phenylbicyclo[2.2.2]octan-2-ol which was used directly without purification.
To a solution of 4-(benzylamino)-1-(4-bromophenyl)bicyclo[2.2.2]octan-2-ol (2.3 g, 6.0 mmol) dissolved in THF (6 mL) and toluene (12 mL) was added Et₃N (1.6 mL, 12 mmol) followed by dropwise addition of MsCl (0.59 mL, 7.5 mmol). After 2 hr the sample was partitioned between water and EtOAc, and extracted 2× with EtOAc. The organic layer was dried over MgSO₄, filtered and concentrated to furnish 4-(benzylamino)-1-(4-bromophenyl)bicyclo[2.2.2]octan-2-yl methanesulfonate (2.8 g, 6.0 mmol, 100% yield) used directly. MS (ESI) m/z 466.1 (M+H).

Intermediate 152f: N-benzyl-4-(4-bromophenyl)bicyclo[2.2.2]oct-2-en-1-amine

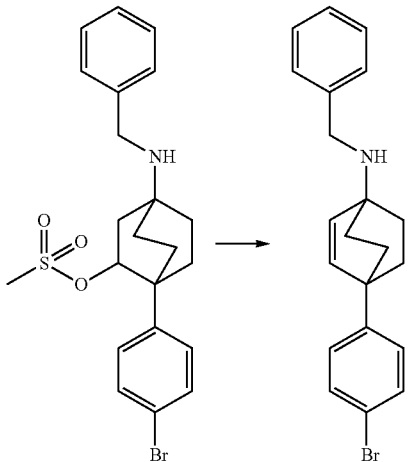 [SMILES: CS(=O)(=O)OC1CC2(NCc3ccccc3)CCC1(c1ccc(Br)cc1)CC2 ; Brc1ccc(C23C=CC(NCc4ccccc4)(CC2)CC3)cc1]

To 4-(benzylamino)-1-(4-bromophenyl)bicyclo[2.2.2]octan-2-yl methanesulfonate (2.8 g, 6.0 mmol) dissolved in a mixture of toluene (22 mL) and DMA (7.4 mL) was added NaI (0.18 g, 1.2 mmol) and DBU (4.5 mL, 30. mmol). The mixture was heated to 120° C. overnight. The reaction was quenched with saturated NH₄Cl, and extracted 2× into EtOAc. The combined organic layers were dried over MgSO₄, filtered and concentrated. The residue was purified via flash chromatography to furnish N-benzyl-4-(4-bromophenyl)bicyclo[2.2.2]oct-2-en-1-amine contaminated with trace impurities, suitable for use as is. MS (ESI) m/z 370.0 (M+H).

Intermediate 152 g: 1-(benzylamino)-4-(4-bromophenyl)bicyclo[2.2.2]octan-2-ol

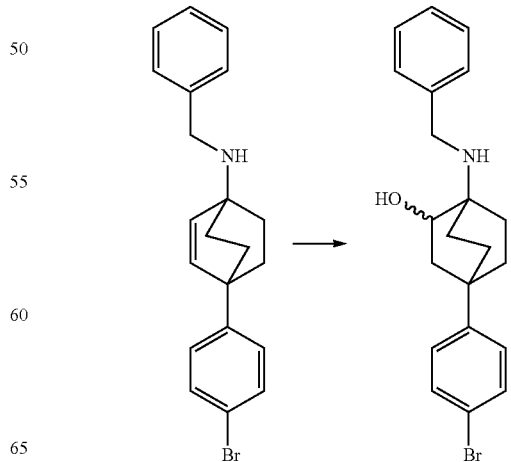

To a solution of N-benzyl-4-(4-bromophenyl)bicyclo[2.2.2]oct-2-en-1-amine (0.20 g, 0.54 mmol) in THF (4.9 mL) was added a solution of borane-THF complex (1.2 mL, 1.2 mmol) at 0° C., and the reaction mixture was warmed to rt. After 2 hours EtOH (2.5 mL) and water (2.5 mL) were added, and then the reaction was treated with hydrogen peroxide (0.08 mL, 3 mmol) and NaOH (0.27 mL, 1.4 mmol). After 2 hours, the reaction mixture was partitioned between EtOAc and water. The organic layer was washed with brine and concentrated. The residue was reconstituted in THF, and 2 mL of 1N HCl were added. The mixture was stirred and heated to reflux for 3 hours. The mixture was concentrated, and partitioned between 1:1 1N NaOH/sat. brine and EtOAc. The organic layer was dried over MgSO$_4$, filtered, concentrated and purified via flash chromatography to furnish 1-(benzylamino)-4-(4-bromophenyl)bicyclo[2.2.2]octan-2-ol (0.15 g, 0.38 mmol, 70% yield). $^1$H NMR (400 MHz, CDCl$_3$) δ 7.48 (d, J=8.4 Hz, 2H), 7.38-7.30 (m, 4H), 7.25-7.18 (m, 3H), 4.24 (td, J=10.3, 5.9 Hz, 1H), 3.89-3.77 (m, 2H), 2.65 (dd, J=10.5, 1.9 Hz, 1H), 2.29 (ddd, J=11.7, 5.9, 2.2 Hz, 1H), 2.23 (br. s., 1H), 1.79-1.56 (m, 7H). MS (ESI) m/z 386.1 (M+H).

Intermediate 152h: 1-amino-4-phenylbicyclo[2.2.2]octan-2-ol, AcOH salt

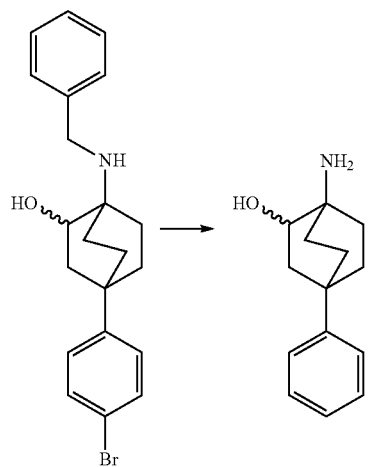 [SMILES: OC1CC2(c3ccc(Br)cc3)CCC1(NCc1ccccc1)CC2 ; NC12CCC(c3ccccc3)(CC1)CC2O]

To 1-(benzylamino)-4-(4-bromophenyl)bicyclo[2.2.2]octan-2-ol (0.15 g, 0.38 mmol) dissolved in EtOH (3.5 mL) and AcOH (0.35 mL) was added Pd/C 10% wt. (0.040 g, 0.38 mmol) and submitted to 55 psi(g) hydrogen over weekend. The sample was filtered and concentrated to furnish 1-amino-4-phenylbicyclo[2.2.2]octan-2-ol, AcOH salt. (0.11 g, 0.38 mmol, 100% yield)$^1$H NMR (400 MHz, CDCl$_3$) δ 7.41-7.19 (m, 5H), 4.26 (td, J=10.3, 6.1 Hz, 1H), 2.73 (d, J=10.6 Hz, 1H), 2.36 (br. s., 2H), 2.08-1.62 (m, 7H). MS (ESI) m/z 218.2 (M+H).

Intermediate 153a: tert-butyl benzyl(4-(4-bromophenyl)-3-oxobicyclo[2.2.2]octan-1-yl)carbamate

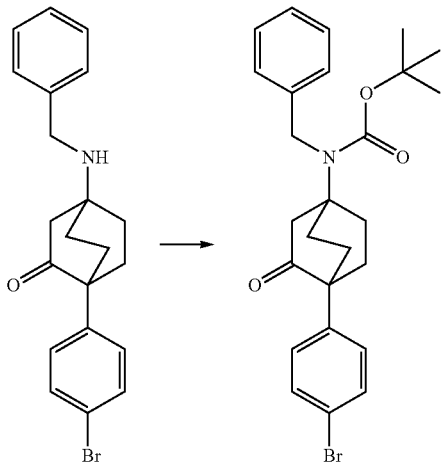 [SMILES: O=C1CC2(NCc3ccccc3)CCC1(c1ccc(Br)cc1)CC2 ; CC(C)(C)OC(=O)N(Cc1ccccc1)C12CCC(c3ccc(Br)cc3)(CC1)C(=O)C2]

To 4-(benzylamino)-1-(4-bromophenyl)bicyclo[2.2.2]octan-2-one (5.0 g, 13 mmol) dissolved in THF (22 mL) was added 1N NaOH (22 mL) followed by Boc$_2$O (3.02 mL, 13.0 mmol). The biphasic mixture was stirred overnight at 50° C. Additional Boc$_2$O (3.02 mL, 13.0 mmol) was added, and the reaction mixture was stirred overnight. The mixture was partitioned between EtOAc and water, and the organic phase was dried over MgSO$_4$, filtered and concentrated. The residue was purified via flash chromatography to furnish tert-butyl benzyl(4-(4-bromophenyl)-3-oxobicyclo[2.2.2]octan-1-yl)carbamate (3.0 g, 6.2 mmol, 48% yield), $^1$H NMR (400 MHz, CDCl$_3$) δ 7.43 (d, J=8.6 Hz, 2H), 7.37-7.30 (m, 2H), 7.30-7.22 (m, 1H), 7.20 (d, J=7.3 Hz, 2H), 7.04-6.93 (m, 2H), 4.63 (s, 2H), 3.06 (s, 2H), 2.37-2.07 (m, 6H), 2.05-1.92 (m, 2H), 1.47 (s, 9H). MS (ESI) m/z 430.0 (M+H-tBu).

Intermediate 153b: tert-butyl benzyl(4-(4-bromophenyl)-3-hydroxybicyclo[2.2.2]octan-1-yl)carbamate

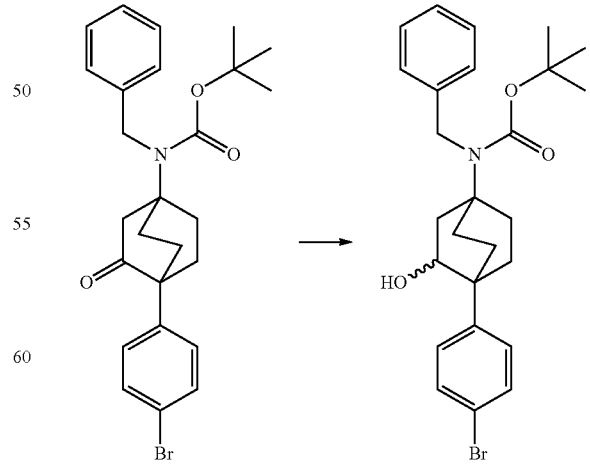

To tert-butyl benzyl(4-(4-bromophenyl)-3-oxobicyclo[2.2.2]octan-1-yl)carbamate (2.0 g, 4.1 mmol) dissolved in EtOH (41 mL) at 0° C. was added NaBH₄ (0.16 g, 4.1 mmol), and the mixture was stirred for 1 hour. The reaction mixture was diluted with water, and the resultant precipitate was filtered and dried under vacuum overnight to furnish tert-butyl benzyl(4-(4-bromophenyl)-3-hydroxybicyclo[2.2.2]octan-1-yl)carbamate (1.6 g, 3.3 mmol, 80% yield), $^1$H NMR (400 MHz, CDCl₃) δ 7.43 (d, J=8.6 Hz, 2H), 7.34-7.28 (m, 2H), 7.24-7.15 (m, 5H), 4.59 (s, 2H), 4.13-4.04 (m, 1H), 2.73 (ddd, J=13.1, 9.5, 3.1 Hz, 1H), 2.40-2.29 (m, 1H), 2.25-2.12 (m, 2H), 2.10-1.98 (m, 2H), 1.94 (dt, J=13.4, 3.1 Hz, 1H), 1.91-1.83 (m, 1H), 1.77-1.62 (m, 2H), 1.44 (s, 9H), 1.23 (d, J=2.6 Hz, 1H). MS (ESI) m/z 386.1/388.1 (M+H-BOC)

Intermediate 153c: 4-(benzyl(tert-butoxycarbonyl)amino)-1-(4-bromophenyl)bicyclo[2.2.2]octan-2-yl methanesulfonate

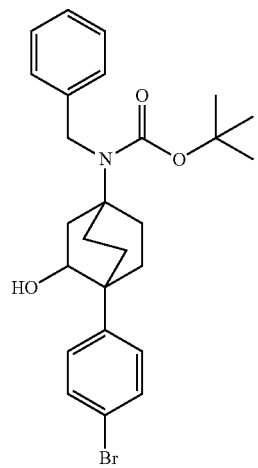
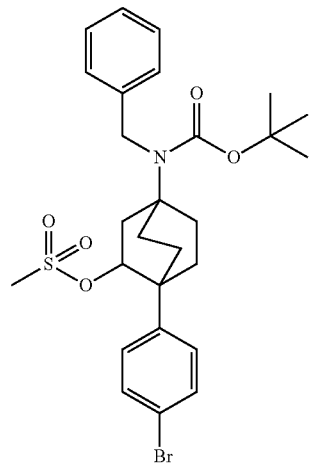

To a solution of tert-butyl benzyl(4-(4-bromophenyl)-3-hydroxybicyclo[2.2.2]octan-1-yl)carbamate (1.3 g, 2.7 mmol) dissolved in THF (2.7 mL) and toluene (5.4 mL) was added Et₃N (0.75 mL, 5.3 mmol) followed by dropwise addition of MsCl (0.26 mL, 3.4 mmol, and the reaction mixture was stirred overnight. The mixture was partitioned between water and EtOAc, and extracted 2× with EtOAc. The organic layer was dried over MgSO₄, filtered and concentrated to furnish 4-(benzyl(tert-butoxycarbonyl)amino)-1-(4-bromophenyl)bicyclo[2.2.2]octan-2-yl methanesulfonate (1.5 g, 2.7 mmol, 100% yield) which was used directly. $^1$H NMR (400 MHz, CDCl₃) δ 7.48-7.40 (m, 2H), 7.36-7.29 (m, 2H), 7.25-7.22 (m, 2H), 7.20-7.13 (m, 9H), 4.95 (d, J=9.0 Hz, 1H), 4.75-4.43 (m, 2H), 2.92 (ddd, J=14.6, 9.2, 3.1 Hz, 1H), 2.46-2.37 (m, 2H), 2.35 (s, 5H), 2.32 (s, 3H), 2.31-2.25 (m, 2H), 2.09-1.85 (m, 3H), 1.84-1.64 (m, 2H), 1.45 (s, 9H). MS (ESI) m/z 466.1 (M+H-Boc).

Intermediate 153d: tert-butyl benzyl(4-(4-bromophenyl)bicyclo[2.2.2]oct-2-en-1-yl)carbamate

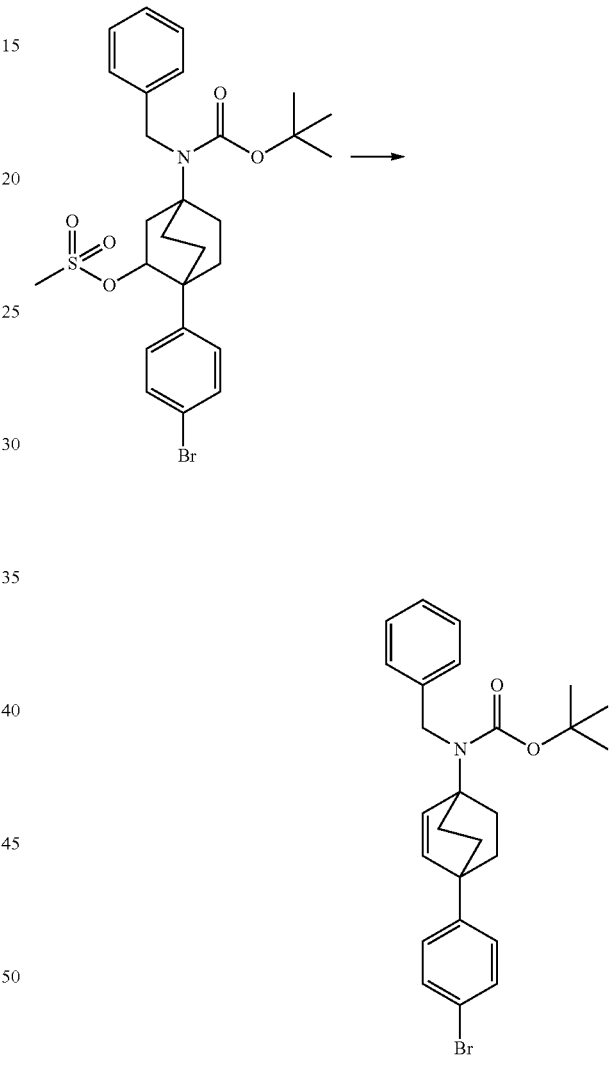

To 4-(benzyl(tert-butoxycarbonyl)amino)-1-(4-bromophenyl)bicyclo[2.2.2]octan-2-yl methanesulfonate (1.5 g, 2.7 mmol) dissolved in a mixture of toluene (10 mL) and DMA (3.3 mL) was added NaI (0.08 g, 0.5 mmol) and DBU (2.0 mL, 13 mmol). The mixture was heated to 90° C. over four days. The reaction was partitioned between EtOAc and water. The organic layer was washed with water and brine, and then dried over MgSO₄, filtered and concentrated. The residue was purified with via flash chromatography to furnish tert-butyl benzyl(4-(4-bromophenyl)bicyclo[2.2.2]oct-2-en-1-yl)carbamate (1.0 g, 2.2 mmol, 81% yield), MS (ESI) m/z 414.0 (M+H-tBu).

Intermediate 153e: tert-butyl benzyl(4-(4-bromophenyl)-2-hydroxybicyclo[2.2.2]octan-1-yl)carbamate

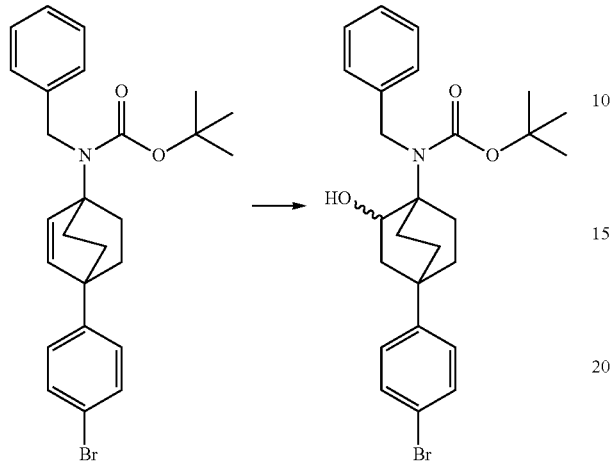

To a solution of tert-butyl benzyl(4-(4-bromophenyl)bicyclo[2.2.2]oct-2-en-1-yl)carbamate (0.50 g, 1.1 mmol) dissolved in THF (9.7 mL) cooled to 0° C. was added a solution of 1 M borane-THF complex (1.3 mL, 1.3 mmol), and the reaction mixture was warmed to rt and stirred overnight. To the mixture were added EtOH (4.9 mL) and water (4.9 mL), followed by hydrogen peroxide (0.16 mL, 5.3 mmol) and 4 M NaOH (0.53 mL, 2.7 mmol). After 2 hours, the reaction mixture was partitioned between EtOAc and water. The organic layer was washed with brine, dried over $MgSO_4$, filtered, concentrated and purified via flash chromatography to furnish tert-butyl benzyl(4-(4-bromophenyl)-2-hydroxybicyclo[2.2.2]octan-1-yl)carbamate (0.27 g, 0.56 mmol, 52% yield). $^1$H NMR (400 MHz, $CDCl_3$) δ 7.45 (d, J=8.4 Hz, 2H), 7.34-7.28 (m, 2H), 7.25-7.19 (m, 3H), 7.15 (d, J=8.6 Hz, 2H), 4.59 (s, 2H), 4.21-4.15 (m, 1H), 2.77-2.64 (m, 1H), 2.55 (d, J=10.3 Hz, 1H), 2.40 (d, J=6.6 Hz, 1H), 2.13 (br. s., 1H), 2.00-1.92 (m, 1H), 1.91-1.79 (m, 2H), 1.63-1.54 (m, 3H), 1.37 (d, J=4.4 Hz, 1H).

Intermediate 153f: tert-butyl benzyl(4-(4-bromophenyl)-2-methoxybicyclo[2.2.2]octan-1-yl)carbamate

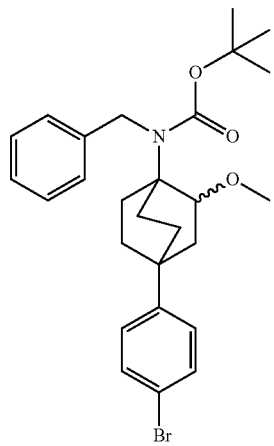

To a solution of tert-butyl benzyl(4-(4-bromophenyl)-2-hydroxybicyclo[2.2.2]octan-1-yl)carbamate (0.10 g, 0.21 mmol) dissolved in THF (0.7 mL) cooled to 0° C. was added NaH 60% wt. (9.0 mg, 0.21 mmol). The resulting solution was warmed to room temperature over 30 minutes, and methyl iodide (0.013 mL, 0.21 mmol) was added. The resulting solution was stirred overnight. The solution was concentrated and purified via flash chromatography to furnish tert-butyl benzyl(4-(4-bromophenyl)-2-methoxybicyclo[2.2.2]octan-1-yl)carbamate (0.046 g, 0.092 mmol, 45% yield). $^1$H NMR (400 MHz, $CDCl_3$) δ 7.41 (d, J=8.6 Hz, 2H), 7.34-7.28 (m, 2H), 7.23 (d, J=7.9 Hz, 3H), 7.08 (d, J=8.4 Hz, 2H), 4.69-4.48 (m, 2H), 3.66 (td, J=10.4, 5.8 Hz, 1H), 3.28 (s, 3H), 2.87 (td, J=5.8, 3.2 Hz, 1H), 2.62 (dd, J=10.6, 2.0 Hz, 1H), 2.48-2.33 (m, 1H), 2.11 (br. s., 1H), 1.96-1.77 (m, 3H), 1.53-1.40 (m, 12H), MS (ESI) m/z 400.1 (M+H-Boc).

Intermediate 153 g: tert-butyl (2-methoxy-4-phenylbicyclo[2.2.2]octan-1-yl)carbamate

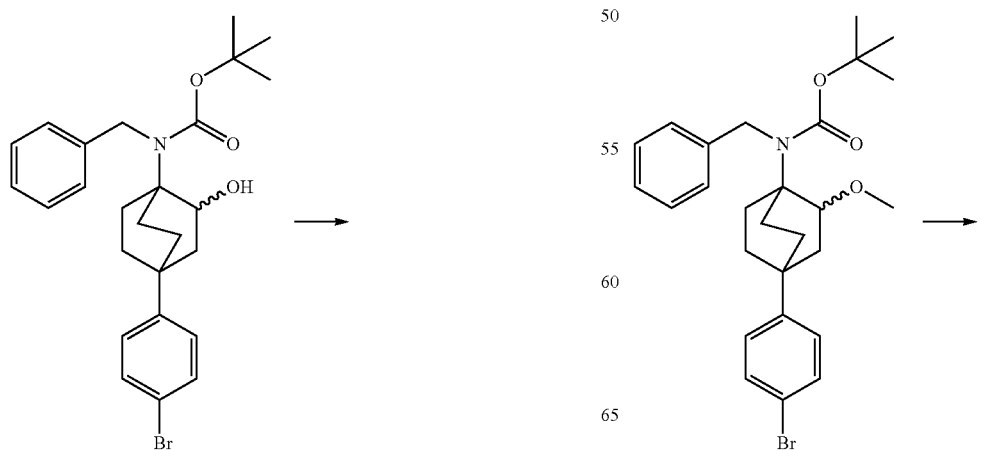

-continued

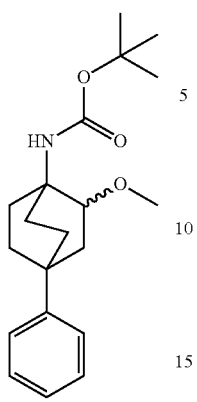

To tert-butyl benzyl(4-(4-bromophenyl)-2-methoxybicyclo[2.2.2]octan-1-yl)carbamate (0.045 g, 0.089 mmol) dissolved in EtOH (9 mL) was added Pd/C 10% wt. (9 mg, 9 μmol) and 3 drops of AcOH. The solution was degassed, and charged with 50 psi(g) hydrogen. The reaction mixture was stirred overnight. The mixture was filtered, and concentrated to furnish tert-butyl (2-methoxy-4-phenylbicyclo[2.2.2]octan-1-yl)carbamate (0.029 g, 0.089 mmol, 100% yield), suitable for direct use. MS (ESI) m/z 276.1 (M+H-tBu).

Intermediate 153h: 2-methoxy-4-phenylbicyclo[2.2.2]octan-1-amine, TFA salt

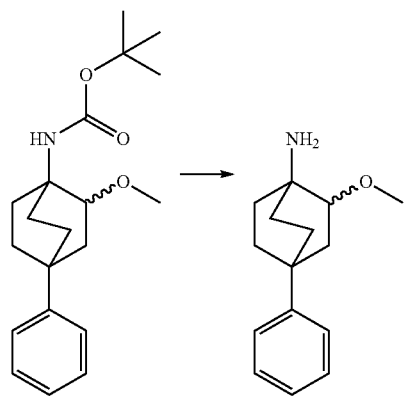 [SMILES: COC1CC2(c3ccccc3)CCC1(NC(=O)OC(C)(C)C)CC2 ; COC1CC2(c3ccccc3)CCC1(N)CC2]

To tert-butyl (2-methoxy-4-phenylbicyclo[2.2.2]octan-1-yl)carbamate (0.035 g, 0.11 mmol) dissolved in DCM (1.1 mL) was added TFA (0.26 mL), and the mixture was stirred overnight. The reaction mixture was concentrated to furnish crude 2-methoxy-4-phenylbicyclo[2.2.2]octan-1-amine, TFA salt (0.037 g, 0.11 mmol, 100% yield). $^1$H NMR (400 MHz, MeOH-d$_4$) δ 7.38-7.25 (m, 4H), 7.25-7.14 (m, 1H), 4.07-3.89 (m, 1H), 3.30 (s, 3H), 2.78 (dd, J=10.7, 1.9 Hz, 1H), 2.50 (ddd, J=11.5, 6.0, 2.8 Hz, 1H), 2.33 (t, J=4.8 Hz, 1H), 2.06-1.87 (m, 3H), 1.85-1.73 (m, 2H), 1.72-1.57 (m, 2H).

Intermediate 154a: 4-(benzylamino)-1-phenylbicyclo[2.2.2]octan-2-ol

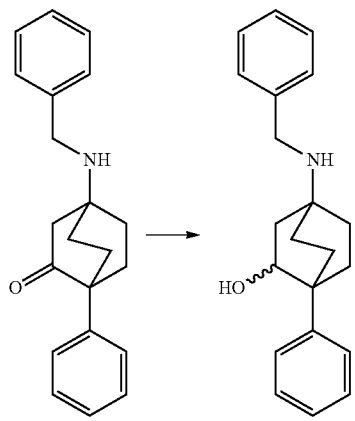 [SMILES: O=C1CC2(NCc3ccccc3)CCC1(c1ccccc1)CC2 ; OC1CC2(NCc3ccccc3)CCC1(c1ccccc1)CC2]

To 4-(benzylamino)-1-phenylbicyclo[2.2.2]octan-2-one (0.50 g, 1.6 mmol) dissolved in MeOH (5.5 mL) was added NaBH$_4$ (0.12 g, 3.3 mmol), and the mixture was stirred overnight. The reaction mixture was partitioned between EtOAc and water. The organic layer was dried over MgSO$_4$, filtered and concentrated to furnish 4-(benzylamino)-1-phenylbicyclo[2.2.2]octan-2-ol (0.47 g, 1.5 mmol, 93% yield). $^1$H NMR (400 MHz, CDCl$_3$) δ 7.43-7.29 (m, 9H), 7.24-7.19 (m, 1H), 4.23 (d, J=8.6 Hz, 1H), 3.76 (s, 2H), 2.51-2.41 (m, 1H), 2.18 (ddd, J=13.1, 9.6, 3.4 Hz, 1H), 2.03-1.97 (m, 1H), 1.93-1.62 (m, 6H), 1.32 (br. s., 1H). MS (ESI) m/z 308.2 (M+H).

Intermediate 154b: 4-amino-1-phenylbicyclo[2.2.2]octan-2-ol

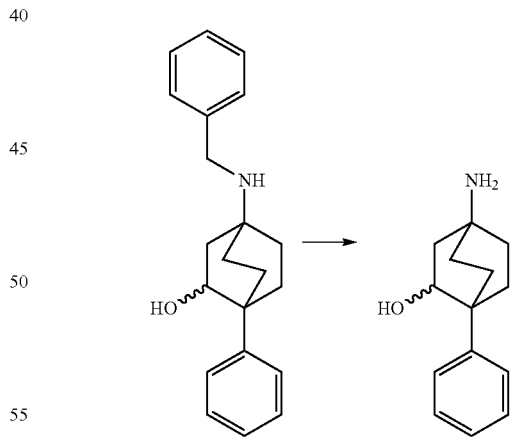

To a solution of 4-(benzylamino)-1-phenylbicyclo[2.2.2]octan-2-ol (0.2 g, 0.7 mmol) dissolved in EtOH (6.5 mL) was added Pd/C 10% wt. (0.07 g, 0.07 mmol), and the mixture was stirred under 55 psi(g) hydrogen overnight. The mixture was filtered and concentrated to furnish 4-amino-1-phenylbicyclo[2.2.2]octan-2-ol (0.1 g, 0.5 mmol, 80% yield). $^1$H NMR (400 MHz, CDCl$_3$) δ 7.43-7.30 (m, 4H), 7.23 (dd, J=5.8, 3.0 Hz, 1H), 4.25-4.13 (m, 1H), 2.45 (dtd, J=11.2, 8.1, 4.6 Hz, 1H), 2.20-1.93 (m, 3H), 1.89-1.58 (m, 6H). MS (ESI) m/z 218.1 (M+H).

General Route 8 (see Scheme 8):

Intermediate 8-1. 3-(3-trityl-5-(tritylamino)-3H-[1,2,3]triazolo[4,5-b]pyridin-7-yl)prop-2-yn-1-ol

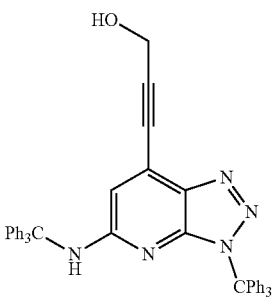

To a solution of 7-bromo-N,3-ditrityl-3H-[1,2,3]triazolo[4,5-b]pyridin-5-amine (10.0 g, 14.3 mmol) in DMF (48 mL), was added bis(triphenylphosphine)palladium(II) chloride (0.402 g, 0.573 mmol), prop-2-yn-1-ol (1.61 g, 28.6 mmol), copper(I) iodide (0.109 g, 0.573 mmol), and TEA (6.0 mL, 43 mmol) in a pressure rated sealed tube under an Ar atmosphere. The reaction mixture was heated to 85° C. for 18 hours, and then cooled to rt. The mixture was filtered over celite and concentrated. The residue was purified by chromatography on silica gel (preflushed with 1% TEA/hexanes) to provide the product, (6.75 g, 10.0 mmol, 70% yield). MS(ESI) m/z 674.4 (M+H).

Intermediate 8-2: (Z)-3-iodo-3-(3-trityl-5-(tritylamino)-3H-[1,2,3]triazolo[4,5-b]pyridin-7-yl)prop-2-en-1-ol

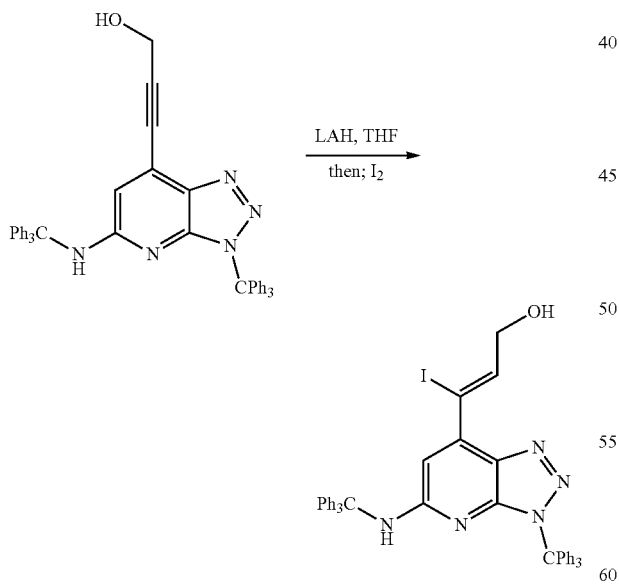

A solution of 3-(3-trityl-5-(tritylamino)-3H-[1,2,3]triazolo[4,5-b]pyridin-7-yl)prop-2-yn-1-ol (6.83 g, 10.1 mmol) in anhydrous THF (43 mL) was added dropwise to a solution of 1 M LiAlH$_4$ in THF (21.3 mL, 21.3 mmol) and sodium methoxide (55 mg, 1.0 mmol) in THF (43 mL) at 0° C. under Ar. The reaction mixture was stirred for 1 h at 0° C. Dimethyl carbonate (1.83 g, 20.3 mmol) was added at 0° C., and the mixture was stirred for 10 min at 0° C. The reaction mixture was cooled to −78° C., and iodine (5.15 g, 20.3 mmol) in 20 mL of anhydrous THF was added dropwise. The reaction mixture was warmed to rt and stirred for 1 h. The reaction was quenched with 20 mL of MeOH. The mixture was diluted with water and EtOAc. The layers were separated, and the aqueous phase was extracted 4× with EtOAc. The combined organics were washed with brine, dried with Na$_2$SO$_4$, filtered and concentrated. The residue was purified by chromatography on silica gel (preflushed with 1% TEA/hexanes) to provide the title compound, (3.65 g, 4.55 mmol, 45% yield). MS(ESI) m/z 802.4 (M+H). Major regioisomer $^1$H NMR (400 MHz, CDCl$_3$) δ 7.26-7.14 (m, 30H), 6.28 (s, 1H), 5.85 (s, 1H), 4.37 (d, J=5.3 Hz, 2H).

Intermediate 171a: (E)-3-(3-hydroxy-1-(3-trityl-5-(tritylamino)-3H-[1,2,3]triazolo[4,5-b]pyridin-7-yl)prop-1-en-1-yl)benzonitrile

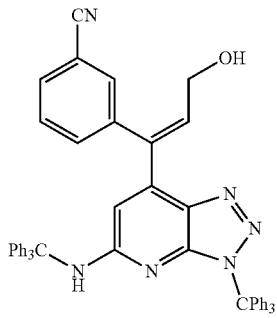

A solution of Intermediate 8-2 (200 mg, 0.25 mmol), (3-cyanophenyl)boronic acid (55 mg, 0.37 mmol), Cs$_2$CO$_3$ (244 mg, 0.75 mmol) and PdCl$_2$(dppf)-DCM adduct (41 mg, 0.050 mmol) in THF (1.8 mL) and H$_2$O (1.8 mL) under Ar atm was heated at 80° C. for 4 hours. The reaction mixture was partitioned between EtOAc and H$_2$O, and the phases were separated. The aqueous layer was extracted twice with EtOAc, and the combined organic layers were washed with brine, dried over Na$_2$SO$_4$, and concentrated. The residue was purified by chromatography on silica gel (preflushed with 1% TEA/hexanes) to provide the title compound, (160 mg, 0.21 mmol, 82%). MS(ESI) m/z 777.8 (M+H).

Intermediate 171b: (E)-3-(3-oxo-1-(3-trityl-5-(tritylamino)-3H-[1,2,3]triazolo[4,5-b]pyridin-7-yl)prop-1-en-1-yl)benzonitrile

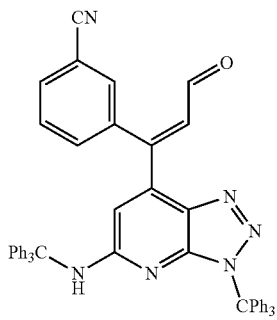

To a solution of Intermediate 171a (160 mg, 0.21 mmol) in DCM (4.1 mL) was added MnO$_2$ (304 mg, 3.5 mmol). The reaction mixture was stirred at rt overnight, and filtered through a pad of Celite. The solids were washed with DCM. The filtrate was evaporated to give a dark yellow foam as the title compound (160 mg, 0.21 mmol, 100%). MS(ESI) m/z 775.7 (M+H).

Intermediate 171c: (E)-3-(3-((4-phenylbicyclo[2.2.2]octan-1-yl)amino)-1-(3-trityl-5-(tritylamino)-3H-[1,2,3]triazolo[4,5-b]pyridin-7-yl)prop-1-en-1-yl)benzonitrile

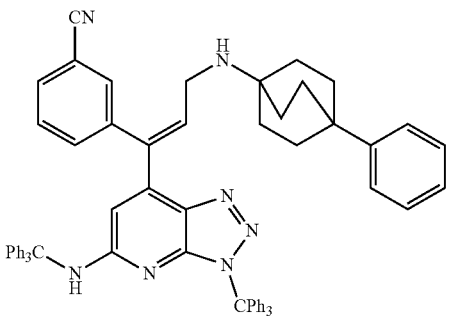

To a solution of Intermediate 171b (160 mg, 0.21 mmol) and Et$_3$N (260 µL, 1.8 mmol) in EtOH (2.0 mL) was added 4-phenylbicyclo[2.2.2]octan-1-amine (150 mg, 0.47 mmol). The reaction mixture was heated to 60° C. for 4 hours. After the reaction mixture was cooled to rt, THF (2.0 mL) and NaBH$_4$ (43 mg, 1.1 mmol) were added. The reaction solution was stirred at rt for 18 h. The mixture was partitioned between EtOAc and 1N NaOH, and the phases were separated. The aqueous layer was extracted twice with EtOAc, and the combined organic layers were washed with brine, dried over Na$_2$SO$_4$, and concentrated to provide the product, (0.197 g, 0.21 mmol, 100%). MS(ESI) m/z 960.9 (M+H).

Example 171: 7-(1-(3-cyanophenyl)-3-((4-phenylbicyclo[2.2.2]octan-1-yl)amino)propyl)-3H-[1,2,3]triazolo[4,5-b]pyridin-5-amine

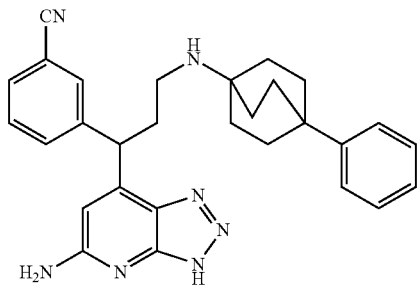 [SMILES: N#Cc1cccc(C(CCNC23CCC(c4ccccc4)(CC2)CC3)c2cc(N)nc3[nH]nnc23)c1]

To a solution of Intermediate 171c (0.197 g, 0.210 mmol) in DCM (7.1 mL) was added TFA (1.8 mL). The reaction solution was stirred for 1 h at rt before it was quenched with a few drops of Et$_3$SiH. The reaction mixture was concentrated in vacuo, and the solid residue was washed with hexanes and dried to provide the deprotected product (0.120 g, 0.21 mmol, 100% yield). MS(ESI) m/z 476.6 (M+H).

To a solution of the above product (120 mg, 0.21 mmol) in EtOH (9.2 mL) and EtOAc (1.0 mL) was added Pt$_2$O (12 mg, 0.051 mmol). The solution was degassed and pressurized with 20 psi hydrogen overnight. The reaction mixture was filtered and concentrated to give crude product, which was purified by preparative HPLC to give Example 171 (3.5 mg, 0.0048 mmol, 2% yield). MS (ESI) m/z 478.6 (M+H). Analytical HPLC Col A: 5.59 min, 98.5%; Col B: 6.75 min, 96.9%. $^1$H NMR (500 MHz, MEOH-d4) δ 7.84 (s, 1H), 7.74 (d, J=8.3 Hz, 1H), 7.62-7.55 (m, 1H), 7.52-7.42 (m, 1H), 7.26-7.13 (m, 4H), 7.10-7.02 (m, 1H), 6.43 (br. s., 1H), 4.53 (t, J=7.4 Hz, 1H), 2.95-2.87 (m, 1H), 2.86-2.70 (m, 2H), 2.54 (s, 1H), 1.95-1.88 (m, 6H), 1.84-1.74 (m, 6H). LC: 5.59 min, Method A Example 172. 7-(1-(3-(aminomethyl)phenyl)-3-((4-phenylbicyclo[2.2.2]octan-1-yl)amino)propyl)-3H-[1,2,3]triazolo[4,5-b]pyridin-5-amine

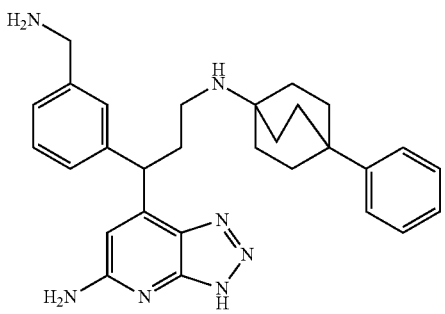 [SMILES: NCc1cccc(C(CCNC23CCC(c4ccccc4)(CC2)CC3)c2cc(N)nc3[nH]nnc23)c1]

Example 172 was an additional product from the reduction of Example 171. It was purified by preparative HPLC (10% ACN-90% H2O-0.1% TFA solvent A, 90% ACN-10% H20-0.1% TFA solvent B, 5-100% solvent B, XBridge Prep 19×100 mm C18 5u, 10 minutes) to give Example 172 (14 mg, 0.014 mmol, 6% yield). MS (ESI) m/z 482.7 (M+H). Analytical HPLC Col A: 4.04 min, 100%; Col B: 5.08 min, 85%. $^1$H NMR (500 MHz, MEOH-d4) δ 7.66-7.58 (m, 2H), 7.55-7.46 (m, 1H), 7.44-7.36 (m, 1H), 7.36-7.25 (m, 4H), 7.21-7.14 (m, 1H), 6.64-6.57 (m, 1H), 4.68-4.60 (m, 1H), 4.18-4.07 (m, 2H), 3.08-2.93 (m, 2H), 2.92-2.80 (m, 1H), 2.69-2.60 (m, 1H), 2.08-1.99 (m, 6H), 1.94-1.85 (m, 6H). LC: 4.04 min, Method A Examples 155-163, and 165-168 were made by similar procedures as Example 171, using commercial boronic acids in the conversion of intermediates 8-2 to 8-3, and the appropriate amine in the reductive amination.

Example 164 was prepared from the trityl protected intermediate of Example 163, using standard LiAlH$_4$ reduction conditions.

General Route 9 (see Scheme 9):

Intermediate 9-2: 3-3-phenyl-3-(3-trityl-5-(tritylamino)-3H-[1,2,3]triazolo[4,5-b]pyridin-7-yl)propan-1-ol

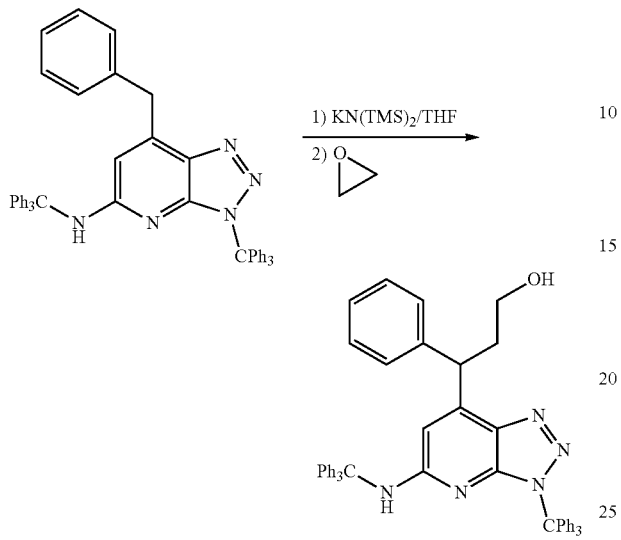

To an oven-dried flask was added a solution of 7-benzyl-N,3-ditrityl-3H-[1,2,3]triazolo[4,5-b]pyridin-5-amine (1.0 g, 1.4 mmol) in toluene (10 mL) and DCM (10 mL). The reaction solution was filtered through a pad of alumina, concentrated under reduced pressure and dried in vacuo for 2 h. A solution of Ar-sparged anhydrous THF (25 mL) was added to the reaction flask, which was evacuated and purged with Ar (3×). A solution of KN(TMS)$_2$ (3.5 mL, 3.5 mmol, 1.0 M in THF) was added to the reaction flask under Ar, which was evacuated and back filled with Ar (3×). After the mixture was stirred for 10 min, a solution of oxirane (2.9 mL, 2.9 mmol, 1 M in THF) was added to the reaction flask. The reaction mixture was stirred at rt for 10 h. The mixture was treated with a saturated solution of NH$_4$Cl, extracted with EtOAc, washed with brine, and dried over MgSO$_4$. The crude was purified by column chromatography (EtOAc/hexanes from 0-100%) to obtain 3-3-phenyl-3-(3-trityl-5-(tritylamino)-3H-[1,2,3]triazolo[4,5-b]pyridin-7-yl)propan-1-ol (0.78 g, 1.0 mmol, 73% yield) as a white solid. MS (ESI) m/z 754.3 (M+H). 3-3-phenyl-3-(3-trityl-5-(tritylamino)-3H-[1,2,3]triazolo[4,5-b]pyridin-7-yl)propan-1-ol was separated into enantiomers using SFC HPLC (Instrument: Agilent Aurora Analytical SFC, Column: (R,R)-Whelk-O 1, 4.6×250 mm, 5 micron, Mobile Phase: 30% MeOH-0.1% DEA/70% CO$_2$, Flow Conditions: 2 mL/min, 150 Bar, 40° C., Detector Wavelength: 220 nm. Injection Details: 10 μL of 1 mg/mL in MeOH:CAN). The R enantiomer was the first peak that eluted.

Intermediate 9-3: (R)-methyl 3-phenyl-3-(3-trityl-5-(tritylamino)-3H-[1,2,3]triazolo[4,5-b]pyridin-7-yl)propanoate Step A:

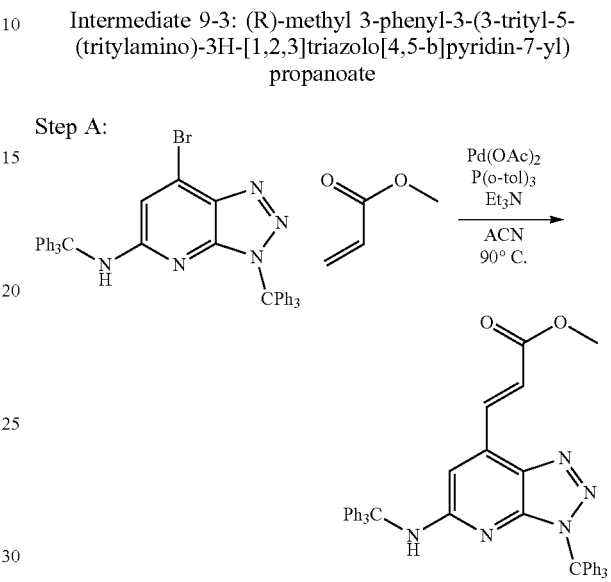

A solution of 7-bromo-N,3-ditrityl-3H-[1,2,3]triazolo[4,5-b]pyridin-5-amine (3.0 g, 4.3 mmol), Et$_3$N (2.4 mL, 17 mmol), methyl acrylate (1.6 mL, 17 mmol), tri-o-tolylphosphine (0.37 g, 1.2 mmol) and PdOAc$_2$ (0.14 g, 0.60 mmol) in acetonitrile (7 mL) in a pressure-released vessel was evacuated, and the vessel was back-filled with Ar (3×), sealed and heated at 90° C. for 3 days. The reaction mixture was diluted with EtOAc, washed with brine, dried over MgSO$_4$, and concentrated in vacuo. The residue was purified by column chromatography (EtOAc/hexanes loading in DCM+0.3 mL TEA) to obtain (E)-methyl 3-(3-trityl-5-(tritylamino)-3H-[1,2,3]triazolo[4,5-b]pyridin-7-yl)acrylate (2.3 g, 3.2 mmol, 74% yield) as a yellow solid. MS (ESI) m/z 704.3 (M+H).

Step B:

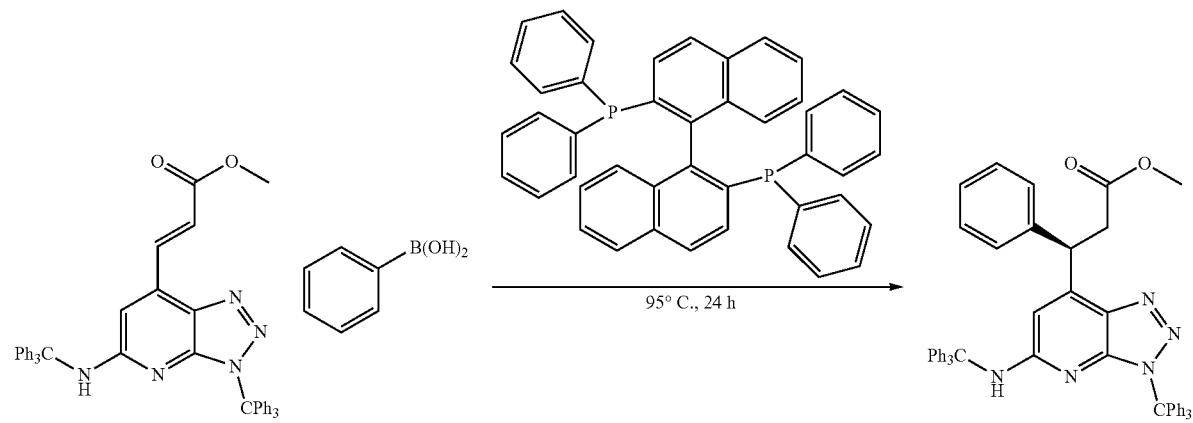

Bis(Norbonadiene)Rhodium(I) tetrafluoroborate (0.18 g, 0.47 mmol) and (S)-(−)-2,2′-bis(diphenylphosphino)-1,1′-binaphthyl (0.29 g, 0.47 mmol) were added to a mixture of phenylboronic acid (1.4 g, 12 mmol) in Ar sparged dioxane (12 mL) under Ar. The reaction vessel was evacuated and backfilled with Ar (3×). After 1 h of agitation at ambient temperature, a solution of (E)-methyl 3-(3-trityl-5-(tritylamino)-3H-[1,2,3]triazolo[4,5-b]pyridin-7-yl)acrylate (3.3 g, 4.7 mmol) in dioxane (15 mL) was added via a syringe, followed by Et₃N (3.3 mL, 23 mmol). The reaction mixture was heated at 85° C. overnight. The mixture was diluted with EtOAc, washed with brine (2×), dried over MgSO₄ and concentrated in vacuo. The crude was purified by column chromatography (EtOAc/hexanes) to obtain (R)-methyl 3-phenyl-3-(3-trityl-5-(tritylamino)-3H-[1,2,3]triazolo[4,5-b]pyridin-7-yl)propanoate (2.9 g, 2.6 mmol, 55% yield) as a yellow solid. MS (ESI) m/z 782.3 (M+H).

Intermediate 9-2 (alternate preparation): (R)-3-phenyl-3-(3-trityl-5-(tritylamino)-3H-[1,2,3]triazolo[4,5-b]pyridin-7-yl)propan-1-ol

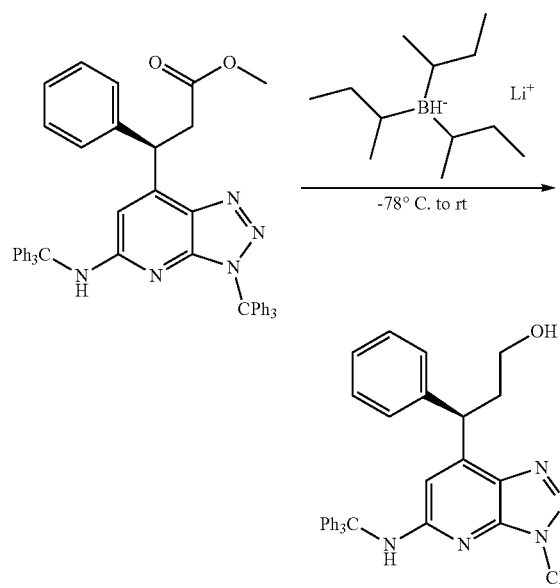

To a solution of (R)-methyl 3-phenyl-3-(3-trityl-5-(tritylamino)-3H-[1,2,3]triazolo[4,5-b]pyridin-7-yl)propanoate (770 mg, 0.985 mmol)) in THF (10 mL) cooled to −78° C. was added L-Selectride (1 M in THF, 3.0 mL, 3.0 mmol). The cooling bath was removed, and the reaction mixture was stirred at rt overnight. The mixture was quenched with saturated NH₄Cl. After extraction with EtOAc, the organics were washed with brine, dried over MgSO₄ and concentrated to obtain a colorless crude residue. The crude material was dissolved in minimal amount of DCM, loaded onto a 40-g Silica gel chromatography column and eluted with EtOAc/hexanes from 0-30% to afford (R)-3-phenyl-3-(3-trityl-5-(tritylamino)-3H-[1,2,3]triazolo[4,5-b]pyridin-7-yl)propan-1-ol (638 mg, 0.847 mmol, 86% yield).

Intermediate 9-4: (R)-7-(3-bromo-1-phenylpropyl)-N,3-ditrityl-3H-[1,2,3]triazolo[4,5-b]pyridin-5-amine

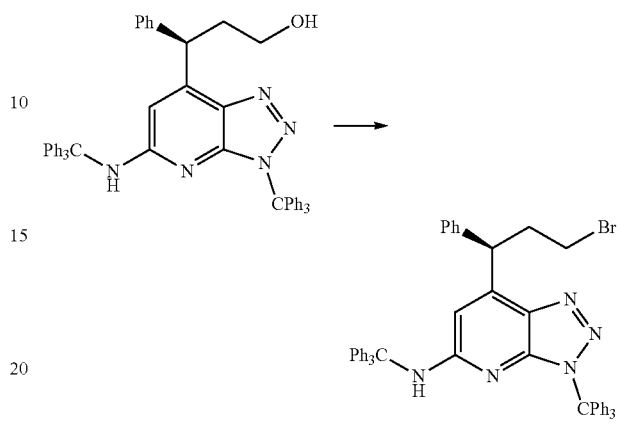

To a solution of (R)-3-phenyl-3-(3-trityl-5-(tritylamino)-3H-[1,2,3]triazolo[4,5-b]pyridin-7-yl)propan-1-ol (0.370 g, 0.491 mmol) in DCM (4.9 mL) were added NaHCO₃ (0.062 g, 0.74 mmol), PPh₃ (0.257 g, 0.982 mmol) and CBr₄ (0.325 g, 0.982 mmol), and the reaction mixture was stirred overnight. The reaction mixture was filtered through silica gel (eluted with EtOAc) and concentrated, and the residue was purified by silica gel chromatography (0-20% EtOAc-loaded in 4:1 DCM/TEA-pulled dry) to furnish (R)-7-(3-bromo-1-phenylpropyl)-N,3-ditrityl-3H-[1,2,3]triazolo[4,5-b]pyridin-5-amine (0.383 g, 0.469 mmol, 96% yield).

Intermediate 178a: ethyl 4-phenylcyclohexylcarbamate

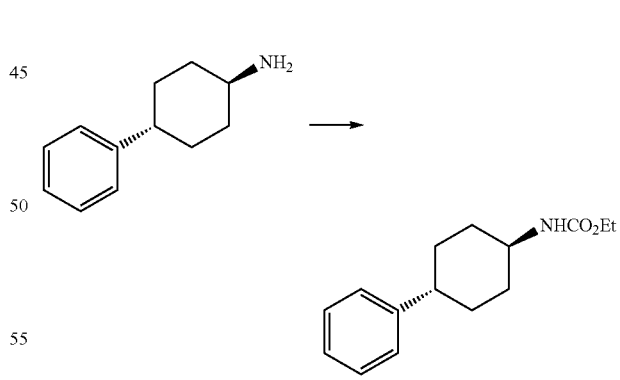

To a solution of (4)-4-phenylcyclohexanamine (0.770 g, 4.39 mmol) in DCM (44 mL) was added Hinig's base (2.3 mL, 13 mmol) followed by EtO₂CCl (0.46 mL, 4.8 mmol) at 0° C. The reaction mixture was allowed to warm to rt overnight. The mixture was diluted with DCM and washed with 10% HCl. The organic layer was concentrated to furnish ethyl 4-phenylcyclohexylcarbamate (1.09 g, 4.39 mmol, 100% yield) which was used as is. MS (ESI) m/z=248.5

Intermediate 178b: N-methyl-4-phenylcyclohexanamine

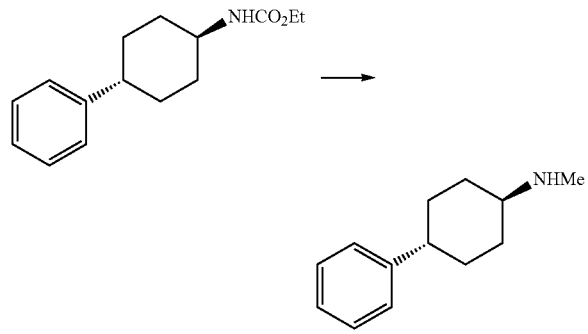

To a solution of ethyl 4-phenylcyclohexylcarbamate (1.09 g, 4.39 mmol) in THF (18 mL) was added LiAlH₄ (0.833 g, 21.9 mmol). The reaction mixture was heated to 60° C. in a sealed vessel overnight. The reaction was quenched with Rochelle's salt and extracted with EtOAc. The organic layer was concentrated and used as is as N-methyl-4-phenylcyclohexanamine (0.420 g, 2.22 mmol, 50.5% yield) in the subsequent alkylation step. MS (ESI) m/z=190.4

Example 178: 7-(3-(methyl(4-phenylcyclohexyl)amino)-1-phenylpropyl)-3H-[1,2,3]triazolo[4,5-b]pyridin-5-amine

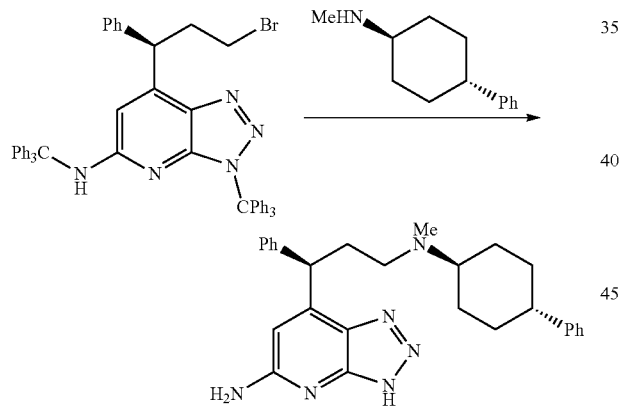

To a solution of 7-(3-bromo-1-phenylpropyl)-N,3-ditrityl-3H-[1,2,3]triazolo[4,5-b]pyridin-5-amine (0.100 g, 0.122 mmol) and N-methyl-4-phenylcyclohexanamine (0.070 g, 0.37 mmol) in DMF (1.2 mL) were added K₂CO₃ (0.085 g, 0.61 mmol) and KI (0.020 g, 0.12 mmol), and the reaction mixture was heated to 80° C. overnight. The reaction mixture was extracted from water with EtOAc. The organic layer was washed with water and brine, the dried over Na₂SO₄. The mixture was filtered and concentrated to furnish 7-(3-(methyl(4-phenylcyclohexyl)amino)-1-phenylpropyl)-N,3-ditrityl-3H-[1,2,3]triazolo[4,5-b]pyridin-5-amine (0.113 g, 0.122 mmol, 100% yield), which was used without further manipulation. The trityl intermediate (0.065 g, 0.070 mmol) was dissolved in DCM (2.8 mL)/TFA (0.70 mL) followed by addition of TES-H (0.11 mL, 0.70 mmol), and the reaction mixture was stirred overnight. The reaction mixture was concentrated, and the residue purified via preparative HPLC to furnish 7-(3-(methyl(4-phenylcyclohexyl)amino)-1-phenylpropyl)-3H-[1,2,3]triazolo[4,5-b]pyridin-5-amine (27.4 mg, 0.0610 mmol, 87%). LC: 1.37 min, Method C The amine intermediate for Examples 175-176, 180-185 were either known, commercially available or prepared as follows. The amine intermediate for Example 179 was prepared analogously to that for Example 178 described above.

Example 177: 4-((3-(5-amino-3H-[1,2,3]triazolo[4,5-b]pyridin-7-yl)-3-phenylpropyl)amino)-1-phenylcyclohexane-1-carbonitrile

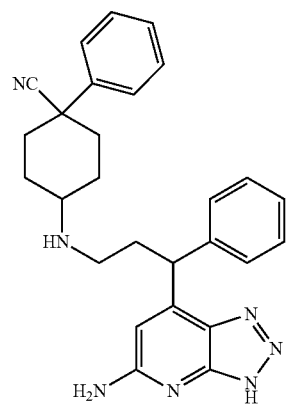 [SMILES: N#CC1(c2ccccc2)CCC(NCCC(c2ccccc2)c2cc(N)nc3[nH]nnc23)CC1]

Intermediate 177a: 7-(3-amino-1-phenylpropyl)-N,3-ditrityl-3H-[1,2,3]triazolo[4,5-b]pyridin-5-amine

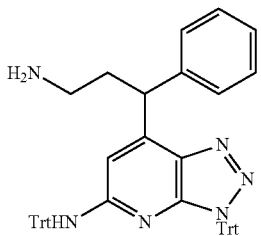

A solution of 7-(3-bromo-1-phenylpropyl)-N,3-ditrityl-3H-[1,2,3]triazolo[4,5-b]pyridin-5-amine (0.10 g, 0.12 mmol) and NH₃ (1.4 mL, 9.8 mmol) in MeOH with DMF (0.5 mL) was heated overnight at 80° C. The mixture was partially concentrated and diluted with EtOAc. The mixture was washed with water and brine, dried over Na₂SO₄ and concentrated in vacuo. The crude product was purified by flash chromatography (0% to 20% MeOH in DCM over 10 min using a 4 g silica gel column) to yield 7-(3-amino-1-phenylpropyl)-N,3-ditrityl-3H-[1,2,3]triazolo[4,5-b]pyridin-5-amine (34 mg, 37% yield). MS (ESI) m/z 753.4 (M+H).

Example 177: 4-((3-(5-amino-3H-[1,2,3]triazolo[4,5-b]pyridin-7-yl)-3-phenylpropyl)amino)-1-phenyl-cyclohexane-1-carbonitrile

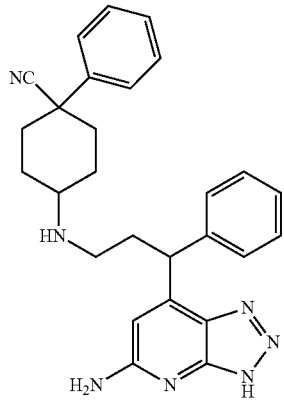 [SMILES: N#CC1(c2ccccc2)CCC(NCCC(c2ccccc2)c2cc(N)nc3[nH]nnc23)CC1]

A mixture of 7-(3-amino-1-phenylpropyl)-N,3-ditrityl-3H-[1,2,3]triazolo[4,5-b]pyridin-5-amine (0.03 g, 0.040 mmol), 4-oxo-1-phenylcyclohexanecarbonitrile (7.9 mg, 0.040 mmol), sodium cyanoborohydride (0.013 g, 0.20 mmol) and formic acid (2 μL) in MeOH (0.5 mL) was heated in the microwave for 1 h at 90° C. The mixture was concentrated, and the trityls were removed using the General Deprotection Procedure to yield the title compound (4.4 mg, 23% yield). $^1$H NMR (500 MHz, DMSO-d6) δ 8.79-8.61 (m, 1H), 7.52-7.46 (m, 4H), 7.43 (m, 2H), 7.39-7.31 (m, 3H), 7.25 (m, 1H), 6.46 (s, 1H), 4.48 (t, J=7.9 Hz, 1H), 3.57-3.47 (m, 1H), 3.24-3.13 (m, 1H), 3.01-2.80 (m, 2H), 2.77-2.67 (m, 1H), 2.24-2.08 (m, 4H), 2.00-1.86 (m, 2H), 1.76-1.63 (m, 2H). MS (ESI) m/z 452.1 (M+H). LC: 1.22 min, Method C General Route 10 (see Scheme 10):

Intermediate 10-1: (R)-3-phenyl-3-(3-trityl-5-(tritylamino)-3H-[1,2,3]triazolo[4,5-b]pyridin-7-yl)propanal

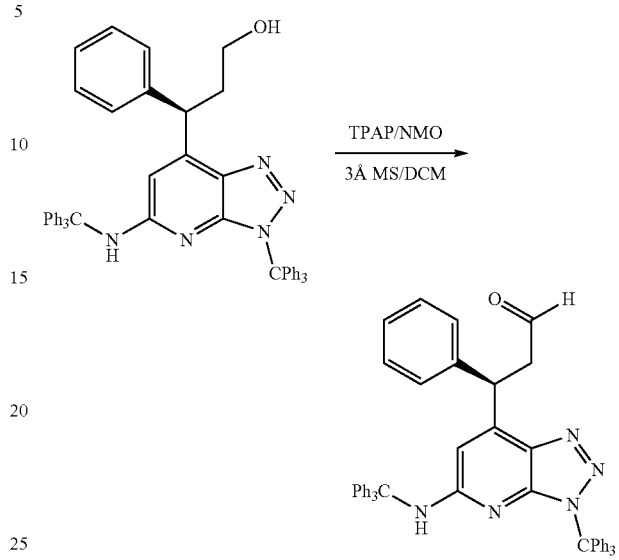

To (R)-3-phenyl-3-(3-trityl-5-(tritylamino)-3H-[1,2,3]triazolo[4,5-b]pyridin-7-yl)propan-1-ol (3.3 g, 4.4 mmol), NMO (0.77 g, 6.6 mmol), TPAP (0.13 g, 0.31 mmol) and 3 Å mol sieves (powdered) (300 mg, 4.4 mmol) under nitrogen was added DCM (5 mL), and the mixture was stirred at rt overnight. The reaction mixture was filtered through Celite with the aid of additional DCM and concentrated in vacuo. The crude product was purified by column chromatography (EtOAc/hexanes with a column pretreated with TEA) to yield (R)-3-phenyl-3-(3-trityl-5-(tritylamino)-3H-[1,2,3]triazolo[4,5-b]pyridin-7-yl)propanal (1.2 g, 1.6 mmol, 36% yield). MS (ESI) m/z 752.3 (M+H).

Example 190: (R)-2-((3-(5-amino-3H-[1,2,3]triazolo[4,5-b]pyridin-7-yl)-3-phenylpropyl)(4-phenylbicyclo[2.2.2]octan-1-yl)amino)acetamide

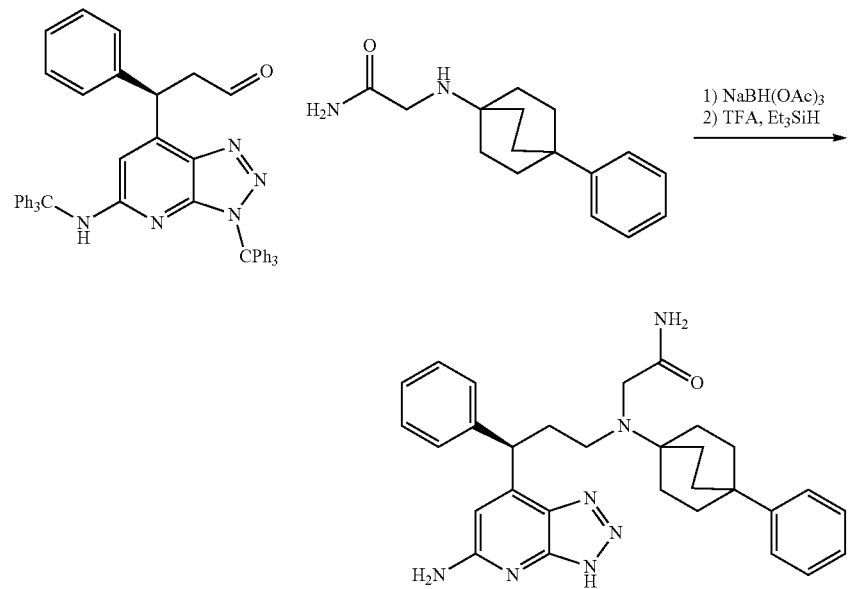

To (R)-3-phenyl-3-(3-trityl-5-(tritylamino)-3H-[1,2,3]triazolo[4,5-b]pyridin-7-yl)propanal (0.070 g, 0.093 mmol) dissolved in DCM (8 mL) was added 2-((4-phenylbicyclo[2.2.2]octan-1-yl)amino)acetamide (0.026 g, 0.10 mmol) and AcOH (6 μL, 0.1 mmol) followed by sodium triacetoxyborohydride (0.024 g, 0.11 mmol). The reaction mixture was stirred overnight, concentrated and (R)-2-((3-phenyl-3-(3-trityl-5-(tritylamino)-3H-[1,2,3]triazolo[4,5-b]pyridin-7-yl)propyl)(4-phenylbicyclo[2.2.2]octan-1-yl)amino)acetamide (0.093 g, 0.094 mmol, 100% yield) was used directly. MS (ESI) m/z 994.5 (M+H). Trityl groups were removed using the General Deprotection Procedures followed by preparative HPLC to furnish (R)-2-((3-(5-amino-3H-[1,2,3]triazolo[4,5-b]pyridin-7-yl)-3-phenylpropyl)(4-phenylbicyclo[2.2.2]octan-1-yl)amino)acetamide (0.0061 g, 11 μmol, 12% yield). ¹H NMR (500 MHz, MeOH-d4) δ 7.35 (d, J=7.7 Hz, 2H), 7.20 (t, J=7.6 Hz, 2H), 7.16-7.07 (m, 5H), 7.02-6.93 (m, 1H), 6.47 (s, 1H), 4.52 (t, J=7.6 Hz, 1H), 3.15-3.02 (m, 2H), 2.53-2.47 (m, 2H), 2.37 (dd, J=13.5, 5.5 Hz, 1H), 2.24-2.14 (m, 1H), 1.75-1.68 (m, 6H), 1.54 (d, J=5.8 Hz, 6H). MS (ESI) m/z 510.2 (M+H). LC: 1.32 min, Method C Intermediate 196: N-(2-methoxyethyl)-4-phenylbicyclo[2.2.2]octan-1-amine

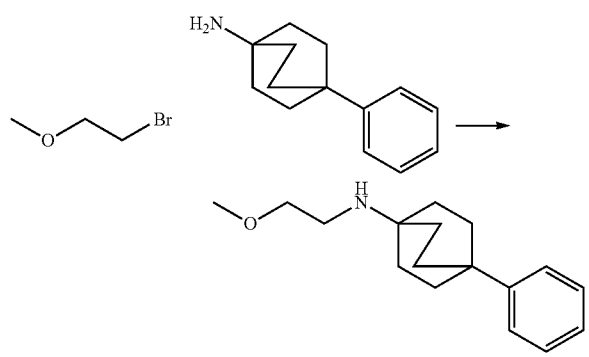

To 4-phenylbicyclo[2.2.2]octan-1-amine (0.10 g, 0.50 mmol) dissolved in acetonitrile (1.5 mL) with K₂CO₃ (0.096 g, 0.70 mmol) was added 1-bromo-2-methoxyethane (0.069 g, 0.50 mmol), and the mixture was stirred overnight in a sealed tube at 80° C. overnight. The reaction mixture was filtered and concentrated to furnish N-(2-methoxyethyl)-4-phenylbicyclo[2.2.2]octan-1-amine (0.13 g, 0.50 mmol, 100% yield), suitable for direct use. MS (ESI) m/z 260.2 (M+H).

Intermediates 189, 191-193, 195, and 198 were prepared analogously to Intermediate 196 outlined above.

Intermediate 199a: 2-fluoro-N-(4-phenylbicyclo[2.2.2]octan-1-yl)acetamide

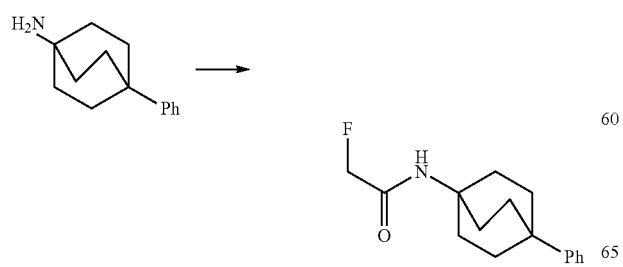

To a solution of 4-phenylbicyclo[2.2.2]octan-1-amine (0.100 g, 0.497 mmol), and Hünig's Base (0.17 mL, 0.98 mmol) was added 2-fluoroacetyl chloride (0.048 g, 0.50 mmol) in DCM (5.0 mL) at 0° C., and the reaction mixture was stirred overnight. The mixture was diluted with DCM and extracted with water. The organic layer was concentrated to furnish 2-fluoro-N-(4-phenylbicyclo[2.2.2]octan-1-yl)acetamide (0.130 g, 0.497 mmol, 100% yield). MS (ESI) m/z=262.1

Intermediate 199b: 4-phenyl-N-(2-fluoroethyl)bicyclo[2.2.2]octan-1-amine

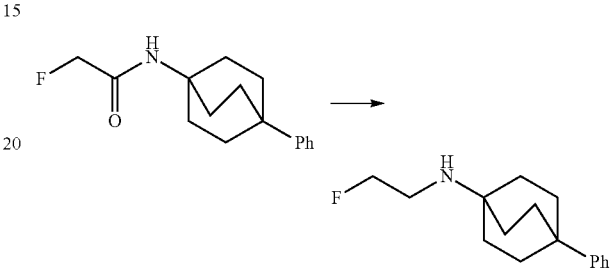

To a solution of 2-fluoro-N-(4-phenylbicyclo[2.2.2]octan-1-yl)acetamide (0.130 g, 0.497 mmol) in THF (2.5 ml) was added BH₃•THF (2.5 ml, 2.5 mmol), and the solution was stirred overnight at 60° C. The mixture was partitioned between water and EtOAc. The organic layer was concentrated, and the residue purified by silica gel chromatography to furnish N-(2-fluoroethyl)-4-phenylbicyclo[2.2.2]octan-1-amine (0.056 g, 0.226 mmol, 45.6% yield). MS (ESI) m/z=248.2

The amine intermediate for Example 197 was prepared analogously to that for Example 199 above.

General Route 11 (see Scheme 11):

Intermediate 11-1: (R)-methyl 3-phenyl-3-(3-trityl-5-(tritylamino)-3H-[1,2,3]triazolo[4,5-b]pyridin-7-yl)propanoic acid

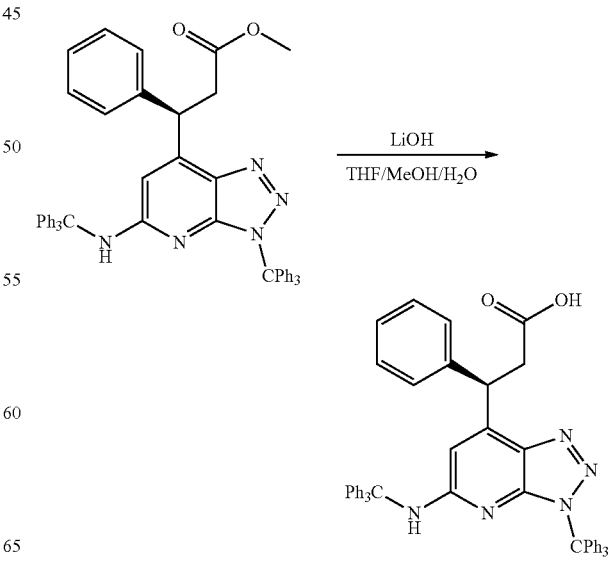

A mixture of (R)-methyl 3-phenyl-3-(3-trityl-5-(tritylamino)-3H-[1,2,3]triazolo[4,5-b]pyridin-7-yl)propanoate (500 mg, 0.64 mmol), and lithium hydroxide monohydrate (270 mg, 6.4 mmol) in THF (10 mL), MeOH (2.5 mL) and water (2.5 mL) was stirred at rt for 24 h. The reaction mixture was diluted with EtOAc, washed with brine (2×), dried over MgSO₄ and concentrated to obtain a yellow solid. MS (ESI) m/z 767.3 (M+H).

Intermediate 200a: (R)-3-phenyl-N-(4-phenylbicyclo[2.2.2]octan-1-yl)-3-(3-trityl-5-(tritylamino)-3H-[1,2,3]triazolo[4,5-b]pyridin-7-yl)propanamide

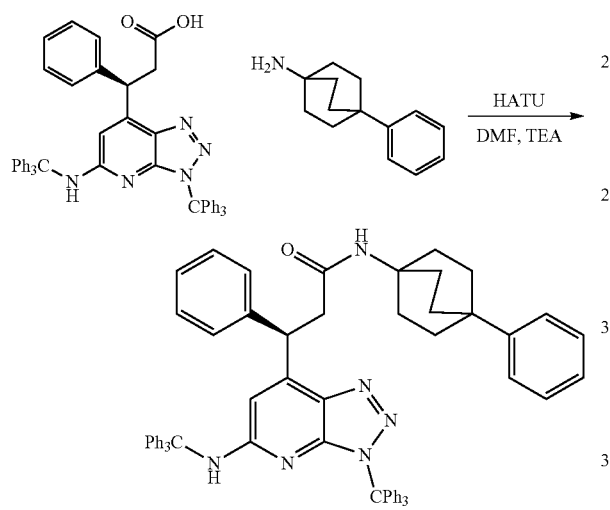

A mixture of (R)-3-phenyl-3-(3-trityl-5-(tritylamino)-3H-[1,2,3]triazolo[4,5-b]pyridin-7-yl)propanoic acid (45 mg, 0.059 mmol), 4-phenylbicyclo[2.2.2]octan-1-amine (24 mg, 0.12 mmol), o-benzotriazol-1-yl-N,N,N',N'-tetramethyluronium hexafluorophosphate (44 mg, 0.120 mmol) and TEA (18 mg, 0.18 mmol) in DMF (2 mL) was stirred for 2 h. The crude material was subjected to subsequent step without workup and characterization.

Example 200: (R)-3-(5-amino-3H-[1,2,3]triazolo[4,5-b]pyridin-7-yl)-3-phenyl-N-(4-phenylbicyclo[2.2.2]octan-1-yl)propanamide

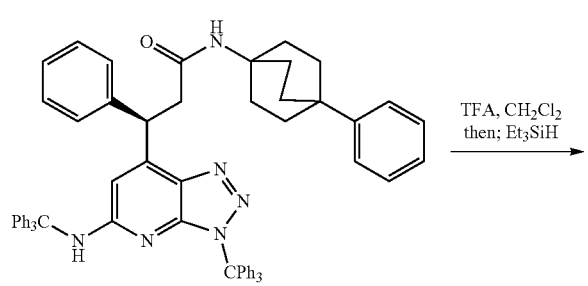

(R)-3-phenyl-N-(4-phenylbicyclo[2.2.2]octan-1-yl)-3-(3-trityl-5-(tritylamino)-3H-[1,2,3]triazolo[4,5-b]pyridin-7-yl)propanamide was deprotected according to the General Deprotection Procedure then purified by preparative HPLC to furnish Example 200 (2.2 mg, 25% yield). MS (ESI) m/z 467.3 (M+H). ¹H NMR (500 MHz, DMSO-d₆) δ 7.52-7.38 (m, 3H), 7.33-7.02 (m, 7H), 6.45 (s, 1H), 4.84 (t, J=7.9 Hz, 1H), 3.55 (d, J=6.1 Hz, 1H), 3.02 (d, J=7.6 Hz, 2H), 1.75 (s, 12H). LC: 1.68 min, Method C Examples 201-203 were prepared analogously to the procedure outlined for Example 200 above.

General Route 12 (see Scheme 12):

Intermediate 12-2: 7-(4-((tert-butyldimethylsilyl)oxy)-1-phenylbutyl)-N,3-ditrityl-3H-[1,2,3]triazolo[4,5-b]pyridin-5-amine

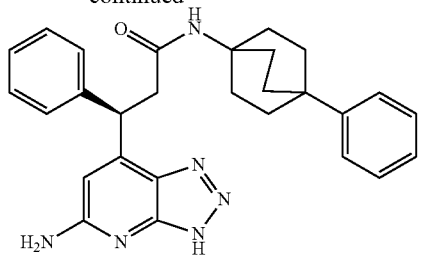

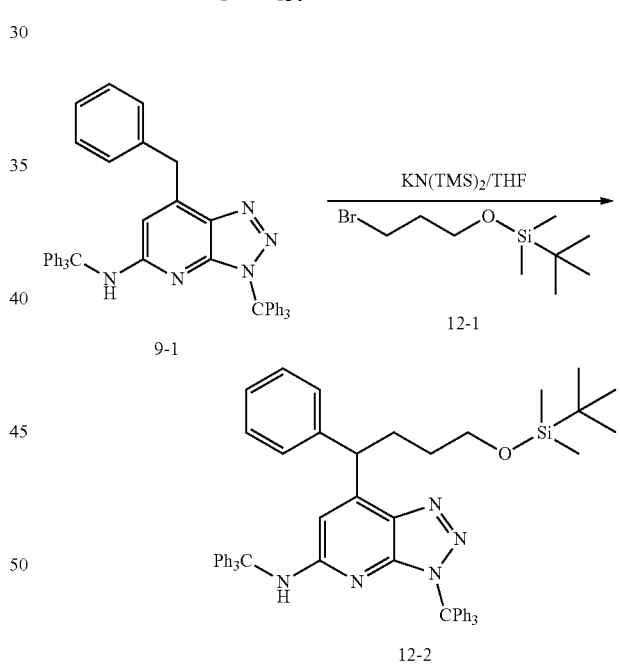

To an oven dried round bottomed flask was charged 7-benzyl-N,3-ditrityl-3H-[1,2,3]triazolo[4,5-b]pyridin-5-amine (1.96 g, 2.76 mmol), and the vial was thoroughly flushed with Ar. To the flask was added anhydrous THF (35 mL), a solution of (3-bromopropoxy)(tert-butyl)dimethylsilane (0.77 mL, 3.3 mmol) in anhydrous THF (5 mL), and lastly KN(TMS)₂ (1.0 M in THF, 8.3 mL, 8.3 mmol) was added dropwise. Stirring was continued under Ar at rt overnight. The reaction was quenched with brine. The phases separated, and the aqueous was extracted with EtOAc (3×). The combined organics were washed with brine, dried (Na₂SO₄), filtered and evaporated to give a residue that was purified by silica gel chromatography eluting with a gradient from 1-15% EtOAc (which contains 1% MeOH and 0.2% conc. aq. NH₃) in hexane to give 7-(4-((tert-butyldimethylsilyl)oxy)-1-phenylbutyl)-N,3-ditrityl-3H-[1,2,3]triazolo[4,5-b]pyridin-5-amine (1.53 g, 1.73 mmol, 62.9% yield). ¹H NMR (500 MHz, DCM-d2) δ 7.35-7.20 (m, 19H), 7.17-7.13 (m, 14H), 6.98 (dd, J=7.6, 1.8 Hz, 2H), 5.89 (s, 1H), 5.79 (s, 1H), 4.36 (t, J=7.8 Hz, 1H), 3.52-3.39 (m, 2H), 1.77 (q, J=7.9 Hz, 2H), 1.33-1.18 (m, 2H), 0.91-0.81 (m, 9H), −0.03 (d, J=0.8 Hz, 6H). MS (ESI) m/z: 882.6 (M+H)+.

Intermediate 12-3: (R)-4-phenyl-4-(3-trityl-5-(tritylamino)-3H-[1,2,3]triazolo[4,5-b]pyridin-7-yl)butan-1-ol

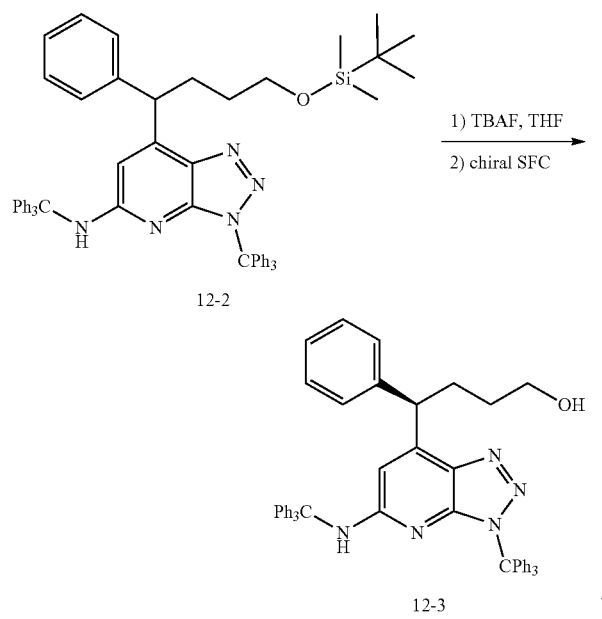

To 7-(4-((tert-butyldimethylsilyl)oxy)-1-phenylbutyl)-N,3-ditrityl-3H-[1,2,3]triazolo[4,5-b]pyridin-5-amine (1.53 g, 1.73 mmol) in anhydrous THF (10 mL) under nitrogen was added TBAF (1 M in THF, 2.1 mL, 2.1 mmol). The mixture was stirred at ambient temperature for 1 h. The reaction was quenched with water, the phases separated, aqueous extracted thrice with EtOAc and all organics combined and washed with brine, dried (Na₂SO₄), filtered and evaporated to give a residue which was purified by silica gel chromatography eluting with a gradient from 0-35% EtOAc in hexane and then with 100% EtOAc (EtOAc mobile phase contains 1% MeOH and 0.2% NH₄OH) to give 4-phenyl-4-(3-trityl-5-(tritylamino)-3H-[1,2,3]triazolo[4,5-b]pyridin-7-yl)butan-1-ol (1039 mg, 78.1% yield). ¹H NMR (500 MHz, DMSO-d₆) δ 7.56-7.50 (m, 1H), 7.30-7.25 (m, 4H), 7.22-7.13 (m, 10H), 7.11-7.06 (m, 3H), 7.02 (t, J=7.7 Hz, 6H), 6.91 (t, J=7.8 Hz, 13H), 4.40-4.32 (m, 2H), 3.40-3.32 (m, 2H), 2.07-1.99 (m, 2H), 1.33-1.21 (m, 2H). MS (ESI) m/z: 768.5 (M+H)+. 4-phenyl-4-(3-trityl-5-(tritylamino)-3H-[1,2,3]triazolo[4,5-b]pyridin-7-yl)butan-1-ol (1039 mg) was subjected to preparative SFC utilizing the following conditions: instrument: Burger Multigram II SFC; column: (R,R) Whelk-O1, 21×250 mm, 5 micron; mobile Phase: 35% MeOH/65% CO₂; flow conditions: 45 mL/min, 150 Bar, 40° C.; detector Wavelength: 220 nm; injection Details: 0.5 mL of 36 mg/mL in MeOH/DMF) to give as the first eluting compound (S)-4-phenyl-4-(3-trityl-5-(tritylamino)-3H-[1,2,3]triazolo[4,5-b]pyridin-7-yl)butan-1-ol (464 mg) and as the second eluting compound (R)-4-phenyl-4-(3-trityl-5-(tritylamino)-3H-[1,2,3]triazolo[4,5-b]pyridin-7-yl)butan-1-ol (474 mg). Structure was assigned based on conversion to active final product.

Intermediate 12-4: (R)-4-phenyl-4-(3-trityl-5-(tritylamino)-3H-[1,2,3]triazolo[4,5-b]pyridin-7-yl)butanal

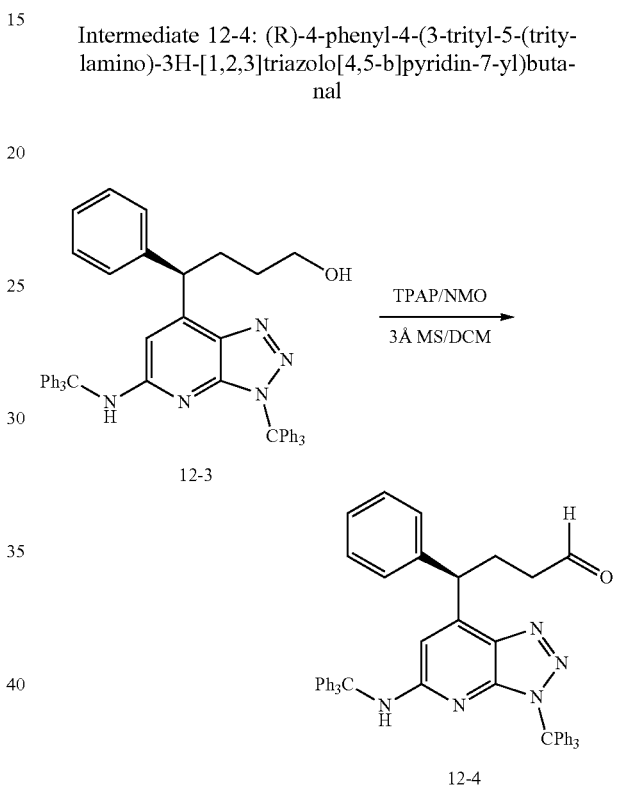

To (R)-4-phenyl-4-(3-trityl-5-(tritylamino)-3H-[1,2,3]triazolo[4,5-b]pyridin-7-yl)butan-1-ol (319 mg, 0.416 mmol), NMO (73 mg, 0.62 mmol), TPAP (12 mg, 0.033 mmol) and 3 Å mol sieves (powdered) (50 mg) under nitrogen was added DCM (anhydrous, 5 mL), and the mixture was stirred overnight at rt. Additional NMO (73 mg) and TPAP (20 mg, 0.13 eq) were added, and the mixture was stirred for an additional 6 h at rt. The reaction mixture was evaporated under reduced pressure to ~2 mL and purified by silica gel chromatography eluting with a gradient from 0-30% EtOAc in hexane (column pre-treated with hexanes containing 1% TEA) to give (R)-4-phenyl-4-(3-trityl-5-(tritylamino)-3H-[1,2,3]triazolo[4,5-b]pyridin-7-yl)butanal (110.5 mg, 0.144 mmol, 34.7% yield). ¹H NMR (500 MHz, DCM-d2) δ 9.54 (s, 1H), 7.27-7.20 (m, 17H), 7.19-7.11 (m, 15H), 7.03-6.99 (m, 2H), 5.85 (s, 1H), 5.82 (s, 1H), 4.36-4.31 (m, 1H), 2.17-2.01 (m, 3H), 1.26 (s, 1H). MS (ESI) m/z: 766.5 (M+H)+.

147

Example 204: (R)-7-(1-phenyl-4-(4-phenylpiperidin-1-yl)butyl)-3H-[1,2,3]triazolo[4,5-b]pyridin-5-amine

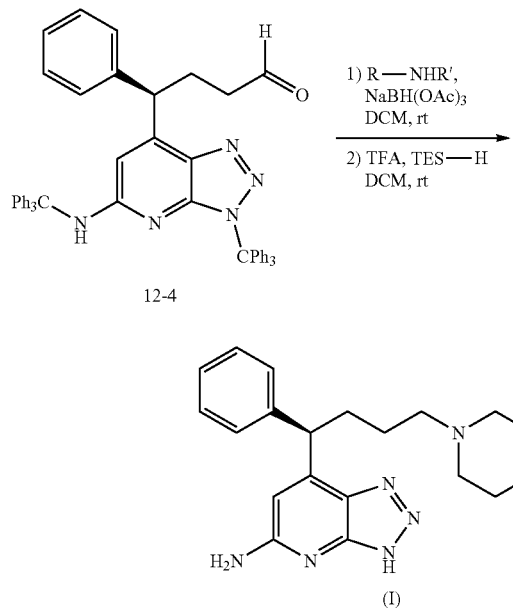

To (R)-4-phenyl-4-(3-trityl-5-(tritylamino)-3H-[1,2,3]triazolo[4,5-b]pyridin-7-yl)butanal (9.0 mg, 0.012 mmol) under nitrogen was added a solution of 4-phenylpiperidine (2.0 mg, 0.013 mmol) and AcOH (glacial, 0.7 μL, 0.01 mmol) in DCM (anhydrous, 1 mL). The mixture was stirred for 15 min followed by the addition of sodium triacetoxyborohydride (2.99 mg, 0.014 mmol), and stirring was continued overnight at rt. The reaction was quenched with saturated NaHCO$_3$(3 mL), phases were separated and the aqueous was extracted twice with DCM (2 mL). The combined organics were washed with brine, dried (Na$_2$SO$_4$), filtered and evaporated to a residue for (R)-7-(1-phenyl-4-(4-phenylpiperidin-1-yl)butyl)-N,3-ditrityl-3H-[1,2,3]triazolo[4,5-b]pyridin-5-amine (13.2 mg, 90% purity). MS (ESI) m/z: 911.6 (M+H)+. The trityl groups were removed using the General Deprotection Procedure followed by purification by preparative HPLC to give (R)-7-(1-phenyl-4-(4-phenylpiperidin-1-yl)butyl)-3H-[1,2,3]triazolo[4,5-b]pyridin-5-amine, TFA (3.97 mg, 6.98 μmol, 58.1% yield) as a colorless solid. $^1$H NMR (500 MHz, DCM-d2) δ 8.04 (br. s., 2H), 7.37-7.32 (m, 2H), 7.30-7.25 (m, 4H), 7.24-7.17 (m, 3H), 7.16-7.13 (m, 2H), 6.87 (s, 1H), 4.43 (t, J=7.7 Hz, 1H), 3.87 (d, J=11.6 Hz, 1H), 3.76 (d, J=11.6 Hz, 1H), 3.28-3.15 (m, 2H), 2.89-2.80 (m, 2H), 2.80-2.70 (m, 1H), 2.55-2.44 (m, 1H), 2.27-2.14 (m, 1H), 2.13-2.00 (m, 4H), 2.00-1.84 (m, 2H). MS (ESI) m/z: 427.1 (M+H)+. LC: 1.34 min, Method C Examples 205-222 were prepared analogously to the procedure outlined for Example 204 above.

148

General Route 13 (see Scheme 13):

Intermediate 223a: (4-(allyloxy)cyclohexyl)benzene

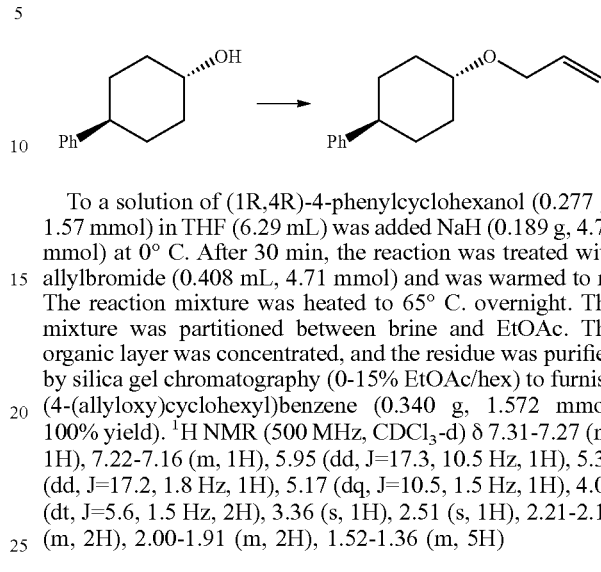

To a solution of (1R,4R)-4-phenylcyclohexanol (0.277 g, 1.57 mmol) in THF (6.29 mL) was added NaH (0.189 g, 4.71 mmol) at 0° C. After 30 min, the reaction was treated with allylbromide (0.408 mL, 4.71 mmol) and was warmed to rt. The reaction mixture was heated to 65° C. overnight. The mixture was partitioned between brine and EtOAc. The organic layer was concentrated, and the residue was purified by silica gel chromatography (0-15% EtOAc/hex) to furnish (4-(allyloxy)cyclohexyl)benzene (0.340 g, 1.572 mmol, 100% yield). $^1$H NMR (500 MHz, CDCl$_3$-d) δ 7.31-7.27 (m, 1H), 7.22-7.16 (m, 1H), 5.95 (dd, J=17.3, 10.5 Hz, 1H), 5.30 (dd, J=17.2, 1.8 Hz, 1H), 5.17 (dq, J=10.5, 1.5 Hz, 1H), 4.06 (dt, J=5.6, 1.5 Hz, 2H), 3.36 (s, 1H), 2.51 (s, 1H), 2.21-2.13 (m, 2H), 2.00-1.91 (m, 2H), 1.52-1.36 (m, 5H)

Intermediate 223b: 3-((4-phenylcyclohexyl)oxy)propane-1,2-diol

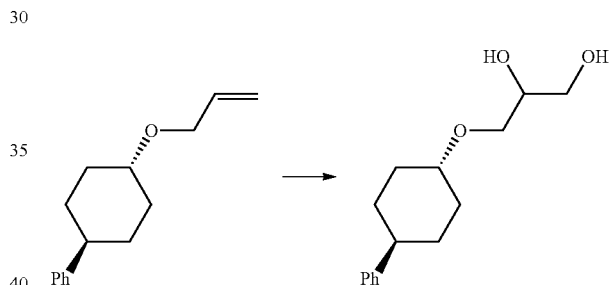

To a solution of (4-(allyloxy)cyclohexyl)benzene (0.340 g, 1.57 mmol) in acetone (2.4 mL) was added NMO (0.737 g, 6.29 mmol) in H$_2$O (0.786 mL) followed by OsO$_4$ (9.87 μL, 0.031 mmol) (added as a few drops in aq. solution), and the mixture was stirred overnight. The mixture was partitioned between brine and EtOAc. The organic layer was concentrated to furnish 3-((4-phenylcyclohexyl)oxy)propane-1,2-diol (0.394 g, 1.57 mmol, 100% yield) was used as is. MS (ESI) m/z=251.2

Intermediate 223c: 2-((4-phenylcyclohexyl)oxy)acetaldehyde

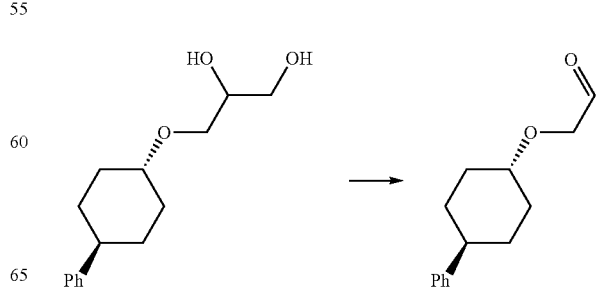

To a solution of 3-((4-phenylcyclohexyl)oxy)propane-1,2-diol (0.394 g, 1.57 mmol) in THF (7.9 mL) was added NaIO₄ (0.437 g, 2.04 mmol) in H₂O (7.9 mL) and the reaction mixture was stirred overnight. The solution was partitioned between brine and EtOAc. The organic layer was concentrated and the residue used as is as 2-((4-phenylcyclohexyl)oxy)acetaldehyde (0.343 g, 1.57 mmol, 100% yield). MS (ESI) m/z=150.0 (cyclohexyl cation)

Intermediate 223d:
2-((4-phenylcyclohexyl)oxy)ethanol

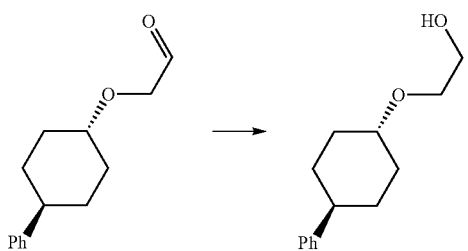 [SMILES: O=CCO[C@H]1CC[C@H](c2ccccc2)CC1 ; OCCO[C@H]1CC[C@H](c2ccccc2)CC1]

To a solution of 2-((4-phenylcyclohexyl)oxy)acetaldehyde (0.335 g, 1.54 mmol) in MeOH (15 mL) was added NaBH₄ (0.058 g, 1.5 mmol), and the mixture was stirred overnight. The mixture was partitioned between EtOAc and brine. The organic layer was filtered through silica gel and concentrated to furnish 2-((4-phenylcyclohexyl)oxy)ethanol which was used as is without further manipulation. MS (ESI) m/z=150.0 (cyclohexyl cation)

Intermediate 223e:
(4-(2-bromoethoxy)cyclohexyl)benzene

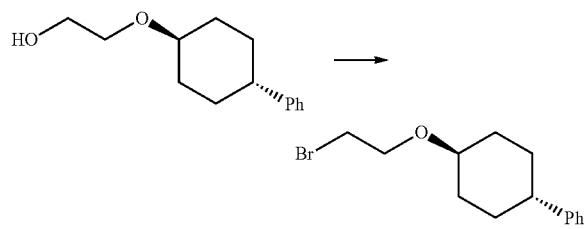

To a solution of 2-((4-phenylcyclohexyl)oxy)ethanol (0.511 g, 2.32 mmol) in THF (11.6 mL) was added CBr₄ (0.923 g, 2.78 mmol) followed by PPh₃ (0.730 g, 2.78 mmol), and the reaction mixture was stirred overnight. The reaction mixture was diluted with ether and adsorbed on silica gel. The resulting solid was placed on top of a silica gel plug and washed with ether. The filtrate was concentrated, and the residue was purified by silica gel chromatography (0-10% EtOAc/hex) to furnish (4-(2-bromoethoxy)cyclohexyl)benzene (0.245 g, 0.865 mmol, 37.3% yield).

Intermediate 223f: 7-(1-phenyl-3-(((1R,4R)-4-phenylcyclohexyl)oxy)propyl)-N,3-ditrityl-3H-[1,2,3]triazolo[4,5-b]pyridin-5-amine

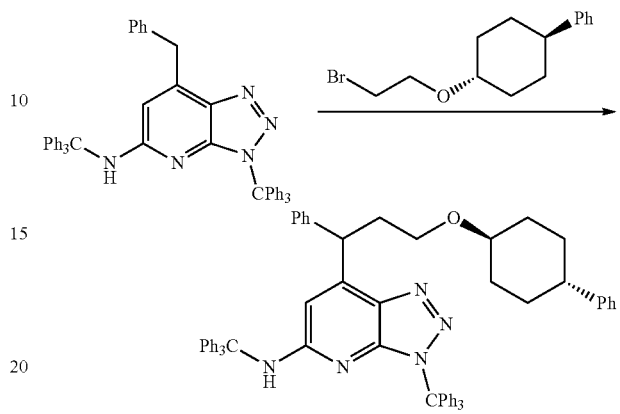

To a solution of 7-benzyl-N,3-ditrityl-3H-[1,2,3]triazolo[4,5-b]pyridin-5-amine (0.150 g, 0.211 mmol) in Ar sparged THF (2.1 mL) was added (4-(2-bromoethoxy)cyclohexyl)benzene (0.072 g, 0.25 mmol). After 10 min the solution was treated with (4-(2-bromoethoxy)cyclohexyl)benzene (0.072 g, 0.25 mmol) and the reaction was stirred for 1 h. The solution was extracted from brine with EtOAc. The organic layer was concentrated and used as is as 7-(1-phenyl-3-((4-phenylcyclohexyl)oxy)propyl)-N,3-ditrityl-3H-[1,2,3]triazolo[4,5-b]pyridin-5-amine (0.193 g, 0.211 mmol, 100% yield). MS (ESI) m/z=913.0

Example 223: 7-(1-phenyl-3-((4-phenylcyclohexyl)oxy)propyl)-3H-[1,2,3]triazolo[4,5-b]pyridin-5-amine

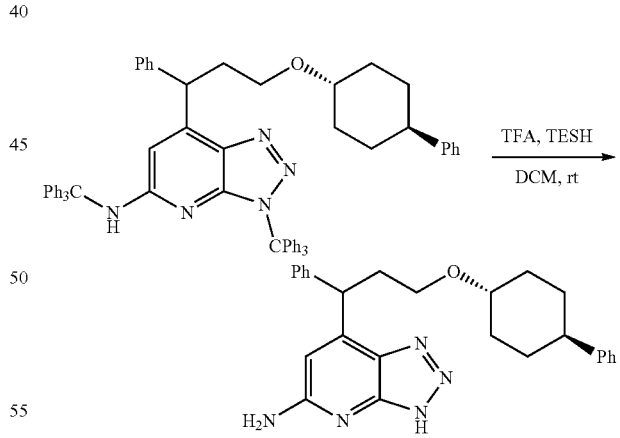

To a solution of 7-(1-phenyl-3-((4-phenylcyclohexyl)oxy)propyl)-N,3-ditrityl-3H-[1,2,3]triazolo[4,5-b]pyridin-5-amine (0.192 g, 0.211 mmol) in DCM (8.44 mL)/TFA (2.110 mL) was added TES-H (0.337 mL, 2.110 mmol). After 60 min, the mixture was concentrated and the residue purified by preparative HPLC to furnish 7-(1-phenyl-3-((4-phenylcyclohexyl)oxy)propyl)-3H-[1,2,3]triazolo[4,5-b]pyridin-5-amine (0.0209 g, 0.047 mmol, 22.24% yield). MS (ESI) m/z=428.3. ¹H NMR (500 MHz, DMSO-d₆) δ 7.43 (d, J=7.3 Hz, 2H), 7.30 (t, J=7.2 Hz, 2H), 7.26-7.08 (m, 6H), 6.70 (s, 1H), 4.55 (t, J=7.5 Hz, 1H), 3.37 (d, J=5.5 Hz, 2H), 3.12 (br. s., 1H), 2.46-2.27 (m, 2H), 1.91 (br. s., 2H), 1.72 (br. s., 2H), 1.43-1.28 (m, 2H), 1.25-1.07 (m, 2H). LC: 1.78 min, Method C Intermediate 224a: ethyl 4-(2-phenyl-2-(2-tosylhydrazono)ethyl)benzoate

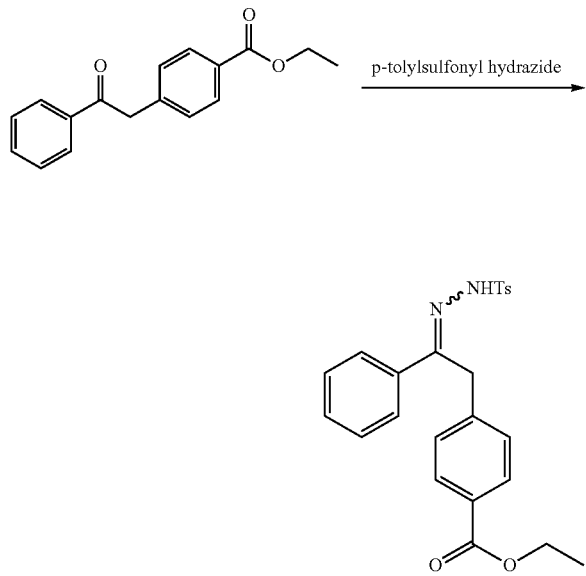

To ethyl 4-(2-oxo-2-phenylethyl)benzoate (1.0 g, 3.7 mmol) dissolved in EtOH (3.7 mL) was added 4-methylbenzenesulfonohydrazide (0.69 g, 3.7 mmol), and the mixture was heated to reflux overnight. The mixture was filtered to isolate the white solid ethyl 4-(2-phenyl-2-(2-tosylhydrazono)ethyl)benzoate (1.47 g, 3.20 mmol, 86% yield), MS (ESI) m/z 437.0 (M+H). $^1$H NMR (400 MHz, CDCl$_3$-d) δ 7.87 (d, J=8.3 Hz, 2H), 7.76-7.64 (m, 4H), 7.38 (t, J=8.1 Hz, 4H), 7.31-7.27 (m, 2H), 7.03 (d, J=8.6 Hz, 2H), 4.39 (q, J=7.2 Hz, 2H), 4.05 (s, 2H), 2.45 (s, 3H), 1.41 (t, J=7.1 Hz, 3H).

Intermediate 224b: ethyl 4-(2-(2,6-bis(2,5-dimethyl-1H-pyrrol-1-yl)pyridin-4-yl)-2-phenylvinyl)benzoate To ethyl 4-(2-phenyl-2-(2-tosylhydrazono)ethyl)benzoate (0.558 g, 1.28 mmol), chloro(2-dicyclohexylphosphino-2′,4′,6′-tri-i-propyl-1,1′-biphenyl)[2-(aminoethyl)phenyl]palladium(II) methyl-t-butylether adduct (0.038 g, 0.046 mmol), and 4-bromo-2,6-bis(2,5-dimethyl-1H-pyrrol-1-yl)pyridine (0.400 g, 1.16 mmol) in dioxane (4.65 mL) blanketed under Ar was added lithium 2-methylpropan-2-olate (0.223 g, 2.79 mmol), and the mixture was heated to 80° C. overnight. The reaction was cooled, and iodoethane (0.094 mL, 1.2 mmol) was added. The mixture was stirred overnight. The crude reaction was partitioned between EtOAc and water, and the aqueous was washed with EtOAc. The organics were dried over MgSO$_4$, filtered and concentrated. Crude material was purified via flash chromatography to furnish ethyl 4-(2-(2,6-bis(2,5-dimethyl-1H-pyrrol-1-yl)pyridin-4-yl)-2-phenylvinyl)benzoate (0.184 g, 30.7% yield). MS (ESI) m/z 516.1. $^1$H NMR (400 MHz, CDCl$_3$-d) δ 7.87 (d, J=8.2 Hz, 2H), 7.45-7.34 (m, 3H), 7.32-7.28 (m, 2H), 7.21-7.14 (m, 3H), 7.05 (s, 2H), 5.84 (s, 4H), 4.36 (q, J=7.1 Hz, 2H), 2.03 (s, 12H), 1.38 (t, J=7.1 Hz, 3H).

Intermediate 224c: ethyl 4-(2-(2,6-diaminopyridin-4-yl)-2-phenylvinyl)benzoate

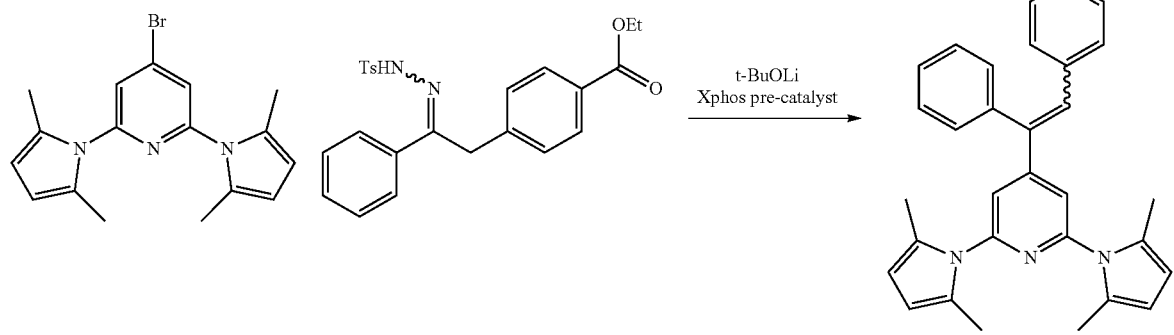

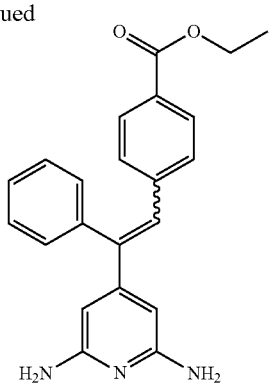

To ethyl 4-(2-(2,6-bis(2,5-dimethyl-1H-pyrrol-1-yl)pyridin-4-yl)-2-phenylvinyl)benzoate (0.184 g, 0.357 mmol) dissolved in EtOH (3.6 mL) was added TEA (0.50 mL, 3.6 mmol) and hydroxylamine hydrochloride (0.496 g, 7.14 mmol), and the mixture was heated to 80° C. overnight. Reaction was concentrated, partitioned between EtOAc and water, and aqueous was extracted 3× with EtOAc. The organic layer was dried over MgSO₄, filtered, concentrated and purified via flash chromatography to furnish ethyl 4-(2-(2,6-diaminopyridin-4-yl)-2-phenylvinyl)benzoate (0.226 g, 0.353 mmol, 99% yield) contaminated with residual EtOAc and TEA.

Intermediate 224d: ethyl 4-(2-(2,6-diaminopyridin-4-yl)-2-phenylethyl)benzoate

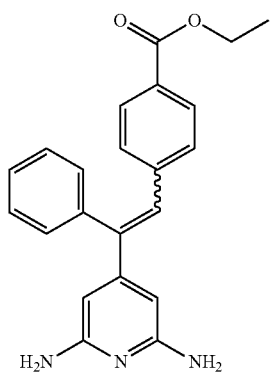

Pd/C, H₂

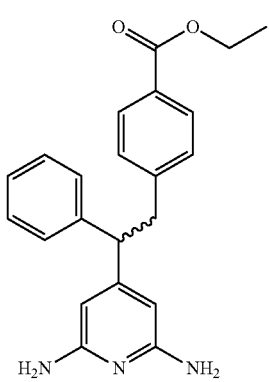

To ethyl 4-(2-(2,6-diaminopyridin-4-yl)-2-phenylvinyl)benzoate (0.226 g, 0.629 mmol) dissolved in EtOH (6.3 mL), was added AcOH (0.11 mL, 1.9 mmol) and Pd/C (0.067 g, 0.063 mmol). The flask was purged and evacuated with nitrogen 3×, and placed under 55 psi(g) atmosphere of hydrogen overnight. Filtered off Pd/C and concentrated to furnish ethyl 4-(2-(2,6-diaminopyridin-4-yl)-2-phenylethyl)benzoate (0.125 g, 0.346 mmol, 55.0% yield) MS (ESI) m/z 362.1 (M+H).

Intermediate 224e: (4-(2-(2,6-diaminopyridin-4-yl)-2-phenylethyl)phenyl)methanol, TFA

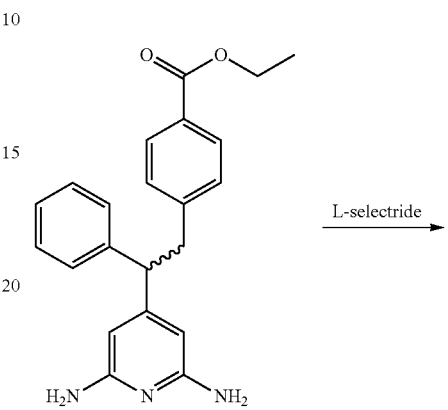

L-selectride

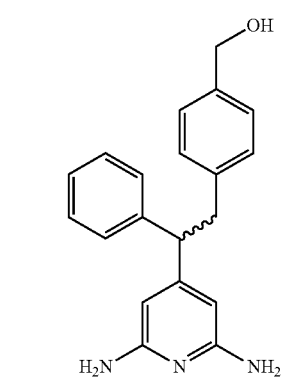

To ethyl 4-(2-(2,6-diaminopyridin-4-yl)-2-phenylethyl)benzoate (0.125 g, 0.346 mmol) in THF (3.5 mL) added L-Selectride (2.1 mL, 2.1 mmol), and the mixture was stirred overnight. The reaction was quenched with dilute HCl in MeOH, and concentrated. The crude product was purified via preparative reverse phase chromatography to furnish (4-(2-(2,6-diaminopyridin-4-yl)-2-phenylethyl)phenyl)methanol, TFA (0.0454 g, 30% yield). MS (ESI) m/z 320.0 (M+H).

Example 224: (4-(2-(5-amino-3H-[1,2,3]triazolo[4,5-b]pyridin-7-yl)-2-phenylethyl)phenyl)methanol

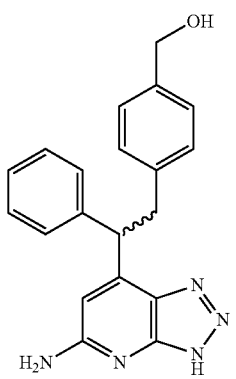 [SMILES: Nc1cc(C(Cc2ccc(CO)cc2)c2ccccc2)c2nn[nH]c2n1]

Example 224 was prepared from Intermediate 224e by methods described in the General procedures, Examples 2 and 11. MS (ESI) m/z 346.1 (M+H). ¹H NMR (400 MHz, CD₃CN) δ 7.50 (d, J=7.1 Hz, 2H), 7.32-7.22 (m, 2H), 7.21-7.11 (m, 5H), 6.52 (s, 1H), 5.37 (br. s., 2H), 4.83 (t, J=8.0 Hz, 1H), 4.45 (s, 2H), 3.76 (dd, J=13.7, 8.2 Hz, 1H), 3.58-3.43 (m, 1H). LC: 5.82 min, Method A Intermediate 225a: (Z)-1-(2,6-bis(2,5-dimethyl-1H-pyrrol-1-yl)pyridin-4-yl)-1,5-diphenylpent-1-en-3-ol

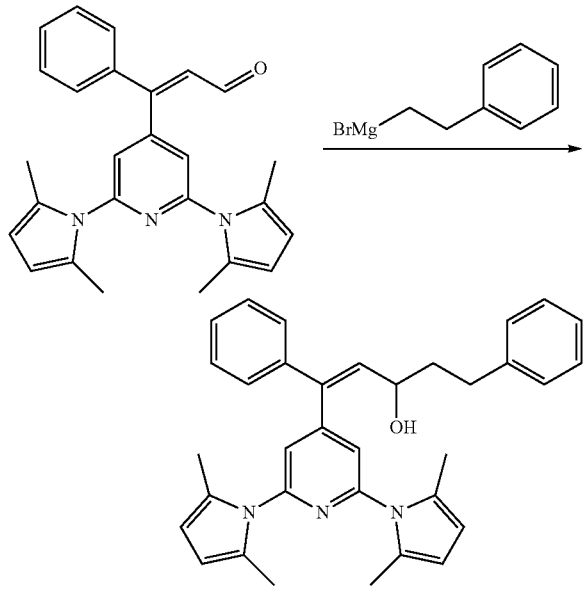

To a solution of (Z)-3-(2,6-bis(2,5-dimethyl-1H-pyrrol-1-yl)pyridin-4-yl)-3-phenylacrylaldehyde (Intermediate 4-1, 0.80 g, 2.0 mmol) in THF (10 mL) was added phenethylmagnesium bromide (6.1 mL, 3.0 mmol) at −78° C. After 1 h, the reaction was warmed to rt. The solution was then quenched via addition of brine and partitioned with EtOAc. The organic layer was concentrated, and the residue was purified by silica gel chromatography to furnish (Z)-1-(2,6-bis(2,5-dimethyl-1H-pyrrol-1-yl)pyridin-4-yl)-1,5-diphenylpent-1-en-3-ol (0.503 g, 1.00 mmol, 49.6% yield). MS (ESI) m/z=502.0. ¹H NMR (500 MHz, CDCL₃-d) δ 7.41-7.32 (m, 1H), 7.26-7.19 (m, 1H), 7.18-7.11 (m, 1H), 7.09 (s, 1H), 6.22 (d, J=9.4 Hz, 1H), 5.91 (s, 4H), 4.38-4.20 (m, 1H), 2.82-2.62 (m, 2H), 2.20-2.13 (m, 12H), 2.11-1.74 (m, 3H)

Intermediate 225b: (Z)-1-(2,6-diaminopyridin-4-yl)-1,5-diphenylpent-1-en-3-ol

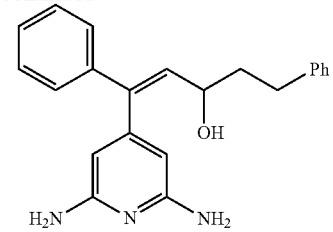

A slurry of (Z)-1-(2,6-bis(2,5-dimethyl-1H-pyrrol-1-yl)pyridin-4-yl)-1,5-diphenylpent-1-en-3-ol (0.503 g, 1.00 mmol), hydroxylamine hydrochloride (1.39 g, 20.0 mmol), TEA (1.4 mL, 10 mmol) in IPA (8.0 mL)/water (2.0 mL) was prepared and heated to 80° C. in a sealed vessel with stirring overnight. The reaction mixture was partitioned between saturated aq. NaHCO₃ and EtOAc. The organic layer was concentrated and the residue purified by silica gel chromatography to furnish 0.55 g of (Z)-1-(2,6-diaminopyridin-4-yl)-1,5-diphenylpent-1-en-3-ol that was contaminated with an oxime impurity. MS (ESI) m/z=346.0

Example 225: 1-(5-amino-3H-[1,2,3]triazolo[4,5-b]pyridin-7-yl)-1,5-diphenylpentan-3-ol, TFA

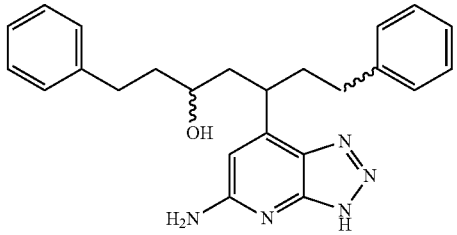 [SMILES: Nc1cc(C(CCc2ccccc2)CC(O)CCc2ccccc2)c2nn[nH]c2n1]

Example 225 was prepared from Intermediate 225b as described in the General Procedures and Examples 2 and 11. MS (ESI) m/z=374.0. ¹H NMR (500 MHz, MeOH-d4) δ 7.53-7.05 (m, 10H), 6.89 (s, 1H), 4.75 (dd, J=9.9, 5.8 Hz, 1H), 3.47-3.37 (m, 1H), 2.82-2.49 (m, 3H), 2.21 (ddd, J=14.2, 8.7, 5.8 Hz, 1H), 1.95-1.74 (m, 2H). LC: 6.31 min, Method A Intermediate 226a: tert-butyl (2-(2,6-bis(2,5-dimethyl-1H-pyrrol-1-yl)pyridin-4-yl)-2-phenylethyl)carbamate

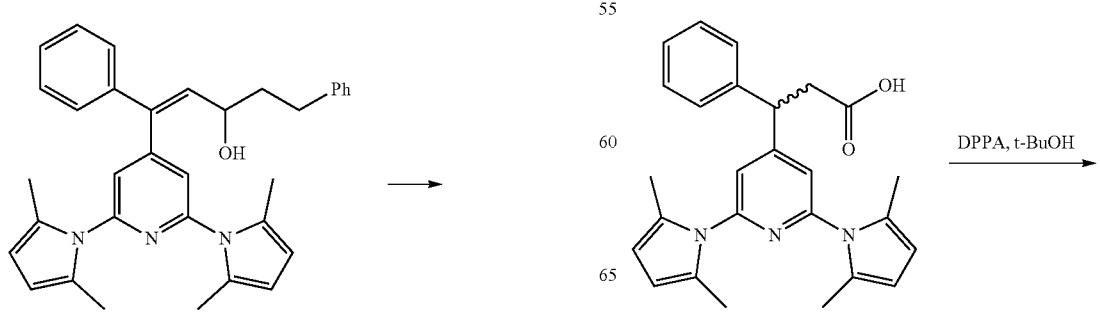

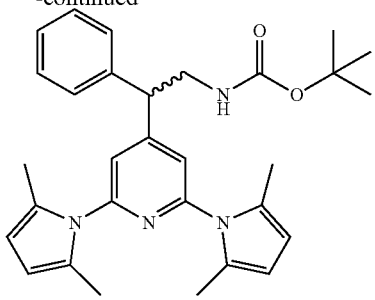

To 3-(2,6-bis(2,5-dimethyl-1H-pyrrol-1-yl)pyridin-4-yl)-3-phenylpropanoic acid (2.68 g, 6.48 mmol) dissolved in t-butanol (21 mL) was added TEA (1.8 mL, 13 mmol). The solution was heated to 80° C. Diphenyl phosphorazidate (1.47 mL, 6.48 mmol) was added dropwise, and the mixture was stirred overnight. The reaction mixture was concentrated, and partitioned between saturated NaHCO$_3$ and EtOAc. The aqueous layer was washed 3× with EtOAc. The organics were dried over MgSO$_4$, filtered, concentrated and purified via flash chromatography to furnish tert-butyl (2-(2,6-bis(2,5-dimethyl-1H-pyrrol-1-yl)pyridin-4-yl)-2-phenylethyl)carbamate (2.46 g, 5.08 mmol, 78% yield). MS (ESI) m/z 485.1 (M+H).

Intermediate 226b: tert-butyl (2-(2,6-diaminopyridin-4-yl)-2-phenylethyl)carbamate

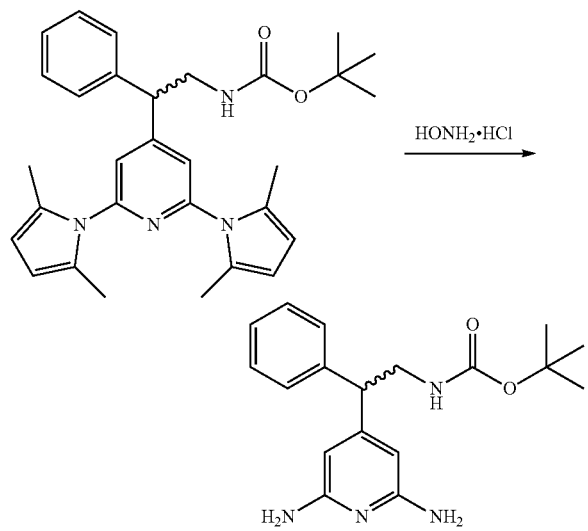

To tert-butyl (2-(2,6-bis(2,5-dimethyl-1H-pyrrol-1-yl)pyridin-4-yl)-2-phenylethyl)carbamate (0.102 g, 0.210 mmol) suspended in EtOH (2.1 mL) were added TEA (0.29 mL, 2.1 mmol) and hydroxylamine hydrochloride (0.292 g, 4.21 mmol), and the mixture was heated to 80° C. for overnight. The reaction mixture was partitioned between DCM and 1N NaOH, and the aqueous layers were washed 2× with DCM. The organics were dried over MgSO$_4$, filtered and concentrated to furnish tert-butyl (2-(2,6-diaminopyridin-4-yl)-2-phenylethyl)carbamate (0.069 g, 0.21 mmol), which was used crude. MS (ESI) m/z 329.0 (M+H).

Intermediate 226c: 4-(2-amino-1-phenylethyl)pyridine-2,6-diamine, HCl

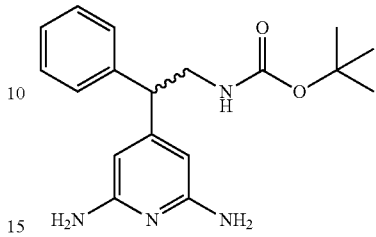

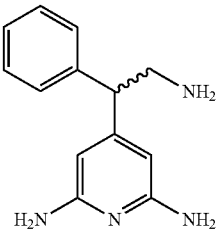

To tert-butyl (2-(2,6-diaminopyridin-4-yl)-2-phenylethyl)carbamate (0.069 g, 0.21 mmol) dissolved in DCM (1.75 mL) was added TFA (0.35 mL), and the mixture was stirred overnight. The reaction mixture was concentrated. The residue was dissolved in a minimal volume of 2-propanol followed by addition of 0.21 mL of 2N HCl (2 eq) and dilution with ether. The solvents were evaporated to furnish a white gummy solid 4-(2-amino-1-phenylethyl)pyridine-2,6-diamine, HCl (0.056 g, 0.21 mmol) that was taken forward as crude product. MS (ESI) m/z 229.2 (M+H).

Intermediate 226d: N-(2-(2,6-diaminopyridin-4-yl)-2-phenylethyl)-2,2-difluoro-2-phenylacetamide

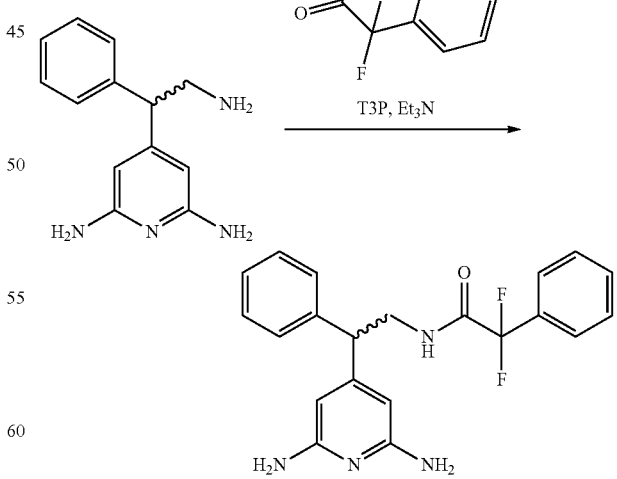

To 4-(2-amino-1-phenylethyl)pyridine-2,6-diamine, HCl (0.056 g, 0.210 mmol), TEA (0.176 mL, 1.260 mmol) and 2,2-difluoro-2-phenylacetic acid (0.036 g, 0.21 mmol) dissolved in THF (2.1 mL) was added T3P in EtOAc (0.25 mL, 0.42 mmol), and the mixture was stirred overnight. To this was added saturated NaHCO₃, and the product was extracted into EtOAc×2. The organics were dried over Na₂SO₄, filtered concentrated and purified via flash chromatography to furnish N-(2-(2,6-diaminopyridin-4-yl)-2-phenylethyl)-2,2-difluoro-2-phenylacetamide (0.058 g, 0.14 mmol, 67% yield) contaminated with residual MeOH. MS (ESI) m/z 383.2. ¹H NMR (500 MHz, CDCl₃) δ 7.49-7.38 (m, 5H), 7.34-7.24 (m, 3H), 7.21-7.15 (m, 2H), 6.45 (br. s., 1H), 5.71 (s, 2H), 4.18 (br. s., 4H), 3.98-3.91 (m, 1H), 3.90-3.81 (m, 2H).

Intermediate 226e: 4-(2-((2,2-difluoro-2-phenylethyl)amino)-1-phenylethyl)pyridine-2,6-diamine

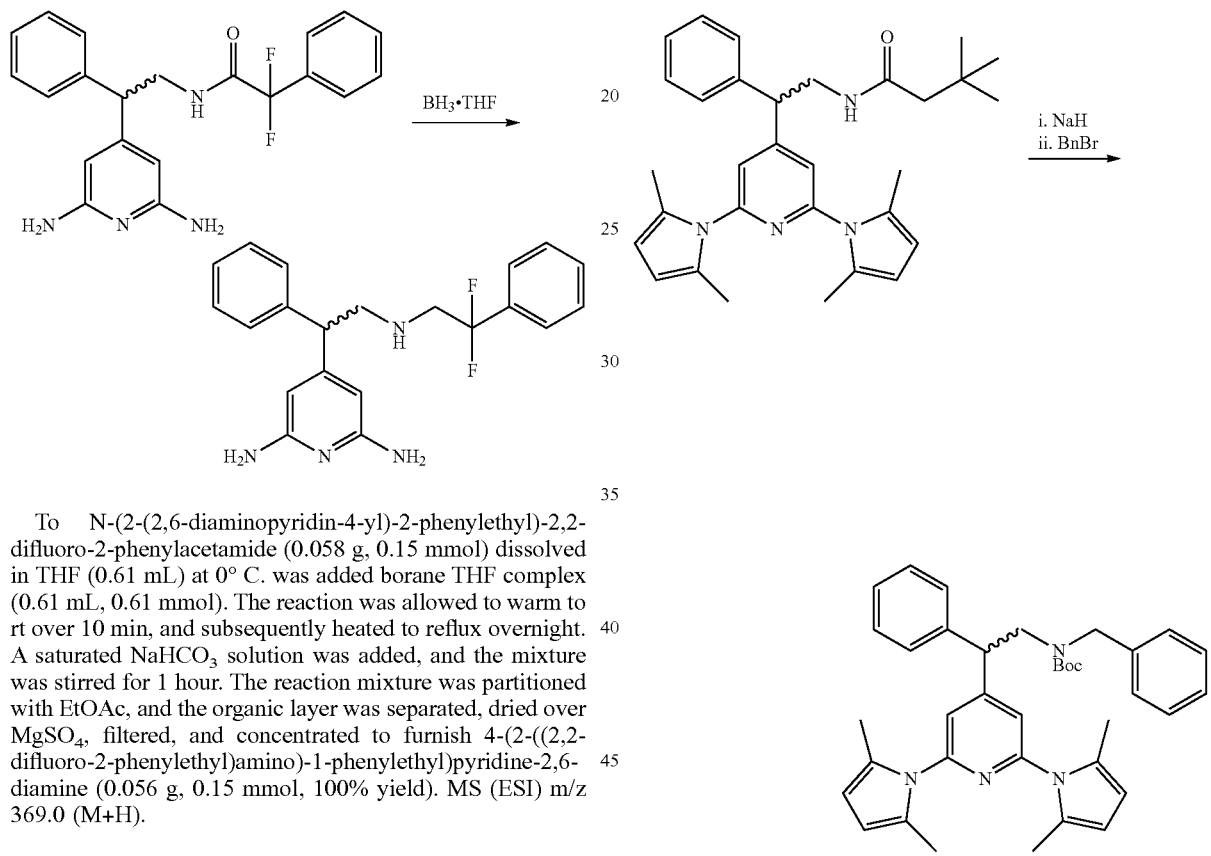

To N-(2-(2,6-diaminopyridin-4-yl)-2-phenylethyl)-2,2-difluoro-2-phenylacetamide (0.058 g, 0.15 mmol) dissolved in THF (0.61 mL) at 0° C. was added borane THF complex (0.61 mL, 0.61 mmol). The reaction was allowed to warm to rt over 10 min, and subsequently heated to reflux overnight. A saturated NaHCO₃ solution was added, and the mixture was stirred for 1 hour. The reaction mixture was partitioned with EtOAc, and the organic layer was separated, dried over MgSO₄, filtered, and concentrated to furnish 4-(2-((2,2-difluoro-2-phenylethyl)amino)-1-phenylethyl)pyridine-2,6-diamine (0.056 g, 0.15 mmol, 100% yield). MS (ESI) m/z 369.0 (M+H).

Example 226: 7-(2-((2,2-difluoro-2-phenylethyl)amino)-1-phenylethyl)-3H-[1,2,3]triazolo[4,5-b]pyridin-5-amine

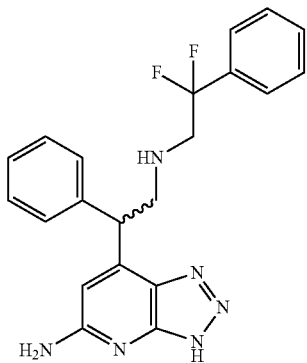 [SMILES: Nc1cc(C(CNCC(F)(F)c2ccccc2)c2ccccc2)c2nn[nH]c2n1]

Example 226 was prepared from Intermediate 226e as described in the General Procedures and Examples 2 and 11. MS (ESI) m/z 395.25 (M+H). ¹H NMR (500 MHz, MeOH-d4) δ 7.43-7.34 (m, 7H), 7.31 (t, J=7.6 Hz, 2H), 7.27-7.17 (m, 1H), 6.46 (s, 1H), 4.71-4.66 (m, 1H), 3.64 (dd, J=12.4, 7.4 Hz, 1H), 3.48 (dd, J=12.2, 7.8 Hz, 1H), 3.27 (t, J=14.4 Hz, 2H). LC: 1.10 min, Method C Intermediate 227a: tert-butyl benzyl(2-(2,6-bis(2,5-dimethyl-1H-pyrrol-1-yl)pyridin-4-yl)-2-phenylethyl)carbamate To tert-butyl (2-(2,6-bis(2,5-dimethyl-1H-pyrrol-1-yl)pyridin-4-yl)-2-phenylethyl)carbamate (0.300 g, 0.619 mmol) in DMF (2.1 mL) at 0° C. was added NaH (0.030 g, 0.74 mmol) and allowed to stir for 30 min. Benzyl bromide (0.09 mL, 0.7 mmol) was added and the solution allowed to warm to room temperature over weekend. The reaction was partitioned between EtOAc and water, aqueous layer separated and washed with EtOAc, organic layers combined, combined organics washed with water, brine, dried over Na₂SO₄, filtered, concentrated, and purified via flash chromatography to furnish tert-butyl benzyl(2-(2,6-bis(2,5-dimethyl-1H-pyrrol-1-yl)pyridin-4-yl)-2-phenylethyl)carbamate (0.185 g, 0.322 mmol, 52.0% yield). MS (ESI) m/z 575.2 (M+H).

Example 227: 7-(2-(benzylamino)-1-phenylethyl)-3H-[1,2,3]triazolo[4,5-b]pyridin-5-amine, TFA

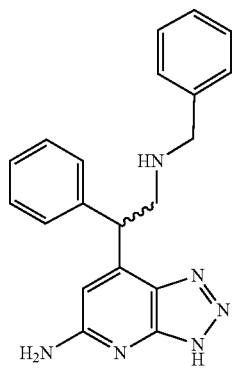 [SMILES: Nc1cc(C(CNCc2ccccc2)c2ccccc2)c2nn[nH]c2n1]

Example 227 was prepared as described from Intermediate 227a by methods described in General Procedures and Examples 2 and 11 with the addition of a final treatment with TFA in DCM to remove the Boc protecting group. MS (ESI) m/z 345.2 (M+H). $^1$H NMR (500 MHz, CD$_3$CN) δ 7.51-7.30 (m, 10H), 6.73 (s, 1H), 4.91 (t, J=7.4 Hz, 1H), 4.26 (s, 2H), 4.08 (dd, J=12.8, 8.1 Hz, 1H), 3.79 (dd, J=12.8, 6.7 Hz, 1H). LC: 4.243 min, Method A Example 228 was prepared analogously to Example 227.

Intermediate 229a: 4-benzyl-2,6-bis(2,5-dimethyl-1H-pyrrol-1-yl)pyridine

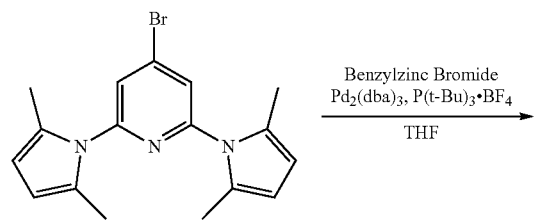

To a solution of 4-bromo-2,6-bis(2,5-dimethyl-1H-pyrrol-1-yl)pyridine (1.0 g, 2.9 mmol), tri-t-butylphosphonium tetrafluoroborate (0.084 g, 0.29 mmol) and tris(dibenzylideneacetone)dipalladium(0) (0.133 g, 0.145 mmol) dissolved in THF (5.8 mL) was added a 1 M THF solution of benzylzinc(II) bromide (8.7 mL, 8.7 mmol), and the mixture was stirred at rt overnight. The reaction was quenched with sat. NH$_4$Cl, and extracted into EtOAc. The organic layer was dried over Na$_2$SO$_4$, filtered, concentrated, and purified via flash chromatography to furnish 4-benzyl-2,6-bis(2,5-dimethyl-1H-pyrrol-1-yl)pyridine (1.1 g, 3.1 mmol, contaminated with trace impurities) MS (ESI) m/z 356.2 (M+H). $^1$H NMR (400 MHz, CDCl$_3$) δ 7.38-7.31 (m, 2H), 7.30-7.26 (m, 1H), 7.23-7.16 (m, 2H), 7.00 (s, 2H), 5.86 (s, 4H), 4.10 (s, 2H), 2.10 (s, 12H).

Intermediate 229b: 4-(2-(4-(benzyloxy)phenyl)-1-phenylethyl)-2,6-bis(2,5-dimethyl-1H-pyrrol-1-yl)pyridine

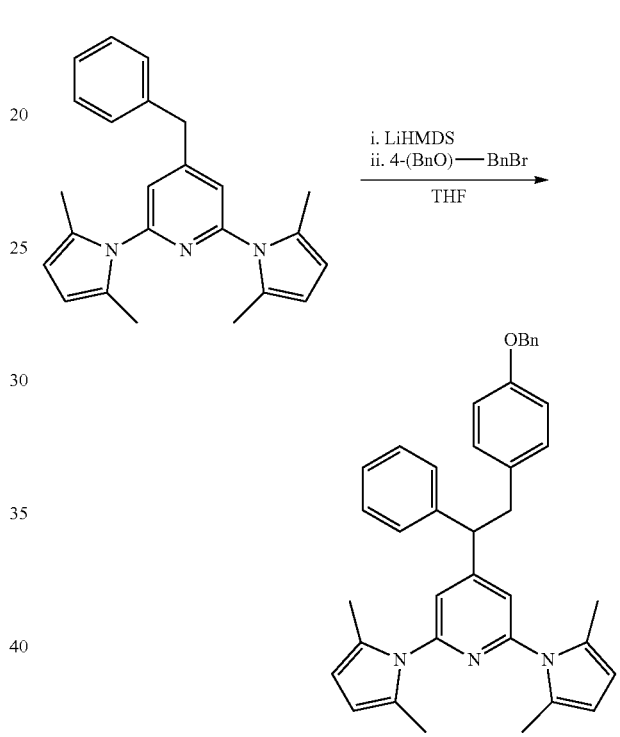

To 4-benzyl-2,6-bis(2,5-dimethyl-1H-pyrrol-1-yl)pyridine (0.100 g, 0.281 mmol) dissolved in THF (2.8 mL), sparged with Ar, and cooled to 0° C. was added LiHMDS (0.28 mL, 0.28 mmol). The mixture was stirred for 10 min, followed by addition of 1-(benzyloxy)-4-(bromomethyl)benzene (0.078 g, 0.28 mmol) dissolved in 1 mL of Ar sparged THF. The reaction mixture warmed to rt over 1 hour. The reaction was quenched with sat. NH$_4$Cl solution and extracted into EtOAc. The organic layer was dried over MgSO$_4$, concentrated and purified via flash chromatography to furnish 4-(2-(4-(benzyloxy)phenyl)-1-phenylethyl)-2,6-bis(2,5-dimethyl-1H-pyrrol-1-yl)pyridine (0.104 g, 0.189 mmol, 67.1% yield). MS (ESI) m/z 552.3 (M+H). $^1$H NMR (400 MHz, CDCl$_3$-d) δ 7.45-7.30 (m, 7H), 7.28-7.20 (m, 3H), 6.96 (s, 2H), 6.93-6.87 (m, 2H), 6.83-6.74 (m, 2H), 5.84 (s, 4H), 4.98 (s, 2H), 4.28 (dd, J=9.5, 6.4 Hz, 1H), 3.42 (dd, J=13.6, 6.4 Hz, 1H), 3.26 (dd, J=13.6, 9.7 Hz, 1H), 2.00 (s, 12H).

Intermediate 229c: 7-(2-(4-(benzyloxy)phenyl)-1-phenylethyl)-3H-[1,2,3]triazolo[4,5-b]pyridin-5-amine, TFA

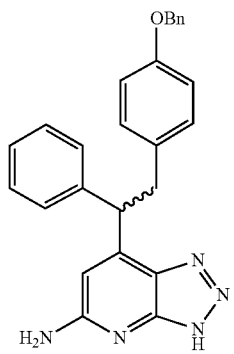 [SMILES: Nc1cc(C(Cc2ccc(OCc3ccccc3)cc2)c2ccccc2)c2nn[nH]c2n1]

Intermediate 229c was prepared from Intermediate 229b by methods described in the General Procedures and Examples 2 and 11. MS (ESI) m/z 422.1 (M+H). $^1$H NMR (400 MHz, CD$_3$CN) δ 7.49-7.16 (m, 10H), 7.12-7.00 (m, 2H), 6.85-6.71 (m, 3H), 4.99 (s, 2H), 4.78 (t, J=8.0 Hz, 1H), 3.59 (dd, J=14.1, 7.5 Hz, 1H), 3.41 (dd, J=14.0, 8.5 Hz, 1H).

Example 229: 4-(2-(5-amino-3H-[1,2,3]triazolo[4,5-b]pyridin-7-yl)-2-phenylethyl)phenol

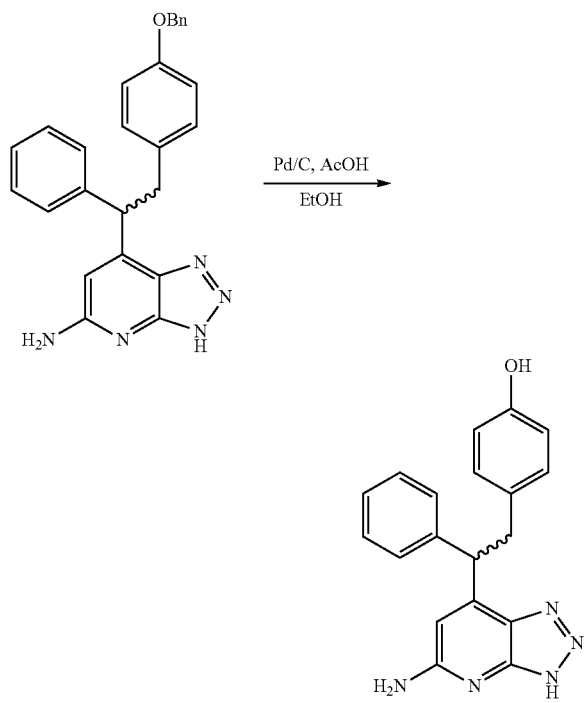

To a solution of 7-(2-(4-(benzyloxy)phenyl)-1-phenylethyl)-3H-[1,2,3]triazolo[4,5-b]pyridin-5-amine, TFA (0.02 g, 0.04 mmol) dissolved in EtOH (0.37 mL) was added AcOH (11 μL, 0.19 mmol) and Pd/C (4.0 mg, 3.7 μmol). The vessel was evacuated and placed under 50 psi(g) hydrogen overnight. The reaction mixture was filtered, concentrated and purified via preparative HPLC to furnish 4-(2-(5-amino-3H-[1,2,3]triazolo[4,5-b]pyridin-7-yl)-2-phenylethyl)phenol (0.0071 g, 0.021 mmol, 57% yield). MS (ESI) m/z 332.2 (M+H). $^1$H NMR (500 MHz, MeOH-d4) δ 7.38 (d, J=7.4 Hz, 2H), 7.22 (t, J=7.6 Hz, 2H), 7.16-7.10 (m, 1H), 6.90 (d, J=8.5 Hz, 2H), 6.61-6.51 (m, 3H), 4.72 (t, J=7.8 Hz, 1H), 3.58 (dd, J=13.9, 7.8 Hz, 1H), 3.35 (dd, J=13.9, 8.1 Hz, 1H). LC: 1.12 min, Method C Intermediate 230a: 7-(2-(3-(benzyloxy)phenyl)-1-phenylethyl)-3H-[1,2,3]triazolo[4,5-b]pyridin-5-amine, TFA

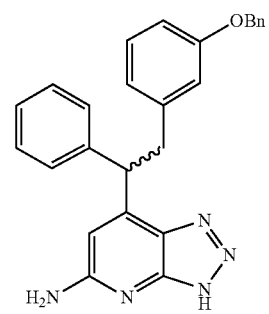 [SMILES: Nc1cc(C(Cc2cccc(OCc3ccccc3)c2)c2ccccc2)c2nn[nH]c2n1]

Intermediate 230a was prepared from 4-benzyl-2,6-bis(2,5-dimethyl-1H-pyrrol-1-yl)pyridine and 1-(benzyloxy)-3-(bromomethyl)benzene by Example 229: 7-(2-(4-(benzyloxy)phenyl)-1-phenylethyl)-3H-[1,2,3]triazolo[4,5-b]pyridin-5-amine, TFA). MS (ESI) m/z 422.1 (M+H). $^1$H NMR (400 MHz, CD$_3$CN) δ 7.48-7.01 (m, 11H), 6.84-6.66 (m, 4H), 4.97 (s, 2H), 4.82 (t, J=8.0 Hz, 1H), 3.63 (dd, J=13.9, 7.5 Hz, 1H), 3.44 (dd, J=13.8, 8.5 Hz, 1H).

Example 230: 3-(2-(5-amino-3H-[1,2,3]triazolo[4,5-b]pyridin-7-yl)-2-phenylethyl)phenol

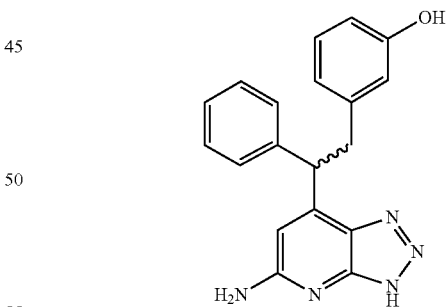

Example 230 was prepared from 4-benzyl-2,6-bis(2,5-dimethyl-1H-pyrrol-1-yl)pyridine and 1-(benzyloxy)-3-(bromomethyl)benzene by methods described in Example 229. MS (ESI) m/z 332.20 (M+H). $^1$H NMR (500 MHz, DMSO-d$_6$) δ 9.14 (br. s., 1H), 7.47 (d, J=7.4 Hz, 2H), 7.26 (t, J=7.7 Hz, 2H), 7.19-7.10 (m, 1H), 6.94 (t, J=7.8 Hz, 1H), 6.65-6.54 (m, 2H), 6.52-6.33 (m, 4H), 4.67 (t, J=7.8 Hz, 1H), 3.66 (dd, J=13.8, 8.3 Hz, 1H), 3.35 (m, 1H). LC: 1.18 min, Method C

Intermediate 231a: 2-((2,3-dihydro-1H-inden-1-yl)oxy)ethanol

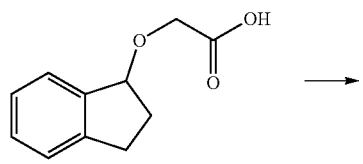

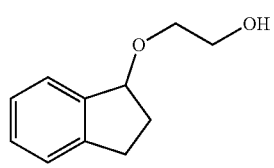

2-((2,3-dihydro-1H-inden-1-yl)oxy)acetic acid was prepared similar to methods described in WO 2007/121471 A2. To 2-((2,3-dihydro-1H-inden-1-yl)oxy)acetic acid (2.0 g, 10 mmol) dissolved in THF (35 mL) was added LiAlH$_4$ (3.0 mL, 11 mmol), and the mixture was heated to reflux for 2 hours. The reaction was quenched with 1N NaOH, and extracted into ether. The organics were dried over MgSO$_4$, filtered and concentrated, and purified via flash chromatography to furnish 2-((2,3-dihydro-1H-inden-1-yl)oxy)ethanol (0.43 g, 2.5 mmol, 23% yield), MS (ESI) m/z 201.1 (M+Na) $^1$H NMR (400 MHz, CDCl$_3$) δ 7.43-7.36 (m, 1H), 7.29-7.25 (m, 2H), 7.25-7.19 (m, 1H), 4.98 (dd, J=6.6, 4.2 Hz, 1H), 3.79-3.72 (m, 2H), 3.70-3.62 (m, 2H), 3.16-3.02 (m, 1H), 2.83 (ddd, J=15.9, 8.5, 5.3 Hz, 1H), 2.43-2.30 (m, 1H), 2.10 (dddd, J=13.5, 8.3, 5.3, 4.2 Hz, 1H)

Intermediate 231b: 1-(2-bromoethoxy)-2,3-dihydro-1H-indene

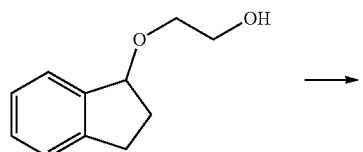

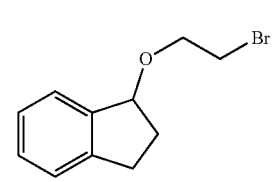

To 2-((2,3-dihydro-1H-inden-1-yl)oxy)ethanol (0.10 g, 0.56 mmol) and CBr$_4$ (0.37 g, 1.1 mmol) dissolved in THF (1.3 mL) was added PPh$_3$ (0.30 g, 1.1 mmol) followed by THF (1.5 mL), and the mixture was stirred overnight. The reaction mixture was diluted with ether, filtered, concentrated, and purified via flash chromatography equipped with ELSD detector to furnish 1-(2-bromoethoxy)-2,3-dihydro-1H-indene (0.12 g, 0.50 mmol, 89% yield). MS (ESI) m/z 265.0 (M+Na). $^1$H NMR (400 MHz, CDCl$_3$) δ 7.41 (d, J=6.8 Hz, 1H), 7.29-7.19 (m, 3H), 5.01 (dd, J=6.6, 4.2 Hz, 1H), 3.89-3.82 (m, 2H), 3.48 (t, J=6.5 Hz, 2H), 3.14-3.03 (m, 1H), 2.88-2.77 (m, 1H), 2.42-2.30 (m, 1H), 2.11 (dddd, J=13.5, 8.3, 5.4, 4.3 Hz, 1H).

Intermediate 231c: 4-(3-((2,3-dihydro-1H-inden-1-yl)oxy)-1-phenylpropyl)-2,6-bis(2,5-dimethyl-1H-pyrrol-1-yl)pyridine

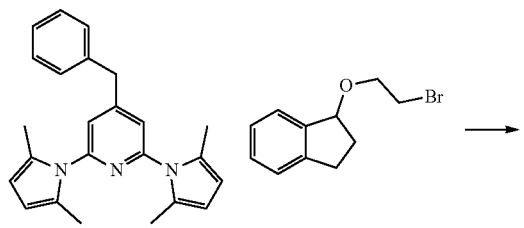

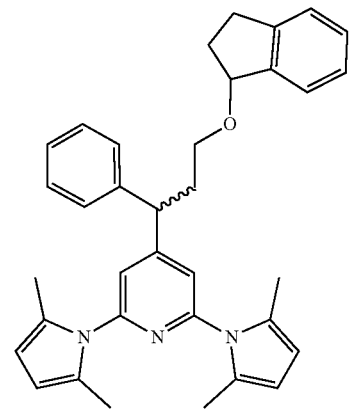

To 4-benzyl-2,6-bis(2,5-dimethyl-1H-pyrrol-1-yl)pyridine (0.10 g, 0.28 mmol) dissolved in THF (2.8 mL) and sparged with Ar and cooled to 0° C. was added 1 M LiHMDS (0.28 mL, 0.28 mmol). The mixture was stirred for 10 min, followed by addition of 1-(2-bromoethoxy)-2,3-dihydro-1H-indene (0.068 g, 0.281 mmol) dissolved in 0.25 mL of Ar sparged THF. The mixture was allowed to warm to rt. Upon complete conversion at 1 hour saturated NH$_4$Cl was added, and the product was extracted into EtOAc. The organics were dried over MgSO$_4$, filtered, concentrated, and purified via flash chromatography to furnish 4-(3-((2,3-dihydro-1H-inden-1-yl)oxy)-1-phenylpropyl)-2,6-bis(2,5-dimethyl-1H-pyrrol-1-yl)pyridine (0.094 g, 0.18 mmol, 65% yield)$^1$H NMR (400 MHz, CDCl$_3$) δ 7.39-7.11 (m, 9H), 7.11-7.02 (m, 2H), 5.86 (s, 4H), 4.89-4.70 (m, 1H), 4.37-4.22 (m, 1H), 3.64-3.35 (m, 2H), 3.13-2.95 (m, 1H), 2.85-2.66 (m, 1H), 2.53-2.18 (m, 3H), 2.16-1.90 (m, 13H). MS (ESI) m/z 516.0 (M+H).

Example 231 & Example 232: 7-(3-((2,3-dihydro-1H-inden-1-yl)oxy)-1-phenylpropyl)-3H-[1,2,3]triazolo[4,5-b]pyridin-5-amine

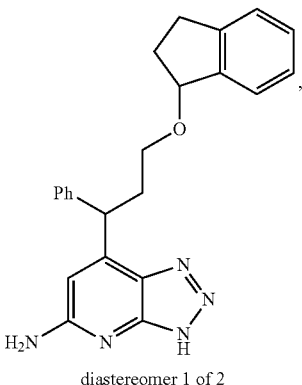

diastereomer 1 of 2

231

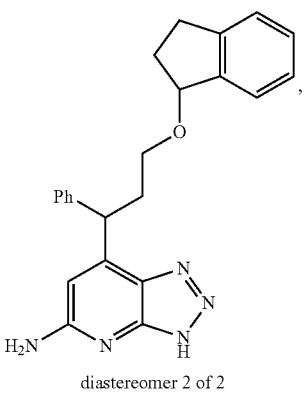

diastereomer 2 of 2

232

Examples 231 and 232 were prepared from Intermediate 231c by the methods described in the General Procedures and Examples 2 and 11. The diastereomers were separated via preparative HPLC via standard gradient on a Sunfire 5m C18 30×100 mm column.

Example 231: Peak 1: MS (ESI) m/z 386.2 (M+H). $^1$H NMR (400 MHz, CD$_3$CN) δ 7.48-7.39 (m, 2H), 7.33 (t, J=7.6 Hz, 2H), 7.29-7.16 (m, 4H), 7.12 (td, J=5.0, 2.8 Hz, 1H), 6.75 (d, J=4.6 Hz, 1H), 4.75 (dd, J=6.2, 4.0 Hz, 1H), 4.64 (t, J=7.8 Hz, 1H), 3.50 (t, J=5.9 Hz, 2H), 3.04-2.87 (m, 1H), 2.81-2.68 (m, 1H), 2.65-2.50 (m, 1H), 2.44-2.30 (m, 1H), 2.27-2.14 (m, 1H), 1.92-1.82 (m, 1H). LC: 7.03 min, Method A Example 232: Peak 2: MS (ESI) m/z 386.1 (M+H). $^1$H NMR (400 MHz, CD$_3$CN) δ 7.50-7.38 (m, 2H), 7.36-7.10 (m, 7H), 6.81-6.72 (m, 1H), 4.77 (dd, J=6.3, 4.3 Hz, 1H), 4.64 (t, J=7.8 Hz, 1H), 3.62-3.37 (m, 2H), 3.02-2.87 (m, 1H), 2.82-2.69 (m, 1H), 2.66-2.54 (m, 1H), 2.44-2.30 (m, 1H), 2.22 (ddt, J=13.1, 8.3, 6.4 Hz, 1H), 1.91-1.83 (m, 1H). LC: 7.19 min, Method A Intermediate 233a:
2-benzyl-2-(2-bromoethyl)-1,3-dioxolane

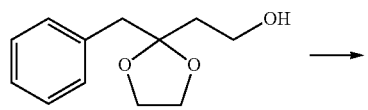

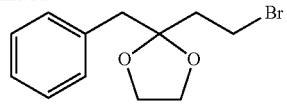

To 1.0 g (4.8 mmol) of 2-(2-benzyl-1,3-dioxolan-2-yl)ethanol (*J. Org. Chem.*, 2010, 75, 3113-6) and CBr$_4$ (3.2 g, 9.6 mmol) dissolved in THF (24 mL) was added PPh$_3$ (2.5 g, 9.7 mmol), and the mixture was stirred overnight. The reaction mixture was diluted with ether, filtered, concentrated and purified via flash chromatography to furnish 2-benzyl-2-(2-bromoethyl)-1,3-dioxolane (1.2 g, 4.4 mmol, 92% yield). $^1$H NMR (400 MHz, CDCl$_3$) δ 7.34-7.18 (m, 5H), 3.94-3.83 (m, 2H), 3.79-3.67 (m, 2H), 3.46-3.35 (m, 2H), 2.88 (s, 2H), 2.29-2.17 (m, 2H) MS (ESI) m/z 270.9 (M+H).

Intermediate 233b: 4-(3-(2-benzyl-1,3-dioxolan-2-yl)-1-phenylpropyl)-2,6-bis(2,5-dimethyl-1H-pyrrol-1-yl)pyridine

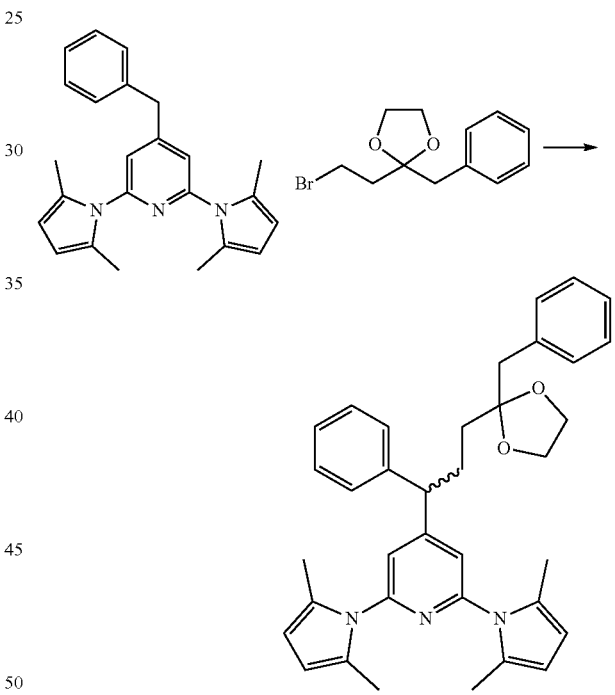

To 4-benzyl-2,6-bis(2,5-dimethyl-1H-pyrrol-1-yl)pyridine (0.47 g, 1.3 mmol) dissolved in THF (13 mL) and sparged with Ar and cooled to 0° C. was added 1 M LiHMDS (1.33 mL, 1.33 mmol). The mixture was stirred for 5 min, followed by addition of 2-benzyl-2-(2-bromoethyl)-1,3-dioxolane (0.36 g, 1.33 mmol) dissolved in 1 mL of sparged THF. The mixture warmed to rt for 1 hour. The reaction was quenched with saturated NH$_4$Cl, and extracted into EtOAc. The organic layer was dried over MgSO$_4$, filtered, concentrated, and purified via flash chromatography to furnish 4-(3-(2-benzyl-1,3-dioxolan-2-yl)-1-phenylpropyl)-2,6-bis(2,5-dimethyl-1H-pyrrol-1-yl)pyridine (0.24 g, 0.44 mmol, 33% yield)$^1$H NMR (400 MHz, CDCl$_3$) δ 7.35-7.12 (m, 10H), 7.03 (s, 2H), 5.86 (s, 4H), 3.94 (t, J=7.8 Hz, 1H), 3.88-3.79 (m, 2H), 3.76-3.65 (m, 2H), 2.94-2.76

(m, 2H), 2.20 (q, J=7.8 Hz, 2H), 2.12-2.05 (m, 12H), 1.67-1.56 (m, 2H). MS (ESI) m/z 546.2 (M+H).

Intermediate 233c: 7-(3-(2-benzyl-1,3-dioxolan-2-yl)-1-phenylpropyl)-3H-[1,2,3]triazolo[4,5-b]pyridin-5-amine

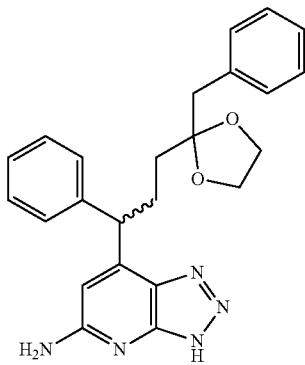 [SMILES: Nc1cc(C(CCC2(Cc3ccccc3)OCCO2)c2ccccc2)c2nn[nH]c2n1]

Intermediate 233c was prepared from Intermediate 233b as described in the General Procedures and Examples 2 and 11. MS (ESI) m/z 416.25 (M+H).

Example 233: 5-(5-amino-3H-[1,2,3]triazolo[4,5-b]pyridin-7-yl)-1,5-diphenylpentan-2-one

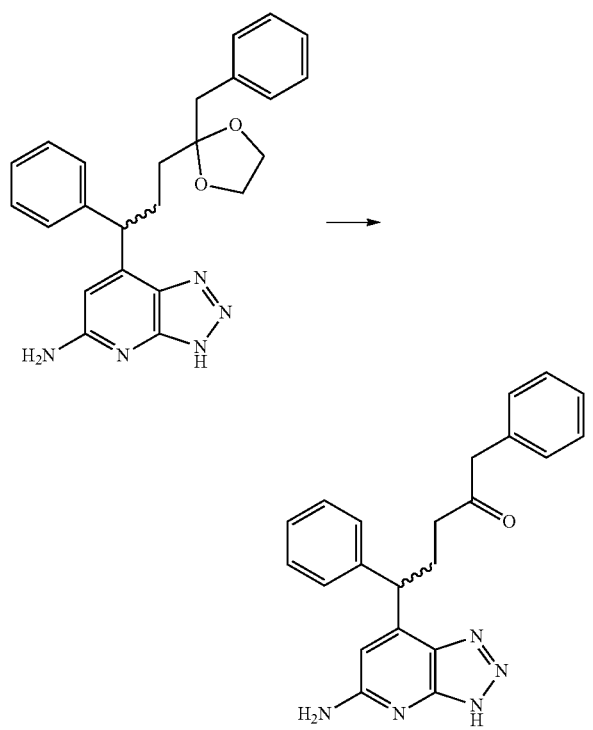

To 7-(3-(2-benzyl-1,3-dioxolan-2-yl)-1-phenylpropyl)-3H-[1,2,3]triazolo[4,5-b]pyridin-5-amine (0.094 g, 0.23 mmol) dissolved in acetone (2.3 mL) were added 0.2 mL of water and TsOH (40 mg, 0.02 mmol), and the solution was stirred for 2 days. The reaction mixture was concentrated, reconstituted in ACN, and purified via AXIA Luna column HPLC ACN/water/TFA to furnish 5-(5-amino-3H-[1,2,3]triazolo[4,5-b]pyridin-7-yl)-1,5-diphenylpentan-2-one (0.048 g, 0.098 mmol, 43% yield). $^1$H NMR (400 MHz, CD$_3$CN) δ 7.48-7.06 (m, 10H), 6.67 (s, 1H), 4.47-4.35 (m, 1H), 3.65 (s, 2H), 2.61-2.24 (m, 4H). MS (ESI) m/z 372.1 (M+H). LC: 6.51 min, Method A Example 234: 5-(5-amino-3H-[1,2,3]triazolo[4,5-b]pyridin-7-yl)-1,5-diphenylpentan-2-ol

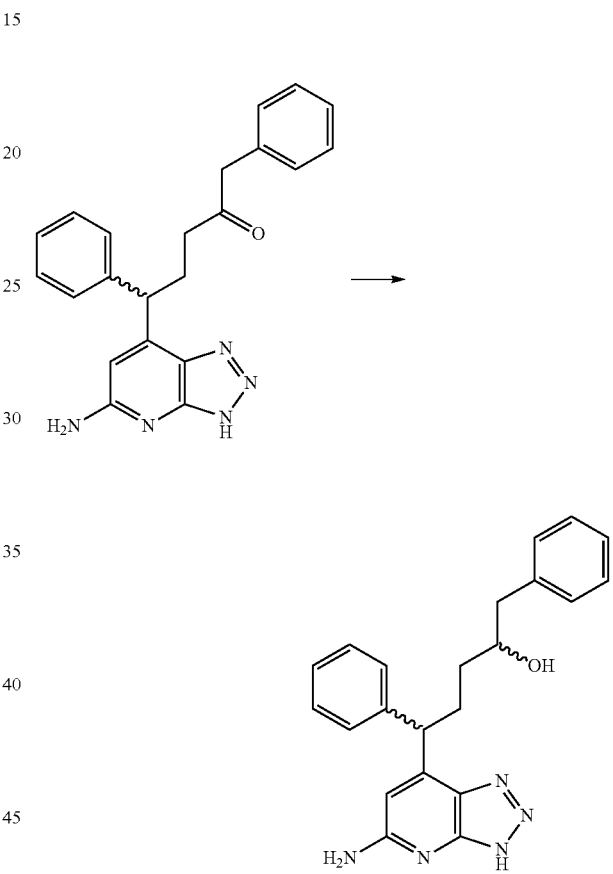

To 5-(5-amino-3H-[1,2,3]triazolo[4,5-b]pyridin-7-yl)-1,5-diphenylpentan-2-one (0.0082 g, 0.022 mmol) dissolved in MeOH (0.22 mL) was added NaBH$_4$ (0.8 mg, 0.02 mmol), and the mixture was stirred for 5 minutes. The reaction mixture was partitioned between pH 7.4 phosphate buffer and DCM, and the aqueous phase was washed with DCM. The combined organic phase was dried over MgSO$_4$, filtered and concentrated to furnish 5-(5-amino-3H-[1,2,3]triazolo[4,5-b]pyridin-7-yl)-1,5-diphenylpentan-2-ol (0.0036 g, 9.35 μmol, 42% yield). MS (ESI) m/z 374.1 (M+H). $^1$H NMR (400 MHz, CD$_3$CN) δ 7.44 (t, J=6.7 Hz, 2H), 7.35-7.09 (m, 8H), 6.49 (d, J=4.4 Hz, 1H), 5.33 (br. s., 2H), 4.45 (td, J=7.8, 3.4 Hz, 1H), 3.89-3.71 (m, 1H), 2.80-2.48 (m, 2H), 2.37 (q, J=7.6 Hz, 1H), 2.27-2.04 (m, 1H), 1.52-1.13 (m, 2H). LC: 6.03 min, Method A

Example 235: 7-(4-amino-1,5-diphenylpentyl)-3H-[1,2,3]triazolo[4,5-b]pyridin-5-amine

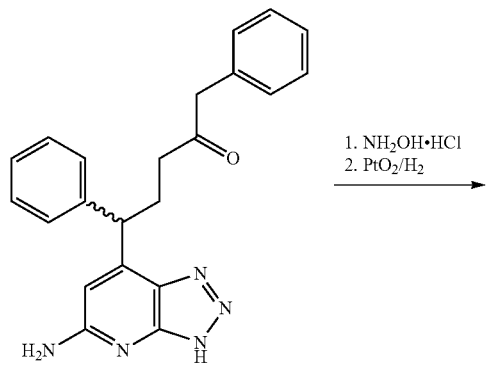

To a solution of 5-(5-amino-3H-[1,2,3]triazolo[4,5-b]pyridin-7-yl)-1,5-diphenylpentan-2-one (0.010 g, 0.027 mmol) dissolved in EtOH (0.27 mL) was added hydroxylamine hydrochloride (1.9 mg, 0.027 mmol), and the mixture was stirred over night. MS (ESI) m/z 387.1 (M+H). To the reaction solution was added AcOH (270 μL) and $PtO_2$ (0.6 mg, 3 μmol). The vessel was evacuated, and charged with 15 psi (g) hydrogen and allowed to stir overnight. The reaction mixture was filtered, and the crude material was purified via preparative LC/MS with the following conditions: Column: Waters XBridge C18, 19×200 mm, 5 μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 20 minutes, then a 5-minute hold at 100% B; Flow: 20 mL/min. Fractions containing the desired product were combined and dried via centrifugal evaporation to furnish 7-(4-amino-1,5-diphenylpentyl)-3H-[1,2,3]triazolo[4,5-b]pyridin-5-amine (3.3 mg, 8.8 μmol, 33% yield). MS (ESI) m/z 373.25 (M+H). $^1$H NMR (500 MHz, DMSO-$d_6$) δ 7.42 (dd, J=12.1, 7.7 Hz, 2H), 7.32-7.06 (m, 8H), 6.49 (br. s., 2H), 6.40 (d, J=10.5 Hz, 1H), 4.37-4.29 (m, 1H), 2.60 (d, J=12.7 Hz, 1H), 2.45-2.25 (m, 2H), 1.38-1.10 (m, 2H) remaining protons obscured by water signal. LC: 1.10 min, Method C

Example 236: (R)-2-((3-(5-amino-3H-[1,2,3]triazolo[4,5-b]pyridin-7-yl)-3-phenylpropyl)amino)-5-phenylpentan-1-ol

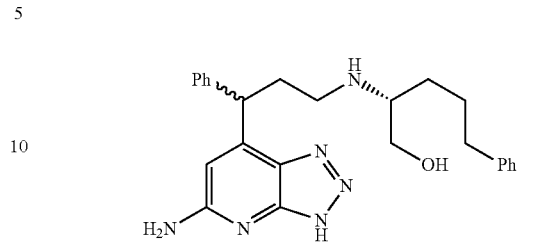

Example 236 was isolated as an over-reduced byproduct during the production of Example 140.

Example 237: (R)-3-(5-amino-3H-[1,2,3]triazolo[4,5-b]pyridin-7-yl)-3-phenylpropan-1-ol

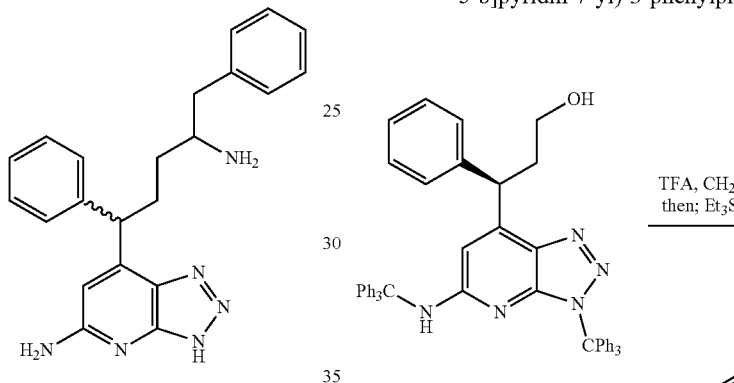

TFA (1.0 mL) was added to a solution of 3-phenyl-3-(3-trityl-5-(tritylamino)-3H-[1,2,3]triazolo[4,5-b]pyridin-7-yl)propan-1-ol (Intermediate 9-2.15 mg, 0.020 mmol) and triethylsilane (0.013 mL, 0.080 mmol) in DCM (4 mL). After stirring for 1 h, the reaction mixture was concentrated, and the crude was purified via preparative LC/MS (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-45% B over 20 minutes, then a 5-minute hold at 100% B; Flow: 20 mL/min. Fractions containing the desired product were combined and dried via centrifugal evaporation to yield the title compound (2.8 mg, 52% yield). MS (ESI) m/z 270.1 (M+H). $^1$H NMR (500 MHz, DMSO-$d_6$) δ 7.44 (m, 2H), 7.35-7.23 (m, 3H), 6.48 (br. s., 1H), 4.54 (t, J=7.7 Hz, 1H), 3.34 (t, J=6.4 Hz, 2H), 2.63-2.45 (m, 2H), 2.29 (m, 1H). LC: 0.91 min, Method C

Example 238: (R)-7-(1-phenyl-2-(7-phenyl-1H-benzo[d]imidazol-2-yl)ethyl)-3H-[1,2,3]triazolo[4,5-b]pyridin-5-amine

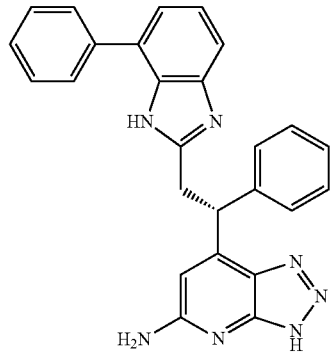 [SMILES: Nc1cc([C@H](Cc2nc3cccc(-c4ccccc4)c3[nH]2)c2ccccc2)c2nn[nH]c2n1]

Intermediate 238a: 2-nitro-[1,1'-biphenyl]-3-amine

A mixture of 3-bromo-2-nitroaniline (520 mg, 2.4 mmol), phenylboronic acid (351 mg, 2.88 mmol), PdCl₂(dppf) (175 mg, 0.240 mmol) and tripotassium phosphate (2030 mg, 9.58 mmol) in dioxane (5 mL) and water (0.2 mL) was purged with argon and subjected to irradiation in a microwave for 45 min at 110° C. The solvent was evaporated, and the crude mixture was purified by column chromatography (eluted with EtOAc/Hexanes from 0-100%) to obtain 2-nitro-[1,1'-biphenyl]-3-amine (500 mg, 2.3 mmol, 98% yield) as a bright orange-red solid. MS (ESI) m/z 215.0 (M+H). ¹H NMR (400 MHz, CDCl₃-d) δ 7.40-7.27 (m, 3H), 7.26-7.18 (m, 3H), 6.72 (dd, J=8.4, 1.1 Hz, 1H), 6.62 (dd, J=7.5, 1.1 Hz, 1H), 4.90 (br. s., 2H).

Intermediate 238b: [1,1'-biphenyl]-2,3-diamine

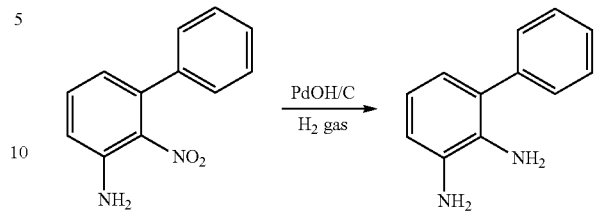

To a solution of 2-nitro-[1,1'-biphenyl]-3-amine (500 mg, 2.3 mmol) in MeOH (5 mL) under argon was added palladium hydroxide on carbon (40 mg, 0.28 mmol), and the mixture was blanketed with H₂ gas. The mixture was filtered through a pad of celite. The solid material was washed three times with MeOH. The filtrates were combined, and concentrated to obtain [1,1'-biphenyl]-2,3-diamine (350 mg, 1.9 mmol, 81% yield) as a dark red solid. MS (ESI) m/z 185.0 (M+H). ¹H NMR (400 MHz, CDCl₃-d) δ 7.49-7.33 (m, 4H), 7.31-7.24 (m, 1H), 6.77-6.57 (m, 3H).

Example 238: (R)-7-(1-phenyl-2-(7-phenyl-1H-benzo[d]imidazol-2-yl)ethyl)-3H-[1,2,3]triazolo[4,5-b]pyridin-5-amine

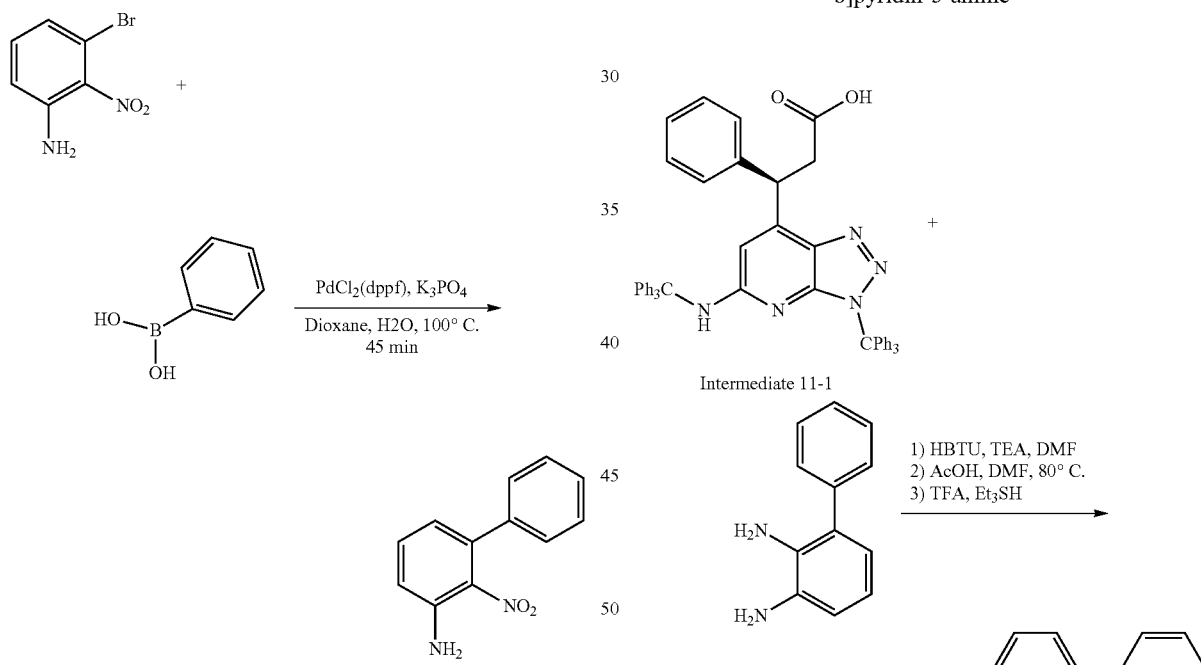

A mixture of Intermediate 11-1 (100 mg, 0.13 mmol), [1,1'-biphenyl]-2,3-diamine (48 mg, 0.26 mmol), o-Benzotriazol-1-yl-N,N,N',N'-tetramethyluronium hexafluorophosphate (HBTU) (99 mg, 0.26 mmol) and TEA (0.18 mL, 1.3 mmol) in DMF (2 mL) was stirred at rt overnight. The reaction mixture was taken up in EtOAc, washed with brine, dried over MgSO$_4$, and concentrated under vacuum to afford crude residue. The crude (R)—N-(3-amino-[1,1'-biphenyl]-2-yl)-3-phenyl-3-(3-trityl-5-(tritylamino)-3H-[1,2,3]triazolo[4,5-b]pyridin-7-yl)propanamide was taken forward without further characterization. MS (ESI) m/z 934.5 (M+H).

The crude residue was dissolved in acetic acid (2 mL) and DMF (1.5 mL), and the solution was stirred at 80° C. for 2 h. The solvents were evaporated, and the crude material (88 mgs) was taken on to next step without further purification or characterization.

The crude residue was dissolved in DMF and THF co-solvents (5 mL) and 1 mL of TFA was slowly added. After stirring for 5 min, triethylsilane (0.209 mL, 1.30 mmol) was slowly added. After stirring for 1 h, the reaction mixture was concentrated in vacuo. The crude material was purified via preparative LCMS with the following conditions: Column: XBridge Phenyl, 19×200 mm, 5 µm particles; Mobile Phase A: 5:95 acetonitrile: water with 0.1% TFA; Mobile Phase B: 95:5 acetonitrile: water with 0.1% TFA; Gradient: 20-60% B over 20 minutes, then a 5-minute hold at 100% B; Flow: 20 mL/min. The fractions containing the desired product were combined and evaporated via centrifugal evaporation. The material was further purified via preparative LC/MS with the following conditions: Column: XBridge C18, 19×200 mm, 5 µm particles; Mobile Phase A: 5:95 acetonitrile: water with 0.1% TFA; Mobile Phase B: 95:5 acetonitrile: water with 0.1% TFA; Gradient: 10-60% B over 20 minutes, then a 5-minute hold at 100% B. Flow: 20 mL/min. After evaporation of the solvents the title compound (17.5 mg, 30% yield), 97% purity) was obtained. MS (ESI) m/z 432.0 (M+H). $^1$H NMR (500 MHz, DMSO-d$_6$) δ 7.59-7.46 (m, 4H), 7.44-7.35 (m, 3H), 7.31-7.23 (m, 4H), 7.22-7.11 (m, 2H), 6.66-6.52 (m, 1H), 5.28-5.14 (m, 1H), 4.06-3.81 (m, 2H)

Intermediate 239a: (R)-7-(2-(benzo[d]thiazol-2-yl)-1-phenylethyl)-N,3-ditrityl-3H-[1,2,3]triazolo[4,5-b]pyridin-5-amine A solution of (R)-3-phenyl-3-(3-trityl-5-(tritylamino)-3H-[1,2,3]triazolo[4,5-b]pyridin-7-yl)propanoic acid (Intermediate 11-1, 14 mg, 0.019 mmol), pyridine (4.55 µL, 0.056 mmol) and 2-aminobenzenethiol (2.0 µL, 0.019 mmol) in DCM (1 mL) was placed under nitrogen and cooled to 0° C. A solution of 1-propylphosphonic acid cyclic anhydride (50% wt solution, 0.017 mL, 0.028 mmol) in EtOAc was added. The solution warmed to rt and was stirred overnight. The reaction mixture was diluted with water and thrice extracted with EtOAc. The combined extracts were washed with water, brine, dried over anhydrous sodium sulfate, filtered and evaporated to give (R)-7-(2-(benzo[d]thiazol-2-yl)-1-phenylethyl)-N,3-ditrityl-3H-[1,2,3]triazolo[4,5-b]pyridin-5-amine (17.3 mg). HPLC estimated purity 50%. MS (ESI) m/z 857.3 (M+H).

Example 239: (R)-7-(2-(benzo[d]thiazol-2-yl)-1-phenylethyl)-3H-[1,2,3]triazolo[4,5-b]pyridin-5-amine To a solution of (R)-7-(2-(benzo[d]thiazol-2-yl)-1-phenylethyl)-N,3-ditrityl-3H-[1,2,3]triazolo[4,5-b]pyridin-5-amine (17.3 mg, 0.020 mmol) in DCM (1 mL) was added triethylsilane (0.016 mL, 0.10 mmol) followed by TFA (0.3 mL, 3.89 mmol). The mixture was stirred at rt for 1 h. The reaction mixture was concentrated, and the crude was purified via preparative LC/MS (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 18-58% B over 25 minutes, then a 5-minute hold at 100% B; Flow: 20 mL/min) to yield the title compound (3.8 mg, 50.5% yield). MS (ESI) m/z 373.3 (M+H). $^1$H NMR (500 MHz, DMSO-$d_6$) δ 7.92 (d, J=8.2 Hz, 1H), 7.85 (d, J=7.9 Hz, 1H), 7.52 (d, J=7.0 Hz, 2H), 7.42-7.36 (m, 1H), 7.31 (t, J=7.5 Hz, 1H), 7.26 (t, J=7.2 Hz, 2H), 7.20-6.97 (m, 2H), 6.46 (br. s., 1H), 5.00 (t, J=7.6 Hz, 1H), 4.33-4.23 (m, 1H), 4.01 (dd, J=15.1, 7.8 Hz, 1H). LC: 1.36 min, Method C Intermediate 240a: (R)-7-(2-(benzo[d]oxazol-2-yl)-1-phenylethyl)-N-trityl-3H-[1,2,3]triazolo[4,5-b]pyridin-5-amine

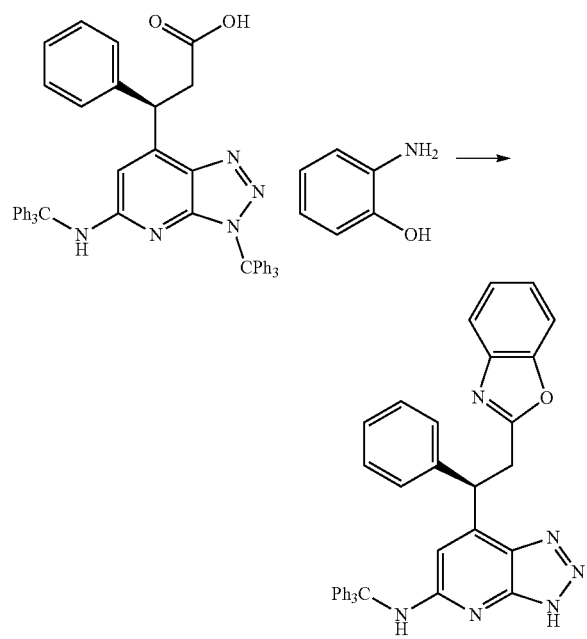

To a solution of (R)-3-phenyl-3-(3-trityl-5-(tritylamino)-3H-[1,2,3]triazolo[4,5-b]pyridin-7-yl)propanoic acid (Intermediate 11-1, 25.6 mg, 0.033 mmol), pyridine (8.1 μL, 0.10 mmol) and 2-aminophenol (4.0 mg, 0.037 mmol) in DCM (1 mL) cooled to 0° C. was added a solution of 1-propylphosphonic acid cyclic anhydride (50% wt solution in EtOAc) (0.030 mL, 0.050 mmol). The mixture was allowed to warm to rt, and was stirred overnight. The reaction mixture was diluted with brine and extracted 3× with EtOAc. The combined extracts were washed with water, brine, dried (Na$_2$SO$_4$), filtered and evaporated to give (R)—N-(2-hydroxyphenyl)-3-phenyl-3-(3-trityl-5-(tritylamino)-3H-[1,2,3]triazolo[4,5-b]pyridin-7-yl)propanamide (28.4 mg). MS (ESI) m/z 859.4 (M+H). (R)—N-(2-hydroxyphenyl)-3-phenyl-3-(3-trityl-5-(tritylamino)-3H-[1,2,3]triazolo[4,5-b]pyridin-7-yl)propanamide (28.4 mg, 0.033 mmol) was combined with AcOH (glacial) (2 mL), and the mixture was heated to 80° C. overnight. The reaction mixture was evaporated to dryness to give (R)-7-(2-(benzo[d]oxazol-2-yl)-1-phenylethyl)-N-trityl-3H-[1,2,3]triazolo[4,5-b]pyridin-5-amine (32.9 mg). Estimated HPLC purity 47%. MS (ESI) m/z 599.4 (M+H).

Example 240: (R)-7-(2-(benzo[d]oxazol-2-yl)-1-phenylethyl)-3H-[1,2,3]triazolo[4,5-b]pyridin-5-amine

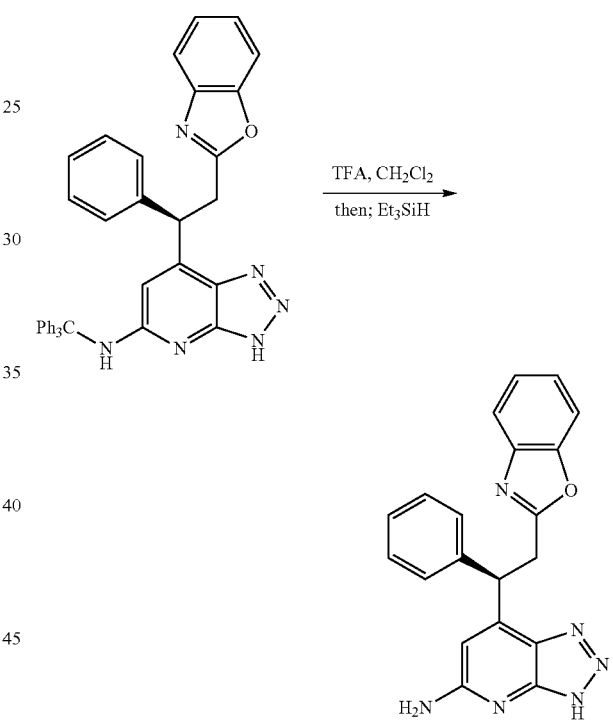

Example 240 was prepared from (R)-7-(2-(benzo[d]oxazol-2-yl)-1-phenylethyl)-N-trityl-3H-[1,2,3]triazolo[4,5-b]pyridin-5-amine as described for Example 239 and was purified by preparatory LC/MS (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min.) to yield the title compound (1.5 mg, 6.8% yield). MS (ESI) m/z 357.0 (M+H). $^1$H NMR (500 MHz, DMSO-$d_6$) δ 7.63-7.57 (m, 2H), 7.54 (d, J=7.6 Hz, 2H), 7.32-7.23 (m, 5H), 7.18-7.14 (m, 1H), 6.43 (s, 1H), 6.28 (br. s., 1H), 5.09 (t, J=7.9 Hz, 1H), 4.16 (dd, J=15.9, 7.6 Hz, 1H), 3.94 (dd, J=16.0, 8.4 Hz, 1H). LC: 1.51 min, Method C.

179

Intermediate 241a: 4-amino-[1,1'-biphenyl]-3-carboxamide

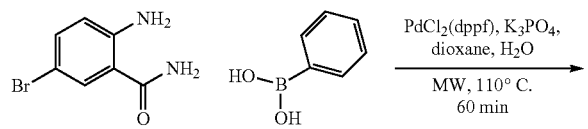

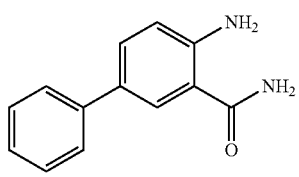

A mixture of 2-amino-5-bromobenzamide (400 mg, 1.86 mmol), phenylboronic acid (227 mg, 1.86 mmol), PdCl₂(dppf) (136 mg, 0.186 mmol) and tripotassium phosphate (1180 mg, 5.58 mmol) in dioxane (10 mL) and water (1 mL) was purged with argon and treated with microwave irradiation for 60 min at 110° C. The aqueous layer was decanted. The organic layer was concentrated and purified via column chromatography with EtOAc/Hexanes from 0-100% to obtain 4-amino-[1,1'-biphenyl]-3-carboxamide (310 mg, 1.5 mmol, 80% yield) as a white solid. ¹H NMR (400 MHz, CDCl₃) δ 7.50 (d, J=2.0 Hz, 1H), 7.46-7.40 (m, 3H), 7.38-7.31 (m, 2H), 7.27-7.20 (m, 1H), 6.70 (d, J=8.4 Hz, 1H), 5.66 (br. s., 2H).

Example 241: (R)-4-(3-phenyl-3-(3-trityl-5-(tritylamino)-3H-[1,2,3]triazolo[4,5-b]pyridin-7-yl)propanamido)-[1,1'-biphenyl]-3-carboxamide

180

A mixture of (R)-3-phenyl-3-(3-trityl-5-(tritylamino)-3H-[1,2,3]triazolo[4,5-b]pyridin-7-yl)propanoic acid (Intermediate 11-1, 100 mg, 0.130 mmol), 4-amino-[1,1'-biphenyl]-3-carboxamide (55.3 mg, 0.260 mmol), o-Benzotriazol-1-yl-N,N,N',N' tetramethyluroniuhexafluorophosphate (99 mg, 0.260 mmol) and TEA (0.182 mL, 1.302 mmol) in DMF (1 mL) was stirred at rt overnight. Then the reaction mixture was heated at 75° C. for an additional 16 hours. The solvents were evaporated and the mixture was taken to the next step without further purification.

The crude material was taken up in EtOH (2 mL) and DMF (1 mL) followed by addition of KOH (227 mg, 4.05 mmol). The reaction mixture was subjected to irradiation in a microwave for 2 h at 110° C. After cooling, reaction contents were diluted with water, extracted with DCM (3×), washed with brine, dried over MgSO₄ and then concentrated to obtain a brown solid. The crude material was dissolved in a mixture of DCM (4 mL) and TFA (1 mL), followed by addition of triethylsilane (0.107 mL, 0.667 mmol). The reaction mixture was stirred at rt for 1 h. The mixture was concentrated, and the residue was purified by LCMS to afford the title compound (2.5 mg, 7% yield, 86% purity). MS (ESI) m/z 460.1 (M+H). ¹H NMR (500 MHz, DMSO-d₆) δ 7.66-7.08 (m, 13H), 6.65-6.53 (m, 1H), 5.25-5.14 (m, 1H), 4.03-3.79 (m, 2H)¹H NMR (500 MHz, DMSO-d₆) δ 7.29 (s, 5H), 7.19 (s, 4H), 7.08 (s, 4H), 6.53 (br. s., 1H), 5.28 (t, J=7.5 Hz, 1H), 3.71 (d, J=7.3 Hz, 1H), 3.64 (d, J=8.9 Hz, 1H).

Examples 242-263 were prepared by methods similar to those described for Examples 238-241.

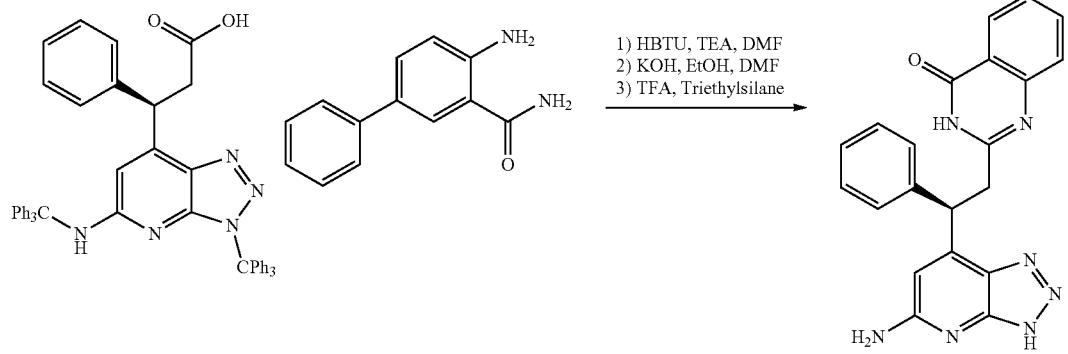

| Ex. No. | Structure | Name | MS (ESI) (M + H) | ¹H NMR | LC RT$^a$ (min) |
|---|---|---|---|---|---|
| 3 | 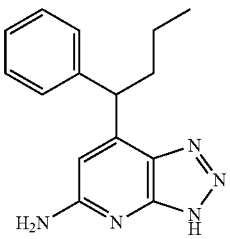 [SMILES: CCCC(c1ccccc1)c1cc(N)nc2[nH]nnc12] | 7-(1-phenylbutyl)-3H-[1,2,3]triazolo[4,5-b]pyridin-5-amine | 268.0 | (400 MHz, CD$_3$CN) δ 7.47-7.41 (m, 2H), 7.32 (t, J = 7.7 Hz, 2H), 7.27-7.20 (m, 1H), 6.70 (s, 1H), 4.48 (t, J = 8.0 Hz, 1H), 2.27 (dd, J = 13.2, 8.2 Hz, 1H), 2.19-2.05 (m, 1H), 1.31 (sxt, J = 7.4 Hz, 2H), 0.94 (t, J = 7.4 Hz, 4H) | 6.91 |
| 4 | 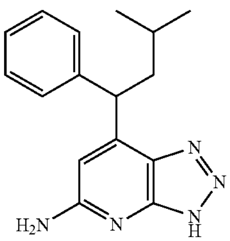 [SMILES: CC(C)CC(c1ccccc1)c1cc(N)nc2[nH]nnc12] | 7-(3-methyl-1-phenylbutyl)-3H-[1,2,3]triazolo[4,5-b]pyridin-5-amine | 282.0 | (400 MHz, CD$_3$CN) δ 7.48-7.42 (m, 2H), 7.37-7.30 (m, 2H), 7.26-7.19 (m, 1H), 6.73 (s, 1H), 4.59 (t, J = 8.0 Hz, 1H), 2.26-1.97 (m, 2H), 1.51-1.39 (m, 1H), 1.07-0.81 (m, 6H) | 7.34 |
| 5 | 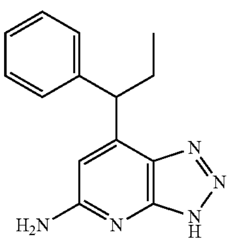 [SMILES: CCC(c1ccccc1)c1cc(N)nc2[nH]nnc12] | 7-(1-phenylpropyl)-3H-[1,2,3]triazolo[4,5-b]pyridin-5-amine | 254.0 | (400 MHz, CD$_3$CN) δ 7.43 (d, J = 7.3 Hz, 2H), 7.33 (t, J = 7.5 Hz, 2H), 7.27-7.18 (m, 1H), 6.69 (s, 1H), 4.37 (t, J = 7.7 Hz, 1H), 2.40-2.28 (m, 1H), 2.23-2.11 (m, 1H), 0.93 (t, J = 7.2 Hz, 3H) | 6.22 |
| 6 | 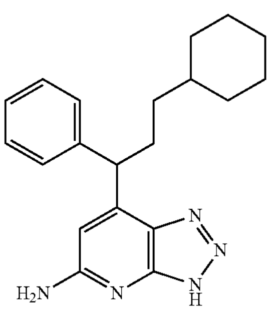 [SMILES: Nc1cc(C(CCC2CCCCC2)c2ccccc2)c2nn[nH]c2n1] | 7-(3-cyclohexyl-1-phenylpropyl)-3H-[1,2,3]triazolo[4,5-b]pyridin-5-amine | 336.1 | (400 MHz, CD$_3$CN) δ 7.42 (d, J = 7.6 Hz, 2H), 7.33 (t, J = 7.5 Hz, 2H), 7.28-7.19 (m, 1H), 6.74 (s, 1H), 4.41 (t, J = 7.7 Hz, 1H), 2.39-2.24 (m, 1H), 2.22-2.06 (m, 1H), 1.77-1.55 (m, 6H), 1.35-1.07 (m, 5H), 0.86 (d, J = 10.9 Hz, 2H) | 9.54 |
| 14 | 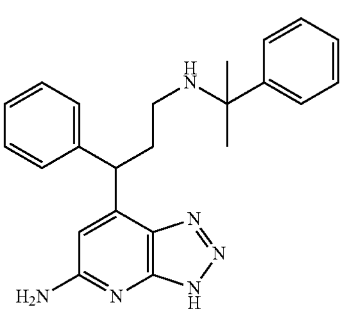 [SMILES: CC(C)(NCCC(c1ccccc1)c1cc(N)nc2[nH]nnc12)c1ccccc1] | 7-{1-phenyl-3-[(2-phenylpropan-2-yl)amino]propyl}-3H-[1,2,3]triazolo[4,5-b]pyridin-5-amine | 387.1 | (400 MHz, CD$_3$CN) δ 7.53-7.47 (m, 2H), 7.42-7.19 (m, 8H), 6.83 (s, 1H), 4.60-4.43 (m, 1H), 2.84-2.59 (m, 3H), 2.54-2.34 (m, 1H), 1.80-1.65 (m, 6H) | 4.17 |

-continued

| Ex. No. | Structure | Name | MS (ESI) (M + H) | $^1$H NMR | LC RT$^a$ (min) |
|---|---|---|---|---|---|
| 16 | 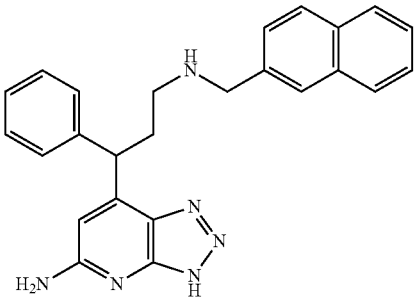 [SMILES: Nc1cc(C(CCNCc2ccc3ccccc3c2)c2ccccc2)c2nn[nH]c2n1] | 7-(3-{[(naphthalen-2-yl)methyl]amino}-1-phenylpropyl)-3H-[1,2,3]triazolo[4,5-b]pyridin-5-amine | 408.9 | (500 MHz, CD$_3$CN) δ 7.97-7.85 (m, 4H), 7.61-7.54 (m, 2H), 7.52 (dd, J = 8.4, 1.8 Hz, 1H), 7.43-7.38 (m, 2H), 7.36-7.31 (m, 2H), 7.29-7.24 (m, 1H), 6.79 (s, 1H), 4.58 (t, J = 7.8 Hz, 1H), 4.29 (s, 2H), 3.19-2.97 (m, 2H), 2.83-2.68 (m, 1H), 2.63-2.49 (m, 1H) | 4.02 |
| 18 | 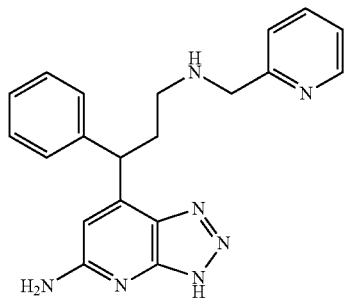 [SMILES: Nc1cc(C(CCNCc2ccccn2)c2ccccc2)c2nn[nH]c2n1] | 7-(1-phenyl-3-{[(pyridin-2-yl)methyl]amino}propyl)-3H-[1,2,3]triazolo[4,5-b]pyridin-5-amine | 360.0 | (500 MHz, CD$_3$CN) δ 8.53 (dt, J = 4.7, 1.4 Hz, 1H), 7.83 (td, J = 7.8, 1.8 Hz, 1H), 7.48-7.42 (m, 2H), 7.41-7.34 (m, 4H), 7.32-7.25 (m, 1H), 6.81 (s, 1H), 4.61 (t, J = 7.8 Hz, 1H), 4.30 (s, 2H), 3.18-3.04 (m, 2H), 2.87-2.75 (m, 1H), 2.69-2.56 (m, 1H) | 6.31$^b$ |
| 19 | 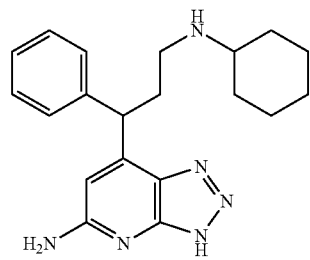 [SMILES: Nc1cc(C(CCNC2CCCCC2)c2ccccc2)c2nn[nH]c2n1] | 7-[3-(cyclohexylamino)-1-phenylpropyl]-3H-[1,2,3]triazolo[4,5-b]pyridin-5-amine | 351.1 | (500 MHz, CD$_3$CN) δ 7.48-7.41 (m, 2H), 7.39-7.33 (m, 2H), 7.31-7.24 (m, 1H), 6.81 (s, 1H), 4.60 (t, J = 7.8 Hz, 1H), 2.99 (br. s., 2H), 2.80-2.66 (m, 1H), 2.59-2.47 (m, 1H), 1.82-1.69 (m, 3H), 1.67-1.53 (m, 2H), 1.39-1.04 (m, 8H) | 8.16$^b$ |
| 20 | 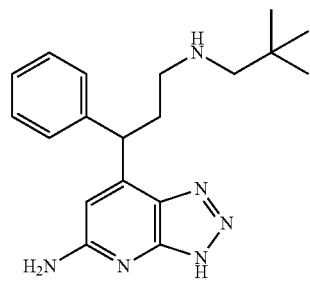 [SMILES: CC(C)(C)CNCCC(c1ccccc1)c1cc(N)nc2[nH]nnc12] | 7-{3-[(2,2-dimethylpropyl)amino]-1-phenylpropyl}-3H-[1,2,3]triazolo[4,5-b]pyridin-5-amine | 339.0 | (500 MHz, CD$_3$CN) δ 7.47-7.41 (m, 2H), 7.40-7.33 (m, 2H), 7.32-7.24 (m, 1H), 6.74 (s, 1H), 4.58 (t, J = 7.8 Hz, 1H), 3.12-2.90 (m, 2H), 2.83-2.72 (m, 3H), 2.69-2.55 (m, 1H), 1.01 (s, 9H) | 8.35$^b$ |
| 21 | 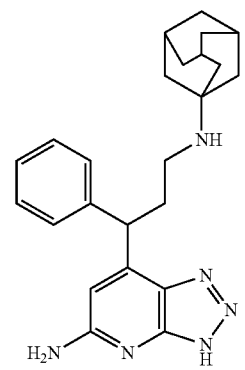 [SMILES: Nc1cc(C(CCNC23CC4CC(CC(C4)C2)C3)c2ccccc2)c2nn[nH]c2n1] | 7-{3-[(adamantan-1-yl)amino]-1-phenylpropyl}-3H-[1,2,3]triazolo[4,5-b]pyridin-5-amine | 403.0 | (500 MHz, CD$_3$CN) δ 7.45-7.39 (m, 2H), 7.35 (t, J = 7.6 Hz, 2H), 7.30-7.24 (m, 1H), 6.96 (s, 1H), 4.63 (t, J = 7.8 Hz, 1H), 2.99 (br. s., 2H), 2.77-2.65 (m, 1H), 2.56-2.43 (m, 1H), 2.12 (br. s., 3H), 1.84 (d, J = 2.2 Hz, 6H), 1.75-1.65 (m, 3H), 1.64-1.56 (m, 3H) | 4.76 |

-continued

| Ex. No. | Structure | Name | MS (ESI) (M + H) | ¹H NMR | LC RT$^a$ (min) |
|---|---|---|---|---|---|
| 22 | 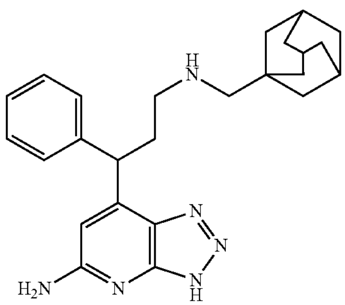 [SMILES: Nc1cc(C(CCNCC23CC4CC(CC(C4)C2)C3)c2ccccc2)c2nn[nH]c2n1] | 7-(3-{[(adamantan-1-yl)methyl]amino}-1-phenylpropyl)-3H-[1,2,3]triazolo[4,5-b]pyridin-5-amine | 417.0 | (500 MHz, CD$_3$CN) δ 7.46-7.41 (m, 2H), 7.40-7.34 (m, 2H), 7.32-7.26 (m, 1H), 6.76 (s, 1H), 4.58 (t, J = 7.7 Hz, 1H), 3.10-2.87 (m, 2H), 2.81-2.68 (m, 1H), 2.67-2.53 (m, 3H), 1.98 (br. s., 3H), 1.78-1.70 (m, 3H), 1.68-1.62 (m, 3H), 1.57 (d, J = 2.2 Hz, 6H) | 8.36 |
| 23 | 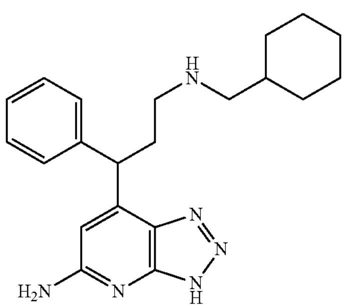 [SMILES: Nc1cc(C(CCNCC2CCCCC2)c2ccccc2)c2nn[nH]c2n1] | 7-{3-[(cyclohexylmethyl)amino]-1-phenylpropyl}-3H-[1,2,3]triazolo[4,5-b]pyridin-5-amine | 365.1 | (500 MHz, CD$_3$CN) δ 7.45-7.40 (m, 2H), 7.35 (t, J = 7.6 Hz, 2H), 7.30-7.25 (m, 1H), 6.82 (s, 1H), 4.59 (t, J = 7.8 Hz, 1H), 3.06-2.90 (m, 2H), 2.82-2.67 (m, 3H), 2.61-2.50 (m, 1H), 1.76-1.60 (m, 6H), 1.30-1.11 (m, 3H), 1.02-0.90 (m, 2H) | 4.58 |
| 24 | 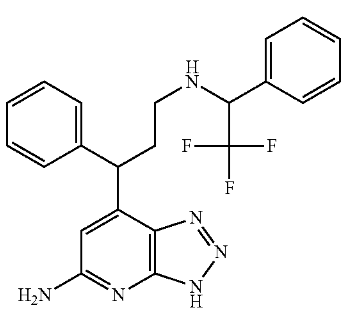 [SMILES: Nc1cc(C(CCNC(c2ccccc2)C(F)(F)F)c2ccccc2)c2nn[nH]c2n1] | 7-{1-phenyl-3-[(2,2,2-trifluoro-1-phenylethyl)amino]propyl}-3H-[1,2,3]triazolo[4,5-b]pyridin-5-amine | 427.1 | (500 MHz, CD$_3$CN) δ 7.49-7.39 (m, 5H), 7.38-7.28 (m, 3H), 7.27-7.16 (m, 2H), 6.79 (s, 1H), 4.65-4.50 (m, 2H), 2.81-2.14 (m, 4H) | 5.63 |
| 25 | 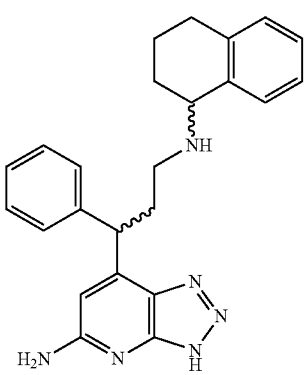 [SMILES: Nc1cc(C(CCNC2CCCc3ccccc32)c2ccccc2)c2nn[nH]c2n1] | 7-{1-phenyl-3-[(1,2,3,4-tetrahydronaphthalen-1-yl)amino]propyl}-3H-[1,2,3]triazolo[4,5-b]pyridin-5-amine | 399.2 | (400 MHz, CD$_3$CN) δ 7.44-7.40 (m, 2H), 7.38-7.25 (m, 5H), 7.22-7.13 (m, 2H), 6.91 (d, J = 15.0 Hz, 1H), 4.60 (td, J = 7.7, 4.4 Hz, 1H), 4.42 (d, J = 4.0 Hz, 1H), 3.24-2.99 (m, 2H), 2.91-2.68 (m, 3H), 2.62-2.51 (m, 1H), 2.17-1.97 (m, 2H), 1.91-1.74 (m, 2H) | 4.06 |

-continued

| Ex. No. | Structure | Name | MS (ESI) (M + H) | $^1$H NMR | LC RT$^a$ (min) |
|---|---|---|---|---|---|
| 26 | 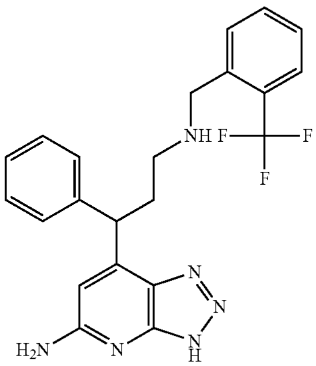 [SMILES: Nc1cc(C(CCNCc2ccccc2C(F)(F)F)c2ccccc2)c2nn[nH]c2n1] | 7-[1-phenyl-3-({[2-(trifluoromethyl)phenyl]methyl}amino)propyl]-3H-[1,2,3]triazolo[4,5-b]pyridin-5-amine | 427.0 | (500 MHz, CDCl$_3$ and CD$_3$OD) δ 7.64 (d, J = 7.7 Hz, 1H), 7.55-7.49 (m, 2H), 7.44 (d, J = 7.4 Hz, 2H), 7.42-7.36 (m, 1H), 7.31 (t, J = 7.7 Hz, 2H), 7.25-7.18 (m, 1H), 6.51 (s, 1H), 4.61 (m, 1H), 3.91 (s, 2H), 2.74-2.64 (m, 2H), 2.62-2.53 (m, 1H), 2.50-2.39 (m, 1H) | 1.10$^c$ |
| 27 | 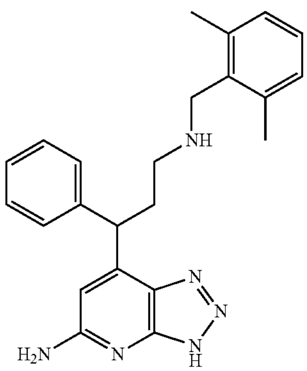 [SMILES: Cc1cccc(C)c1CNCCC(c1ccccc1)c1cc(N)nc2[nH]nnc12] | 7-(3-{[(2,6-dimethylphenyl)methyl]amino}-1-phenylpropyl)-3H-[1,2,3]triazolo[4,5-b]pyridin-5-amine | 387.3 | (500 MHz, DMSO-d6) δ 8.53 (br. s., 2H), 7.50 (d, J = 7.4 Hz, 2H), 7.36 (t, J = 7.6 Hz, 2H), 7.29-7.17 (m, 2H), 7.10 (d, J = 7.7 Hz, 2H), 6.42 (br. s., 1H), 4.50 (t, J = 7.8 Hz, 1H), 4.16 (t, J = 6.1 Hz, 2H), 3.14-2.97 (m, 2H), 2.80 (d, J = 5.0 Hz, 1H), 2.71-2.63 (m, 1H), 2.36 (s, 6H) | 1.13$^c$ |
| 28 | 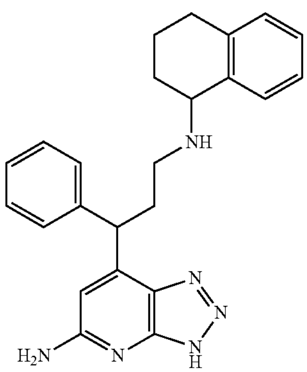 [SMILES: Nc1cc(C(CCNC2CCCc3ccccc32)c2ccccc2)c2nn[nH]c2n1] | 7-{1-phenyl-3-[(1,2,3,4-tetrahydronaphthalen-1-yl)amino]propyl}-3H-[1,2,3]triazolo[4,5-b]pyridin-5-amine | 399.3 | (500 MHz, DMSO-d6) δ 7.46 (d, J = 7.4 Hz, 2H), 7.36-7.26 (m, 3H), 7.23-7.16 (m, 1H), 7.12-7.00 (m, 3H), 6.53 (br. s., 2H), 6.49 (s, 1H), 4.62 (t, J = 7.0 Hz, 1H), 3.62 (br. s., 1H), 2.73-2.54 (m, 5H), 2.33-2.23 (m, 1H), 1.85 (dd, J = 8.0, 5.5 Hz, 1H), 1.74-1.66 (m, 1H), 1.64-1.51 (m, 2H) | 1.13$^c$ |
| 29 | 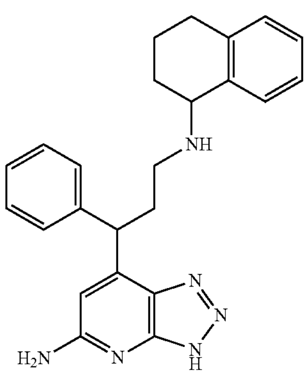 [SMILES: Nc1cc(C(CCNC2CCCc3ccccc32)c2ccccc2)c2nn[nH]c2n1] | 7-{1-phenyl-3-[(1,2,3,4-tetrahydronaphthalen-1-yl)amino]propyl}-3H-[1,2,3]triazolo[4,5-b]pyridin-5-amine | 398.9 | (400 MHz, CD$_3$OD) δ 7.49-7.42 (m, 2H), 7.31 (t, J = 7.6 Hz, 2H), 7.25-7.16 (m, 2H), 7.16-7.01 (m, 3H), 6.48 (s, 1H), 4.61 (t, J = 7.9 Hz, 1H), 3.87 (t, J = 4.6 Hz, 1H), 2.86-2.64 (m, 4H), 2.63-2.40 (m, 2H), 1.97-1.80 (m, 3H), 1.76-1.64 (m, 1H) | 9.28 |

-continued

| Ex. No. | Structure | Name | MS (ESI) (M + H) | ¹H NMR | LC RT$^a$ (min) |
|---|---|---|---|---|---|
| 30 | 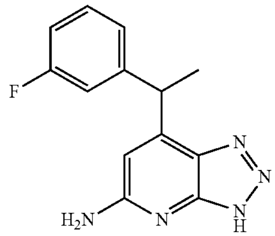 [SMILES: CC(c1cccc(F)c1)c1cc(N)nc2[nH]nnc12] | 7-[1-(3-fluorophenyl) ethyl]-3H-[1,2,3] triazolo[4,5-b] pyridin-5-amine | 258.0 | (400 MHz, CD$_3$CN) δ 7.35 (td, J = 8.0, 6.0 Hz, 1H), 7.20 (d, J = 7.7 Hz, 1H), 7.15 (dt, J = 10.4, 1.9 Hz, 1H), 7.00 (td, J = 8.5, 2.7 Hz, 1H), 6.65 (s, 1H), 4.69 (q, J = 7.1 Hz, 1H), 1.74 (d, J = 7.1 Hz, 3H) | 6.07 |
| 31 | 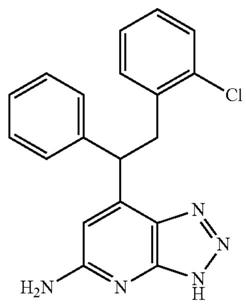 [SMILES: Nc1cc(C(Cc2ccccc2Cl)c2ccccc2)c2nn[nH]c2n1] | 7-[2-(2-chlorophenyl)-1-phenylethyl]-3H-[1,2,3]triazolo [4,5-b]pyridin-5-amine | 350.0 | (400 MHz, CD$_3$CN) δ 7.45-7.39 (m, 2H), 7.38-7.20 (m, 4H), 7.18-7.11 (m, 1H), 7.10-7.00 (m, 2H), 6.90-6.80 (m, 1H), 4.92 (t, J = 8.0 Hz, 1H), 3.79-3.69 (m, 1H), 3.67-3.53 (m, 1H) | 7.30 |
| 32 | 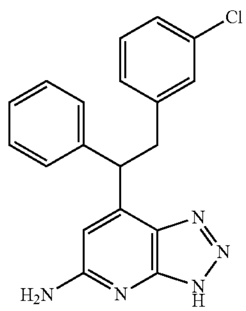 [SMILES: Nc1cc(C(Cc2cccc(Cl)c2)c2ccccc2)c2nn[nH]c2n1] | 7-[2-(3-chlorophenyl)-1-phenylethyl]-3H-[1,2,3]triazolo [4,5-b]pyridin-5-amine | 350.0 | (400 MHz, CD$_3$CN) δ 7.46-7.40 (m, 2H), 7.35-7.27 (m, 2H), 7.26-7.06 (m, 5H), 6.72 (s, 1H), 4.81 (t, J = 8.2 Hz, 1H), 3.67 (dd, J = 13.7, 7.7 Hz, 1H), 3.48 (dd, J = 13.7, 8.8 Hz, 1H) | 7.43 |
| 33 | 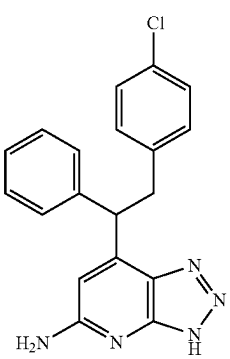 [SMILES: Nc1cc(C(Cc2ccc(Cl)cc2)c2ccccc2)c2nn[nH]c2n1] | 7-[2-(4-chlorophenyl)-1-phenylethyl]-3H-[1,2,3]triazolo [4,5-b]pyridin-5-amine | 350.0 | (400 MHz, CD$_3$CN) δ 7.46-7.38 (m, 2H), 7.33-7.26 (m, 2H), 7.25-7.10 (m, 5H), 6.71 (s, 1H), 4.78 (t, J = 8.0 Hz, 1H), 3.67 (dd, J = 13.7, 7.7 Hz, 1H), 3.47 (dd, J = 14.0, 8.5 Hz, 1H) | 7.46 |
| 35 | 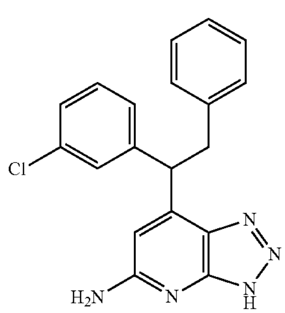 [SMILES: Nc1cc(C(Cc2ccccc2)c2cccc(Cl)c2)c2nn[nH]c2n1] | 7-[1-(3-chlorophenyl)-2-phenylethyl]-3H-[1,2,3]triazolo [4,5-b]pyridin-5-amine | 350.0 | (400 MHz, CD$_3$CN) δ 7.48-7.44 (m, 1H), 7.39-7.33 (m, 1H), 7.30-7.10 (m, 7H), 6.74 (s, 1H), 4.82 (t, J = 8.2 Hz, 1H), 3.66 (dd, J = 14.0, 7.4 Hz, 1H), 3.46 (dd, J = 13.7, 8.8 Hz, 1H) | 7.68 |

-continued

| Ex. No. | Structure | Name | MS (ESI) (M + H) | ¹H NMR | LC RT[a] (min) |
|---|---|---|---|---|---|
| 36 | 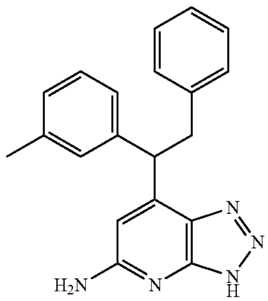 [SMILES: Cc1cccc(C(Cc2ccccc2)c2cc(N)nc3[nH]nnc23)c1] | 7-[1-(3-methylphenyl)-2-phenylethyl]-3H-[1,2,3]triazolo[4,5-b]pyridin-5-amine | 330.1 | (400 MHz, CD$_3$CN) δ 7.31-7.08 (m, 8H), 7.03 (d, J = 7.1 Hz, 1H), 6.69 (s, 1H), 4.79 (t, J = 8.0 Hz, 1H), 3.66 (dd, J = 14.0, 8.0 Hz, 1H), 3.47 (dd, J = 13.7, 8.2 Hz, 1H), 2.27 (s, 3H) | 7.27 |
| 37 | 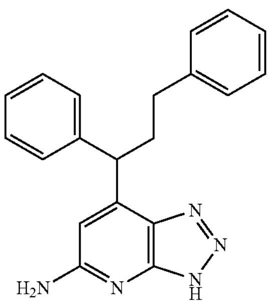 [SMILES: Nc1cc(C(CCc2ccccc2)c2ccccc2)c2nn[nH]c2n1] | 7-(1,3-diphenylpropyl)-3H-[1,2,3]triazolo[4,5-b]pyridin-5-amine | 330.1 | (400 MHz, CD$_3$CN) δ 7.44 (d, J = 7.1 Hz, 2H), 7.38-7.23 (m, 5H), 7.21-7.10 (m, 3H), 6.79 (s, 1H), 4.53-4.40 (m, 1H), 2.71-2.54 (m, 3H), 2.50-2.37 (m, 1H) | 6.98 |
| 39 | 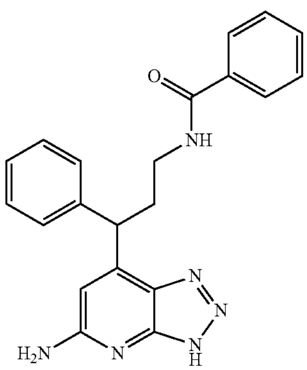 [SMILES: Nc1cc(C(CCNC(=O)c2ccccc2)c2ccccc2)c2nn[nH]c2n1] | N-(3-{5-amino-3H-[1,2,3]triazolo[4,5-b]pyridin-7-yl}-3-phenylpropyl)benzamide | 317.1 | (400 MHz, THF-d8) δ 7.88 (br. s., 1H), 7.85-7.81 (m, 2H), 7.52 (d, J = 7.7 Hz, 2H), 7.45-7.33 (m, 3H), 7.27 (t, J = 7.7 Hz, 2H), 7.20-7.12 (m, 1H), 6.38 (s, 1H), 4.62 (t, J = 7.7 Hz, 1H), 3.47-3.37 (m, 1H), 3.33-3.22 (m, 1H), 2.76-2.48 (m, 2H) | 6.27 |
| 40 | 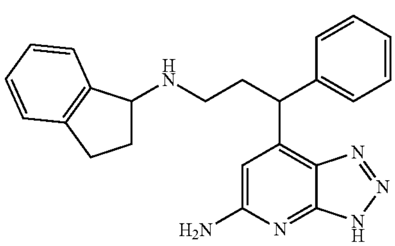 [SMILES: Nc1cc(C(CCNC2CCc3ccccc32)c2ccccc2)c2nn[nH]c2n1] | 7-{3-[(2,3-dihydro-1H-inden-1-yl)amino]-1-phenylpropyl}-3H-[1,2,3]triazolo[4,5-b]pyridin-5-amine | 385.0 | (500 MHz, CD$_3$OD) δ 7.57-7.22 (m, 9H), 6.78-6.68 (m, 1H), 4.82-4.75 (m, 1H), 4.64 (ddd, J = 9.4, 6.2, 3.4 Hz, 1H), 3.25-2.93 (m, 4H), 2.90-2.62 (m, 2H), 2.59-2.46 (m, 1H), 2.29-2.13 (m, 1H) | 4.56 |
| 41 | 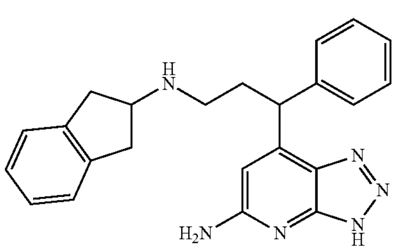 [SMILES: Nc1cc(C(CCNC2Cc3ccccc3C2)c2ccccc2)c2nn[nH]c2n1] | 7-{3-[(2,3-dihydro-1H-inden-2-yl)amino]-1-phenylpropyl}-3H-[1,2,3]triazolo[4,5-b]pyridin-5-amine | 385.0 | (500 MHz, CD$_3$OD) δ 7.56-7.49 (m, 2H), 7.43-7.39 (m, 2H), 7.35-7.30 (m, 1H), 7.28-7.18 (m, 4H), 6.81 (s, 1H), 4.65 (dd, J = 9.1, 6.6 Hz, 1H), 4.17-3.96 (m, 1H), 3.38 (ddd, J = 16.5, 7.7, 1.7 Hz, 2H), 3.18 (td, J = 11.7, 5.2 Hz, 1H), 3.13-2.99 (m, 3H), 2.92-2.81 (m, 1H), 2.75-2.63 (m, 1H) | 4.66 |

-continued

| Ex. No. | Structure | Name | MS (ESI) (M + H) | ¹H NMR | LC RT<sup>a</sup> (min) |
|---|---|---|---|---|---|
| 42 | 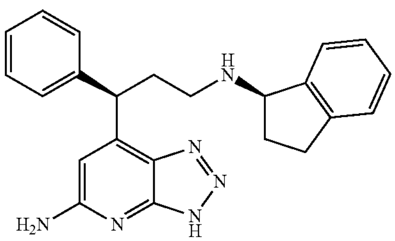 [SMILES: Nc1cc([C@H](CCN[C@@H]2CCc3ccccc32)c2ccccc2)c2nn[nH]c2n1] | 7-[(1R)-3-{[(1R)-2,3-dihydro-1H-inden-1-yl]amino}-1-phenylpropyl]-3H-[1,2,3]triazolo[4,5-b]pyridin-5-amine | 385.0 | (500 MHz, CD₃OD) δ 7.56-7.25 (m, 9H), 6.57 (s, 1H), 4.78 (dd, J = 7.7, 3.9 Hz, 1H), 4.62 (dd, J = 9.4, 6.3 Hz, 1H), 3.22-3.12 (m, 2H), 3.11-3.04 (m, 1H), 2.99 (ddd, J = 16.4, 8.9, 4.4 Hz, 1H), 2.89-2.77 (m, 1H), 2.75-2.64 (m, 1H), 2.60-2.48 (m, 1H), 2.19 (ddt, J = 14.2, 8.4, 4.2 Hz, 1H) | 3.85 |
| 43 | 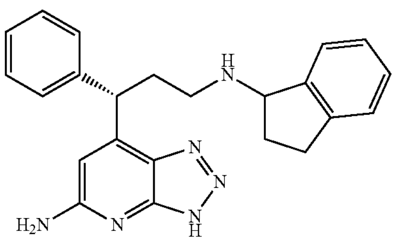 [SMILES: Nc1cc([C@@H](CCNC2CCc3ccccc32)c2ccccc2)c2nn[nH]c2n1] | 7-[(1S)-3-[(2,3-dihydro-1H-inden-1-yl)amino]-1-phenylpropyl]-3H-[1,2,3]triazolo[4,5-b]pyridin-5-amine | 385.0 | 500 MHz, CD₃OD) δ 7.60-7.21 (m, 9H), 6.58 (br. s., 1H), 4.81-4.75 (m, 1H), 4.65-4.56 (m, 1H), 3.21-3.12 (m, 2H), 3.12-3.04 (m, 1H), 3.03-2.95 (m, 1H), 2.93-2.78 (m, 1H), 2.74-2.61 (m, 1H), 2.59-2.47 (m, 1H), 2.23-2.11 (m, 1H) | 3.81 |
| 44 | 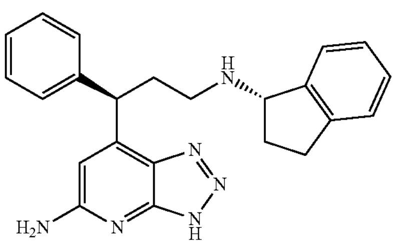 [SMILES: Nc1cc([C@H](CCN[C@H]2CCc3ccccc32)c2ccccc2)c2nn[nH]c2n1] | 7-[(1R)-3-{[(1S)-2,3-dihydro-1H-inden-1-yl]amino}-1-phenylpropyl]-3H-[1,2,3]triazolo[4,5-b]pyridin-5-amine | 385.0 | (500 MHz, CD₃OD) δ 7.55-7.48 (m, 3H), 7.46-7.36 (m, 6H), 7.35-7.25 (m, br. s., 1H), 6.60 (br. s., 1H), 4.79 (dd, J = 7.7, 3.9 Hz, 1H), 4.62 (t, J = 7.8 Hz, 1H), 3.21-3.11 (m, 2H), 3.07 (td, J = 11.7, 5.0 Hz, 1H), 2.99 (ddd, J = 16.4, 8.9, 4.7 Hz, 1H), 2.87 (tt, J = 12.0, 6.1 Hz, 1H), 2.73-2.61 (m, 1H), 2.58-2.47 (m, 1H), 2.24-2.13 (m, 1H) | 3.83 |
| 45 | 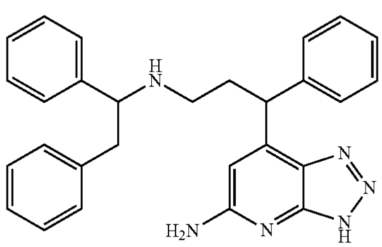 [SMILES: Nc1cc(C(CCNC(Cc2ccccc2)c2ccccc2)c2ccccc2)c2nn[nH]c2n1] | 7-{3-[(1,2-diphenylethyl)amino]-1-phenylpropyl}-3H-[1,2,3]triazolo[4,5-b]pyridin-5-amine | 448.9 | (500 MHz, CD₃OD) δ 7.45-7.24 (m, 10H), 7.20-7.12 (m, 3H), 7.05-6.96 (m, 2H), 6.69 (d, J = 8.0 Hz, 1H), 4.55-4.42 (m, 2H), 3.45 (dt, J = 13.2, 4.4 Hz, 1H), 3.22 (dd, J = 13.1, 10.9 Hz, 1H), 3.02-2.95 (m, 1H), 2.95-2.65 (m, 3H), 3.04-2.52 (m, 1H) | 5.21 |
| 46 | 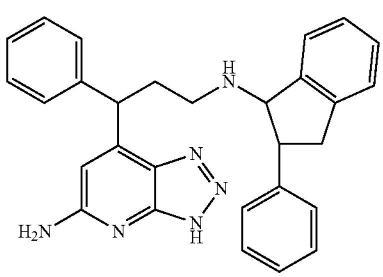 [SMILES: Nc1cc(C(CCNC2c3ccccc3CC2c2ccccc2)c2ccccc2)c2nn[nH]c2n1] | 7-{1-phenyl-3-[(2-phenyl-2,3-dihydro-1H-inden-1-yl)amino]propyl}-3H-[1,2,3]triazolo[4,5-b]pyridin-5-amine | 460.9 | (500 MHz, CD₃OD) δ 7.52-7.24 (m, 14H), 6.61 (d, J = 2.8 Hz, 1H), 4.91 (dd, J = 6.7, 2.1 Hz, 2H), 4.46-4.32 (m, 1H), 4.15-4.04 (m, 1H), 3.62 (dd, J = 16.0, 9.9 Hz, 1H), 3.31-3.22 (m, 1H), 2.99-2.83 (m, 1H), 2.76-2.35 (m, 2H) | 5.16 |
| 47 | 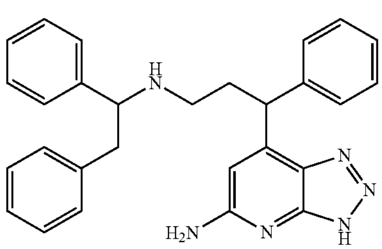 [SMILES: Nc1cc(C(CCNC(Cc2ccccc2)c2ccccc2)c2ccccc2)c2nn[nH]c2n1] | 7-{3-[(1,2-diphenylethyl)amino]-1-phenylpropyl}-3H-[1,2,3]triazolo[4,5-b]pyridin-5-amine | 448.9 | (500 MHz, CD₃OD) δ 7.38-7.30 (m, 2H), 7.28-7.07 (m, 13H), 7.04-6.97 (m, 2H), 6.45-6.39 (m, 1H), 4.56-4.41 (m, 1H), 3.87 (t, J = 7.2 Hz, 1H), 3.09-2.78 (m, 2H), 2.51-2.28 (m, 3H) | 5.19 |

-continued

| Ex. No. | Structure | Name | MS (ESI) (M + H) | ¹H NMR | LC RT[a] (min) |
|---|---|---|---|---|---|
| 48 | 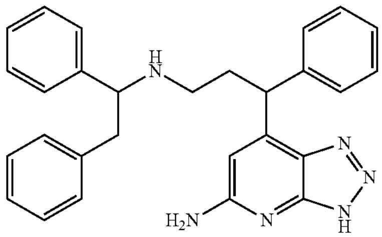 [SMILES: Nc1cc(C(CCNC(Cc2ccccc2)c2ccccc2)c2ccccc2)c2nn[nH]c2n1] | 7-{3-[(1,2-diphenylethyl)amino]-1-phenylpropyl}-3H-[1,2,3]triazolo[4,5-b]pyridin-5-amine | 448.9 | (500 MHz, CD$_3$OD) δ 7.39-7.33 (m, 2H), 7.24 (t, J = 7.7 Hz, 2H), 7.20-7.10 (m, 7H), 7.10-7.04 (m, 2H), 7.04-6.98 (m, 2H), 6.38 (s, 1H), 4.52 (t, J = 7.8 Hz, 1H), 3.78 (t, J = 7.2 Hz, 1H), 3.02 (dd, J = 13.2, 6.6 Hz, 1H), 2.90-2.77 (m, 1H), 2.56-2.45 (m, 1H), 2.41 (t, J = 7.0 Hz, 2H), 2.32-2.19 (m, 1H) | 5.17 |
| 51 | 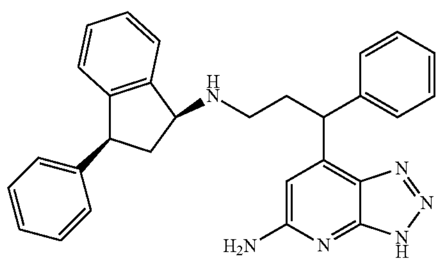 [SMILES: Nc1cc(C(CCN[C@H]2C[C@@H](c3ccccc3)c3ccccc32)c2ccccc2)c2nn[nH]c2n1] | 7-(1-phenyl-3-{[(1S,3S)-3-phenyl-2,3-dihydro-1H-inden-1-yl]amino}propyl)-3H-[1,2,3]triazolo[4,5-b]pyridin-5-amine | 460.9 | (500 MHz, CD$_3$OD) δ 7.62-7.57 (m, 1H), 7.56-7.49 (m, 2H), 7.45-7.28 (m, 9H), 7.26-7.20 (m, 2H), 6.96 (d, J = 5.8 Hz, 1H), 6.67-6.58 (m, 1H), 4.98-4.90 (m, 2H), 4.64 (q, J = 7.7 Hz, 1H), 4.37 (t, J = 8.9 Hz, 1H), 3.30-3.08 (m, 2H), 3.08-2.95 (m, 1H), 2.93-2.77 (m, 1H), 2.10-1.93 (m, 1H) | 5.55 |
| 52 | 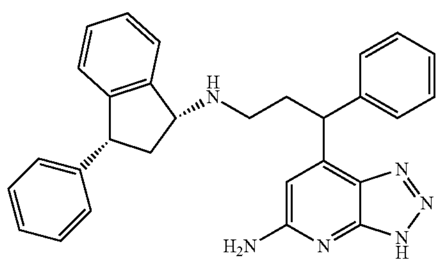 [SMILES: Nc1cc(C(CCN[C@@H]2C[C@H](c3ccccc3)c3ccccc32)c2ccccc2)c2nn[nH]c2n1] | 7-(1-phenyl-3-{[(1S,3S)-3-phenyl-2,3-dihydro-1H-inden-1-yl]amino}propyl)-3H-[1,2,3]triazolo[4,5-b]pyridin-5-amine | 460.9 | (500 MHz, CD$_3$OD) δ 7.63-7.49 (m, 3H), 7.45-7.18 (m, 11H), 7.03-6.91 (m, 1H), 6.64 (d, J = 15.7 Hz, 1H), 4.97-4.89 (m, 1H), 4.70-4.56 (m, 1H), 4.37 (t, J = 8.8 Hz, 1H), 3.30-2.96 (m, 3H), 2.90-2.80 (m, 1H), 2.76-2.59 (m, 1H) | 5.52 |
| 53 | 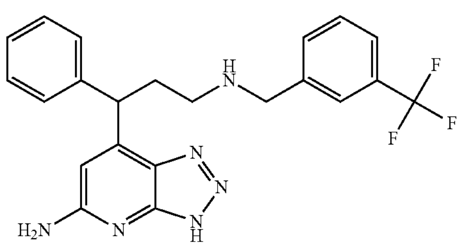 [SMILES: Nc1cc(C(CCNCc2cccc(C(F)(F)F)c2)c2ccccc2)c2nn[nH]c2n1] | 7-[1-phenyl-3-({[3-(trifluoromethyl)phenyl]methyl}amino)propyl]-3H-[1,2,3]triazolo[4,5-b]pyridin-5-amine | 427.2 | (500 MHz, DMSO-d6) δ 7.66 (br. s., 1H), 7.58 (t, J = 7.2 Hz, 2H), 7.54-7.47 (m, 1H), 7.43 (d, J = 7.7 Hz, 2H), 7.27 (t, J = 7.4 Hz, 2H), 7.21-7.14 (m, 1H), 6.52 (br. s., 2H), 6.43 (s, 1H), 4.57-4.48 (m, 1H), 3.79 (br. s., 2H), 2.36 (br. s., 1H) | 1.20[c] |
| 54 | 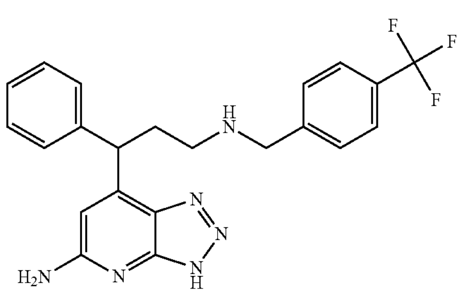 [SMILES: Nc1cc(C(CCNCc2ccc(C(F)(F)F)cc2)c2ccccc2)c2nn[nH]c2n1] | 7-[1-phenyl-3-({[4-(trifluoromethyl)phenyl]methyl}amino)propyl]-3H-[1,2,3]triazolo[4,5-b]pyridin-5-amine | 427.2 | (500 MHz, DMSO-d6) δ 7.59 (d, J = 8.0 Hz, 2H), 7.48 (d, J = 8.0 Hz, 2H), 7.43 (d, J = 7.4 Hz, 2H), 7.27 (t, J = 7.6 Hz, 2H), 7.21-7.13 (m, 1H), 6.52 (br. s., 2H), 6.45 (s, 1H), 4.55 (t, J = 7.4 Hz, 1H), 3.74 (s, 2H), 2.43 (t, J = 6.2 Hz, 2H), 2.35-2.23 (m, 1H) | 1.21[c] |

| Ex. No. | Structure | Name | MS (ESI) (M + H) | ¹H NMR | LC RT[a] (min) |
|---|---|---|---|---|---|
| 55 | 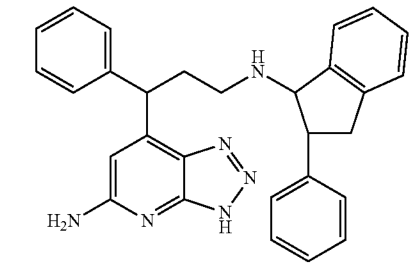 [SMILES: Nc1cc(C(CCNC2c3ccccc3CC2c2ccccc2)c2ccccc2)c2nn[nH]c2n1] | 7-{1-phenyl-3-[(2-phenyl-2,3-dihydro-1H-inden-1-yl)amino]propyl}-3H-[1,2,3]triazolo[4,5-b]pyridin-5-amine | 460.9 | (400 MHz, CD$_3$OD) δ 7.55-7.20 (m, 14H), 6.45 (s, 1H), 4.89 (d, J = 6.6 Hz, 1H), 4.33 (t, J = 7.6 Hz, 1H), 4.21- 3.98 (m, 1H), 3.59 (dd, J = 16.1, 10.1 Hz, 1H), 3.25 (dd, J = 16.4, 7.6 Hz, 1H), 2.97-2.79 (m, 1H), 2.72-2.50 (m, 2H), 2.49-2.26 (m, 1H) | 5.11 |
| 56 | 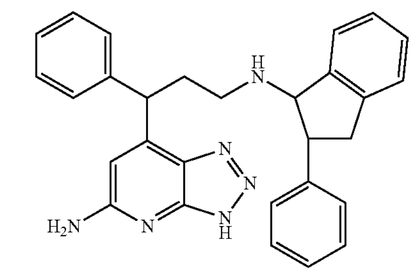 [SMILES: Nc1cc(C(CCNC2c3ccccc3CC2c2ccccc2)c2ccccc2)c2nn[nH]c2n1] | 7-{1-phenyl-3-[(2-phenyl-2,3-dihydro-1H-inden-1-yl)amino]propyl}-3H-[1,2,3]triazolo[4,5-b]pyridin-5-amine | 460.9 | (400 MHz, CD$_3$OD) δ 7.52-7.19 (m, 14H), 6.49 (s, 1H), 4.89 (d, J = 6.6 Hz, 1H), 4.36 (dd, J = 8.6, 6.6 Hz, 1H), 4.07 (dt, J = 9.5, 7.3 Hz, 1H), 3.59 (dd, J = 16.1, 9.9 Hz, 1H), 3.29-3.19 (m, 1H), 2.96-2.81 (m, 1H), 2.75-2.35 (m, 3H) | 5.16 |
| 57 | 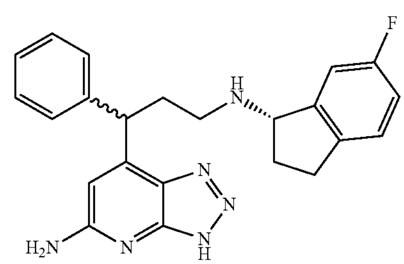 [SMILES: Nc1cc(C(CCN[C@H]2CCc3ccc(F)cc32)c2ccccc2)c2nn[nH]c2n1] | 7-(3-{[(1S)-6-fluoro-2,3-dihydro-1H-inden-1-yl]amino}-1-phenylpropyl)-3H-[1,2,3]triazolo[4,5-b]pyridin-5-amine | 403.2 | (500 MHz, CD$^3$OD) δ 7.56-7.50 (m, 1H), 7.49-7.44 (m, 1H), 7.41 (td, J = 7.5, 1.5 Hz, 2H), 7.36-7.27 (m, 2H), 7.11 (dd, J = 8.8, 2.2 Hz, 1H), 7.06-6.99 (m, 1H), 6.87-6.77 (m, 1H), 4.75 (td, J = 7.2, 3.6 Hz, 1H), 4.69-4.59 (m, 1H), 3.25-3.12 (m, 2H), 3.10-2.93 (m, 2H), 2.93-2.78 (m, 1H), 2.77-2.63 (m, 1H), 2.62-2.52 (m, 1H), 2.31-2.19 (m, 1H) | 4.40 |
| 58 | 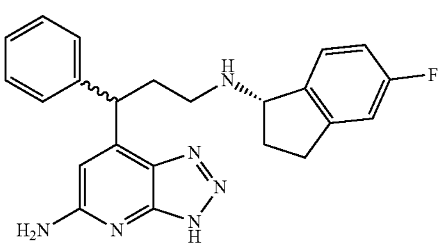 [SMILES: Nc1cc(C(CCN[C@H]2CCc3cc(F)ccc32)c2ccccc2)c2nn[nH]c2n1] | 7-(3-{[(1S)-5-fluoro-2,3-dihydro-1H-inden-1-yl]amino}-1-phenylpropyl)-3H-[1,2,3]triazolo[4,5-b]pyridin-5-amine | 403.2 | (500 MHz, CD$_3$OD) δ 7.60-7.25 (m, 6H), 7.16-6.94 (m, 2H), 6.86-6.71 (m, 1H), 4.75 (td, J = 7.2, 3.6 Hz, 1H), 4.68-4.62 (m, 1H), 3.28-2.93 (m, 4H), 2.91-2.49 (m, 3H), 2.35-2.10 (m, 1H) | 4.44 |
| 59 | 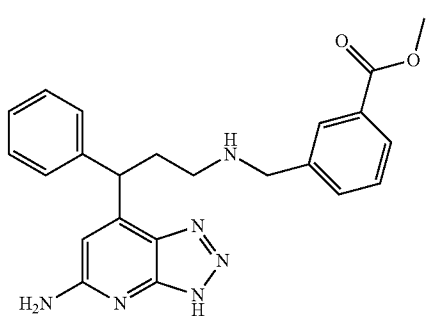 [SMILES: COC(=O)c1cccc(CNCCC(c2ccccc2)c2cc(N)nc3[nH]nnc23)c1] | methyl 3-{[(3-{5-amino-3H-[1,2,3]triazolo[4,5-b]pyridin-7-yl}-3-phenylpropyl)amino]methyl}benzoate | 416.9 | (500 MHz, CD$_3$OD) δ 8.16 (s, 1H), 8.10 (dd, J = 7.7, 1.1 Hz, 1H), 7.70 (d, J = 7.7 Hz, 1H), 7.63-7.55 (m, 2H), 7.54-7.46 (m, 2H), 7.40 (t, J = 7.7 Hz, 2H), 7.33 (d, J = 7.2 Hz, 1H), 6.80-6.62 (m, 1H), 4.68-4.55 (m, 1H), 4.28 (s, 2H), 3.95 (s, 3H), 3.22-3.11 (m, 1H), 3.06 (td, J = 11.7, 5.0 Hz, 1H), 2.91-2.78 (m, 1H), 2.78-2.63 (m, 1H) | 4.02 |

-continued

| Ex. No. | Structure | Name | MS (ESI) (M + H) | ¹H NMR | LC RT$^a$ (min) |
|---|---|---|---|---|---|
| 60 | 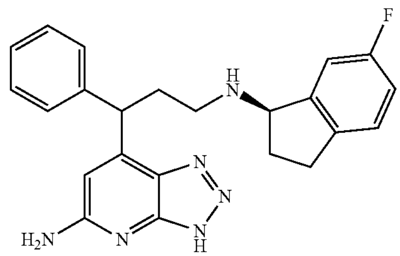 [SMILES: Nc1cc(C(CCN[C@@H]2CCc3ccc(F)cc32)c2ccccc2)c2nn[nH]c2n1] | 7-(3-{[(1R)-6-fluoro-2,3-dihydro-1H-inden-1-yl]amino}-1-phenylpropyl)-3H-[1,2,3]triazolo[4,5-b]pyridin-5-amine | 402.9 | (500 MHz, CD$_3$OD) δ 7.57-7.48 (m, 2H), 7.46-7.30 (m, 4H), 7.23 (td, J = 9.0, 2.3 Hz, 1H), 7.19-7.10 (m, 1H), 6.68 (d, J = 7.4 Hz, 1H), 4.81-4.75 (m, 1H), 4.68-4.60 (m, 1H), 3.23-3.15 (m, 1H), 3.15-3.01 (m, 2H), 3.00-2.78 (m, 2H), 2.77-2.63 (m, 1H), 2.63-2.50 (m, 1H), 2.33-2.11 (m, 1H) | 4.36 |
| 61 | 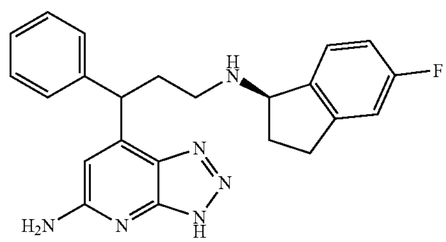 [SMILES: Nc1cc(C(CCN[C@@H]2CCc3cc(F)ccc32)c2ccccc2)c2nn[nH]c2n1] | 7-(3-{[(1R)-5-fluoro-2,3-dihydro-1H-inden-1-yl]amino}-1-phenylpropyl)-3H-[1,2,3]triazolo[4,5-b]pyridin-5-amine | 402.9 | (500 MHz, CD$_3$OD) δ 7.56-7.37 (m, 5H), 7.37-7.29 (m, 1H), 7.12 (dd, J = 8.9, 2.3 Hz, 1H), 7.03 (td, J = 8.8, 1.7 Hz, 1H), 6.61 (d, J = 7.7 Hz, 1H), 4.78-4.71 (m, 1H), 4.68-4.56 (m, 1H), 3.22-3.12 (m, 2H), 3.10-2.94 (m, 2H), 2.92-2.77 (m, 1H), 2.76-2.63 (m, 1H), 2.62-2.50 (m, 1H), 2.29-2.15 (m, 1H) | 4.39 |
| 62 | 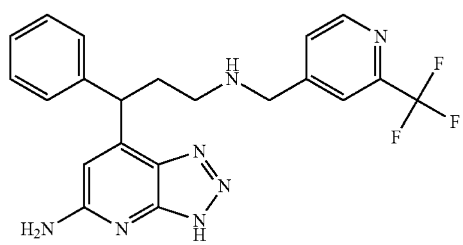 [SMILES: Nc1cc(C(CCNCc2ccnc(C(F)(F)F)c2)c2ccccc2)c2nn[nH]c2n1] | 7-[1-phenyl-3-({[2-(trifluoromethyl)pyridin-4-yl]methyl}amino)propyl]-3H-[1,2,3]triazolo[4,5-b]pyridin-5-amine | 428.2 | (500 MHz, DMSO-d6) δ 8.60 (d, J = 5.0 Hz, 1H), 7.80 (s, 1H), 7.59 (d, J = 4.7 Hz, 1H), 7.43 (d, J = 7.7 Hz, 2H), 7.27 (t, J = 7.6 Hz, 2H), 7.20-7.12 (m, 1H), 6.51 (br. s., 2H), 6.43 (s, 1H), 4.54 (t, J = 7.7 Hz, 1H), 3.78 (s, 2H), 2.41 (t, J = 6.6 Hz, 2H), 2.37-2.25 (m, 1H) | 1.02$^c$ |
| 63 | 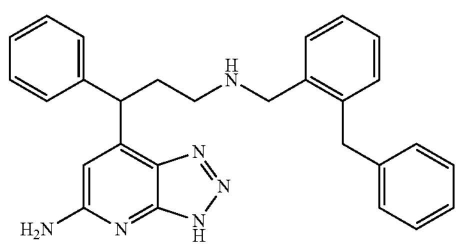 | 7-(3-{[(2-benzylphenyl)methyl]amino}-1-phenylpropyl)-3H-[1,2,3]triazolo[4,5-b]pyridin-5-amine | 449.2 | (500 MHz, CD$_3$OD) δ 7.48 (d, J = 7.4 Hz, 2H), 7.45-7.29 (m, 7H), 7.27-7.21 (m, 2H), 7.20-7.13 (m, 1H), 7.10 (d, J = 7.2 Hz, 2H), 6.57 (s, 1H), 4.58-4.49 (m, 1H), 4.24-4.07 (m, 4H), 3.04-2.90 (m, 2H), 2.84-2.74 (m, 1H), 2.65-2.56 (m, 1H) | 1.39$^c$ |
| 64 | 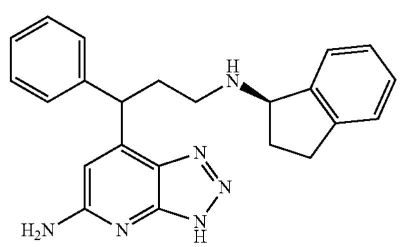 [SMILES: Nc1cc(C(CCN[C@@H]2CCc3ccccc32)c2ccccc2)c2nn[nH]c2n1] | 7-(3-{[(1R)-2,3-dihydro-1H-inden-1-yl]amino}-1-phenylpropyl)-3H-[1,2,3]triazolo[4,5-b]pyridin-5-amine | 384.9 | (500 MHz, CD$_3$OD) δ 7.55-7.49 (m, 2H), 7.47-7.23 (m, 7H), 6.60 (d, J = 6.6 Hz, 1H), 4.80-4.75 (m, 1H), 4.65- 4.59 (m, 1H), 3.21-3.12 (m, 2H), 3.11-3.03 (m, 1H), 3.03-2.94 (m, 1H), 2.91-2.77 (m, 1H), 2.75-2.61 (m, 1H), 2.59-2.46 (m, 1H), 2.18 (ddt, J = 18.4, 14.1, 4.2 Hz, 1H) | 4.18 |
| 65 | 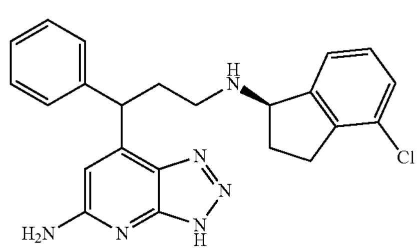 [SMILES: Nc1cc(C(CCN[C@@H]2CCc3c(Cl)cccc32)c2ccccc2)c2nn[nH]c2n1] | 7-(3-{[(1R)-4-chloro-2,3-dihydro-1H-inden-1-yl]amino}-1-phenylpropyl)-3H-[1,2,3]triazolo[4,5-b]pyridin-5-amine | 418.8 | (500 MHz, CD$_3$OD) δ 7.55-7.49 (m, 2H), 7.47-7.39 (m, 4H), 7.38-7.24 (m, 2H), 6.67 (d, J = 6.9 Hz, 1H), 4.85-4.80 (m, 1H), 4.68-4.57 (m, 1H), 3.25-3.12 (m, 2H), 3.11-2.97 (m, 2H), 2.94-2.77 (m, 1H), 2.78-2.63 (m, 1H), 2.62-2.51 (m, 1H), 2.28-2.14 (m, 1H) | 4.77 |

-continued

| Ex. No. | Structure | Name | MS (ESI) (M + H) | ¹H NMR | LC RT$^a$ (min) |
|---|---|---|---|---|---|
| 66 | 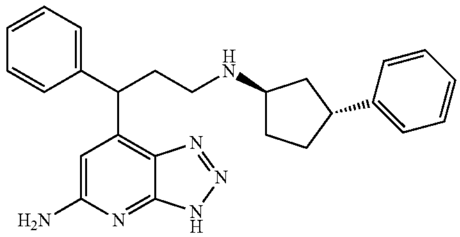 [SMILES: Nc1cc(C(CCN[C@@H]2CC[C@@H](c3ccccc3)C2)c2ccccc2)c2nn[nH]c2n1] | 7-(1-phenyl-3-{[(1R,3R)-3-phenylcyclopentyl]amino}propyl)-3H-[1,2,3]triazolo[4,5-b]pyridin-5-amine | 413.3 | (500 MHz, CD$_3$OD) δ 7.51 (d, J = 7.4 Hz, 2H), 7.38 (t, J = 7.4 Hz, 2H), 7.33-7.21 (m, 5H), 7.20-7.14 (m, 1H), 6.75 (s, 1H), 4.62 (t, J = 7.6 Hz, 1H), 3.69 (d, J = 5.2 Hz, 1H), 3.17-3.03 (m, 2H), 2.74-2.62 (m, 1H), 2.46 (dd, J = 12.7, 6.6 Hz, 1H), 2.30-2.04 (m, 3H), 1.92-1.58 (m, 5H) | 1.287$^c$ |
| 67 | 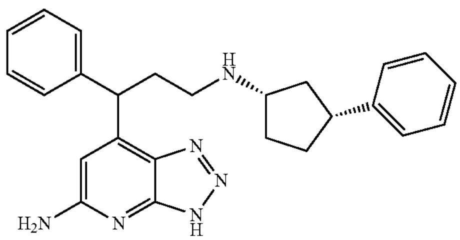 [SMILES: Nc1cc(C(CCN[C@H]2CC[C@@H](c3ccccc3)C2)c2ccccc2)c2nn[nH]c2n1] | 7-(1-phenyl-3-{[(1S,3R)-3-phenylcyclopentyl]amino}propyl)-3H-[1,2,3]triazolo[4,5-b]pyridin-5-amine | 413.0 | (500 MHz, CD$_3$OD) δ 7.97 (s, 1H), 7.51 (d, J = 7.7 Hz, 2H), 7.38 (t, J = 7.4 Hz, 2H), 7.33-7.12 (m, 6H), 6.75 (s, 1H), 4.62 (t, J = 7.6 Hz, 1H), 3.77(d, J = 9.1 Hz, 1H), 3.11 (br. s., 1H), 2.68 (d, J = 11.0 Hz, 1H), 2.39-2.26 (m, 1H), 2.22-1.49 (m, 9H), | 1.286$^c$ |
| 68 | 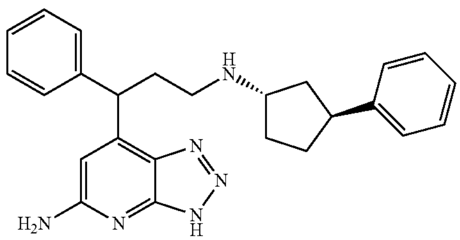 [SMILES: Nc1cc(C(CCN[C@H]2CC[C@H](c3ccccc3)C2)c2ccccc2)c2nn[nH]c2n1] | 7-(1-phenyl-3-{[(1S,3S)-3-phenylcyclopentyl]amino}propyl)-3H-[1,2,3]triazolo[4,5-b]pyridin-5-amine | 413.3 | (500 MHz, CD$_3$OD) δ 7.51 (d, J = 7.7 Hz, 2H), 7.39 (t, J = 7.4 Hz, 2H), 7.33-7.14 (m, 6H), 6.61 (br. s., 1H), 4.60 (t, J = 7.8 Hz, 1H), 3.80-3.72 (m, 1H), 3.28 (d, J = 9.1 Hz, 1H), 3.16-3.05 (m, 1H), 3.01-2.93 (m, 1H), 2.89-2.78 (m, 1H), 2.66 (d, J = 9.1 Hz, 1H), 2.37-2.26 (m, 1H), 2.24-2.05 (m, 2H), 1.86-1.62 (m, 3H) | 1.28$^c$ |
| 69 | 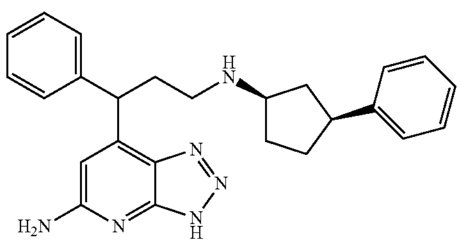 [SMILES: Nc1cc(C(CCN[C@@H]2CC[C@H](c3ccccc3)C2)c2ccccc2)c2nn[nH]c2n1] | 7-(1-phenyl-3-{[(1R,3S)-3-phenylcyclopentyl]amino}propyl)-3H-[1,2,3]triazolo[4,5-b]pyridin-5-amine | 413.3 | (500 MHz, CD$_3$OD) δ 7.51 (d, J = 7.4 Hz, 2H), 7.37 (t, J = 7.4 Hz, 2H), 7.31-7.13 (m, 6H), 6.78 (s, 1H), 4.62 (t, J = 7.7 Hz, 1H), 3.75-3.64 (m, 1H), 3.11 (dd, J = 10.6, 4.8 Hz, 2H), 2.78-2.58 (m, 1H), 2.46 (dd, J = 12.7, 6.6 Hz, 1H), 2.26-2.15 (m, 1H), 2.16-2.02 (m, 1H), 1.94-1.57 (m, 4H), 1.32-1.07 (m, 1H) | 1.29$^c$ |
| 70 | 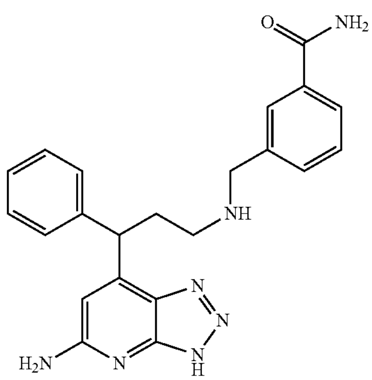 [SMILES: NC(=O)c1cccc(CNCCC(c2ccccc2)c2cc(N)nc3[nH]nnc23)c1] | 3-{[(3-{5-amino-3H-[1,2,3]triazolo[4,5-b]pyridin-7-yl}-3-phenylpropyl)amino]methyl}benzamide | 402 | (500 MHz, CD$_3$CN) δ 8.06 (br. s., 1H), 7.85 (d, J = 7.4 Hz, 1H), 7.61 (d, J = 7.2 Hz, 1H), 7.54-7.48 (m, 1H), 7.44 (d, J = 7.2 Hz, 2H), 7.37 (t, J = 7.2 Hz, 2H), 7.31 (d, J = 7.4 Hz, 1H), 7.12 (br. s., 1H), 6.75 (br. s., 1H), 6.21 (br. s., 1H), 4.62 (t, J = 7.3 Hz, 1H), 4.21 (br. s., 2H), 3.85 (s, 1H), 3.17-2.98 (m, 2H), 2.77 (d, J = 10.2 Hz, 1H), 2.62 (br. s., 1H). | 0.90$^c$ |
| 72 | 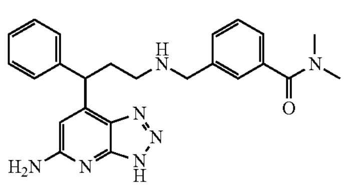 [SMILES: CN(C)C(=O)c1cccc(CNCCC(c2ccccc2)c2cc(N)nc3[nH]nnc23)c1] | 3-{[(3-{5-amino-3H-[1,2,3]triazolo[4,5-b]pyridin-7-yl}-3-phenylpropyl)amino]methyl}-N,N-dimethylbenzamide | 430.3 | (500 MHz, CD$_3$CN) δ 7.47 (d, J = 7.4 Hz, 2H), 7.38-7.26 (m, 5H), 7.26-7.17 (m, 2H), 6.50 (br. s., 1H), 5.46 (br. s., 2H), 4.68-4.59 (m, 1H), 3.83-3.70 (m, 2H), 3.05 (br. s., 3H), 2.89 (br. s., 3H), 2.51-2.18 (m, 2H) | 1.00$^c$ |

-continued

| Ex. No. | Structure | Name | MS (ESI) (M + H) | 1H NMR | LC RT$^a$ (min) |
|---|---|---|---|---|---|
| 73 | 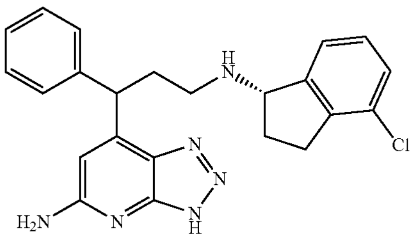 [SMILES: Nc1cc(C(CCN[C@H]2CCc3c(Cl)cccc32)c2ccccc2)c2nn[nH]c2n1] | 7-(3-{[(1S)-4-chloro-2,3-dihydro-1H-inden-1-yl]amino}-1-phenylpropyl)-3H-[1,2,3]triazolo[4,5-b]pyridin-5-amine | 419.2 | (500 MHz, CD$_3$OD) δ 7.52 (d, J = 6.9 Hz, 2H), 7.47-7.38 (m, 4H), 7.33 (d, J = 3.9 Hz, 2H),, 6.57 (d, J = 6.9 Hz, 1H), 4.86 (br. s., 1H), 4.62 (d, J = 5.2 Hz, 1H), 3.25-3.04 (m, 4H), 2.83 (d, J = 6.6 Hz, 1H), 2.70 (br. s., 1H), 2.57 (br. s., 1H), 2.29-2.15 (m, 1H) | 1.24$^c$ |
| 74 | 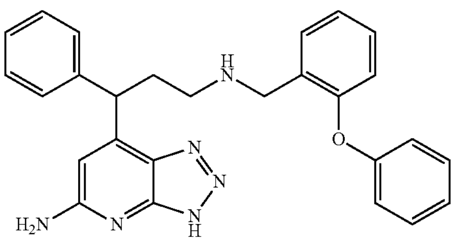 [SMILES: Nc1cc(C(CCNCc2ccccc2Oc2ccccc2)c2ccccc2)c2nn[nH]c2n1] | 7-(3-{[(2-phenoxyphenyl)methyl]amino}-1-phenylpropyl)-3H-[1,2,3]triazolo[4,5-b]pyridin-5-amine | 451.3 | (500 MHz, CD$_3$CN) δ 7.48-7.40 (m, 3H), 7.38-7.18 (m, 6H), 7.17-7.03 (m, 2H), 6.96-6.79 (m, 3H), 6.50 (br. s., 1H), 5.37 (br. s., 2H), 4.70-4.55 (m, 1H), 3.75 (br. s., 2H), 2.65-2.50 (m, 3H), 2.45-2.25 (m, 1H) | 1.36$^c$ |
| 75 | 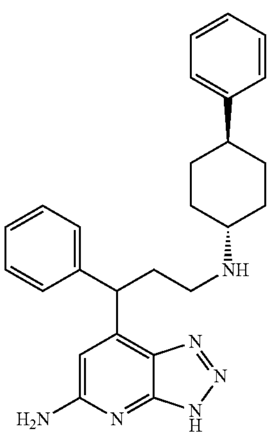 [SMILES: Nc1cc(C(CCN[C@H]2CC[C@H](c3ccccc3)CC2)c2ccccc2)c2nn[nH]c2n1] | 7-(1-phenyl-3-{[(trans)-4-phenylcyclohexyl]amino}propyl)-3H-[1,2,3]triazolo[4,5-b]pyridin-5-amine | 427.2 | (500 MHz, DMSO-d6) δ 15.20 (br. s., 1H), 8.49 (br. s., 2H), 7.51 (d, J = 7.4 Hz, 2H), 7.37 (t, J = 7.6 Hz, 2H), 7.32-7.24 (m, 3H), 7.24-7.16 (m, 3H), 6.65 (br. s., 2H), 6.41 (br. s., 1H), 4.49 (t, J = 7.7 Hz, 1H), 3.11 (br. s., 1H), 2.94 (d, J = 4.7 Hz, 1H), 2.87 (d, J = 11.0 Hz, 1H), 2.75 (s, 1H), 2.62 (br. s., 1H), 2.49-2.45 (m, 1H), 2.13-1.98 (m, 2H), 1.86 (d, J = 10.7 Hz, 2H), 1.57-1.32 (m, 4H) | 1.30$^c$ |
| 76 | 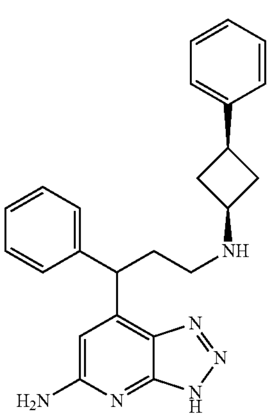 [SMILES: Nc1cc(C(CCN[C@H]2C[C@@H](c3ccccc3)C2)c2ccccc2)c2nn[nH]c2n1] | 7-(1-phenyl-3-{[(1s,3s)-3-phenylcyclobutyl]amino}propyl)-3H-[1,2,3]triazolo[4,5-b]pyridin-5-amine | 399.2 | (500 MHz, CD$_3$OD) δ 7.52 (d, J = 7.4 Hz, 2H), 7.40 (t, J = 7.6 Hz, 2H), 7.36-7.19 (m, 6H), 6.48 (s, 1H), 4.58 (t, J = 7.8 Hz, 1H), 3.78 (quin, J = 8.0 Hz, 1H), 3.42-3.35 (m, 1H), 3.01-2.91 (m, 2H), 2.88-2.80 (m, 1H), 2.79-2.71 (m, 2H), 2.69-2.59 (m, 1H), 2.22 (d, J = 9.4 Hz, 2H) | 1.17$^c$ |

-continued

| Ex. No. | Structure | Name | MS (ESI) (M + H) | ¹H NMR | LC RT$^a$ (min) |
|---|---|---|---|---|---|
| 78 | 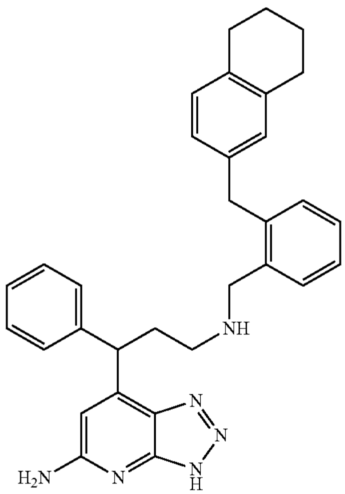 [SMILES: Nc1cc(C(CCNCc2ccccc2Cc2ccc3c(c2)CCCC3)c2ccccc2)c2nn[nH]c2n1] | 7-{1-phenyl-3-[({2-[(5,6,7,8-tetrahydronaphthalen-2-yl)methyl]phenyl}methyl)amino]propyl}-3H-[1,2,3]triazolo[4,5-b]pyridin-5-amine | 503.3 | (500 MHz, CD$_3$CN) δ 7.51-7.43 (m, 2H), 7.34-7.29 (m, 3H), 7.27-7.15 (m, 4H), 6.93 (d, J = 7.7 Hz, 1H), 6.84-6.77 (m, 2H), 6.52 (s, 1H), 5.37 (br. s., 2H), 4.63 (t, J = 7.8 Hz, 1H), 4.00 (s, 2H), 3.10 (q, J = 7.4 Hz, 2H), 2.93-2.88 (m, 2H), 2.60-2.55 (m, 2H), 2.50 (td, J = 13.8, 7.2 Hz, 1H), 2.35-2.26 (m, 1H), 1.27 (t, J = 7.3 Hz, 2H), 1.18 (t, J = 7.3 Hz, 2H) | 1.67$^c$ |
| 80 | 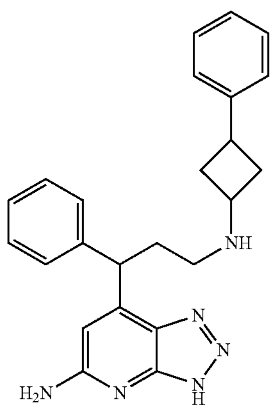 [SMILES: Nc1cc(C(CCNC2CC(c3ccccc3)C2)c2ccccc2)c2nn[nH]c2n1] | 7-{1-phenyl-3-[(3-phenylcyclobutyl)amino]propyl}-3H-[1,2,3]triazolo[4,5-b]pyridin-5-amine | 399.3 | (500 MHz, CD$_3$OD) δ 7.56-7.50 (m, 2H), 7.41 (t, J = 7.7 Hz, 2H), 7.36-7.29 (m, 3H), 7.28-7.19 (m, 3H), 6.64 (s, 1H), 4.61 (dd, J = 8.8, 6.6 Hz, 1H), 3.83-3.74 (m, 1H), 3.42-3.35 (m, 1H), 3.09-3.03 (m, 1H), 2.95 (td, J = 11.6, 5.0 Hz, 1H), 2.87-2.81 (m, 1H), 2.79-2.61 (m, 3H), 2.29-2.19 (m, 2H) | 1.22$^c$ Peak 2 |
| 81 | 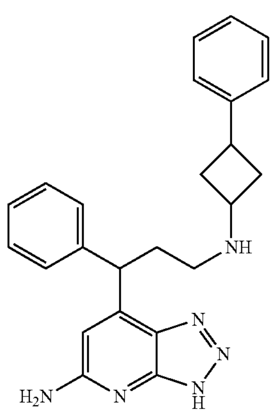 [SMILES: Nc1cc(C(CCNC2CC(c3ccccc3)C2)c2ccccc2)c2nn[nH]c2n1] | 7-{1-phenyl-3-[(3-phenylcyclobutyl)amino]propyl}-3H-[1,2,3]triazolo[4,5-b]pyridin-5-amine | 399.3 | (500 MHz, CD$_3$OD) δ 7.56-7.50 (m, 2H), 7.41 (t, J = 7.7 Hz, 2H), 7.36-7.16 (m, 6H), 6.61 (s, 1H), 4.60 (dd, J = 8.5, 6.9 Hz, 1H), 3.83-3.74 (m, 1H), 3.37 (d, J = 3.6 Hz, 1H), 3.03 (br. s., 1H), 2.95 (td, J = 11.5, 4.8 Hz, 1H), 2.88-2.81 (m, 1H), 2.80-2.61 (m, 3H), 2.29-2.19 (m, 2H) | 1.08$^c$ Peak 1 |

-continued

| Ex. No. | Structure | Name | MS (ESI) (M + H) | ¹H NMR | LC RT$^a$ (min) |
|---|---|---|---|---|---|
| 82 | 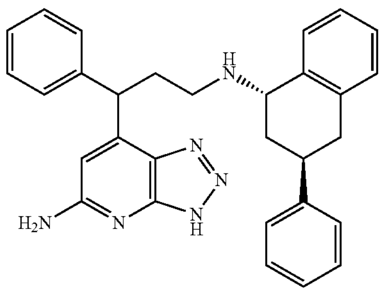 [SMILES: Nc1cc(C(CCN[C@H]2C[C@H](c3ccccc3)Cc3ccccc32)c2ccccc2)c2nn[nH]c2n1] | 7-(1-phenyl-3-{[(1S,3R)-3-phenyl-1,2,3,4-tetrahydronaphthalen-1-yl]amino}propyl)-3H-[1,2,3]triazolo[4,5-b]pyridin-5-amine | 475.3 | (500 MHz, CD$_3$CN) δ 7.66-7.58 (m, 1H), 7.52 (dd, J = 7.0, 4.3 Hz, 2H), 7.40-7.04 (m, 11H), 6.57 (d, J = 3.9 Hz, 1H), 5.39 (br. s., 2H), 4.90-4.73 (m, 1H), 4.04 (dd, J = 10.6, 5.6 Hz, 1H), 2.65 (d, J = 5.8 Hz, 1H), 2.48-2.36 (m, 3H), 1.91-1.64 (m, 3H), 1.40-0.88 (m, 2H) | 1.45$^c$ |
| 83 | 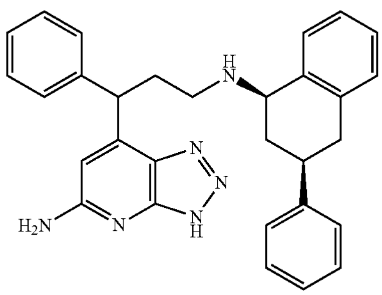 [SMILES: Nc1cc(C(CCN[C@@H]2C[C@H](c3ccccc3)Cc3ccccc32)c2ccccc2)c2nn[nH]c2n1] | 7-(1-phenyl-3-{[(1R,3R)-3-phenyl-1,2,3,4-tetrahydronaphthalen-1-yl]amino}propyl)-3H-[1,2,3]triazolo[4,5-b]pyridin-5-amine | 475.3 | (500 MHz, CD$_3$CN) δ 7.63 (d, J = 7.4 Hz, 1H), 7.50-7.43 (m, 1H), 7.41-7.19 (m, 12H), 6.85 (d, J = 8.8 Hz, 1H), 4.94-4.81 (m, 1H), 4.70-4.59 (m, 1H), 3.23-2.96 (m, 4H), 2.72-2.56 (m, 1H), 2.51-2.40 (m, 1H), 2.16-2.05 (m, 1H), 1.55-1.40 (m, 2H) | 1.50$^c$ |
| 84 | 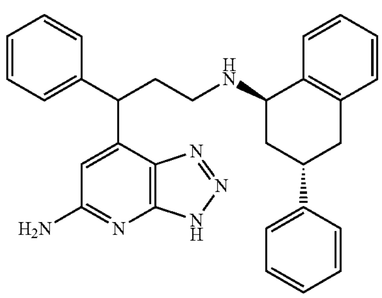 [SMILES: Nc1cc(C(CCN[C@@H]2C[C@@H](c3ccccc3)Cc3ccccc32)c2ccccc2)c2nn[nH]c2n1] | 7-(1-phenyl-3-{[(1R,3S)-3-phenyl-1,2,3,4-tetrahydronaphthalen-1-yl]amino}propyl)-3H-[1,2,3]triazolo[4,5-b]pyridin-5-amine | 475.3 | (500 MHz, DMSO-d$_6$) δ 7.51 (d, J = 6.9 Hz, 2H), 7.46-7.19 (m, 12H), 6.42 (d, J = 16.2 Hz, 1H), 4.60-4.49 (m, 2H), 3.33-3.17 (m, 3H), 3.15-3.04 (m, 2H), 3.03-2.86 (m, 2H), 2.33-2.09 (m, 2H), 1.97-1.59 (m, 2H) | 1.42$^c$ |
| 85 | 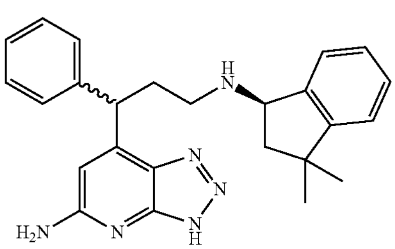 [SMILES: CC1(C)C[C@@H](NCCC(c2ccccc2)c2cc(N)nc3[nH]nnc23)c2ccccc21] | 7-(3-{[(1R)-3,3-dimethyl-2,3-dihydro-1H-inden-1-yl]amino}-1-phenylpropyl)-3H-[1,2,3]triazolo[4,5-b]pyridin-5-amine | 413.3 | (500 MHz, DMSO-d$_6$) δ 7.59-7.48 (m, 3H), 7.42-7.23 (m, 6H), 6.44 (br. s., 1H), 4.90 (br. s., 1H), 4.60-4.46 (m, 1H), 3.08-2.93 (m, 3H), 2.88-2.77 (m, 1H), 2.40-2.23 (m, 1H), 1.93-1.80 (m, 1H), 1.37 (d, J = 8.3 Hz, 3H), 1.13 (d, J = 3.9 Hz, 3H) | 1.20$^c$ |
| 86 | 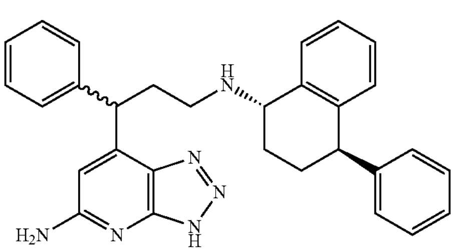 [SMILES: Nc1cc(C(CCN[C@H]2CC[C@H](c3ccccc3)c3ccccc32)c2ccccc2)c2nn[nH]c2n1] | 7-(1-phenyl-3-{[(1S,4R)-4-phenyl-1,2,3,4-tetrahydronaphthalen-1-yl]amino}propyl)-3H-[1,2,3]triazolo[4,5-b]pyridin-5-amine | 475.3 | (500 MHz, DMSO-d$_6$) δ 7.58-7.48 (m, 2H), 7.36 (t, J = 7.2 Hz, 2H), 7.32-7.18 (m, 6H), 7.03-6.94 (m, 2H), 6.86 (d, J = 6.1 Hz, 1H), 6.44 (br. s., 1H), 4.66 (br. s., 1H), 4.53 (br. s., 1H), 4.22 (d, J = 4.7 Hz, 1H), 3.02 (br. s., 1H), 2.98-2.92 (m, 1H), 2.89-2.83 (m, 1H), 2.63 (d, J = 9.4 Hz, 1H), 2.27 (br. s., 1H), 2.07 (d, J = 14.3 Hz, 1H), 1.91 (br. s., 1H), 1.79 (br. s., 1H) | 1.50$^c$ |

-continued

| Ex. No. | Structure | Name | MS (ESI) (M + H) | ¹H NMR | LC RT$^a$ (min) |
|---|---|---|---|---|---|
| 87 | 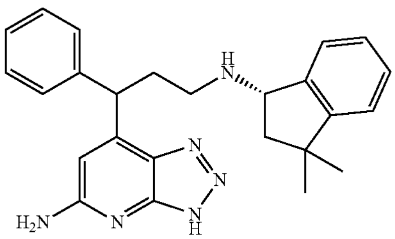 [SMILES: CC1(C)C[C@H](NCCC(c2ccccc2)c2cc(N)nc3[nH]nnc23)c2ccccc21] | 7-(3-{[(1S)-3,3-dimethyl-2,3-dihydro-1H-inden-1-yl]amino}-1-phenylpropyl)-3H-[1,2,3]triazolo[4,5-b]pyridin-5-amine | 413.3 | (500 MHz, DMSO-d6) δ 7.68-7.21 (m, 9H), 6.42 (br. s., 1H), 4.91 (br. s., 1H), 4.52 (br. s., 1H), 2.96 (br. s., 2H), 2.40-2.20 (m, 1H), 1.93-1.75 (m, 1H), 1.45-1.28 (m, 3H), 1.20-1.05 (m, 3H) | 1.30$^c$ |
| 88 | 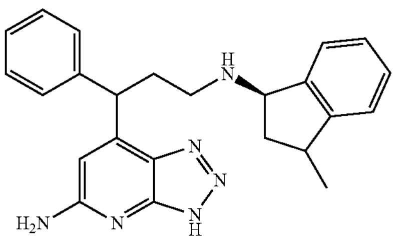 [SMILES: CC1C[C@@H](NCCC(c2ccccc2)c2cc(N)nc3[nH]nnc23)c2ccccc21] | 7-(3-{[(1R)-3-methyl-2,3-dihydro-1H-inden-1-yl]amino}-1-phenylpropyl)-3H-[1,2,3]triazolo[4,5-b]pyridin-5-amine | 399.3 | (500 MHz, DMSO-d6) δ 7.54-7.22 (m, 9H), 6.39 (d, J = 7.7 Hz, 1H), 4.75 (d, J = 5.2 Hz, 1H), 4.58-4.47 (m, 1H), 2.98 (br. s., 1H), 2.67 (d, J = 18.2 Hz, 1H), 2.44-2.29 (m, 1H), 2.01-1.86 (m, 1H), 1.23 (dd, J = 6.9, 2.2 Hz, 3H) | 1.11$^c$ |
| 89 | 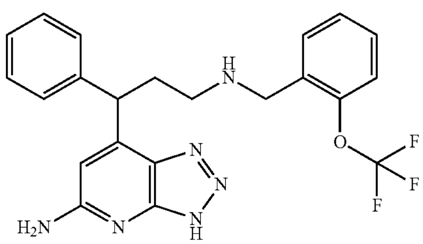 [SMILES: Nc1cc(C(CCNCc2ccccc2OC(F)(F)F)c2ccccc2)c2nn[nH]c2n1] | 7-[1-phenyl-3-({[2-(trifluoromethoxy)phenyl]methyl}amino)propyl]-3H-[1,2,3]triazolo[4,5-b]pyridin-5-amine | 443.2 | (500 MHz, CD$_3$CN) δ 7.68-7.24 (m, 10H), 6.61 (s, 1H), 4.86 (br. s., 1H), 4.62 (br. s., 1H), 4.32-4.20 (m, 3H), 3.06 (br. s., 2H), 2.67 (br. s., 2H) | 1.11$^c$ |
| 90 | 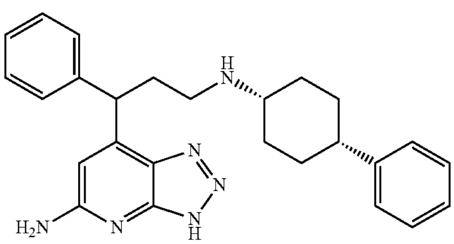 [SMILES: Nc1cc(C(CCN[C@H]2CC[C@@H](c3ccccc3)CC2)c2ccccc2)c2nn[nH]c2n1] | 7-(1-phenyl-3-{[(1s,4s)-4-phenylcyclohexyl]amino}propyl)-3H-[1,2,3]triazolo[4,5-b]pyridin-5-amine | 427.3 | (500 MHz, DMSO-d$_6$) δ 7.51 (d, J = 7.4 Hz, 2H), 7.39-7.15 (m, 8H), 6.42 (br. s., 1H), 4.48 (t, J = 7.7 Hz, 1H), 3.34-3.29 (m, 1H), 2.96 (d, J = 5.0 Hz, 1H), 2.87 (d, J = 11.3 Hz, 1H), 2.78 (d, J = 11.0 Hz, 1H), 2.72-2.62 (m, 2H), 1.97-1.58 (m, 8H) | 1.37$^c$ |
| 91 | 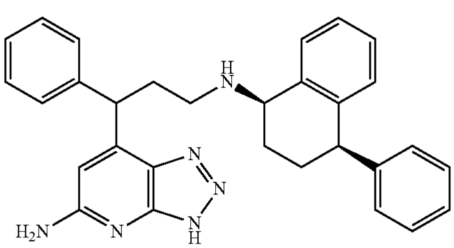 [SMILES: Nc1cc(C(CCN[C@@H]2CC[C@H](c3ccccc3)c3ccccc32)c2ccccc2)c2nn[nH]c2n1] | 7-(1-phenyl-3-{[(trans)-4-phenyl-1,2,3,4-tetrahydronaphthalen-1-yl]amino}propyl)-3H-[1,2,3]triazolo[4,5-b]pyridin-5-amine | 475.3 | (500 MHz, DMSO-d6) δ 7.53-7.44 (m, 3H), 7.36-6.96 (m, 10H), 6.71 (t, J = 7.0 Hz, 1H), 6.55 (br. s., 2H), 6.49 (d, J = 5.8 Hz, 1H), 4.64 (t, J = 7.4 Hz, 1H), 4.12 (q, J = 6.9 Hz, 1H), 3.86 (br. s., 1H), 2.70-2.55 (m, 2H), 2.47-1.96 (m, 2H), 1.87 (br. s., 1H), 1.76-1.65 (m, 1H), 1.58 (br. s., 1H) | 1.48$^c$ |
| 92 | 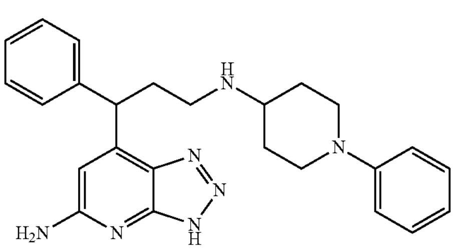 [SMILES: Nc1cc(C(CCNC2CCN(c3ccccc3)CC2)c2ccccc2)c2nn[nH]c2n1] | N-(3-{5-amino-3H-[1,2,3]triazolo[4,5-b]pyridin-7-yl}-3-phenylpropyl)-1-phenylpiperidin-4-amine | 427.3 | (500 MHz, DMSO-d6) δ 7.50 (d, J = 7.4 Hz, 2H), 7.37 (t, J = 7.7 Hz, 2H), 7.31-7.17 (m, 3H), 6.95 (d, J = 8.0 Hz, 2H), 6.78 (t, J = 7.3 Hz, 1H), 6.42 (br. s., 1H), 4.49 (t, J = 7.7 Hz, 1H), 3.32-3.18 (m, 2H), 3.06-2.92 (m, 2H), 2.89-2.81 (m, 1H), 2.74-2.66 (m, 2H), 2.64-2.56 (m, 1H), 2.03-1.89 (m, 2H), 1.61-1.48 (m, 2H) | 1.04$^c$ |

| Ex. No. | Structure | Name | MS (ESI) (M + H) | ¹H NMR | LC RT$^a$ (min) |
|---|---|---|---|---|---|
| 93 | 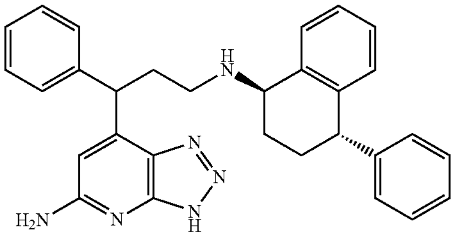 [SMILES: Nc1cc(C(CCN[C@@H]2CC[C@@H](c3ccccc3)c3ccccc32)c2ccccc2)c2nn[nH]c2n1] | 7-(1-phenyl-3-{[(1R,4S)-4-phenyl-1,2,3,4-tetrahydronaphthalen-1-yl]amino}propyl)-3H-[1,2,3]triazolo[4,5-b]pyridin-5-amine | 475.3 | (500 MHz, DMSO-d6) δ 7.53-7.44 (m, 3H), 7.36-6.96 (m, 10H), 6.71 (t, J = 7.0 Hz, 1H), 6.55 (br. s., 2H), 6.49 (d, J = 5.8 Hz, 1H), 4.64 (t, J = 7.4 Hz, 1H), 4.12 (q, J = 6.9 Hz, 1H), 3.86 (br. s., 1H), 2.70-2.55 (m, 2H), 2.47-1.96 (m, 3H), 1.87 (br. s., 1H), 1.76-1.65 (m, 1H), 1.58 (br. s., 1H). | 1.50$^c$ |
| 94 | 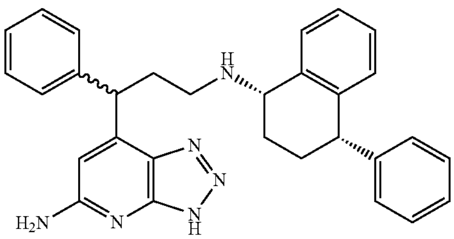 [SMILES: Nc1cc(C(CCN[C@H]2CC[C@@H](c3ccccc3)c3ccccc32)c2ccccc2)c2nn[nH]c2n1] | 7-(1-phenyl-3-{[(1S,4R)-4-phenyl-1,2,3,4-tetrahydronaphthalen-1-yl]amino}propyl)-3H-[1,2,3]triazolo[4,5-b]pyridin-5-amine | 475.3 | (500 MHz, DMSO-d6) δ 7.47 (dd, J = 6.9, 5.2 Hz, 2H), 7.38 (d, J = 7.7 Hz, 1H), 7.29 (q, J = 7.5 Hz, 4H), 7.24-7.18 (m, 2H), 7.17-7.09 (m, 3H), 7.09-7.02 (m, 1H), 6.68 (d, J = 7.7 Hz, 1H), 6.54 (br. s., 1H), 6.49 (d, J = 6.1 Hz, 1H), 4.72-4.56 (m, 1H), 4.05-3.95 (m, 1H), 3.73 (br. s, 1H) 2.70-2.55 (m, 2H), 2.08-1.96 (m, 2H), 1.91-1.84 (m, 1H), 1.83-1.63 (m, 2H) | 1.50$^c$ |
| 95 | 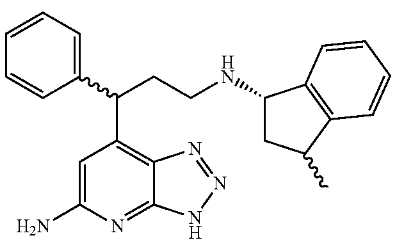 [SMILES: CC1C[C@H](NCCC(c2ccccc2)c2cc(N)nc3[nH]nnc23)c2ccccc21] | 7-(3-{[(1S)-3-methyl-2,3-dihydro-1H-inden-1-yl]amino}-1-phenylpropyl)-3H-[1,2,3]triazolo[4,5-b]pyridin-5-amine | 399.3 | (500 MHz, CD₃OD) δ 7.58-7.21 (m, 9H), 6.55-6.48 (m, 1H), 4.69-4.55 (m, 2H), 3.70-3.53 (m, 1H), 3.25-3.03 (m, 2H), 2.79-2.67 (m, 2H), 2.65-2.55 (m, 1H), 1.48 (ddt, J = 15.6, 12.6, 9.2 Hz, 1H), 1.40-1.31 (m, 3H) | 1.22$^c$ |
| 96 | 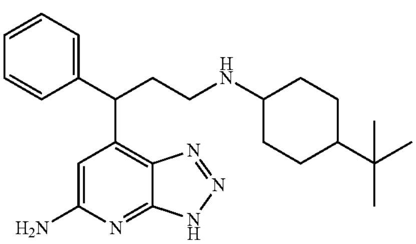 [SMILES: CC(C)(C)C1CCC(NCCC(c2ccccc2)c2cc(N)nc3[nH]nnc23)CC1] | 7-{3-[(4-tert-butylcyclohexyl)amino]-1-phenylpropyl}-3H-[1,2,3]triazolo[4,5-b]pyridin-5-amine | 407.3 | (500 MHz, CD₃OD) δ 7.56-7.50 (m, 2H), 7.41 (t, J = 7.7 Hz, 2H), 7.33 (d, J = 7.4 Hz, 1H), 6.57 (s, 1H), 4.64-4.56 (m, 1H), 3.09 (d, J = 5.0 Hz, 1H), 3.01-2.95 (m, 1H), 2.87-2.78 (m, 1H), 2.70-2.56 (m, 1H), 2.19-2.07 (m, 2H), 2.06-1.98 (m, 1H), 1.93 (d, J = 12.9 Hz, 2H), 1.78-1.66 (m, 1H), 1.38-0.97 (m, 5H), 0.94-0.85 (m, 9H) | 1.49$^c$ |
| 97 | 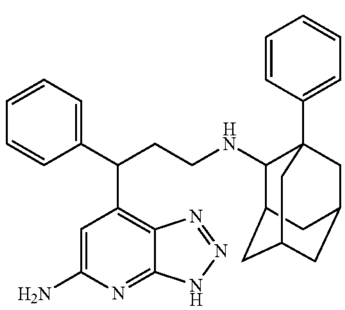 [SMILES: Nc1cc(C(CCNC2C3CC4CC(C3)CC2(c2ccccc2)C4)c2ccccc2)c2nn[nH]c2n1] | 7-{1-phenyl-3-[(3-phenyladamantan-1-yl)amino]propyl}-3H-[1,2,3]triazolo[4,5-b]pyridin-5-amine | 479.2 | (500 MHz, CD₃OD) δ 7.52 (d, J = 7.2 Hz, 2H), 7.44-7.27 (m, 7H), 7.25-7.16 (m, 1H), 6.45 (s, 1H), 4.62 (t, J = 7.8 Hz, 1H), 3.12 (td, J = 11.3, 5.4 Hz, 1H), 3.02-2.95 (m, 1H), 2.87-2.75 (m, 1H), 2.70-2.56 (m, 1H), 2.39 (br. s, 2H), 2.03-1.66 (m, 12H) | 1.53$^c$ |
| 98 | 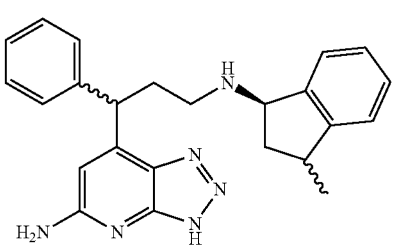 [SMILES: CC1C[C@@H](NCCC(c2ccccc2)c2cc(N)nc3[nH]nnc23)c2ccccc21] | 7-(3-{[(1R)-3-methyl-2,3-dihydro-1H-inden-1-yl]amino}-1-phenylpropyl)-3H-[1,2,3]triazolo[4,5-b]pyridin-5-amine | 399.3 | (500 MHz, CD₃OD) δ 7.53 (t, J = 8.3 Hz, 2H), 7.47-7.35 (m, 4H), 7.35-7.24 (m, 3H), 6.50 (d, J = 16.2 Hz, 1H), 4.70-4.58 (m, 2H), 3.26-3.04 (m, 3H), 2.83-2.70 (m, 2H), 2.63 (ddd, J = 10.5, 5.2, 2.5 Hz, 1H), 1.50 (ddt, J = 15.2, 12.6, 9.1 Hz, 1H), 1.38 (t, J = 6.6 Hz, 3H) | 1.23$^c$ |

| Ex. No. | Structure | Name | MS (ESI) (M + H) | ¹H NMR | LC RT$^a$ (min) |
|---|---|---|---|---|---|
| 99 | 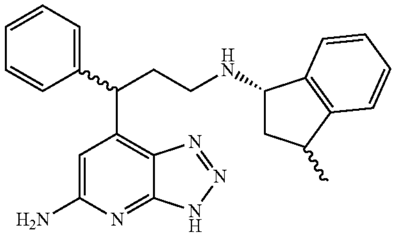 [SMILES: CC1C[C@H](NCCC(c2ccccc2)c2cc(N)nc3[nH]nnc23)c2ccccc21] | 7-(3-{[(1S)-3-methyl-2,3-dihydro-1H-inden-1-yl]amino}-1-phenylpropyl)-3H-[1,2,3]triazolo[4,5-b]pyridin-5-amine | 399.3 | (500 MHz, DMSO-d$_6$) δ 7.55-7.21 (m, 9H), 6.39 (br. s., 1H), 4.74 (d, J = 5.0 Hz, 1H), 4.50 (t, J = 7.4 Hz, 1H), 3.39 (br. s., 1H), 3.07-2.93 (m, 1H), 2.83-2.75 (m, 1H), 2.71-2.63 (m, 1H), 2.62-2.54 (m, 1H), 2.41-2.30 (m, 1H), 2.00-1.82 (m, 1H), 1.22 (dd, J = 7.0, 2.3 Hz, 3H) | 1.22$^c$ |
| 100 | 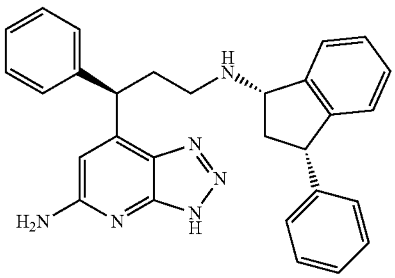 [SMILES: Nc1cc([C@H](CCN[C@H]2C[C@@H](c3ccccc3)c3ccccc32)c2ccccc2)c2nn[nH]c2n1] | 7-[(1R)-1-phenyl-3-{[(1S,3S)-3-phenyl-2,3-dihydro-1H-inden-1-yl]amino}propyl]-3H-[1,2,3]triazolo[4,5-b]pyridin-5-amine | 461.2 | (400 MHz, CD$_3$OD) δ 7.47 (d, J = 7.3 Hz, 2H), 7.38 (d, J = 7.5 Hz, 1H), 7.33-7.24 (m, 4H), 7.23-7.09 (m, 7H), 6.77 (d, J = 7.5 Hz, 1H), 6.48 (s, 1H), 4.67 (t, J = 7.8 Hz, 1H), 4.31-4.22 (m, 1H), 4.13 (dd, J = 10.5, 7.4 Hz, 1H), 2.79-2.64 (m, 2H), 2.58-2.40 (m, 2H), 1.72 (dt, J = 11.8, 10.2 Hz, 1H) | 5.53 |
| 101 | 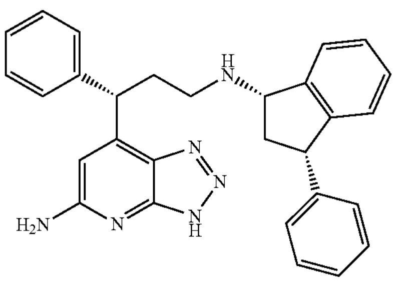 [SMILES: Nc1cc([C@@H](CCN[C@H]2C[C@@H](c3ccccc3)c3ccccc32)c2ccccc2)c2nn[nH]c2n1] | 7-[(1S)-1-phenyl-3-{[(1S,3S)-3-phenyl-2,3-dihydro-1H-inden-1-yl]amino}propyl]-3H-[1,2,3]triazolo[4,5-b]pyridin-5-amine | 461.2 | (400 MHz, CD$_3$OD) δ 7.51-7.43 (m, 2H), 7.36 (d, J = 7.5 Hz, 1H), 7.32-7.24 (m, 4H), 7.23-7.04 (m, 7H), 6.76 (d, J = 7.5 Hz, 1H), 6.48 (s, 1H), 4.67 (t, J = 7.7 Hz, 1H), 4.33-4.24 (m, 1H), 4.13 (t, J = 8.9 Hz, 1H), 2.77-2.70 (m, 3H), 2.69-2.56 (m, 1H), 2.50-2.35 (m, 1H), 1.69 (dt, J = 11.8, 10.2 Hz, 1H) | 5.51 |
| 102 | 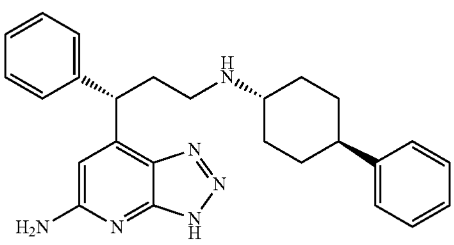 [SMILES: Nc1cc([C@@H](CCN[C@H]2CC[C@H](c3ccccc3)CC2)c2ccccc2)c2nn[nH]c2n1] | 7-[(1S)-1-phenyl-3-{[(trans)-4-phenylcyclohexyl]amino}propyl]-3H-[1,2,3]triazolo[4,5-b]pyridin-5-amine | 426.3 | (400 MHz, CD$_3$OD) δ 7.52 (d, J = 7.3 Hz, 2H), 7.40 (t, J = 7.5 Hz, 2H), 7.35-7.22 (m, 3H), 7.23-7.10 (m, 3H), 6.80 (br. s., 1H), 4.67-4.58 (m, 1H), 3.21-3.08 (m, 2H), 3.00 (td, J = 11.6, 5.0 Hz, 1H), 2.88-2.76 (m, 1H), 2.73-2.60 (m, 1H), 2.59-2.47 (m, 1H), 2.23-2.09 (m, 2H), 1.97 (d, J = 13.0 Hz, 2H), 1.67-1.43 (m, 4H) | 5.48 |
| 103 | 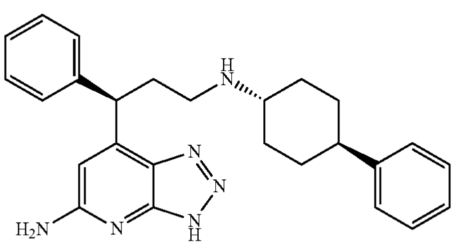 [SMILES: Nc1cc([C@H](CCN[C@H]2CC[C@H](c3ccccc3)CC2)c2ccccc2)c2nn[nH]c2n1] | 7-[(1R)-1-phenyl-3-{[(trans)-4-phenylcyclohexyl]amino}propyl]-3H-[1,2,3]triazolo[4,5-b]pyridin-5-amine | 426.3 | (400 MHz, CD$_3$OD) δ 7.52 (d, J = 7.3 Hz, 2H), 7.40 (t, J = 7.5 Hz, 2H), 7.33-7.22 (m, 3H), 7.22-7.11 (m, 3H), 6.88-6.73 (m, 1H), 4.67-4.56 (m, 1H), 3.23-3.07 (m, 2H), 3.00 (td, J = 11.6, 5.0 Hz, 1H), 2.88-2.77 (m, 1H), 2.73-2.60 (m, 1H), 2.59-2.47 (m, 1H), 2.22-2.08 (m, 2H), 1.97 (d, J = 13.0 Hz, 2H), 1.69-1.39 (m, 4H) | 5.48 |
| 104 | 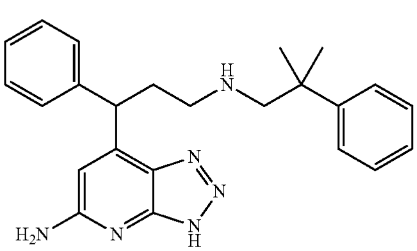 [SMILES: CC(C)(CNCCC(c1ccccc1)c1cc(N)nc2[nH]nnc12)c1ccccc1] | 7-{3-[(2-methyl-2-phenylpropyl)amino]-1-phenylpropyl}-3H-[1,2,3]triazolo[4,5-b]pyridin-5-amine | 401.3 | (500 MHz, CD$_3$OD) δ 7.54-7.35 (m, 8H), 7.33-7.25 (m, 2H), 6.57 (br. s., 1H), 4.49 (t, J = 7.8 Hz, 1H), 3.00-2.90 (m, 2H), 2.79 (tt, J = 11.9, 5.8 Hz, 1H), 2.69-2.56 (m, 1H), 1.91-1.64 (m, 2H), 1.47 (s, 3H), 0.98 (s, 3H) | 1.22$^c$ |

| Ex. No. | Name | MS (ESI) (M + H) | 1H NMR | LC RT$^a$ (min) |
|---|---|---|---|---|
| 105 | 7-(3-{[4-(3-chlorophenyl)cyclohexyl]amino}-1-phenylpropyl)-3H-[1,2,3]triazolo[4,5-b]pyridin-5-amine | 461.2 | (500 MHz, DMSO-d$_6$) δ 7.51 (d, J = 7.7 Hz, 2H), 7.41-7.22 (m, 7H), 6.43 (br. s., 1H), 4.56-4.42 (m, 1H), 2.97 (d, J = 6.3 Hz, 2H), 2.87-2.77 (m, 1H), 2.71-2.55 (m, 2H), 1.92-1.56 (m, 7H), 1.53-1.34 (m, 2H) | 1.51$^c$ |
| 106 | 7-{1-phenyl-3-[(3-phenylpropyl)amino]propyl}-3H-[1,2,3]triazolo[4,5-b]pyridin-5-amine | 387.3 | (500 MHz, CD$_3$OD) δ 7.51 (d, J = 7.7 Hz, 2H), 7.39 (t, J = 7.3 Hz, 2H), 7.30 (d, J = 6.3 Hz, 3H), 7.22 (d, J = 7.2 Hz, 3H), 6.46 (s, 1H), 4.57 (t, J = 7.7 Hz, 1H), 3.06-2.87 (m, 4H), 2.83-2.74 (m, 1H), 2.69 (m, 2H), 2.65-2.56 (m, 1H), 2.01-1.88 (m, 2H). | 1.15$^c$ |
| 107 | 7-(1-phenyl-3-{[(1s,4s)-4-(4-chlorophenyl)cyclohexyl]amino}propyl)-3H-[1,2,3]triazolo[4,5-b]pyridin-5-amine | 463.3 | (500 MHz, CD$_3$OD) δ 7.53 (d, J = 6.6 Hz, 2H), 7.41 (br. s., 2H), 7.33 (br. s., 5H), 6.51 (br. s., 1H), 4.59 (br. s., 1H), 3.41 (br. s., 1H), 3.22-3.09 (m, 1H), 2.83-2.59 (m, 2H), 1.99-1.63 (m, 9H), 1.46-1.25 (m, 1H) | 1.43$^c$ |
| 108 | 7-(1-phenyl-3-{[(trans)-4-(4-chlorophenyl)cyclohexyl]amino}propyl)-3H-[1,2,3]triazolo[4,5-b]pyridin-5-amine | 463.2 | (500 MHz, CD$_3$OD) δ 7.53 (d, J = 7.4 Hz, 2H), 7.40 (t, J = 7.7 Hz, 2H), 7.33-7.26 (m, 3H), 7.25-7.16 (m, 2H), 6.50 (br. s., 1H), 4.65-4.51 (m, 1H), 3.21-2.99 (m, 3H), 2.91-2.81 (m, 1H), 2.73-2.52 (m, 2H), 2.23-2.12 (m, 2H), 2.03-1.94 (m, 2H), 1.63-1.46 (m, 4H) | 1.47$^c$ |
| 109 | 7-{1-phenyl-3-[(2-phenylethyl)amino]propyl}-3H-[1,2,3]triazolo[4,5-b]pyridin-5-amine | 373.3 | (500 MHz, DMSO-d$_6$) δ 7.50 (d, J = 7.2 Hz, 2H), 7.42-7.30 (m, 4H), 7.28-7.18 (m, 4H), 6.42 (br. s., 1H), 4.47 (t, J = 7.6 Hz, 1H), 3.17 (br. s., 2H), 2.93-2.83 (m, 4H), 2.75 (br. s., 1H), 2.60 (br. s., 1H) | 1.09$^c$ |
| 110 | 7-{3-[(1-methyl-2,3-dihydro-1H-inden-1-yl)amino]-1-phenylpropyl}-3H-[1,2,3]triazolo[4,5-b]pyridin-5-amine | 399.3 | (500 MHz, CD$_3$OD) δ 7.53-7.18 (m, 9H), 6.40 (br. s., 1H), 4.52 (d, J = 7.4 Hz, 1H), 3.10-2.89 (m, 3H), 2.84-2.49 (m, 3H), 2.47-2.20 (m, 2H), 1.71 (br. s., 3H) | 1.13$^c$ |

-continued

| Ex. No. | Structure | Name | MS (ESI) (M + H) | ¹H NMR | LC RT[a] (min) |
|---|---|---|---|---|---|
| 111 | 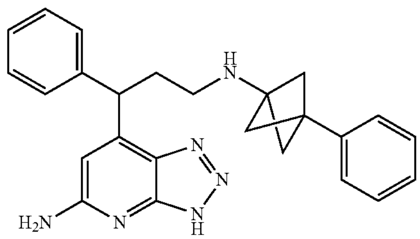 [SMILES: Nc1cc(C(CCNC23CC(c4ccccc4)(C2)C3)c2ccccc2)c2nn[nH]c2n1] | 7-[1-phenyl-3-({3-phenylbicyclo[1.1.1]pentan-1-yl}amino)propyl]-3H-[1,2,3]triazolo[4,5-b]pyridin-5-amine | 411.3 | (500 MHz, CD$_3$OD) δ 7.51 (d, J = 7.4 Hz, 2H), 7.39 (t, J = 7.6 Hz, 2H), 7.35-7.28 (m, 3H), 7.28-7.18 (m, 3H), 6.52 (s, 1H), 4.63-4.57 (m, 1H), 3.13-3.05 (m, 1H), 3.04-2.96 (m, 1H), 2.92-2.81 (m, 1H), 2.72-2.60 (m, 1H), 2.32 (s, 6H). | 1.20[c] |
| 112 | 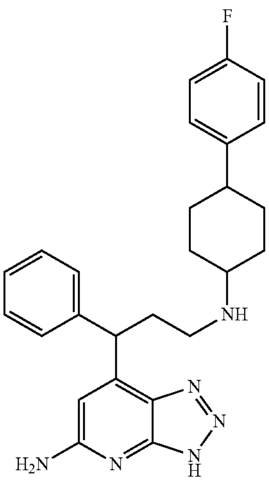 [SMILES: Nc1cc(C(CCNC2CCC(c3ccc(F)cc3)CC2)c2ccccc2)c2nn[nH]c2n1] | 7-(3-{[4-(4-fluorophenyl)cyclohexyl]amino}-1-phenylpropyl)-3H-[1,2,3]triazolo[4,5-b]pyridin-5-amine | 445.3 | (500 MHz, CD$_3$OD) δ 7.52 (d, J = 7.4 Hz, 2H), 7.40 (t, J = 7.6 Hz, 2H), 7.35-7.29 (m, 3H), 7.09-6.99 (m, 2H), 6.61 (s, 1H), 4.64-4.57 (m, 1H), 3.40 (d, J = 3.9 Hz, 1H), 3.18-3.09 (m, 1H), 3.07-2.97 (m, 1H), 2.93-2.83 (m, 1H), 2.82-2.69 (m, 2H), 1.95-1.77 (m, 8H) | 1.39[c] |
| 113 | 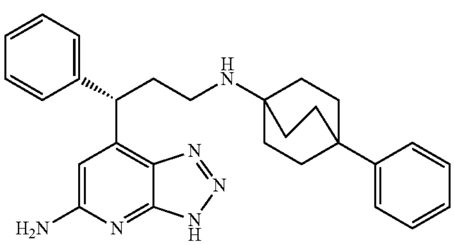 [SMILES: Nc1cc([C@@H](CCNC23CCC(c4ccccc4)(CC2)CC3)c2ccccc2)c2nn[nH]c2n1] | 7-[(1S)-1-phenyl-3-({4-phenylbicyclo[2.2.2]octan-1-yl}amino)propyl]-3H-[1,2,3]triazolo[4,5-b]pyridin-5-amine | 453.4 | (500 MHz, CD$_3$OD) δ 7.50 (d, J = 7.4 Hz, 2H), 7.39 (t, J = 7.6 Hz, 2H), 7.33-7.21 (m, 5H), 7.18-7.08 (m, 1H), 6.61 (s, 1H), 4.61 (dd, J = 8.8, 6.6 Hz, 1H), 3.09-3.00 (m, 1H), 2.91 (td, J = 11.4, 5.0 Hz, 1H), 2.79 (tt, J = 12.1, 5.8 Hz, 1H), 2.68-2.57 (m, 1H), 2.06-1.95 (m, 6H), 1.93-1.80 (m, 6H). | 1.32[c] |
| 115 | 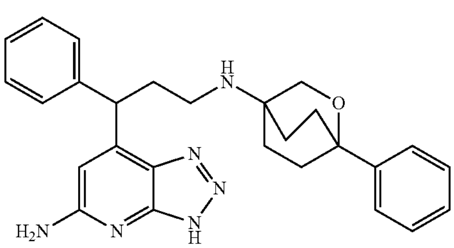 | 7-[1-phenyl-3-({1-phenyl-2-oxabicyclo[2.2.2]octan-4-yl}amino)propyl]-3H-[1,2,3]triazolo[4,5-b]pyridin-5-amine | 455.3 | (500 MHz, CD$_3$OD) δ 7.47 (d, J = 7.7 Hz, 2H), 7.43-7.31 (m, 4H), 7.30-7.12 (m, 4H), 6.50 (s, 1H), 4.60 (t, J = 7.8 Hz, 1H), 3.88 (s, 2H), 2.82-2.66 (m, 2H), 2.63-2.53 (m, 1H), 2.50-2.36 (m, 1H), 2.23-2.11 (m, 2H), 2.02 (td, J = 11.3, 5.0 Hz, 2H), 1.96-1.84 (m, 2H), 1.83-1.71 (m, 2H). | 1.27[c] |
| 116 | 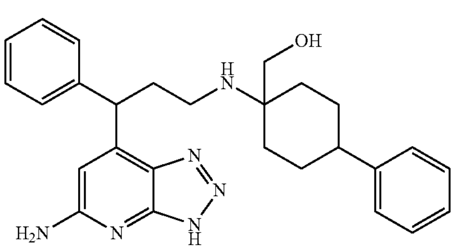 [SMILES: Nc1cc(C(CCNC2(CO)CCC(c3ccccc3)CC2)c2ccccc2)c2nn[nH]c2n1] | {1-[(3-{5-amino-3H-[1,2,3]triazolo[4,5-b]pyridin-7-yl}-3-phenylpropyl)amino]-4-phenylcyclohexyl}methanol | 457.3 | (500 MHz, CD$_3$OD) δ 7.50 (d, J = 7.7 Hz, 2H), 7.38 (t, J = 7.6 Hz, 2H), 7.31-7.24 (m, 3H), 7.23-7.13 (m, 3H), 6.46 (s, 1H), 4.61 (t, J = 7.8 Hz, 1H), 3.78 (s, 2H), 3.14-2.95 (m, 2H), 2.85-2.74 (m, 1H), 2.72-2.48 (m, 2H), 2.12 (t, J = 9.4 Hz, 2H), 1.85 (br. s., 2H), 1.68-1.58 (m, 4H) | 1.28[c] |

-continued

| Ex. No. | Structure | Name | MS (ESI) (M + H) | ¹H NMR | LC RT$^a$ (min) |
|---|---|---|---|---|---|
| 117 | 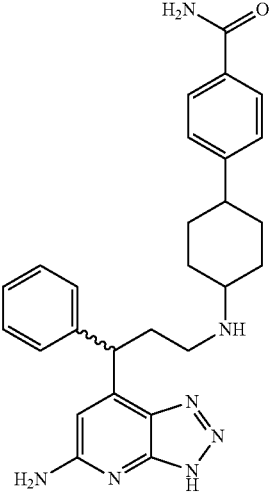 [SMILES: NC(=O)c1ccc(C2CCC(NCCC(c3ccccc3)c3cc(N)nc4[nH]nnc34)CC2)cc1] | 4-{4-[(3-{5-amino-3H-[1,2,3]triazolo[4,5-b]pyridin-7-yl}-3-phenylpropyl)amino]cyclohexyl}benzamide | 470.4 | (500 MHz, CD$_3$OD) δ 7.80 (d, J = 8.0 Hz, 2H), 7.51 (d, J = 7.7 Hz, 2H), 7.39 (t, J = 7.6 Hz, 2H), 7.33-7.24 (m, 3H), 6.56 (br. s., 1H), 4.59 (t, J = 7.8 Hz, 1H), 3.23-3.08 (m, 2H), 3.06-3.00 (m, 1H), 2.89-2.79 (m, 1H), 2.72-2.55 (m, 2H), 2.24-2.14 (m, 2H), 2.00 (d, J = 11.0 Hz, 2H), 1.68-1.41 (m, 4H) | 0.96$^c$ |
| 118 | 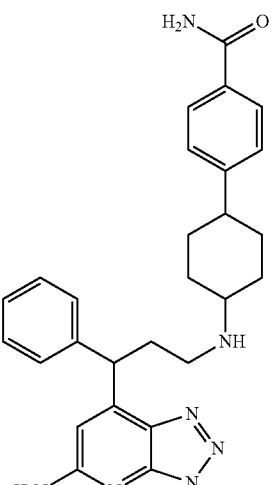 | 4-{4-[(3-{5-amino-3H-[1,2,3]triazolo[4,5-b]pyridin-7-yl}-3-phenylpropyl)amino]cyclohexyl}benzamide | 470.4 | (500 MHz, CD$_3$OD) δ 7.82 (d, J = 8.3 Hz, 2H), 7.50 (d, J = 7.7 Hz, 2H), 7.43-7.34 (m, 4H), 7.33-7.26 (m, 1H), 6.60 (br. s., 1H), 4.59 (t, J = 7.7 Hz, 1H), 3.39 (br. s., 1H), 3.19-3.09 (m, 1H), 3.06-3.00 (m, 1H), 2.91-2.83 (m, 2H), 2.74-2.63 (m, 1H), 2.06-1.78 (m, 8H) | 1.00$^c$ |
| 119 | 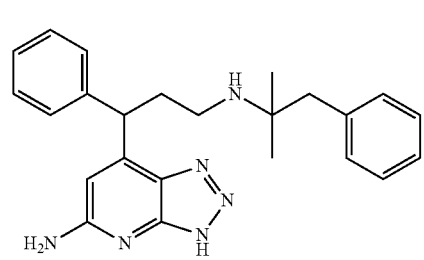 [SMILES: CC(C)(Cc1ccccc1)NCCC(c1ccccc1)c1cc(N)nc2[nH]nnc12] | 7-{3-[(2-methyl-1-phenylpropan-2-yl)amino]-1-phenylpropyl}-3H-[1,2,3]triazolo[4,5-b]pyridin-5-amine | 401.3 | (500 MHz, CD$_3$OD) δ 7.55 (d, J = 7.4 Hz, 2H), 7.43 (t, J = 7.4 Hz, 2H), 7.39-7.28 (m, 4H), 7.20 (d, J = 6.9 Hz, 2H), 6.62 (br. s., 1H), 4.64 (t, J = 7.6 Hz, 1H), 3.19 (td, J = 11.3, 5.1 Hz, 1H), 3.10-3.03 (m, 1H), 2.93 (s, 2H), 2.88-2.78 (m, 1H), 2.67 (d, J = 12.4 Hz, 1H), 1.29 (s, 6H) | 1.16$^c$ |
| 120 | 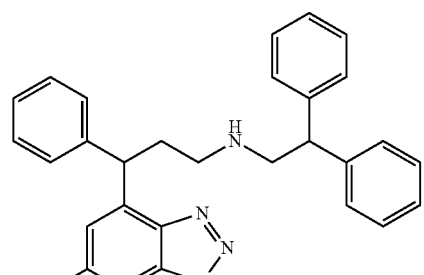 | 7-{3-[(2,2-diphenylethyl)amino]-1-phenylpropyl}-3H-[1,2,3]triazolo[4,5-b]pyridin-5-amine | 449.2 | (500 MHz, CD$_3$OD) δ 7.52-7.44 (m, 2H), 7.43-7.22 (m, 17H), 6.58 (s, 1H), 4.60-4.48 (m, 1H), 4.34 (t, J = 8.0 Hz, 1H), 3.77 (d, J = 8.0 Hz, 2H), 3.42 (dd, J = 12.7, 4.4 Hz, 1H), 3.13-2.96 (m, 2H), 2.86-2.76 (m, 1H), 2.71-2.59 (m, 2H), 1.97-1.89 (m, 1H), 1.82-1.76 (m, 1H), 1.67-1.58 (m, 2H), 1.44-1.28 (m, 2H), 1.24-1.10 (m, 2H), 1.04 (dd, J = 11.6, 3.6 Hz, 1H) | 1.29$^c$ |

-continued

| Ex. No. | Structure | Name | MS (ESI) (M + H) | ¹H NMR | LC RT$^a$ (min) |
|---|---|---|---|---|---|
| 121 | 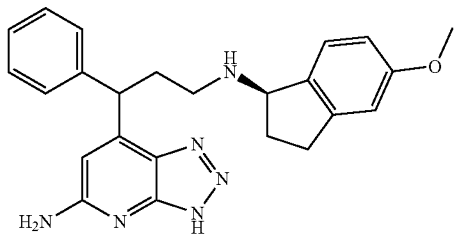 [SMILES: COc1ccc2c(c1)CC[C@H]2NCCC(c1ccccc1)c1cc(N)nc2[nH]nnc12] | 7-(3-{[(1R)-5-methoxy-2,3-dihydro-1H-inden-1-yl]amino}-1-phenylpropyl)-3H-[1,2,3]triazolo[4,5-b]pyridin-5-amine | 415.2 | (500 MHz, CD$_3$OD) δ 7.50 (d, J = 8.3 Hz, 2H), 7.40 (t, J = 7.7 Hz, 2H), 7.35-7.26 (m, 2H), 6.91 (s, 1H), 6.82 (d, J = 8.5 Hz, 1H), 6.57 (d, J = 5.8 Hz, 1H), 4.69 (dt, J = 7.6, 3.7 Hz, 1H), 4.60 (t, J = 7.8 Hz, 1H), 3.88-3.72 (m, 3H), 3.20-2.99 (m, 3H), 2.97-2.91 (m, 1H), 2.86-2.75 (m, 1H), 2.71-2.58 (m, 1H), 2.55-2.42 (m, 1H), 2.26-2.11 (m, 1H) | 1.10$^c$ |
| 122 | 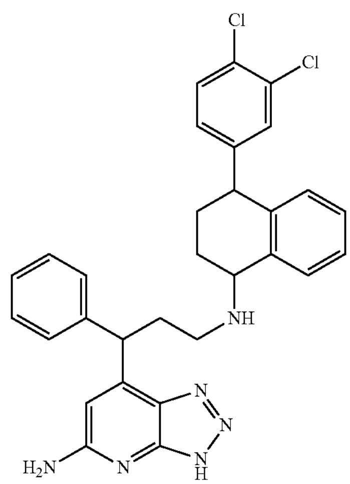 [SMILES: Nc1cc(C(CCNC2CCC(c3ccc(Cl)c(Cl)c3)c3ccccc32)c2ccccc2)c2nn[nH]c2n1] | 7-(3-{[4-(3,4-dichlorophenyl)-1,2,3,4-tetrahydronaphthalen-1-yl]amino}-1-phenylpropyl)-3H-[1,2,3]triazolo[4,5-b]pyridin-5-amine | 542.3 | (500 MHz, DMSO-d$_6$) δ 7.64-7.55 (m, 2H), 7.53-7.42 (m, 4H), 7.40-7.32 (m, 2H), 7.30-7.17 (m, 4H), 6.78 (br. s., 1H), 6.50 (br. s., 1H), 4.52 (br. s., 2H), 4.14 (br. s., 1H), 3.59 (br. s., 1H), 3.13-2.94 (m, 2H), 2.77 (d, J = 7.6 Hz, 1H), 2.16-1.85 (m, 3H) | 2.13$^c$ |
| 123 | 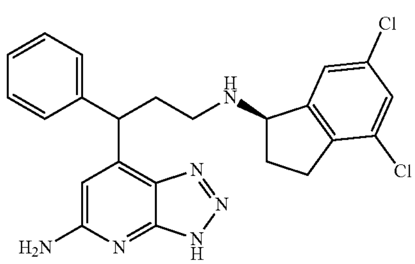 [SMILES: Nc1cc(C(CCN[C@@H]2CCc3c(Cl)cc(Cl)cc32)c2ccccc2)c2nn[nH]c2n1] | 7-(3-{[(1R)-4,6-dichloro-2,3-dihydro-1H-inden-1-yl]amino}-1-phenylpropyl)-3H-[1,2,3]triazolo[4,5-b]pyridin-5-amine | 450.9 | (500 MHz, CD$_3$OD) δ 7.55-7.47 (m, 4H), 7.41 (td, J = 7.6, 4.1 Hz, 2H), 7.36-7.27 (m, 1H), 6.64 (d, J = 9.1 Hz, 1H), 4.68-4.58 (m, 1H), 3.24-3.03 (m, 3H), 2.99-2.95 (m, 1H), 2.87-2.77 (m, 2H), 2.75-2.64 (m, 1H), 2.63-2.51 (m, 1H), 2.34-2.11 (m, 1H) | 1.28$^c$ |
| 124 | 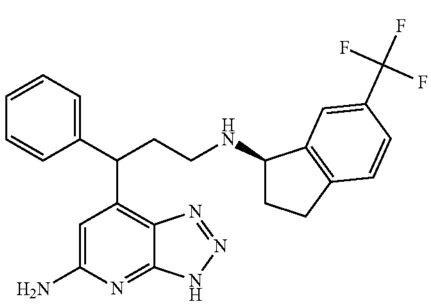 [SMILES: Nc1cc(C(CCN[C@@H]2CCc3ccc(C(F)(F)F)cc32)c2ccccc2)c2nn[nH]c2n1] | 7-(1-phenyl-3-{[(1R)-6-(trifluoromethyl)-2,3-dihydro-1H-inden-1-yl]amino}propyl)-3H-[1,2,3]triazolo[4,5-b]pyridin-5-amine | 453.2 | (500 MHz, CD$_3$OD) δ 7.88-7.79 (m, 1H), 7.71 (d, J = 8.0 Hz, 1H), 7.63-7.45 (m, 4H), 7.43-7.25 (m, 3H), 6.60-6.49 (m, 1H), 4.61 (s, 1H), 3.27-3.02 (m, 6H), 2.97-2.89 (m, 1H), 2.59 (d, J = 8.5 Hz, 1H), 2.22 (d, J = 5.0 Hz, 1H) | 1.25$^c$ |

-continued

| Ex. No. | Structure | Name | MS (ESI) (M + H) | $^1$H NMR | LC RT$^a$ (min) |
|---|---|---|---|---|---|
| 125 | 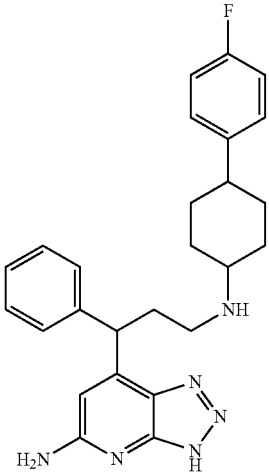 [SMILES: Nc1cc(C(CCNC2CCC(c3ccc(F)cc3)CC2)c2ccccc2)c2nn[nH]c2n1] | 7-(3-{[4-(4-fluorophenyl)cyclohexyl]amino}-1-phenylpropyl)-3H-[1,2,3]triazolo[4,5-b]pyridin-5-amine | 445.3 | (500 MHz, CD$_3$OD) δ 7.53 (d, J = 7.7 Hz, 2H), 7.41 (t, J = 7.6 Hz, 2H), 7.35-7.29 (m, 1H), 7.26-7.19 (m, 2H), 7.06-6.96 (m, 2H), 6.68 (s, 1H), 4.62 (dd, J = 8.8, 6.9 Hz, 1H), 3.23-3.10 (m, 2H), 3.07-2.98 (m, 1H), 2.91-2.80 (m, 1H), 2.74-2.63 (m, 1H), 2.61-2.53 (m, 1H), 2.22-2.13 (m, 2H), 2.04-1.94 (m, 2H), 1.63-1.45 (m, 4H) | 1.34$^c$ |
| 126 | 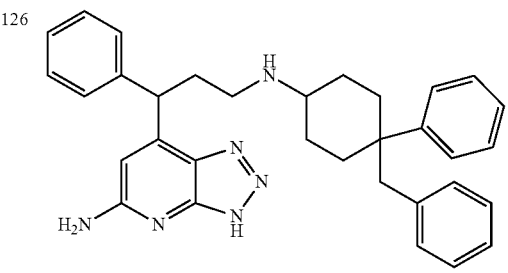 | 7-{3-[(4-benzyl-4-phenylcyclohexyl)amino]-1-phenylpropyl}-3H-[1,2,3]triazolo[4,5-b]pyridin-5-amine | 517.3 | (500 MHz, DMSO-d6) δ 8.47 (br. s., 2H), 7.93 (s, 1H), 7.45 (d, J = 7.3 Hz, 2H), 7.39-7.29 (m, 5H), 7.28-7.19 (m, 5H), 7.16-7.08 (m, 2H), 6.42 (s, 1H), 4.43 (t, J = 7.8 Hz, 1H), 3.57-3.40 (m, 2H), 2.93 (br. s., 1H), 2.79 (br. s., 2H), 2.67 (br. s., 1H), 2.20-2.10 (m, 1H), 1.90-1.80 (m, 2H), 1.50 (d, J = 12.7 Hz, 2H), 1.30-1.14 (m, 2H), 0.88 (q, J = 12.7 Hz, 2H) | 1.64$^c$ |
| 127 | 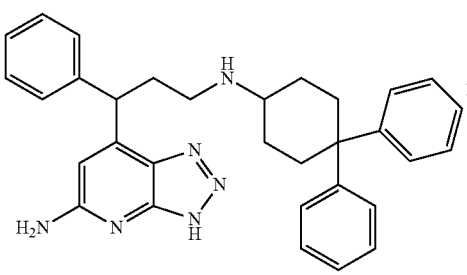 [SMILES: Nc1cc(C(CCNC2CCC(c3ccccc3)(c3ccccc3)CC2)c2ccccc2)c2nn[nH]c2n1] | 7-{3-[(4,4-diphenylcyclohexyl)amino]-1-phenylpropyl}-3H-[1,2,3]triazolo[4,5-b]pyridin-5-amine | 503.3 | (500 MHz, CD$_3$OD) δ 7.49 (d, J = 7.4 Hz, 2H), 7.45 (d, J = 7.4 Hz, 2H), 7.38 (q, J = 7.8 Hz, 4H), 7.33-7.27 (m, 1H), 7.24-7.17 (m, 5H), 7.15-7.06 (m, 1H), 6.65 (s, 1H), 4.57 (dd, J = 8.8, 6.9 Hz, 1H), 3.29-3.20 (m, 1H), 3.11-3.00 (m, 1H), 2.98-2.83 (m, 3H), 2.81-2.70 (m, 1H), 2.65-2.53 (m, 1H), 2.18-1.97 (m, 4H), 1.67-1.49 (m, 2H) | 1.51$^c$ |
| 128 | 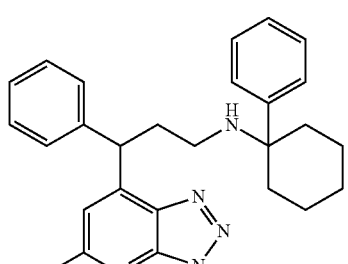 | 7-{1-phenyl-3-[(1-phenylcyclohexyl)amino]propyl}-3H-[1,2,3]triazolo[4,5-b]pyridin-5-amine | 427.3 | (500 MHz, CD$_3$OD) δ 7.51 (d, J = 6.9 Hz, 2H), 7.48-7.37 (m, 3H), 7.33-7.22 (m, 5H), 6.49 (s, 1H), 4.44-4.35 (m, 1H), 2.77-2.57 (m, 5H), 2.49-2.39 (m, 1H), 1.91-1.71 (m, 4H), 1.65 (d, J = 12.7 Hz, 1H), 1.47-1.17 (m, 3H) | 1.25$^c$ |
| 129 | 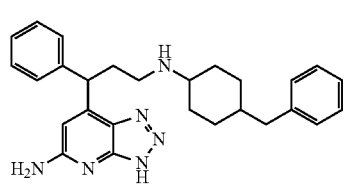 [SMILES: Nc1cc(C(CCNC2CCC(Cc3ccccc3)CC2)c2ccccc2)c2nn[nH]c2n1] | 7-{3-[(4-benzylcyclohexyl)amino]-1-phenylpropyl}-3H-[1,2,3]triazolo[4,5-b]pyridin-5-amine | 441.3 | (500 MHz, CD$_3$OD) δ 7.57-7.47 (m, 2H), 7.44-7.36 (m, 2H), 7.34-7.22 (m, 3H), 7.21-7.11 (m, 3H), 6.57 (d, J = 7.7 Hz, 1H), 4.65-4.54 (m, 1H), 3.19 (dt, J = 8.3, 4.2 Hz, 1H), 3.14-2.93 (m, 2H), 2.91-2.75 (m, 1H), 2.72-2.58 (m, 2H), 2.52 (d, J = 7.2 Hz, 1H), 2.10-1.99 (m, 1H), 1.93 (d, J = 4.1 Hz, 1H), 1.86-1.68 (m, 3H), | 1.41$^c$ |

-continued

| Ex. No. | Structure | Name | MS (ESI) (M + H) | ¹H NMR | LC RT$^a$ (min) |
|---|---|---|---|---|---|
| | | | | 1.63-1.46 (m, 3H), 1.35-1.23 (m, 1H), 1.15-1.01 (m, 1H) | |
| 130 | 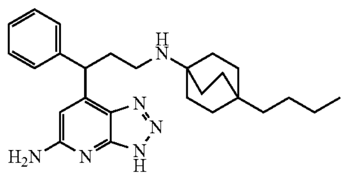 [SMILES: CCCCC12CCC(NCCC(c3ccccc3)c3cc(N)nc4[nH]nnc34)(CC1)CC2] | 7-[3-({4-butylbicyclo[2.2.2]octan-1-yl}amino)-1-phenylpropyl]-3H-[1,2,3]triazolo[4,5-b]pyridin-5-amine | 431.3 | (500 MHz, CD$_3$OD) δ 7.48 (d, J = 7.4 Hz, 2H), 7.37 (t, J = 7.7 Hz, 2H), 7.29 (d, J = 7.4 Hz, 1H), 6.53 (s, 1H), 4.57 (dd, J = 8.7, 7.0 Hz, 1H), 2.97 (d, J = 5.2 Hz, 1H), 2.84 (br. s., 1H), 2.80-2.69 (m, 1H), 2.63-2.53 (m, 1H), 1.71 (dd, J = 9.5, 5.6 Hz, 6H), 1.59-1.48 (m, 6H), 1.32-1.20 (m, 2H), 1.19-1.06 (m, 4H), 0.88 (t, J = 7.3 Hz, 3H) | 1.62$^c$ |
| 131 | 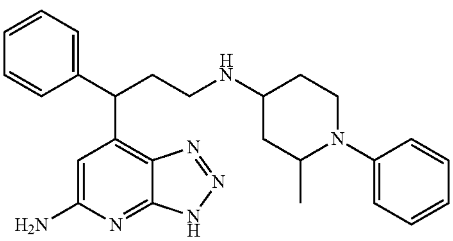 [SMILES: CC1CC(NCCC(c2ccccc2)c2cc(N)nc3[nH]nnc23)CCN1c1ccccc1] | N-(3-{5-amino-3H-[1,2,3]triazolo[4,5-b]pyridin-7-yl}-3-phenylpropyl)-2-methyl-1-phenylpiperidin-4-amine | 442.3 | (500 MHz, CD$_3$OD) δ 7.54 (d, J = 7.4 Hz, 2H), 7.45-7.38 (m, 2H), 7.36-7.26 (m, 3H), 7.07 (d, J = 7.7 Hz, 2H), 6.95 (s, 1H), 6.76 (d, J = 4.4 Hz, 1H), 4.65 (t, J = 7.7 Hz, 1H), 4.32 (d, J = 6.1 Hz, 1H), 3.63-3.51 (m, 2H), 3.26-3.15 (m, 2H), 3.08 (d, J = 4.7 Hz, 1H), 2.88 (s, 1H), 2.78-2.66 (m, 1H), 2.22 (br. s., 1H), 2.10 (br. s., 1H), 2.04-1.96 (m, 1H), 1.83-1.69 (m, 1H), 1.05 (d, J = 6.9 Hz, 3H) | 0.90$^c$ |
| 132 | 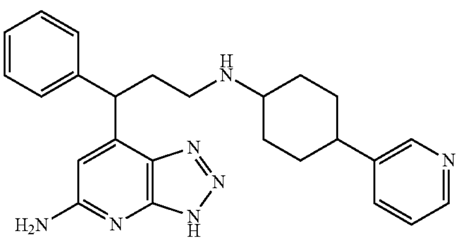 [SMILES: Nc1cc(C(CCNC2CCC(c3cccnc3)CC2)c2ccccc2)c2nn[nH]c2n1] | 7-(1-phenyl-3-{[4-(pyridin-3-yl)cyclohexyl]amino}propyl)-3H-[1,2,3]triazolo[4,5-b]pyridin-5-amine | 428.3 | (500 MHz, CD$_3$OD) δ 8.49-8.33 (m, 2H), 7.83-7.69 (m, 1H), 7.53-7.43 (m, 2H), 7.40-7.18 (m, 4H), 6.45 (d, J = 8.5 Hz, 1H), 4.64-4.55 (m, 1H), 3.17 (br. s., 1H), 3.05-2.82 (m, 2H), 2.77 (br. s., 1H), 2.59 (d, J = 3.9 Hz, 2H), 2.13 (br. s., 1H), 2.02-1.69 (m, 5H), 1.67-1.53 (m, 1H), 1.46 (br. s., 1H). | 0.67$^c$ |
| 133 | 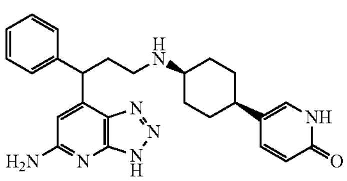 [SMILES: Nc1cc(C(CCN[C@H]2CC[C@@H](c3ccc(=O)[nH]c3)CC2)c2ccccc2)c2nn[nH]c2n1] | 5-[(cis)-4-[(3-{5-amino-3H-[1,2,3]triazolo[4,5-b]pyridin-7-yl}-3-phenylpropyl)amino]cyclohexyl]-1,2-dihydropyridin-2-one | 444.2 | (500 MHz, CD$_3$OD) δ 7.67-7.60 (m, 1H), 7.48 (d, J = 7.7 Hz, 2H), 7.35 (t, J = 7.4 Hz, 2H), 7.29-7.20 (m, 2H), 6.53 (d, J = 9.6 Hz, 1H), 6.48-6.42 (m, 1H), 4.63-4.52 (m, 1H), 3.08-2.88 (m, 3H), 2.83-2.73 (m, 1H), 2.67-2.52 (m, 2H), 1.87-1.66 (m, 6H), 1.65-1.38 (m, 2H) | 0.91$^c$ |
| 134 | 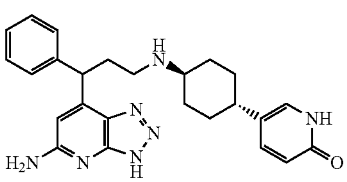 [SMILES: Nc1cc(C(CCN[C@H]2CC[C@H](c3ccc(=O)[nH]c3)CC2)c2ccccc2)c2nn[nH]c2n1] | 5-[(trans)-4-[(3-{5-amino-3H-[1,2,3]triazolo[4,5-b]pyridin-7-yl}-3-phenylpropyl)amino]cyclohexyl]-1,2-dihydropyridin-2-one | 444.3 | (500 MHz, CD$_3$OD) δ 7.56 (d, J = 9.9 Hz, 1H), 7.49 (d, J = 8.0 Hz, 2H), 7.36 (t, J = 7.4 Hz, 2H), 7.31-7.24 (m, 1H), 7.22 (s, 1H), 6.51 (d, J = 9.4 Hz, 1H), 6.45 (s, 1H), 4.57 (t, J = 7.8 Hz, 1H), 3.09-2.92 (m, 3H), 2.80 (d, J = 6.6 Hz, 1H), 2.61 (d, J = 5.5 Hz, 1H), 2.40 (br. s., 1H), 2.12 (br. s., 2H), 1.92 (s, 3H), 1.57-1.35 (m, 4H) | 0.88$^c$ |
| 135 | 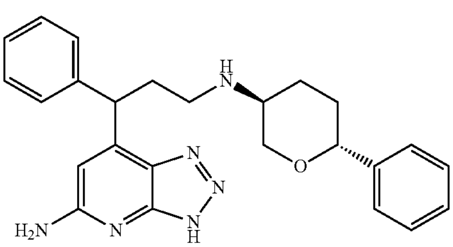 [SMILES: Nc1cc(C(CCN[C@H]2CC[C@H](c3ccccc3)OC2)c2ccccc2)c2nn[nH]c2n1] | 7-(1-phenyl-3-{[(3S,6R)-6-phenyloxan-3-yl]amino}propyl)-3H-[1,2,3]triazolo[4,5-b]pyridin-5-amine | 429.3 | (500 MHz, CD$_3$OD) δ 7.48 (d, J = 7.7 Hz, 2H), 7.38-7.27 (m, 6H), 7.26-7.20 (m, 2H), 6.51 (s, 1H), 4.58 (t, J = 7.7 Hz, 1H), 4.31 (d, J = 11.0 Hz, 1H), 4.21-4.11 (m, 1H), 3.38-3.32 (m, 1H), 2.99-2.90 (m, 1H), 2.90-2.72 (m, 2H), 2.71-2.58 (m, 1H), 2.56-2.44 (m, 1H), 2.16 (br. s., 1H), 1.70-1.59 (m, 1H), 1.59-1.48 (m, 1H), 1.59-1.47 (m, 1H) | 1.17$^c$ |

-continued

| Ex. No. | Structure | Name | MS (ESI) (M + H) | ¹H NMR | LC RT$^a$ (min) |
|---|---|---|---|---|---|
| 136 | 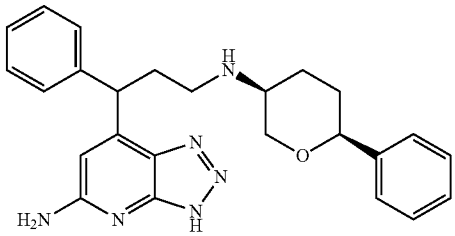 [SMILES: Nc1cc(C(CCN[C@H]2CC[C@@H](c3ccccc3)OC2)c2ccccc2)c2nn[nH]c2n1] | 7-(1-phenyl-3-{[(3S,6S)-6-phenyloxan-3-yl]amino}propyl)-3H-[1,2,3]triazolo[4,5-b]pyridin-5-amine | 429.3 | (500 MHz, CD$_3$OD) δ 7.54 (d, J = 8.0 Hz, 2H), 7.45-7.38 (m, 4H), 7.37-7.24 (m, 4H), 6.59 (br. s., 1H), 4.66-4.57 (m, 1H), 4.54-4.46 (m, 1H), 4.29-4.17 (m, 1H), 3.96-3.87 (m, 1H), 3.38 (br. s., 1H), 3.25-3.16 (m, 1H), 3.11 (d, J = 12.1 Hz, 1H), 2.93 (br. s., 1H), 2.77 (br. s., 1H), 2.24-2.15 (m, 2H), 1.91 (br. s., 2H) | 1.21$^c$ |
| 137 | 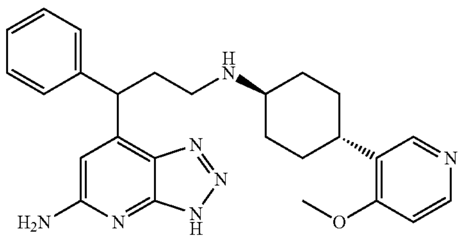 [SMILES: COc1ccncc1[C@H]1CC[C@H](NCCC(c2ccccc2)c2cc(N)nc3[nH]nnc23)CC1] | 7-(1-phenyl-3-{[(trans)-4-(4-methoxypyridin-3-yl)cyclohexyl]amino}propyl)-3H-[1,2,3]triazolo[4,5-b]pyridin-5-amine | 458.3 | (500 MHz, CD$_3$OD) δ 8.31 (d, J = 5.8 Hz, 1H), 8.20 (s, 1H), 7.58-7.48 (m, 2H), 7.39 (t, J = 7.4 Hz, 2H), 7.34-7.27 (m, 1H), 7.04 (d, J = 6.1 Hz, 1H), 6.50 (s, 1H), 4.59 (t, J = 8.0 Hz, 1H), 3.94 (s, 3H), 3.22-3.03 (m, 2H), 2.98-2.85 (m, 1H), 2.67 (br. s., 1H), 2.19 (br. s., 2H), 1.96 (d, J = 8.0 Hz, 1H), 1.89-1.75 (m, 1H), 1.74-1.59 (m, 2H), 1.58-1.45 (m, 2H), 1.41-1.27 (m, 2H). | 0.88$^c$ |
| 138 | 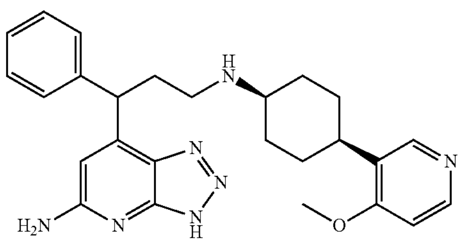 [SMILES: COc1ccncc1[C@H]1CC[C@@H](NCCC(c2ccccc2)c2cc(N)nc3[nH]nnc23)CC1] | 7-(1-phenyl-3-{[(1s,4s)-4-(4-methoxypyridin-3-yl)cyclohexyl]amino}propyl)-3H-[1,2,3]triazolo[4,5-b]pyridin-5-amine | 458.2 | (500 MHz, CD$_3$OD) δ 8.38 (br. s., 1H), 7.53 (d, J = 7.7 Hz, 2H), 7.39 (t, J = 7.4 Hz, 2H), 7.32-7.26 (m, 1H), 7.18-7.08 (m, 1H), 6.50 (s, 1H), 4.60 (t, J = 7.8 Hz, 1H), 4.01-3.95 (m, 3H), 3.52-3.42 (m, 1H), 3.24-3.02 (m, 2H), 2.98-2.89 (m, 1H), 2.74 (br. s., 1H), 2.09-1.47 (m, 9H). | 0.91$^c$ |
| 139 | 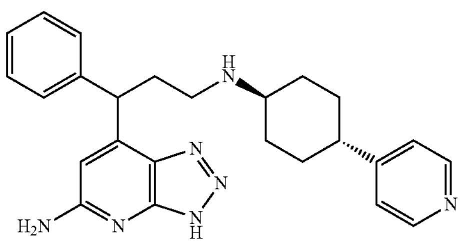 [SMILES: Nc1cc(C(CCN[C@H]2CC[C@H](c3ccncc3)CC2)c2ccccc2)c2nn[nH]c2n1] | 7-(1-phenyl-3-{[(trans)-4-(pyridin-4-yl)cyclohexyl]amino}propyl)-3H-[1,2,3]triazolo[4,5-b]pyridin-5-amine | 429.2 | (500 MHz, CD$_3$OD) δ 8.43 (d, J = 5.5 Hz, 2H), 7.51 (d, J = 7.7 Hz, 2H), 7.44-7.21 (m, 5H), 6.46 (s, 1H), 4.61 (t, J = 8.0 Hz, 1H), 3.07-2.47 (m, 6H), 2.19-2.08 (m, 2H), 1.69-1.37 (m, 6H) | 0.85$^c$ |
| 140 | 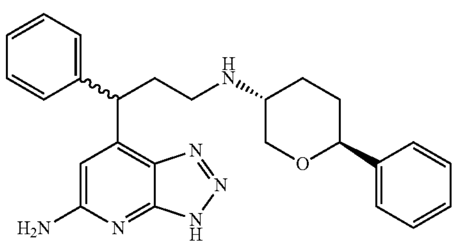 [SMILES: Nc1cc(C(CCN[C@@H]2CC[C@@H](c3ccccc3)OC2)c2ccccc2)c2nn[nH]c2n1] | 7-(1-phenyl-3-{[(3R,6S)-6-phenyloxan-3-yl]amino}propyl)-3H-[1,2,3]triazolo[4,5-b]pyridin-5-amine | 429.2 | (500 MHz, CD$_3$OD) δ 7.53-7.47 (m, 2H), 7.39-7.28 (m, 6H), 7.25 (s, 2H), 6.54 (s, 1H), 4.64-4.57 (m, 1H), 4.32 (d, J = 10.7 Hz, 1H), 4.19-4.11 (m, 1H), 3.38-3.34 (m, 1H), 2.96-2.72 (m, 3H), 2.69-2.57 (m, 1H), 2.55-2.43 (m, 2H), 2.16 (t, J = 11.1 Hz, 1H), 1.72-1.59 (m, 1H), 1.52 (ddd, J = 11.9, 7.6, 4.1 Hz, 1H) | 1.18$^c$ |
| 141 | 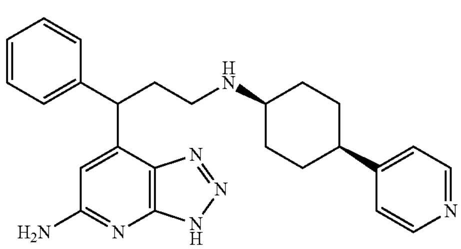 [SMILES: Nc1cc(C(CCN[C@H]2CC[C@@H](c3ccncc3)CC2)c2ccccc2)c2nn[nH]c2n1] | 7-(1-phenyl-3-{[(1s,4s)-4-(pyridin-4-yl)cyclohexyl]amino}propyl)-3H-[1,2,3]triazolo[4,5-b]pyridin-5-amine | 428.3 | (500 MHz, CD$_3$OD) δ 8.60 (d, J = 5.5 Hz, 2H), 7.68 (d, J = 5.5 Hz, 2H), 7.52 (d, J = 7.7 Hz, 2H), 7.39 (t, J = 7.7 Hz, 2H), 7.33-7.27 (m, 1H), 6.49 (s, 1H), 4.59 (t, J = 7.7 Hz, 1H), 3.44 (br. s., 1H), 3.18-2.96 (m, 3H), 2.93-2.83 (m, 1H), 2.76-2.68 (m, 2H), 2.06-1.85 (m, 7H) | 0.87$^c$ |

-continued

| Ex. No. | Structure | Name | MS (ESI) (M + H) | $^1$H NMR | LC RT$^a$ (min) |
|---|---|---|---|---|---|
| 142 | 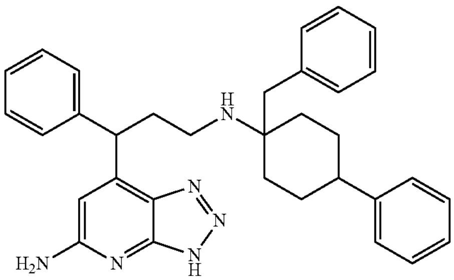 [SMILES: Nc1cc(C(CCNC2(Cc3ccccc3)CCC(c3ccccc3)CC2)c2ccccc2)c2nn[nH]c2n1] | 7-{3-[(1-benzyl-4-phenylcyclohexyl) amino]-1-phenylpropyl}-3H-[1,2,3]triazolo[4,5-b]pyridin-5-amine | 517.4 | (500 MHz, CD$_3$OD) δ 7.54 (d, J = 7.7 Hz, 2H), 7.45-7.11 (m, 13H), 6.61 (br. s., 1H), 4.62 (t, J = 7.6 Hz, 1H), 3.21 (dt, J = 11.6, 5.8 Hz, 1H), 3.12 (td, J = 11.6, 4.1 Hz, 1H), 2.98-2.88 (m, 1H), 2.73 (d, J = 12.7 Hz, 1H), 2.46 (br. s., 1H), 2.13-1.99 (m, 2H), 1.92-1.70 (m, 8H) | 1.66$^c$ |
| 143 | 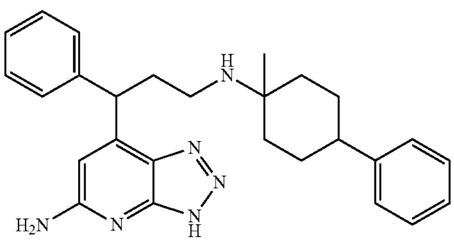 [SMILES: CC1(NCCC(c2ccccc2)c2cc(N)nc3[nH]nnc23)CCC(c2ccccc2)CC1] | 7-{3-[(1-methyl-4-phenylcyclohexyl) amino]-1-phenylpropyl}-3H-[1,2,3]triazolo[4,5-b]pyridin-5-amine | 441.5 | (500 MHz, CD$_3$OD) δ 7.52 (d, J = 7.2 Hz, 2H), 7.39 (t, J = 7.6 Hz, 2H), 7.33-7.27 (m, 5H), 7.23-7.16 (m, 1H), 6.47 (s, 1H), 4.60 (t, J = 7.7 Hz, 1H), 3.14-3.04 (m, 1H), 3.00 (td, J = 11.2, 4.8 Hz, 1H), 2.95-2.86 (m, 1H), 2.78-2.61 (m, 2H), 2.02 (dd, J = 11.1, 4.5 Hz, 1H), 1.91-1.64 (m, 7H), 1.30 (s, 3H) (3:1 mixture of diastereomers) | 1.37$^c$ |
| 144 | 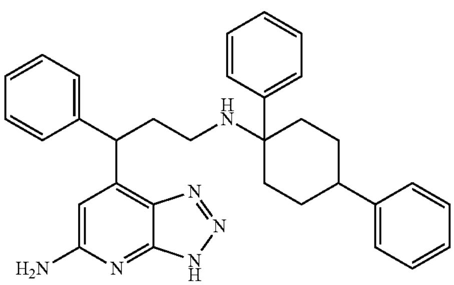 [SMILES: Nc1cc(C(CCNC2(c3ccccc3)CCC(c3ccccc3)CC2)c2ccccc2)c2nn[nH]c2n1] | 7-{3-[(1,4-diphenylcyclohexyl) amino]-1-phenylpropyl}-3H-[1,2,3]triazolo[4,5-b]pyridin-5-amine | 503.3 | (500 MHz, CD$_3$OD) δ 7.49 (d, J = 7.2 Hz, 2H), 7.43-7.15 (m, 14H), 6.33 (s, 1H), 4.41 (t, J = 7.6 Hz, 1H), 2.78-2.52 (m, 4H), 2.50-2.36 (m, 3H), 2.12 (br. s., 2H), 2.06-1.87 (m, 5H) | 1.54$^c$ |
| 145 | 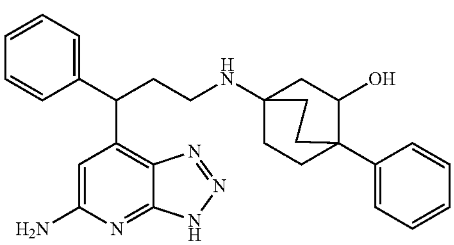 [SMILES: Nc1cc(C(CCNC23CCC(c4ccccc4)(CC2)C(O)C3)c2ccccc2)c2nn[nH]c2n1] | 4-[(3-{5-amino-3H-[1,2,3]triazolo[4,5-b]pyridin-7-yl}-3-phenylpropyl) amino]-1-phenylbicyclo [2.2.2]octan-2-ol | 469.4 | (500 MHz, CD$_3$OD) δ 7.50 (d, J = 7.4 Hz, 2H), 7.42-7.33 (m, 4H), 7.32-7.24 (m, 3H), 7.21-7.13 (m, 1H), 6.46 (s, 1H), 4.62 (t, J = 7.8 Hz, 1H), 4.27 (d, J = 8.5 Hz, 1H), 2.99-2.79 (m, 2H), 2.78-2.69 (m, 1H), 2.61-2.51 (m, 1H), 2.51-2.41 (m, 1H), 2.27 (ddd, J = 12.9, 9.4, 3.3 Hz, 1H), 2.05-1.96 (m, 1H), 1.92-1.84 (m, 2H), 1.82-1.60 (m, 5H) | 1.18$^c$ |
| 146 | 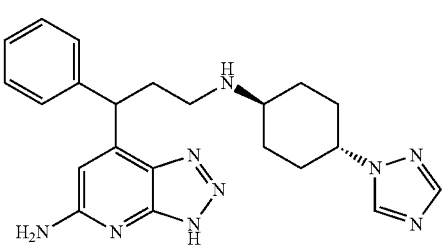 [SMILES: Nc1cc(C(CCN[C@H]2CC[C@H](n3cncn3)CC2)c2ccccc2)c2nn[nH]c2n1] | 7-(1-phenyl-3-{[(trans)-4-(1H-1,2,4-triazol-1-yl) cyclohexyl]amino} propyl)-3H-[1,2,3] triazolo[4,5-b] pyridin-5-amine | 418.4 | (500 MHz, CD$_3$OD) δ 8.52 (s, 1H), 8.02 (s, 1H), 7.54 (d, J = 7.4 Hz, 2H), 7.42 (t, J = 7.7 Hz, 2H), 7.36-7.29 (m, 1H), 6.74 (s, 1H), 4.64 (dd, J = 9.1, 6.6 Hz, 1H), 4.45-4.34 (m, 1H), 3.28-3.12 (m, 2H), 3.09-2.98 (m, 1H), 2.91-2.80 (m, 1H), 2.75-2.64 (m, 1H), 2.26 (d, J = 10.5 Hz, 4H), 2.03-1.90 (m, 2H), 1.68-1.53 (m, 2H) | 0.88$^c$ |

-continued

| Ex. No. | Structure | Name | MS (ESI) (M + H) | ¹H NMR | LC RT$^a$ (min) |
|---|---|---|---|---|---|
| 147 | 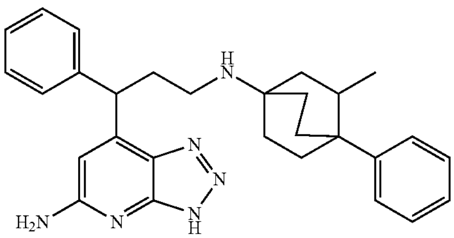 [SMILES: CC1CC2(NCCC(c3ccccc3)c3cc(N)nc4[nH]nnc34)CCC1(c1ccccc1)CC2] | 7-[3-({3-methyl-4-phenylbicyclo[2.2.2]octan-1-yl}amino)-1-phenylpropyl]-3H-[1,2,3]triazolo[4,5-b]pyridin-5-amine | 467.3 | (500 MHz, CD$_3$OD) δ 7.51 (d, J = 7.4 Hz, 2H), 7.39 (t, J = 7.7 Hz, 2H), 7.33-7.19 (m, 5H), 7.18-7.12 (m, 1H), 6.64 (s, 1H), 4.62 (dd, J = 8.9, 6.5 Hz, 1H), 3.11-3.00 (m, 1H), 2.96-2.86 (m, 1H), 2.80 (td, J = 12.1, 5.8 Hz, 1H), 2.68-2.56 (m, 1H), 2.40-2.25 (m, 1H), 2.22-2.10 (m, 2H), 2.01-1.77 (m, 5H), 1.76-1.67 (m, 1H), 1.41-1.29 (m, 1H), 0.63 (dd, J = 6.9, 2.5 Hz, 3H) | 1.46$^c$ |
| 148 | 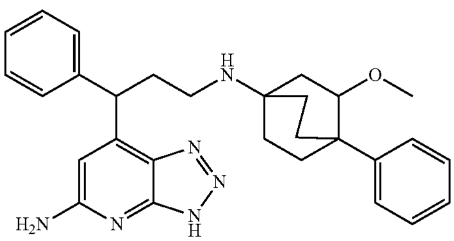 [SMILES: COC1CC2(NCCC(c3ccccc3)c3cc(N)nc4[nH]nnc34)CCC1(c1ccccc1)CC2] | 7-[3-({3-methoxy-4-phenylbicyclo[2.2.2]octan-1-yl}amino)-1-phenylpropyl]-3H-[1,2,3]triazolo[4,5-b]pyridin-5-amine | 483.3 | (500 MHz, CD$_3$OD) δ 7.49 (d, J = 7.4 Hz, 2H), 7.41-7.22 (m, 7H), 7.19-7.12 (m, 1H), 6.46 (d, J = 2.8 Hz, 1H), 4.60 (t, J = 7.2 Hz, 1H), 3.83 (d, J = 8.5 Hz, 1H), 3.07 (d, J = 1.9 Hz, 3H), 2.97-2.82 (m, 2H), 2.81-2.71 (m, 1H), 2.64-2.54 (m, 1H), 2.44-2.34 (m, 1H), 2.24-2.14 (m, 1H), 1.90-1.49 (m, 7H), 1.23-1.06 (m, 1H) | 1.33$^c$ |
| 149 | 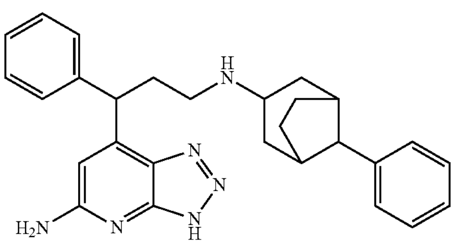 [SMILES: Nc1cc(C(CCNC2CC3CCC(C2)C3c2ccccc2)c2ccccc2)c2nn[nH]c2n1] | 7-[1-phenyl-3-({8-phenylbicyclo[3.2.1]octan-3-yl}amino)propyl]-3H-[1,2,3]triazolo[4,5-b]pyridin-5-amine | 453.3 | (500 MHz, CD$_3$OD) δ 7.46 (d, J = 7.2 Hz, 2H), 7.41-7.34 (m, 6H), 7.32-7.25 (m, 1H), 7.23-7.17 (m, 1H), 6.41 (s, 1H), 4.49 (t, J = 8.0 Hz, 1H), 3.10-3.04 (m, 1H), 2.95-2.82 (m, 5H), 2.56-2.44 (m, 1H), 2.05-1.97 (m, 2H), 1.82-1.60 (m, 7H) | 1.40$^c$ |
| 150 | 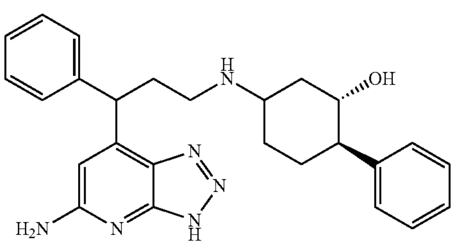 [SMILES: Nc1cc(C(CCNC2CC[C@H](c3ccccc3)[C@@H](O)C2)c2ccccc2)c2nn[nH]c2n1] | (1S,2R)-5-[(3-{5-amino-3H-[1,2,3]triazolo[4,5-b]pyridin-7-yl}-3-phenylpropyl)amino]-2-phenylcyclohexan-1-ol | 443.2 | (500 MHz, CD$_3$OD) δ 7.56-7.47 (m, 2H), 7.43-7.35 (m, 2H), 7.33-7.25 (m, 5H), 7.23-7.13 (m, 2H), 6.62 (s, 1H), 4.64-4.53 (m, 1H), 4.12 (dt, J = 8.3, 4.2 Hz, 1H), 3.63-3.54 (m, 1H), 3.13 (td, J = 11.9, 5.9 Hz, 1H), 3.07-2.95 (m, 1H), 2.85 (d, J = 6.1 Hz, 1H), 2.68 (br. s., 1H), 2.47-2.34 (m, 1H), 2.13-1.78 (m, 6H) | 1.09$^c$ |
| 151 | 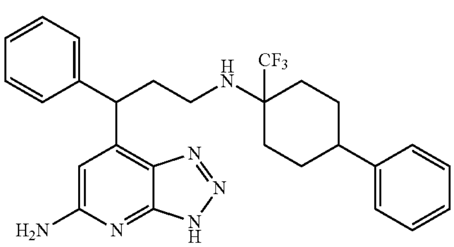 [SMILES: Nc1cc(C(CCNC2(C(F)(F)F)CCC(c3ccccc3)CC2)c2ccccc2)c2nn[nH]c2n1] | 7-(1-phenyl-3-{[4-phenyl-1-(trifluoromethyl)cyclohexyl]amino}propyl)-3H-[1,2,3]triazolo[4,5-b]pyridin-5-amine | 495.3 | (500 MHz, CD$_3$OD) δ 7.56-7.47 (m, 2H), 7.40 (t, J = 7.7 Hz, 2H), 7.35-7.13 (m, 6H), 6.81 (d, J = 8.0 Hz, 1H), 6.60 (br. s., 1H), 4.67 (t, J = 7.8 Hz, 1H), 4.07-3.94 (m, 1H), 3.21-3.08 (m, 1H), 3.02 (d, J = 7.2 Hz, 2H), 2.93-2.73 (m, 2H), 2.67-2.58 (m, 1H), 2.46-2.27 (m, 2H), 1.88-1.74 (m, 5H) | 1.51$^c$ |
| 152 | 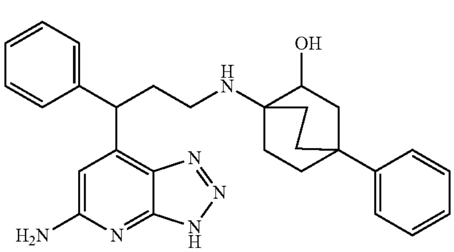 [SMILES: Nc1cc(C(CCNC23CCC(c4ccccc4)(CC2)CC3O)c2ccccc2)c2nn[nH]c2n1] | 1-[(3-{5-amino-3H-[1,2,3]triazolo[4,5-b]pyridin-7-yl}-3-phenylpropyl)amino]-4-phenylbicyclo[2.2.2]octan-2-ol | 369.3 | (500 MHz, CD$_3$OD) δ 7.52 (d, J = 7.7 Hz, 2H), 7.39 (t, J = 7.7 Hz, 2H), 7.35-7.26 (m, 5H), 7.24-7.17 (m, 1H), 6.48 (d, J = 1.7 Hz, 1H), 4.63 (t, J = 7.8 Hz, 1H), 4.27 (td, J = 10.3, 6.1 Hz, 1H), 3.10-2.85 (m, 2H), 2.78 (dt, J = 13.3, 6.5 Hz, 1H), 2.72-2.66 (m, 1H), 2.61 (dd, J = 13.1, 8.1 Hz, 1H), 2.32 (br. s., 1H), 2.20 (d, J = 2.5 Hz, 1H), 1.92-1.80 (m, 3H), 1.79-1.58 (m, 4H) | 1.14$^c$ |

-continued

| Ex. No. | Structure | Name | MS (ESI) (M + H) | ¹H NMR | LC RT[a] (min) |
|---|---|---|---|---|---|
| 153 | 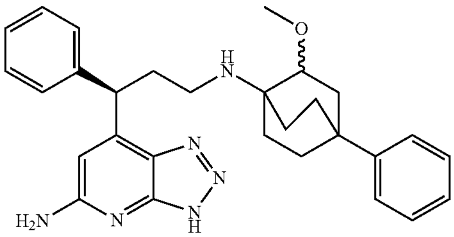 [SMILES: COC1CC2(c3ccccc3)CCC1(NCC[C@H](c1ccccc1)c1cc(N)nc3[nH]nnc13)CC2] | 7-[(1R)-3-({2-methoxy-4-phenylbicyclo[2.2.2]octan-1-yl}amino)-1-phenylpropyl]-3H-[1,2,3]triazolo[4,5-b]pyridin-5-amine | 483.3 | (500 MHz, CD₃OD) δ 7.52 (d, J = 7.4 Hz, 2H), 7.39 (t, J = 7.7 Hz, 2H), 7.34-7.26 (m, 5H), 7.23-7.18 (m, 1H), 6.48 (d, J = 2.8 Hz, 1H), 4.64 (td, J = 7.8, 3.4 Hz, 1H), 3.94 (td, J = 10.1, 5.9 Hz, 1H), 3.29 (d, J = 1.7 Hz, 3H), 3.15-2.89 (m, 2H), 2.86-2.72 (m, 2H), 2.61 (dt, J = 13.3, 8.0 Hz, 1H), 2.48-2.39 (m, 1H), 2.31 (br. s., 1H), 1.93-1.82 (m, 3H), 1.80-1.69 (m, 2H), 1.68-1.59 (m, 1H), 1.58-1.49 (m, 1H) | 1.29[c] |
| 154 | 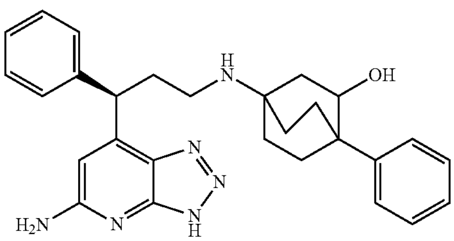 [SMILES: Nc1cc([C@H](CCNC23CCC(c4ccccc4)(CC2)C(O)C3)c2ccccc2)c2nn[nH]c2n1] | 4-{[(3R)-3-{5-amino-3H-[1,2,3]triazolo[4,5-b]pyridin-7-yl}-3-phenylpropyl]amino}-1-phenylbicyclo[2.2.2]octan-2-ol | 469.5 | (500 MHz, CD₃OD) δ 7.49 (d, J = 7.4 Hz, 2H), 7.40-7.33 (m, 4H), 7.29 (t, J = 8.0 Hz, 3H), 7.20-7.14 (m, 1H), 6.44 (s, 1H), 4.63 (t, J = 8.0 Hz, 1H), 4.26 (d, J = 9.1 Hz, 1H), 2.90-2.80 (m, 1H), 2.79-2.71 (m, 1H), 2.65-2.60 (m, 1H), 2.55-2.38 (m, 2H), 2.26-2.17 (m, 1H), 1.98 (d, J = 14.3 Hz, 1H), 1.90-1.79 (m, 2H), 1.77-1.57 (m, 5H) | 1.19[c] |
| 155 | 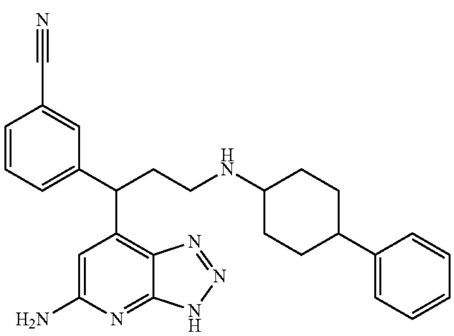 [SMILES: N#Cc1cccc(C(CCNC2CCC(c3ccccc3)CC2)c2cc(N)nc3[nH]nnc23)c1] | 3-(1-{5-amino-3H-[1,2,3]triazolo[4,5-b]pyridin-7-yl}-3-[(4-phenylcyclohexyl)amino]propyl)benzonitrile | 452.3 | (400 MHz, CD₃OD) δ 7.98 (s, 1H), 7.90-7.85 (m, 1H), 7.74-7.69 (m, 1H), 7.64-7.57 (m, 1H), 7.33-7.26 (m, 2H), 7.24-7.16 (m, 3H), 6.74 (s, 1H), 4.69 (t, J = 7.8 Hz, 1H), 3.26-3.11 (m, 2H), 3.10-3.00 (m, J = 4.8 Hz, 1H), 2.97-2.87 (m, 1H), 2.76-2.64 (m, 1H), 2.62-2.53 (m, J = 3.1 Hz, 1H), 2.26-2.15 (m, 2H), 2.05-1.98 (m, 2H), 1.69-1.48 (m, 4H), 1.37-1.30 (m, 1H). | 5.52 |
| 156 | 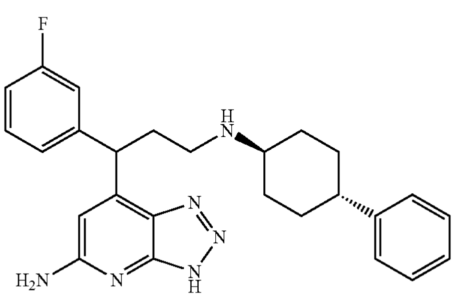 [SMILES: Nc1cc(C(CCN[C@H]2CC[C@H](c3ccccc3)CC2)c2cccc(F)c2)c2nn[nH]c2n1] | 7-[1-(3-fluorophenyl)-3-{[(trans)-4-phenylcyclohexyl]amino}propyl]-3H-[1,2,3]triazolo[4,5-b]pyridin-5-amine | 445.0 | (400 MHz, CD₃OD) δ 7.56-7.46 (m, 1H), 7.39 (dd, J = 7.8, 5.8 Hz, 1H), 7.33 (d, J = 7.0 Hz, 1H), 7.30-7.24 (m, 2H), 7.23-7.14 (m, 3H), 7.09-6.98 (m, 1H), 6.52 (s, 1H), 4.59 (t, J = 7.8 Hz, 1H), 3.24-2.98 (m, 3H), 2.92-2.79 (m, 1H), 2.70-2.60 (m, 1H), 2.60-2.50 (m, 1H), 2.25-2.11 (m, 2H), 2.04-1.93 (m, 2H), 1.66-1.42 (m, 4H), 1.35-1.26 (m, 1H) | 10.03 |
| 157 | 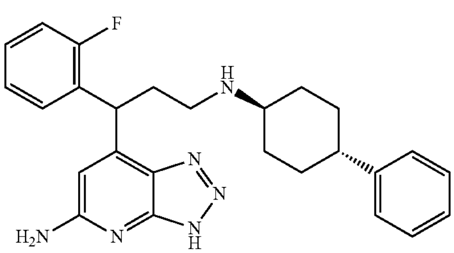 [SMILES: Nc1cc(C(CCN[C@H]2CC[C@H](c3ccccc3)CC2)c2ccccc2F)c2nn[nH]c2n1] | 7-[1-(2-fluorophenyl)-3-{[(trans)-4-phenylcyclohexyl]amino}propyl]-3H-[1,2,3]triazolo[4,5-b]pyridin-5-amine | 445.3 | (500 MHz, DMSO-d₆) δ 8.54 (br. s., 2H), 7.68 (t, J = 7.3 Hz, 1H), 7.37-7.31 (m, 1H), 7.31-7.14 (m, 7H), 6.37 (br. s., 1H), 4.75 (t, J = 7.7 Hz, 1H), 3.11 (m, 1H), 3.00-2.88 (m, 2H), 2.85-2.74 (m, 1H), 2.65-2.54 (m, 2H), 2.05 (t, J = 13.8 Hz, 2H), 1.85 (d, J = 10.7 Hz, 2H), 1.55-1.34 (m, 4H) | 1.31[c] |

| Ex. No. | Structure | Name | MS (ESI) (M + H) | ¹H NMR | LC RT$^a$ (min) |
|---|---|---|---|---|---|
| 158 | 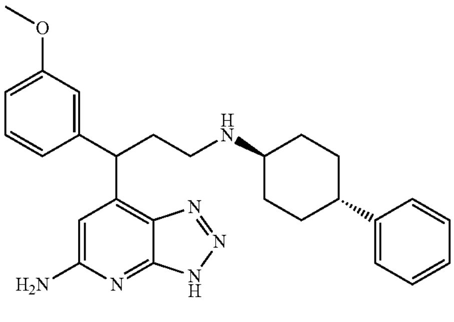 [SMILES: COc1cccc(C(CCN[C@H]2CC[C@H](c3ccccc3)CC2)c2cc(N)nc3[nH]nnc23)c1] | 7-[1-(3-methoxyphenyl)-3-{[(trans)-4-phenylcyclohexyl]amino}propyl]-3H-[1,2,3]triazolo[4,5-b]pyridin-5-amine | 457.3 | (500 MHz, CD$_3$OD) δ 7.33-7.13 (m, 6H), 7.07 (d, J = 7.7 Hz, 2H), 6.86 (d, J = 8.3 Hz, 1H), 6.46 (s, 1H), 4.55-4.50 (m, 1H), 3.78 (s, 3H), 3.19-2.99 (m, 3H), 2.83-2.76 (m, 1H), 2.68-2.59 (m, 1H), 2.58-2.49 (m, 1H), 2.22-2.09 (m, 2H), 2.03-1.92 (m, 2H), 1.66-1.43 (m, 4H) | 1.39$^c$ |
| 159 | 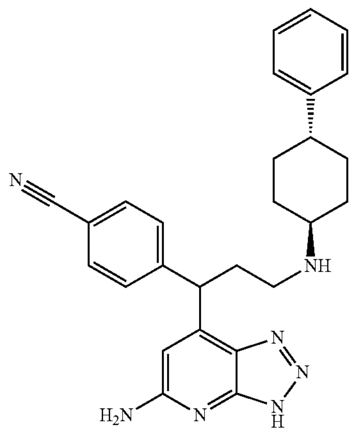 [SMILES: N#Cc1ccc(C(CCN[C@H]2CC[C@H](c3ccccc3)CC2)c2cc(N)nc3[nH]nnc23)cc1] | 4-(1-{5-amino-3H-[1,2,3]triazolo[4,5-b]pyridin-7-yl}-3-{[(trans)-4-phenylcyclohexyl]amino}propyl)benzonitrile | 452.3 | (500 MHz, DMSO-d6) δ 7.78 (d, J = 8.3 Hz, 2H), 7.66 (d, J = 8.0 Hz, 2H), 7.29-7.22 (m, 2H), 7.22-7.06 (m, 3H), 6.58 (br. s, 2H), 6.46 (s, 1H), 4.72-4.56 (m, 1H), 2.47-2.25 (m, 4H), 1.92-1.64 (m, 5H), 1.50-1.03 (m, 5H) | 1.34$^c$ |
| 160 | 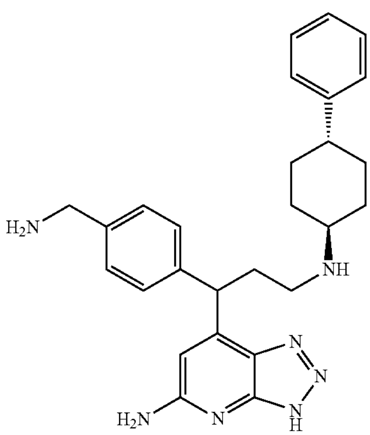 [SMILES: NCc1ccc(C(CCN[C@H]2CC[C@H](c3ccccc3)CC2)c2cc(N)nc3[nH]nnc23)cc1] | 7-{1-[4-(aminomethyl)phenyl]-3-{[(trans)-4-phenylcyclohexyl]amino}propyl}-3H-[1,2,3]triazolo[4,5-b]pyridin-5-amine | 456.35 | (500 MHz, CD3OD) δ 7.62 (d, J = 7.7 Hz, 2H), 7.49-7.38 (m, 2H), 7.31-7.24 (m, 2H), 7.22-7.14 (m, 3H), 6.64 (s, 1H), 4.66-4.55 (m, 1H), 4.09 (s, 2H), 3.22-3.12 (m, 1H), 3.10-3.00 (m, 2H), 2.94-2.81 (m, 1H), 2.73-2.61 (m, 1H), 2.58-2.48 (m, 1H), 2.14 (d, J = 8.8 Hz, 2H), 1.97 (d, J = 11.6 Hz, 2H), 1.68-1.51 (m, 4H) | 1.02$^c$ |
| 161 | 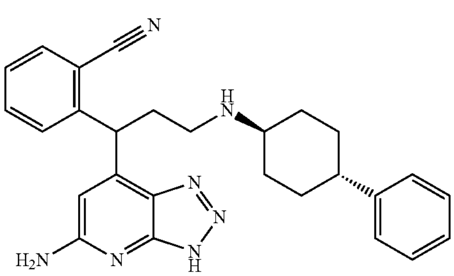 [SMILES: N#Cc1ccccc1C(CCN[C@H]1CC[C@H](c2ccccc2)CC1)c1cc(N)nc2[nH]nnc12] | 2-(1-{5-amino-3H-[1,2,3]triazolo[4,5-b]pyridin-7-yl}-3-{[(trans)-4-phenylcyclohexyl]amino}propyl)benzonitrile | 452.3 | (500 MHz, CD$_3$OD) δ 7.92 (d, J = 8.0 Hz, 1H), 7.77 (d, J = 7.7 Hz, 1H), 7.71 (t, J = 7.8 Hz, 1H), 7.47 (t, J = 7.7 Hz, 1H), 7.28-7.24 (m, 2H), 7.21-7.15 (m, 3H), 6.44 (s, 1H), 4.95 (t, J = 7.3 Hz, 1H), 3.19-2.82 (m, 4H), 2.68-2.48 (m, 2H), 2.18-2.06 (m, 2H), 1.95 (s, 2H), 1.72-1.40 (m, 4H) | 1.29$^c$ |

| Ex. No. | Structure | Name | MS (ESI) (M + H) | ¹H NMR | LC RT$^a$ (min) |
|---|---|---|---|---|---|
| 162 | 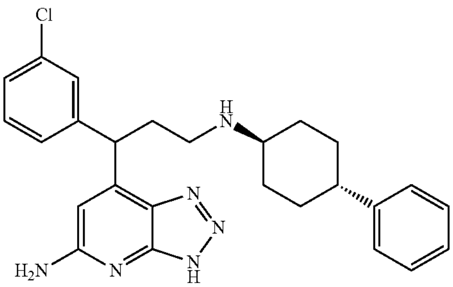 [SMILES: Nc1cc(C(CCN[C@H]2CC[C@H](c3ccccc3)CC2)c2cccc(Cl)c2)c2nn[nH]c2n1] | 7-[1-(3-chlorophenyl)-3-{[(trans)-4-phenylcyclohexyl]amino}propyl]-3H-[1,2,3]triazolo[4,5-b]pyridin-5-amine | 461.3 | (500 MHz, CD$_3$OD) δ 7.59 (s, 1H), 7.46 (d, J = 7.4 Hz, 1H), 7.37 (t, J = 7.8 Hz, 1H), 7.34-7.30 (m, 1H), 7.28-7.25 (m, 2H), 7.23-7.13 (m, 3H), 6.62 (s, 1H), 4.58 (t, J = 7.7 Hz, 1H), 3.19-3.07 (m, 2H), 3.02 (d, J = 5.0 Hz, 1H), 2.86-2.80 (m, 1H), 2.68-2.60 (m, 1H), 2.57-2.50 (m, 1H), 2.22-2.12 (m, 2H), 1.98 (d, J = 12.9 Hz, 2H), 1.64-1.46 (m, 4H) | 1.39$^c$ |
| 163 | 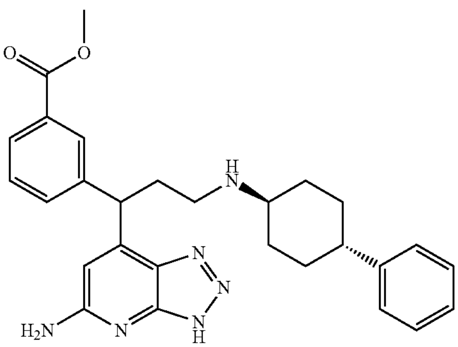 [SMILES: COC(=O)c1cccc(C(CCN[C@H]2CC[C@H](c3ccccc3)CC2)c2cc(N)nc3[nH]nnc23)c1] | methyl 3-(1-{5-amino-3H-[1,2,3]triazolo[4,5-b]pyridin-7-yl}-3-{[(trans)-4-phenylcyclohexyl]amino}propyl)benzoate | 485.25 | (500 MHz, DMSO-d6) δ 8.03 (s, 1H), 7.79 (d, J = 8.0 Hz, 1H), 7.76 (d, J = 7.7 Hz, 1H), 7.46 (t, J = 7.8 Hz, 1H), 7.29-7.22 (m, 2H), 7.21-7.11 (m, 3H), 6.56 (br. s., 2H), 6.48 (s, 1H), 4.63 (t, J = 7.2 Hz, 1H), 3.83 (s, 3H), 2.46-2.33 (m, 3H), 2.33-2.26 (m, 1H), 1.88 (s, 3H), 1.73 (d, J = 10.5 Hz, 2H), 1.46-1.34 (m, 2H), 1.23 (s, 1H), 1.16-1.03 (m, 2H) | 1.36$^c$ |
| 164 | 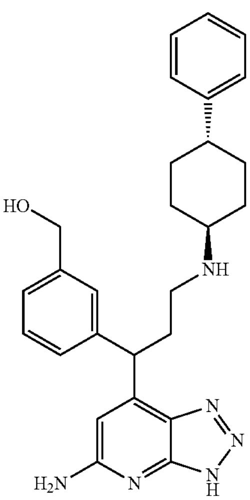 [SMILES: Nc1cc(C(CCN[C@H]2CC[C@H](c3ccccc3)CC2)c2cccc(CO)c2)c2nn[nH]c2n1] | [3-(1-{5-amino-3H-[1,2,3]triazolo[4,5-b]pyridin-7-yl}-3-{[(trans)-4-phenylcyclohexyl]amino}propyl)phenyl]methanol | 457.25 | (500 MHz, DMSO-d6) δ 7.39-7.33 (m, 2H), 7.29-7.24 (m, 3H), 7.22-7.11 (m, 4H), 6.54 (s, 1H), 6.46 (s, 1H), 4.52 (s, 1H), 4.45 (s, 2H), 2.60-2.54 (m, 2H), 2.48-2.39 (m, 3H), 2.35-2.27 (m, 1H), 1.90-1.86 (m, 2H), 1.75 (d, J = 9.4 Hz, 2H), 1.47-1.36 (m, J = 12.9 Hz, 2H), 1.20-1.08 (m, J = 4.1 Hz, 2H) | 1.19$^c$ |
| 165 | 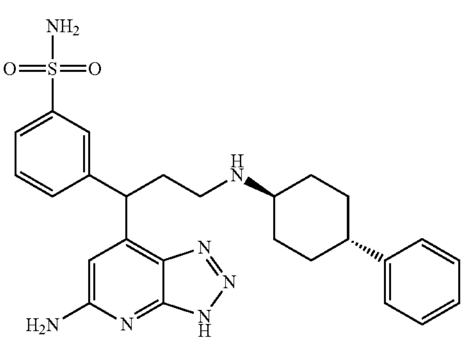 [SMILES: Nc1cc(C(CCN[C@H]2CC[C@H](c3ccccc3)CC2)c2cccc(S(N)(=O)=O)c2)c2nn[nH]c2n1] | 3-(1-{5-amino-3H-[1,2,3]triazolo[4,5-b]pyridin-7-yl}-3-{[(trans)-4-phenylcyclohexyl]amino}propyl)benzene-1-sulfonamide | 506.25 | (500 MHz, DMSO-d6) δ 7.87 (s, 1H), 7.74 (d, J = 7.7 Hz, 1H), 7.68 (d, J = 8.0 Hz, 1H), 7.53 (t, J = 7.8 Hz, 1H), 7.33 (br. s., 2H), 7.28-7.23 (m, 2H), 7.21-7.11 (m, 3H), 6.60 (br. s, 2H), 6.49 (s, 1H), 4.63 (t, J = 7.4 Hz, 1H), 2.63-2.52 (m, 3H), 2.49-2.39 (m, 2H), 2.37-2.28 (m, 1H), 1.93-1.84 (m, 2H), 1.79-1.71 (m, 2H), 1.42 (q, J = 12.9 Hz, 2H), 1.21-1.08 (m, 2H) | 1.17$^c$ |

-continued

| Ex. No. | Structure | Name | MS (ESI) (M + H) | ¹H NMR | LC RT[a] (min) |
|---|---|---|---|---|---|
| 166 | 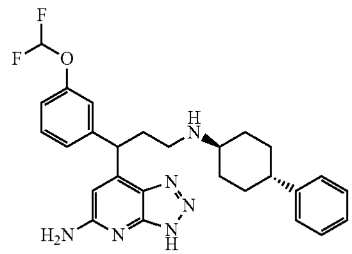 [SMILES: Nc1cc(C(CCN[C@H]2CC[C@H](c3ccccc3)CC2)c2cccc(OC(F)F)c2)c2nn[nH]c2n1] | 7-{1-[3-(difluoromethoxy)phenyl]-3-{[(trans)-4-phenylcyclohexyl]amino}propyl}-3H-[1,2,3]triazolo[4,5-b]pyridin-5-amine | 493.25 | (500 MHz, CD₃OD) δ 7.40-7.33 (m, 2H), 7.30 (s, 1H), 7.27-7.21 (m, 2H), 7.20-7.11 (m, 3H), 7.04 (d, J = 7.4 Hz, 1H), 6.97-6.64 (m, J = 75.4 Hz, 1H), 6.44 (s, 1H), 4.59 (t, J = 7.8 Hz, 1H), 2.94-2.85 (m, 2H), 2.72 (d, J = 9.4 Hz, 1H), 2.58-2.46 (m, 2H), 2.13-2.03 (m, 2H), 1.96-1.86 (m, 2H), 1.60-1.49 (m, 2H), 1.46-1.34 (m, 2H), 1.29 (d, J = 6.6 Hz, 1H) | 1.43[c] |
| 168 | 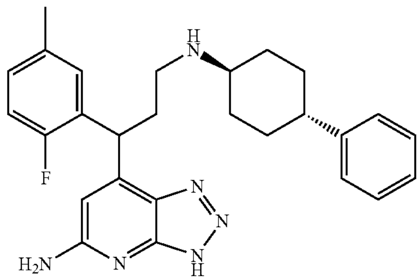 [SMILES: Cc1ccc(F)c(C(CCN[C@H]2CC[C@H](c3ccccc3)CC2)c2cc(N)nc3[nH]nnc23)c1] | 7-[1-(2-fluoro-5-methylphenyl)-3-{[(trans)-4-phenylcyclohexyl]amino}propyl]-3H-[1,2,3]triazolo[4,5-b]pyridin-5-amine | 459.25 | (500 MHz, CD₃OD) δ 7.43 (d, J = 5.2 Hz, 1H), 7.28-7.23 (m, 2H), 7.22-7.12 (m, 4H), 7.02 (dd, J = 10.3, 8.4 Hz, 1H), 6.49 (s, 1H), 4.88-4.86 (m, 1H), 3.22-3.01 (m, 4H), 2.67-2.59 (m, 1H), 2.59-2.50 (m, 1H), 2.33 (s, 3H), 2.21-2.13 (m, 2H), 2.01-1.95 (m, 2H), 1.64-1.46 (m, 4H) | 1.40[c] |
| 174 | 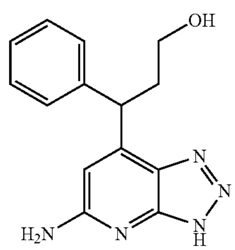 [SMILES: Nc1cc(C(CCO)c2ccccc2)c2nn[nH]c2n1] | 3-{5-amino-3H-[1,2,3]triazolo[4,5-b]pyridin-7-yl}-3-phenylpropan-1-ol | 270.1 | (400 MHz, CD₃CN) δ 7.50-7.40 (m, 2H), 7.38-7.30 (m, 2H), 7.28-7.20 (m, 1H), 6.73 (s, 1H), 4.67 (t, J = 7.6 Hz, 1H), 3.48 (td, J = 6.4, 1.9 Hz, 2H), 2.55-2.45 (m, 1H), 2.39-2.25 (m, 1H) | 4.26 |
| 175 | 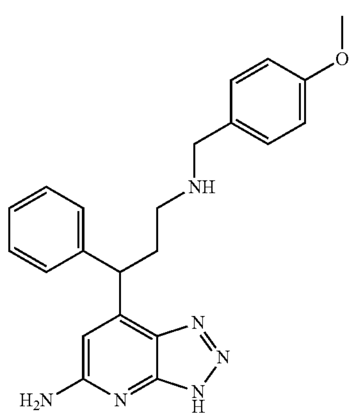 [SMILES: COc1ccc(CNCCC(c2ccccc2)c2cc(N)nc3[nH]nnc23)cc1] | 7-(3-{[(4-methoxyphenyl)methyl]amino}-1-phenylpropyl)-3H-[1,2,3]triazolo[4,5-b]pyridin-5-amine | 389.2 | (500 MHz, DMSO-d₆) δ 7.46 (d, J = 7.6 Hz, 2H), 7.39-7.28 (m, 4H), 7.26-7.16 (m, 1H), 7.01-6.87 (m, 2H), 6.41 (br. s., 1H), 4.46 (t, J = 7.6 Hz, 1H), 4.05 (br. s., 2H), 3.75 (s, 3H), 2.95-2.80 (m, 2H), 2.58-2.44 (m, 2H). | 1.05[c] |
| 176 | 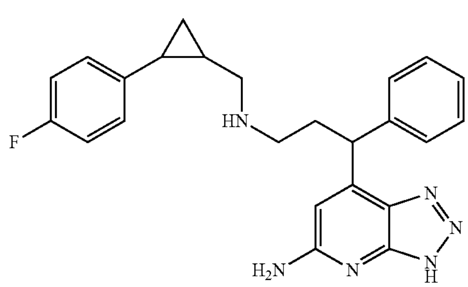 [SMILES: Nc1cc(C(CCNCC2CC2c2ccc(F)cc2)c2ccccc2)c2nn[nH]c2n1] | 7-[3-({[2-(4-fluorophenyl)cyclopropyl]methyl}amino)-1-phenylpropyl]-3H-[1,2,3]triazolo[4,5-b]pyridin-5-amine | 417.4 | (500 MHz, DMSO-d₆) δ 7.42 (m, 2H), 7.28 (m, 2H), 7.20-7.15 (m, 1H), 7.02 (m, 4H), 6.51 (s, 2H), 6.44 (s, 1H), 4.49 (t, J = 7.3 Hz, 1H), 2.63 (m, 1H), 2.45-2.37 (m, 4H), 2.34-2.23 (m, 2H), 1.74-1.64 (m, 1H), 1.06 (br. s., 1H), 0.77 (m, 2H) | 1.24[c] |

| Ex. No. | Structure | Name | MS (ESI) (M + H) | ¹H NMR | LC RT[a] (min) |
|---|---|---|---|---|---|
| 179 | 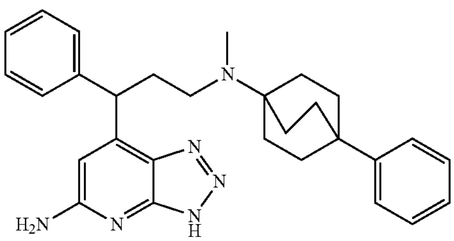 [SMILES: CN(CCC(c1ccccc1)c1cc(N)nc2[nH]nnc12)C12CCC(c3ccccc3)(CC1)CC2] | 7-{3-[methyl({4-phenylbicyclo[2.2.2]octan-1-yl})amino]-1-phenylpropyl}-3H-[1,2,3]triazolo[4,5-b]pyridin-5-amine | 467.3 | (500 MHz, CD₃OD) δ 7.54 (d, J = 7.4 Hz, 2H), 7.41 (br. s., 2H), 7.36-7.24 (m, 5H), 7.17 (s, 1H), 6.62 (br. s., 1H), 4.67-4.48 (m, 1H), 3.60-3.39 (m, 1H), 3.20-3.03 (m, 1H), 2.86 (m, 5H), 2.67 (s, 1H), 2.12-1.89 (m, 12H) | 1.40[c] |
| 180 | 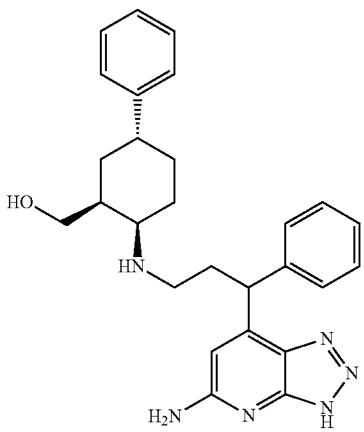 [SMILES: Nc1cc(C(CCN[C@@H]2CC[C@@H](c3ccccc3)C[C@@H]2CO)c2ccccc2)c2nn[nH]c2n1] | [(1S,2R,5R)-2-[(3-{5-amino-3H-[1,2,3]triazolo[4,5-b]pyridin-7-yl}-3-phenylpropyl)amino]-5-phenylcyclohexyl]methanol | 457.2 | (500 MHz, DMSO-d₆) δ 7.49 (m, 2H), 7.34 (m, 2H), 7.25 (m, 4H), 7.21-7.11 (m, 4H), 7.05 (s, 1H), 6.43 (br. s., 1H), 4.45 (m, 1H), 3.94-3.80 (m, 1H), 3.67-3.52 (m, 1H), 3.41 (br. s., 2H), 3.33 (br. s., 1H), 2.62 (br. s., 3H), 2.30 (br. s., 1H), 1.82 (br. s., 3H), 1.75 (br. s., 1H), 1.60 (br. s., 1H), 1.45 (d, J = 12.8 Hz, 1H) | 1.29[c] |
| 181 | 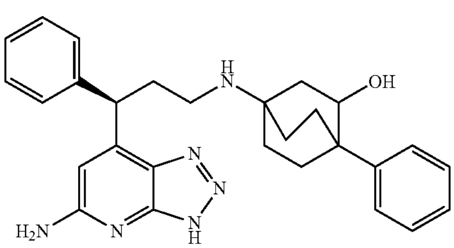 [SMILES: Nc1cc([C@H](CCNC23CCC(c4ccccc4)(CC2)C(O)C3)c2ccccc2)c2nn[nH]c2n1] | 4-{[(3R)-3-{5-amino-3H-[1,2,3]triazolo[4,5-b]pyridin-7-yl}-3-phenylpropyl]amino}-1-phenylbicyclo[2.2.2]octan-2-ol | 469.2 | (500 MHz, CD₃OD) δ 7.49 (d, J = 7.4 Hz, 2H), 7.40-7.32 (m, 4H), 7.31-7.23 (m, 3H), 7.19-7.11 (m, 1H), 6.42 (s, 1H), 4.59 (t, J = 7.7 Hz, 1H), 4.26 (d, J = 9.1 Hz, 1H), 2.93 (td, J = 11.3, 5.0 Hz, 1H), 2.86 (td, J = 11.3, 5.1 Hz, 1H), 2.78-2.67 (m, 1H), 2.64-2.51 (m, 1H), 2.48-2.38 (m, 1H), 2.26 (t, J = 12.7 Hz, 1H), 2.05-1.95 (m, 1H), 1.90-1.58 (m, 7H) | 4.72 |
| 182 | 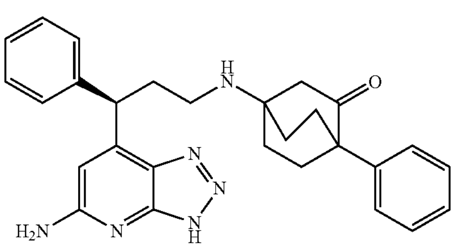 [SMILES: Nc1cc([C@H](CCNC23CCC(c4ccccc4)(CC2)C(=O)C3)c2ccccc2)c2nn[nH]c2n1] | 4-{[(3R)-3-{5-amino-3H-[1,2,3]triazolo[4,5-b]pyridin-7-yl}-3-phenylpropyl]amino}-1-phenylbicyclo[2.2.2]octan-2-one | 467.3 | (500 MHz, CD₃OD) δ 7.53 (d, J = 7.6 Hz, 2H), 7.41 (t, J = 7.6 Hz, 2H), 7.36-7.29 (m, 3H), 7.27-7.15 (m, 3H), 6.68 (br. s., 1H), 4.65 (t, J = 7.5 Hz, 1H), 3.16 (td, J = 11.4, 5.0 Hz, 1H), 3.03 (td, J = 11.2, 4.7 Hz, 1H), 2.87 (td, J = 11.6, 5.8 Hz, 1H), 2.74 (s, 2H), 2.44-2.26 (m, 2H), 2.24-2.10 (m, 4H), 2.05 (d, J = 4.6 Hz, 3H) | 1.15[c] |
| 183 | 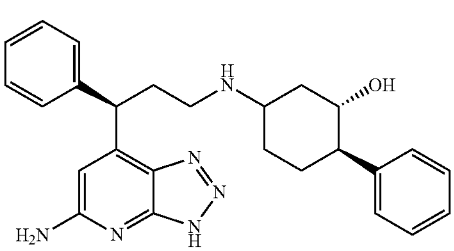 [SMILES: Nc1cc([C@H](CCNC2CC[C@H](c3ccccc3)[C@@H](O)C2)c2ccccc2)c2nn[nH]c2n1] | (1S,2R)-5-{[(3R)-3-{5-amino-3H-[1,2,3]triazolo[4,5-b]pyridin-7-yl}-3-phenylpropyl]amino}-2-phenylcyclohexan-1-ol | 443.3 | (500 MHz, CD₃OD) δ 7.59-7.48 (m, 2H), 7.42-7.18 (m, 8H), 6.49 (br. s., 1H), 4.59 (t, J = 7.8 Hz, 1H), 4.19-4.10 (m, 1H), 3.65-3.57 (m, 1H), 3.18-2.98 (m, 2H), 2.92-2.80 (m, 1H), 2.72 (m., 2H), 2.14-1.80 (m, 7H) | 1.06[c] |

| Ex. No. | Structure | Name | MS (ESI) (M + H) | ¹H NMR | LC RT[a] (min) |
|---|---|---|---|---|---|
| 184 | 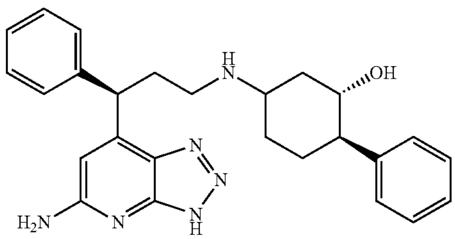 [SMILES: Nc1cc([C@H](CCNC2CC[C@H](c3ccccc3)[C@@H](O)C2)c2ccccc2)c2nn[nH]c2n1] | (1S,2R)-5-{[(3R)-3-{5-amino-3H-[1,2,3]triazolo[4,5-b]pyridin-7-yl}-3-phenylpropyl]amino}-2-phenylcyclohexan-1-ol | 443.3 | (500 MHz, CD$_3$OD) δ 7.53 (d, J = 7.6 Hz, 2H), 7.40 (t, J = 7.6 Hz, 2H), 7.34-7.27 (m, 3H), 7.27-7.18 (m, 3H), 6.51 (s, 1H), 4.60 (t, J = 7.8 Hz, 1H), 3.78 (td, J = 10.4, 4.0 Hz, 1H), 3.19-3.00 (m, 2H), 2.96-2.78 (m, 1H), 2.72-2.59 (m, 2H), 2.51-2.35 (m, 2H), 2.10 (d, J = 11.9 Hz, 1H), 1.92 (dd, J = 14.0, 3.4 Hz, 1H), 1.71-1.40 (m, 3H) | 1.13[c] |
| 185 | 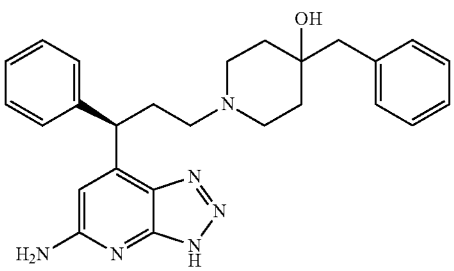 [SMILES: Nc1cc([C@H](CCN2CCC(O)(Cc3ccccc3)CC2)c2ccccc2)c2nn[nH]c2n1] | 1-[(3R)-3-{5-amino-3H-[1,2,3]triazolo[4,5-b]pyridin-7-yl}-3-phenylpropyl]-4-benzylpiperidin-4-ol | 443.3 | (500 MHz, CD$_3$OD) δ 8.23 (d, J = 7.6 Hz, 2H), 8.12-7.94 (m, 8H), 7.33 (br. s., 2H), 7.25 (s, 1H), 5.29-5.14 (m, 1H), 3.45 (s, 1H), 3.35-3.21 (m, 3H), 3.09-2.95 (m, 4H), 2.26 (br. s., 2H), 2.14 (d, J = 12.5 Hz, 2H) | 1.08[c] |
| 186 | 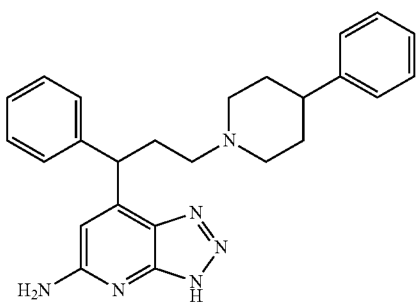 [SMILES: Nc1cc(C(CCN2CCC(c3ccccc3)CC2)c2ccccc2)c2nn[nH]c2n1] | 7-[1-phenyl-3-(4-phenylpiperidin-1-yl)propyl]-3H-[1,2,3]triazolo[4,5-b]pyridin-5-amine | 413.3 | (500 MHz, CD$_3$OD) δ 7.51 (d, J = 7.7 Hz, 2H), 7.38-7.21 (m, 7H), 7.21-7.16 (m, 1H), 6.57 (s, 1H), 4.54 (t, J = 7.6 Hz, 1H), 3.25 (t, J = 12.1 Hz, 2H), 2.79-2.70 (m, 1H), 2.69-2.50 (m, 4H), 2.41 (t, J = 11.7 Hz, 2H), 1.97-1.77 (m, 4H) | 1.16[c] |
| 187 | 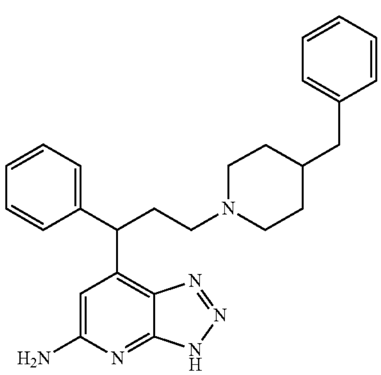 [SMILES: Nc1cc(C(CCN2CCC(Cc3ccccc3)CC2)c2ccccc2)c2nn[nH]c2n1] | 7-[3-(4-benzylpiperidin-1-yl)-1-phenylpropyl]-3H-[1,2,3]triazolo[4,5-b]pyridin-5-amine | 427.2 | (500 MHz, CD$_3$OD) δ 7.49 (d, J = 7.4 Hz, 2H), 7.36 (t, J = 7.6 Hz, 2H), 7.31-7.23 (m, 3H), 7.21-7.11 (m, 3H), 6.62 (s, 1H), 4.51 (t, J = 7.8 Hz, 1H), 3.56 (t, J = 10.6 Hz, 2H), 3.20-2.81 (m, 4H), 2.74-2.63 (m, 1H), 2.60 (d, J = 6.6 Hz, 2H), 1.95-1.78 (m, 3H), 1.47 (d, J = 13.2 Hz, 2H) | 1.29[c] |
| 188 | 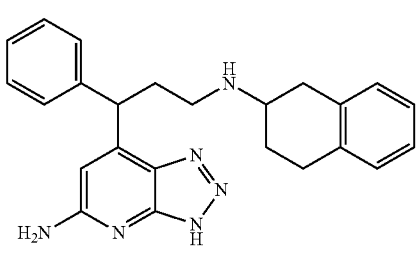 [SMILES: Nc1cc(C(CCNC2CCc3ccccc3C2)c2ccccc2)c2nn[nH]c2n1] | 7-{1-phenyl-3-[(1,2,3,4-tetrahydronaphthalen-2-yl)amino]propyl}-3H-[1,2,3]triazolo[4,5-b]pyridin-5-amine | 399.2 | (500 MHz, DMSO-d$_6$) δ 7.50 (d, J = 7.6 Hz, 2H), 7.41-7.21 (m, 3H), 7.16-6.96 (m, J = 11.9, 3.7 Hz, 4H), 6.45 (br. s., 1H), 4.50 (t, 1H), 3.16-2.91 (m, 3H), 2.76 (m, 4H), 2.20-2.05 (m, 2H), 1.75-1.54 (m, 2H). | 1.17[c] |

-continued

| Ex. No. | Structure | Name | MS (ESI) (M + H) | ¹H NMR | LC RT[a] (min) |
|---|---|---|---|---|---|
| 189 | 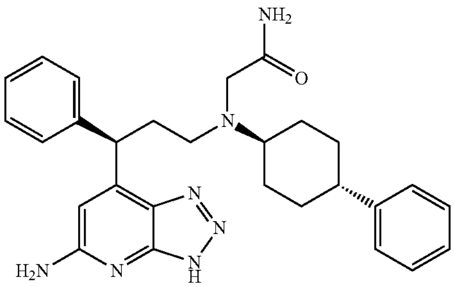 [SMILES: NC(=O)CN(CC[C@H](c1ccccc1)c1cc(N)nc2[nH]nnc12)[C@H]1CC[C@H](c2ccccc2)CC1] | 2-{[(3R)-3-{5-amino-3H-[1,2,3]triazolo[4,5-b]pyridin-7-yl}-3-phenylpropyl][(trans)-4-phenylcyclohexyl]amino}acetamide | 484.2 | (500 MHz, CD₃OD) δ 7.41 (d, J = 7.6 Hz, 2H), 7.32-7.13 (m, 5H), 7.13-7.03 (m, 3H), 6.50 (br. s., 1H), 4.43 (t, J = 7.5 Hz, 1H), 3.91 (br. s., 2H), 3.38 (br. s., 1H), 3.13 (td, J = 12.1, 5.2 Hz, 1H), 2.85 (br. s., 1H), 2.67-2.57 (m, 1H), 2.50-2.40 (m, 2H), 1.97 (br. s., 2H), 1.89 (br. s., 2H), 1.52 (br. s., 4H). | 1.29[c] |
| 191 | 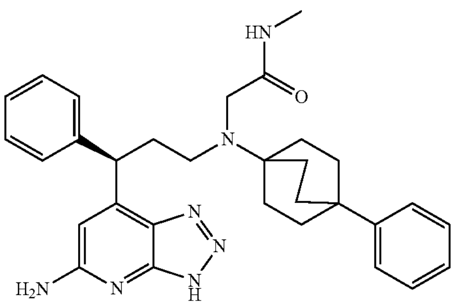 [SMILES: CNC(=O)CN(CC[C@H](c1ccccc1)c1cc(N)nc2[nH]nnc12)C12CCC(c3ccccc3)(CC1)CC2] | 2-{[(3R)-3-{5-amino-3H-[1,2,3]triazolo[4,5-b]pyridin-7-yl}-3-phenylpropyl]({4-phenylbicyclo[2.2.2]octan-1-yl})amino}-N-methylacetamide | 524 | (500 MHz, CD₃OD) δ 7.35 (d, J = 7.7 Hz, 2H), 7.20 (t, J = 7.7 Hz, 2H), 7.15-7.06 (m, 5H), 7.02-6.95 (m, 1H), 6.44 (s, 1H), 4.53 (t, J = 7.2 Hz, 1H), 3.27-3.10 (m, 4H), 2.67 (s, 3H), 2.42-2.28 (m, 1H), 2.23-2.10 (m, 1H), 1.80-1.64 (m, 6H), 1.54 (br. s., 6H) | 1.39[c] |
| 192 | 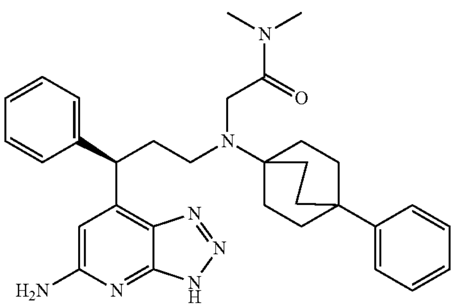 [SMILES: CN(C)C(=O)CN(CC[C@H](c1ccccc1)c1cc(N)nc2[nH]nnc12)C12CCC(c3ccccc3)(CC1)CC2] | 2-{[(3R)-3-{5-amino-3H-[1,2,3]triazolo[4,5-b]pyridin-7-yl}-3-phenylpropyl]({4-phenylbicyclo[2.2.2]octan-1-yl})amino}-N,N-dimethylacetamide | 538.1 | (500 MHz, CD₃OD) δ 7.34 (d, J = 7.7 Hz, 2H), 7.20 (t, J = 7.6 Hz, 2H), 7.17-7.07 (m, 5H), 7.02-6.95 (m, 1H), 6.43 (s, 1H), 4.41 (t, J = 7.7 Hz, 1H), 3.49 (br. s., 2H), 3.04 (s, 3H), 2.80 (s, 3H), 2.63 (br.s., 2H), 2.41 (d, J = 8.5 Hz, 1H), 2.27-2.15 (m, 1H), 1.78-1.69 (m, 6H), 1.62 (d, J = 8.0 Hz, 6H). | 1.51[c] |
| 193 | 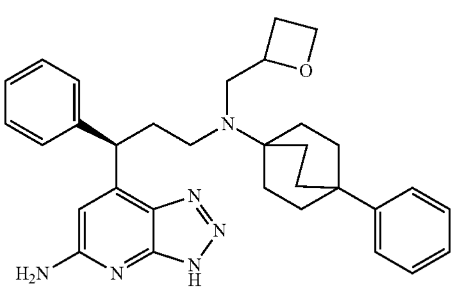 [SMILES: Nc1cc([C@H](CCN(CC2CCO2)C23CCC(c4ccccc4)(CC2)CC3)c2ccccc2)c2nn[nH]c2n1] | 7-[(1R)-3-{[(oxetan-2-yl)methyl]({4-phenylbicyclo[2.2.2]octan-1-yl})amino}-1-phenylpropyl]-3H-[1,2,3]triazolo[4,5-b]pyridin-5-amine | 523.2 | (500 MHz, CD₃OD) δ 7.37 (d, J = 7.7 Hz, 2H), 7.25-7.07 (m, 7H), 7.03-6.96 (m, 1H), 6.47 (s, 1H), 4.57-4.46 (m, 1H), 4.40-4.30 (m, 2H), 3.01 (dd, J = 14.3, 7.4 Hz, 1H), 2.83 (dd, J = 14.3, 3.9 Hz, 1H), 2.72-2.59 (m, 2H), 2.34-2.21 (m, 1H), 1.83 (s, 1H), 1.80-1.71 (m, 7H), 1.68-1.55 (m, 6H) | 1.41[c] |
| 195 | 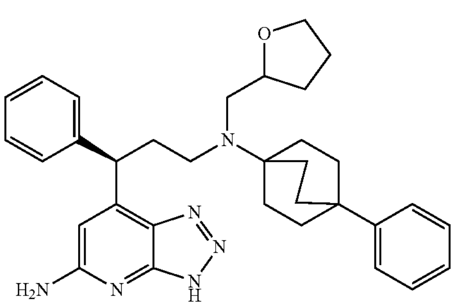 [SMILES: Nc1cc([C@H](CCN(CC2CCCO2)C23CCC(c4ccccc4)(CC2)CC3)c2ccccc2)c2nn[nH]c2n1] | 7-[(1R)-3-{[(oxolan-2-yl)methyl]({4-phenylbicyclo[2.2.2]octan-1-yl})amino}-1-phenylpropyl]-3H-[1,2,3]triazolo[4,5-b]pyridin-5-amine | 537.2 | (500 MHz, CD₃OD) δ 8.24 (d, J = 6.4 Hz, 2H), 8.08 (br. s., 2H), 8.02-7.91 (m, 5H), 7.89-7.78 (m, 1H), 7.27 (br. s., 1H), 5.20 (br. s., 1H), 4.92-4.08 (m, 5H), 3.93-3.57 (m, 3H), 2.71 (br. s., 14H), 2.28 (br. s., 1H) | 1.56[c] |

| Ex. No. | Structure | Name | MS (ESI) (M + H) | ¹H NMR | LC RT[a] (min) |
|---|---|---|---|---|---|
| 196 | 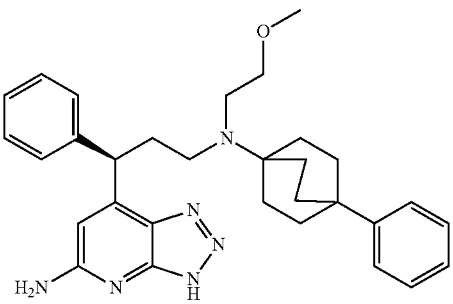 [SMILES: COCCN(CC[C@H](c1ccccc1)c1cc(N)nc2[nH]nnc12)C12CCC(c3ccccc3)(CC1)CC2] | 7-[(1R)-3-[(2-methoxyethyl)({4-phenylbicyclo[2.2.2]octan-1-yl})amino]-1-phenylpropyl]-3H-[1,2,3]triazolo[4,5-b]pyridin-5-amine | 511.1 | (500 MHz, CD³OD) δ 7.44 (d, J = 7.4 Hz, 2H), 7.33-7.26 (m, 2H), 7.24-7.13 (m, 5H), 7.05 (br. s., 1H), 6.63 (s, 1H), 4.44 (br. s., 1H), 3.71-3.42 (m, 2H), 3.31 (s, 2H), 3.26 (s, 2H), 3.22-3.15 (m, 3H), 3.14-3.03 (m, 1H), 2.84-2.68 (m, 1H), 2.08-1.80 (m, 12H) | 1.61[c] |
| 197 | 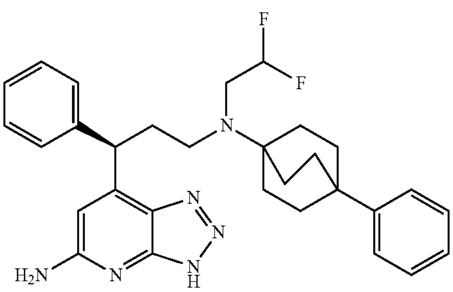 [SMILES: Nc1cc([C@H](CCN(CC(F)F)C23CCC(c4ccccc4)(CC2)CC3)c2ccccc2)c2nn[nH]c2n1] | 7-[(1R)-3-[(2,2-difluoroethyl)({4-phenylbicyclo[2.2.2]octan-1-yl})amino]-1-phenylpropyl]-3H-[1,2,3]triazolo[4,5-b]pyridin-5-amine | 517.1 | (500 MHz, CD₃OD) δ 7.36 (d, J = 7.4 Hz, 2H), 7.24-7.06 (m, 7H), 6.99 (s, 1H), 6.50 (s, 1H), 5.82-5.49 (m, 1H), 4.44 (t, J = 7.7 Hz, 1H), 3.41-3.30 (m, 2H), 2.96-2.78 (m, 2H), 2.39 (dd, J = 14.9, 6.3 Hz, 1H), 2.28-2.18 (m, 1H), 1.78-1.68 (m, 5H), 1.58-1.45 (m, 7H) | 1.49[c] |
| 198 | 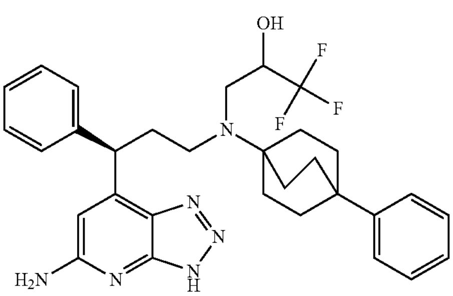 [SMILES: Nc1cc([C@H](CCN(CC(O)C(F)(F)F)C23CCC(c4ccccc4)(CC2)CC3)c2ccccc2)c2nn[nH]c2n1] | 3-{[(3R)-3-{5-amino-3H-[1,2,3]triazolo[4,5-b]pyridin-7-yl}-3-phenylpropyl]({4-phenylbicyclo[2.2.2]octan-1-yl})amino}-1,1,1-trifluoropropan-2-ol | 565.1 | (500 MHz, CD₃OD) δ 7.37 (d, J = 7.4 Hz, 2H), 7.25-7.07 (m, 7H), 7.04-6.95 (m, 1H), 6.46 (s, 1H), 4.40 (t, J = 7.7 Hz, 1H), 3.77 (br. s., 1H), 2.81 (dd, J = 14.2, 2.6 Hz, 1H), 2.65 (dd, J = 14.2, 9.5 Hz, 1H), 2.58 (br. s., 2H), 2.48-2.22 (m, 2H), 1.80-1.69 (m, 6H), 1.59 (d, J = 11.0 Hz, 6H) | 1.61[c] |
| 199 | 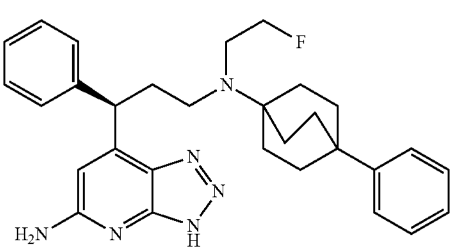 [SMILES: Nc1cc([C@H](CCN(CCF)C23CCC(c4ccccc4)(CC2)CC3)c2ccccc2)c2nn[nH]c2n1] | 7-[(1R)-3-[(2-fluoroethyl)({4-phenylbicyclo[2.2.2]octan-1-yl})amino]-1-phenylpropyl]-3H-[1,2,3]triazolo[4,5-b]pyridin-5-amine | 499.1 | (500 MHz, CD₃OD) δ 7.44 (d, J = 7.4 Hz, 2H), 7.30 (t, J = 7.6 Hz, 2H), 7.24-7.12 (m, 5H), 7.09-7.00 (m, 1H), 6.64 (br. s., 1H), 4.63 (m, 1H), 4.46 (m, 1H), 3.94-3.58 (m, 1H), 3.35 (m, 1H), 3.06-2.91 (m, 2H), 2.66 (br. s., 1H), 2.03-1.80 (m, 14H) | 1.44[c] |
| 200 | 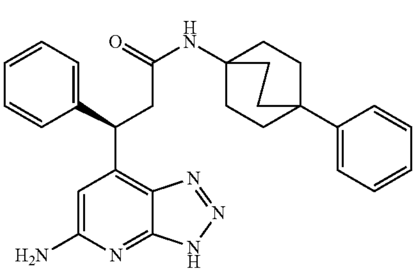 [SMILES: Nc1cc([C@H](CC(=O)NC23CCC(c4ccccc4)(CC2)CC3)c2ccccc2)c2nn[nH]c2n1] | (3R)-3-{5-amino-3H-[1,2,3]triazolo[4,5-b]pyridin-7-yl}-3-phenyl-N-{4-phenylbicyclo[2.2.2]octan-1-yl}propanamide | 467.3 | (500 MHz, DMSO-d₆) δ 7.52-7.38 (m, 3H), 7.33-7.02 (m, 7H), 6.45 (s, 1H), 4.84 (t, J = 7.9 Hz, 1H), 3.55 (d, J = 6.1 Hz, 1H), 3.02 (d, J = 7.6 Hz, 2H), 1.75 (s, 12H). | 1.68[c] |

| Ex. No. | Structure | Name | MS (ESI) (M + H) | ¹H NMR | LC RT$^a$ (min) |
|---|---|---|---|---|---|
| 201 | 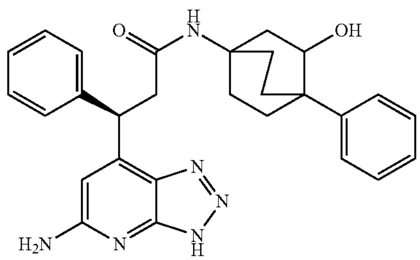 [SMILES: Nc1cc([C@H](CC(=O)NC23CCC(c4ccccc4)(CC2)C(O)C3)c2ccccc2)c2nn[nH]c2n1] | (3R)-3-{5-amino-3H-[1,2,3]triazolo[4,5-b]pyridin-7-yl}-N-{3-hydroxy-4-phenylbicyclo[2.2.2]octan-1-yl}-3-phenylpropanamide | 483.3 | (500 MHz, DMSO-d$_6$) δ 7.39 (s, 1H), 7.34-7.22 (m, 5H), 7.17-7.04 (m, 3H), 6.85-6.72 (m, 2H), 6.62-6.54 (m, 1H), 6.45 (br. s., 1H), 4.76 (t, J = 7.8 Hz, 1H), 3.02-2.88 (m, 3H), 1.77 (s, 13H) | 1.36$^c$ |
| 202 | 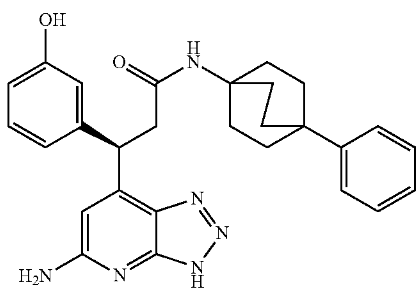 [SMILES: Nc1cc([C@H](CC(=O)NC23CCC(c4ccccc4)(CC2)CC3)c2cccc(O)c2)c2nn[nH]c2n1] | (3R)-3-{5-amino-3H-[1,2,3]triazolo[4,5-b]pyridin-7-yl}-3-(3-hydroxyphenyl)-N-{4-phenylbicyclo[2.2.2]octan-1-yl}propanamide | 483.3 | (500 MHz, DMSO-d$_6$) δ 7.34-7.22 (m, 5H), 7.15-7.02 (m, 2H), 6.88-6.74 (m, 2H), 6.64-6.52 (m, 1H), 6.49-6.28 (m, 1H), 4.76 (t, J = 7.8 Hz, 1H), 3.14-2.87 (m, 2H), 1.77 (s, 12H). | 1.57$^c$ |
| 203 | 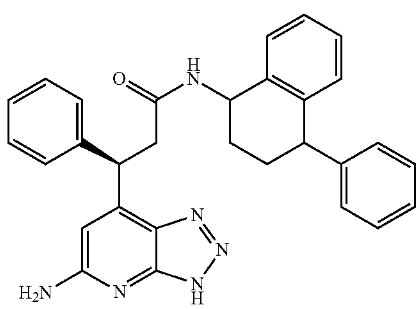 [SMILES: Nc1cc([C@H](CC(=O)NC2CCC(c3ccccc3)c3ccccc32)c2ccccc2)c2nn[nH]c2n1] | (3R)-3-{5-amino-3H-[1,2,3]triazolo[4,5-b]pyridin-7-yl}-3-phenyl-N-(4-phenyl-1,2,3,4-tetrahydronaphthalen-1-yl)propanamide | 489.4 | (500 MHz, DMSO-d$_6$) δ 8.29 (m, 1H), 7.47 (m, 2H), 7.33-7.23 (m, 4H), 7.19 (m, 2H), 7.09-6.94 (m, 4H), 6.64 (m, 1H), 6.68 (m, 1H), 6.55 (br. s., 2H), 6.43 (br. s., 1H), 5.03-4.88 (m, 2H), 4.06 (t, J = 6.7 Hz, 1H), 3.09 (m, 1H), 2.06 (m, 1H), 1.80-1.64 (m, 2H), 1.57-1.40 (m, 1H) | 1.69$^c$ |
| 205 | 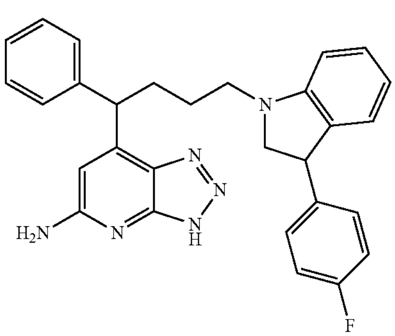 [SMILES: Nc1cc(C(CCCN2CC(c3ccc(F)cc3)c3ccccc32)c2ccccc2)c2nn[nH]c2n1] | 7-{4-[3-(4-fluorophenyl)-2,3-dihydro-1H-indol-1-yl]-1-phenylbutyl}-3H-[1,2,3]triazolo[4,5-b]pyridin-5-amine | 479.5 | (500 MHz, CD$_3$OD) δ 7.47-7.41 (m, 2H), 7.37-7.33 (m, 1H), 7.30 (t, J = 7.4 Hz, 1H), 7.28-7.18 (m, 3H), 7.04 (t, J = 7.7 Hz, 1H), 7.02-6.95 (m, 2H), 6.82-6.76 (m, 2H), 6.65-6.61 (m, 1H), 6.55 (dd, J = 8.0, 2.2 Hz, 1H), 4.57 (ddd, J = 8.9, 6.6, 2.3 Hz, 1H), 4.34 (t, J = 8.3 Hz, 1H), 3.65 (td, J = 8.9, 7.4 Hz, 1H), 3.25-3.06 (m, 3H), 2.52-2.42 (m, 1H), 2.39-2.30 (m, 1H), 1.72-1.63 (m, 2H). | 8.65 |

| Ex. No. | Structure | Name | MS (ESI) (M + H) | ¹H NMR | LC RT[a] (min) |
|---|---|---|---|---|---|
| 206 | 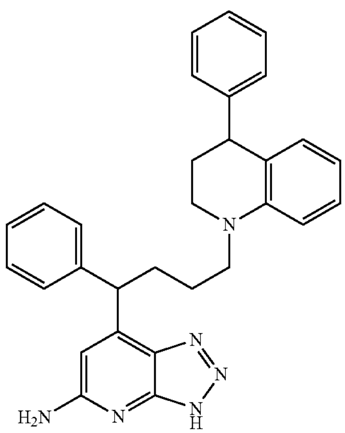 [SMILES: Nc1cc(C(CCCN2CCC(c3ccccc3)c3ccccc32)c2ccccc2)c2nn[nH]c2n1] | 7-[1-phenyl-4-(4-phenyl-1,2,3,4-tetrahydroquinolin-1-yl)butyl]-3H-[1,2,3]triazolo[4,5-b]pyridin-5-amine | 475.5 | (500 MHz, DMSO-d6) δ 7.79 (d, J = 7.6 Hz, 2H), 7.68-7.61 (m, 2H), 7.58-7.52 (m, 3H), 7.51-7.46 (m, 1H), 7.32 (d, J = 7.6 Hz, 2H), 7.24 (t, J = 7.5 Hz, 1H), 6.97 (br. s., 1H), 6.89 (d, J = 7.3 Hz, 1H), 6.82 (d, J = 8.2 Hz, 1H), 6.71 (t, J = 7.3 Hz, 1H), 4.82-4.75 (m, 1H), 4.37 (t, J = 5.2 Hz, 1H), 3.73-3.64 (m, 1H), 3.64-3.55 (m, 1H), 3.50-3.42 (m, 1H), 3.38-3.29 (m, 1H), 2.72-2.62 (m, 1H), 2.56-2.47 (m, 1H), 2.40-2.32 (m, 1H), 2.28-2.20 (m, 1H), 1.89-1.77 (m, 2H). | 2.22[d] |
| 207 | 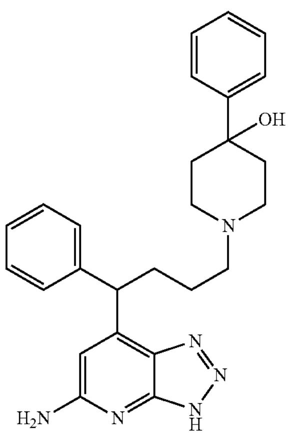 [SMILES: Nc1cc(C(CCCN2CCC(O)(c3ccccc3)CC2)c2ccccc2)c2nn[nH]c2n1] | 1-(4-{5-amino-3H-[1,2,3]triazolo[4,5-b]pyridin-7-yl}-4-phenylbutyl)-4-phenylpiperidin-4-ol | 443.5 | (500 MHz, DMSO-d6) δ 7.48 (d, J = 7.6 Hz, 2H), 7.44-7.40 (m, 2H), 7.34 (dt, J = 14.5, 7.4 Hz, 4H), 7.24 (dt, J = 15.1, 7.4 Hz, 2H), 6.52 (br. s., 1H), 4.42 (t, J = 7.8 Hz, 1H), 3.36 (d, J = 9.8 Hz, 2H), 3.24-3.13 (m, 4H), 2.43-2.34 (m, 1H), 2.27-2.19 (m, 1H), 2.17-2.08 (m, 2H), 1.82-1.75 (m, 2H), 1.65 (d, J = 7.3 Hz, 2H). | 1.06[d] |
| 208 | 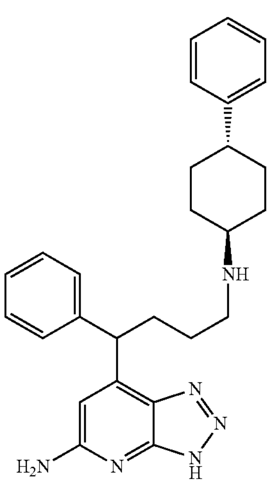 [SMILES: Nc1cc(C(CCCN[C@H]2CC[C@H](c3ccccc3)CC2)c2ccccc2)c2nn[nH]c2n1] | 7-(1-phenyl-4-{[(trans)-4-phenylcyclohexyl]amino}butyl)-3H-[1,2,3]triazolo[4,5-b]pyridin-5-amine | 441.3 | (500 MHz, CD3OD) δ 7.49 (d, J = 7.4 Hz, 2H), 7.37 (t, J = 7.7 Hz, 2H), 7.30-7.25 (m, 4H), 7.22-7.15 (m, 4H), 6.66 (s, 1H), 4.58-4.53 (m, 1H), 3.12 (t, J = 7.8 Hz, 3H), 2.58-2.46 (m, 2H), 2.40-2.31 (m, 1H), 2.20 (d, J = 8.8 Hz, 2H), 1.99 (d, J = 13.2 Hz, 2H), 1.72 (dt, J = 15.7, 7.9 Hz, 2H), 1.65-1.43 (m, 6H). | 2.15[d] |

-continued

| Ex. No. | Structure | Name | MS (ESI) (M + H) | ¹H NMR | LC RT$^a$ (min) |
|---|---|---|---|---|---|
| 209 | 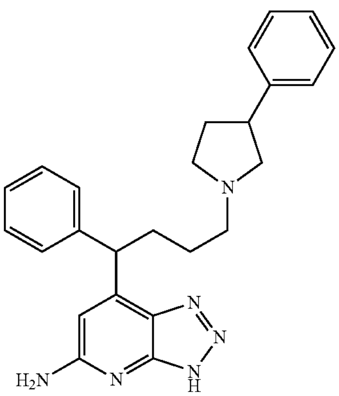 [SMILES: Nc1cc(C(CCCN2CCC(c3ccccc3)C2)c2ccccc2)c2nn[nH]c2n1] | 7-[1-phenyl-4-(3-phenylpyrrolidin-1-yl)butyl]-3H-[1,2,3]triazolo[4,5-b]pyridin-5-amine | 413.3 | (500 MHz, DMSO-d6) δ 7.47 (d, J = 7.4 Hz, 2H), 7.38-7.24 (m, 9H), 7.24-7.19 (m, 1H), 7.16 (s, 1H), 7.05 (s, 1H), 6.44 (br. s., 1H), 4.40 (t, J = 7.4 Hz, 1H), 3.88-3.80 (m, 1H), 3.73-3.34 (m, 2H), 3.27 (br. s., 2H), 3.17-2.97 (m, 1H), 2.40 (br. s., 2H), 2.28-2.17 (m, 1H), 2.12-2.00 (m, 1H), 1.96-1.84 (m, 1H), 1.61 (br. s., 2H) | 1.13$^d$ |
| 210 | 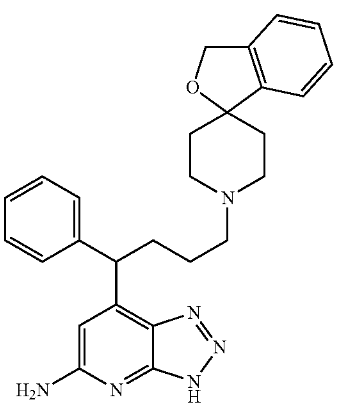 [SMILES: Nc1cc(C(CCCN2CCC3(CC2)OCc2ccccc23)c2ccccc2)c2nn[nH]c2n1] | 7-(1-phenyl-4-{3H-spiro[2-benzofuran-1,4'-piperidine]-1'-yl}butyl)-3H-[1,2,3]triazolo[4,5-b]pyridin-5-amine | 455.2 | (500 MHz, DMSO-d6) δ 7.45 (d, J = 7.4 Hz, 2H), 7.30 (t, J = 7.6 Hz, 2H), 7.26-7.16 (m, 5H), 6.55 (br. s., 2H), 6.46 (s, 1H), 4.93 (s, 2H), 4.40 (t, J = 7.7 Hz, 1H), 2.68 (br. s., 2H), 2.38 (br. s., 3H), 2.27-2.11 (m, 3H), 1.84 (br. s., 2H), 1.56 (d, J = 12.8 Hz, 2H), 1.46-1.37 (m, 2H) | 1.31$^d$ |
| 211 | 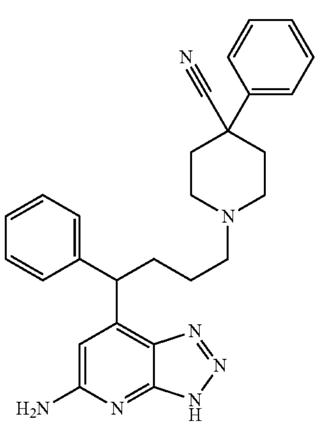 [SMILES: N#CC1(c2ccccc2)CCN(CCCC(c2ccccc2)c2cc(N)nc3[nH]nnc23)CC1] | 1-(4-{5-amino-3H-[1,2,3]triazolo[4,5-b]pyridin-7-yl}-4-phenylbutyl)-4-phenylpiperidine-4-carbonitrile | 452.1 | (500 MHz, DMSO-d6) δ 7.53-7.48 (m, 2H), 7.47-7.39 (m, 5H), 7.36 (d, J = 7.1 Hz, 1H), 7.30 (t, J = 7.6 Hz, 2H), 7.21-7.16 (m, 1H), 6.55 (br. s., 2H), 6.46 (br. s., 1H), 4.40 (t, J = 7.7 Hz, 1H), 3.02-2.89 (m, 2H), 2.39-2.30 (m, 2H), 2.30-2.21 (m, 1H), 2.20-2.13 (m, 1H), 2.08 (d, J = 12.1 Hz, 2H), 1.98 (br. s., 2H), 1.48-1.38 (m, 2H) | 1.18$^d$ |

| Ex. No. | Structure | Name | MS (ESI) (M + H) | ¹H NMR | LC RT[a] (min) |
|---|---|---|---|---|---|
| 212 | 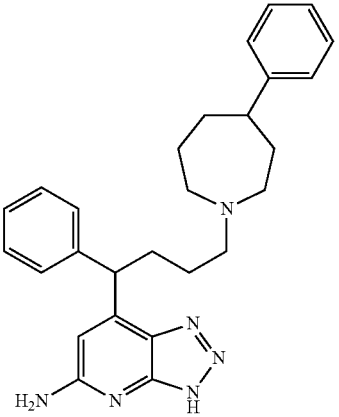 [SMILES: Nc1cc(C(CCCN2CCCC(c3ccccc3)CC2)c2ccccc2)c2nn[nH]c2n1] | 7-[1-phenyl-4-(4-phenylazepan-1-yl)butyl]-3H-[1,2,3]triazolo[4,5-b]pyridin-5-amine | 441.1 | (500 MHz, DMSO-d6) δ 7.45 (d, J = 7.4 Hz, 2H), 7.30 (t, J = 7.2 Hz, 2H), 7.26-7.22 (m, 2H), 7.21-7.10 (m, 4H), 6.52 (s, 2H), 6.46 (s, 1H), 4.40 (t, J = 7.7 Hz, 1H), 2.72 (d, J = 4.7 Hz, 1H), 2.65 (d, J = 4.7 Hz, 1H), 2.62-2.52 (m, 3H), 2.31 (d, J = 7.2 Hz, 1H), 2.18 (br. s., 1H), 1.78-1.64 (m, 6H), 1.58 (d, J = 5.5 Hz, 1H), 1.38 (quin, J = 7.3 Hz, 2H) | 1.33[d] |
| 213 | 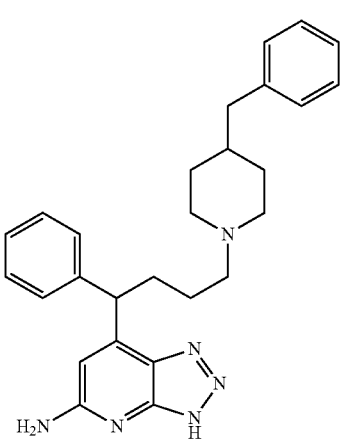 [SMILES: Nc1cc(C(CCCN2CCC(Cc3ccccc3)CC2)c2ccccc2)c2nn[nH]c2n1] | 7-[4-(4-benzylpiperidin-1-yl)-1-phenylbutyl]-3H-[1,2,3]triazolo[4,5-b]pyridin-5-amine | 441.5 | (500 MHz, DMSO-d6) δ 7.48-7.42 (m, 2H), 7.34-7.24 (m, 5H), 7.23-7.12 (m, 5H), 6.46 (br. s, 1H), 4.37 (t, J = 7.8 Hz, 1H), 3.53-3.42 (m, 2H), 3.40-3.31 (m, 2H), 3.04 (br. s., 2H), 2.81-2.71 (m, 2H), 2.34 (dd, J = 13.6, 7.2 Hz, 1H), 2.22-2.11 (m, 1H), 1.77-1.66 (m, 3H), 1.61-1.53 (m, 2H), 1.36-1.25 (m, 2H). | 1.35[d] |
| 214 | 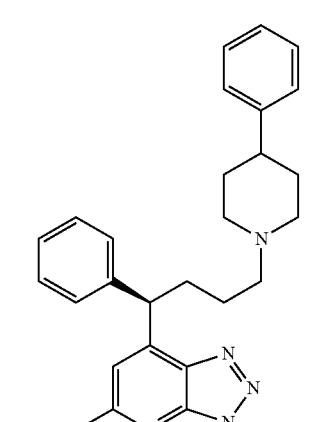 | 7-[(1R)-1-phenyl-4-(4-phenylpiperidin-1-yl)butyl]-3H-[1,2,3]triazolo[4,5-b]pyridin-5-amine | 427.1 | (500 MHz, CD2Cl2) δ 9.96 (br. s., 1H), 8.04 (br. s., 2H), 7.37-7.32 (m, 2H), 7.30-7.25 (m, 4H), 7.24-7.17 (m, 3H), 7.16-7.13 (m, 2H), 6.87 (s, 1H), 4.43 (t, J = 7.7 Hz, 1H), 3.87 (d, J = 11.6 Hz, 1H), 3.76 (d, J = 11.6 Hz, 1H), 3.28-3.15 (m, 2H), 2.89-2.80 (m, 2H), 2.80-2.70 (m, 1H), 2.55-2.44 (m, 1H), 2.27-2.14 (m, 1H), 2.13-2.00 (m, 4H), 2.00-1.84 (m, 2H). | 5.99 |

-continued

| Ex. No. | Structure | Name | MS (ESI) (M + H) | ¹H NMR | LC RT$^a$ (min) |
|---|---|---|---|---|---|
| 215 | 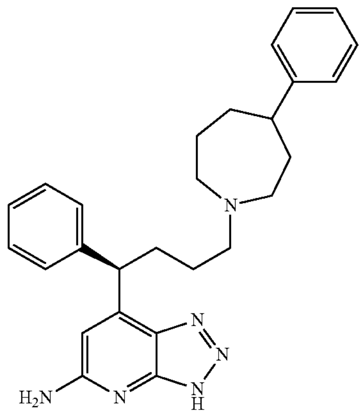 [SMILES: Nc1cc([C@H](CCCN2CCCC(c3ccccc3)CC2)c2ccccc2)c2nn[nH]c2n1] | 7-[(1R)-1-phenyl-4-(4-phenylazepan-1-yl)butyl]-3H-[1,2,3]triazolo[4,5-b]pyridin-5-amine | 441.1 | (500 MHz, CD$_2$Cl$_2$) δ 10.20 (d, J = 17.9 Hz, 1H), 8.44 (br. s., 2H), 7.36-7.32 (m, 2H), 7.31-7.10 (m, 9H), 6.87 (d, J = 5.2 Hz, 1H), 4.46-4.39 (m, 1H), 3.83-3.57 (m, 2H), 3.39-3.16 (m, 3H), 3.08-2.92 (m, 1H), 2.89-2.71 (m, 1H), 2.52-2.43 (m, 1H), 2.26-1.57 (m, 9H). | 6.35 |
| 216 | 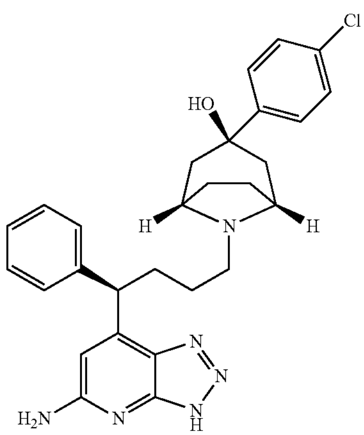 [SMILES: Nc1cc([C@H](CCCN2[C@@H]3CC[C@H]2C[C@](O)(c2ccc(Cl)cc2)C3)c2ccccc2)c2nn[nH]c2n1] | (1R,3R,5S)-8-[(4R)-4-{5-amino-3H-[1,2,3]triazolo[4,5-b]pyridin-7-yl}-4-phenylbutyl]-3-(4-chlorophenyl)-8-azabicyclo[3.2.1]octan-3-ol | 503.2 | (500 MHz, DMSO-d6) δ 7.48 (dd, J = 12.4, 8.1 Hz, 4H), 7.37 (d, J = 8.5 Hz, 2H), 7.31 (t, J = 7.5 Hz, 2H), 7.23-7.18 (m, 1H), 6.54 (br. s., 2H), 6.47 (s, 1H), 4.40 (t, J = 7.8 Hz, 1H), 3.01-2.88 (m, 2H), 2.39 (br. s., 3H), 2.26 (d, J = 14.0 Hz, 3H), 2.00 (br. s., 2H), 1.90 (d, J = 14.0 Hz, 2H), 1.61 (br. s., 2H) | 1.33$^d$ |
| 217 | 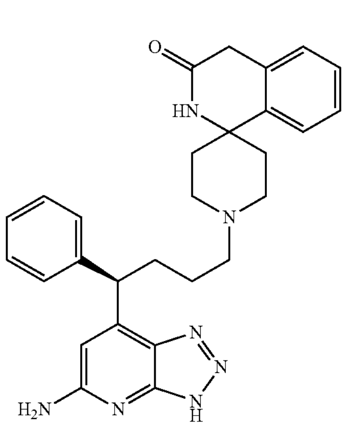 [SMILES: Nc1cc([C@H](CCCN2CCC3(CC2)NC(=O)Cc2ccccc23)c2ccccc2)c2nn[nH]c2n1] | 1'-[(4R)-4-{5-amino-3H-[1,2,3]triazolo[4,5-b]pyridin-7-yl}-4-phenylbutyl]-3,4-dihydro-2H-spiro[isoquinoline-1,4'-piperidine]-3-one | 482.3 | (500 MHz, DMSO-d6) δ 7.94 (s, 1H), 7.71 (s, 1H), 7.45 (d, J = 7.3 Hz, 2H), 7.40 (d, J = 7.0 Hz, 1H), 7.30 (t, J = 7.5 Hz, 2H), 7.27-7.15 (m, 4H), 6.52 (br. s., 2H), 6.47 (s, 1H), 4.40 (t, J = 7.8 Hz, 1H), 2.65 (d, J = 11.3 Hz, 2H), 2.44-2.29 (m, 5H), 2.21-2.11 (m, 1H), 1.99 (d, J = 12.5 Hz, 2H), 1.67 (d, J = 13.4 Hz, 2H), 1.41 (quin, J = 7.2 Hz, 2H) | 1.12$^d$ |

| Ex. No. | Structure | Name | MS (ESI) (M + H) | ¹H NMR | LC RT[a] (min) |
|---|---|---|---|---|---|
| 218 | 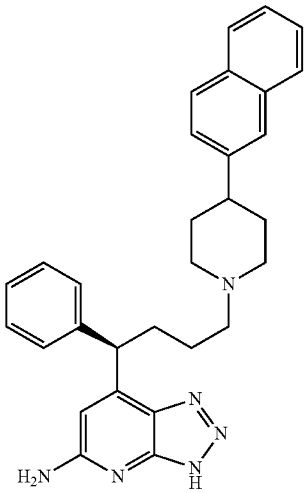 [SMILES: Nc1cc([C@H](CCCN2CCC(c3ccc4ccccc4c3)CC2)c2ccccc2)c2nn[nH]c2n1] | 7-[(1R)-4-[4-(naphthalen-2-yl)piperidin-1-yl]-1-phenylbutyl]-3H-[1,2,3]triazolo[4,5-b]pyridin-5-amine | 477.3 | (500 MHz, DMSO-d6) δ 7.83 (t, J = 8.4 Hz, 3H), 7.69 (s, 1H), 7.48-7.39 (m, 5H), 7.30 (t, J = 7.6 Hz, 2H), 7.21-7.17 (m, 1H), 6.53 (s, 2H), 6.48 (s, 1H), 4.41 (t, J = 7.8 Hz, 1H), 2.95 (d, J = 9.8 Hz, 2H), 2.63 (br. s., 1H), 2.42 (br. s., 2H), 2.37-2.30 (m, 1H), 2.18 (br. s., 1H), 2.06 (br. s., 2H), 1.84-1.66 (m, 4H), 1.43 (quin, J = 7.2 Hz, 2H) | 1.53[d] |
| 219 | 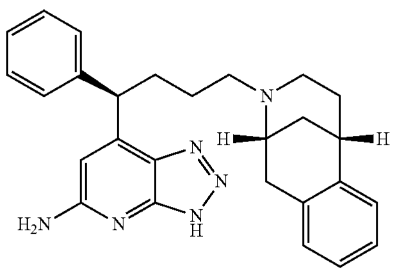 [SMILES: Nc1cc([C@H](CCCN2CC[C@H]3C[C@@H]2Cc2ccccc23)c2ccccc2)c2nn[nH]c2n1] | 7-((R)-1-phenyl-4-((2R,6S)-1,4,5,6-tetrahydro-2,6-methanobenzo[d]azocin-3(2H)-yl)butyl)-3H-[1,2,3]triazolo[4,5-b]pyridin-5-amine | 439.3 | (500 MHz, DMSO-d6) δ 7.44 (d, J = 7.3 Hz, 2H), 7.29 (t, J = 7.6 Hz, 2H), 7.21-7.16 (m, 1H), 7.08-6.99 (m, 4H), 6.52 (s, 2H), 6.46 (s, 1H), 4.40 (t, J = 7.8 Hz, 1H), 3.11 (br. s., 1H), 2.96-2.89 (m, 2H), 2.65-2.55 (m, 1H), 2.40 (br. s., 2H), 2.36-2.27 (m, 1H), 2.21-2.11 (m, 1H), 1.93 (br. s., 2H), 1.72 (br. s., 1H), 1.41-1.29 (m, 3H) | 1.18[d] |
| 220 | 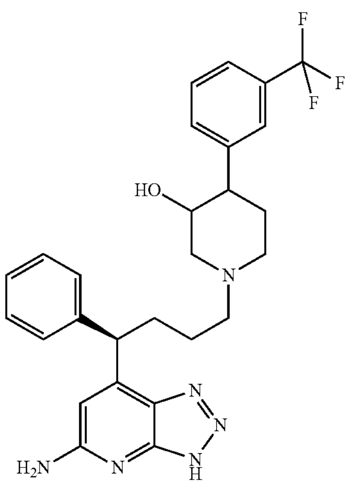 [SMILES: Nc1cc([C@H](CCCN2CCC(c3cccc(C(F)(F)F)c3)C(O)C2)c2ccccc2)c2nn[nH]c2n1] | 1-[(4R)-4-{5-amino-3H-[1,2,3]triazolo[4,5-b]pyridin-7-yl}-4-phenylbutyl]-4-[3-(trifluoromethyl)phenyl]piperidin-3-ol | 511.2 | (500 MHz, DMSO-d6) δ 7.77 (s, 1H), 7.71 (d, J = 6.7 Hz, 1H), 7.58-7.52 (m, 2H), 7.45 (d, J = 7.6 Hz, 2H), 7.29 (t, J = 7.5 Hz, 2H), 7.21-7.16 (m, 1H), 6.51 (br. s., 2H), 6.48 (s, 1H), 4.40 (t, J = 7.8 Hz, 1H), 3.58-3.51 (m, 3H), 2.70 (br. s., 1H), 2.47-2.39 (m, 2H), 2.38-2.28 (m, 1H), 2.21-2.12 (m, 1H), 1.95 (br. s., 2H), 1.57 (d, J = 13.1 Hz, 2H), 1.44 (br. s., 2H) | 1.36[d] |
| 221 | 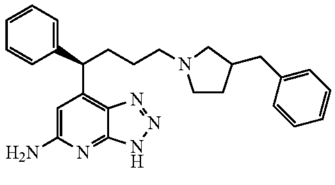 [SMILES: Nc1cc([C@H](CCCN2CCC(Cc3ccccc3)C2)c2ccccc2)c2nn[nH]c2n1] | 7-[(1R)-4-(3-benzylpyrrolidin-1-yl)-1-phenylbutyl]-3H-[1,2,3]triazolo[4,5-b]pyridin-5-amine | 427.2 | (500 MHz, DMSO-d6) δ 7.41 (d, J = 7.9 Hz, 2H), 7.29-7.21 (m, 5H), 7.19-7.11 (m, 4H), 6.47 (d, J = 4.6 Hz, 2H), 4.35 (t, J = 7.8 Hz, 1H), 3.79-3.72 (m, 3H), 2.57 (d, J = 7.3 Hz, 6H), 2.38 (d, J = 7.6 Hz, 1H), 2.26 (d, J = 7.6 Hz, 2H), 2.14 (d, J = 8.2 Hz, 1H), 1.82-1.75 (m, 1H), 1.45-1.33 (m, 2H) | 1.24[d] |

-continued

| Ex. No. | Structure | Name | MS (ESI) (M + H) | ¹H NMR | LC RT[a] (min) |
|---|---|---|---|---|---|
| 222 | 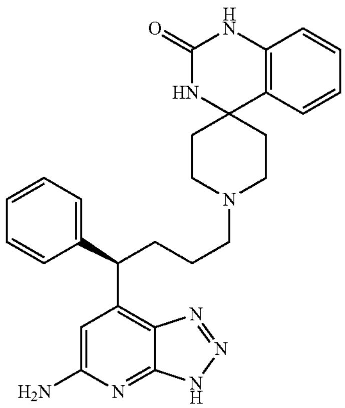 [SMILES: Nc1cc([C@H](CCCN2CCC3(CC2)NC(=O)Nc2ccccc23)c2ccccc2)c2nn[nH]c2n1] | 1-[(4R)-4-{5-amino-3H-[1,2,3]triazolo[4,5-b]pyridin-7-yl}-4-phenylbutyl]-2',3'-dihydro-1'H-spiro[piperidine-4,4'-quinazoline]-2'-one | 483.1 | (500 MHz, DMSO-d6) δ 9.15 (s, 1H), 7.44 (d, J = 7.3 Hz, 2H), 7.29 (t, J = 7.6 Hz, 2H), 7.22 (d, J = 7.6 Hz, 1H), 7.20-7.16 (m, 1H), 7.11 (t, J = 7.3 Hz, 1H), 6.88 (t, J = 7.5 Hz, 1H), 6.79 (d, J = 7.6 Hz, 1H), 6.68 (s, 1H), 6.49 (s, 2H), 6.47 (s, 1H), 4.39 (t, J = 7.8 Hz, 1H), 2.41-2.27 (m, 6H), 2.19-2.09 (m, 1H), 1.87 (d, J = 12.5 Hz, 2H), 1.63 (d, J = 13.1 Hz, 2H), 1.42-1.35 (m, 2H) | 1.09[d] |
| 228 | 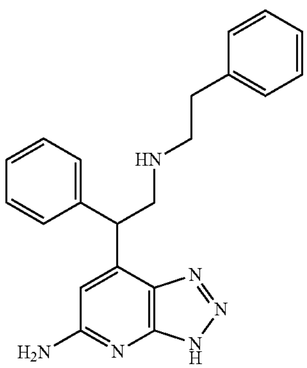 [SMILES: Nc1cc(C(CNCCc2ccccc2)c2ccccc2)c2nn[nH]c2n1] | 7-{1-phenyl-2-[(2-phenylethyl)amino]ethyl}-3H-[1,2,3]triazolo[4,5-b]pyridin-5-amine | 359.3 | (500 MHz, CD₃OD) δ 7.49 (d, J = 7.4 Hz, 2H), 7.43-7.38 (m, 2H), 7.37-7.24 (m, 4H), 7.20 (d, J = 7.2 Hz, 2H), 6.51 (s, 1H), 4.80 (t, J = 7.4 Hz, 1H), 4.20 (dd, J = 12.7, 7.7 Hz, 1H), 3.90 (dd, J = 12.7, 7.2 Hz, 1H), 3.32-3.26 (m, 2H), 3.03-2.98 (m, 2H) | 1.07[c] |
| 236 | 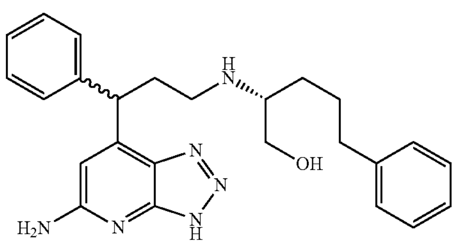 [SMILES: Nc1cc(C(CCN[C@@H](CO)CCCc2ccccc2)c2ccccc2)c2nn[nH]c2n1] | (2R)-2-[(3-{5-amino-3H-[1,2,3]triazolo[4,5-b]pyridin-7-yl}-3-phenylpropyl)amino]-5-phenylpentan-1-ol | 431.3 | (500 MHz, CD₃OD) δ 7.47 (d, J = 8.0 Hz, 2H), 7.35 (t, J = 7.7 Hz, 2H), 7.28-7.17 (m, 3H), 7.14 (d, J = 6.9 Hz, 3H), 6.44 (d, J = 1.4 Hz, 1H), 4.58-4.48 (m, 1H), 3.78-3.65 (m, 1H), 3.59-3.52 (m, 2H), 3.35 (s, 2H), 3.16 (s, 1H), 3.02 (br. s, 1H), 2.91 (d, J = 6.6 Hz, 2H), 2.74 (br. s, 1H), 2.65-2.48 (m, 1H), 1.80-1.49 (m, 2H), | 1.18[c] |
| 242 | 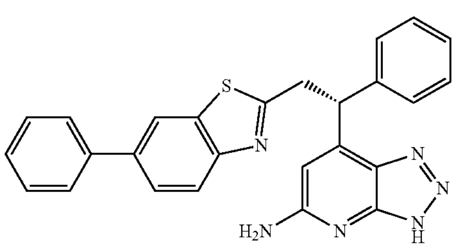 [SMILES: Nc1cc([C@H](Cc2nc3ccc(-c4ccccc4)cc3s2)c2ccccc2)c2nn[nH]c2n1] | (R)-7-(1-phenyl-2-(6-phenylbenzo[d]thiazol-2-yl)ethyl)-3H-[1,2,3]triazolo[4,5-b]pyridin-5-amine | 449.0 | (500 MHz, DMSO-d₆) δ 8.26 (s, 1H), 7.94 (s, 1H), 7.73 (d, J = 8.2 Hz, 1H), 7.68 (d, J = 7.6 Hz, 2H), 7.57 (d, J = 7.6 Hz, 2H), 7.46 (t, J = 7.5 Hz, 2H), 7.39-7.34 (m, 1H), 7.31 (t, J = 7.5 Hz, 2H), 7.26-7.01 (m, 2H), 6.61 (br. s., 1H), 5.07 (t, J = 7.9 Hz, 1H), 4.31 (dd, J = 15.1, 8.1 Hz, 1H), 4.07 (dd, J = 15.1, 7.8 Hz, 1H). | 2.04[d] |
| 243 | 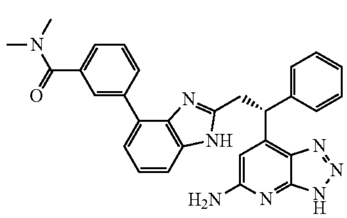 [SMILES: CN(C)C(=O)c1cccc(-c2cccc3[nH]c(C[C@H](c4ccccc4)c4cc(N)nc5[nH]nnc45)nc23)c1] | (R)-3-(2-(2-(5-amino-3H-[1,2,3]triazolo[4,5-b]pyridin-7-yl)-2-phenylethyl)-1H-benzo[d]imidazol-4-yl)-N,N-dimethylbenzamide | 503.1 | (500 MHz, DMSO-d₆) δ 8.01 (br. s, 2H), 7.54 (m, 3H), 7.41 (m, 2H), 7.31 (m, 1H), 7.26 (m, 2H), 7.22-7.09 (m, 2H), 6.56 (s, 1H), 6.52 (br. s., 2H), 5.22 (t, J = 7.9 Hz, 1H), 4.01-3.82 (m, 2H), 3.06 (s, 6H) | 1.55[c] |

-continued

| Ex. No. | Structure | Name | MS (ESI) (M + H) | ¹H NMR | LC RT$^a$ (min) |
|---|---|---|---|---|---|
| 244 | 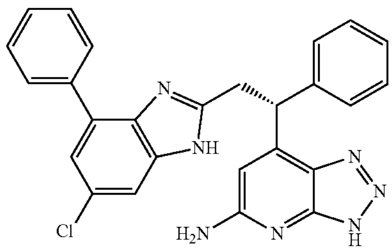 [SMILES: Nc1cc([C@H](Cc2nc3c(-c4ccccc4)cc(Cl)cc3[nH]2)c2ccccc2)c2nn[nH]c2n1] | (R)-7-(2-(6-chloro-4-phenyl-1H-benzo[d]imidazol-2-yl)-1-phenylethyl)-3H-[1,2,3]triazolo[4,5-b]pyridin-5-amine | 466.3 | (500 MHz, DMSO-d$_6$) δ 7.79 (d, J = 6.7 Hz, 2H), 7.59-7.48 (m, 3H), 7.48-7.42 (m, 1H), 7.34 (s, 1H), 7.32-7.24 (m, 3H), 7.23-7.14 (m, 2H), 7.07 (s, 2H), 6.60 (s, 1H), 5.19 (t, J = 7.9 Hz, 1H), 4.06-3.90 (m, 2H) | 1.53$^c$ |
| 245 | 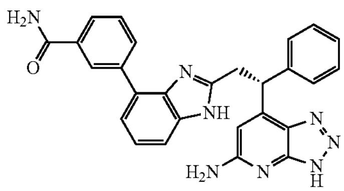 [SMILES: NC(=O)c1cccc(-c2cccc3[nH]c(C[C@H](c4ccccc4)c4cc(N)nc5[nH]nnc45)nc23)c1] | (R)-3-(2-(2-(5-amino-3H-[1,2,3]triazolo[4,5-b]pyridin-7-yl)-2-phenylethyl)-1H-benzo[d]imidazol-4-yl)benzamide | 475.1 | ¹H NMR (500 MHz, DMSO-d$_6$) δ 8.13 (m, 1H), 7.91 (m, 2H), 7.61 (m, 1H), 7.54 (m, 2H), 7.47 (m, 1H), 7.41 (m, 1H), 7.37-7.27 (m, 4H), 6.59 (s, 1H), 5.21 (m, 1H), 4.03 (m, 2H) | 1.13$^c$ |
| 246 | 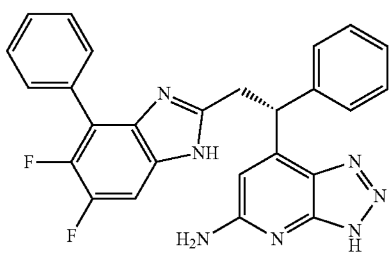 [SMILES: Nc1cc([C@H](Cc2nc3c(-c4ccccc4)c(F)c(F)cc3[nH]2)c2ccccc2)c2nn[nH]c2n1] | (R)-7-(2-(5,6-difluoro-4-phenyl-1H-benzo[d]imidazol-2-yl)-1-phenylethyl)-3H-[1,2,3]triazolo[4,5-b]pyridin-5-amine | 468.3 | ¹H NMR (500 MHz, DMSO-d$_6$) δ 7.63-7.58 (m, 2H), 7.56 (m, 3H), 7.51 (m, 4H), 7.29 (m, 1H), 7.19 (m, 1H), 6.56 (s, 1H), 5.15 (t, J = 7.8 Hz, 1H), 3.99-3.79 (m, 2H) | 1.47$^c$ |
| 247 | 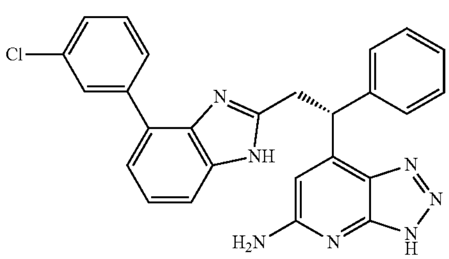 [SMILES: Nc1cc([C@H](Cc2nc3c(-c4cccc(Cl)c4)cccc3[nH]2)c2ccccc2)c2nn[nH]c2n1] | (R)-7-(2-(4-(3-chlorophenyl)-1H-benzo[d]imidazol-2-yl)-1-phenylethyl)-3H-[1,2,3]triazolo[4,5-b]pyridin-5-amine | 466.3 | ¹H NMR (500 MHz, DMSO-d$_6$) δ 7.75 (m, 1H), 7.69-7.50 (m, 5H), 7.50-7.39 (m, 2H), 7.35-7.23 (m, 3H), 7.23-7.18 (m, 1H), 7.16 (s, 1H), 7.06 (s, 1H), 6.56 (s, 1H), 5.20 (t, J = 8.1 Hz, 1H), 4.23-4.03 (m, 2H) | 1.49$^c$ |
| 248 | 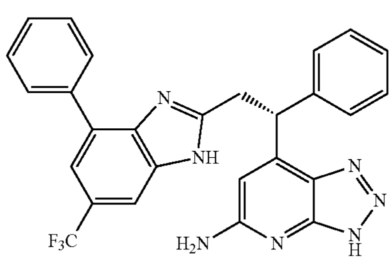 | (R)-7-(1-phenyl-2-(4-phenyl-6-(trifluoromethyl)-1H-benzo[d]imidazol-2-yl)ethyl)-3H-[1,2,3]triazolo[4,5-b]pyridin-5-amine | 500.2 | ¹H NMR (500 MHz, DMSO-d$_6$) δ 7.76 (m, 1H), 7.54 (m, 6H), 7.45 (m, 2H), 7.28 (m, 2H), 7.17 (m, 1H), 6.57 (s, 1H), 5.20 (m, 1H), 4.02-3.87 (m, 2H) | 1.65$^c$ |

| Ex. No. | Structure | Name | MS (ESI) (M + H) | ¹H NMR | LC RT$^a$ (min) |
|---|---|---|---|---|---|
| 249 | 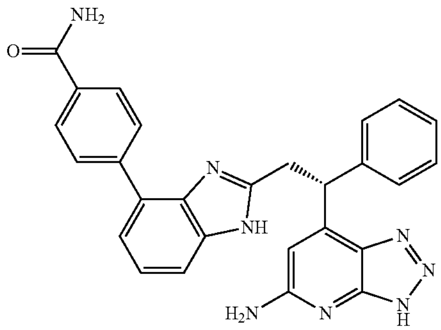 [SMILES: NC(=O)c1ccc(-c2cccc3[nH]c(C[C@H](c4ccccc4)c4cc(N)nc5[nH]nnc45)nc23)cc1] | (R)-4-(2-(2-(5-amino-3H-[1,2,3]triazolo[4,5-b]pyridin-7-yl)-2-phenylethyl)-1H-benzo[d]imidazol-4-yl)benzamide | 475.0 | ¹H NMR (500 MHz, DMSO-d₆) δ 8.13-8.00 (m, 4H), 7.86 (m, 1H), 7.54 (m, 3H), 7.48-7.35 (m, 3H), 7.30 (m, 2H), 7.24-7.19 (m, 1H), 6.57 (m, 1H), 5.30-5.15 (m, 1H), 4.11-3.90 (m, 2H) | 1.10$^e$ |
| 250 | 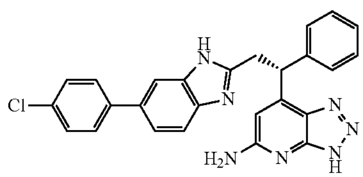 [SMILES: Nc1cc([C@H](Cc2nc3ccc(-c4ccc(Cl)cc4)cc3[nH]2)c2ccccc2)c2nn[nH]c2n1] | (R)-7-(1-phenyl-2-(6-phenyl-1H-benzo[d]imidazol-2-yl)ethyl)-3H-[1,2,3]triazolo[4,5-b]pyridin-5-amine | 466.2 | ¹H NMR (500 MHz, DMSO-d₆) δ 7.70 (m, 2H), 7.67-7.56 (m, 2H), 7.55-7.45 (m, 4H), 7.34-7.25 (m, 3H), 7.24-7.14 (m, 2H), 7.12-7.04 (m, 1H), 6.56 (s, 1H), 5.17 (t, J = 8.1 Hz, 1H), 4.16-4.00 (m, 2H) | 1.43$^e$ |
| 251 | 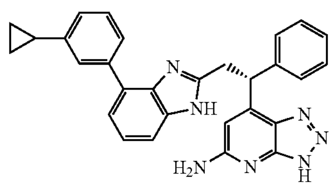 [SMILES: Nc1cc([C@H](Cc2nc3c(-c4cccc(C5CC5)c4)cccc3[nH]2)c2ccccc2)c2nn[nH]c2n1] | (R)-7-(2-(4-(3-cyclopropylphenyl)-1H-benzo[d]imidazol-2-yl)-1-phenylethyl)-3H-[1,2,3]triazolo[4,5-b]pyridin-5-amine | 472.1 | ¹H NMR (500 MHz, DMSO-d₆) δ 7.54 (m, 2H), 7.37 (m, 2H), 7.28 (m, 3H), 7.17 (m, 3H), 7.07 (m, 1H), 6.61 (m, 1H), 6.54 (s, 1H), 5.23 (m, 1H), 3.94 (m, 2H), 2.01 (s, 1H), 1.03 (m, 2H), 0.78 (m, 2H) | 1.55$^e$ |
| 252 | 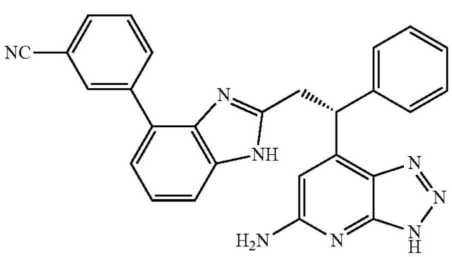 [SMILES: N#Cc1cccc(-c2cccc3[nH]c(C[C@H](c4ccccc4)c4cc(N)nc5[nH]nnc45)nc23)c1] | (R)-3-(2-(2-(5-amino-3H-[1,2,3]triazolo[4,5-b]pyridin-7-yl)-2-phenylethyl)-1H-benzo[d]imidazol-4-yl)benzonitrile | 457.1 | ¹H NMR (500 MHz, DMSO-d₆) δ 8.31-8.20 (m, 2H), 7.86 (m, 1H), 7.71 (m, 1H), 7.58-7.48 (m, 3H), 7.43 (m, 1H), 7.28 (m, 4H), 7.20-7.16 (m, 2H), 6.56 (s, 1H), 5.19 (t, J = 8.1 Hz, 1H), 4.00 (m, 2H) | 1.24$^e$ |
| 253 | 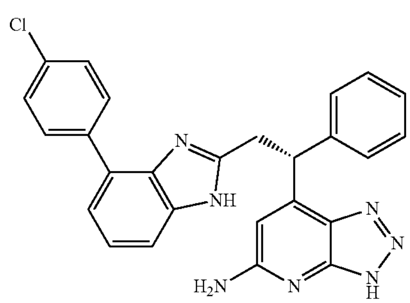 [SMILES: Nc1cc([C@H](Cc2nc3c(-c4ccc(Cl)cc4)cccc3[nH]2)c2ccccc2)c2nn[nH]c2n1] | (R)-7-(2-(4-(4-chlorophenyl)-1H-benzo[d]imidazol-2-yl)-1-phenylethyl)-3H-[1,2,3]triazolo[4,5-b]pyridin-5-amine | 466.2 | ¹H NMR (500 MHz, DMSO-d₆) δ 7.73 (m, 2H), 7.66-7.57 (m, 4H), 7.53 (m, 2H), 7.48-7.36 (m, 3H), 7.36-7.30 (m, 2H), 7.22 (m, 1H), 6.57 (s, 1H), 5.21 (t, J = 7.9 Hz, 1H), 4.13 (m, 2H) | 1.45$^e$ |
| 254 | 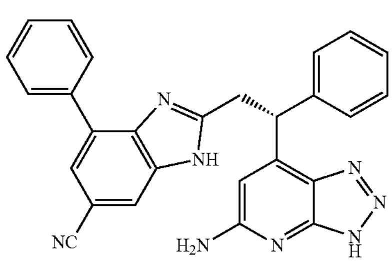 [SMILES: N#Cc1cc(-c2ccccc2)c2nc(C[C@H](c3ccccc3)c3cc(N)nc4[nH]nnc34)[nH]c2c1] | (R)-2-(2-(5-amino-3H-[1,2,3]triazolo[4,5-b]pyridin-7-yl)-2-phenylethyl)-4-phenyl-1H-benzo[d]imidazole-6-carbonitrile | 457.0 | ¹H NMR (500 MHz, DMSO-d₆) δ 7.98 (m, 1H), 7.84 (m, 2H), 7.68 (m, 1H), 7.59-7.49 (m, 4H), 7.47 (m, 1H), 7.30 (m, 2H), 7.23-7.17 (m, 1H), 6.65 (s, 1H), 5.22 (t, J = 7.9 Hz, 1H), 4.04-3.94 (m, 2H) | 1.59$^e$ |

-continued

| Ex. No. | Structure | Name | MS (ESI) (M + H) | ¹H NMR | LC RT[a] (min) |
|---|---|---|---|---|---|
| 255 | 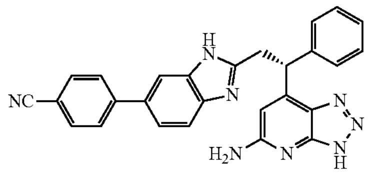 [SMILES: N#Cc1ccc(-c2ccc3nc(C[C@H](c4ccccc4)c4cc(N)nc5[nH]nnc45)[nH]c3c2)cc1] | (R)-4-(2-(2-(5-amino-3H-[1,2,3]triazolo[4,5-b]pyridin-7-yl)-2-phenylethyl)-1H-benzo[d]imidazol-6-yl)benzonitrile | 457.0 | ¹H NMR (500 MHz, DMSO-d₆) δ 8.00-7.89 (m, 7H), 7.80-7.72 (m, 2H), 7.53 m, 2H), 7.36-7.30 (m, 2H), 7.21 (m, 1H), 6.55 (s, 1H), 5.21 (t, J = 8.1 Hz, 1H), 4.19 (m, 2H) | 1.25[c] |
| 256 | 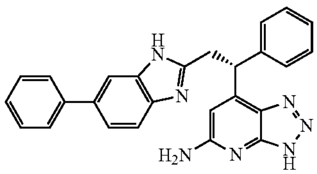 [SMILES: Cn1c(C[C@H](c2ccccc2)c2cc(N)nc3[nH]nnc23)nc2ccc(-c3ccccc3)cc21] | (R)-7-(1-phenyl-2-(6-phenyl-1H-benzo[d]imidazol-2-yl)ethyl)-3H-[1,2,3]triazolo[4,5-b]pyridin-5-amine | 432.2 | ¹H NMR (500 MHz, DMSO-d₆) δ 7.64 (m, 2H), 7.53 (m, 2H), 7.44 (m, 2H), 7.38 (m, 1H), 7.34-7.29 (m, 1H), 7.27 (m, 2H), 7.20-7.11 (m, 1H), 6.58 (m, 2H), 6.55 (s, 1H), 5.21 (t, J = 8.1 Hz, 1H), 4.02-3.80 (m, 2H) | 1.30[c] |
| 257 | 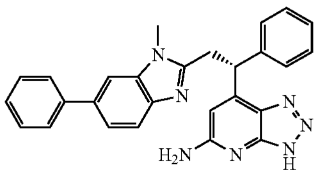 | (R)-7-(2-(1-methyl-6-phenyl-1H-benzo[d]imidazol-2-yl)-1-phenylethyl)-3H-[1,2,3]triazolo[4,5-b]pyridin-5-amine | 446.2 | ¹H NMR (500 MHz, DMSO-d₆) δ 7.80 (m, 1H), 7.72 (m, 2H), 7.55 m, 2H), 7.59 m, 1H), 7.47 (m, 3H), 7.38-7.28 (m, 3H), 7.21 (m, 1H), 6.52 (s, 1H), 5.22 (t, J = 7.8 Hz, 1H), 4.17 (m, 1H), 3.82 (m, 1H), 3.80 (s, 3H) | 1.37[c] |
| 258 | 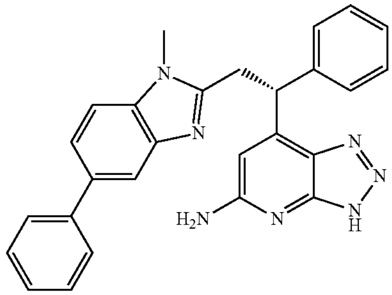 [SMILES: Cn1c(C[C@H](c2ccccc2)c2cc(N)nc3[nH]nnc23)nc2cc(-c3ccccc3)ccc21] | (R)-7-(2-(1-methyl-5-phenyl-1H-benzo[d]imidazol-2-yl)-1-phenylethyl)-3H-[1,2,3]triazolo[4,5-b]pyridin-5-amine | 446.4 | ¹H NMR (500 MHz, DMSO-d₆) δ 7.76 (m, 1H), 7.66 (m, 2H), 7.59-7.47 (m, 4H), 7.45 (m, 2H), 7.36-7.27 (m, 3H), 7.24-7.17 (m, 1H), 6.55 (s, 1H), 5.21 (t, J = 7.6 Hz, 1H), 4.12 (m, 1H), 3.82 (m, 1H), 3.75 (s, 3H) | 1.32[c] |
| 259 | 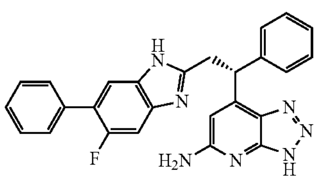 [SMILES: Nc1cc([C@H](Cc2nc3cc(F)c(-c4ccccc4)cc3[nH]2)c2ccccc2)c2nn[nH]c2n1] | (R)-7-(2-(5-fluoro-6-phenyl-1H-benzo[d]imidazol-2-yl)-1-phenylethyl)-3H-[1,2,3]triazolo[4,5-b]pyridin-5-amine | 449.9 | ¹H NMR (500 MHz, DMSO-d₆) δ 7.60-7.44 (m, 7H), 7.40-7.32 (m, 2H), 7.28 (m, 2H), 7.18 (m, 1H), 6.64-6.44 (m, 1H), 5.21 (t, J = 7.7 Hz, 1H), 4.04-3.91 (m, 1H), 3.89-3.77 (m, 1H) | 1.67[d] |
| 260 | 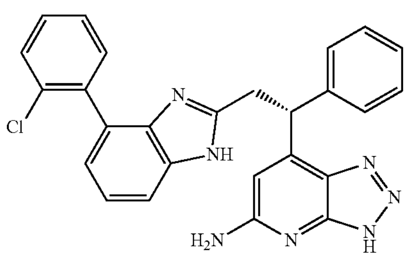 [SMILES: Nc1cc([C@H](Cc2nc3c(-c4ccccc4Cl)cccc3[nH]2)c2ccccc2)c2nn[nH]c2n1] | (R)-7-(2-(4-(2-chlorophenyl)-1H-benzo[d]imidazol-2-yl)-1-phenylethyl)-3H-[1,2,3]triazolo[4,5-b]pyridin-5-amine | 466.0 | ¹H NMR (500 MHz, DMSO-d₆) δ 7.49 (m, 6H), 7.24 (m, 2H), 7.15 (m, 2H), 7.08-6.88 (m, 1H), 6.56 (m, 2H), 5.27-5.02 (m, 1H), 3.84 (m, 2H) | 1.40 |
| 261 | 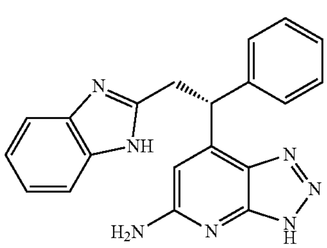 [SMILES: Nc1cc([C@H](Cc2nc3ccccc3[nH]2)c2ccccc2)c2nn[nH]c2n1] | (R)-7-(2-(1H-benzo[d]imidazol-2-yl)-1-phenylethyl)-3H-[1,2,3]triazolo[4,5-b]pyridin-5-amine | 356.3 | ¹H NMR (500 MHz, DMSO-d₆) δ 7.77-7.67 (m, 2H), 7.51 (m, 2H), 7.49-7.44 (m, 2H), 7.30 (m, 2H), 7.23-7.18 (m, 1H), 6.48 (s, 1H), 5.16 (t, J = 8.2 Hz, 1H), 4.25 (m, 2H) | 0.98 |

| Ex. No. | Structure | Name | MS (ESI) (M + H) | $^1$H NMR | LC RT$^a$ (min) |
|---|---|---|---|---|---|
| 262 | 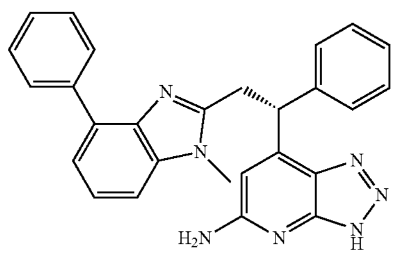 [SMILES: Cn1c(C[C@H](c2ccccc2)c2cc(N)nc3[nH]nnc23)nc2c(-c3ccccc3)cccc21] | (R)-7-(2-(1-methyl-4-phenyl-1H-benzo[d]imidazol-2-yl)-1-phenylethyl)-3H-[1,2,3]triazolo[4,5-b]pyridin-5-amine | 445.9 | $^1$H NMR (500 MHz, DMSO-$d_6$) δ 7.76 (m, 2H), 7.57 (m, 3H), 7.49 (m, 2H), 7.47-7.37 (m, 3H), 7.34 (m, 2H), 7.31-7.21 (m, 3H), 6.61 (s, 1H), 5.20 (t, J = 7.6 Hz, 1H), 4.19 (m, 1H), 3.98 (m, 1H), 3.80 (s, 3H) | 1.29$^c$ |
| 263 | 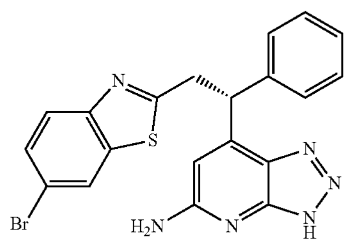 [SMILES: Nc1cc([C@H](Cc2nc3ccc(Br)cc3s2)c2ccccc2)c2nn[nH]c2n1] | (R)-7-(2-(6-bromobenzo[d]thiazol-2-yl)-1-phenylethyl)-3H-[1,2,3]triazolo[4,5-b]pyridin-5-amine | 451/453 | (500 MHz, DMSO-$d_6$) δ 8.26 (d, J = 1.9 Hz, 1H), 7.83 (d, J = 8.5 Hz, 1H), 7.58 (dd, J = 8.7, 2.1 Hz, 1H), 7.57-7.54 (m, 2H), 7.30 (t, J = 7.7 Hz, 2H), 7.22-7.18 (m, 1H), 6.54-6.48 (m, 1H), 5.02 (t, J = 8.0 Hz, 1H), 4.32 (dd, J = 15.8, 8.1 Hz, 1H), 4.08-4.02 (m, 1H). | 6.62 |

$^a$LC method A used unless otherwise specified
$^b$Method B
$^c$Method C
$^d$Method D

What is claimed is:

1. A compound of Formula (I):

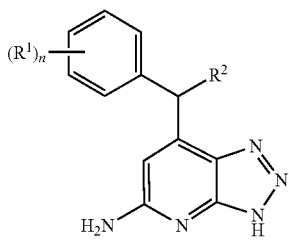

(I)

wherein $R^1$ is independently one or more hydrogen, halogen, $C_{1-4}$ alkyl, $C_{1-4}$ alkoxy, $C_{1-4}$ haloalkyl, $C_{1-4}$ haloalkoxy, CN, $CO_2(C_{1-4}$ alkyl), $CH_2H$, $CH_2NH_2$, $SO_2Me$, or $SO_2NH_2$;

n is 0, 1, or 2;

$R^2$ is benzyl, $C_3$-$C_8$ cycloalkyl $C_1$-$C_6$ alkyl-, hydroxy $C_1$-$C_6$ alkyl-, aryl $C_1$-$C_6$ alkyl-, —$(CH_2)_2$ $C_1$-$C_6$ alkoxy aryl, heteroaryl $C_1$-$C_6$ alkyl-, —$(CH_2)_2$ $C_1$-$C_6$ alkoxy, —$(CH_2)_m$ $NR^3COaryl$, —$(CH_2)_m NR^3$ $C_1$-$C_6$ alkyl, —$(CH_2)_m NR^3$ aryl $C_1$-$C_6$ alkyl; —$(CH_2)_m NR^3$ heteroaryl $C_1$-$C_6$ alkyl, —$(CH_2)_m NR^3$ $C_3$-$C_8$ cycloalkyl, —$(CH_2)_m NR^3$ heterocyclyl, —$(CH_2)_m NR^3$ $C_3$-$C_8$ cycloalkyl $C_1$-$C_6$ alkyl, —$(CH_2)_m NR^3$ $C_3$-$C_8$ cycloalkyl aryl, —$(CH_2)_m$ $NR^3$ $C_9$-$C_{10}$ bicyclic carbocyclyl, —$(CH_2)_m NR^3$ bridged carbocyclyl, —$(CH_2)_m NR^3$ bridged heterocyclyl, —$(CH_2)_m$ $NHSO_2$ aryl, —$(CH_2)_{20}$ $C_3$-$C_{10}$ carbocyclyl, —$(CH_2)_m$ CO aryl $C_1$-$C_6$ alkyl, —$(CH_2)_p$ heterocyclyl, or —$CH_2$ CO $NR^3$ $C_3$-$C_{10}$ carbocyclyl; any of which is substituted with 0-3 $R^4$ groups, m is 1, 2, 3, or 4;

p is 2 or 3;

$R^3$ is hydrogen, $C_{1-4}$ alkyl, 2-($C_{1-4}$ alkoxy)ethyl-, hydroxy $C_2$-$C_4$ alkyl, $C_{1-4}$ haloalkyl, —$CH_2CH(OH)CF_3$, —$(CH_2)$ heterocyclyl or —$CH_2CONR^xR^y$;

$R^x$ is hydrogen or $C_{1-4}$ alkyl;

$R^y$ is hydrogen or $C_{1-4}$ alkyl;

$R^4$ is, independently at each occurrence, one or more hydrogen, halogen, hydroxy, amino, cyano, hydroxy $C_1$-$C_6$ alkyl, halo $C_1$-$C_6$ alkyl, $C_1$-$C_6$ alkyl, $C_1$-$C_4$ alkoxy, —$C_{3-6}$ cycloalkyl, aryl, aryloxy, aryl $C_1$-$C_6$ alkyl-, heterocycle, —COO $C_1$-$C_6$ alkyl, or $CONR^xR^y$;

said —$C_{3-6}$ cycloalkyl substituted with 0-3 $R^a$, aryl substituted with 0-4 $R^a$, or a 5- to 10-membered heterocycle comprising carbon atoms and 1-4 heteroatoms selected from N, $NR^b$, O, and S; wherein said heterocycle is substituted with 0-3 $R^a$;

$R^a$ is, independently at each occurrence, hydrogen, OH, CN, —$CONH_2$, halogen, $C_{1-4}$ alkyl, $C_{1-4}$ alkoxy, $C_{1-4}$ haloalkyl or $C_{1-4}$ haloalkoxy;

$R^b$ is, independently at each occurrence, hydrogen, $C_{1-4}$ alkyl, $C_{1-4}$ haloalkyl, $CO(C_{1-4}$ alkyl), $C_2(C_{1-4}$ alkyl), $SO_2(C_{1-4}$ alkyl) or —$(CH_2)$-phenyl, said —$(CH_2)t$-phenyl substituted with 0-1 $R^d$;

$R^d$ is hydrogen, $C_{1-4}$ alkyl or halogen;

t is 1 or 2;

and/or a pharmaceutically acceptable salt, a stereoisomer, a tautomer, or a solvate thereof.

2. A compound according to claim 1 of Formula (II);

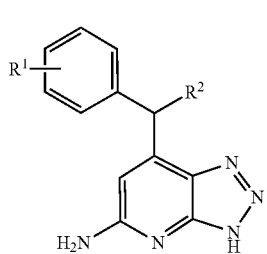

(II)

wherein $R^1$ is hydrogen, halogen, OMe, OCF$_3$, OCF$_2$H, methyl, CH$_2$OH, SO$_2$NH$_2$ or CN;

$R^2$ is benzyl, C$_3$-C$_8$ cycloalkyl C$_1$-C$_6$ alkyl-, hydroxy C$_1$-C$_6$ alkyl-, aryl C$_1$-C$_6$ alkyl-, —(CH$_2$)$_2$ C$_1$-C$_6$ alkoxy aryl, heteroaryl C$_1$-C$_6$ alkyl-, —(CH$_2$)$_2$ C$_1$-C$_6$ alkoxy, —(CH$_2$)$_m$ NR$^3$COaryl, —(CH$_2$)$_m$NR$^3$ C$_1$-C$_6$ alkyl, —(CH$_2$)$_m$NR$^3$ aryl C$_1$-C$_6$ alkyl; —(CH$_2$)$_m$NR$^3$ heteroaryl C$_1$-C$_6$ alkyl, —(CH$_2$)$_m$NR$^3$ C$_3$-C$_8$ cycloalkyl, —(CH$_2$)$_m$NR$^3$ heterocyclyl, —(CH$_2$)$_m$NR$^3$ C$_3$-C$_8$ cycloalkyl C$_1$-C$_6$ alkyl, —(CH$_2$)$_m$NR$^3$ C$_3$-C$_8$ cycloalkyl aryl, —(CH$_2$)$_m$ NR$^3$ C$_9$-C$_{10}$ bicyclic carbocyclyl, —(CH$_2$)$_m$NR$^3$ bridged carbocyclyl, —(CH$_2$)$_m$NR$^3$ bridged heterocyclyl, —(CH$_2$)$_m$ NHSO$_2$ aryl, —(CH$_2$)$_2$ O C$_3$-C$_{10}$ carbocyclyl, —(CH$_2$)$_m$ CO aryl C$_1$-C$_6$ alkyl, —(CH$_2$)$_p$ heterocyclyl, or —CH$_2$CONR$^3$C$_3$-C$_{10}$ carbocyclyl; any of which is substituted with 0-3 R$^4$ groups, m is 2 or 3;

p is 2 or 3;

$R^3$ is hydrogen, C$_{1-4}$ alkyl, 2-(C$_{1-4}$ alkoxy)ethyl-, hydroxy C$_2$-C$_4$ alkyl, C$_{1-4}$ haloalkyl, —(CH$_2$) heterocyclyl or —CH$_2$CONR$^x$R$^y$;

$R^x$ is hydrogen or C$_{1-4}$ alkyl;

$R^y$ is hydrogen or C$_{1-4}$ alkyl;

$R^4$ is, independently at each occurrence, one or more halogen, hydroxy, cyano, hydroxy C$_1$-C$_6$ alkyl, halo C$_1$-C$_6$ alkyl, C$_1$-C$_4$ alkoxy, C$_1$-C$_6$ alkyl, —C$_{3-6}$ cycloalkyl, aryl, aryloxy, aryl C$_1$-C$_6$ alkyl-, —COO C$_1$-C$_6$ alkyl, or CONR$^x$R$^y$;

said —C$_{3-6}$ cycloalkyl is substituted with 0-3 R$^a$; said aryl is substituted with 0-4 R$^a$, or a 5- to 10-membered heterocycle comprising carbon atoms and 1-4 heteroatoms selected from N, NR$^b$, O, and S; wherein said heterocycle is substituted with 0-3 R$^a$;

$R^a$ is, independently at each occurrence, OH, CN, —CONH$_2$, halogen, C$_{1-4}$ alkyl, C$_{1-4}$ alkoxy, C$_{1-4}$ haloalkyl, or C$_{1-4}$ haloalkoxy;

$R^b$ is, independently at each occurrence, hydrogen, C$_{1-4}$ alkyl, C$_{1-4}$ haloalkyl, CO(C$_{1-4}$ alkyl), C$_2$(C$_{1-4}$ alkyl), SO$_2$(C$_{1-4}$ alkyl) or —(CH$_2$)-phenyl, said —(CH$_2$)t-phenyl substituted with 0-1 R$^d$;

$R^d$ is F or Cl;

and/or a pharmaceutically acceptable salt, a stereoisomer, a tautomer, or a solvate thereof.

3. A compound according to claim 2 of Formula (III);

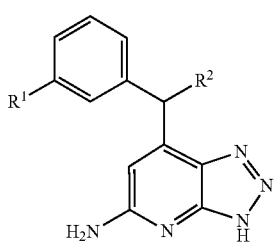

(III)

wherein $R^1$ is hydrogen, halogen, OMe, OCF$_3$, OCF$_2$H, methyl, CH$_2$OH, SO$_2$NH$_2$ or cyano;

$R^3$ is hydrogen, C$_{1-4}$ alkyl, 2-(C$_{1-4}$ alkoxy)ethyl-, hydroxy ethyl, C$_{1-4}$ haloalkyl, —(CH$_2$) heterocyclyl or —CH$_2$CONR$^x$R$^y$;

$R^2$ is 3-phenylpropyl, 2-benzyloxyethyl, 3,3,-diphenylpropyl, 3-cyclohexylethyl, 1-naphthylpropyl, 2-naphthylpropyl, 1-indanylpropyl, 2-(tetrahydro-2H-pyran-4-yl)ethyl, 3-(1,2,3,4-tetrahydroisoquinolin-1-yl) propyl, —(CH$_2$)$_2$NR$^3$ C$_1$-C$_6$ alkyl, —(CH$_2$)$_m$NR$^3$ aryl C$_1$-C$_6$ alkyl; —(CH$_2$)$_m$NR$^3$ heteroaryl C$_1$-C$_6$ alkyl, —(CH$_2$)$_m$NR$^3$ C$_3$-C$_8$ cycloalkyl, —(CH$_2$)$_m$NR$^3$ heterocyclyl, —(CH$_2$)$_m$NR$^3$ C$_3$-C$_8$ cycloalkyl C$_1$-C$_6$ alkyl, —(CH$_2$)$_m$NR$^3$ C$_3$-C$_8$ cycloalkyl aryl, —(CH$_2$)$_m$ NR$^3$ C$_9$-C$_{10}$ bicyclic carbocyclyl, —(CH$_2$)$_m$NR$^3$ bridged carbocyclyl, —(CH$_2$)$_m$NR$^3$ bridged heterocyclyl,

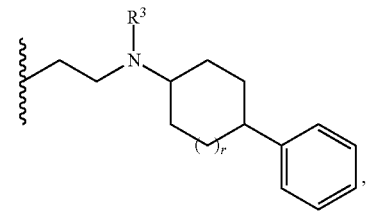

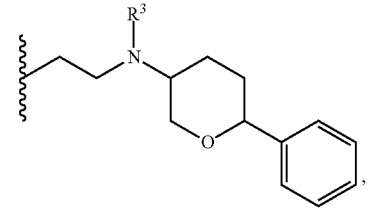

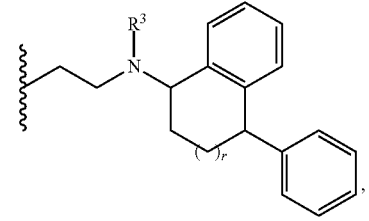

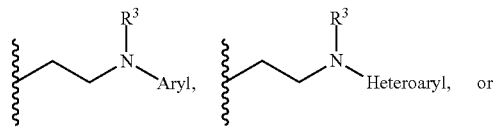

-continued

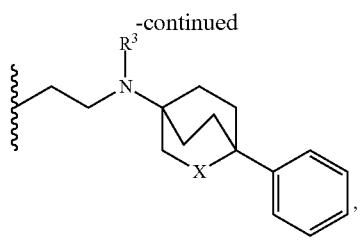

any of which can be substituted with 0-3 R⁴ groups;
m is 2;
R⁴ is hydrogen, halogen, hydroxyl, $C_{1-4}$ alkyl, $C_{1-4}$ alkoxy, $C_{1-2}$ haloalkyl, phenoxy, aryl or benzyl;
said —$C_{3-6}$ cycloalkyl is substituted with 0-3 $R^a$; said aryl is substituted with 0-4 $R^a$,
or a 5- to 10-membered heterocycle comprising carbon atoms and 1-4 heteroatoms selected from N, $NR^b$, O, and S; wherein said heterocycle is substituted with 0-3 $R^a$;
$R^a$ is, independently at each occurrence, OH, CN, —$CONH_2$, halogen, $C_{1-4}$ alkyl, $C_{1-4}$ alkoxy, $C_{1-4}$ haloalkyl, or $C_{1-4}$ haloalkoxy;
r is 0 or 1;
X is $CH_2$ or O;
and/or a pharmaceutically acceptable salt, a stereoisomer, a tautomer, or a solvate thereof.

4. A compound according to claim 3 wherein
R³ is hydrogen, $C_{1-4}$ alkyl, $C_{1-4}$ alkoxyalkyl, $C_{2-4}$ hydroxyalkyl, $C_{1-4}$ haloalkyl, —$CH_2$-heterocyclyl or —$(CH_2)CONH_2$;
R² is

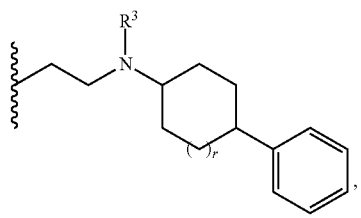

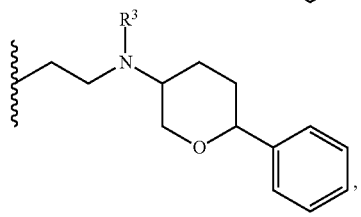

-continued

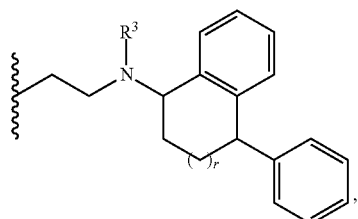

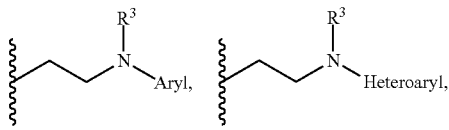

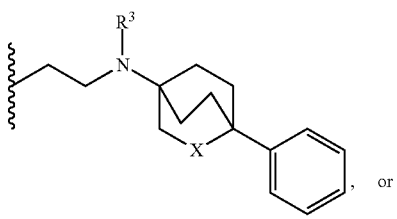

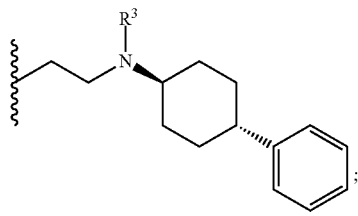

any of which can be substituted with 0-1 R⁴ groups;
r is 0 or 1;
R⁴ is hydrogen, halogen, hydroxyl, $C_{1-4}$ alkyl, $C_{1-4}$ alkoxy, $C_{1-2}$ haloalkyl, phenoxy, aryl or benzyl;
and/or a pharmaceutically acceptable salt, a stereoisomer, a tautomer, or a solvate thereof.

5. A pharmaceutical composition, comprising a pharmaceutically acceptable carrier and a compound according to claim 1, or a stereoisomer, a tautomer, or a pharmaceutically acceptable salt thereof.

* * * * *